United States Patent
Barany et al.

(10) Patent No.: US 10,829,804 B2
(45) Date of Patent: Nov. 10, 2020

(54) METHOD FOR IDENTIFICATION AND ENUMERATION OF NUCLEIC ACID SEQUENCES, EXPRESSION, SPLICE VARIANT, TRANSLOCATION, COPY, OR DNA METHYLATION CHANGES USING COMBINED NUCLEASE, LIGASE, POLYMERASE, TERMINAL TRANSFERASE, AND SEQUENCING REACTIONS

(71) Applicants: The University of North Carolina at Chapel Hill, Chapel Hill, NC (US); Cornell University, Ithaca, NY (US); Board of Supervisors of Louisiana State University and Agricultural and Mechanical College, Baton Rouge, LA (US)

(72) Inventors: Francis Barany, New York, NY (US); John William Efcavitch, San Carlos, CA (US); Steven A. Soper, Baton Rouge, LA (US); Sunggook Park, Baton Rouge, LA (US)

(73) Assignees: The University of North Carolina at Chapel Hill, Chapel Hill, NC (US); Cornell University, Ithaca, NY (US); Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 4 days.

(21) Appl. No.: 15/560,805

(22) PCT Filed: Mar. 23, 2016

(86) PCT No.: PCT/US2016/023814
§ 371 (c)(1),
(2) Date: Sep. 22, 2017

(87) PCT Pub. No.: WO2016/154337
PCT Pub. Date: Sep. 29, 2016

(65) Prior Publication Data
US 2018/0346973 A1    Dec. 6, 2018

Related U.S. Application Data

(60) Provisional application No. 62/137,009, filed on Mar. 23, 2015.

(51) Int. Cl.
C12Q 1/68      (2018.01)
C12Q 1/6827    (2018.01)

(52) U.S. Cl.
CPC .................................. *C12Q 1/6827* (2013.01)

(58) Field of Classification Search
None
See application file for complete search history.

(56) References Cited

U.S. PATENT DOCUMENTS

| | | |
|---|---|---|
| 8,586,301 B2 | 11/2013 | Kokoris et al. |
| 8,652,779 B2 | 2/2014 | Turner et al. |
| 8,889,348 B2 | 11/2014 | Ju |
| 8,975,095 B2 | 3/2015 | Han et al. |
| 2007/0237680 A1 | 10/2007 | Lee et al. |
| 2010/0291548 A1 | 11/2010 | Sharaf et al. |
| 2010/0297709 A1 | 11/2010 | Rashtchian |
| 2010/0331194 A1 | 12/2010 | Turner et al. |
| 2011/0011781 A1 | 1/2011 | Blankenstein et al. |
| 2012/0080361 A1 | 4/2012 | Walavalkar et al. |
| 2012/0100521 A1 | 4/2012 | Soper et al. |
| 2012/0157344 A1 | 6/2012 | Rosenfeld et al. |
| 2012/0164651 A1 | 6/2012 | Kazakov et al. |
| 2012/0220047 A1 | 8/2012 | Seifried et al. |
| 2012/0237997 A1 | 9/2012 | Koser |
| 2013/0022977 A1 | 1/2013 | Lapidus et al. |
| 2013/0244313 A1 | 9/2013 | Dunn et al. |
| 2013/0327644 A1 | 12/2013 | Turner et al. |
| 2014/0134646 A1 | 5/2014 | Martin et al. |
| 2014/0179909 A1 | 6/2014 | O'Halloran et al. |
| 2016/0161378 A1 | 6/2016 | Kim et al. |

FOREIGN PATENT DOCUMENTS

| | | |
|---|---|---|
| DE | 10 2011 081 472 A1 | 2/2013 |
| WO | 2012/170560 | 12/2012 |
| WO | WO 2013/012440 A2 | 1/2013 |
| WO | WO 2013/160408 A2 | 10/2013 |
| WO | WO 2013/191793 A1 | 12/2013 |
| WO | WO 2014/124365 A2 | 8/2014 |
| WO | WO 2014/160199 A1 | 10/2014 |

(Continued)

OTHER PUBLICATIONS

Extended European Search Report corresponding to European Application No. 16769605.3 dated Jan. 3, 2019.
Satake et al , A sensor for blood cell counter using MEMS technology, 2002, Sensors and Actuators B, 83, 77-81 (Year: 2002).
Machine translation in English of Description DE102011081472, printed on Nov. 7, 2018, pp. 1-20. (Year: 2018).
Machine translation in English of Claims DE102011081472, printed on Nov. 7, 2018, pp. 1-2. (Year: 2018).

(Continued)

*Primary Examiner* — James Martinell
(74) *Attorney, Agent, or Firm* — Myers Bigel, P.A.

(57) ABSTRACT

The present invention is directed methods for identifying, in a sample, one or more target nucleotide sequences differing from other nucleotide sequences in the sample by one or more nucleotides, one or more copy numbers, one or more transcript sequences, and/or one or more methylated residues, using ligation detection reactions, polymerase mediated extension reactions, and/or cleavage reactions. The present invention is also directed to methods for identifying, in a sample, one or more nucleotides in a target nucleotide sequence.

18 Claims, 229 Drawing Sheets

Specification includes a Sequence Listing.

(56) References Cited

FOREIGN PATENT DOCUMENTS

| WO | 2016/154302 | 9/2016 |
|---|---|---|
| WO | 2016/154337 | 9/2016 |

OTHER PUBLICATIONS

Partial Supplementary European Search Report corresponding to European Application No. 16769605.1 dated Sep. 4, 2018.
International Search Report corresponding to International Application No. PCT/US2016/023814 dated Sep. 7, 2016.
Written Opinion of the International Searching Authority corresponding to International Application No. PCT/US2016/023814 dated Sep. 7, 2016.
International Search Report and the Written Opinion of the International Searching Authority corresponding to International Patent Application No. PCT/US2016/023769 dated Jul. 21, 2016.
Ashton et al. "MinION nanopore sequencing identifies position and structure of a bacterial antibiotic resistance island" *Nature Biotechnology* 33:296-300 (2015).
Atas et al, "DNA sequencing and bar-coding using solid-state nanopores" *Electrophoresis* 33:3437-3447 (2012).
Brown et al, "Novel, Gasketless, Interconnect Using Parallel Superhydrophobic Surfaces for Modular Microfluidic Systems" *Proceedings of the ASME 2011 International Mechanical Engineering Congress & Exposition* (5 pages) (2011).
Cherf et al. "Automated forward and reverse ratcheting of DNA in a nanopore at 5-Å precision" *Nature Biotechnology* 30(4):344-348 (2012).
Hernandez-Ainsa et al. "DNA Origami Nanopores for Controlling DNA Translocation" *ACS Nano* 7(7):6024-6030 (2013).
Kant et al. "The Influence of Nanopore Dimensions on the Electrochemical Properties of Nanopore Arrays Studied by Impedance Spectroscopy" *Sensors* 14:21316-21328 (2014).
Kumar et al. "PEG-Labeled Nucleotides and Nanopore Detection for Single Molecule DNA Sequencing by Synthesis" *Scientific Reports* 2(684):1-8 (2012).
Langecker et al. "Electrophoretic Time-of-Flight Measurements of Single DNA Molecules with Two Stacked Nanopores" *Nano Letters* 11:5002-5007 (2011).
Laszlo et al. "Nanopore sequencing of the phi X 174 genome" *arXiv* 1406(4214) (39 pages) (2014).
Lee et al. "Single-molecule DNA digestion in various alkanethiol-functionalized gold naopores" *Talanta* 107:297-303 (2013).
Manrao et al. "Reading DNA at single-nucleotide resolution with a mutant MspA nanopore and phi29 DNA polymerase" *Nature Biotechnology* 30(4):349-354 (2012).
Matthews, Jerney M.A. "Nanopore DNA sequencing inches closer to commercial debut" *Physics Today* 65:29-31 (2012).
Pennisi, Elizabeth "Search for Pore-fection" *Science* 336:534-537 (2012).
Quick et al. "Real-time, portable genome sequencing for Ebola surveillance" *Nature* 530:228-232 (2016).
Saleh et al. "An Artificial Nanopore for Molecular Sensing" *Nano Letters* 3(1):37-38 (2003).
Steinbock et al. "The emergence of nanopores in next-generation sequencing" *Nanotechnology* 25:1-5 (2015).
Venta et al. "Differentiation of Short, Single-Stranded DNA Homopolymers in Solid-State Nanopores" *ACS Nano* 7(5):4629-4636 (2013).
Wang et al. "The evolution of nanopore sequencing" *Frontiers in Genetics* 5:1-20 (2015).
Zhang et al. "Programming Nanopore Ion Flow for Encoded Multiplex MicroRNA Detection" *ACS Nano* 8(4):3444-3450 (2014).
Notification Concerning Transmittal of International Preliminary Report on Patentability corresponding to International Application No. PCT/US2016/023814 dated Oct. 5, 2017.
Notification Concerning Transmittal of International Preliminary Report on Patentability corresponding to International Patent Application No. PCT/US2016/023769 dated Oct. 5, 2017.
U.S. Appl. No. 15/560,028, filed Sep. 20, 2017; office action dated Feb. 4, 2019.
Murphy et al. "Technology for Modular Microfluidic Systems" Louisiana State University's Center for Biomodular Multi-Scale Systems Presentation (43 pages) (Dec. 17, 2012).
Examination Report corresponding to European Application No. 16769605.3 dated Aug. 19, 2019.
Examination Report corresponding to European Application No. 16769605.3 dated Apr. 3, 2020.
Examination Report corresponding to European Application No. 16769625.1 dated Jan. 2, 2020.

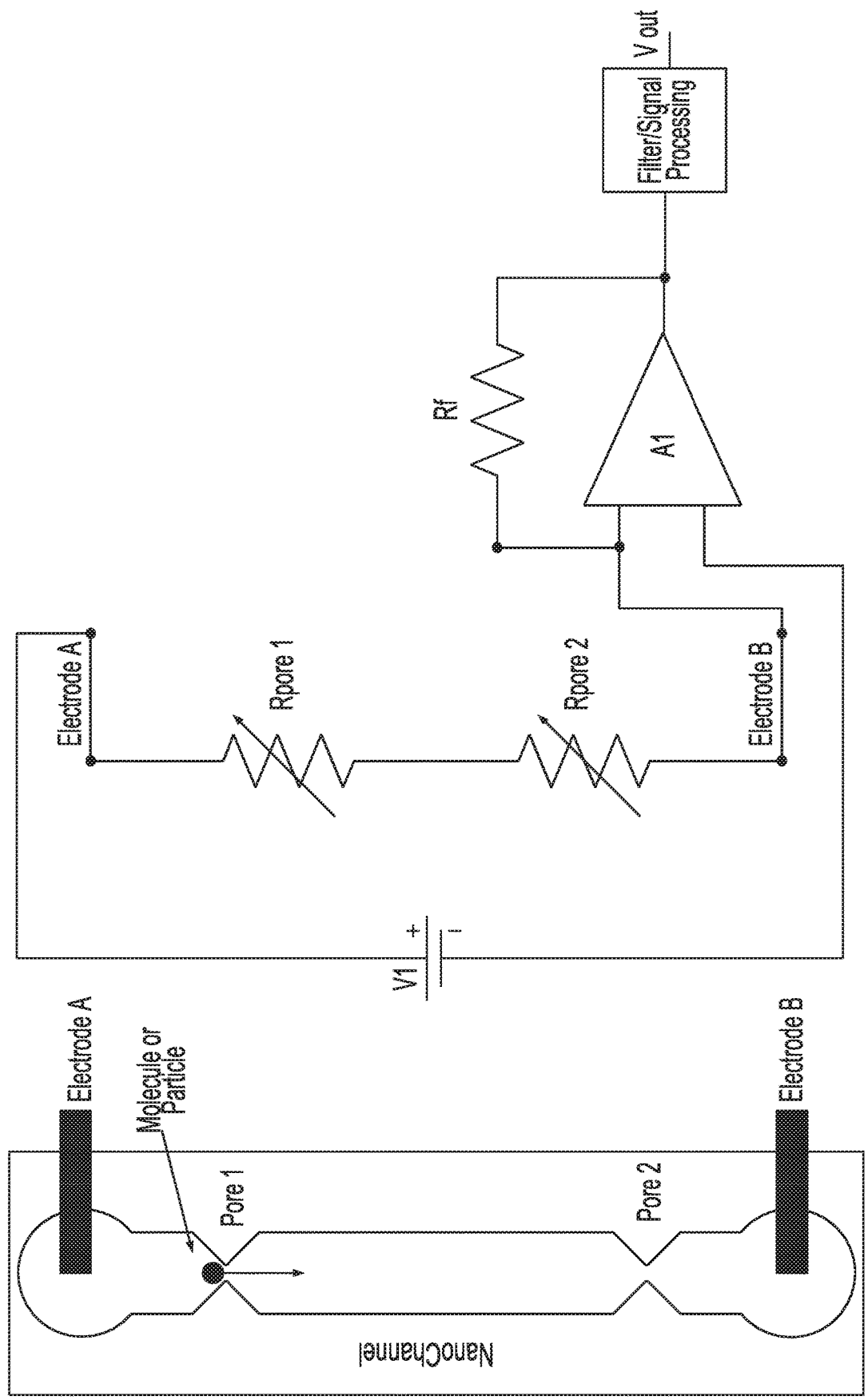

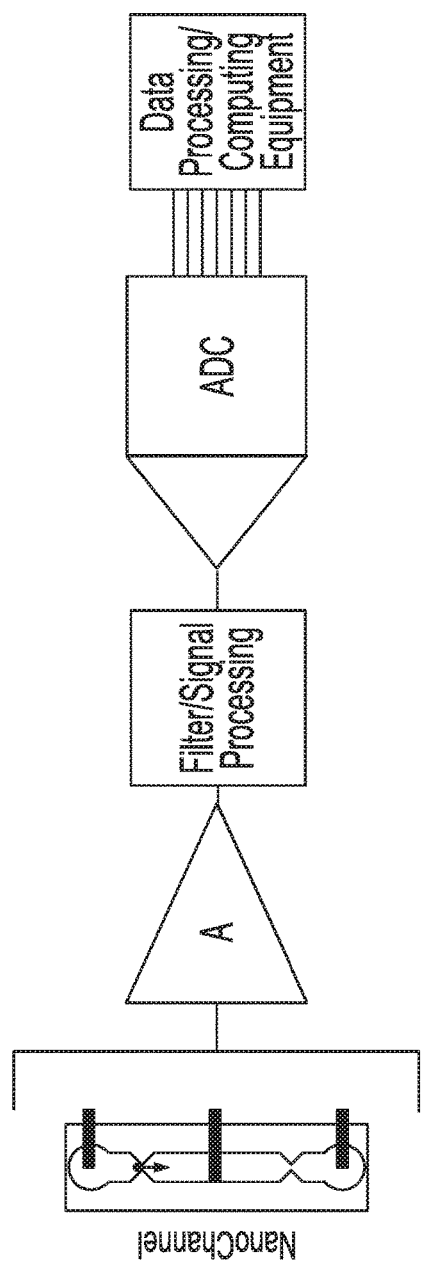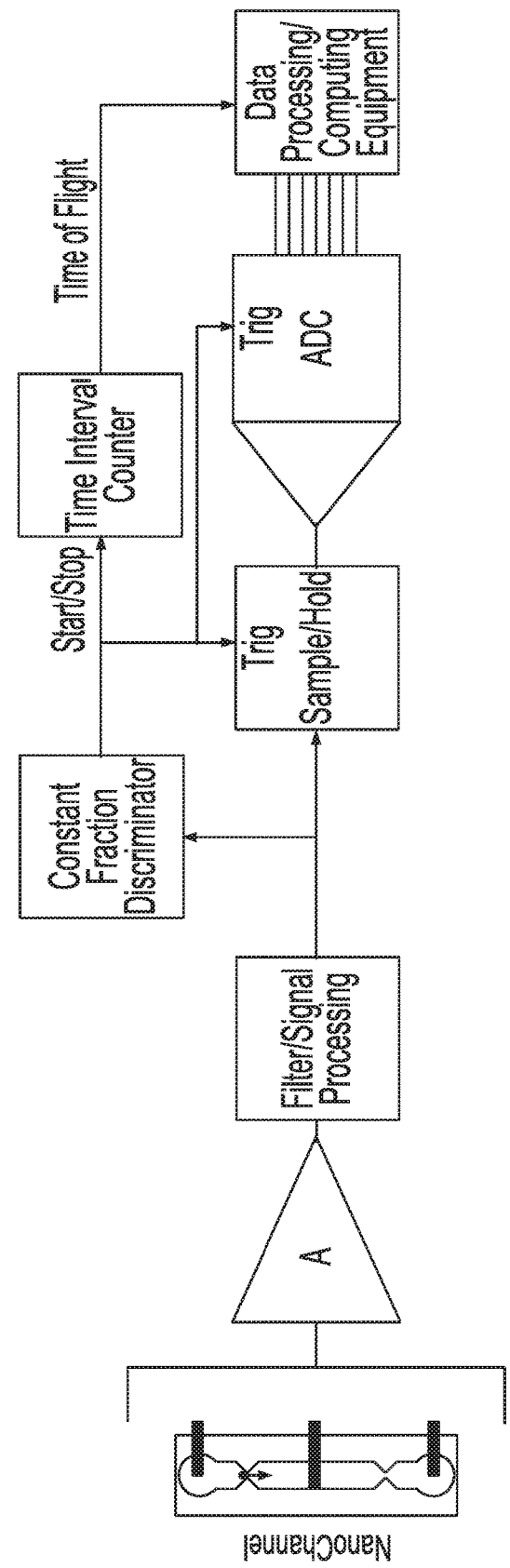
FIG. 15A
FIG. 15B

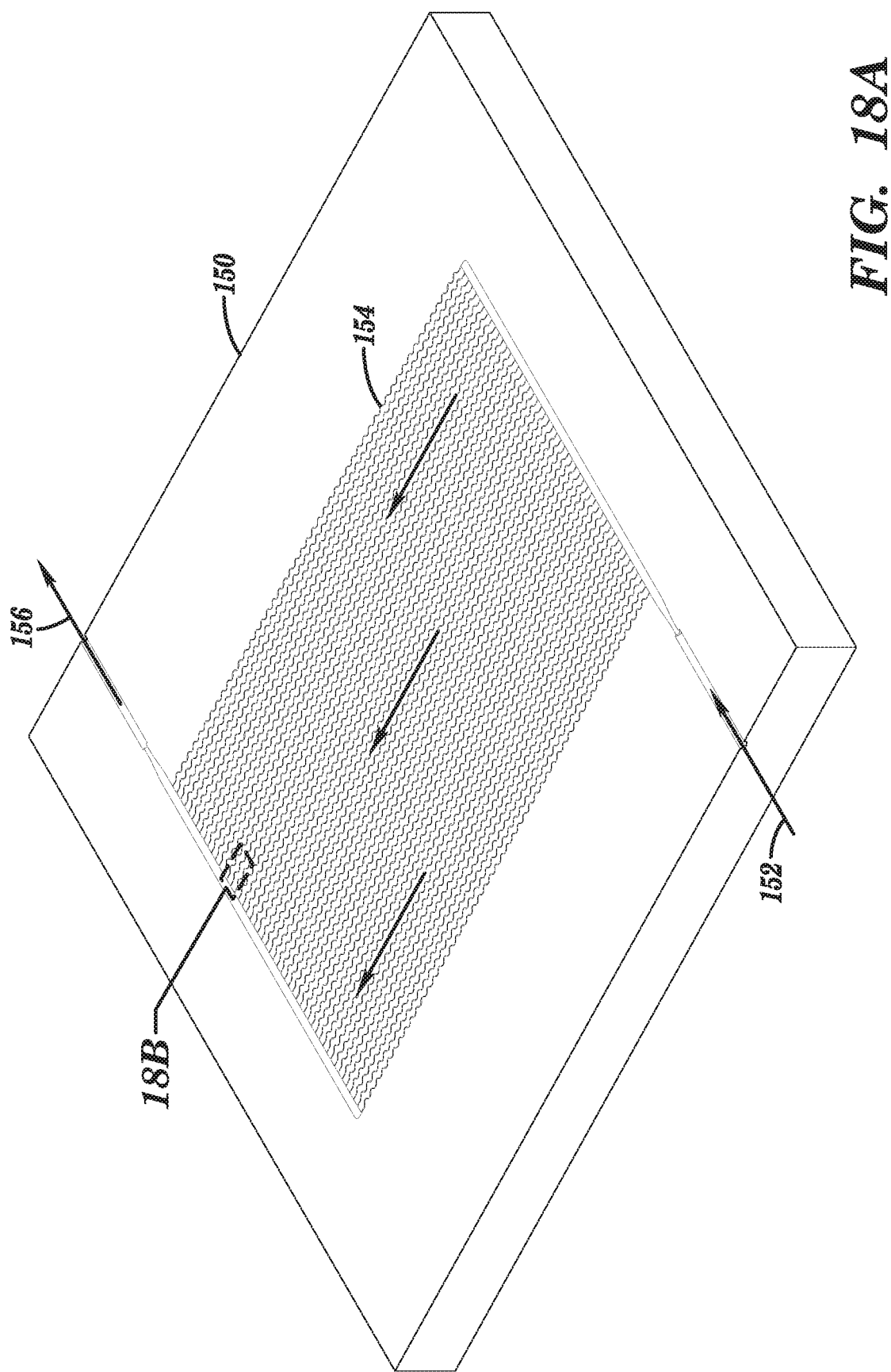

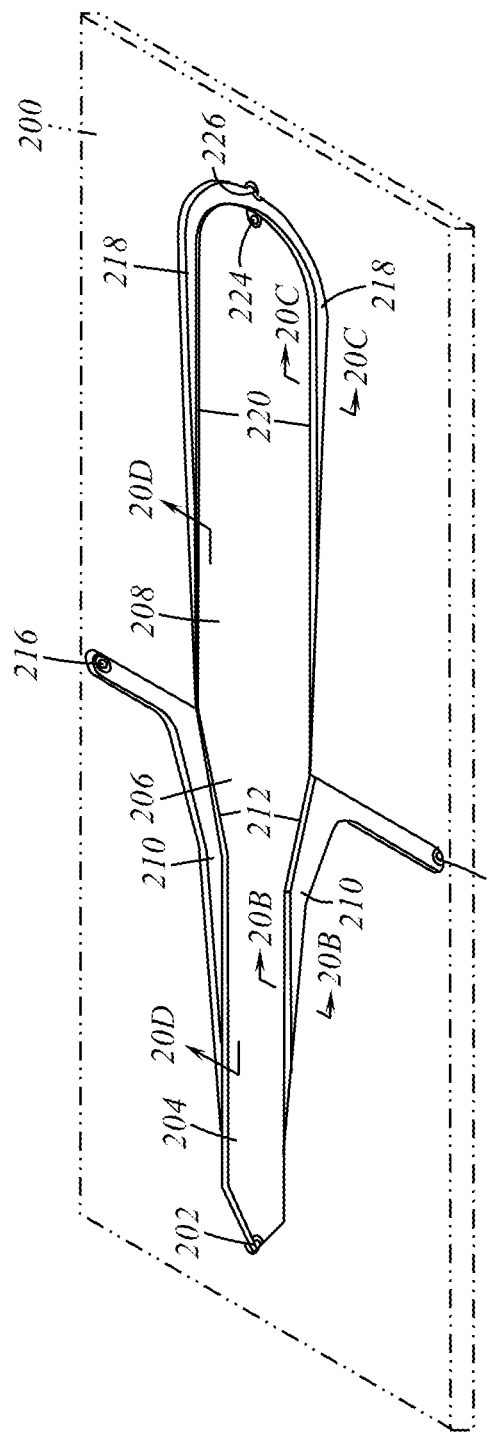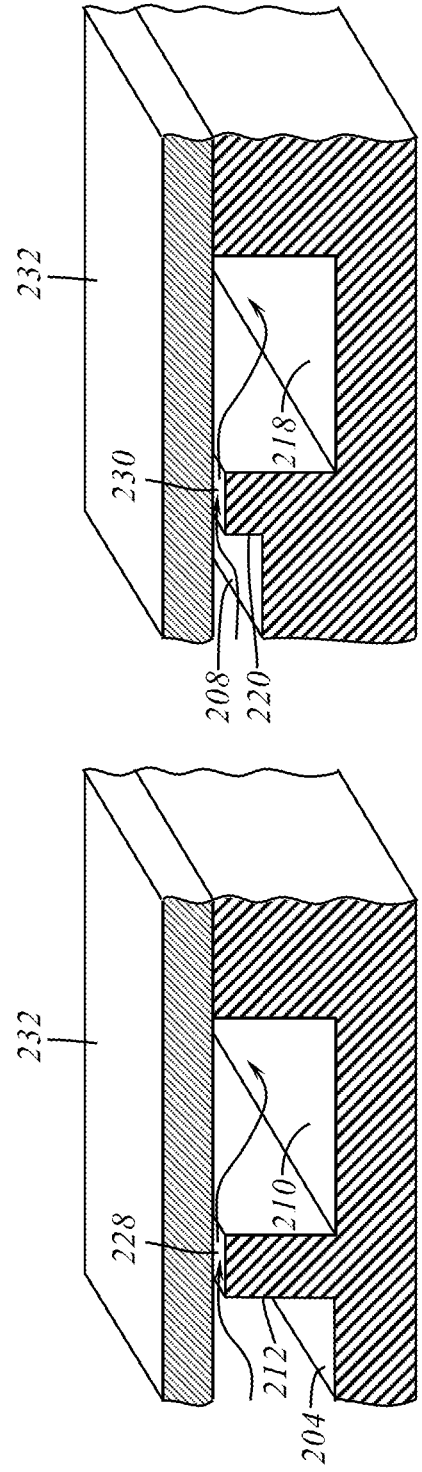
FIG. 20A
FIG. 20B
FIG. 20C

STEP 1
STEP 2
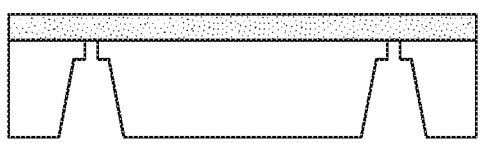
STEP 3
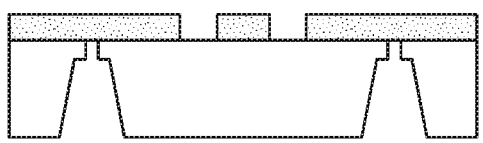
STEP 4
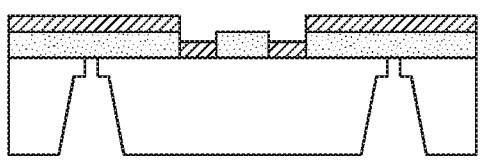
STEP 5
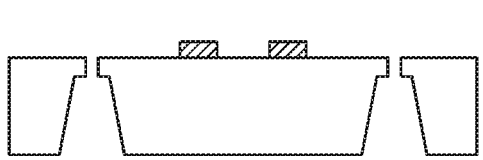
STEP 6
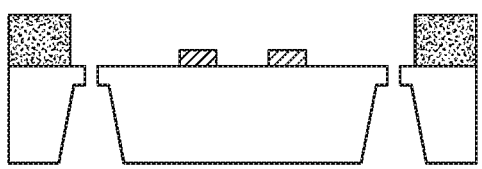
STEP 7
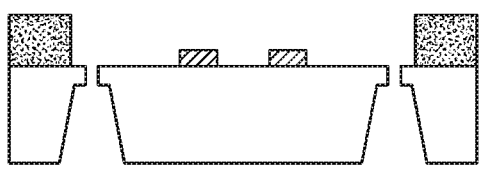
STEP 8
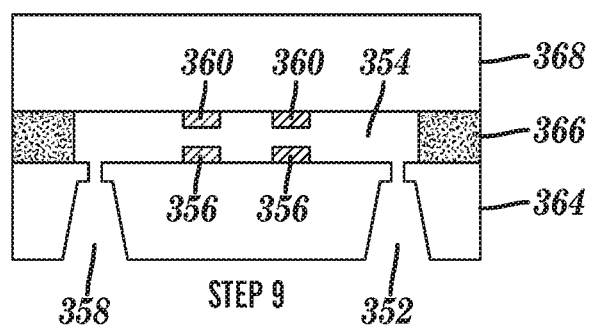
STEP 9
*FIG. 24*

(A) REGULAR MOLD INSERT
(C) MODIFIED POST MOLD INSERT
(B) EMBOSSED POST
(D) EMBOSSED POST

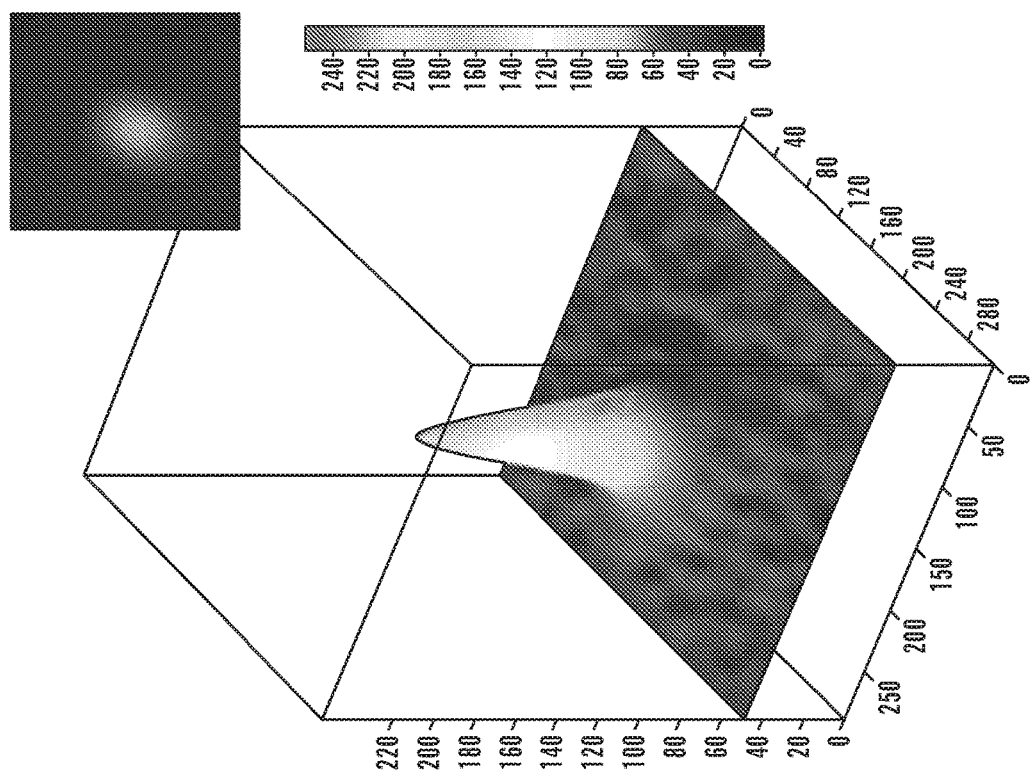
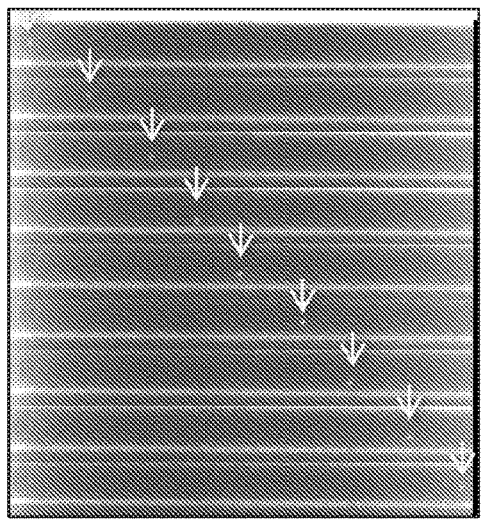
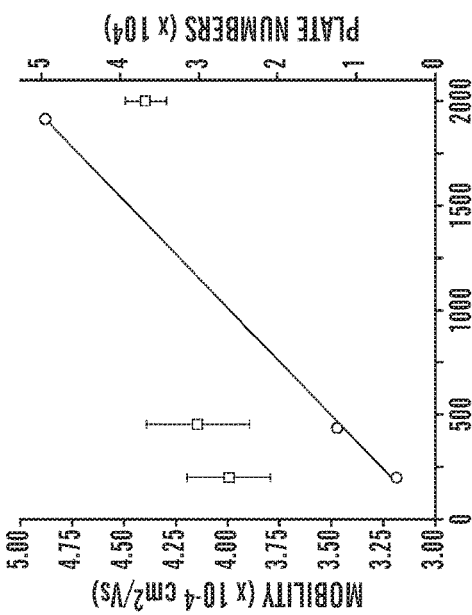
FIG. 40A
FIG. 40B
FIG. 40C

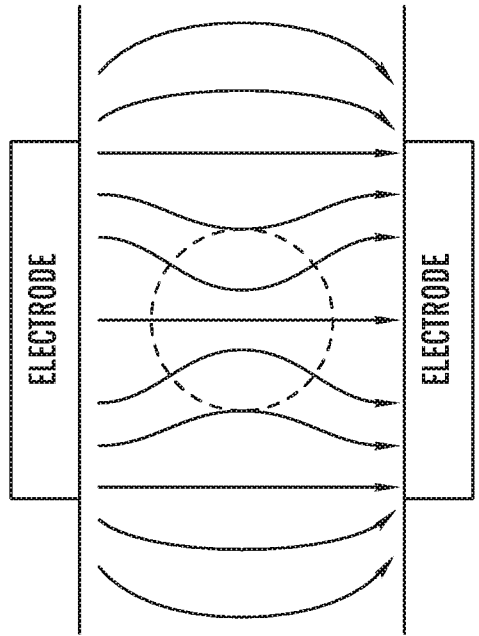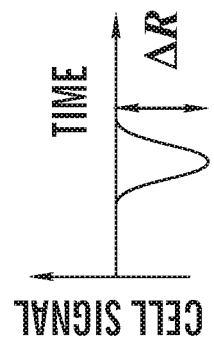
FIG. 44A
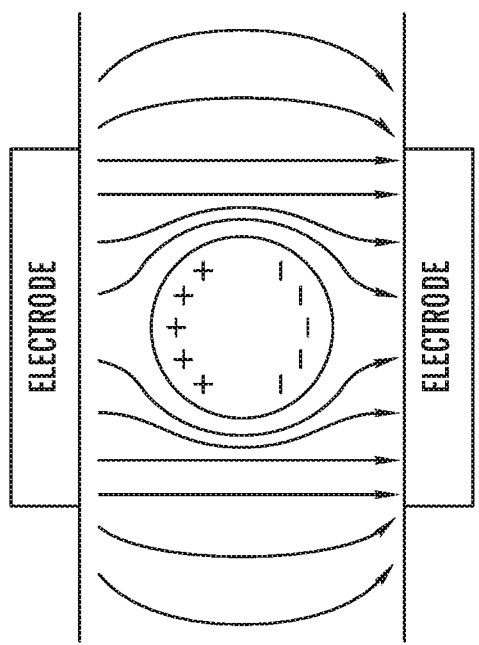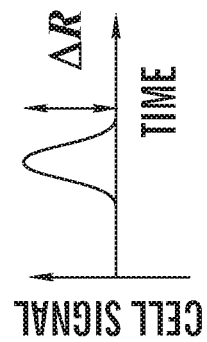
FIG. 44B

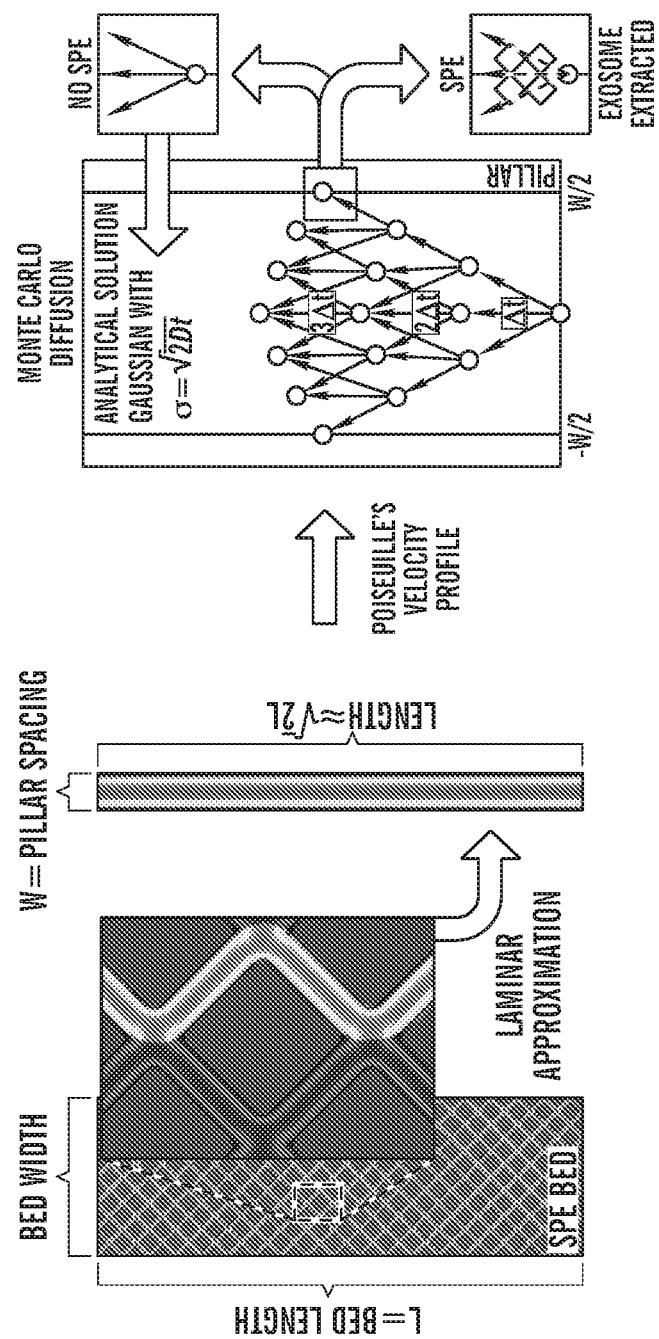
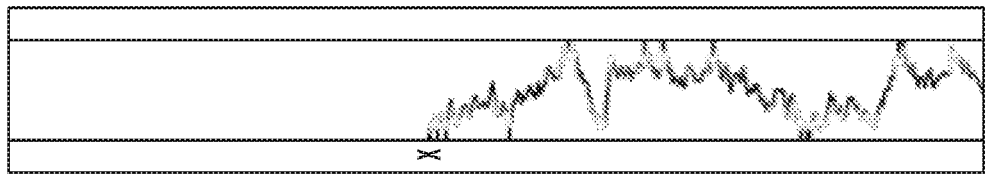
FIG. 45A
FIG. 45B
FIG. 45C

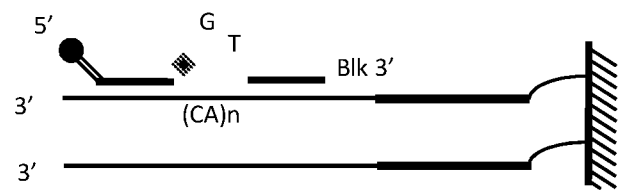
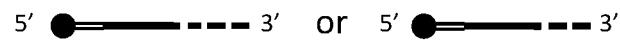
FIG. 64
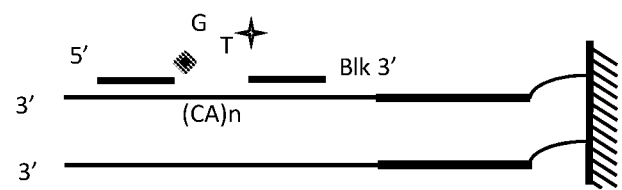
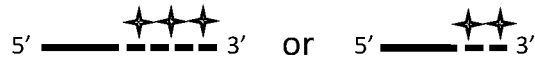
FIG. 65
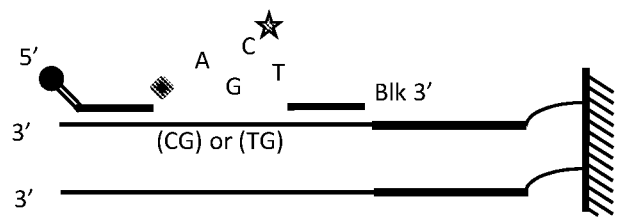
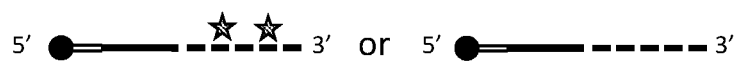
FIG. 66

A. Pixel-LDR to detect mutation or copy number. Isolate genomic or cfDNA.

B. Tail 3' ends with Terminal deoxynucleotidyl transferase (TdT), using TTP to generate T(100-150).

C. Distribute onto an addressable matrix array, such that the T(100) tail hybridizes to dA30 primers immobilized to pillars on a solid support.

D. Extend hybridized primer with strand displacing Bst polymerase at 37oC. When raising the temperature to 55-60oC, the dA portion partially denatures, allowing for an adjacent primer to hybridize and polymerase displace the first primer strand. By this repetitive process, the original strand is "handed-off" to the next primer to achieve a linear amplification of the original DNA.

E. Mutation or gene-specific ligation oligonucleotides contain 5' identifying signature modifiers for subsequent nanopore detection. Ligase covalently seals the two oligonucleotides together.

F. Wash away unligated probes. Denature product from target, then detect, and enumerate signal.

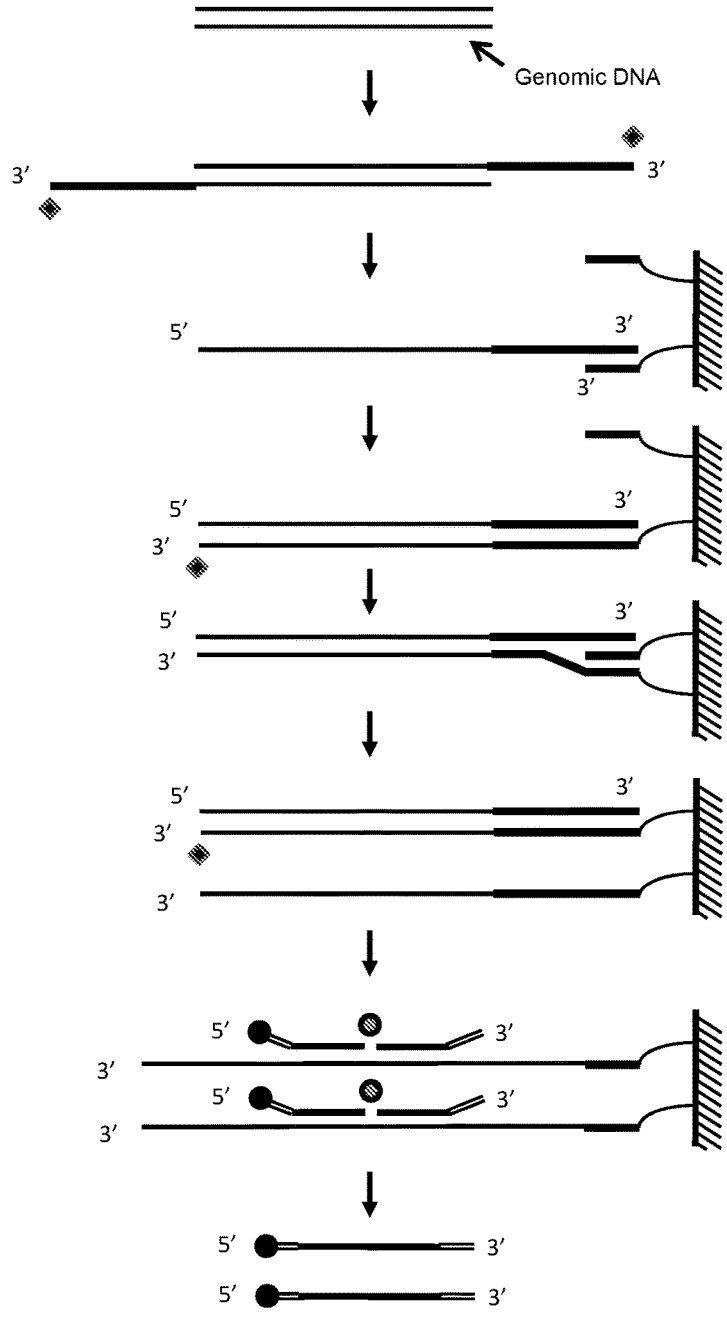

FIG. 74

A. Pixel-LDR to detect mutation. Isolate genomic or cfDNA.

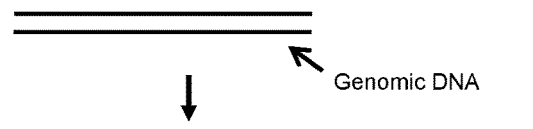
Genomic DNA

B. Tail 3' ends with Terminal deoxynucleotidyl transferase (TdT), using TTP to generate T(100-150).

C. Distribute onto an addressable matrix array, such that the T(100) tail hybridizes to dA30 primers immobilized to pillars on a solid support.

D. Extend hybridized primer with strand displacing Bst polymerase at 37oC. When raising the temperature to 55-60oC, the dA portion partially denatures, allowing for an adjacent primer to hybridize and polymerase displace the first primer strand. By this repetitive process, the original strand is "handed-off" to the next primer to achieve a linear amplification of the original DNA.

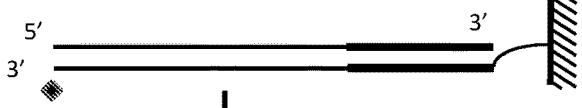

E. Mutation-specific ligation oligonucleotides (Mt) contain 5' identifying signature modifiers for subsequent nanopore detection, while wild-type probe (Wt) does not. Upstream ligation probe contains block, which may be removed by cleaving ribose base with RNaseH2 only when hybridized to target.

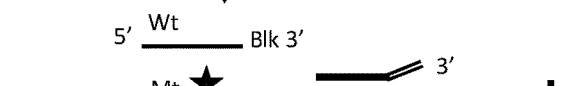

F. Ligase covalently seals the unblocked upstream and phosphorylated downstream oligonucleotides together.

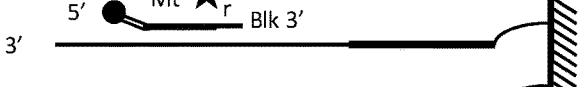

G. Wash away unligated probes. Denature product from target, then detect, and enumerate signal.

*FIG. 75*

A. Pixel-LDR to detect mutation with carryover protection. Isolate genomic or cfDNA. Treat with UDG (uracil DNA glycosylase) and EndoVIII for carryover prevention B. Tail 3' ends with Terminal deoxynucleotidyl transferase (TdT), using dUTP to generate dU(100-150).

C. Distribute onto an addressable matrix array, such that the dU(100) tail hybridizes to dA30 primers immobilized to pillars on a solid support.

D. Extend hybridized primer with strand displacing Bst polymerase at 37oC. When raising the temperature to 55-60oC, the dA portion partially denatures, allowing for an adjacent primer to hybridize and polymerase displace the first primer strand. By this repetitive process, the original strand is "handed-off" to the next primer to achieve a linear amplification of the original DNA.

E. Mutation-specific ligation oligonucleotides (Mt) contain 5' identifying signature modifiers for subsequent nanopore detection, while wild-type probe (Wt) does not. Upstream ligation probe contains block, which may be removed by cleaving ribose base with RNaseH2 only when hybridized to target.

F. Ligase covalently seals the unblocked upstream and phosphorylated downstream oligonucleotides together. Downstream LDR probe contains dU at penultimate 3' position, providing additional protection.

G. Wash away unligated probes. Denature product from target, then detect, and enumerate signal.

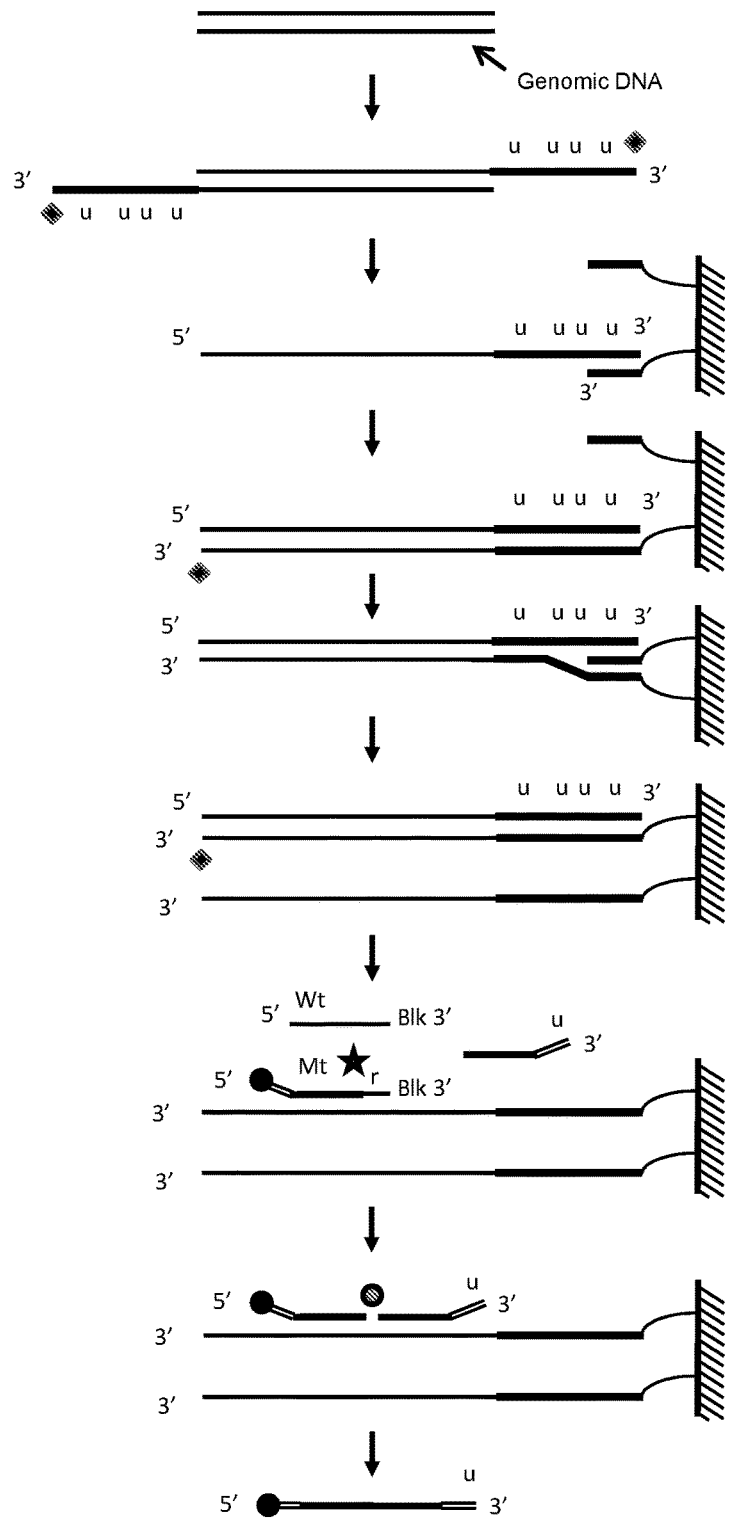

*FIG. 76*

A. Pixel-LDR to detect mutation. Isolate genomic or cfDNA.

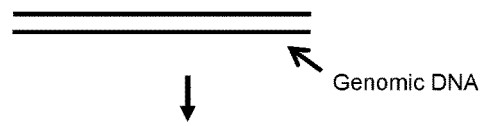
Genomic DNA

B. Tail 3' ends with Terminal deoxynucleotidyl transferase (TdT), using TTP to generate T(100-150).

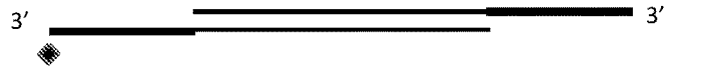

C. Distribute onto an addressable matrix array, such that the T(100) tail hybridizes to dA30 primers immobilized to pillars on a solid support.

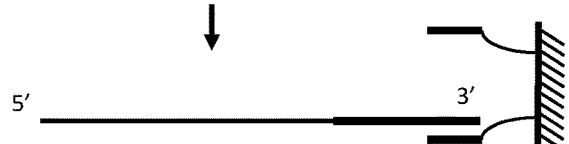

D. Extend hybridized primer with strand displacing Bst polymerase at 37oC. When raising the temperature to 55-60oC, the dA portion partially denatures, allowing for an adjacent primer to hybridize and polymerase displace the first primer strand. By this repetitive process, the original strand is "handed-off" to the next primer to achieve a linear amplification of the original DNA.


E. Mutation-specific ligation oligonucleotides (Mt) overlap at the mutation base, and contain 5' identifying signature modifiers for subsequent nanopore detection, while wild-type probe (Wt) does not. 5'-nuclease activity of polymerase cleaves off only matching 5'-overlapping base and additional flap, leaving ligation-competent 5-phosphate.


F. Ligase covalently seals the upstream and unblocked phosphorylated downstream oligonucleotides together.

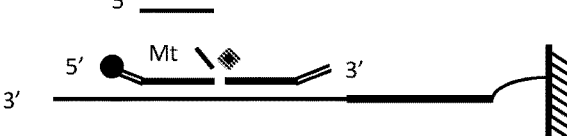

G. Wash away unligated probes. Denature product from target, then detect, and enumerate signal.

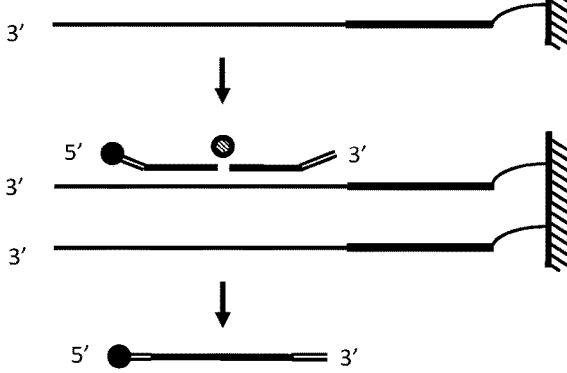

*FIG. 77*

A. Pixel-Cleavage to detect mutation. Isolate genomic or cfDNA.

B. Tail 3' ends with Terminal deoxynucleotidyl transferase (TdT), using TTP to generate T(100-150).

C. Distribute onto an addressable matrix array, such that the T(100) tail hybridizes to dA30 primers immobilized to pillars on a solid support.

D. Extend hybridized primer with strand displacing Bst polymerase at 37oC. When raising the temperature to 55-60oC, the dA portion partially denatures, allowing for an adjacent primer to hybridize and polymerase displace the first primer strand. By this repetitive process, the original strand is "handed-off" to the next primer to achieve a linear amplification of the original DNA.

E. Upstream and downstream oligonucleotides have mutation-specific base, with the mutation-specific flap oligonucleotides (Mt) overlap at the mutation base, and contain 5' identifying signature modifiers for subsequent nanopore detection. 5'-nuclease activity of polymerase or flap endonuclease cleaves off only matching 5'-overlapping base and additional flap; then detect, and enumerate signal.

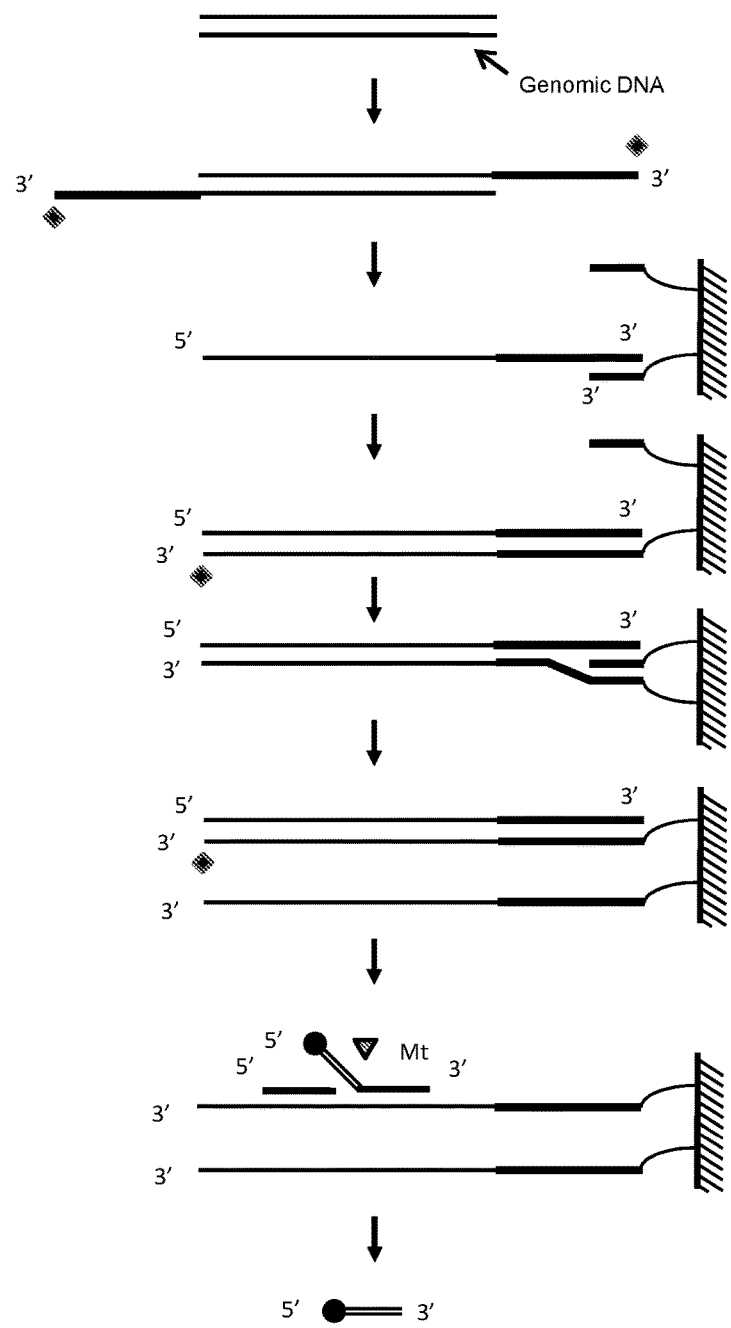

*FIG. 78*

A. Pixel-Nucleotide-Extension to detect mutation. Isolate genomic or cfDNA.

B. Tail 3' ends with Terminal deoxynucleotidyl transferase (TdT), using TTP to generate T(100-150).

C. Distribute onto an addressable matrix array, such that the T(100) tail hybridizes to dA30 primers immobilized to pillars on a solid support.

D. Extend hybridized primer with strand displacing Bst polymerase at 37oC. When raising the temperature to 55-60oC, the dA portion partially denatures, allowing for an adjacent primer to hybridize and polymerase displace the first primer strand. By this repetitive process, the original strand is "handed-off" to the next primer to achieve a linear amplification of the original DNA.

E. Wash away all dNTPs. Hybridize locus-specific oligonucleotides, which contain 5' identifying signature modifiers for subsequent nanopore detection.

F. Extend oligonucleotides with nucleotide analogue terminator dNTPs containing 3' encoding signature modifiers.

G. Wash away unhybridized probes and unincorporated analogues. Denature product from target, then detect, and enumerate signal.

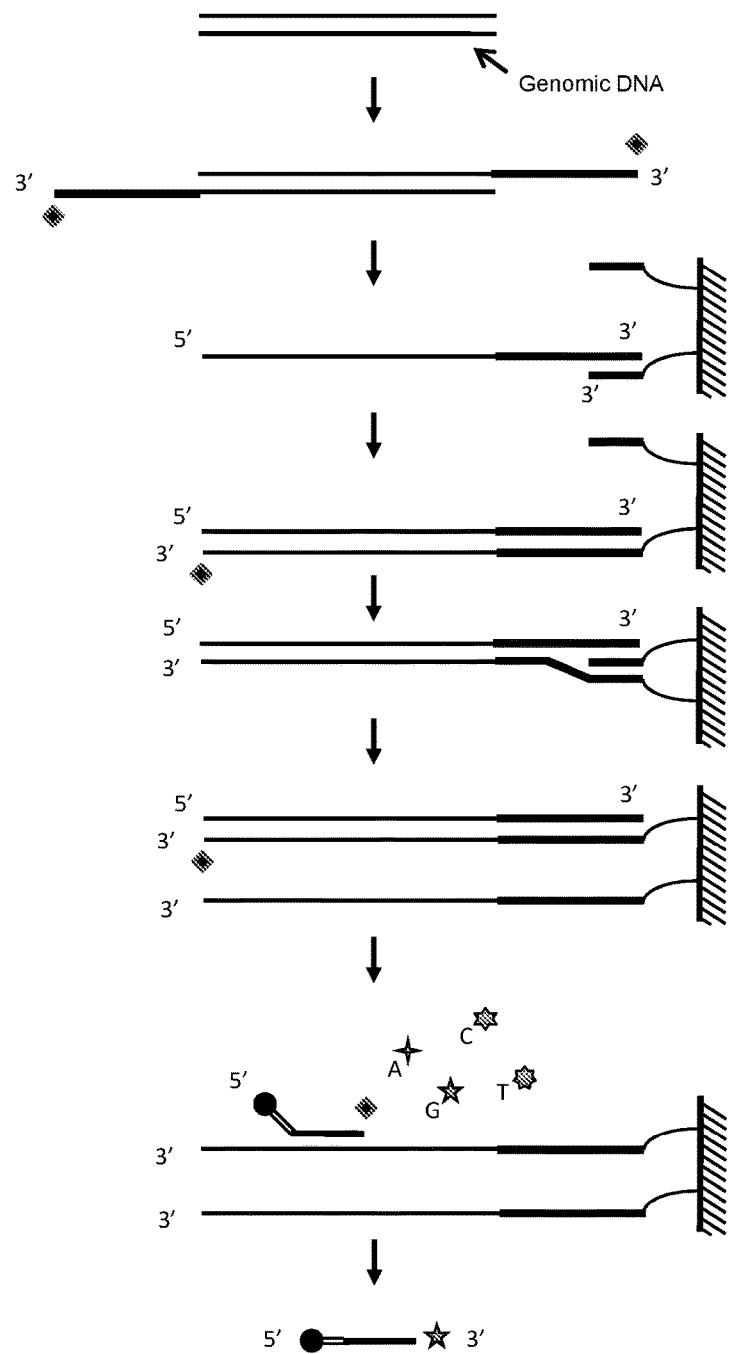

*FIG. 79*

A. Pixel-Primer-Extension to detect repeat polymorphism length. Isolate genomic or cfDNA.

B. Tail 3' ends with Terminal deoxynucleotidyl transferase (TdT), using TTP to generate T(100-150).

C. Distribute onto an addressable matrix array, such that the T(100) tail hybridizes to dA30 primers immobilized to pillars on a solid support.

D. Extend hybridized primer with strand displacing Bst polymerase at 37oC. When raising the temperature to 55-60oC, the dA portion partially denatures, allowing for an adjacent primer to hybridize and polymerase displace the first primer strand. By this repetitive process, the original strand is "handed-off" to the next primer to achieve a linear amplification of the original DNA.

E. Wash away all dNTPs. Hybridize upstream locus-specific oligonucleotides, which contain 5' identifying signature modifiers for subsequent nanopore detection. Downstream primers contain 3' block.

F. Extend upstream oligonucleotides with polymerase lacking 5'-3' nuclease and strand-displacement activity, until extension product abuts downstream primer.

G. Wash away unhybridized probes. Denature product from target, then detect, and enumerate signal.

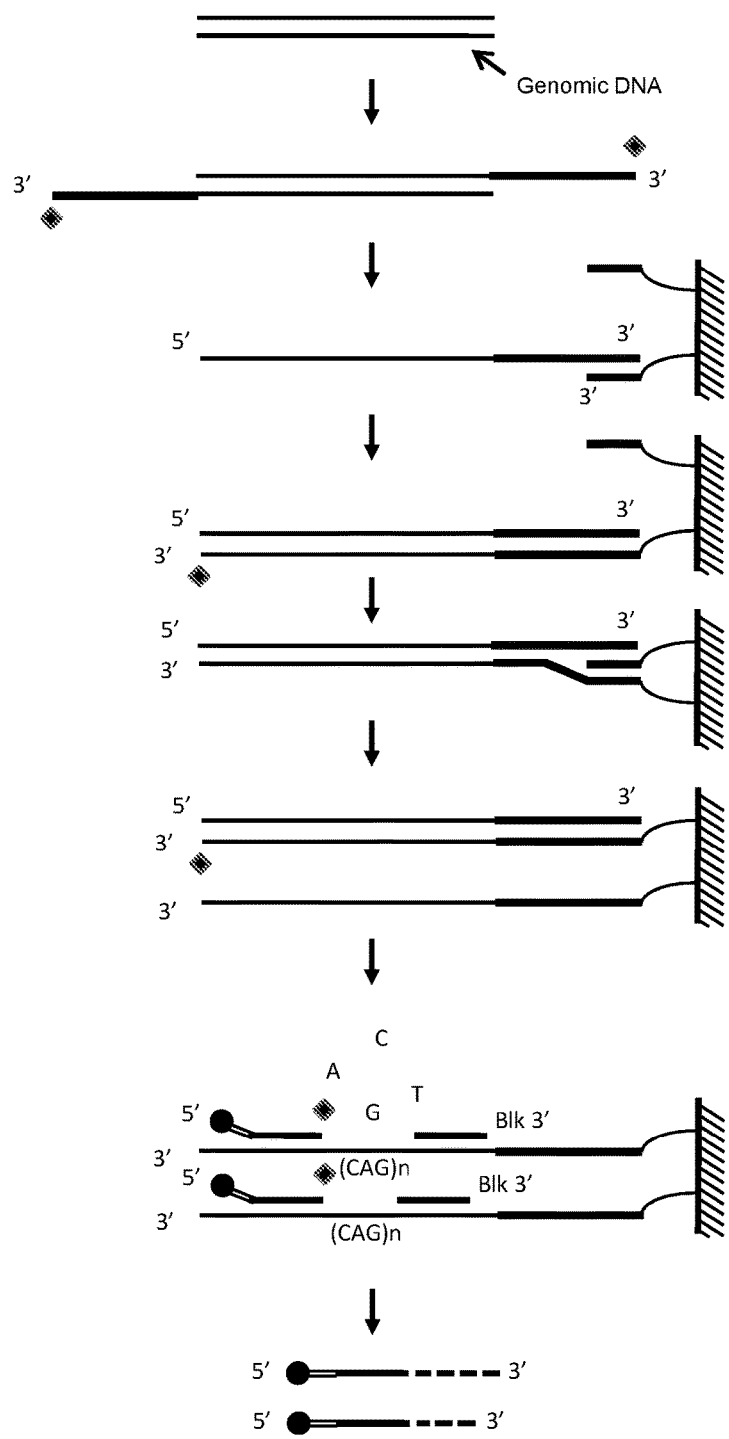

*FIG. 80*

A. Pixel-LDR to detect mutation. Isolate genomic or cfDNA.

B. Repair ends with polymerase, phosphorylate 5' ends, extend 3'ends with a single A base, and ligate on A:T rich linkers with single-base T overhang, and 3'-T30 tails.

C. Distribute onto an addressable matrix array, such that the T30 tail hybridizes to dA30 primers immobilized to pillars on a solid support.

D. Extend hybridized primer with strand displacing Bst polymerase at 37oC. When raising the temperature to 55-60oC, the dA portion partially denatures, allowing for an adjacent primer to hybridize and polymerase displace the first primer strand. By this repetitive process, the original strand is "handed-off" to the next primer to achieve a linear amplification of the original DNA.

E. Mutation-specific ligation oligonucleotides (Mt) contain 5' identifying signature modifiers for subsequent nanopore detection, while wild-type probe (Wt) does not. Upstream ligation probe contains block, which may be removed by cleaving ribose base with RNaseH2 only when hybridized to target.

F. Ligase covalently seals the unblocked upstream and phosphorylated downstream oligonucleotides together.

G. Wash away unligated probes. Denature product from target, then detect, and enumerate signal.

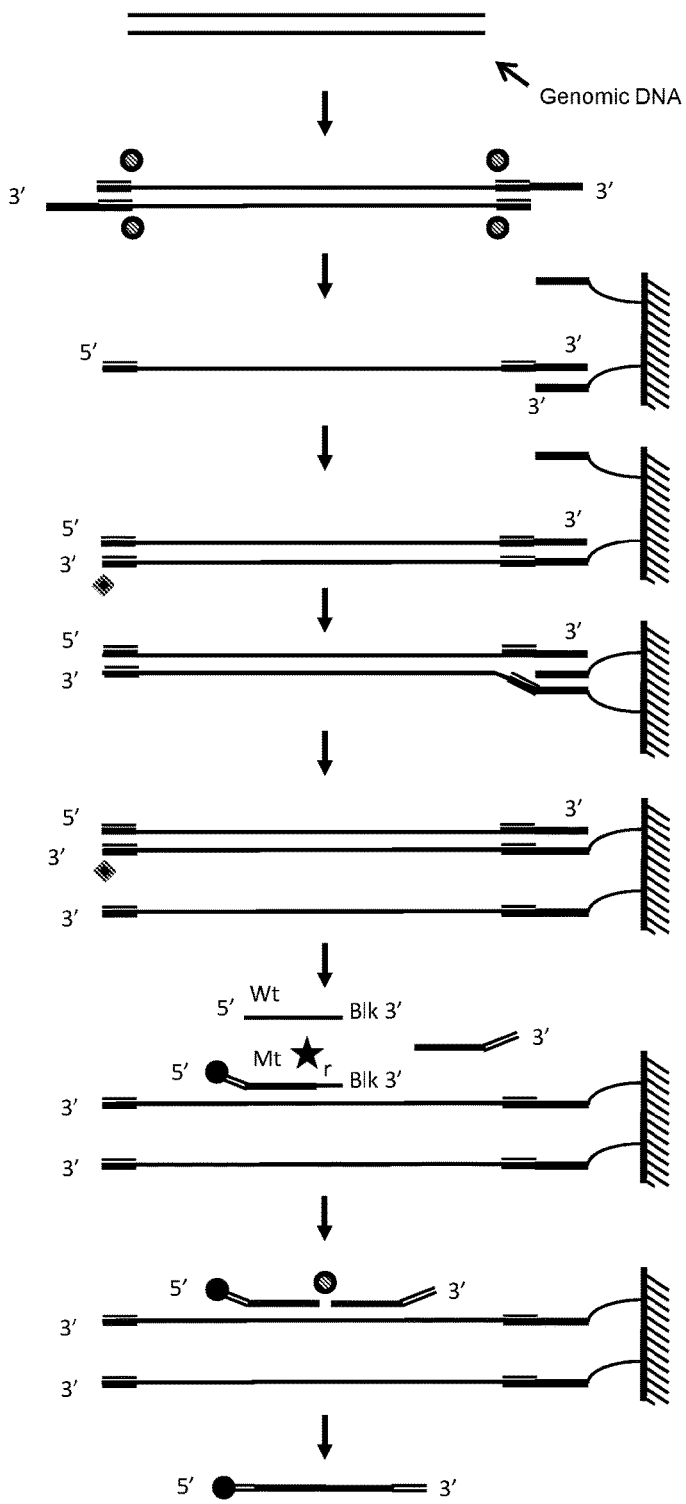

FIG. 81

A. Pixel-Cleavage to detect mutation. Isolate genomic or cfDNA.

B. Repair ends with polymerase, phosphorylate 5' ends, extend 3'ends with a single A base, and ligate on A:T rich linkers with single-base T overhang, and 3'-T30 tails.

C. Distribute onto an addressable matrix array, such that the T30 tail hybridizes to dA30 primers immobilized to pillars on a solid support.

D. Extend hybridized primer with strand displacing Bst polymerase at 37oC. When raising the temperature to 55-60oC, the dA portion partially denatures, allowing for an adjacent primer to hybridize and polymerase displace the first primer strand. By this repetitive process, the original strand is "handed-off" to the next primer to achieve a linear amplification of the original DNA.

E. Upstream and downstream oligonucleotides have mutation-specific base, with the mutation-specific flap oligonucleotides (Mt) overlap at the mutation base, and contain 5' identifying signature modifiers for subsequent nanopore detection. 5'-nuclease activity of polymerase or flap endonuclease cleaves off only matching 5'-overlapping base and additional flap; then detect, and enumerate signal.

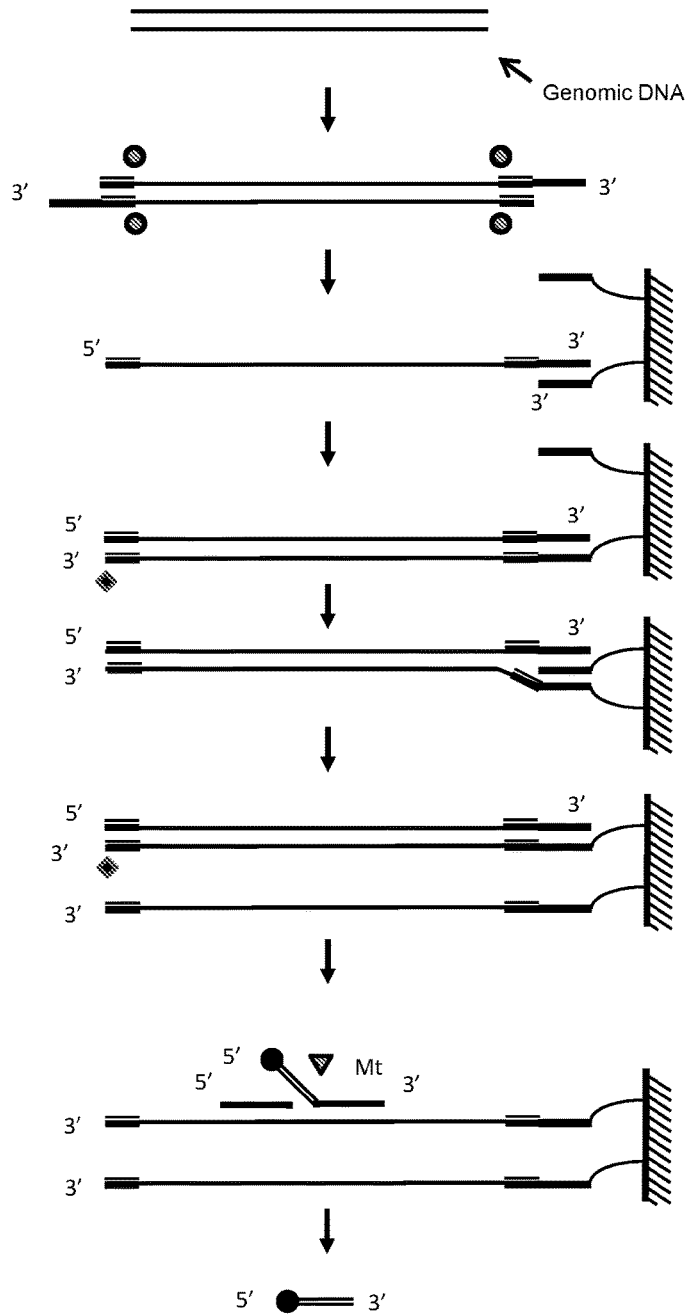

*FIG. 82*

A. Pixel-Nucleotide-Extension to detect mutation. Isolate genomic or cfDNA.

B. Repair ends with polymerase, phosphorylate 5' ends, extend 3'ends with a single A base, and ligate on A:T rich linkers with single-base T overhang, and 3'-T30 tails.

C. Distribute onto an addressable matrix array, such that the T30 tail hybridizes to dA30 primers immobilized to pillars on a solid support.

D. Extend hybridized primer with strand displacing Bst polymerase at 37oC. When raising the temperature to 55-60oC, the dA portion partially denatures, allowing for an adjacent primer to hybridize and polymerase displace the first primer strand. By this repetitive process, the original strand is "handed-off" to the next primer to achieve a linear amplification of the original DNA.

E. Wash away all dNTPs. Hybridize locus-specific oligonucleotides, which contain 5' identifying signature modifiers for subsequent nanopore detection.

F. Extend oligonucleotides with nucleotide analogue terminator dNTPs containing 3' encoding signature modifiers moieties.

G. Wash away unhybridized probes and unincorporated analogues. Denature product from target, then detect, and enumerate signal.

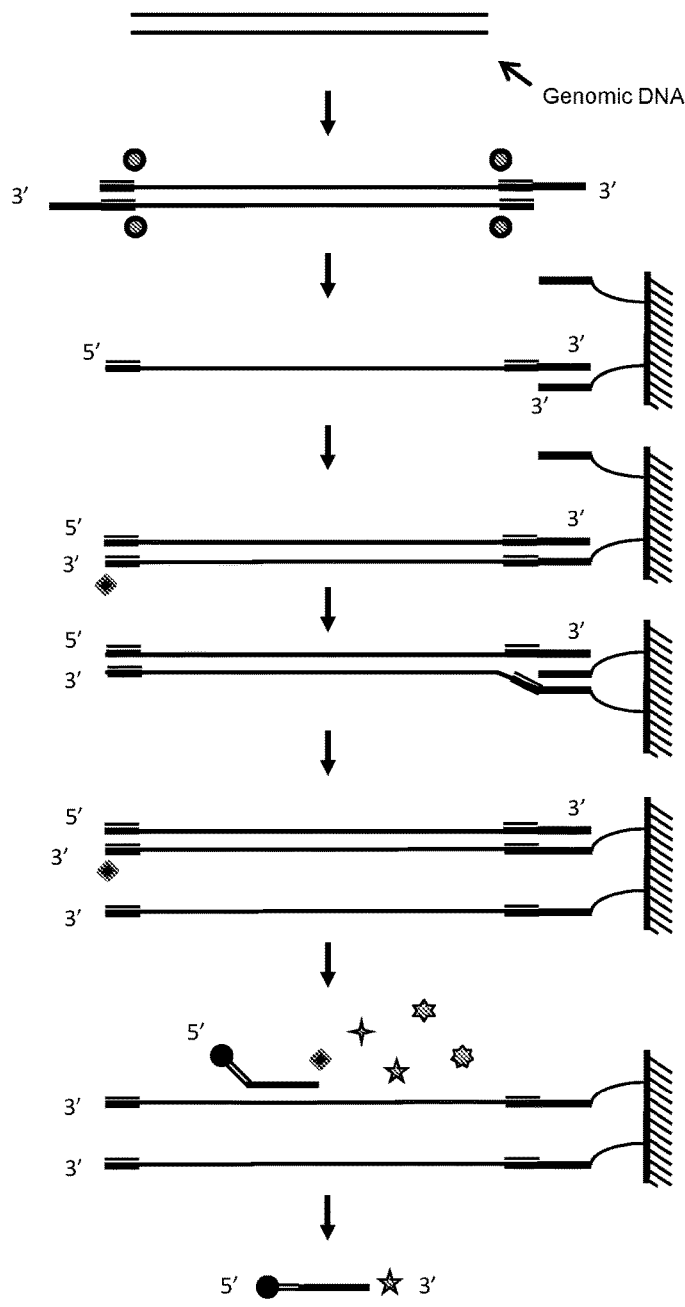

*FIG. 83*

A. Pixel-Primer-Extension to detect repeat polymorphism. Isolate genomic or cfDNA.

B. Repair ends with polymerase, phosphorylate 5' ends, extend 3'ends with a single A base, and ligate on A:T rich linkers with single-base T overhang, and 3'-T30 tails.

C. Distribute onto an addressable matrix array, such that the T30 tail hybridizes to dA30 primers immobilized to pillars on a solid support.

D. Extend hybridized primer with strand displacing Bst polymerase at 37oC. When raising the temperature to 55-60oC, the dA portion partially denatures, allowing for an adjacent primer to hybridize and polymerase displace the first primer strand. By this repetitive process, the original strand is "handed-off" to the next primer to achieve a linear amplification of the original DNA.

E. Wash away all dNTPs. Hybridize upstream locus-specific oligonucleotides, which contain 5' identifying signature modifiers for subsequent nanopore detection. Downstream primers contain 3' block.

F. Extend upstream oligonucleotides with polymerase lacking 5'-3' nuclease and strand-displacement activity, until extension product abuts downstream primer.

G. Wash away unhybridized probes. Denature product from target, then detect, and enumerate signal.

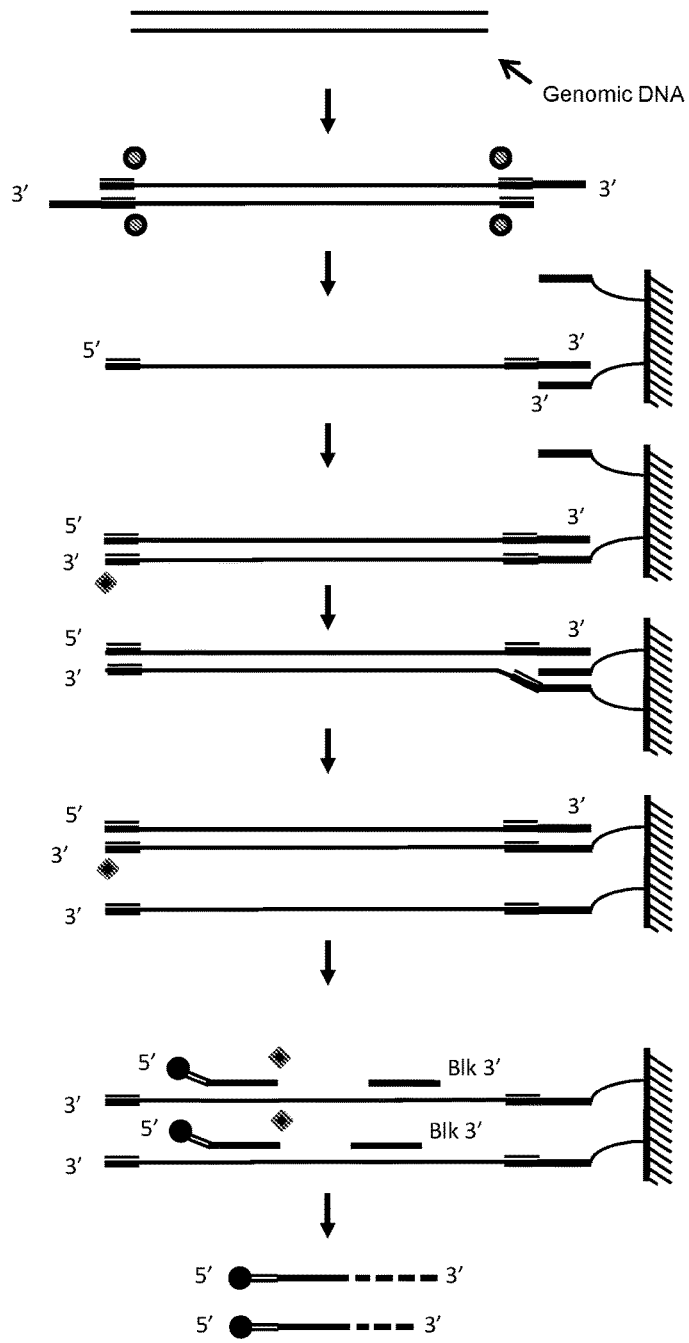

*FIG. 84*

A. Pixel-LDR to detect locus-specific mutation or copy number. Isolate genomic or cfDNA.

B. Tail 3' ends with Terminal deoxynucleotidyl transferase (TdT), using TTP to generate T(100-150).

C. Denature DNA and hybridize locus-specific primer with blocked 3' end. Primers are unblocked with RNaseH2 only when bound to target. Extend with polymerase to incorporate biotin-dCTP.

D. Capture biotinylated strand on solid support, wash, and release enriched target.

E. Distribute onto an addressable matrix array, such that the T(100) tail hybridizes to dA30 primers immobilized to pillars on a solid support.

F. Extend hybridized primer with strand displacing Bst polymerase at 37oC. When raising the temperature to 55-60oC, the dA portion partially denatures, allowing for an adjacent primer to hybridize and polymerase displace the first primer strand. By this repetitive process, the original strand is "handed-off" to the next primer to achieve a linear amplification of the original DNA.

G. Mutation or locus-specific ligation oligonucleotides contain 5' identifying signature modifiers for subsequent nanopore detection. Ligase covalently seals the two oligonucleotides together.

H. Wash away unligated probes. Denature product from target, then detect, and enumerate signal.

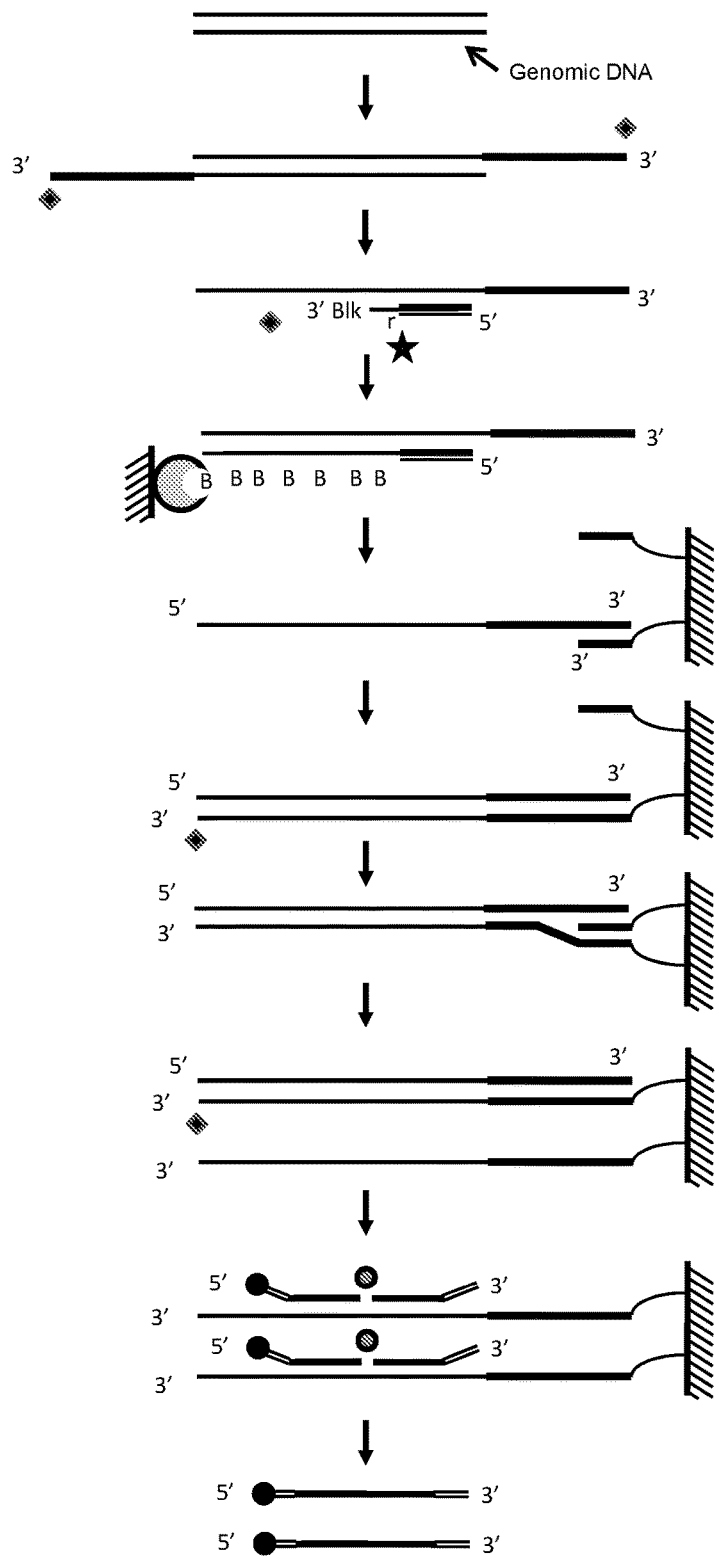

*FIG. 85*

A. Pixel-Cleavage to detect locus-specific mutation or copy number. Isolate genomic or cfDNA.

B. Tail 3' ends with Terminal deoxynucleotidyl transferase (TdT), using TTP to generate T(100-150).

C. Denature DNA and hybridize locus-specific primer with blocked 3' end. Primers are unblocked with RNaseH2 only when bound to target. Extend with polymerase to incorporate biotin-dCTP.

D. Capture biotinylated strand on solid support, wash, and release enriched target.

E. Distribute onto an addressable matrix array, such that the T(100) tail hybridizes to dA30 primers immobilized to pillars on a solid support.

F. Extend hybridized primer with strand displacing Bst polymerase at 37oC. When raising the temperature to 55-60oC, the dA portion partially denatures, allowing for an adjacent primer to hybridize and polymerase displace the first primer strand. By this repetitive process, the original strand is "handed-off" to the next primer to achieve a linear amplification of the original DNA.

G. Upstream and downstream oligonucleotides have locus or mutation-specific base, with the locus or mutation-specific flap oligonucleotides (Mt) overlap at the mutation base, and contain 5' identifying signature modifiers for subsequent nanopore detection. 5'-nuclease activity of polymerase or flap endonuclease cleaves off only matching 5'-overlapping base and additional flap; then detect, and enumerate signal.

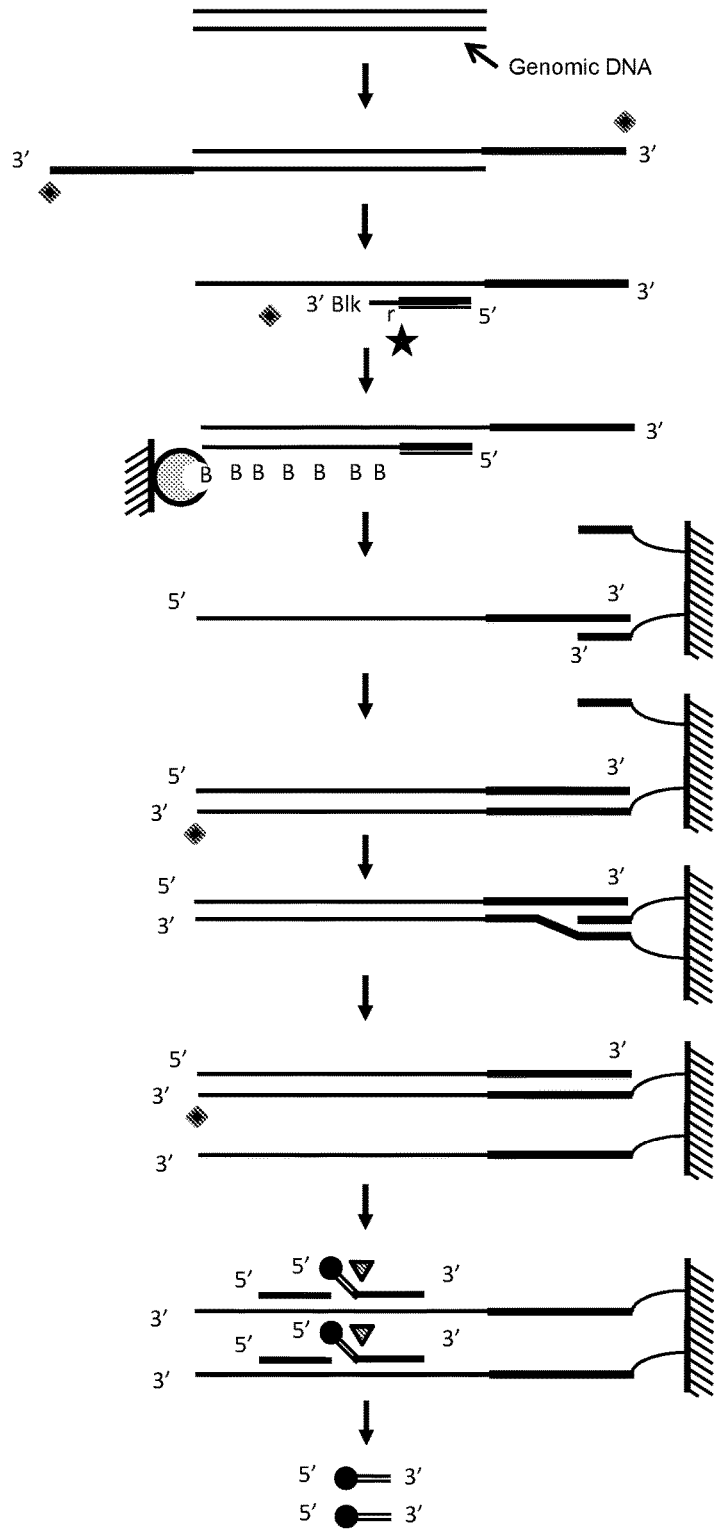

*FIG. 86*

A. Pixel-Nucleotide-Extension to detect locus-specific mutation or copy number. Isolate cfDNA.

B. Tail 3' ends with Terminal deoxynucleotidyl transferase (TdT), using TTP to generate T(100-150).

C. Denature DNA and hybridize locus-specific primer with blocked 3' end. Primers are unblocked with RNaseH2 only when bound to target. Extend with polymerase to incorporate biotin-dCTP.

D. Capture biotinylated strand on solid support, wash, and release enriched target.

E. Distribute onto an addressable matrix array, such that the T(100) tail hybridizes to dA30 primers immobilized to pillars on a solid support.

F. Extend hybridized primer with strand displacing Bst polymerase at 37oC. When raising the temperature to 55-60oC, the dA portion partially denatures, allowing for an adjacent primer to hybridize and polymerase displace the first primer strand. By this repetitive process, the original strand is "handed-off" to the next primer to achieve a linear amplification of the original DNA.

G. Wash away all dNTPs. Hybridize locus-specific oligonucleotides, which contain 5' identifying signature modifiers for subsequent nanopore detection.

H. Extend oligonucleotides with nucleotide analogue terminator dNTPs containing 3' encoding signature modifiers.

I. Wash away unhybridized probes and unincorporated analogues. Denature product from target, then detect, and enumerate signal.

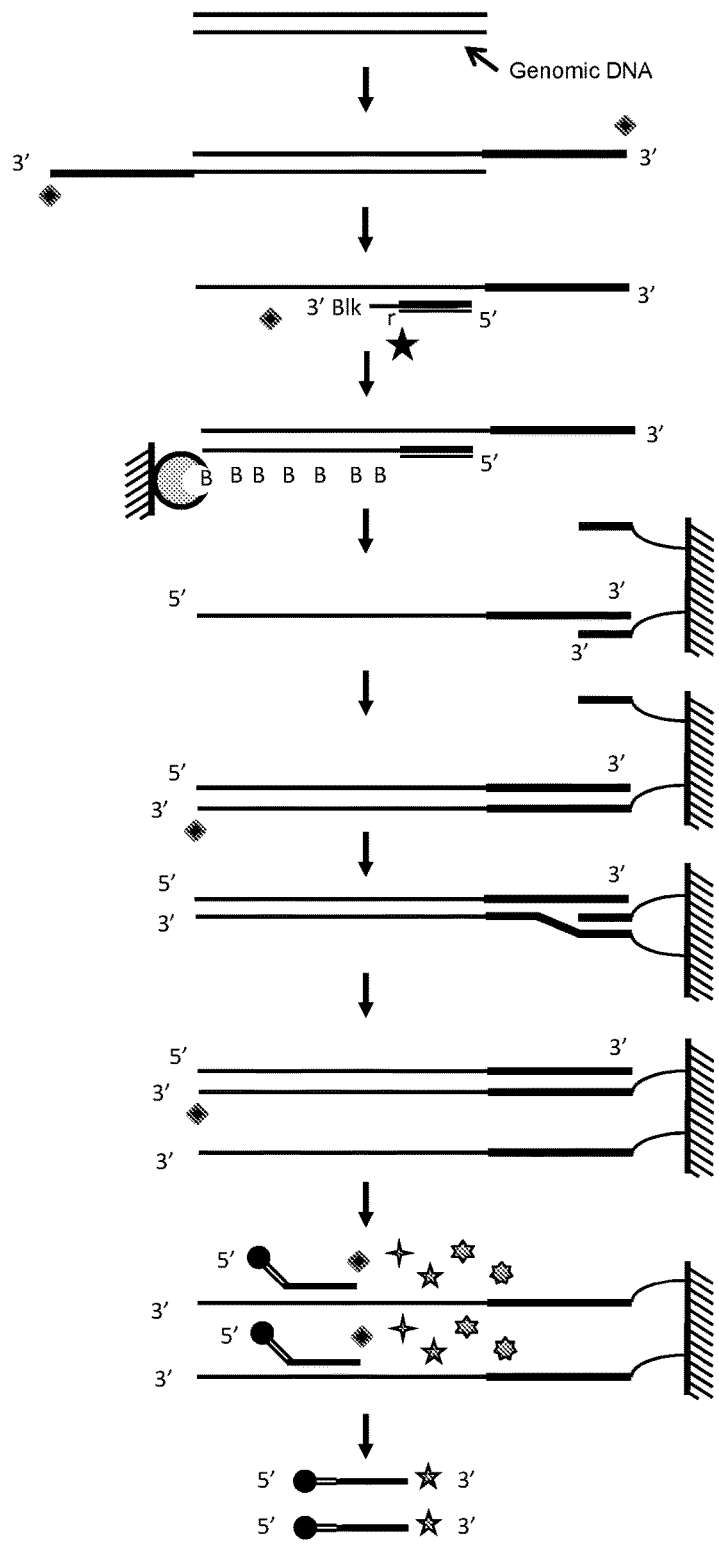

FIG. 87

A. Pixel-Primer-Extension to detect locus-specific mutation or copy number. Isolate cfDNA.

B. Tail 3' ends with Terminal deoxynucleotidyl transferase (TdT), using TTP to generate T(100-150).

C. Denature DNA and hybridize locus-specific primer with blocked 3' end. Primers are unblocked with RNaseH2 only when bound to target. Extend with polymerase to incorporate biotin-dCTP.

D. Capture biotinylated strand on solid support, wash, and release enriched target.

E. Distribute onto an addressable matrix array, such that the T(100) tail hybridizes to dA30 primers immobilized to pillars on a solid support.

F. Extend hybridized primer with strand displacing Bst polymerase at 37oC. When raising the temperature to 55-60oC, the dA portion partially denatures, allowing for an adjacent primer to hybridize and polymerase displace the first primer strand. By this repetitive process, the original strand is "handed-off" to the next primer to achieve a linear amplification of the original DNA.

G. Wash away all dNTPs. Hybridize upstream locus-specific oligonucleotides, which contain 5' identifying signature modifiers for subsequent nanopore detection. Downstream primers contain 3' block.

H. Extend upstream oligonucleotides with polymerase lacking 5'-3' nuclease and strand-displacement activity, until extension product abuts downstream primer.

I. Wash away unhybridized probes. Denature product from target, then detect, and enumerate signal.

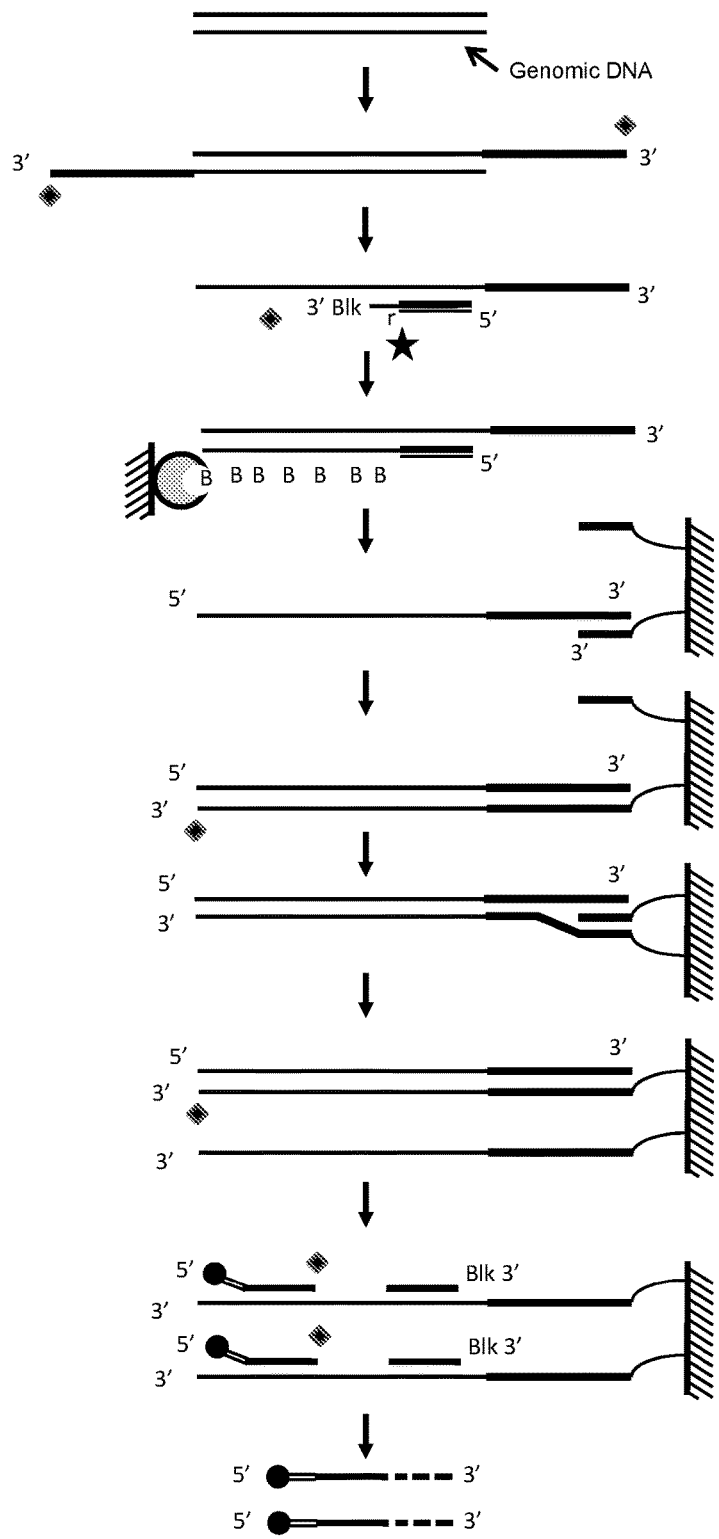

*FIG. 88*

A. Pixel-LDR to detect locus-specific mutation or copy number. Isolate genomic or cfDNA..

B. Repair ends with polymerase, phosphorylate 5' ends, extend 3'ends with a single A base, and ligate on A:T rich linkers with single-base T overhang, and 3'-T30 tails.

C. Denature DNA and hybridize locus-specific primer with blocked 3' end. Primers are unblocked with RNaseH2 only when bound to target. Extend with polymerase to incorporate biotin-dCTP.

D. Capture biotinylated strand on solid support, wash, and release enriched target.

E. Distribute onto an addressable matrix array, such that the T30 tail hybridizes to dA30 primers immobilized to pillars on a solid support.

F. Extend hybridized primer with strand displacing Bst polymerase at 37oC. When raising the temperature to 55-60oC, the dA portion partially denatures, allowing for an adjacent primer to hybridize and polymerase displace the first primer strand. By this repetitive process, the original strand is "handed-off" to the next primer to achieve a linear amplification of the original DNA.

G. Mutation-specific ligation oligonucleotides contain 5' identifying signature modifiers for subsequent nanopore detection. Ligase covalently seals the two oligonucleotides together.

H. Wash away unligated probes. Denature product from target, then detect, and enumerate signal.

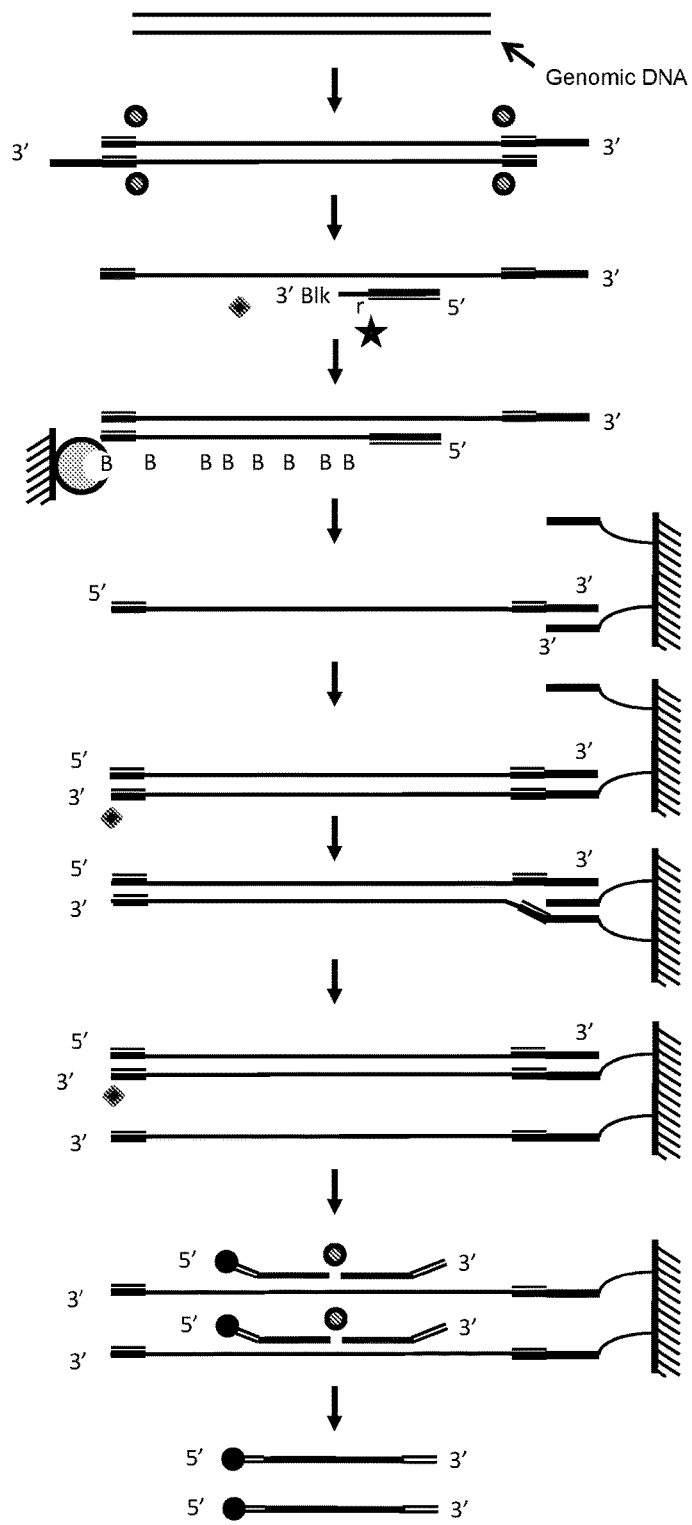

*FIG. 89*

A. Pixel-Cleavage to detect locus-specific mutation or copy number. Isolate genomic or cfDNA.

B. Repair ends with polymerase, phosphorylate 5′ ends, extend 3′ends with a single A base, and ligate on A:T rich linkers with single-base T overhang, and 3′-T30 tails.

C. Denature DNA and hybridize locus-specific primer with blocked 3′ end. Primers are unblocked with RNaseH2 only when bound to target. Extend with polymerase to incorporate biotin-dCTP.

D. Capture biotinylated strand on solid support, wash, and release enriched target.

E. Distribute onto an addressable matrix array, such that the T30 tail hybridizes to dA30 primers immobilized to pillars on a solid support.

F. Extend hybridized primer with strand displacing Bst polymerase at 37oC. When raising the temperature to 55-60oC, the dA portion partially denatures, allowing for an adjacent primer to hybridize and polymerase displace the first primer strand. By this repetitive process, the original strand is "handed-off" to the next primer to achieve a linear amplification of the original DNA.

G. Upstream and downstream oligonucleotides have locus or mutation-specific base, with the locus or mutation-specific flap oligonucleotides (Mt) overlap at the mutation base, and contain 5′ identifying signature modifiers for subsequent nanopore detection. 5′-nuclease activity of polymerase or flap endonuclease cleaves off only matching 5′-overlapping base and additional flap; then detect, and enumerate signal.

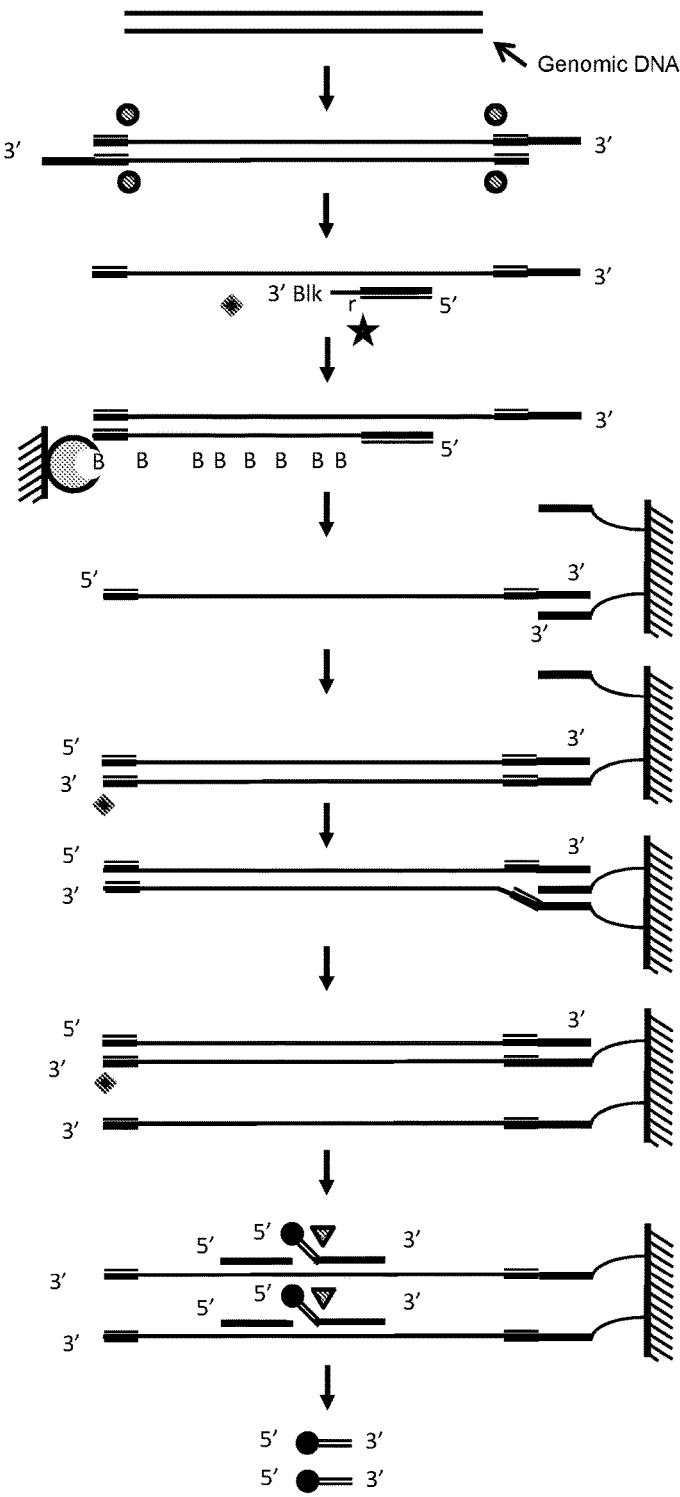

*FIG. 90*

A. Pixel-Nucleotide-Extension to detect locus-specific mutation or copy number. Isolate cfDNA..

B. Repair ends with polymerase, phosphorylate 5' ends, extend 3'ends with a single A base, and ligate on A:T rich linkers with single-base T overhang, and 3'-T30 tails.

C. Denature DNA and hybridize locus-specific primer with blocked 3' end. Primers are unblocked with RNaseH2 only when bound to target. Extend with polymerase to incorporate biotin-dCTP.

D. Capture biotinylated strand on solid support, wash, and release enriched target.

E. Distribute onto an addressable matrix array, such that the T30 tail hybridizes to dA30 primers immobilized to pillars on a solid support.

F. Extend hybridized primer with strand displacing Bst polymerase at 37oC. When raising the temperature to 55-60oC, the dA portion partially denatures, allowing for an adjacent primer to hybridize and polymerase displace the first primer strand. By this repetitive process, the original strand is "handed-off" to the next primer to achieve a linear amplification of the original DNA.

G. Wash away all dNTPs. Hybridize locus-specific oligonucleotides, which contain 5' identifying signature modifiers for subsequent nanopore detection.

H. Extend oligonucleotides with nucleotide analogue terminator dNTPs containing 3' encoding signature modifiers.

I. Wash away unhybridized probes and unincorporated analogues. Denature product from target, then detect, and enumerate signal.

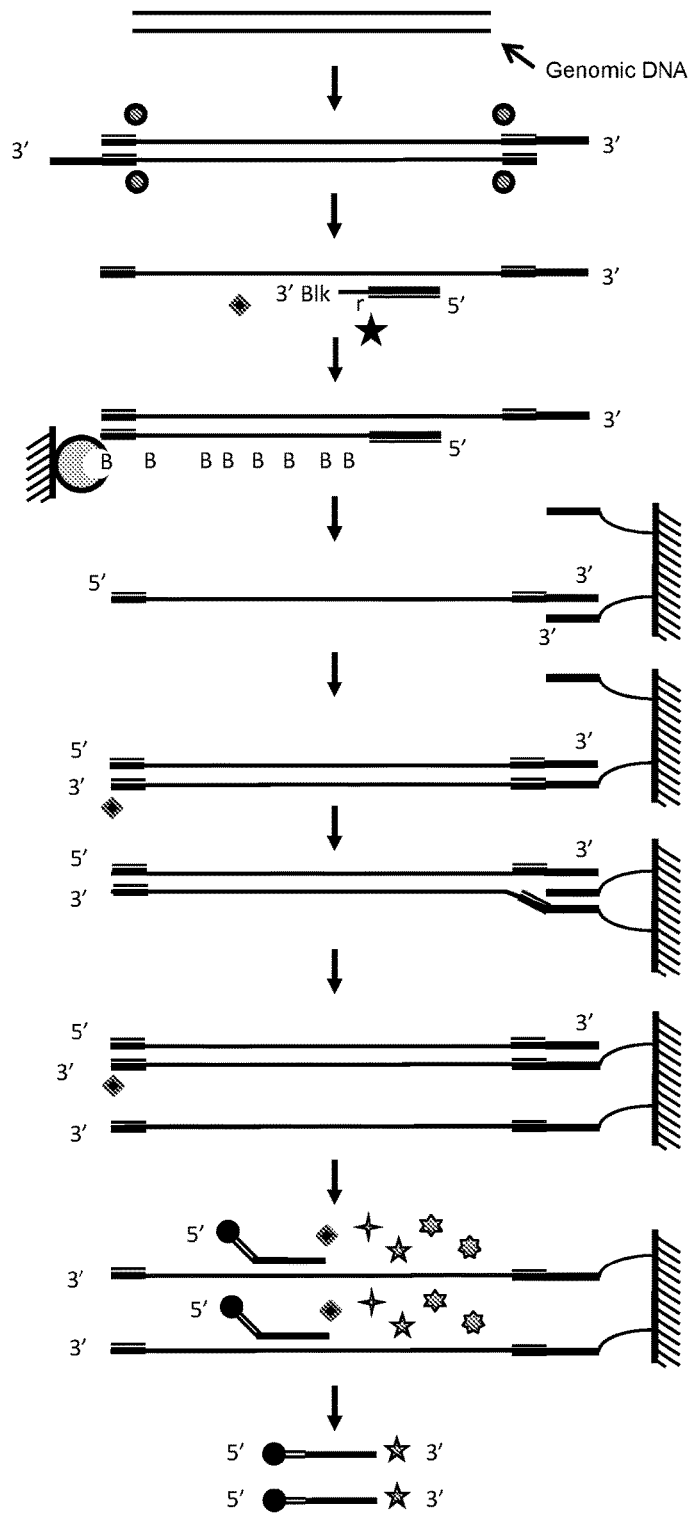

*FIG. 91*

A. Pixel-Primer-Extension to detect locus-specific mutation or copy number. Isolate cfDNA..

B. Repair ends with polymerase, phosphorylate 5' ends, extend 3'ends with a single A base, and ligate on A:T rich linkers with single-base T overhang, and 3'-T30 tails.

C. Denature DNA and hybridize locus-specific primer with blocked 3' end. Primers are unblocked with RNaseH2 only when bound to target. Extend with polymerase to incorporate biotin-dCTP.

D. Capture biotinylated strand on solid support, wash, and release enriched target.

E. Distribute onto an addressable matrix array, such that the T30 tail hybridizes to dA30 primers immobilized to pillars on a solid support.

F. Extend hybridized primer with strand displacing Bst polymerase at 37oC. When raising the temperature to 55-60oC, the dA portion partially denatures, allowing for an adjacent primer to hybridize and polymerase displace the first primer strand. By this repetitive process, the original strand is "handed-off" to the next primer to achieve a linear amplification of the original DNA.

G. Wash away all dNTPs. Hybridize upstream locus-specific oligonucleotides, which contain 5' identifying signature modifiers for subsequent nanopore detection. Downstream primers contain 3' block.

H. Extend upstream oligonucleotides with polymerase lacking 5'-3' nuclease and strand-displacement activity, until extension product abuts downstream primer.

I. Wash away unhybridized probes. Denature product from target, then detect, and enumerate signal.

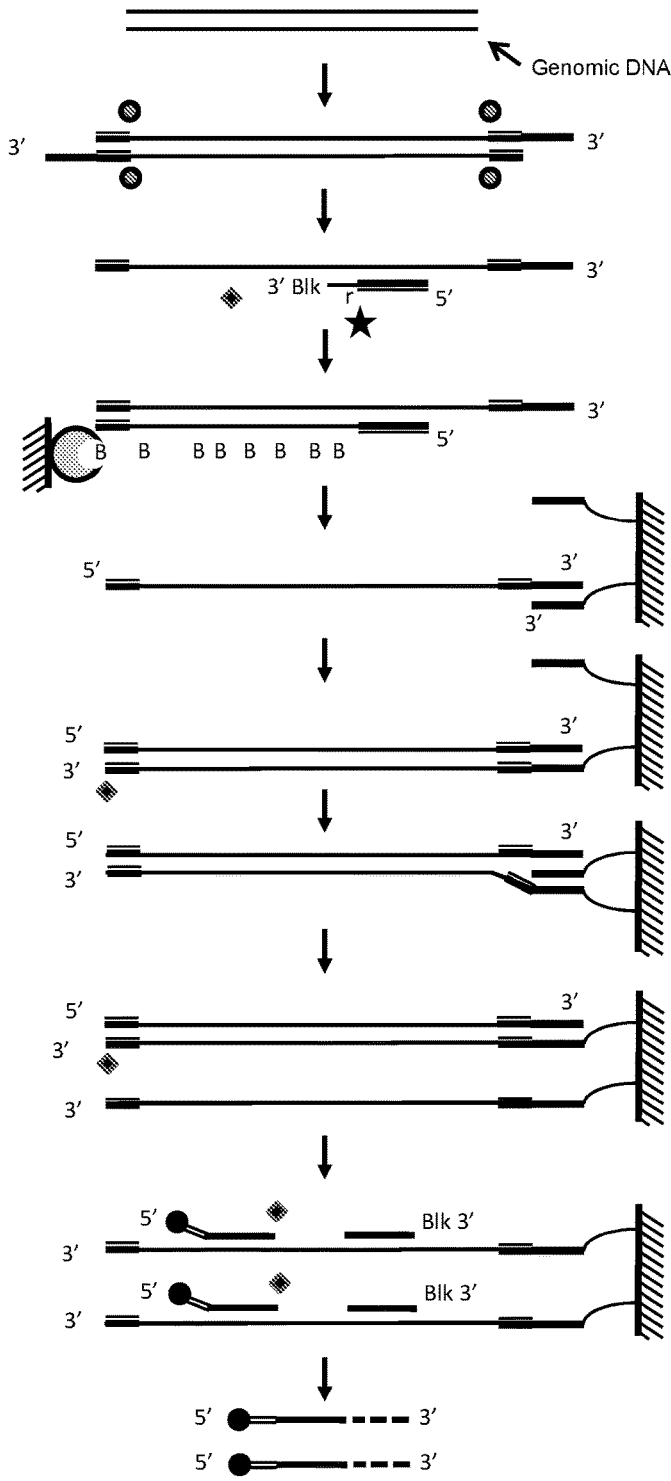

*FIG. 92*

A. Pixel-LDR to enumerate copy number. Isolate CTC DNA.

B. Blunt ends, extend 3'end with a single A base, and ligate on A:T rich linkers with single-base T overhang, and 5'-dA30 tails.

C. Denature DNA and hybridize locus-specific primer with blocked 3' and 5' ends. Primers are unblocked with RNaseH2 only when bound to target. Extend with polymerase, and generate T30 on 3' end. Optional: Degrade dA30 linkers with 5' nuclease.

D. Distribute onto an addressable matrix array, such that the T30 tail hybridizes to dA30 primers immobilized to pillars on a solid support.

E. Extend hybridized primer with strand displacing Bst polymerase at 37oC. When raising the temperature to 55-60oC, the dA portion partially denatures, allowing for an adjacent primer to hybridize and polymerase displace the first primer strand. By this repetitive process, the original strand is "handed-off" to the next primer to achieve a linear amplification of the original DNA.

F. Locus-specific ligation oligonucleotides contain 5' identifying signature modifiers for subsequent nanopore detection. Ligase covalently seals the two oligonucleotides together.

G. Wash away unligated probes. Denature product from target, then detect, and enumerate signal.

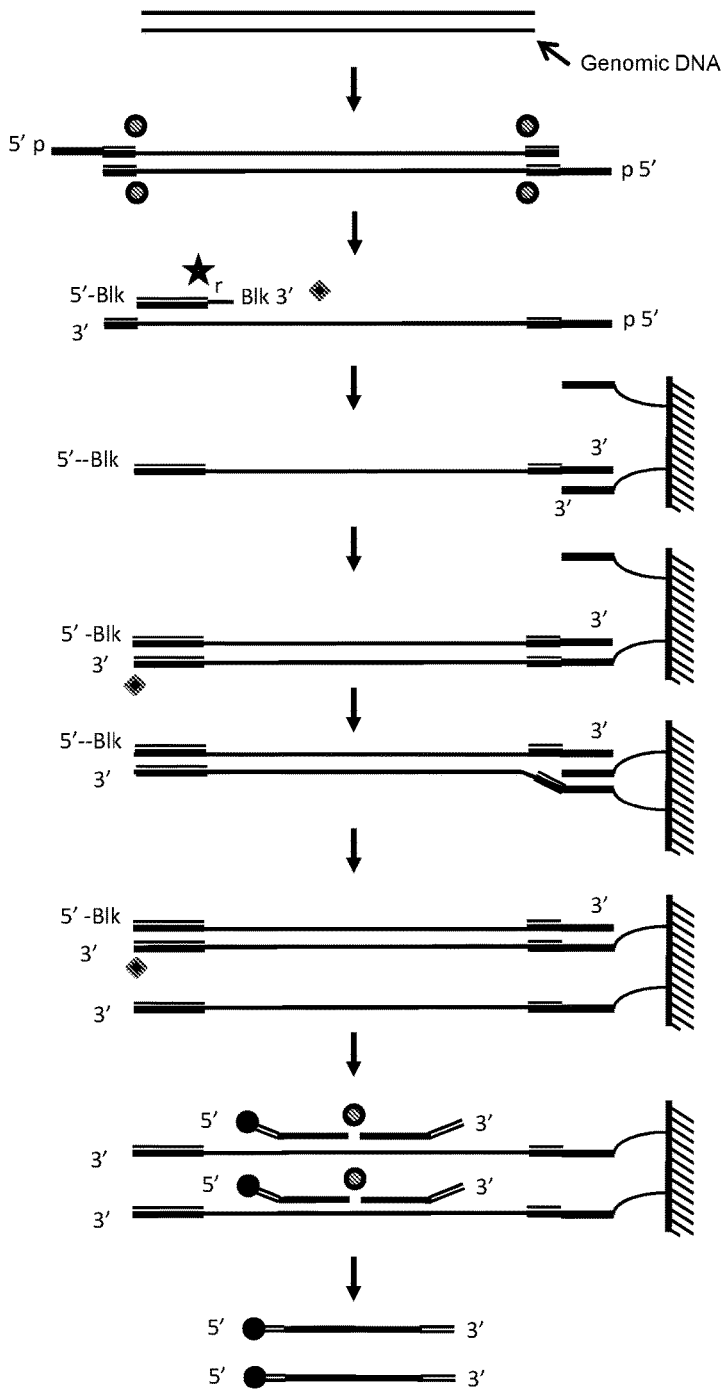

FIG. 93

A. Pixel-Cleavage to enumerate copy number. Isolate CTC DNA.

B. Blunt ends, extend 3'end with a single A base, and ligate on A:T rich linkers with single-base T overhang, and 5'-dA30 tails.

C. Denature DNA and hybridize locus-specific primer with blocked 3' and 5' ends. Primers are unblocked with RNaseH2 only when bound to target. Extend with polymerase, and generate T30 on 3' end. Optional: Degrade dA30 linkers with 5' nuclease.

D. Distribute onto an addressable matrix array, such that the T30 tail hybridizes to dA30 primers immobilized to pillars on a solid support.

E. Extend hybridized primer with strand displacing Bst polymerase at 37oC. When raising the temperature to 55-60oC, the dA portion partially denatures, allowing for an adjacent primer to hybridize and polymerase displace the first primer strand. By this repetitive process, the original strand is "handed-off" to the next primer to achieve a linear amplification of the original DNA.

F. Upstream and downstream oligonucleotides have locus-specific base, with the locus-specific flap oligonucleotides overlap at the locus base, and contain 5' identifying signature modifiers for subsequent nanopore detection. 5'-nuclease activity of polymerase or flap endonuclease cleaves off only matching 5'-overlapping base and additional flap; then detect, and enumerate signal.

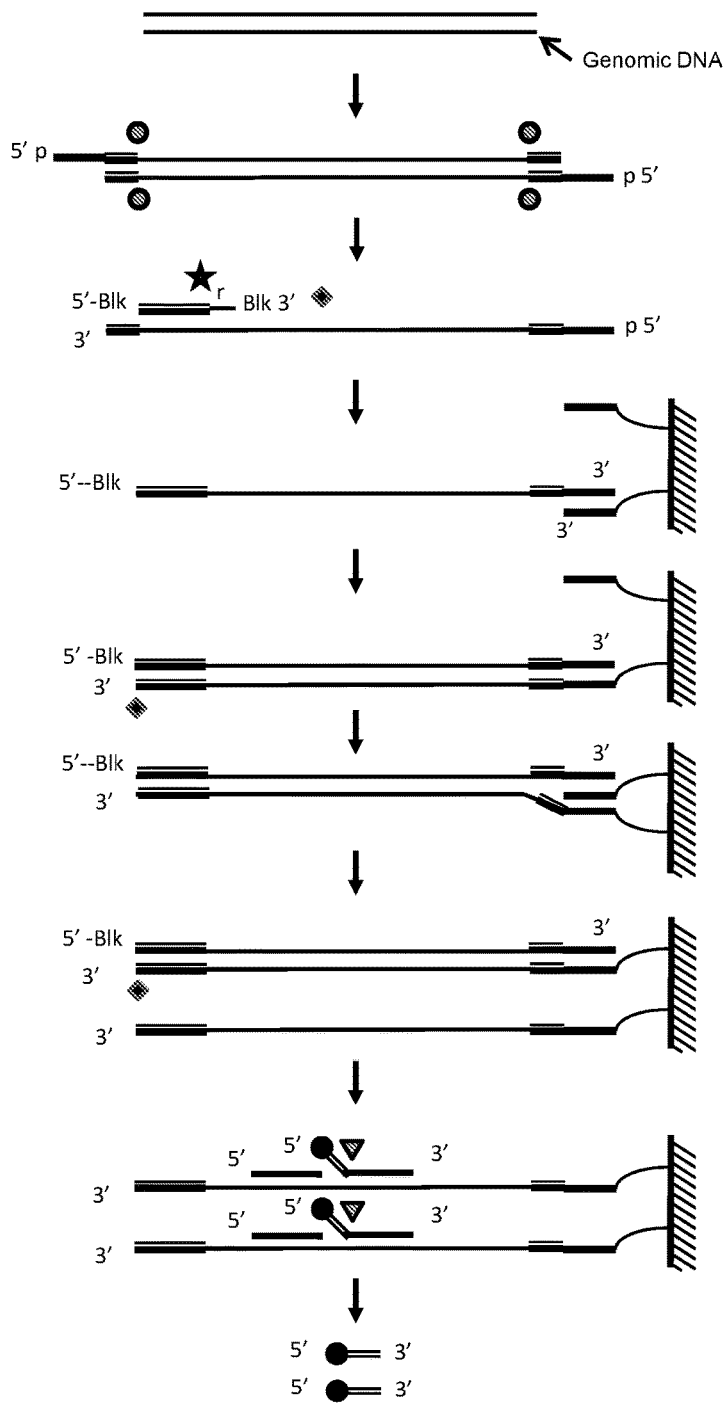

*FIG. 94*

A. Pixel-Nucleotide-Extension to enumerate copy number. Isolate CTC DNA.

B. Blunt ends, extend 3'end with a single A base, and ligate on A:T rich linkers with single-base T overhang, and 5'-dA30 tails.

C. Denature DNA and hybridize locus-specific primer with blocked 3' and 5' ends. Primers are unblocked with RNaseH2 only when bound to target. Extend with polymerase, and generate T30 on 3' end. Optional: Degrade dA30 linkers with 5' nuclease.

D. Distribute onto an addressable matrix array, such that the T30 tail hybridizes to dA30 primers immobilized to pillars on a solid support.

E. Extend hybridized primer with strand displacing Bst polymerase at 37oC. When raising the temperature to 55-60oC, the dA portion partially denatures, allowing for an adjacent primer to hybridize and polymerase displace the first primer strand. By this repetitive process, the original strand is "handed-off" to the next primer to achieve a linear amplification of the original DNA.

F. Wash away all dNTPs. Hybridize locus-specific oligonucleotides, which contain 5' identifying signature modifiers for subsequent nanopore detection.

G. Extend oligonucleotides with nucleotide analogue terminator dNTPs containing 3' encoding signature modifiers.

H. Wash away unhybridized probes and unincorporated analogues. Denature product from target, then detect, and enumerate signal.

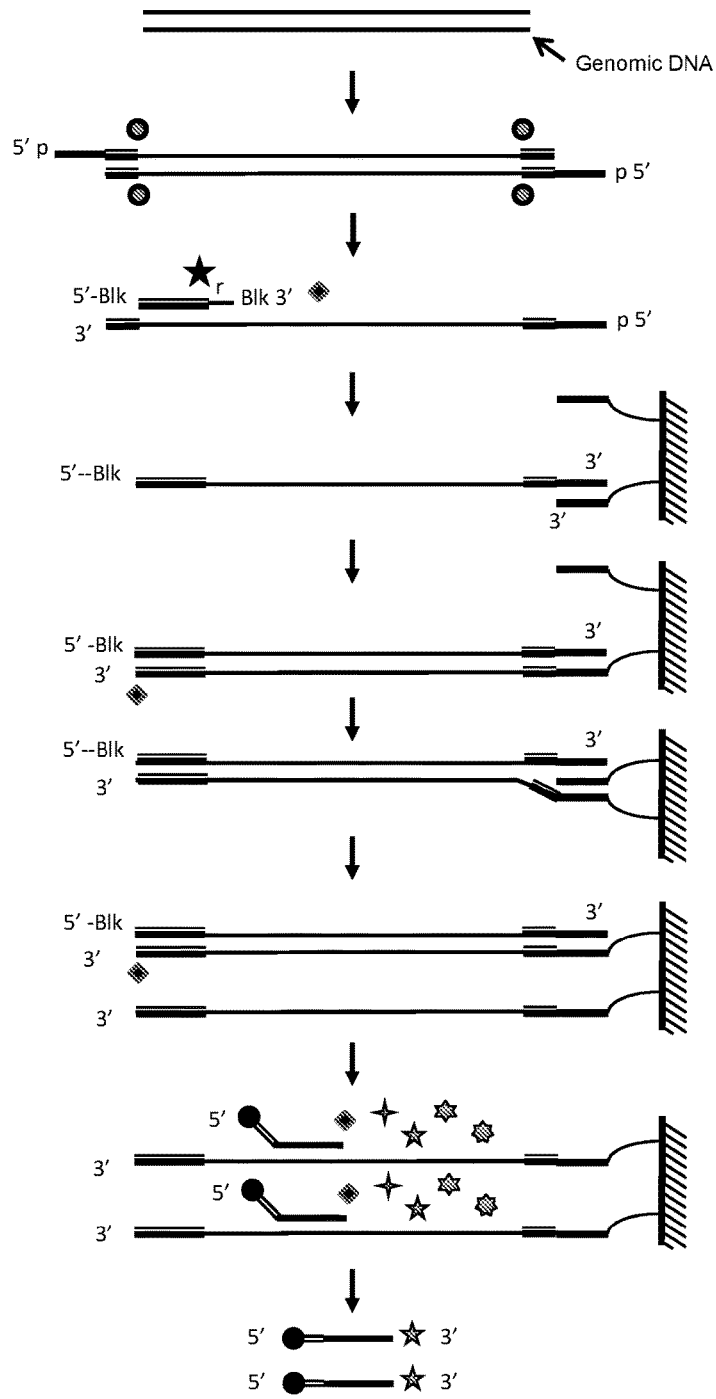

*FIG. 95*

A. Pixel-Primer-Extension to enumerate copy number. Isolate CTC DNA.

B. Blunt ends, extend 3'end with a single A base, and ligate on A:T rich linkers with single-base T overhang, and 5'-dA30 tails.

C. Denature DNA and hybridize locus-specific primer with blocked 3' and 5' ends. Primers are unblocked with RNaseH2 only when bound to target. Extend with polymerase, and generate T30 on 3' end. Optional: Degrade dA30 linkers with 5' nuclease.

D. Distribute onto an addressable matrix array, such that the T30 tail hybridizes to dA30 primers immobilized to pillars on a solid support.

E. Extend hybridized primer with strand displacing Bst polymerase at 37oC. When raising the temperature to 55-60oC, the dA portion partially denatures, allowing for an adjacent primer to hybridize and polymerase displace the first primer strand. By this repetitive process, the original strand is "handed-off" to the next primer to achieve a linear amplification of the original DNA.

F. Wash away all dNTPs. Hybridize upstream locus-specific oligonucleotides, which contain 5' identifying signature modifiers for subsequent nanopore detection. Downstream primers contain 3' block.

G. Extend upstream oligonucleotides with polymerase lacking 5'-3' nuclease and strand-displacement activity, until extension product abuts downstream primer.

H. Wash away unhybridized probes. Denature product from target, then detect, and enumerate signal.

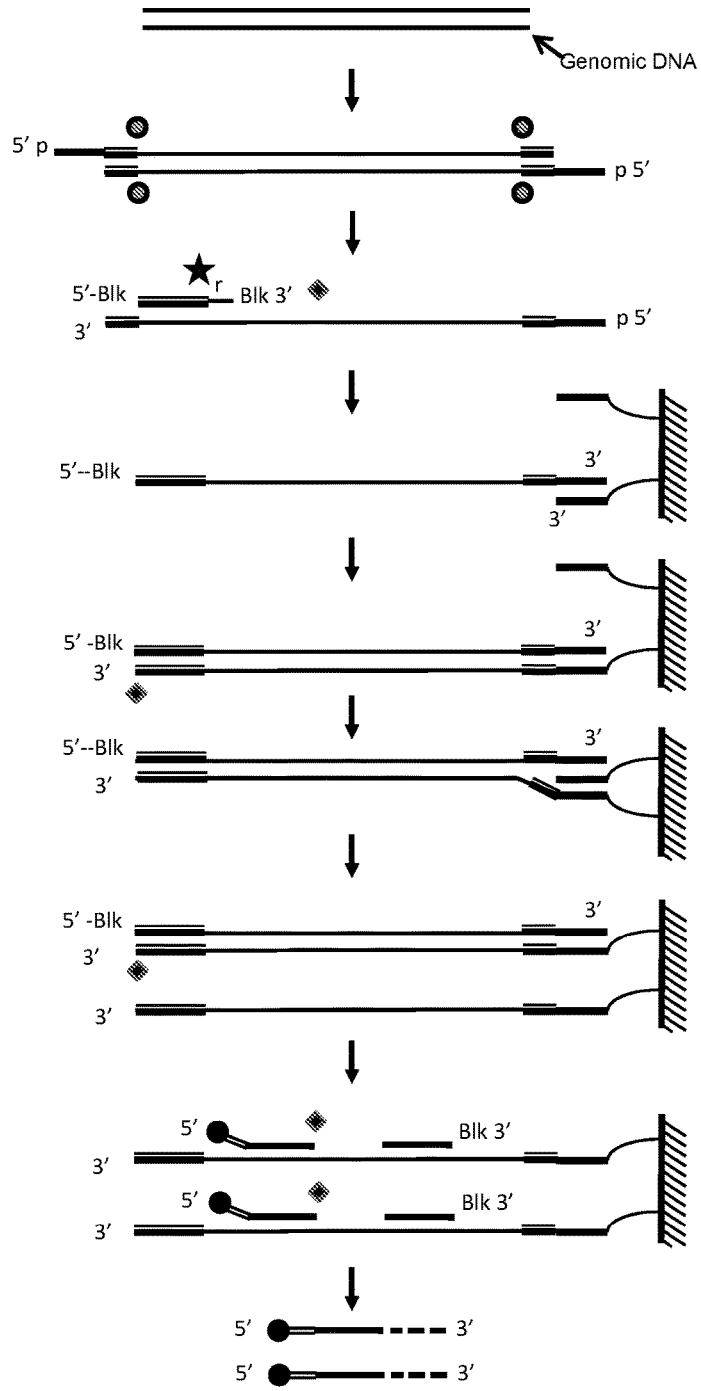

*FIG. 96*

A. Pixel-LDR to enumerate low-abundance DNA. Isolate DNA.

B. Denature DNA and hybridize locus-specific primer with 5'dA30 tails and blocked 3' end. Primers are unblocked with RNaseH2 only when bound to target. Extend with thermostable polymerase.

C. Denature DNA and hybridize locus-specific primer with blocked 3' and 5' ends. Primers are unblocked with RNaseH2 only when bound to target. Extend with polymerase, and generate T30 on 3' end. Optional: Degrade dA30 linkers with 5' nuclease.

D. Distribute onto an addressable matrix array, such that the T30 tail hybridizes to dA30 primers immobilized to pillars on a solid support.

E. Extend hybridized primer with strand displacing Bst polymerase at 37oC. When raising the temperature to 55-60oC, the dA portion partially denatures, allowing for an adjacent primer to hybridize and polymerase displace the first primer strand. By this repetitive process, the original strand is "handed-off" to the next primer to achieve a linear amplification of the original DNA.

F. Target-specific ligation oligonucleotides contain 5' identifying signature modifiers for subsequent nanopore detection. Ligase covalently seals the two oligonucleotides together.

G. Wash away unligated probes. Denature product from target, then detect, and enumerate signal.

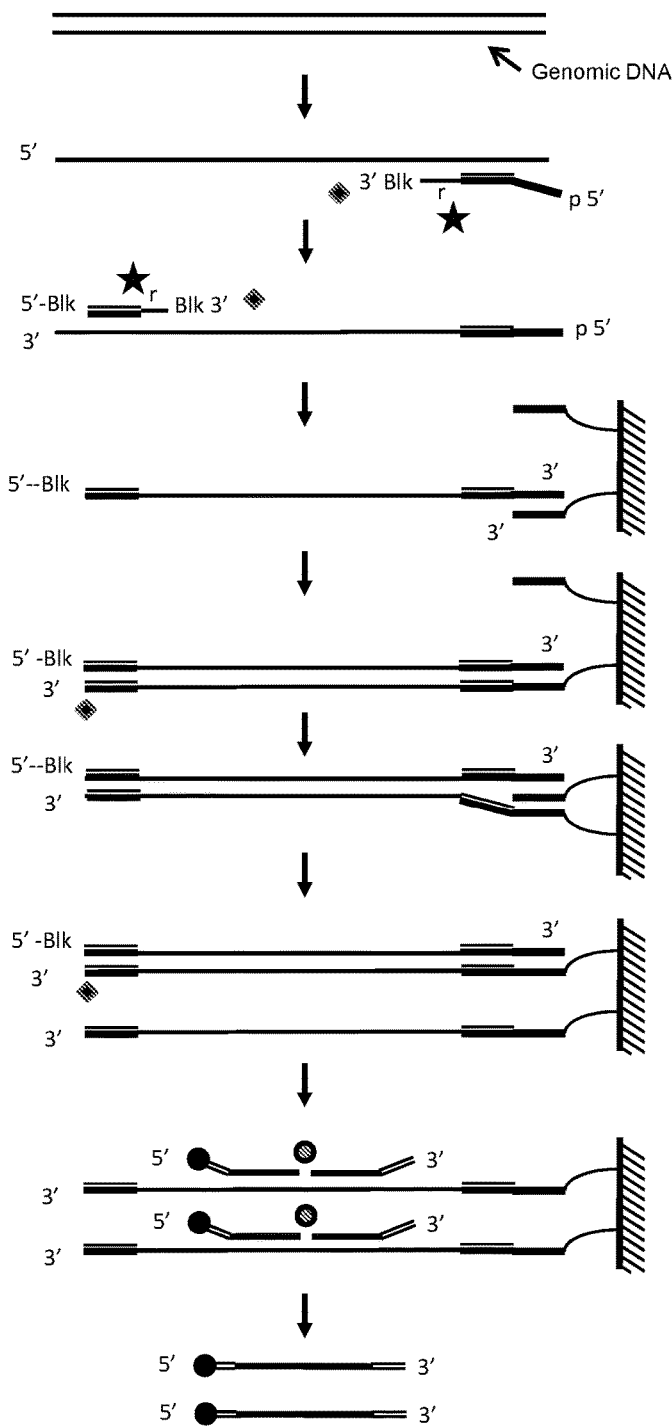

*FIG. 97*

A. Pixel-Cleavage to enumerate low-abundance DNA. Isolate DNA.

B. Denature DNA and hybridize locus-specific primer with 5'dA30 tails and blocked 3' end. Primers are unblocked with RNaseH2 only when bound to target. Extend with thermostable polymerase.

C. Denature DNA and hybridize locus-specific primer with blocked 3' and 5' ends. Primers are unblocked with RNaseH2 only when bound to target. Extend with polymerase, and generate T30 on 3' end. Optional: Degrade dA30 linkers with 5' nuclease.

D. Distribute onto an addressable matrix array, such that the T30 tail hybridizes to dA30 primers immobilized to pillars on a solid support.

E. Extend hybridized primer with strand displacing Bst polymerase at 37oC. When raising the temperature to 55-60oC, the dA portion partially denatures, allowing for an adjacent primer to hybridize and polymerase displace the first primer strand. By this repetitive process, the original strand is "handed-off" to the next primer to achieve a linear amplification of the original DNA.

F. Upstream and downstream oligonucleotides have locus-specific base, with the locus-specific flap oligonucleotides overlap at the locus base, and contain 5' identifying signature modifiers for subsequent nanopore detection. 5'-nuclease activity of polymerase or flap endonuclease cleaves off only matching 5'-overlapping base and additional flap; then detect, and enumerate signal.

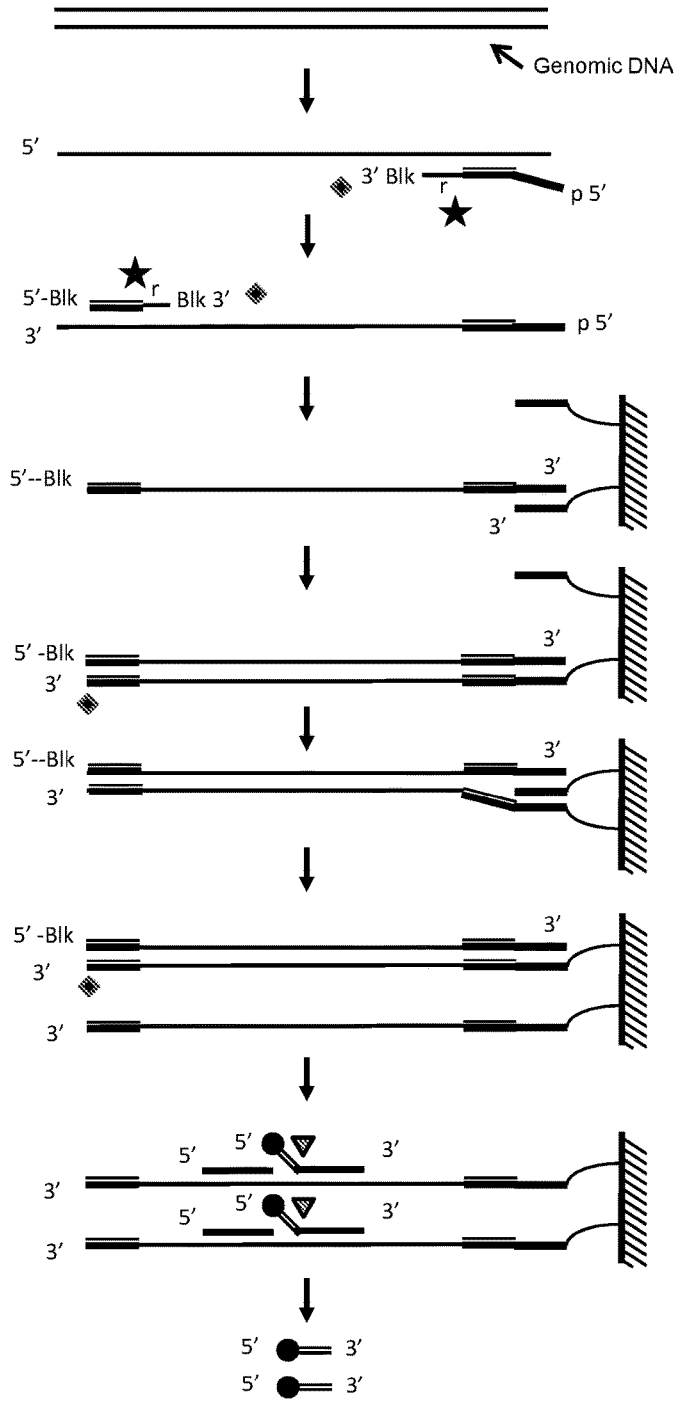

*FIG. 98*

A. Pixel-Nucleotide-Extension to enumerate low-abundance DNA. Isolate DNA.

B. Denature DNA and hybridize locus-specific primer with 5'dA30 tails and blocked 3' end. Primers are unblocked with RNaseH2 only when bound to target. Extend with thermostable polymerase.

C. Denature DNA and hybridize locus-specific primer with blocked 3' and 5' ends. Primers are unblocked with RNaseH2 only when bound to target. Extend with polymerase, and generate T30 on 3' end. Optional: Degrade dA30 linkers with 5' nuclease.

D. Distribute onto an addressable matrix array, such that the T30 tail hybridizes to dA30 primers immobilized to pillars on a solid support.

E. Extend hybridized primer with strand displacing Bst polymerase at 37oC. When raising the temperature to 55-60oC, the dA portion partially denatures, allowing for an adjacent primer to hybridize and polymerase displace the first primer strand. By this repetitive process, the original strand is "handed-off" to the next primer to achieve a linear amplification of the original DNA.

F. Wash away all dNTPs. Hybridize locus-specific oligonucleotides, which contain 5' identifying signature modifiers for subsequent nanopore detection.

G. Extend oligonucleotides with nucleotide analogue terminator dNTPs containing 3' encoding signature modifiers.

H. Wash away unhybridized probes and unincorporated analogues. Denature product from target, then detect, and enumerate signal.

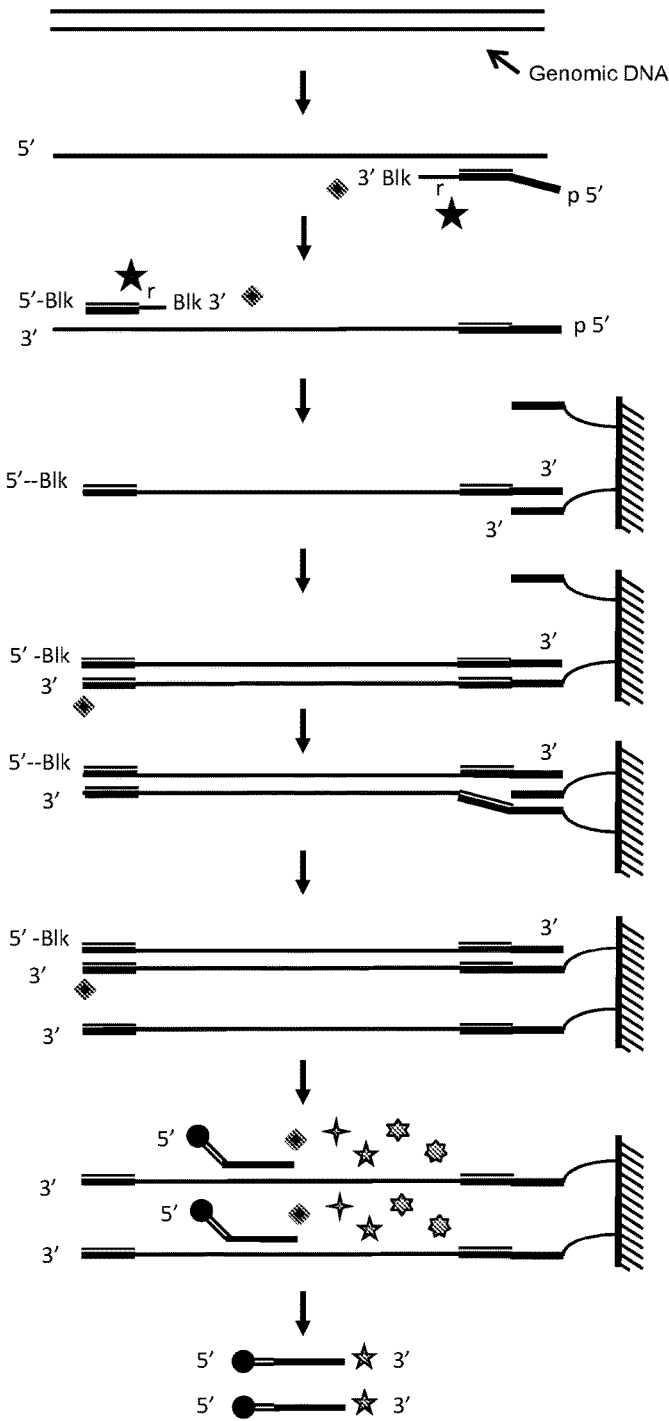

FIG. 99

A. Pixel-Primer-Extension to enumerate low-abundance DNA. Isolate DNA.

B. Denature DNA and hybridize locus-specific primer with 5'dA30 tails and blocked 3' end. Primers are unblocked with RNaseH2 only when bound to target. Extend with thermostable polymerase.

C. Denature DNA and hybridize locus-specific primer with blocked 3' and 5' ends. Primers are unblocked with RNaseH2 only when bound to target. Extend with polymerase, and generate T30 on 3' end. Optional: Degrade dA30 linkers with 5' nuclease.

D. Distribute onto an addressable matrix array, such that the T30 tail hybridizes to dA30 primers immobilized to pillars on a solid support.

E. Extend hybridized primer with strand displacing Bst polymerase at 37oC. When raising the temperature to 55-60oC, the dA portion partially denatures, allowing for an adjacent primer to hybridize and polymerase displace the first primer strand. By this repetitive process, the original strand is "handed-off" to the next primer to achieve a linear amplification of the original DNA.

F. Wash away all dNTPs. Hybridize upstream locus-specific oligonucleotides, which contain 5' identifying signature modifiers for subsequent nanopore detection. Downstream primers contain 3' block.

G. Extend upstream oligonucleotides with polymerase lacking 5'-3' nuclease and strand-displacement activity, until extension product abuts downstream primer.

H. Wash away unhybridized probes. Denature product from target, then detect, and enumerate signal.

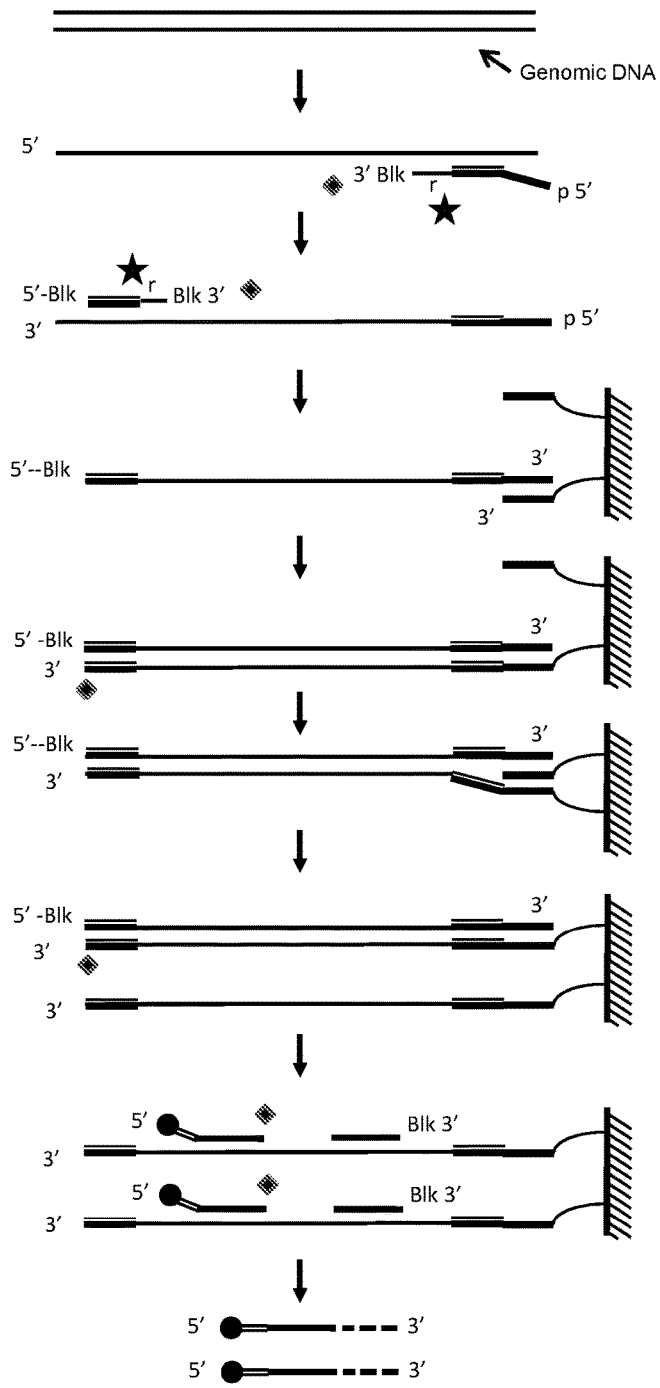

FIG. 100

A. Pixel-LDR to detect methylation. Isolate genomic or cfDNA. Optional: enrich for methylated DNA using antibodies.

B. Tail 3' ends with Terminal deoxynucleotidyl transferase (TdT), using TTP to generate T(100-150).

C. Treat with methyl-sensitive restriction endonucleasesBsh1236I (CG^CG).

D. Distribute onto an addressable matrix array, such that the T(100) tail hybridizes to dA30 primers immobilized to pillars on a solid support.

E. Extend hybridized primer with strand displacing Bst polymerase at 37oC, in presence of BstU1 (CG^CG). When raising the temperature to 55-60oC, the dA portion partially denatures, allowing for an adjacent primer to hybridize and polymerase displaces the first primer strand. By this repetitive process, the original strand is "handed-off" to the next primer to achieve a linear amplification of the original DNA. BstU1 will cleave dsDNA if unmethylated, but not hybrid methyl/unmethyl DNA, nor unmethylated ssDNA.

F. Methylation-specific ligation oligonucleotides contain 5' identifying signature modifiers for subsequent nanopore detection. Ligase covalently seals the two oligonucleotides together.

G. Wash away unligated probes. Denature product from target, then detect, and enumerate signal.

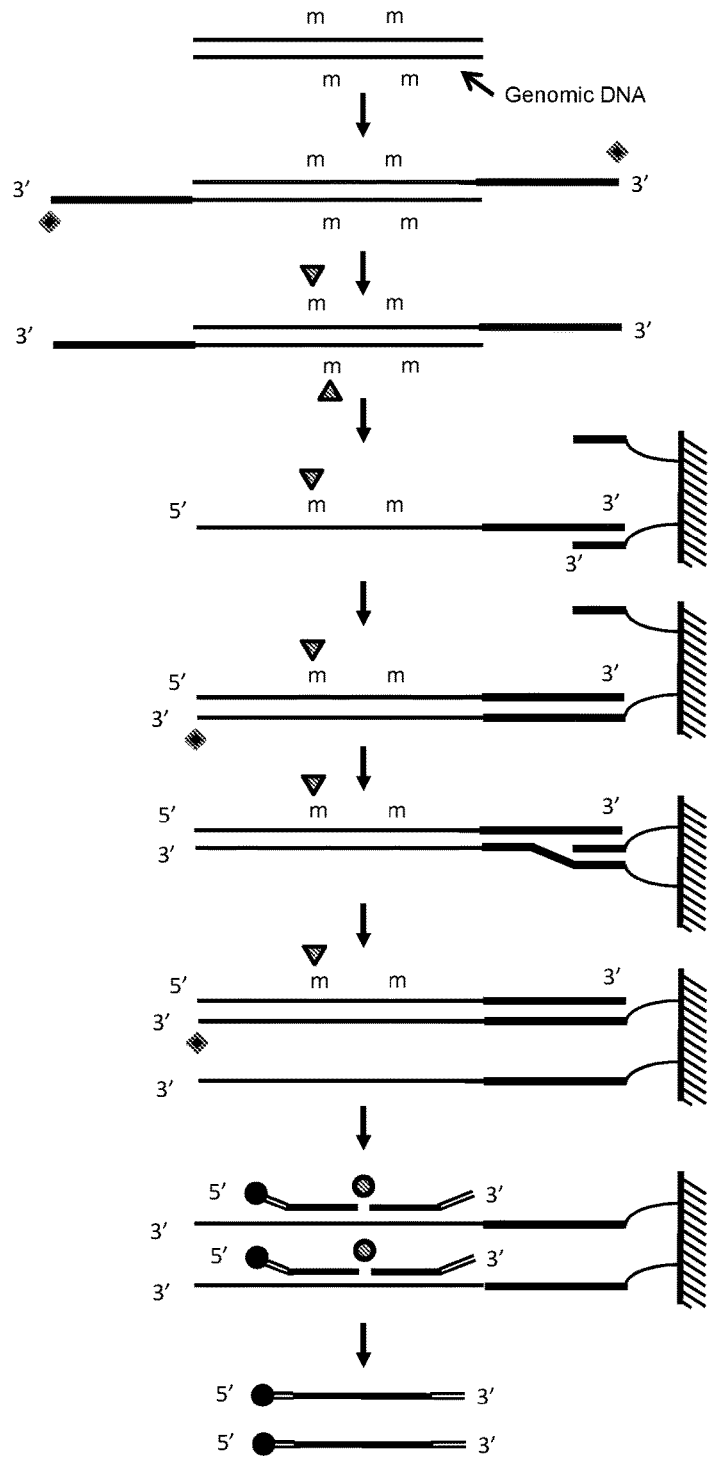

FIG. 101

A. Pixel-Cleavage to detect methylation. Isolate genomic or cfDNA. Optional: enrich for methylated DNA using antibodies.

B. Tail 3' ends with Terminal deoxynucleotidyl transferase (TdT), using TTP to generate T(100-150).

C. Treat with methyl-sensitive restriction endonucleasesBsh1236I (CG^CG).

D. Distribute onto an addressable matrix array, such that the T(100) tail hybridizes to dA30 primers immobilized to pillars on a solid support.

E. Extend hybridized primer with strand displacing Bst polymerase at 37oC, in presence of BstU1 (CG^CG). When raising the temperature to 55-60oC, the dA portion partially denatures, allowing for an adjacent primer to hybridize and polymerase displaces the first primer strand. By this repetitive process, the original strand is "handed-off" to the next primer to achieve a linear amplification of the original DNA. BstU1 will cleave dsDNA if unmethylated, but not hybrid methyl/unmethyl DNA, nor unmethylated ssDNA.

F. Upstream and downstream oligonucleotides have methylation locus-specific base, with the locus-specific flap oligonucleotides overlap at the locus base, and contain 5' identifying signature modifiers for subsequent nanopore detection. 5'-nuclease activity of polymerase or flap endonuclease cleaves off only matching 5'-overlapping base and additional flap; then detect, and enumerate signal.

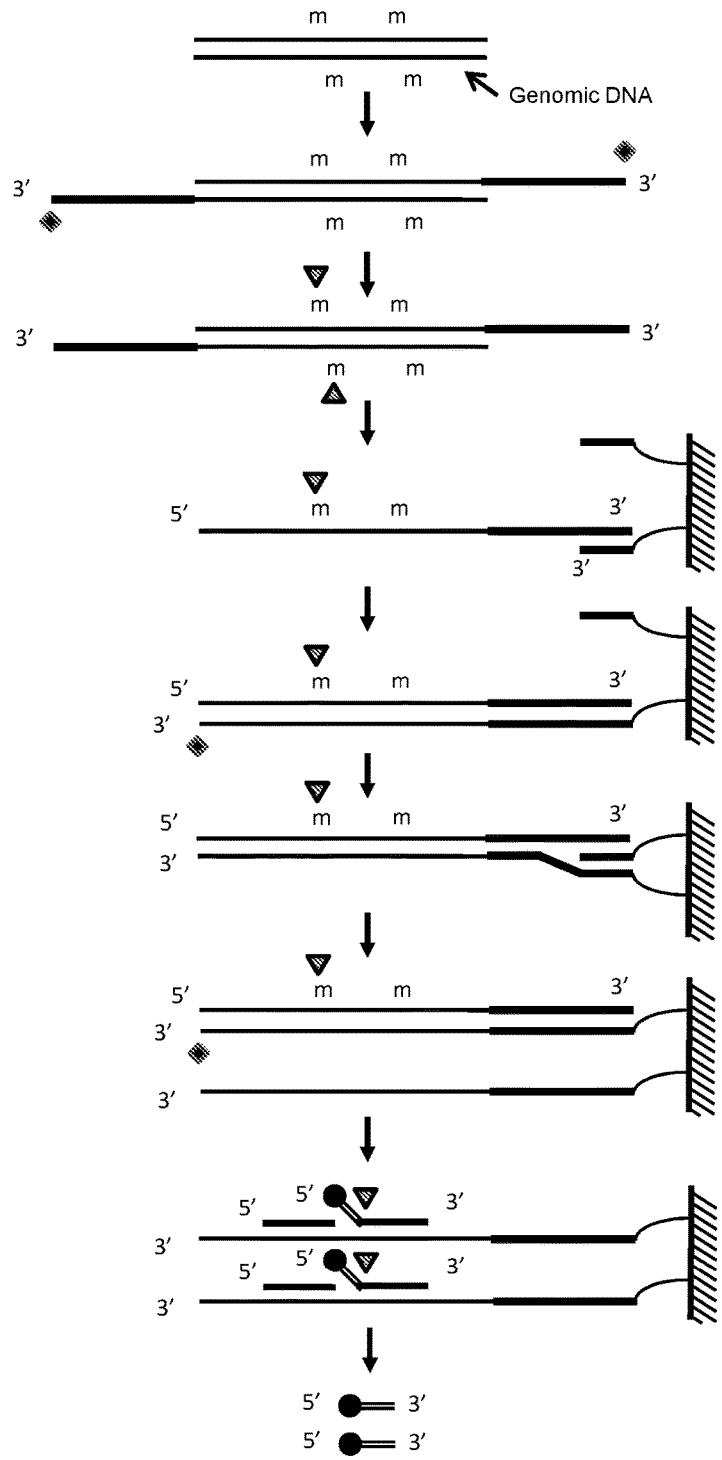

FIG. 102

A. Pixel-Nucleotide-Extension to detect methylation. Isolate genomic or cfDNA. Optional: enrich for methylated DNA using antibodies.

B. Tail 3' ends with Terminal deoxynucleotidyl transferase (TdT), using TTP to generate T(100-150).

C. Treat with methyl-sensitive restriction endonucleasesBsh1236I (CG^CG).

D. Distribute onto an addressable matrix array, such that the T(100) tail hybridizes to dA30 primers immobilized to pillars on a solid support.

E. Extend hybridized primer with strand displacing Bst polymerase at 37oC, in presence of BstU1 (CG^CG). When raising the temperature to 55-60oC, the dA portion partially denatures, allowing for an adjacent primer to hybridize and polymerase displaces the first primer strand. By this repetitive process, the original strand is "handed-off" to the next primer to achieve a linear amplification of the original DNA. BstU1 will cleave dsDNA if unmethylated, but not hybrid methyl/unmethyl DNA, nor unmethylated ssDNA.

F. Wash away all dNTPs. Hybridize methylation locus-specific oligonucleotides, which contain 5' identifying signature modifiers for subsequent nanopore detection.

G. Extend oligonucleotides with nucleotide analogue terminator dNTPs containing 3' encoding signature modifiers.

H. Wash away unhybridized probes and unincorporated analogues. Denature product from target, then detect, and enumerate signal.

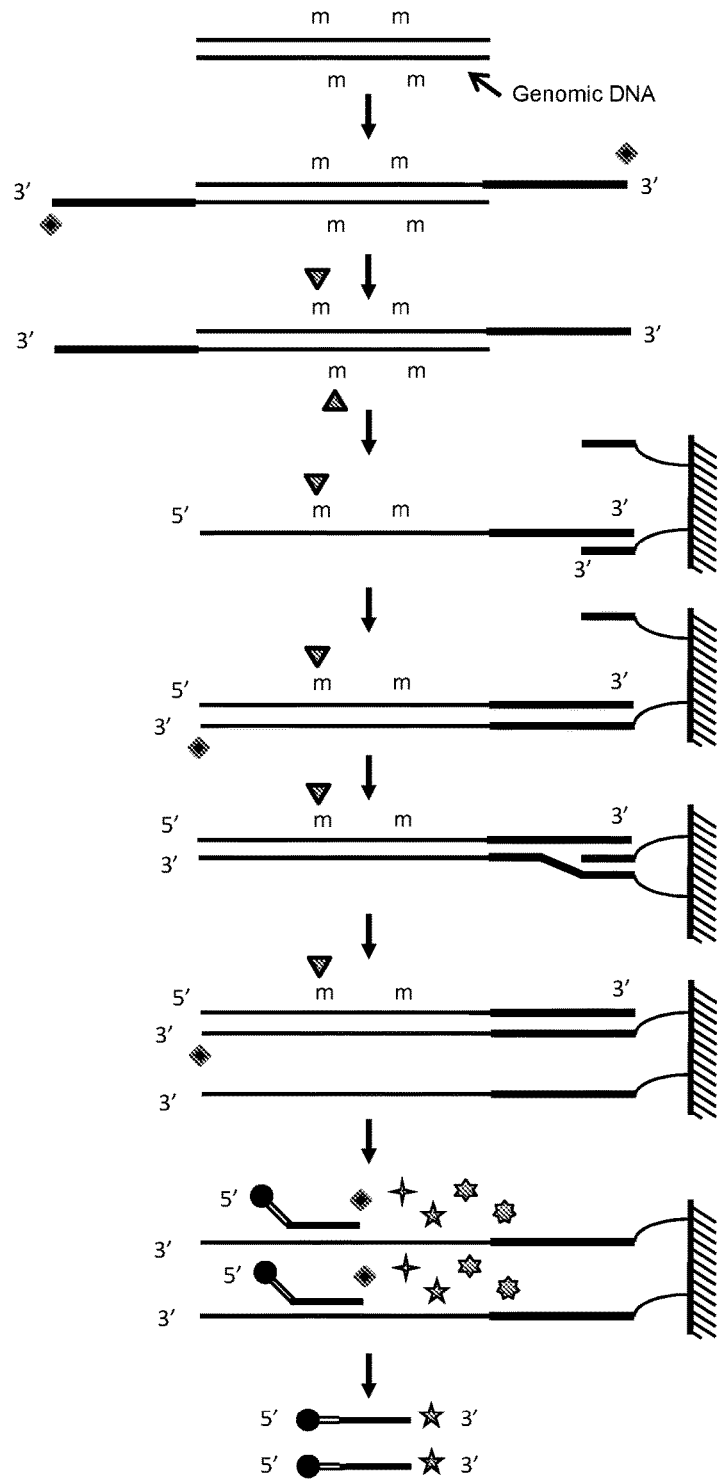

FIG. 103

A. Pixel-Primer-Extension to detect methylation. Isolate genomic or cfDNA. Optional: enrich for methylated DNA using antibodies.

B. Tail 3' ends with Terminal deoxynucleotidyl transferase (TdT), using TTP to generate T(100-150).

C. Treat with methyl-sensitive restriction endonucleasesBsh1236I (CG^CG).

D. Distribute onto an addressable matrix array, such that the T(100) tail hybridizes to dA30 primers immobilized to pillars on a solid support.

E. Extend hybridized primer with strand displacing Bst polymerase at 37oC, in presence of BstU1 (CG^CG). When raising the temperature to 55-60oC, the dA portion partially denatures, allowing for an adjacent primer to hybridize and polymerase displaces the first primer strand. By this repetitive process, the original strand is "handed-off" to the next primer to achieve a linear amplification of the original DNA. BstU1 will cleave dsDNA if unmethylated, but not hybrid methyl/unmethyl DNA, nor unmethylated ssDNA.

F. Wash away all dNTPs. Hybridize upstream methylation locus-specific oligonucleotides, which contain 5' identifying signature modifiers for subsequent nanopore detection. Downstream primers contain 3' block.

G. Extend upstream oligonucleotides with polymerase lacking 5'-3' nuclease and strand-displacement activity, until extension product abuts downstream primer.

H. Wash away unhybridized probes. Denature product from target, then detect, and enumerate signal.

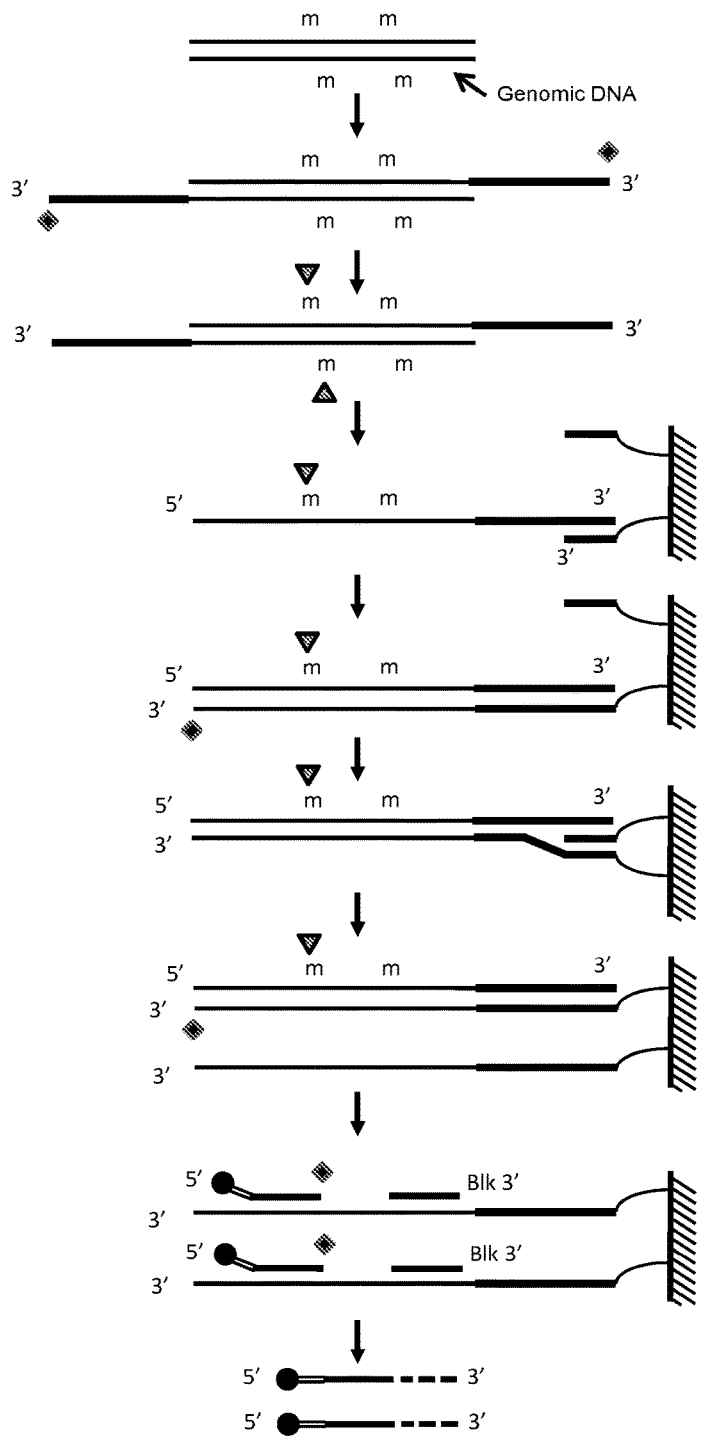

FIG. 104

A. Pixel-LDR to detect locus-specific methylation. Isolate DNA.

B. Tail 3' ends with Terminal deoxynucleotidyl transferase (TdT), using TTP to generate T(100-150). Treat with methyl-sensitive restriction endonucleases Bsh1236I (CG^CG).

C. Denature DNA and hybridize locus-specific primer with blocked 3' end. Primers are unblocked with RNaseH2 only when bound to target. Extend with polymerase to incorporate biotin-dCTP.

D. Capture biotinylated strand on solid support, wash, and release enriched target.

E. Distribute onto an addressable matrix array, such that the T(100) tail hybridizes to dA30 primers immobilized to pillars on a solid support.

F. Extend hybridized primer with strand displacing Bst polymerase at 37oC, in presence of BstU1 (CG^CG). When raising the temperature to 55-60oC, the dA portion partially denatures, allowing for an adjacent primer to hybridize and polymerase displace the first primer strand. By this repetitive process, the original strand is "handed-off" to the next primer to achieve a linear amplification of the original DNA. BstU1 will cleave dsDNA if unmethylated, but not hybrid methyl/unmethyl DNA, nor unmethylated ssDNA.

G. Methylation-specific ligation oligonucleotides contain 5' identifying signature modifiers for subsequent nanopore detection. Ligase covalently seals the two oligonucleotides together.

H. Wash away unligated probes. Denature product from target, then detect, and enumerate signal.

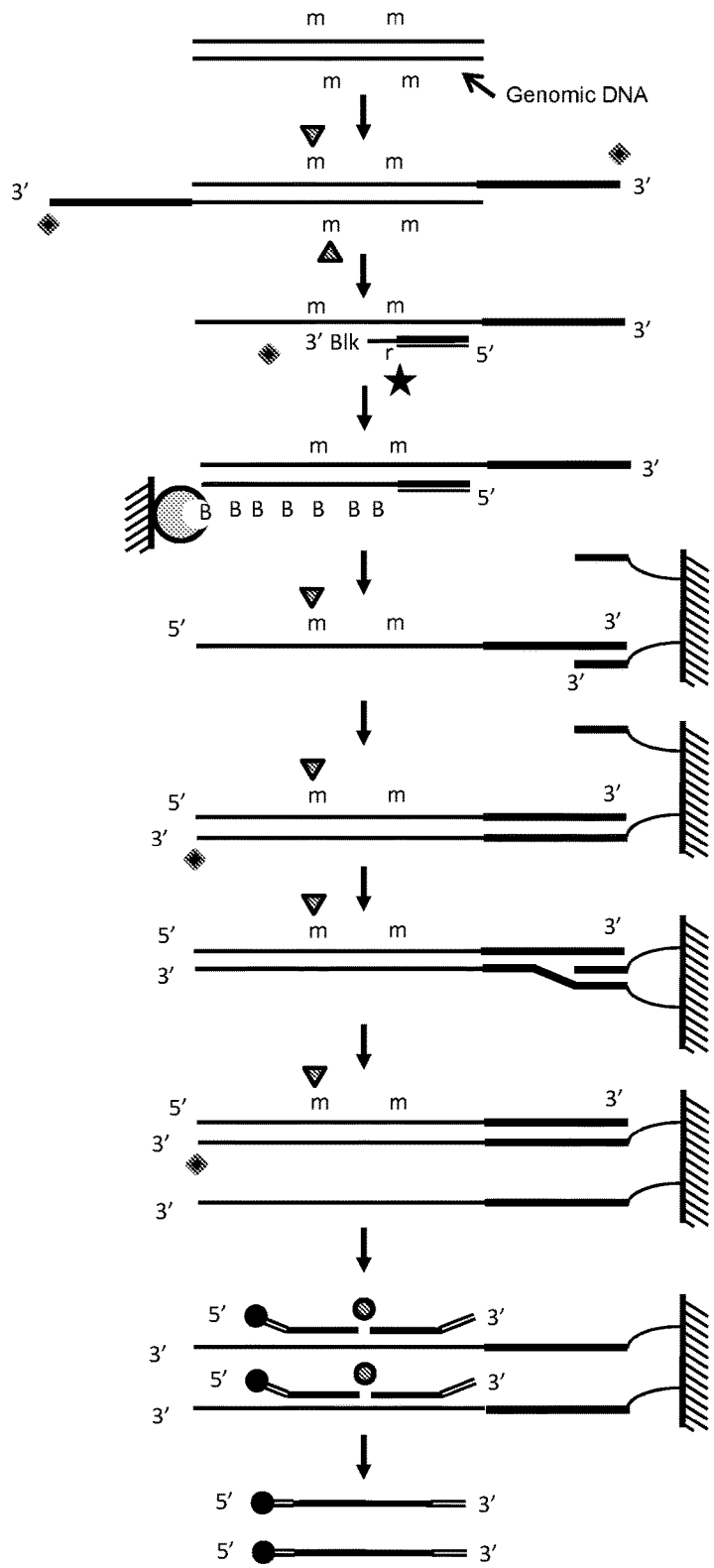

*FIG. 105*

A. Pixel-LDR to detect methylation using bisulfite. Isolate genomic or cfDNA. Optional: enrich for methylated DNA using antibodies.

B. Tail 3' ends with Terminal deoxynucleotidyl transferase (TdT), using TTP to generate dT(100-150).

C. Treat with bisulfite, which converts unmethylated dC to dU, and renders the strands non-complementary.

D. Distribute onto an addressable matrix array, such that the T(100) tail hybridizes to dA30 primers immobilized to pillars on a solid support.

E. Extend hybridized primer with strand displacing Bst polymerase at 37oC. When raising the temperature to 55-60oC, the dA portion partially denatures, allowing for an adjacent primer to hybridize and polymerase displace the first primer strand. By this repetitive process, the original strand is "handed-off" to the next primer to achieve a linear amplification of the original DNA.

F. Methylation-specific ligation oligonucleotides contain 5' identifying signature modifiers for subsequent nanopore detection. Ligase covalently seals the two oligonucleotides together.

G. Wash away unligated probes. Denature product from target, then detect, and enumerate signal.

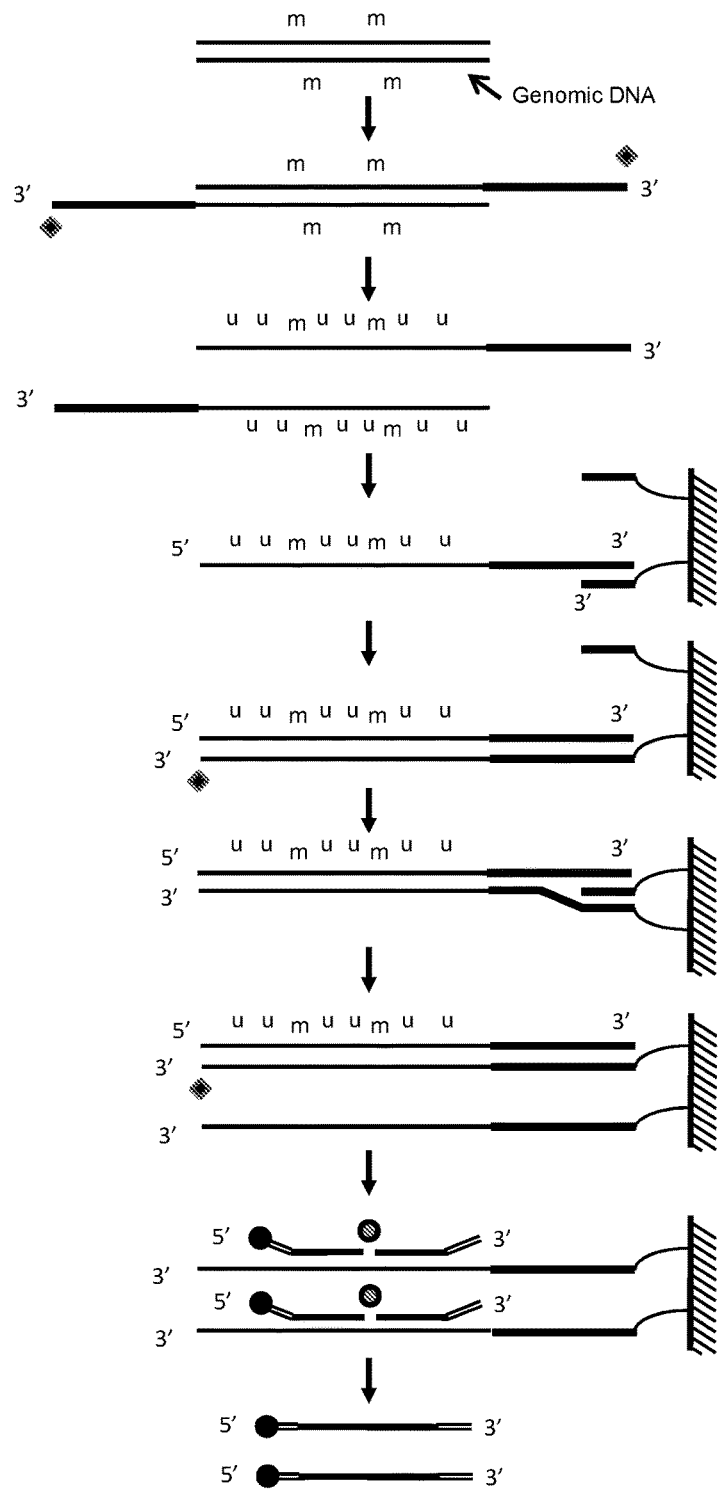

*FIG. 106*

A. Pixel-primer-extension to detect methylation using bisulfite. Isolate genomic or cfDNA. Optional: enrich for methylated DNA using antibodies.

B. Tail 3′ ends with Terminal deoxynucleotidyl transferase (TdT), using TTP to generate dT(100-150).

C. Treat with bisulfite, which converts unmethylated dC to dU, and renders the strands non-complementary.

D. Distribute onto an addressable matrix array, such that the T(100) tail hybridizes to dA30 primers immobilized to pillars on a solid support.

E. Extend hybridized primer with strand displacing Bst polymerase at 37oC. When raising the temperature to 55-60oC, the dA portion partially denatures, allowing for an adjacent primer to hybridize and polymerase displace the first primer strand. By this repetitive process, the original strand is "handed-off" to the next primer to achieve a linear amplification of the original DNA.

F. Wash away all dNTPs. Hybridize upstream methyl region-specific oligonucleotides, which contain 5′ identifying signature modifiers for subsequent nanopore detection. Downstream primers contain 3′ block.

G. Extend upstream oligonucleotides with dATP, dGTP, TTP, and with dCTP analog comprising a 3′ identifying signature modifier, using polymerase lacking 5′-3′ nuclease and strand-displacement activity, until extension product abuts downstream primer.

H. Wash away unhybridized probes. Denature product from target, then detect, and enumerate signal.

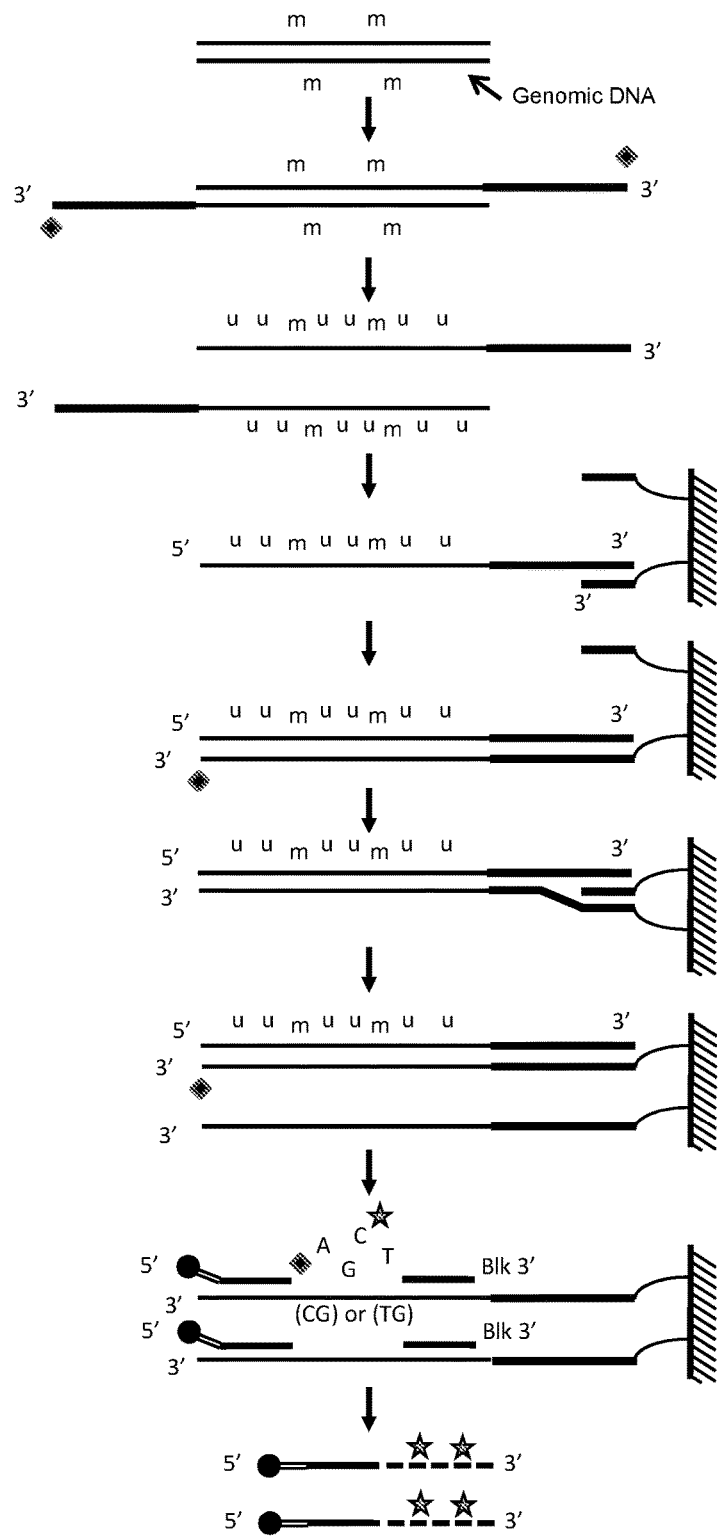

*FIG. 107*

A. Pixel-LDR to detect locus-specific methylation using bisulfite. Isolate genomic or cfDNA.

B. Repair ends with polymerase, phosphorylate 5' ends, extend 3'ends with a single A base, and ligate on A:T rich linkers with single-base T overhang, and 3'-T30 tails. (Optional, cleave with methyl-sensitive restriction enzymes.)

C. Treat with bisulfite, which converts unmethylated dC to dU, and renders the strands non-complementary.

D. Hybridize locus-specific primer with blocked 3' and 5' ends. Primers are unblocked with RNaseH2 only when bound to target. Extend with polymerase, and generate T30 on 3' end. Optional: Degrade dA30 linkers with 5' nuclease.

E. Distribute onto an addressable matrix array, such that the T30 tail hybridizes to dA30 primers immobilized to pillars on a solid support.

F. Extend hybridized primer with strand displacing Bst polymerase at 37oC. When raising the temperature to 55-60oC, the dA portion partially denatures, allowing for an adjacent primer to hybridize and polymerase displace the first primer strand. By this repetitive process, the original strand is "handed-off" to the next primer to achieve a linear amplification of the original DNA.

G. Methylation-specific ligation oligonucleotides contain 5' identifying signature modifiers for subsequent nanopore detection. Ligase covalently seals the two oligonucleotides together.

H. Wash away unligated probes. Denature product from target, then detect, and enumerate signal.

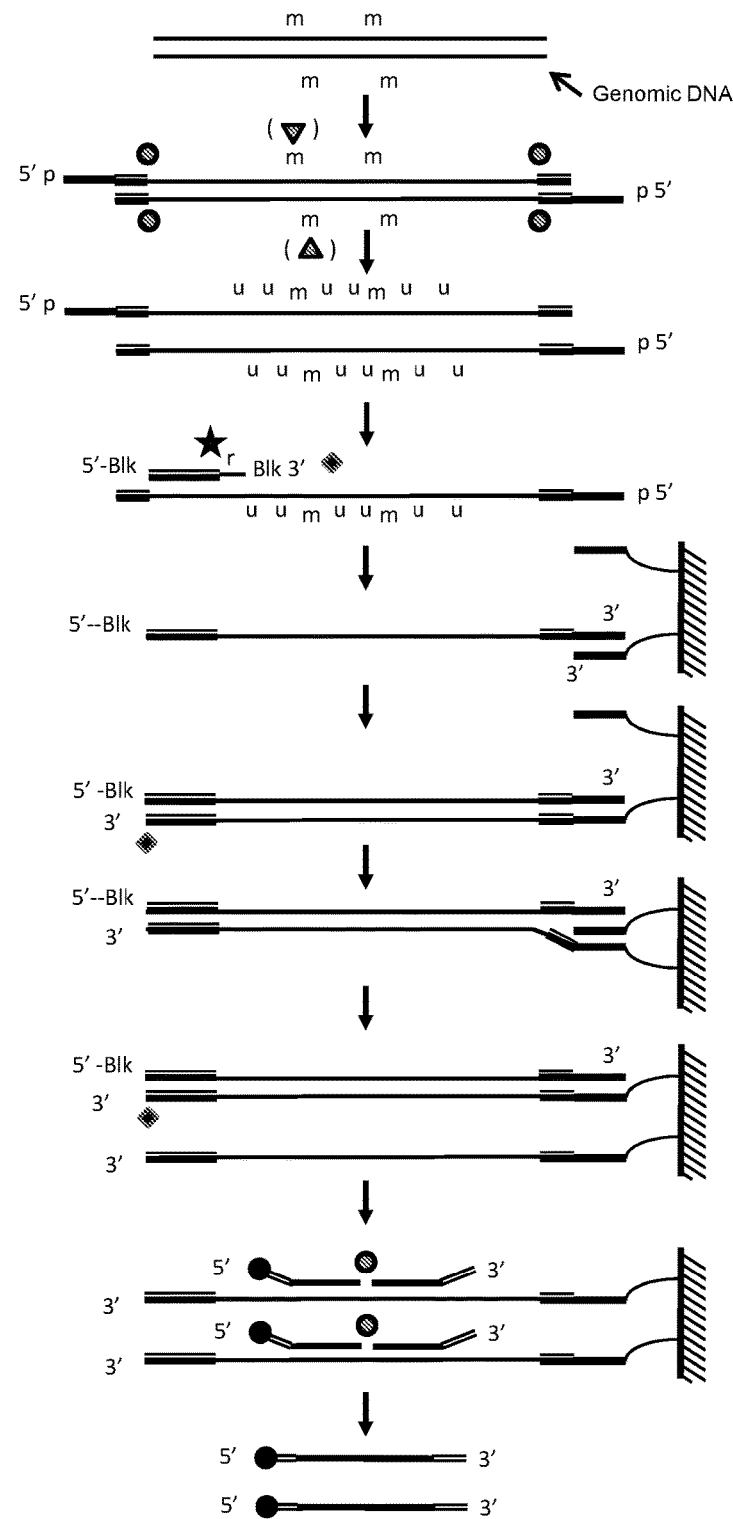

*FIG. 108*

A. Pixel-Nucleotide-Extension to detect locus-specific methylation using bisulfite. Isolate genomic or cfDNA.

B. Repair ends with polymerase, phosphorylate 5' ends, extend 3'ends with a single A base, and ligate on A:T rich linkers with single-base T overhang, and 3'-T30 tails. (Optional, cleave with methyl-sensitive REases.)

C. Treat with bisulfite, which converts unmethylated dC to dU, and renders the strands non-complementary.

D. Hybridize locus-specific primer with blocked 3' and 5' ends. Primers are unblocked with RNaseH2 only when bound to target. Extend with polymerase, and generate T30 on 3' end. Optional: Degrade dA30 linkers with 5' nuclease.

E. Distribute onto an addressable matrix array, such that the T30 tail hybridizes to dA30 primers immobilized to pillars on a solid support.

F. Extend hybridized primer with strand displacing Bst polymerase at 37oC. When raising the temperature to 55-60oC, the dA portion partially denatures, allowing for an adjacent primer to hybridize and polymerase displace the first primer strand. By this repetitive process, the original strand is "handed-off" to the next primer to achieve a linear amplification of the original DNA.

G. Wash away all dNTPs. Hybridize upstream methyl region-specific oligonucleotides, which contain 5' identifying signature modifiers for subsequent nanopore detection. Downstream primers contain 3' block.

H. Extend upstream oligonucleotides with dATP, dGTP, TTP, and with dCTP comprising a 3' identifying signature modifier, using polymerase lacking 5'-3' nuclease and strand-displacement activity, until extension product abuts downstream primer.

I. Wash away unhybridized probes. Denature product from target, then detect, and enumerate signal.

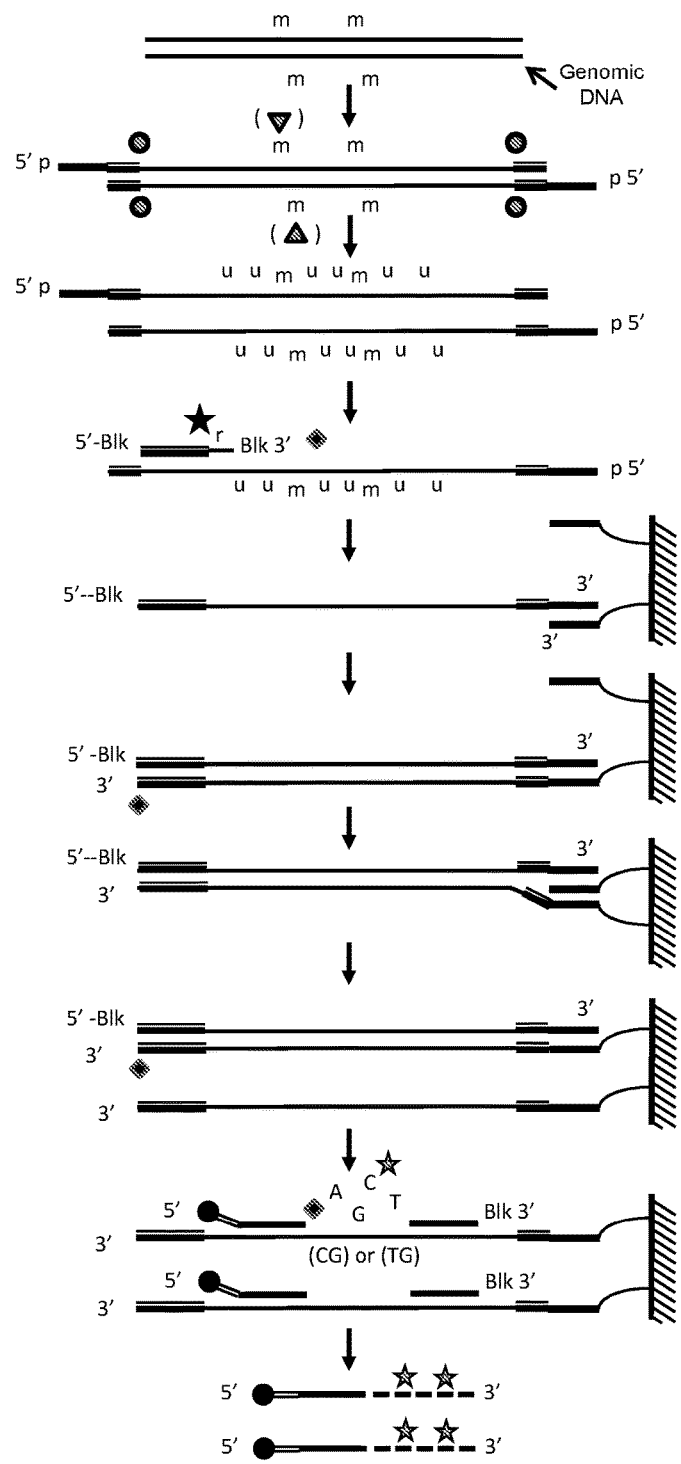

*FIG. 109*

A. Pixel-Cleavage to detect locus-specific methylation using bisulfite. Isolate genomic or cfDNA.

B. Repair ends with polymerase, phosphorylate 5' ends, extend 3'ends with a single A base, and ligate on A:T rich linkers with single-base T overhang, and 3'-T30 tails. (Optional, cleave with methyl-sensitive restriction enzymes.)

C. Treat with bisulfite, which converts unmethylated dC to dU, and renders the strands non-complementary.

D. Hybridize locus-specific primer with blocked 3' and 5' ends. Primers are unblocked with RNaseH2 only when bound to target. Extend with polymerase, and generate T30 on 3' end. Optional: Degrade dA30 linkers with 5' nuclease.

E. Distribute onto an addressable matrix array, such that the T30 tail hybridizes to dA30 primers immobilized to pillars on a solid support.

F. Extend hybridized primer with strand displacing Bst polymerase at 37oC. When raising the temperature to 55-60oC, the dA portion partially denatures, allowing for an adjacent primer to hybridize and polymerase displace the first primer strand. By this repetitive process, the original strand is "handed-off" to the next primer to achieve a linear amplification of the original DNA.

G. Upstream and downstream oligonucleotides have methylation locus-specific base, with the locus-specific flap oligonucleotides overlap at the locus base, and contain 5' identifying signature modifiers for subsequent nanopore detection. 5'-nuclease activity of polymerase or flap endonuclease cleaves off only matching 5'-overlapping base and additional flap; then detect, and enumerate signal.

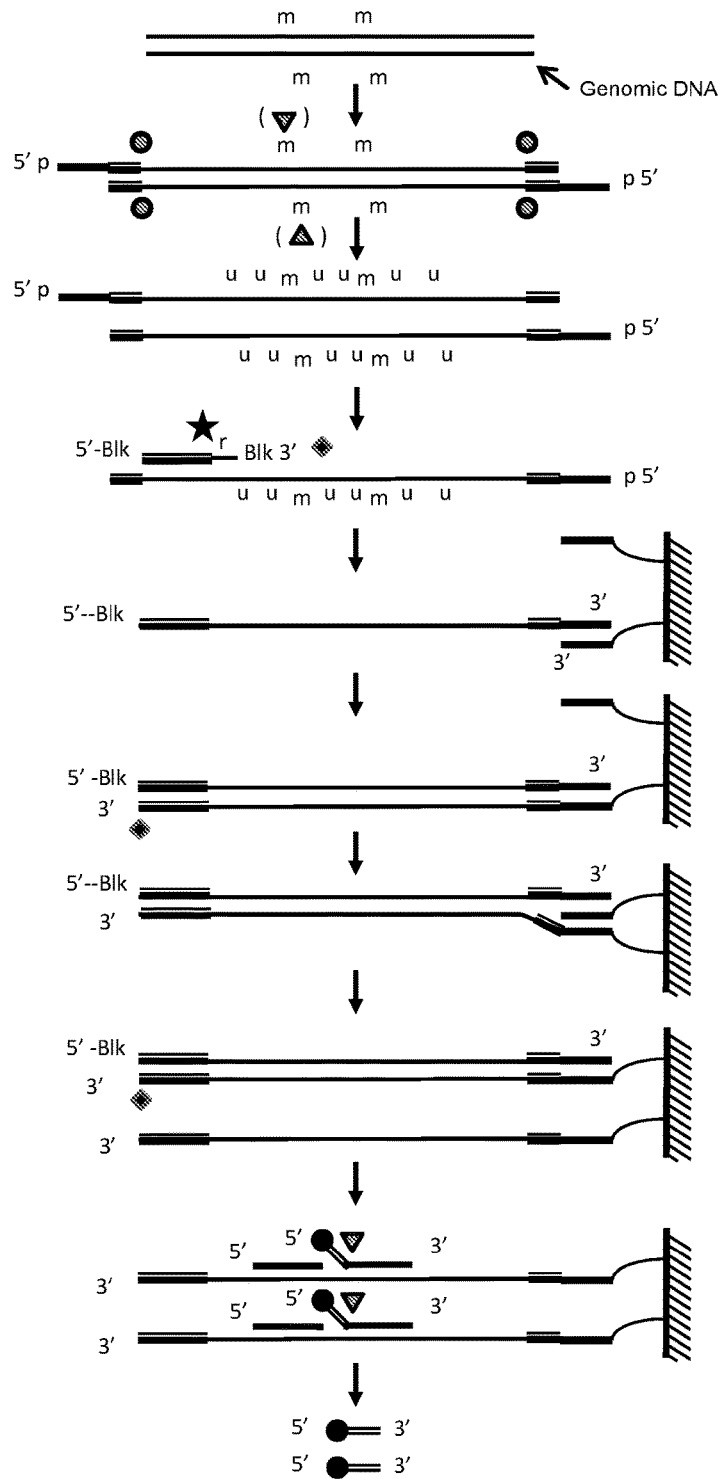

*FIG. 110*

A. Pixel-Nucleotide-Extension to detect locus-specific methylation using bisulfite. Isolate genomic or cfDNA.

B. Repair ends with polymerase, phosphorylate 5' ends, extend 3'ends with a single A base, and ligate on A:T rich linkers with single-base T overhang, and 3'-T30 tails. (Optional, cleave with methyl-sensitive REases.)

C. Treat with bisulfite, which converts unmethylated dC to dU, and renders the strands non-complementary.

D. Hybridize locus-specific primer with blocked 3' and 5' ends. Primers are unblocked with RNaseH2 only when bound to target. Extend with polymerase, and generate T30 on 3' end. Optional: Degrade dA30 linkers with 5' nuclease.

E. Distribute onto an addressable matrix array, such that the T30 tail hybridizes to dA30 primers immobilized to pillars on a solid support.

F. Extend hybridized primer with strand displacing Bst polymerase at 37oC. When raising the temperature to 55-60oC, the dA portion partially denatures, allowing for an adjacent primer to hybridize and polymerase displace the first primer strand. By this repetitive process, the original strand is "handed-off" to the next primer to achieve a linear amplification of the original DNA.

G. Wash away all dNTPs. Hybridize methylation locus-specific oligonucleotides, which contain 5' identifying signature modifiers for subsequent nanopore detection.

H. Extend oligonucleotides with nucleotide analogue terminator dNTPs containing 3' encoding signature modifiers.

I. Wash away unhybridized probes and unincorporated analogues. Denature product from target, then detect, and enumerate signal.

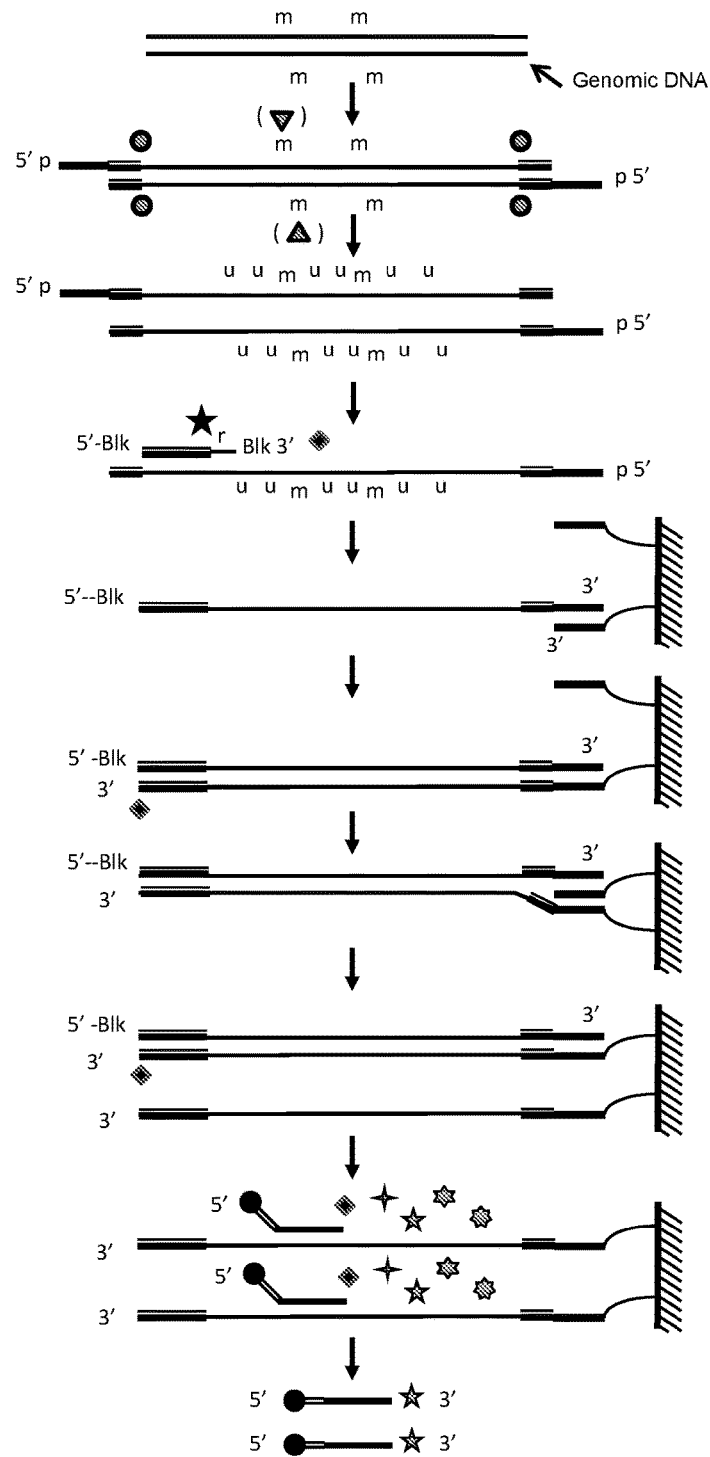

*FIG. 111*

A. Pixel-LDR to detect mRNA. Isolate mRNA.

B. Use reverse-transcriptase to make cDNA copy using dU30 or T30dUV primer.

C. Cleave unused primer with UDG & EndoVIII, degrade RNA with RNaseI & RNaseH, and remove dNTPs and 1-3 base digestion products.

D. Tail 3' ends with Terminal deoxynucleotidyl transferase (TdT), using TTP to generate dT(100-150).

E. Distribute onto an addressable matrix array, such that the T(100) tail hybridizes to dA30 primers immobilized to pillars on a solid support. Extend hybridized primer with strand displacing Bst polymerase at 37oC, then raise the temperature to 55-60oC, allowing for an adjacent primer to hybridize and polymerase to displace primer strands to achieve a linear amplification of the original DNA.

F. mRNA sequence-specific ligation oligonucleotides contain 5' identifying signature modifiers for subsequent nanopore detection. Ligase covalently seals the two oligonucleotides together.

G. Wash away unligated probes. Denature product from target, then detect, and enumerate signal.

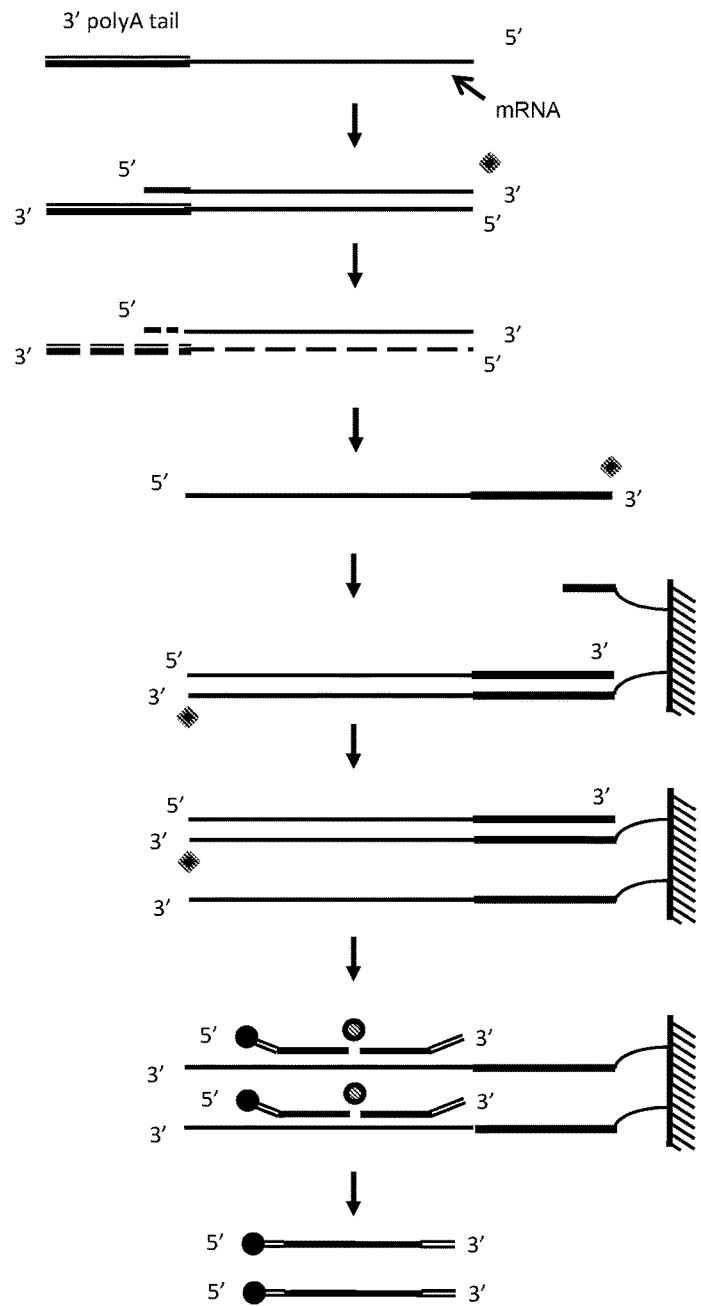

FIG. 112

A. Pixel-LDR to detect mRNA & lncRNA with polyA 3' end. Isolate total RNA, or 3' polyA tail RNA.

B. Distribute onto an addressable matrix array, such that the polyA tail (about 250 bases) hybridizes to dT60 primers immobilized to pillars on a solid support.

C. Extend hybridized primer with strand displacing M-MuLV reverse transcriptase or Pyrophage 3173 DNA polymerase, (which has reverse-transcriptase activity). When raising the temperature to 45-55oC, the dT portion partially denatures from the polyA RNA tail, allowing for an adjacent primer to hybridize and polymerase displace the first primer strand. By this repetitive process, the original RNA strand is "handed-off" to the next primer to achieve a linear amplification of the original RNA.

D. mRNA sequence-specific ligation oligonucleotides contain 5' identifying signature modifiers for subsequent nanopore detection. Ligase covalently seals the two oligonucleotides together.

E. Wash away unligated probes. Denature product from target, then detect, and enumerate signal.

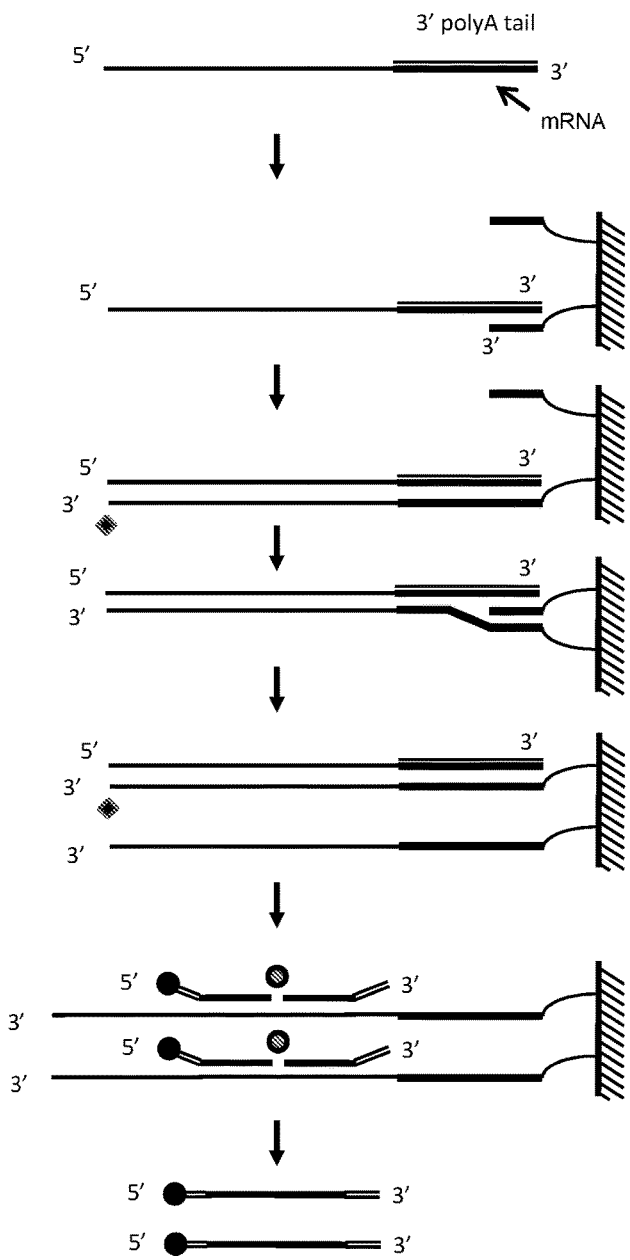

*FIG. 113*

A. Pixel-LDR to detect mRNA or lncRNA with polyA 3' end. Isolate total RNA, or 3' polyA tail RNA.

B. Hybridize (T,dU)30VN primer on polyA tail, and generate cDNA using reverse-transcriptase, which also appends C3 on 3' end of cDNA.

C. Hybridize second primer with 3' rG3, and dA30 tail.

D. Reverse transcriptase undergoes strand switching and copies second primer to generate a T30 tail on the cDNA. Remove original primer by digesting with UDG. Optional: Degrade dA30 primer with 5' nuclease.

E. Distribute onto an addressable matrix array, such that the T(30) tail hybridizes to dA30 primers immobilized to pillars on a solid support. Extend hybridized primer with strand displacing Bst polymerase at 37oC, then raise the temperature to 55-60oC, allowing for an adjacent primer to hybridize and polymerase to displace primer strands to achieve a linear amplification of the original DNA.

F. mRNA sequence-specific ligation oligonucleotides contain 5' identifying signature modifiers for subsequent nanopore detection. Ligase covalently seals the two oligonucleotides together.

G. Wash away unligated probes. Denature product from target, then detect, and enumerate signal.

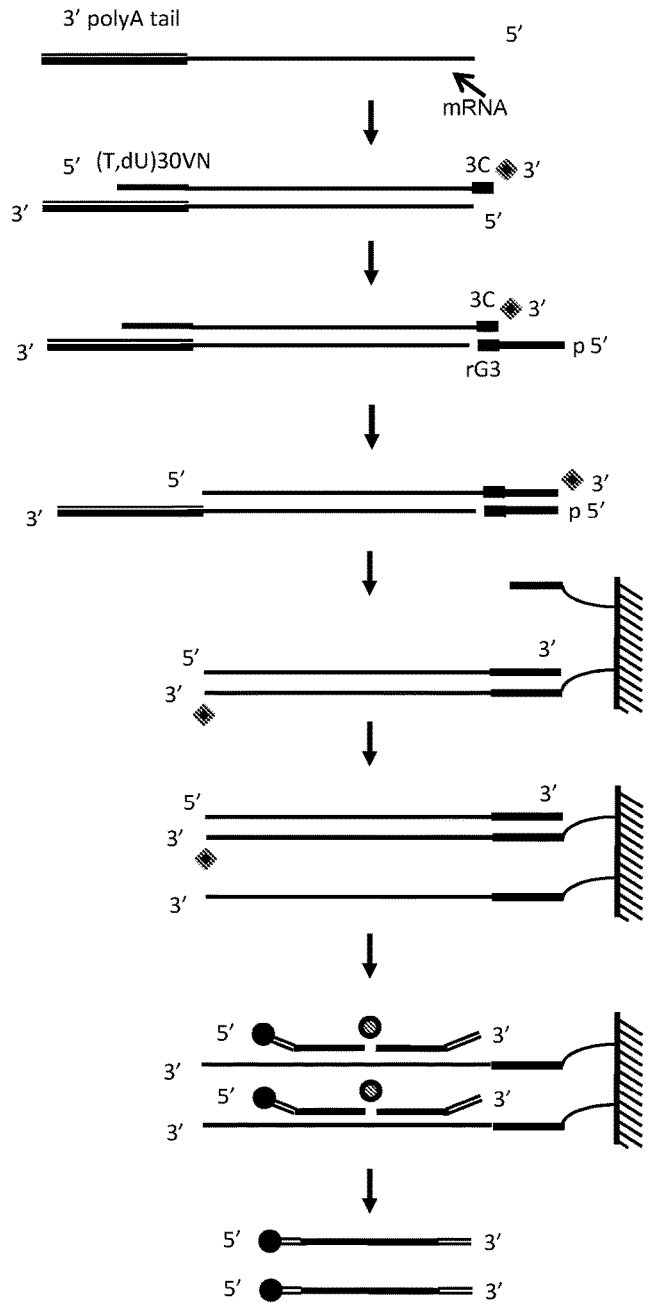

*FIG. 114*

A. Pixel-Cleavage to detect mRNA or lncRNA with polyA 3' end. Isolate total RNA, or 3' polyA tail RNA.

B. Hybridize (T,dU)30VN primer on polyA tail, and generate cDNA using reverse-transcriptase, which also appends C3 on 3' end of cDNA.

C. Hybridize second primer with 3' rG3, and dA30 tail.

D. Reverse transcriptase undergoes strand switching and copies second primer to generate a T30 tail on the cDNA. Remove original primer by digesting with UDG. Optional: Degrade dA30 primer with 5' nuclease.

E. Distribute onto an addressable matrix array, such that the T(30) tail hybridizes to dA30 primers immobilized to pillars on a solid support. Extend hybridized primer with strand displacing Bst polymerase at 37oC, then raise the temperature to 55-60oC, allowing for an adjacent primer to hybridize and polymerase to displace primer strands to achieve a linear amplification of the original DNA.

F. Upstream and downstream oligonucleotides have mRNA locus-specific base, with the locus-specific flap oligonucleotides overlap at the locus base, and contain 5' identifying signature modifiers for subsequent nanopore detection. 5'-nuclease activity of polymerase or flapendonuclease cleaves off only matching 5'-overlapping base and additional flap; then detect, and enumerate signal.

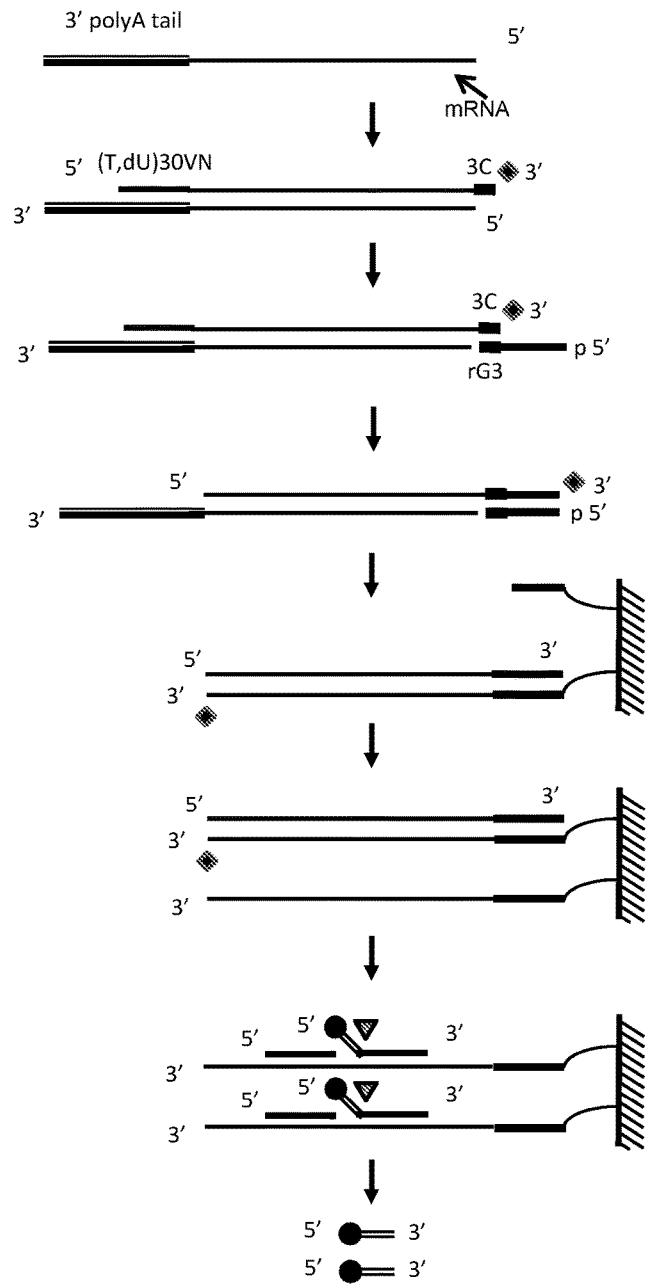

*FIG. 115*

A. Pixel-Nucleotide-Extension to detect mRNA or lncRNA with polyA 3' end. Isolate total RNA, or 3' polyA tail RNA.

B. Hybridize (T,dU)30VN primer on polyA tail, and generate cDNA using reverse-transcriptase, which also appends C3 on 3' end of cDNA.

C. Hybridize second primer with 3' rG3, and dA30 tail.

D. Reverse transcriptase undergoes strand switching and copies second primer to generate a T30 tail on the cDNA. Remove original primer by digesting with UDG. Optional: Degrade dA30 primer with 5' nuclease.

E. Distribute onto an addressable matrix array, such that the T(30) tail hybridizes to dA30 primers immobilized to pillars on a solid support. Extend hybridized primer with strand displacing Bst polymerase at 37oC, then raise the temperature to 55-60oC, allowing for an adjacent primer to hybridize and polymerase to displace primer strands to achieve a linear amplification of the original DNA.

F. Wash away all dNTPs. Hybridize mRNA or lncRNA sequence-specific oligonucleotides, which contain 5' identifying signature modifiers for subsequent nanopore detection.

G. Extend oligonucleotides with nucleotide analogue terminator dNTPs containing 3' encoding signature modifiers.

H. Wash away unhybridized probes and unincorporated analogues. Denature product from target, then detect, and enumerate signal.

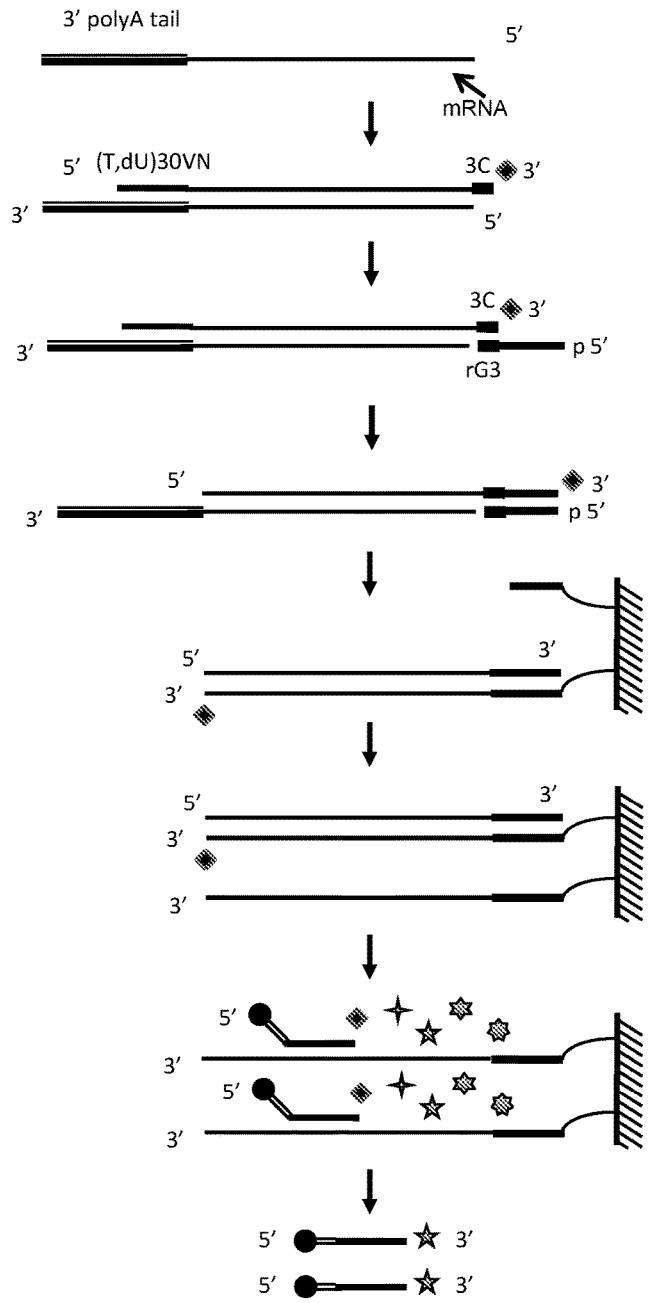

*FIG. 116*

A. Pixel-LDR to detect lncRNA & mRNA. Isolate total RNA.

B. Use reverse-transcriptase to make cDNA copy using random hexamer primer, containing dU in either the 2 or 3 position from the 3' end.

C. Cleave unused primer with UDG & EndoVIII, degrade RNA with RNaseI & RNaseH, and remove dNTPs and 1-3 base digestion products.

D. Tail 3' ends with Terminal deoxynucleotidyl transferase (TdT), using TTP to generate dT(100-150).

E. Distribute onto an addressable matrix array, such that the T(100) tail hybridizes to dA30 primers immobilized to pillars on a solid support. Extend hybridized primer with strand displacing Bst polymerase at 37oC, then raise the temperature to 55-60oC, allowing for an adjacent primer to hybridize and polymerase to displace primer strands to achieve a linear amplification of the original DNA.

F. mRNA sequence-specific ligation oligonucleotides contain 5' identifying signature modifiers for subsequent nanopore detection. Ligase covalently seals the two oligonucleotides together.

G. Wash away unligated probes. Denature product from target, then detect, and enumerate signal.

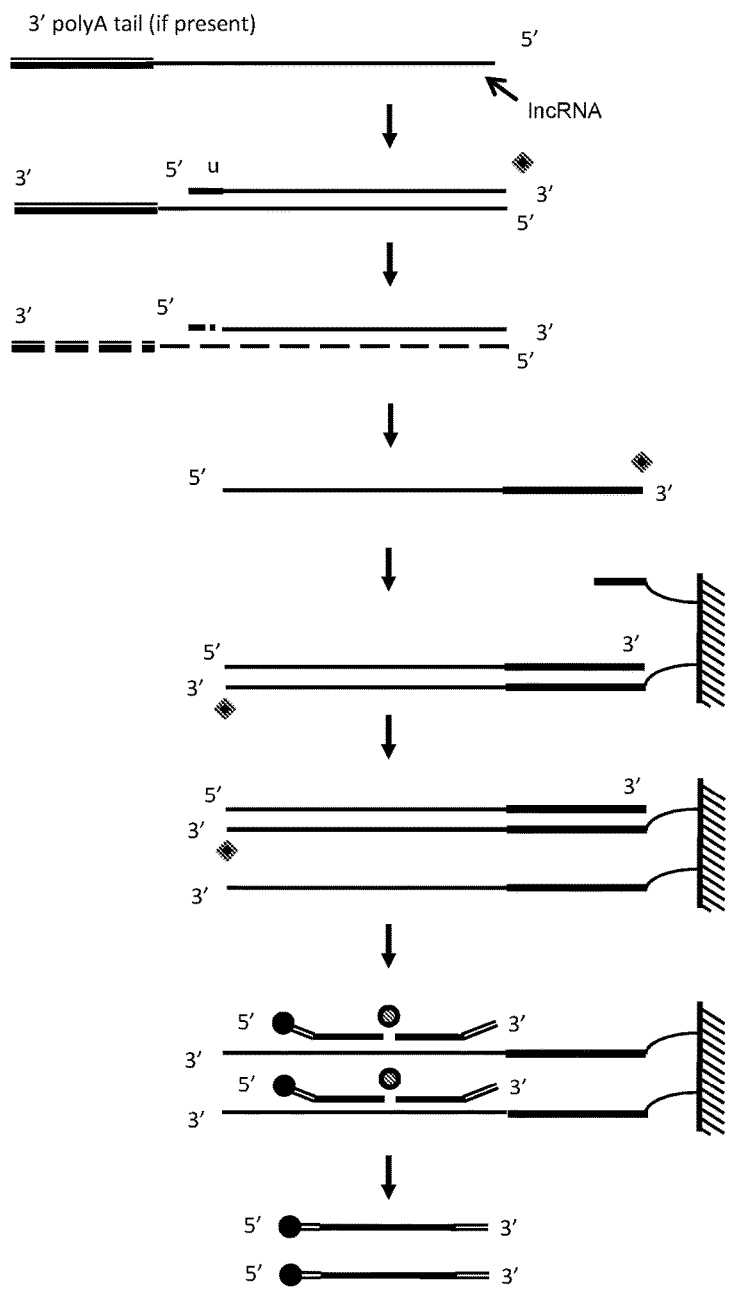

FIG. 117

A. Pixel-LDR to detect mRNA or lncRNA. Isolate total RNA.

B. Hybridize random hexamer primer and use reverse-transcriptase to make cDNA copy, which also appends C3 on 3' end of cDNA.

C. Hybridize second primer with 3' rG3, and dA30 tail.

D. Reverse transcriptase undergoes strand switching and copies second primer to generate a T30 tail on the cDNA. Optional: Degrade dA30 primer with 5' nuclease.

E. Distribute onto an addressable matrix array, such that the T(30) tail hybridizes to dA30 primers immobilized to pillars on a solid support. Extend hybridized primer with strand displacing Bst polymerase at 37oC, then raise the temperature to 55-60oC, allowing for an adjacent primer to hybridize and polymerase to displace primer strands to achieve a linear amplification of the original DNA.

F. mRNA sequence-specific ligation oligonucleotides contain 5' identifying signature modifiers for subsequent nanopore detection. Ligase covalently seals the two oligonucleotides together.

G. Wash away unligated probes. Denature product from target, then detect, and enumerate signal.

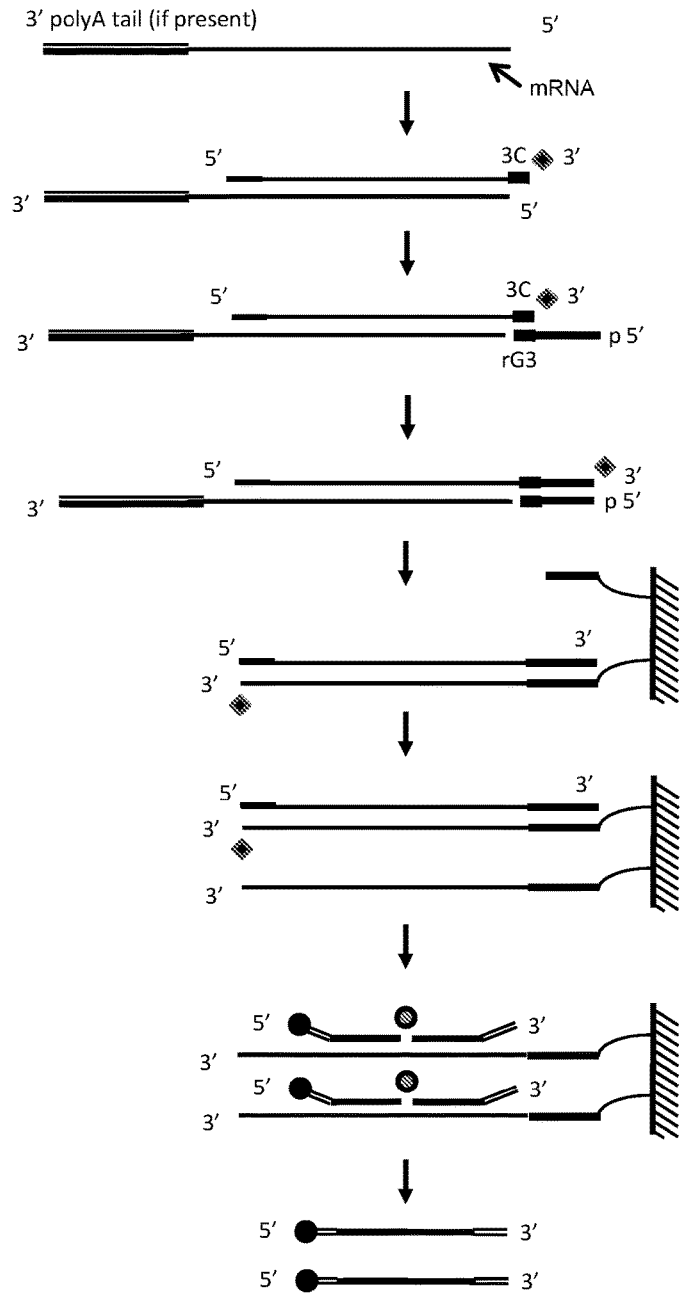

FIG. 118

A. Pixel-Cleavage to detect mRNA or lncRNA. Isolate total RNA.

B. Hybridize random hexamer primer and use reverse-transcriptase to make cDNA copy, which also appends C3 on 3' end of cDNA.

C. Hybridize second primer with 3' rG3, and dA30 tail.

D. Reverse transcriptase undergoes strand switching and copies second primer to generate a T30 tail on the cDNA. Optional: Degrade dA30 primer with 5' nuclease.

E. Distribute onto an addressable matrix array, such that the T(30) tail hybridizes to dA30 primers immobilized to pillars on a solid support. Extend hybridized primer with strand displacing Bst polymerase at 37oC, then raise the temperature to 55-60oC, allowing for an adjacent primer to hybridize and polymerase to displace primer strands to achieve a linear amplification of the original DNA.

F. Upstream and downstream oligonucleotides have mRNA locus-specific base, with the locus-specific flap oligonucleotides overlap at the locus base, and contain 5' identifying signature modifiers for subsequent nanopore detection. 5'-nuclease activity of polymerase or flap endonuclease cleaves off only matching 5'-overlapping base and additional flap; then detect, and enumerate signal.

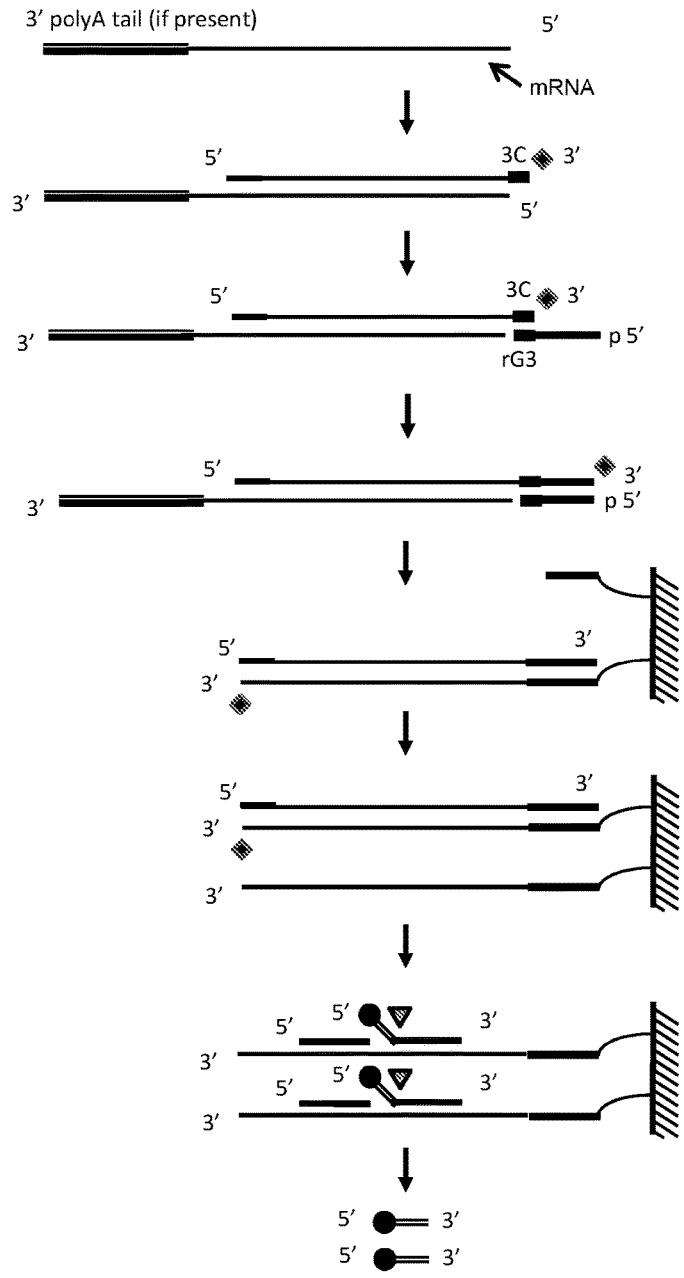

FIG. 119

A. Pixel-Nucleotide-Extension to detect mRNA or lncRNA. Isolate total RNA.

B. Hybridize random hexamer primer and use reverse-transcriptase to make cDNA copy, which also appends C3 on 3' end of cDNA.

C. Hybridize second primer with 3' rG3, and dA30 tail.

D. Reverse transcriptase undergoes strand switching and copies second primer to generate a T30 tail on the cDNA. Optional: Degrade dA30 primer with 5' nuclease.

E. Distribute onto an addressable matrix array, such that the T(30) tail hybridizes to dA30 primers immobilized to pillars on a solid support. Extend hybridized primer with strand displacing Bst polymerase at 37oC, then raise the temperature to 55-60oC, allowing for an adjacent primer to hybridize and polymerase to displace primer strands to achieve a linear amplification of the original DNA.

F. Wash away all dNTPs. Hybridize mRNA or lncRNA sequence-specific oligonucleotides, which contain 5' identifying signature modifiers for subsequent nanopore detection.

G. Extend oligonucleotides with nucleotide analogue terminator dNTPs containing 3' encoding signature modifiers.

H. Wash away unhybridized probes and unincorporated analogues. Denature product from target, then detect, and enumerate signal.

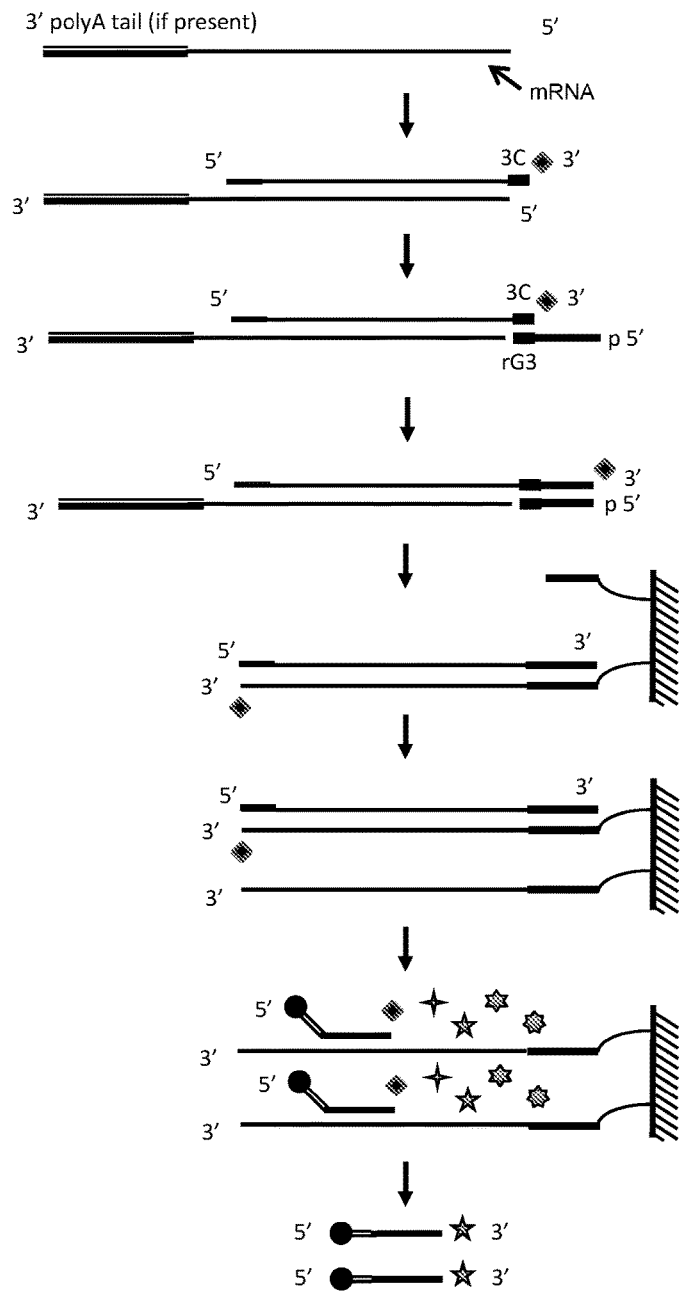

*FIG. 120*

A. Pixel-LDR to detect specific mRNA or lncRNA transcript. Isolate RNA.

B. Use reverse-transcriptase to make cDNA copy with transcript-specific primer, containing dU in either the 2 or 3 position from the 3' end.

C. Cleave unused primer with UDG & EndoVIII, degrade RNA with RNaseI & RNaseH, and remove dNTPs and 1-3 base digestion products.

D. Tail 3' ends with Terminal deoxynucleotidyl transferase (TdT), using TTP to generate dT(100-150).

E. Distribute onto an addressable matrix array, such that the T(100) tail hybridizes to dA30 primers immobilized to pillars on a solid support. Extend hybridized primer with strand displacing Bst polymerase at 37oC, then raise the temperature to 55-60oC, allowing for an adjacent primer to hybridize and polymerase to displace primer strands to achieve a linear amplification of the original DNA.

F. mRNA sequence-specific ligation oligonucleotides contain 5' identifying signature modifiers for subsequent nanopore detection. Ligase covalently seals the two oligonucleotides together.

G. Wash away unligated probes. Denature product from target, then detect, and enumerate signal.

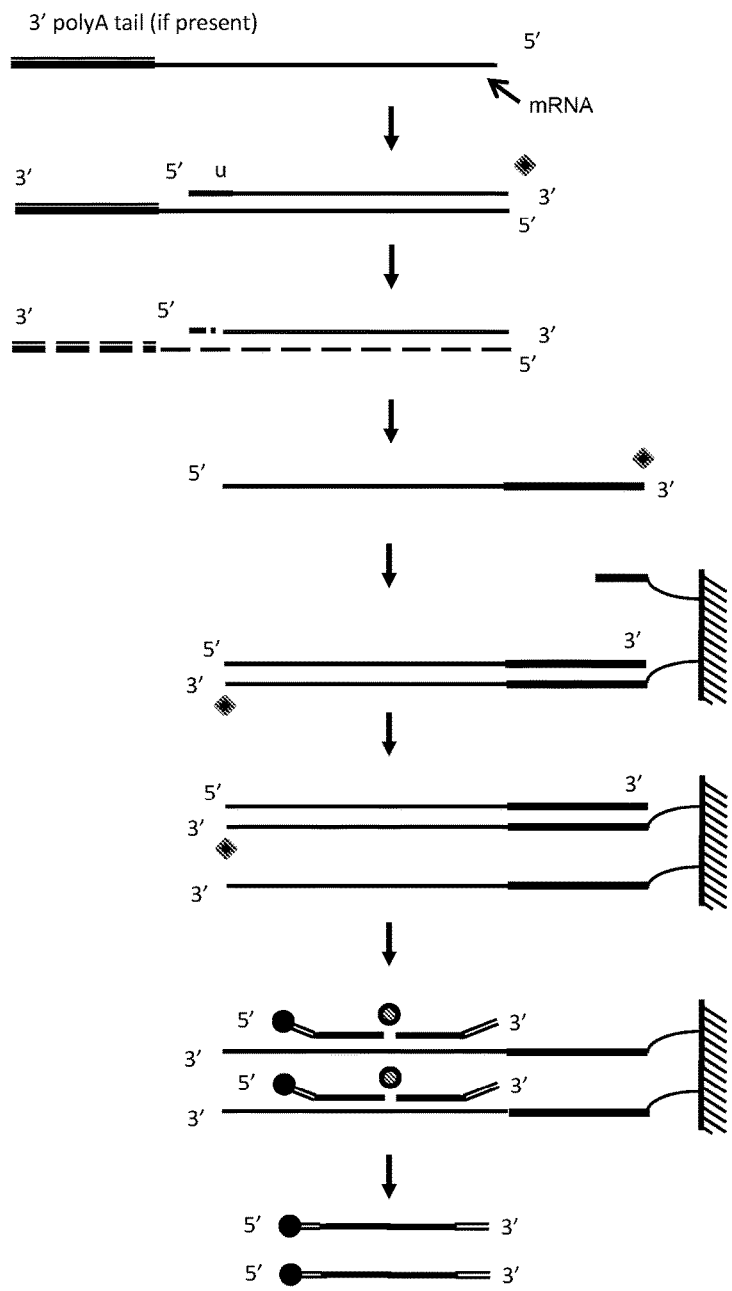

FIG. 121

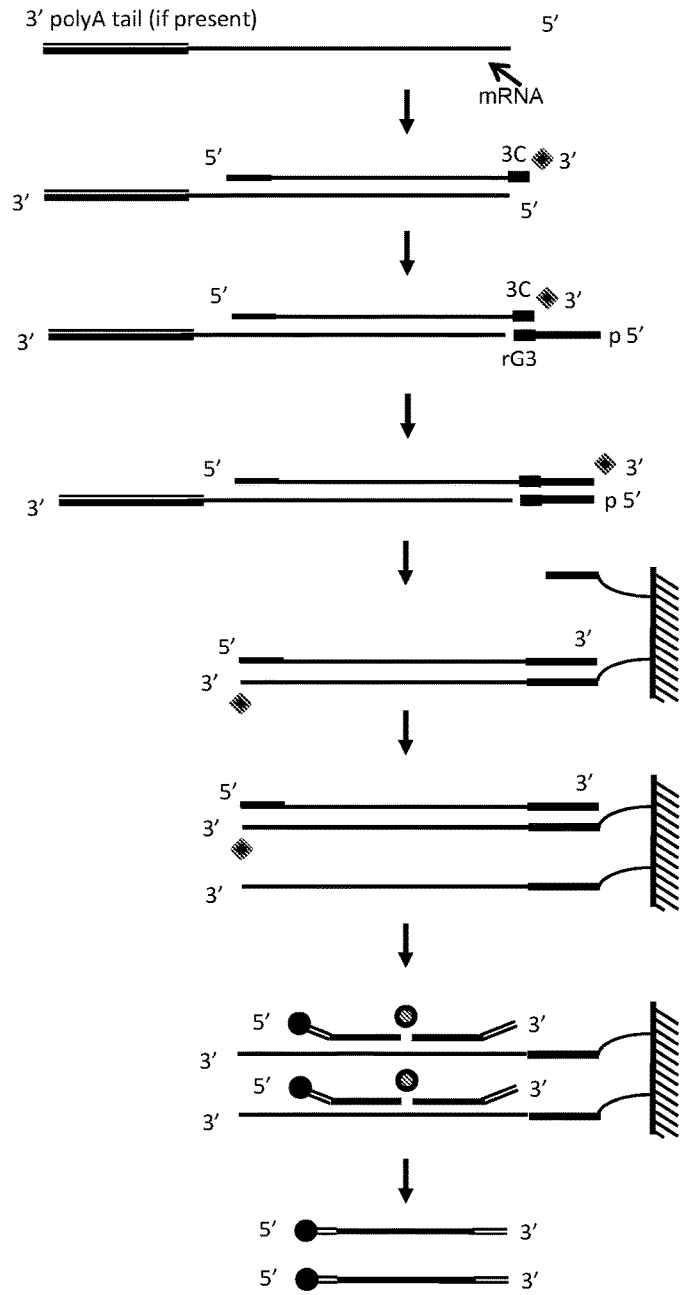

A. Pixel-LDR to detect specific mRNA or lncRNA. Isolate total RNA.

B. Hybridize transcript-specific primer and use reverse-transcriptase to make cDNA copy, which also appends C3 on 3' end of cDNA.

C. Hybridize second primer with 3' rG3, and dA30 tail.

D. Reverse transcriptase undergoes strand switching and copies second primer to generate a T30 tail on the cDNA. Optional: Degrade dA30 primer with 5' nuclease.

E. Distribute onto an addressable matrix array, such that the T(30) tail hybridizes to dA30 primers immobilized to pillars on a solid support. Extend hybridized primer with strand displacing Bst polymerase at 37oC, then raise the temperature to 55-60oC, allowing for an adjacent primer to hybridize and polymerase to displace primer strands to achieve a linear amplification of the original DNA.

F. mRNA sequence-specific ligation oligonucleotides contain 5' identifying signature modifiers for subsequent nanopore detection. Ligase covalently seals the two oligonucleotides together.

G. Wash away unligated probes. Denature product from target, then detect, and enumerate signal.

*FIG. 122*

A. Pixel-Cleavage to detect specific mRNA or lncRNA. Isolate total RNA.

B. Hybridize transcript-specific primer and use reverse-transcriptase to make cDNA copy, which also appends C3 on 3' end of cDNA.

C. Hybridize second primer with 3' rG3, and dA30 tail.

D. Reverse transcriptase undergoes strand switching and copies second primer to generate a T30 tail on the cDNA. Optional: Degrade dA30 primer with 5' nuclease.

E. Distribute onto an addressable matrix array, such that the T(30) tail hybridizes to dA30 primers immobilized to pillars on a solid support. Extend hybridized primer with strand displacing Bst polymerase at 37oC, then raise the temperature to 55-60oC, allowing for an adjacent primer to hybridize and polymerase to displace primer strands to achieve a linear amplification of the original DNA.

F. Upstream and downstream oligonucleotides have mRNA locus-specific base, with the locus-specific flap oligonucleotides overlap at the locus base, and contain 5' identifying signature modifiers for subsequent nanopore detection. 5'-nuclease activity of polymerase or flap endonuclease cleaves off only matching 5'-overlapping base and additional flap; then detect, and enumerate signal.

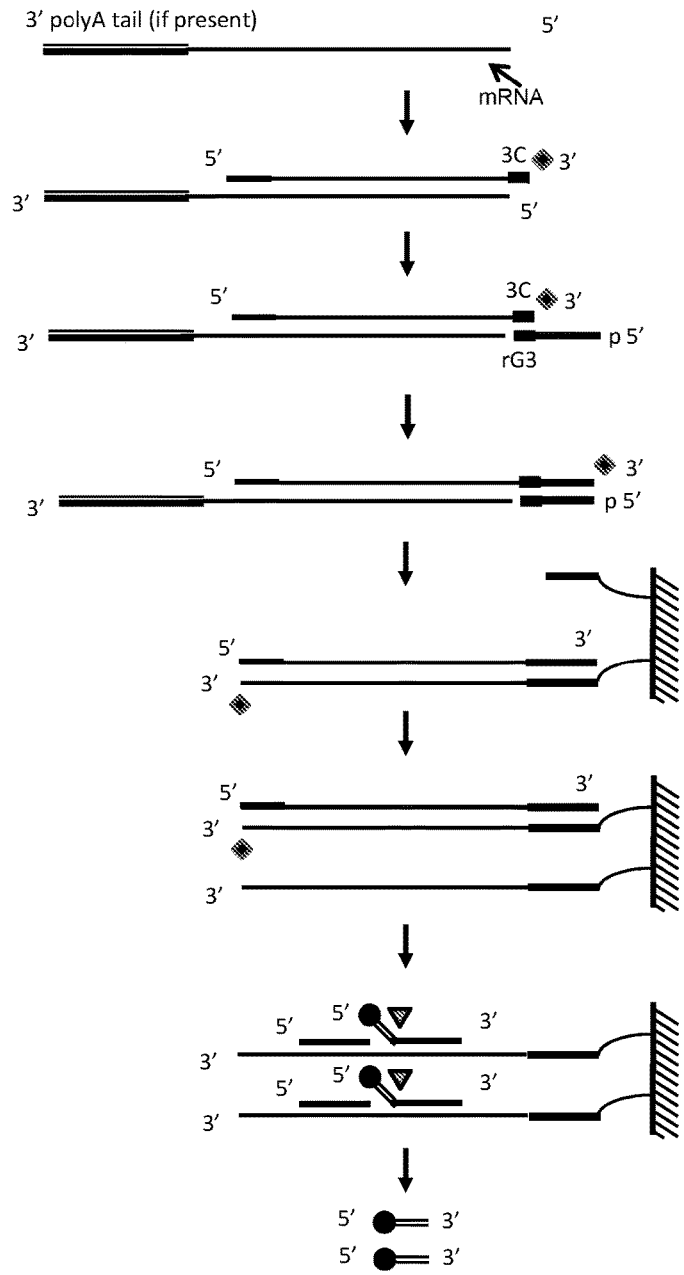

*FIG. 123*

A. Pixel-Nucleotide-Extension to detect specific mRNA or lncRNA. Isolate total RNA.

B. Hybridize transcript-specific primer and use reverse-transcriptase to make cDNA copy, which also appends C3 on 3' end of cDNA.

C. Hybridize second primer with 3' rG3, and dA30 tail.

D. Reverse transcriptase undergoes strand switching and copies second primer to generate a T30 tail on the cDNA. Optional: Degrade dA30 primer with 5' nuclease.

E. Distribute onto an addressable matrix array, such that the T(30) tail hybridizes to dA30 primers immobilized to pillars on a solid support. Extend hybridized primer with strand displacing Bst polymerase at 37oC, then raise the temperature to 55-60oC, allowing for an adjacent primer to hybridize and polymerase to displace primer strands to achieve a linear amplification of the original DNA.

F. Wash away all dNTPs. Hybridize mRNA or lncRNA sequence-specific oligonucleotides, which contain 5' identifying signature modifiers for subsequent nanopore detection.

G. Extend oligonucleotides with nucleotide analogue terminator dNTPs containing 3' encoding signature modifiers.

H. Wash away unhybridized probes and unincorporated analogues. Denature product from target, then detect, and enumerate signal.

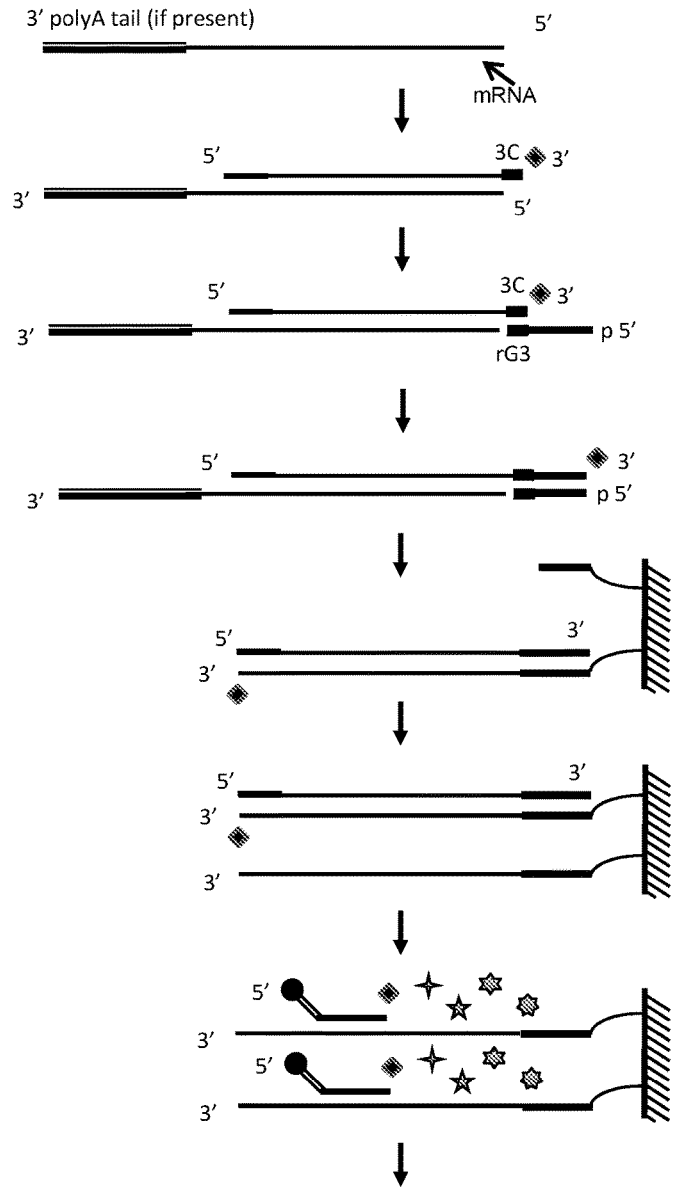

FIG. 124

A. Pixel-LDR to enumerate low-abundance specific mRNA or lncRNA transcript. Isolate RNA.

B. Use reverse-transcriptase to make cDNA copy with transcript-specific primer containing 5' dA30.

C. Denature cDNA and hybridize transcript-specific primer with blocked 3' and 5' ends. Primers are unblocked with RNaseH2 only when bound to target. Extend with polymerase, and generate T30 on 3' end. Optional: Degrade dA30 linkers with 5' nuclease.

D. Distribute onto an addressable matrix array, such that the T30 tail hybridizes to dA30 primers immobilized to pillars on a solid support. Extend hybridized primer with strand displacing Bst polymerase at 37oC, then raise the temperature to 55-60oC, allowing for an adjacent primer to hybridize and polymerase to displace primer strands to achieve a linear amplification of the original DNA.

E. Transcript-specific ligation oligonucleotides contain 5' identifying signature modifiers for subsequent nanopore detection. Ligase covalently seals the two oligonucleotides together.

F. Wash away unligated probes. Denature product from target, then detect, and enumerate signal.

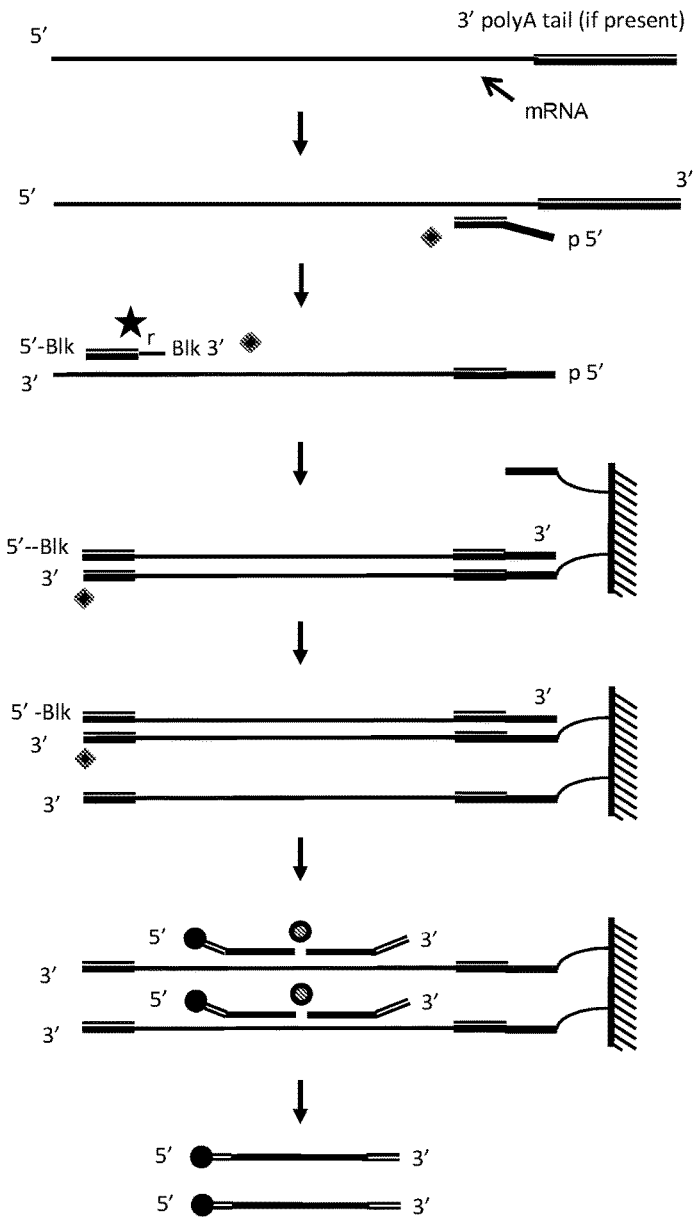

*FIG. 125*

A. Pixel-Cleavage to enumerate low-abundance specific mRNA or lncRNA transcript. Isolate RNA.

B. Use reverse-transcriptase to make cDNA copy with transcript-specific primer containing 5' dA30.

C. Denature cDNA and hybridize transcript-specific primer with blocked 3' and 5' ends. Primers are unblocked with RNaseH2 only when bound to target. Extend with polymerase, and generate T30 on 3' end. Optional: Degrade dA30 linkers with 5' nuclease.

D. Distribute onto an addressable matrix array, such that the T30 tail hybridizes to dA30 primers immobilized to pillars on a solid support. Extend hybridized primer with strand displacing Bst polymerase at 37oC, then raise the temperature to 55-60oC, allowing for an adjacent primer to hybridize and polymerase to displace primer strands to achieve a linear amplification of the original DNA.

E. Upstream and downstream oligonucleotides have mRNA locus-specific base, with the locus-specific flap oligonucleotides overlap at the locus base, and contain 5' identifying signature modifiers for subsequent nanopore detection. 5'-nuclease activity of polymerase or flap endonuclease cleaves off only matching 5'-overlapping base and additional flap; then detect, and enumerate signal.

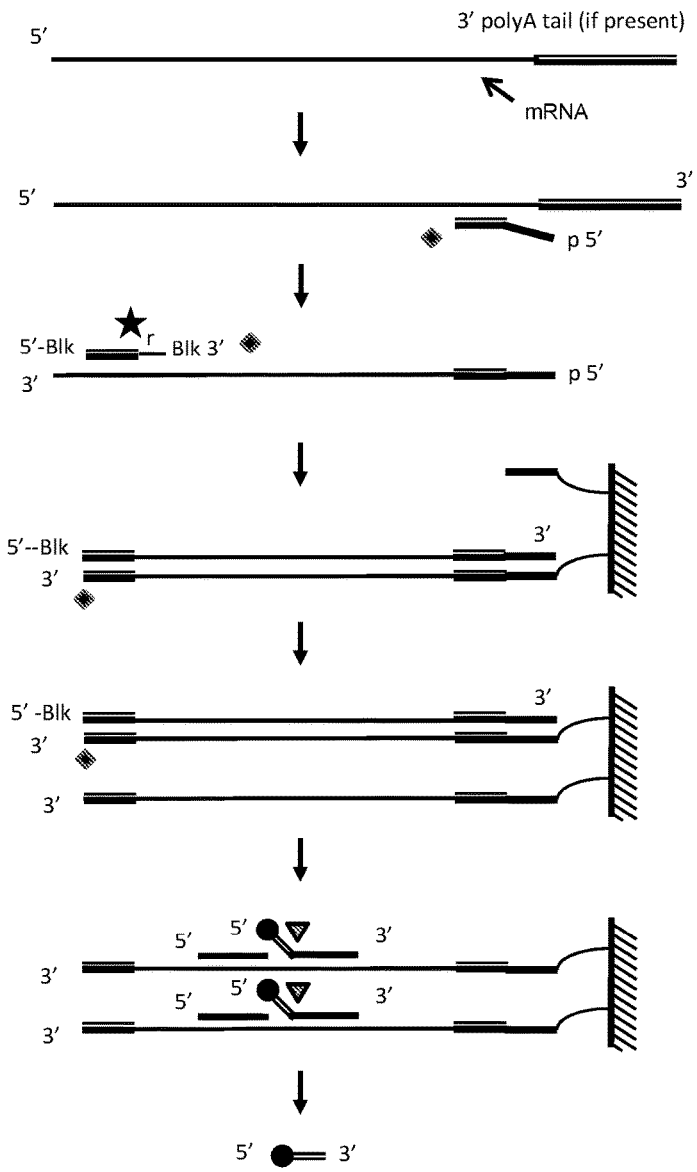

*FIG. 126*

A. Pixel-Nucleotide-Extension to enumerate low-abundance specific mRNA or lncRNA transcript. Isolate RNA.

B. Use reverse-transcriptase to make cDNA copy with transcript-specific primer containing 5' dA30.

C. Denature cDNA and hybridize transcript-specific primer with blocked 3' and 5' ends. Primers are unblocked with RNaseH2 only when bound to target. Extend with polymerase, and generate T30 on 3' end. Optional: Degrade dA30 linkers with 5' nuclease.

D. Distribute onto an addressable matrix array, such that the T30 tail hybridizes to dA30 primers immobilized to pillars on a solid support. Extend hybridized primer with strand displacing Bst polymerase at 37oC, then raise the temperature to 55-60oC, allowing for an adjacent primer to hybridize and polymerase to displace primer strands to achieve a linear amplification of the original DNA.

E. Transcript-specific ligation oligonucleotides contain 5' identifying signature modifiers for subsequent nanopore detection. Ligase covalently seals the two oligonucleotides together.

F. Wash away unligated probes. Denature product from target, then detect, and enumerate signal.

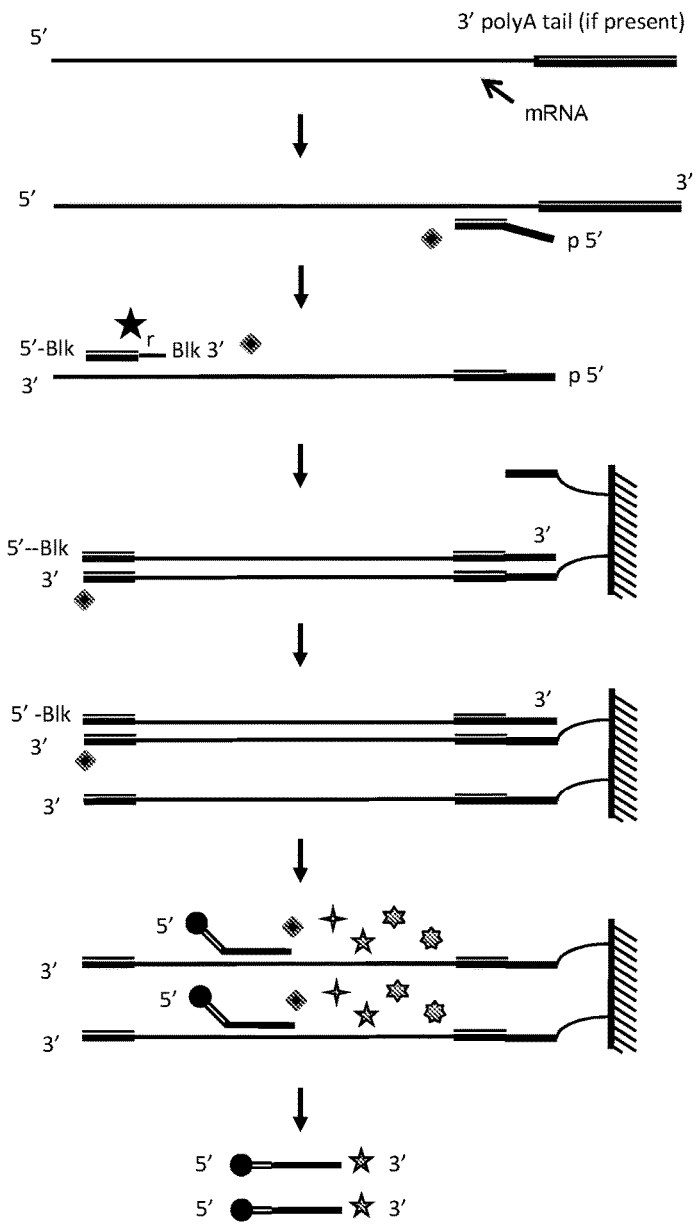

*FIG. 127*

A. Pixel-LDR to detect translocation at the mRNA level. Isolate mRNA.

B. Use reverse-transcriptase to make cDNA copy using transcript-specific primer, containing dU in either the 2 or 3 position from the 3' end.

C. Cleave unused primer with UDG & EndoVIII, degrade RNA with RNaseI & RNaseH, and remove dNTPs and 1-3 base digestion products.

D. Tail 3' ends with Terminal deoxynucleotidyl transferase (TdT), using TTP to generate dT(100-150).

E. Distribute onto an addressable matrix array, such that the T(100) tail hybridizes to dA30 primers immobilized to pillars on a solid support. Extend hybridized primer with strand displacing Bst polymerase at 37oC, then raise the temperature to 55-60oC, allowing for an adjacent primer to hybridize and polymerase to displace primer strands to achieve a linear amplification of the original DNA.

F. Exon junction-specific ligation oligonucleotides contain 5' identifying signature modifiers for subsequent nanopore detection. Ligase covalently seals the two oligonucleotides together.

G. Wash away unligated probes. Denature product from target, then detect, and enumerate signal.

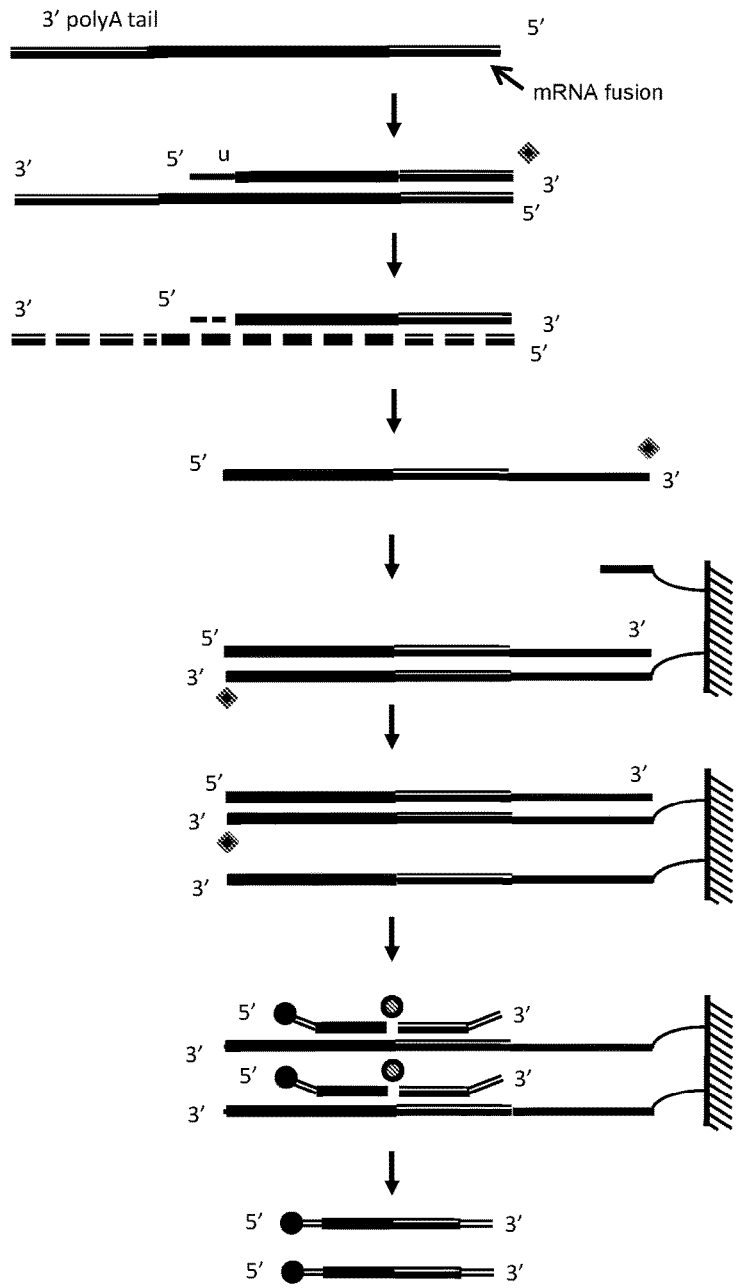

FIG. 128

A. Pixel-LDR to detect translocation at the mRNA level. Isolate mRNA.

B. Hybridize transcript-specific primer and use reverse-transcriptase to make cDNA copy, which also appends C3 on 3' end of cDNA.

C. Hybridize second primer with 3' rG3, and dA30 tail.

D. Reverse transcriptase undergoes strand switching and copies second primer to generate a T30 tail on the cDNA. Optional: Degrade dA30 primer with 5' nuclease.

E. Distribute onto an addressable matrix array, such that the T(30) tail hybridizes to dA30 primers immobilized to pillars on a solid support. Extend hybridized primer with strand displacing Bst polymerase at 37oC, then raise the temperature to 55-60oC, allowing for an adjacent primer to hybridize and polymerase to displace primer strands to achieve a linear amplification of the original DNA.

F. Exon junction-specific ligation oligonucleotides contain 5' identifying signature modifiers for subsequent nanopore detection. Ligase covalently seals the two oligonucleotides together.

G. Wash away unligated probes. Denature product from target, then detect, and enumerate signal.

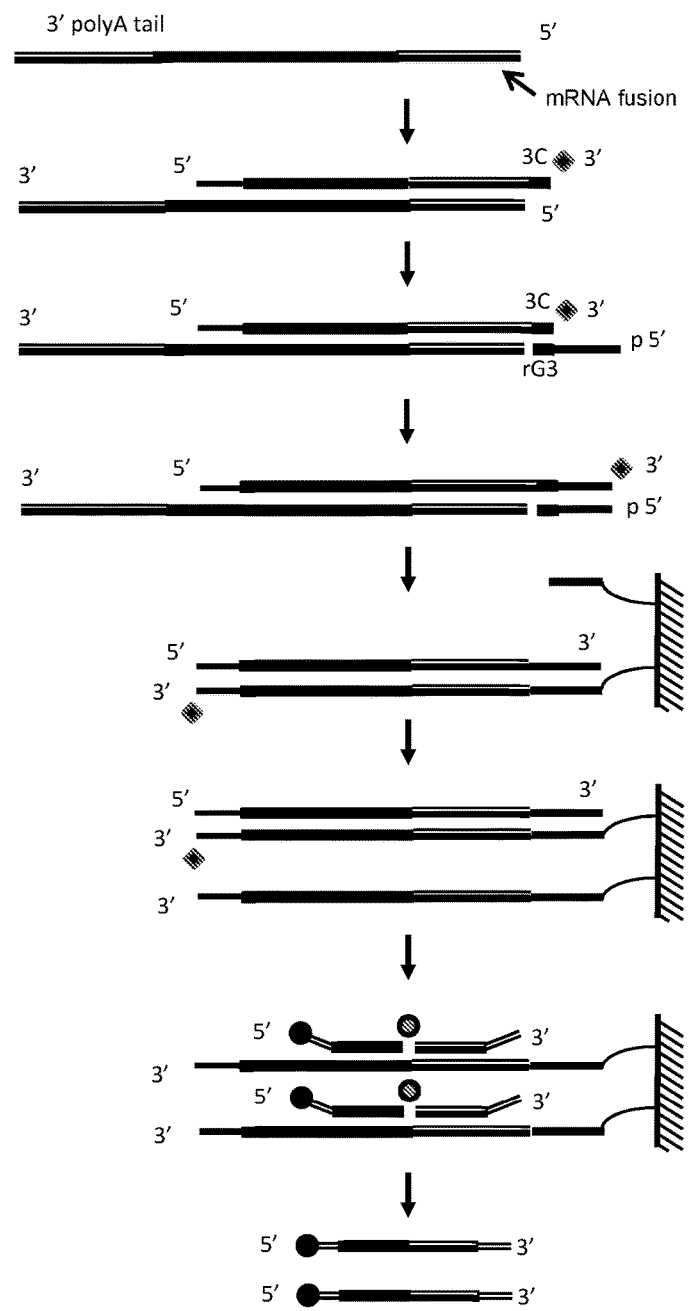

FIG. 129

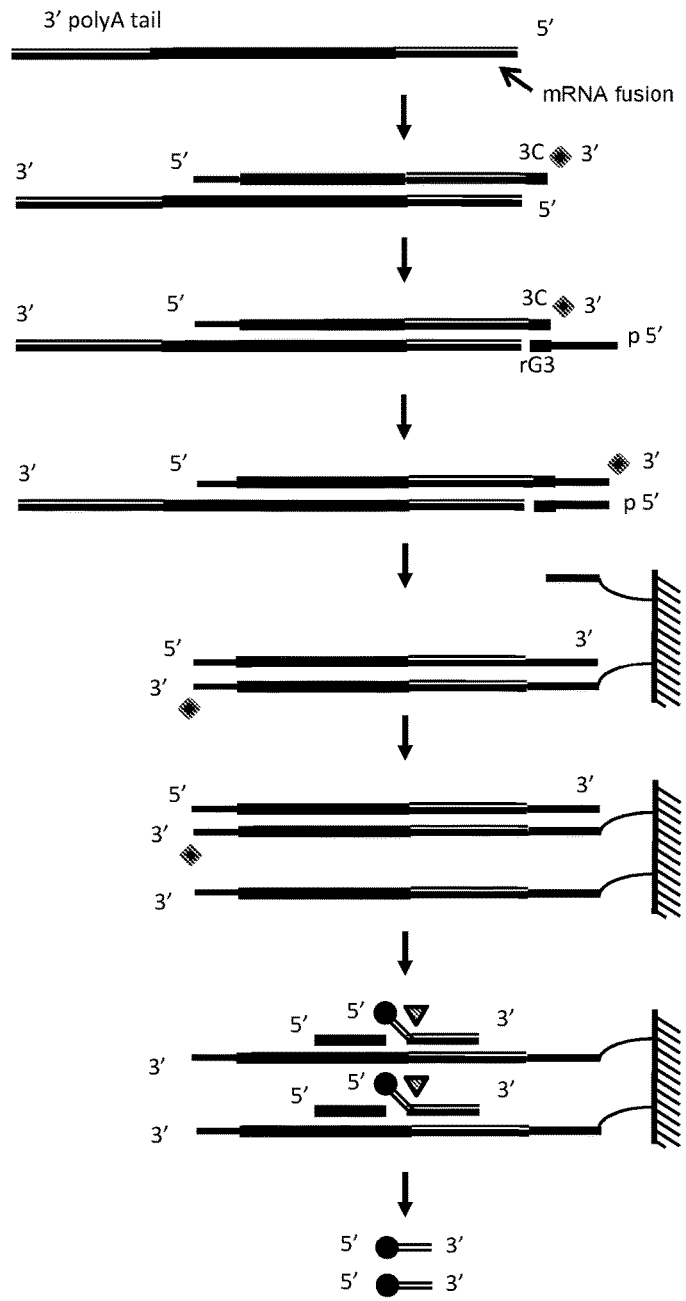

A. Pixel-Cleavage to detect translocation at the mRNA level. Isolate mRNA.

B. Hybridize transcript-specific primer and use reverse-transcriptase to make cDNA copy, which also appends C3 on 3' end of cDNA.

C. Hybridize second primer with 3' rG3, and dA30 tail.

D. Reverse transcriptase undergoes strand switching and copies second primer to generate a T30 tail on the cDNA. Optional: Degrade dA30 primer with 5' nuclease.

E. Distribute onto an addressable matrix array, such that the T(30) tail hybridizes to dA30 primers immobilized to pillars on a solid support. Extend hybridized primer with strand displacing Bst polymerase at 37oC, then raise the temperature to 55-60oC, allowing for an adjacent primer to hybridize and polymerase to displace primer strands to achieve a linear amplification of the original DNA.

F. Upstream and downstream oligonucleotides have mRNA exon junction-specific base, with the junction-specific flap oligonucleotides overlap at the junction base, and contain 5' identifying signature modifiers for subsequent nanopore detection. 5'-nuclease activity of polymerase or flap endonuclease cleaves off only matching 5'-overlapping base and additional flap; then detect, and enumerate signal.

*FIG. 130*

A. Pixel-Nucleotide-Extension to detect translocation at the mRNA level. Isolate mRNA.

B. Hybridize transcript-specific primer and use reverse-transcriptase to make cDNA copy, which also appends C3 on 3' end of cDNA.

C. Hybridize second primer with 3' rG3, and dA30 tail.

D. Reverse transcriptase undergoes strand switching and copies second primer to generate a T30 tail on the cDNA. Optional: Degrade dA30 primer with 5' nuclease.

E. Distribute onto an addressable matrix array, such that the T(30) tail hybridizes to dA30 primers immobilized to pillars on a solid support. Extend hybridized primer with strand displacing Bst polymerase at 37oC, then raise the temperature to 55-60oC, allowing for an adjacent primer to hybridize and polymerase to displace primer strands to achieve a linear amplification of the original DNA.

F. Wash away all dNTPs. Hybridize exon junction-specific oligonucleotides, which contain 5' identifying signature modifiers for subsequent nanopore detection.

G. Extend oligonucleotides with nucleotide analogue terminator dNTPs containing 3' encoding signature modifiers.

H. Wash away unhybridized probes and unincorporated analogues. Denature product from target, then detect, and enumerate signal.

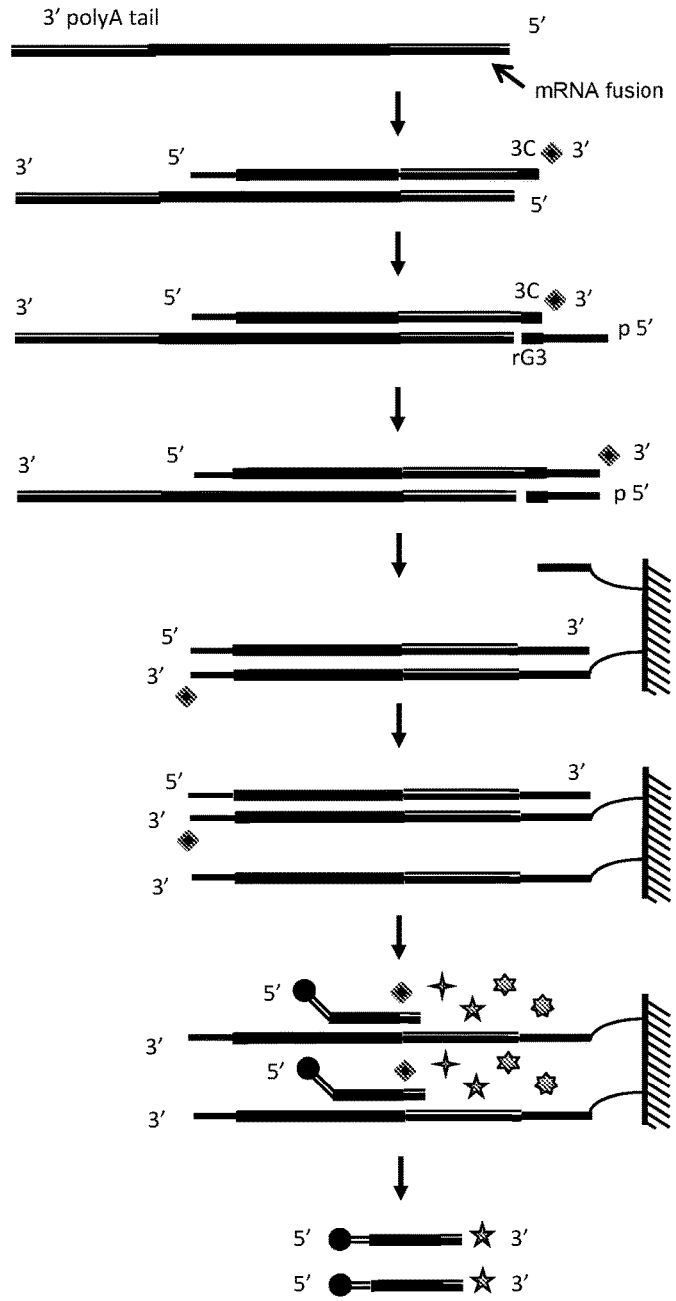

*FIG. 131*

A. Pixel-LDR to enumerate low-abundance translocation at the mRNA level. Isolate RNA.

B. Use reverse-transcriptase to make cDNA copy with transcript-specific primer containing 5' dA30.

C. Denature cDNA and hybridize transcript-specific primer with blocked 3' and 5' ends. Primers are unblocked with RNaseH2 only when bound to target. Extend with polymerase, and generate T30 on 3' end. Optional: Degrade dA30 linkers with 5' nuclease.

D. Distribute onto an addressable matrix array, such that the T30 tail hybridizes to dA30 primers immobilized to pillars on a solid support. Extend hybridized primer with strand displacing Bst polymerase at 37oC, then raise the temperature to 55-60oC, allowing for an adjacent primer to hybridize and polymerase to displace primer strands to achieve a linear amplification of the original DNA.

E. Exon junction-specific ligation oligonucleotides contain 5' identifying signature modifiers for subsequent nanopore detection. Ligase covalently seals the two oligonucleotides together.

F. Wash away unligated probes. Denature product from target, then detect, and enumerate signal.

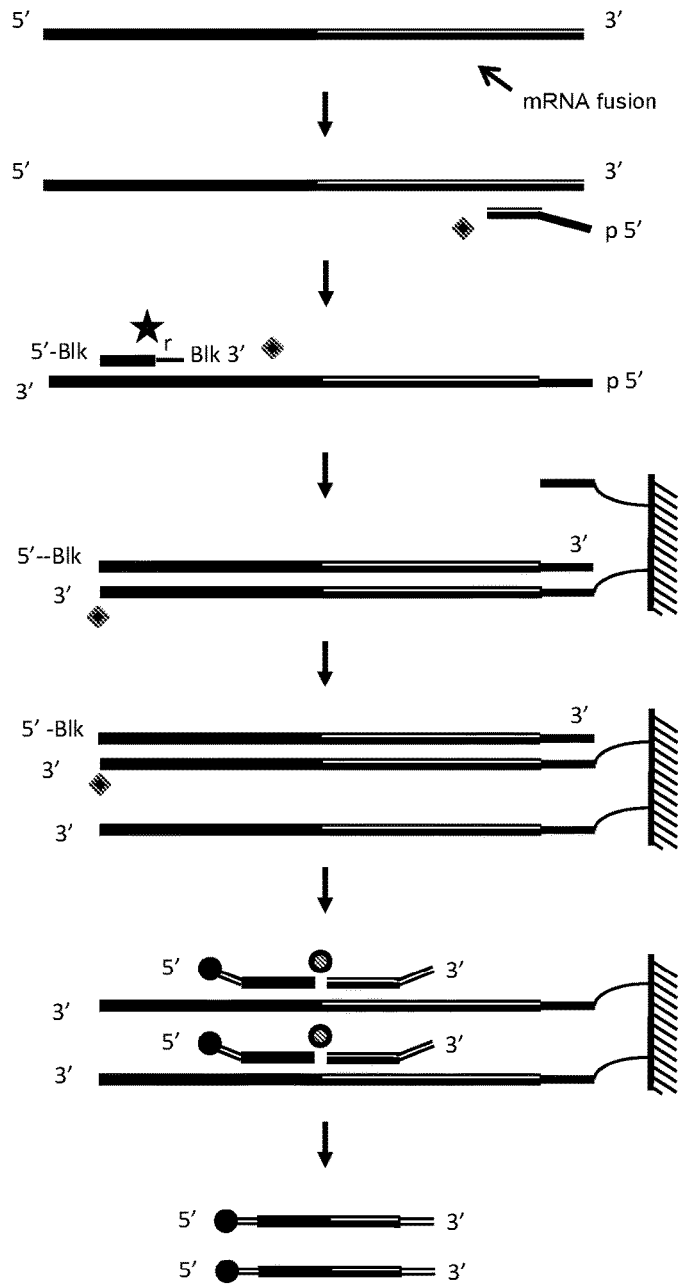

FIG. 132

A. Pixel-Cleavage to enumerate low-abundance translocation at the mRNA level. Isolate RNA.

B. Use reverse-transcriptase to make cDNA copy with transcript-specific primer containing 5' dA30.

C. Denature cDNA and hybridize transcript-specific primer with blocked 3' and 5' ends. Primers are unblocked with RNaseH2 only when bound to target. Extend with polymerase, and generate T30 on 3' end. Optional: Degrade dA30 linkers with 5' nuclease.

D. Distribute onto an addressable matrix array, such that the T30 tail hybridizes to dA30 primers immobilized to pillars on a solid support. Extend hybridized primer with strand displacing Bst polymerase at 37oC, then raise the temperature to 55-60oC, allowing for an adjacent primer to hybridize and polymerase to displace primer strands to achieve a linear amplification of the original DNA.

E. Upstream and downstream oligonucleotides have mRNA exon junction-specific base, with the junction-specific flap oligonucleotides overlap at the junction base, and contain 5' identifying signature modifiers for subsequent nanopore detection. 5'-nuclease activity of polymerase or flap endonuclease cleaves off only matching 5'-overlapping base and additional flap; then detect, and enumerate signal.

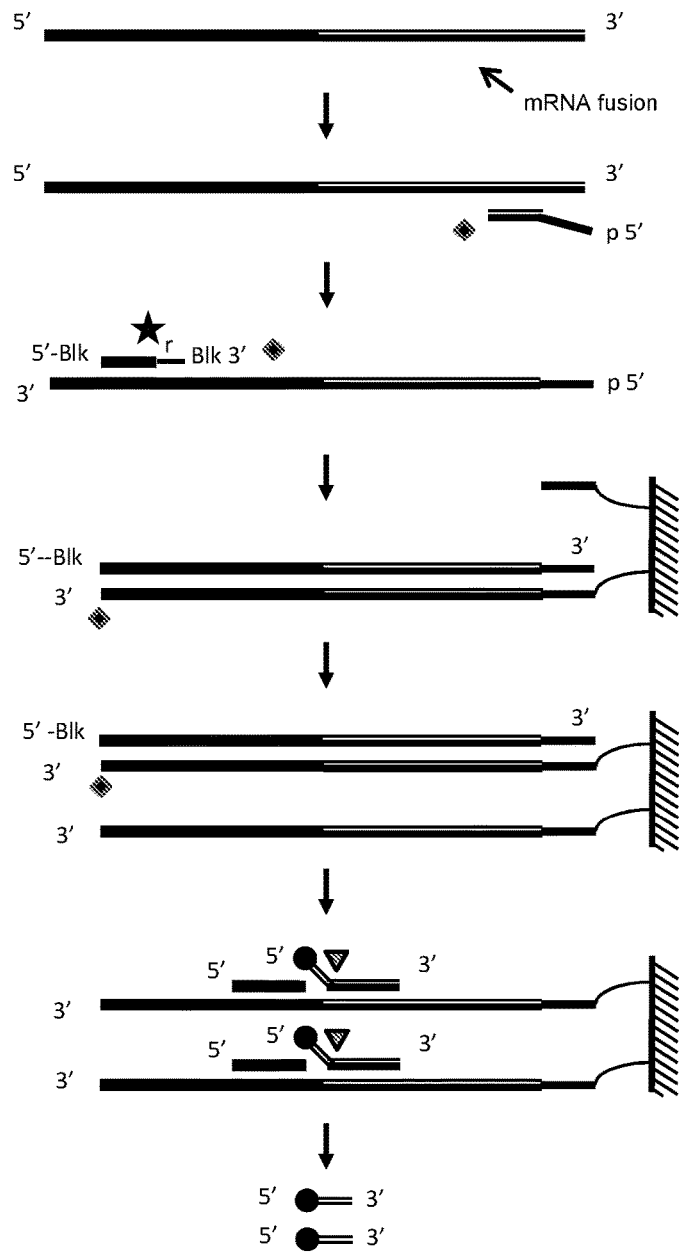

*FIG. 133*

A. Pixel-Nucleotide-Extension to enumerate low-abundance translocation at the mRNA level. Isolate RNA.

B. Use reverse-transcriptase to make cDNA copy with transcript-specific primer containing 5' dA30.

C. Denature cDNA and hybridize transcript-specific primer with blocked 3' and 5' ends. Primers are unblocked with RNaseH2 only when bound to target. Extend with polymerase, and generate T30 on 3' end. Optional: Degrade dA30 linkers with 5' nuclease.

D. Distribute onto an addressable matrix array, such that the T30 tail hybridizes to dA30 primers immobilized to pillars on a solid support. Extend hybridized primer with strand displacing Bst polymerase at 37oC, then raise the temperature to 55-60oC, allowing for an adjacent primer to hybridize and polymerase to displace primer strands to achieve a linear amplification of the original DNA.

E. Wash away all dNTPs. Hybridize exon junction-specific oligonucleotides, which contain 5' identifying signature modifiers for subsequent nanopore detection.

F. Extend oligonucleotides with nucleotide analogue terminator dNTPs containing 3' encoding signature modifiers.

G. Wash away unhybridized probes and unincorporated analogues. Denature product from target, then detect, and enumerate signal.

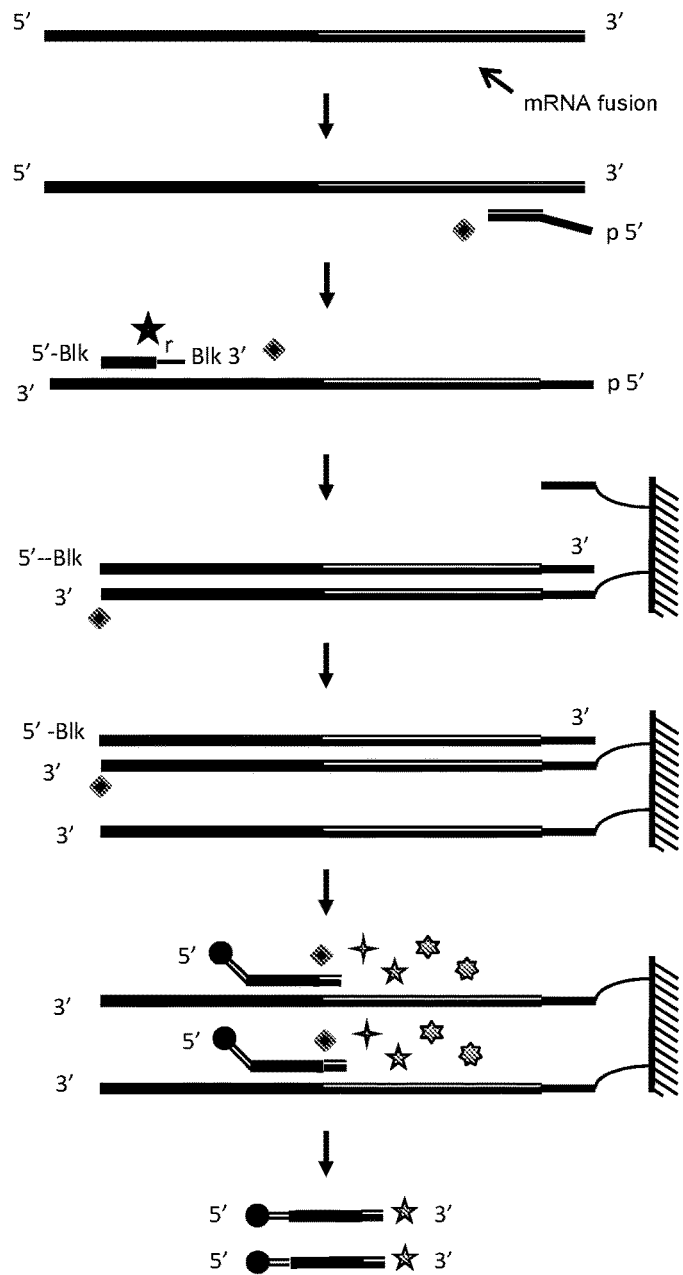

FIG. 134

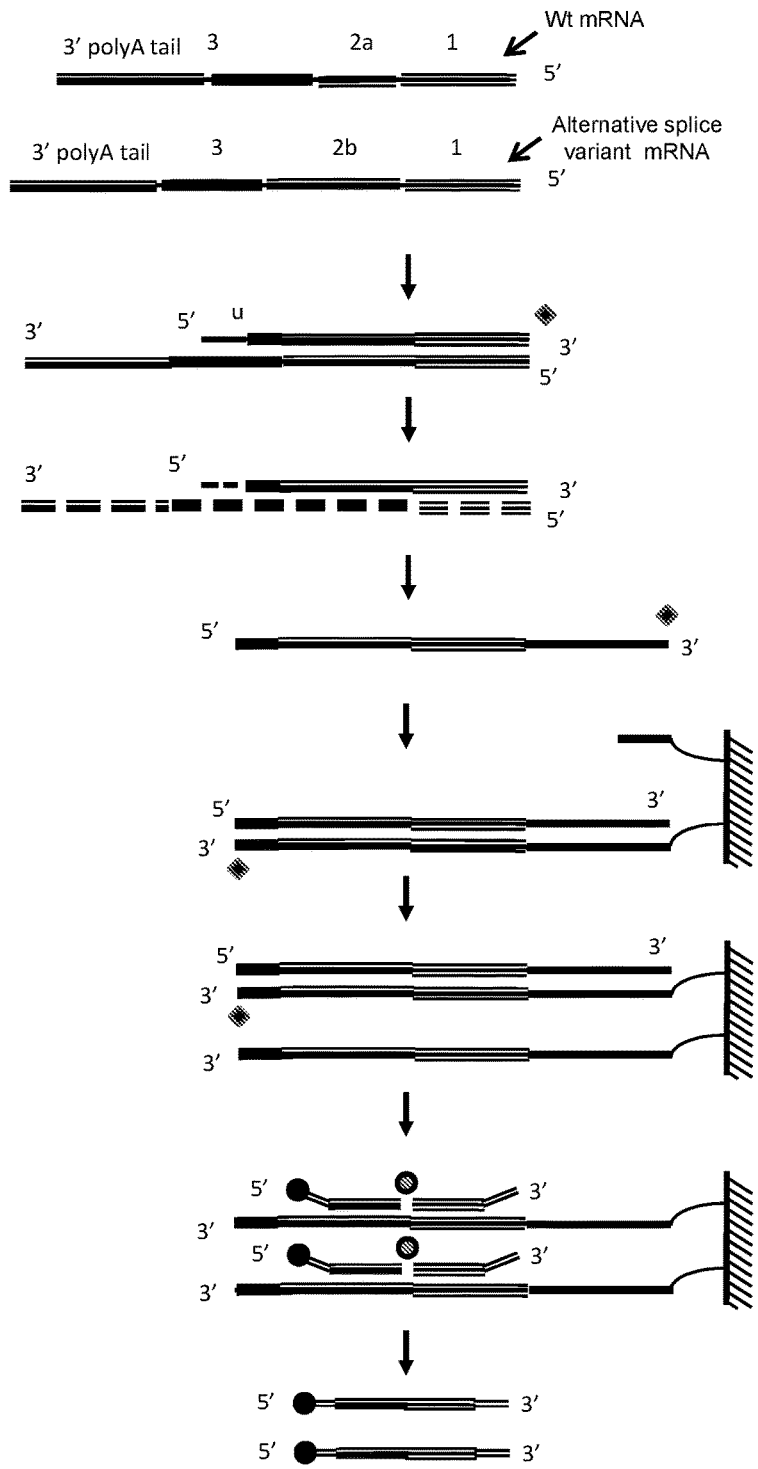

A. Pixel-LDR quantify wt and alternatively spliced (2a vs. 2b) transcript. Isolate mRNA.

B. Use reverse-transcriptase to make cDNA copy using transcript-specific primer, containing dU in either the 2 or 3 position from the 3' end. (Only Exon 2b containing transcript shown.)

C. Cleave unused primer with UDG & EndoVIII, degrade RNA with RNaseI & RNaseH, and remove dNTPs and 1-3 base digestion products.

D. Tail 3' ends with Terminal deoxynucleotidyl transferase (TdT), using TTP to generate dT(100-150).

E. Distribute onto an addressable matrix array, such that the T(100) tail hybridizes to dA30 primers immobilized to pillars on a solid support. Extend hybridized primer with strand displacing Bst polymerase at 37oC, then raise the temperature to 55-60oC, allowing for an adjacent primer to hybridize and polymerase to displace primer strands to achieve a linear amplification of the original DNA.

F. Exon junction-specific ligation oligonucleotides contain 5' identifying signature modifiers for subsequent nanopore detection. Ligase covalently seals the two oligonucleotides together.

G. Wash away unligated probes. Denature product from target, then detect, and enumerate signal.

*FIG. 135*

A. Pixel-LDR quantify wt and alternatively spliced (2a vs. 2b) transcript. Isolate mRNA.

B. Hybridize transcript-specific primer and use reverse-transcriptase to make cDNA copy, which also appends C3 on 3' end of cDNA. (Only Exon 2b containing transcript shown.)

C. Hybridize second primer with 3' rG3, and dA30 tail.

D. Reverse transcriptase undergoes strand switching and copies second primer to generate a T30 tail on the cDNA. Optional: Degrade dA30 primer with 5' nuclease.

E. Distribute onto an addressable matrix array, such that the T(100) tail hybridizes to dA30 primers immobilized to pillars on a solid support. Extend hybridized primer with strand displacing Bst polymerase at 37oC, then raise the temperature to 55-60oC, allowing for an adjacent primer to hybridize and polymerase to displace primer strands to achieve a linear amplification of the original DNA.

F. Exon junction-specific ligation oligonucleotides contain 5' identifying signature modifiers for subsequent nanopore detection. Ligase covalently seals the two oligonucleotides together.

G. Wash away unligated probes. Denature product from target, then detect, and enumerate signal.

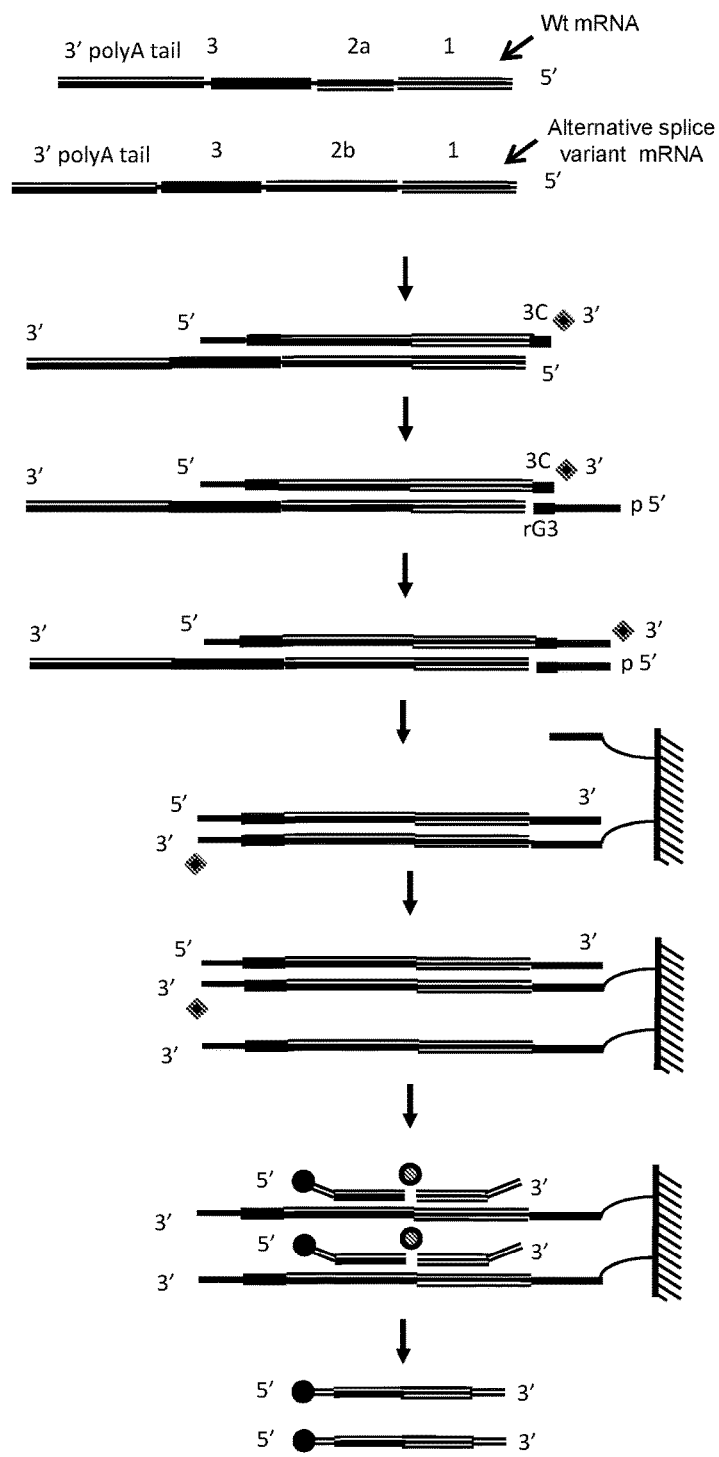

*FIG. 136*

A. Pixel-Cleavage quantify wt and alternatively spliced (2a vs. 2b) transcript. Isolate mRNA.

B. Hybridize transcript-specific primer and use reverse-transcriptase to make cDNA copy, which also appends C3 on 3' end of cDNA. (Only Exon 2b containing transcript shown.)

C. Hybridize second primer with 3' rG3, and dA30 tail.

D. Reverse transcriptase undergoes strand switching and copies second primer to generate a T30 tail on the cDNA. Optional: Degrade dA30 primer with 5' nuclease.

E. Distribute onto an addressable matrix array, such that the T(100) tail hybridizes to dA30 primers immobilized to pillars on a solid support. Extend hybridized primer with strand displacing Bst polymerase at 37oC, then raise the temperature to 55-60oC, allowing for an adjacent primer to hybridize and polymerase to displace primer strands to achieve a linear amplification of the original DNA.

F. Upstream and downstream oligonucleotides have mRNA exon junction-specific base, with the junction-specific flap oligonucleotides overlap at the junction base, and contain 5' identifying signature modifiers for subsequent nanopore detection. 5'-nuclease activity of polymerase or flap endonuclease cleaves off only matching 5'-overlapping base and additional flap; then detect, and enumerate signal.

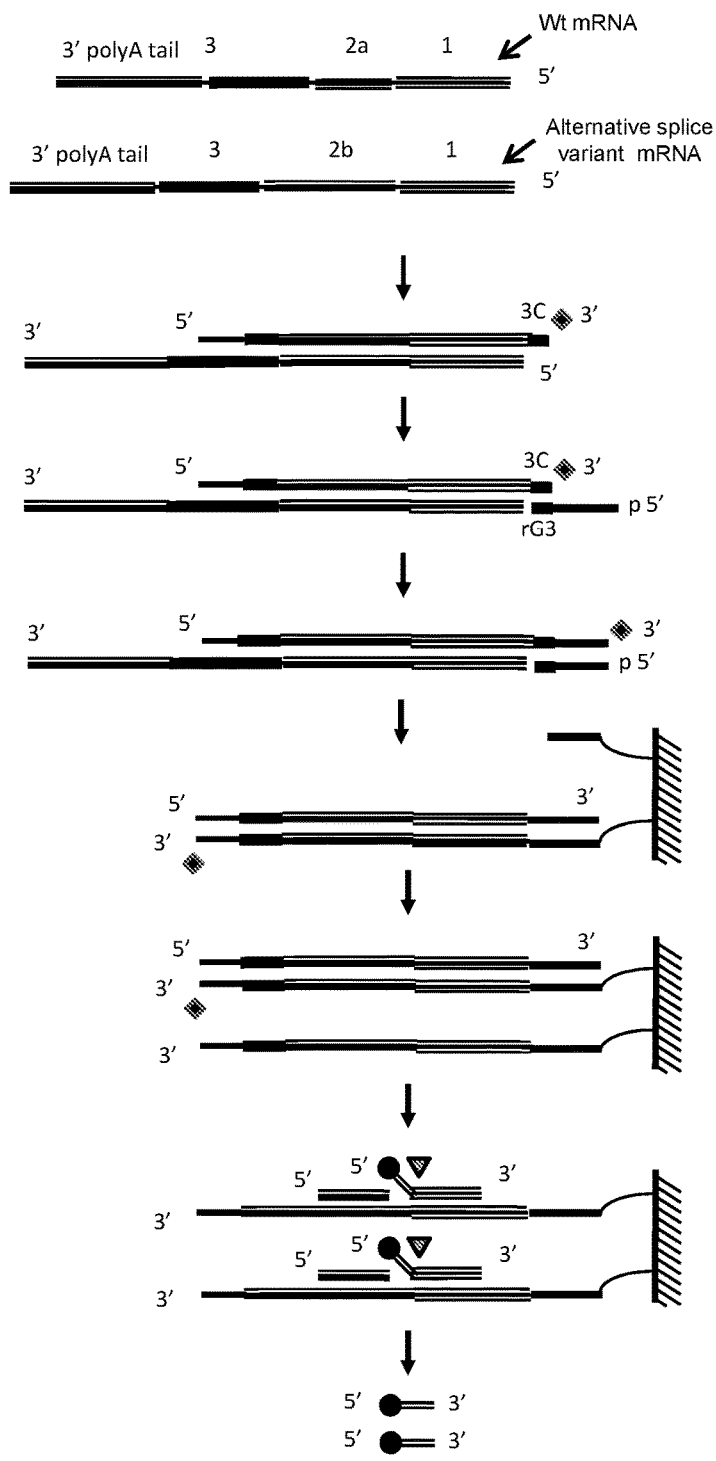

*FIG. 137*

A. Pixel-Nucleotide-Extension quantify wt and alternatively spliced (2a vs. 2b) transcript. Isolate mRNA.

B. Hybridize transcript-specific primer and use reverse-transcriptase to make cDNA copy, which also appends C3 on 3' end of cDNA. (Only Exon 2b containing transcript shown.)

C. Hybridize second primer with 3' rG3, and dA30 tail.

D. Reverse transcriptase undergoes strand switching and copies second primer to generate a T30 tail on the cDNA. Optional: Degrade dA30 primer with 5' nuclease.

E. Distribute onto an addressable matrix array, such that the T(100) tail hybridizes to dA30 primers immobilized to pillars on a solid support. Extend hybridized primer with strand displacing Bst polymerase at 37oC, then raise the temperature to 55-60oC, allowing for an adjacent primer to hybridize and polymerase to displace primer strands to achieve a linear amplification of the original DNA.

F. Wash away all dNTPs. Hybridize exon junction-specific oligonucleotides, which contain 5' identifying signature modifiers for subsequent nanopore detection.

G. Extend oligonucleotides with nucleotide analogue terminator dNTPs containing 3' encoding signature modifiers.

H. Wash away unhybridized probes and unincorporated analogues. Denature product from target, then detect, and enumerate signal.

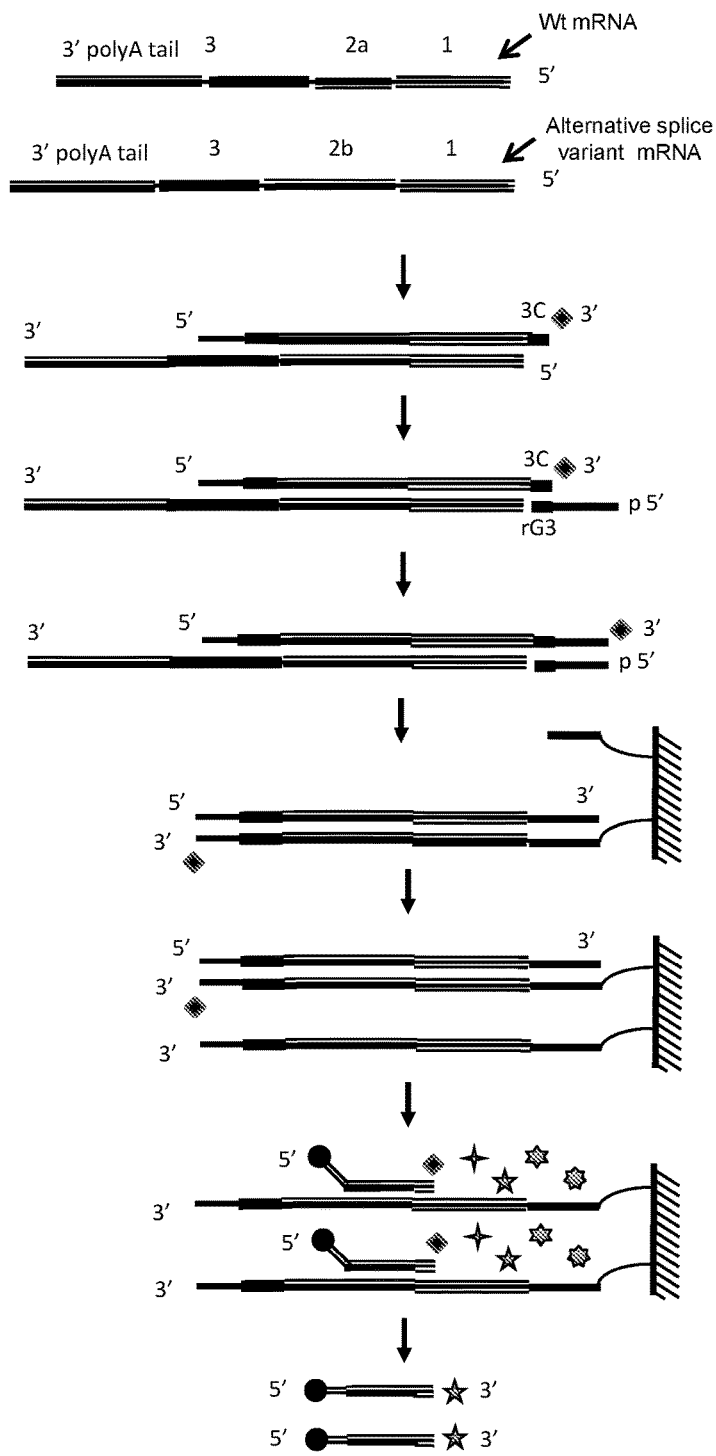

*FIG. 138*

A. Pixel-LDR to enumerate low-level alternatively spliced (e.g. 3b) transcript. Isolate mRNA.

B. Use reverse-transcriptase to make cDNA copy with transcript-specific primer containing 5' dA30.

C. Denature cDNA and hybridize 3b transcript-specific primer with blocked 3' and 5' ends. Primers are unblocked with RNaseH2 only when bound to target. Extend with polymerase, and generate T30 on 3' end. Optional: Degrade dA30 linkers with 5' nuclease.

D. Distribute onto an addressable matrix array, such that the T30 tail hybridizes to dA30 primers immobilized to pillars on a solid support. Extend hybridized primer with strand displacing Bst polymerase at 37oC, then raise the temperature to 55-60oC, allowing for an adjacent primer to hybridize and polymerase to displace primer strands to achieve a linear amplification of the original DNA.

E. Exon junction-specific ligation oligonucleotides contain 5' identifying signature modifiers for subsequent nanopore detection. Ligase covalently seals the two oligonucleotides together.

F. Wash away unligated probes. Denature product from target, then detect, and enumerate signal.

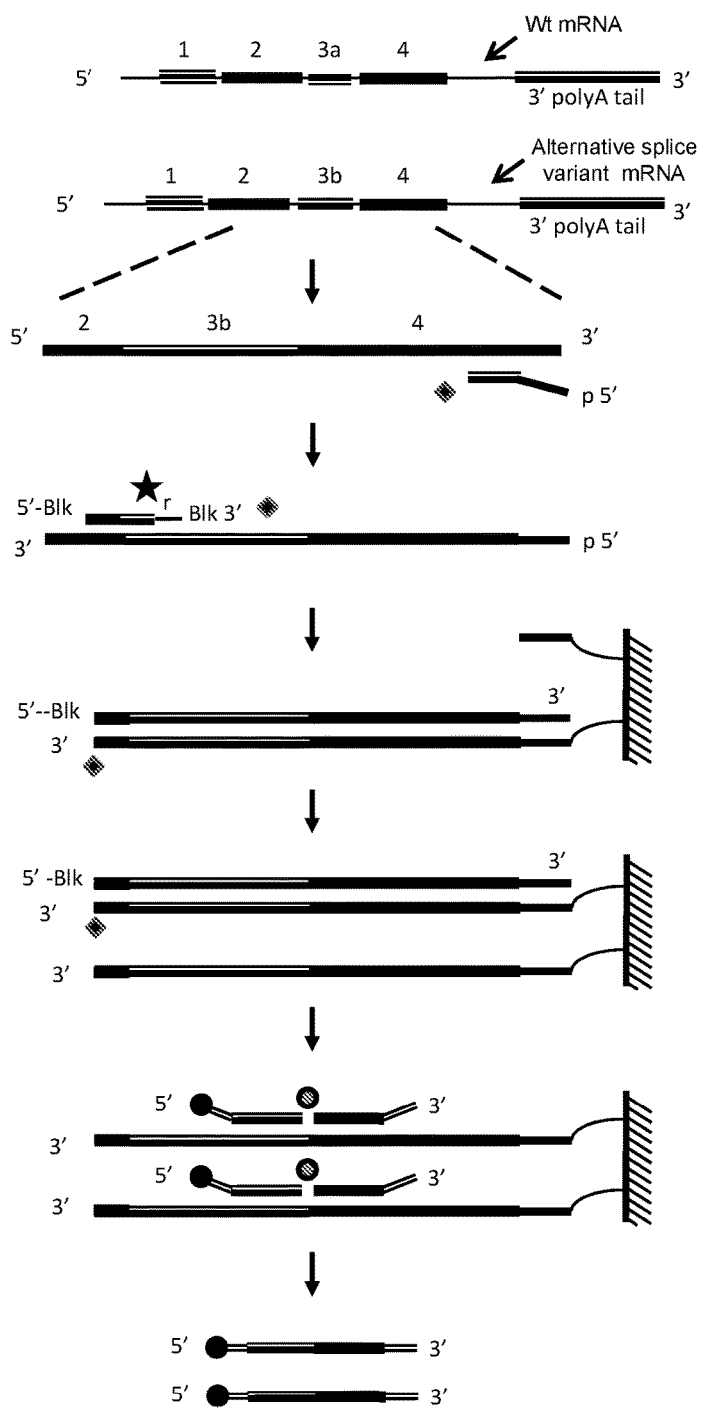

*FIG. 139*

A. Pixel-Cleavage to enumerate low-level alternatively spliced (e.g. 3b) transcript. Isolate mRNA.

B. Use reverse-transcriptase to make cDNA copy with transcript-specific primer containing 5' dA30.

C. Denature cDNA and hybridize 3b transcript-specific primer with blocked 3' and 5' ends. Primers are unblocked with RNaseH2 only when bound to target. Extend with polymerase, and generate T30 on 3' end. Optional: Degrade dA30 linkers with 5' nuclease.

D. Distribute onto an addressable matrix array, such that the T30 tail hybridizes to dA30 primers immobilized to pillars on a solid support. Extend hybridized primer with strand displacing Bst polymerase at 37oC, then raise the temperature to 55-60oC, allowing for an adjacent primer to hybridize and polymerase to displace primer strands to achieve a linear amplification of the original DNA.

E. Upstream and downstream oligonucleotides have mRNA exon junction-specific base, with the junction-specific flap oligonucleotides overlap at the junction base, and contain 5' identifying signature modifiers for subsequent nanopore detection. 5'-nuclease activity of polymerase or flap endonuclease cleaves off only matching 5'-overlapping base and additional flap; then detect, and enumerate signal.

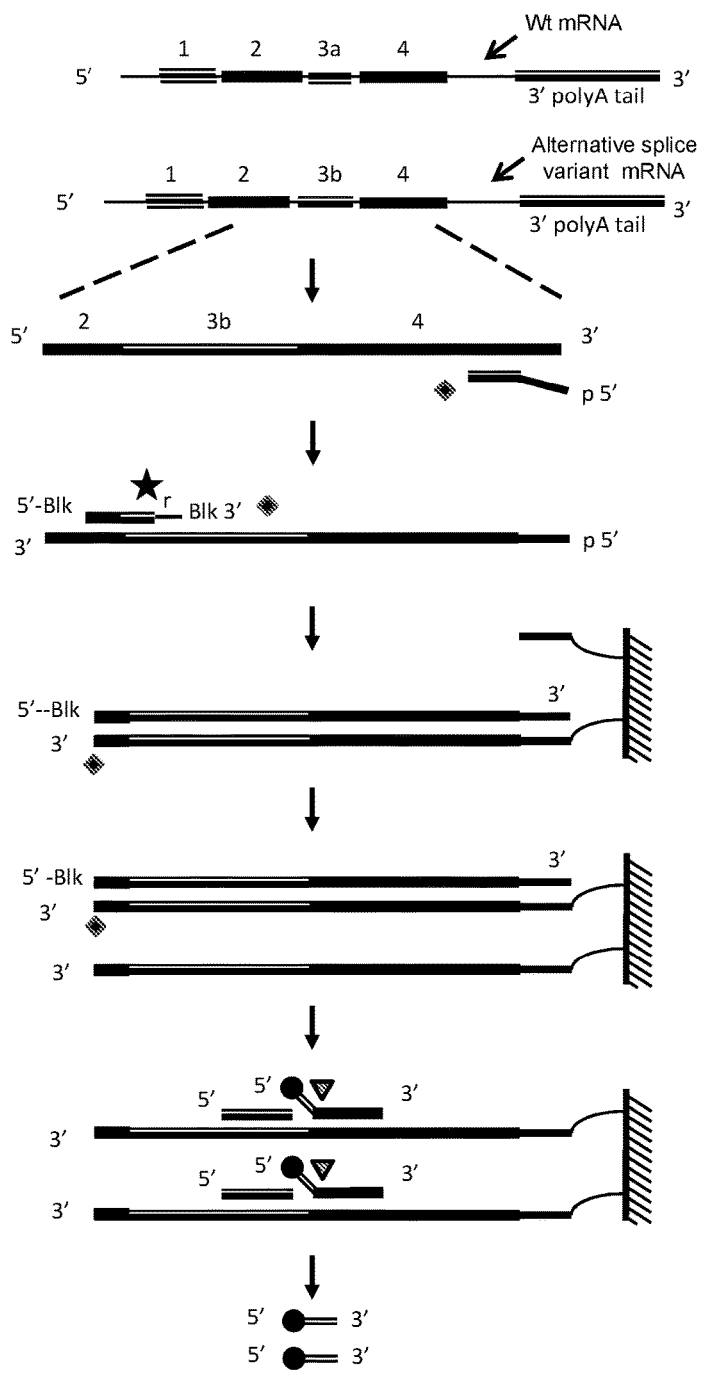

FIG. 140

A. Pixel-Nucleotide-Extension to enumerate low-level alternatively spliced (e.g. 3b) transcript. Isolate mRNA.

B. Use reverse-transcriptase to make cDNA copy with transcript-specific primer containing 5' dA30.

C. Denature cDNA and hybridize 3b transcript-specific primer with blocked 3' and 5' ends. Primers are unblocked with RNaseH2 only when bound to target. Extend with polymerase, and generate T30 on 3' end. Optional: Degrade dA30 linkers with 5' nuclease.

D. Distribute onto an addressable matrix array, such that the T30 tail hybridizes to dA30 primers immobilized to pillars on a solid support. Extend hybridized primer with strand displacing Bst polymerase at 37oC, then raise the temperature to 55-60oC, allowing for an adjacent primer to hybridize and polymerase to displace primer strands to achieve a linear amplification of the original DNA.

E. Wash away all dNTPs. Hybridize exon junction-specific oligonucleotides, which contain 5' identifying signature modifiers for subsequent nanopore detection.

F. Extend oligonucleotides with nucleotide analogue terminator dNTPs containing 3' encoding signature modifiers.

G. Wash away unhybridized probes and unincorporated analogues. Denature product from target, then detect, and enumerate signal.

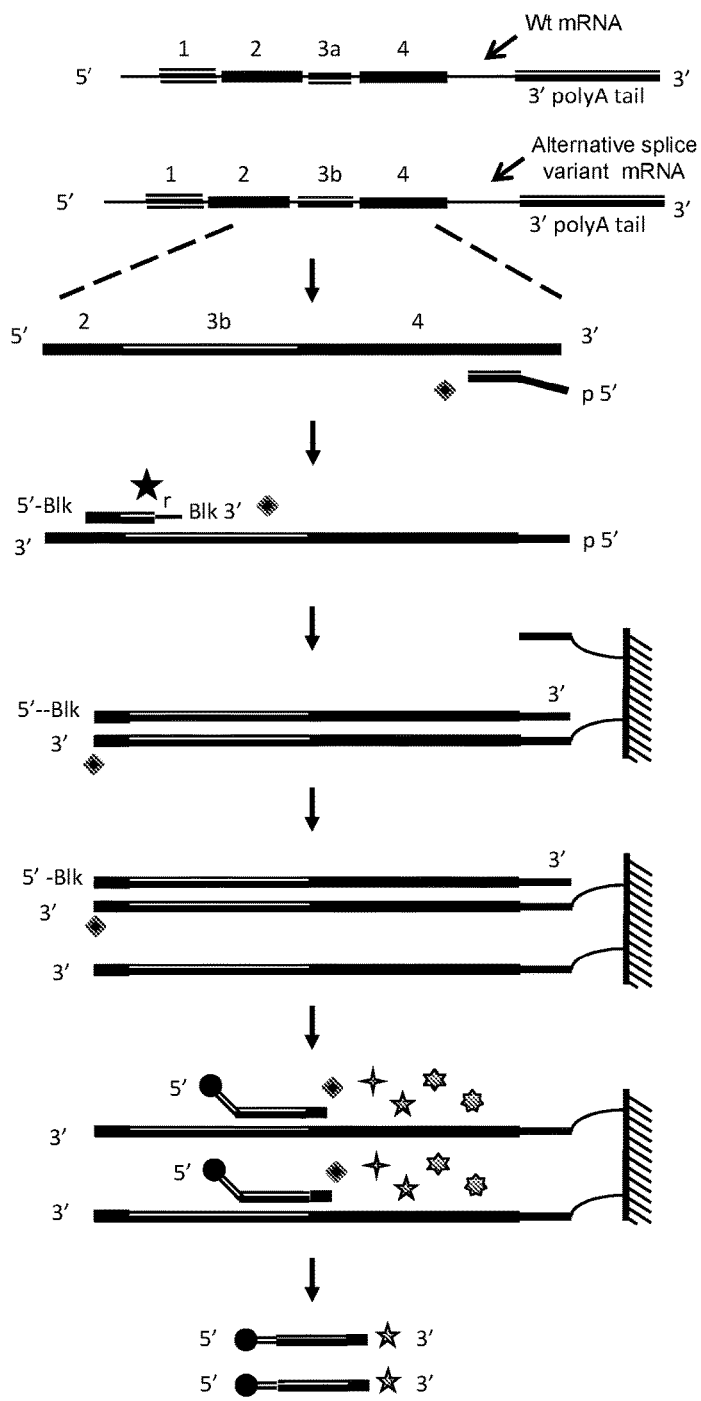

FIG. 141

A. Pixel-LDR to detect miRNA. Isolate miRNA from exosomes.

B. Ligate loop primer with random hexamer complementary to 3' end of target miRNA, containing a stem-loop, an A rich primer binding sequence, and 3' blocking group.

C. Degrade unused loop primer with 5' nuclease. Use dU rich primer and reverse-transcriptase to make cDNA copy.

D. Cleave unused primer with UDG & EndoVIII, degrade RNA with RNaseI & RNaseH, and remove dNTPs and 1-3 base digestion products.

E. Tail 3' ends with Terminal deoxynucleotidyl transferase (TdT), using TTP to generate dT(100-150).

F. Distribute onto an addressable matrix array, such that the T(100) tail hybridizes to dA30 primers immobilized to pillars on a solid support. Extend hybridized primer with strand displacing Bst polymerase at 37oC, then raise the temperature to 55-60oC, allowing for an adjacent primer to hybridize and polymerase to displace primer strands to achieve a linear amplification of the original DNA.

G. miRNA sequence-specific ligation oligonucleotides contain 5' identifying signature modifiers for subsequent nanopore detection. Ligase covalently seals the two oligonucleotides together.

H. Wash away unligated probes. Denature product from target, then detect, and enumerate signal.

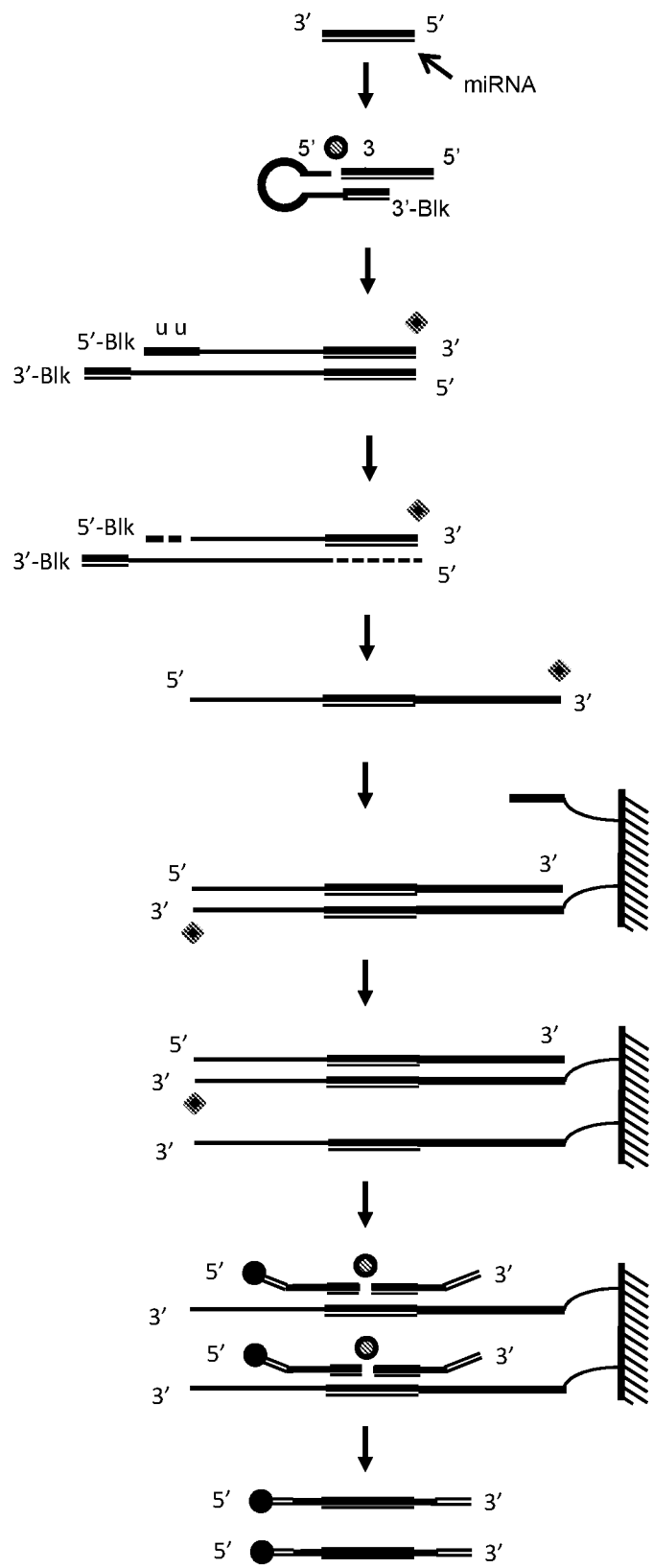

*FIG. 142*

A. Pixel-LDR to detect total miRNA. Isolate miRNA from exosomes.

B. Ligate loop primer with random hexamer complementary to 3' end of target miRNA, containing a stem-loop, a primer binding sequence, and 3' blocking group.

C. Degrade unused loop primer with 5' nuclease. Hybridize loop-specific primer and use reverse-transcriptase to make cDNA copy, which also appends C3 on 3' end of cDNA.

D. Hybridize second primer with 3' rG3, a second primer binding sequence, and dA30 tail.

E. Reverse transcriptase undergoes strand switching and copies second primer to generate a T30 tail on the cDNA. Optional: Degrade dA30 primer with 5' nuclease.

F. Distribute onto an addressable matrix array, such that the T(30) tail hybridizes to dA30 primers immobilized to pillars on a solid support. Extend hybridized primer with strand displacing Bst polymerase at 37oC, then raise the temperature to 55-60oC, allowing for an adjacent primer to hybridize and polymerase to displace primer strands to achieve a linear amplification of the original DNA.

G. miRNA sequence-specific ligation oligonucleotides contain 5' identifying signature modifiers for subsequent nanopore detection. Ligase covalently seals the two oligonucleotides together.

H. Wash away unligated probes. Denature product from target, then detect, and enumerate signal.

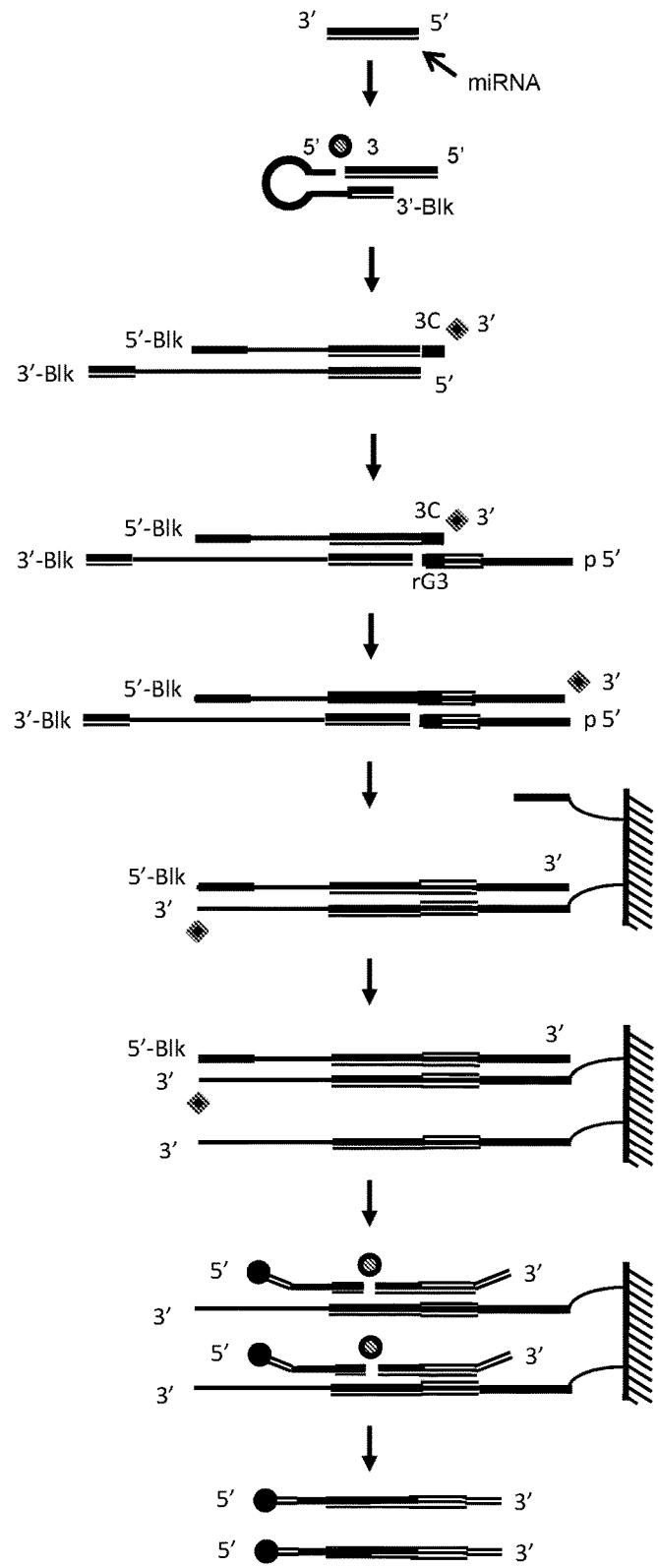

*FIG. 143*

A. Pixel-Cleavage to detect total miRNA. Isolate miRNA from exosomes.

B. Ligate loop primer with random hexamer complementary to 3' end of target miRNA, containing a stem-loop, a primer binding sequence, and 3' blocking group.

C. Degrade unused loop primer with 5' nuclease. Hybridize loop-specific primer and use reverse-transcriptase to make cDNA copy, which also appends C3 on 3' end of cDNA.

D. Hybridize second primer with 3' rG3, a second primer binding sequence, and dA30 tail.

E. Reverse transcriptase undergoes strand switching and copies second primer to generate a T30 tail on the cDNA. Optional: Degrade dA30 primer with 5' nuclease.

F. Distribute onto an addressable matrix array, such that the T(30) tail hybridizes to dA30 primers immobilized to pillars on a solid support. Extend hybridized primer with strand displacing Bst polymerase at 37oC, then raise the temperature to 55-60oC, allowing for an adjacent primer to hybridize and polymerase to displace primer strands to achieve a linear amplification of the original DNA.

G. Upstream and downstream oligonucleotides have miRNA-specific base, with the miRNA-specific flap oligonucleotides overlap at a miRNA base, and contain 5' identifying signature modifiers for subsequent nanopore detection. 5'-nuclease activity of polymerase or flap endonuclease cleaves off only matching 5'-overlapping base and additional flap; then detect, and enumerate signal.

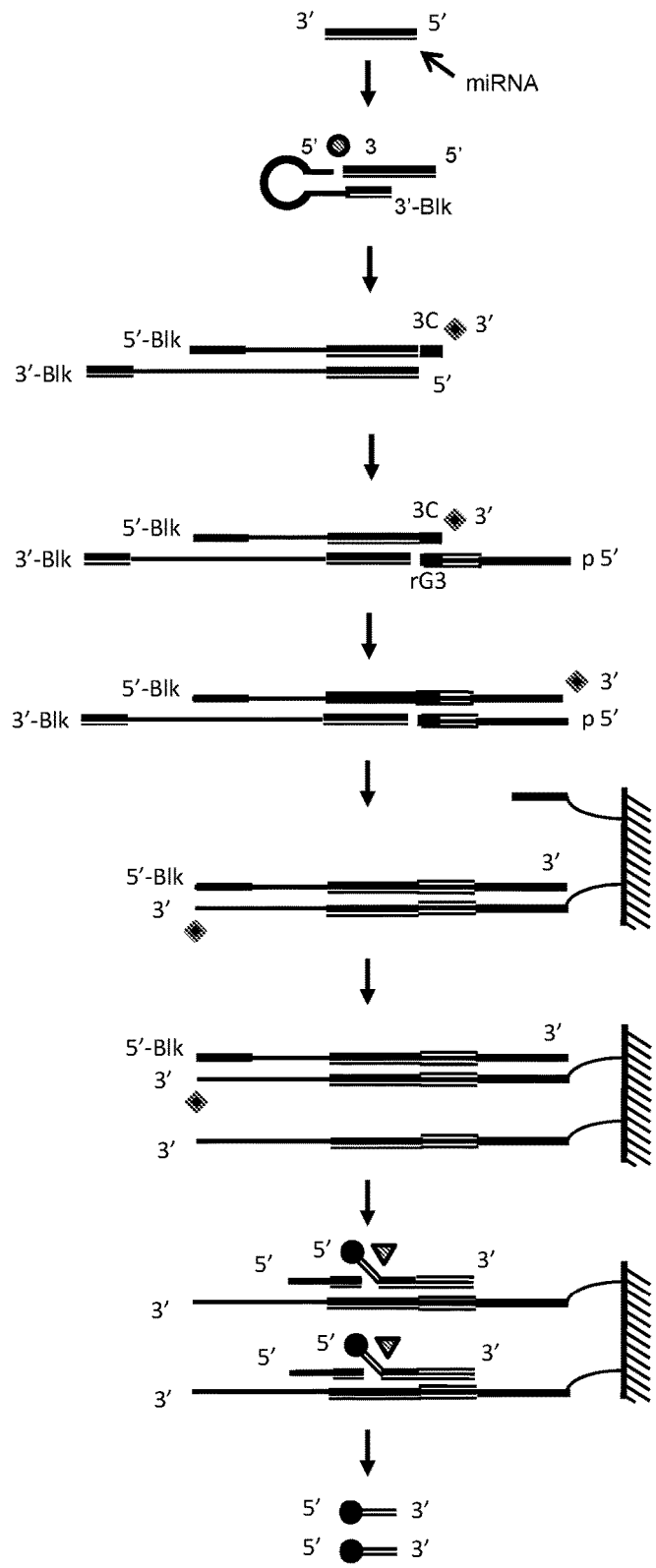

*FIG. 144*

A. Pixel-Nucleotide-Extension to detect total miRNA. Isolate miRNA from exosomes.

B. Ligate loop primer with random hexamer complementary to 3' end of target miRNA, containing a stem-loop, a primer binding sequence, and 3' blocking group.

C. Degrade unused loop primer with 5' nuclease. Hybridize loop-specific primer and use reverse-transcriptase to make cDNA copy, which also appends C3 on 3' end of cDNA.

D. Hybridize second primer with 3' rG3, a second primer binding sequence, and dA30 tail.

E. Reverse transcriptase undergoes strand switching and copies second primer to generate a T30 tail on the cDNA. Optional: Degrade dA30 primer with 5' nuclease.

F. Distribute onto an addressable matrix array, such that the T(30) tail hybridizes to dA30 primers immobilized to pillars on a solid support. Extend hybridized primer with strand displacing Bst polymerase at 37oC, then raise the temperature to 55-60oC, allowing for an adjacent primer to hybridize and polymerase to displace primer strands to achieve a linear amplification of the original DNA.

G. Wash away all dNTPs. Hybridize miRNA-specific oligonucleotides, which contain 5' identifying signature modifiers for subsequent nanopore detection.

H. Extend oligonucleotides with nucleotide analogue terminator dNTPs containing 3' encoding signature modifiers.

I. Wash away unhybridized probes and unincorporated analogues. Denature product from target, then detect, and enumerate signal.

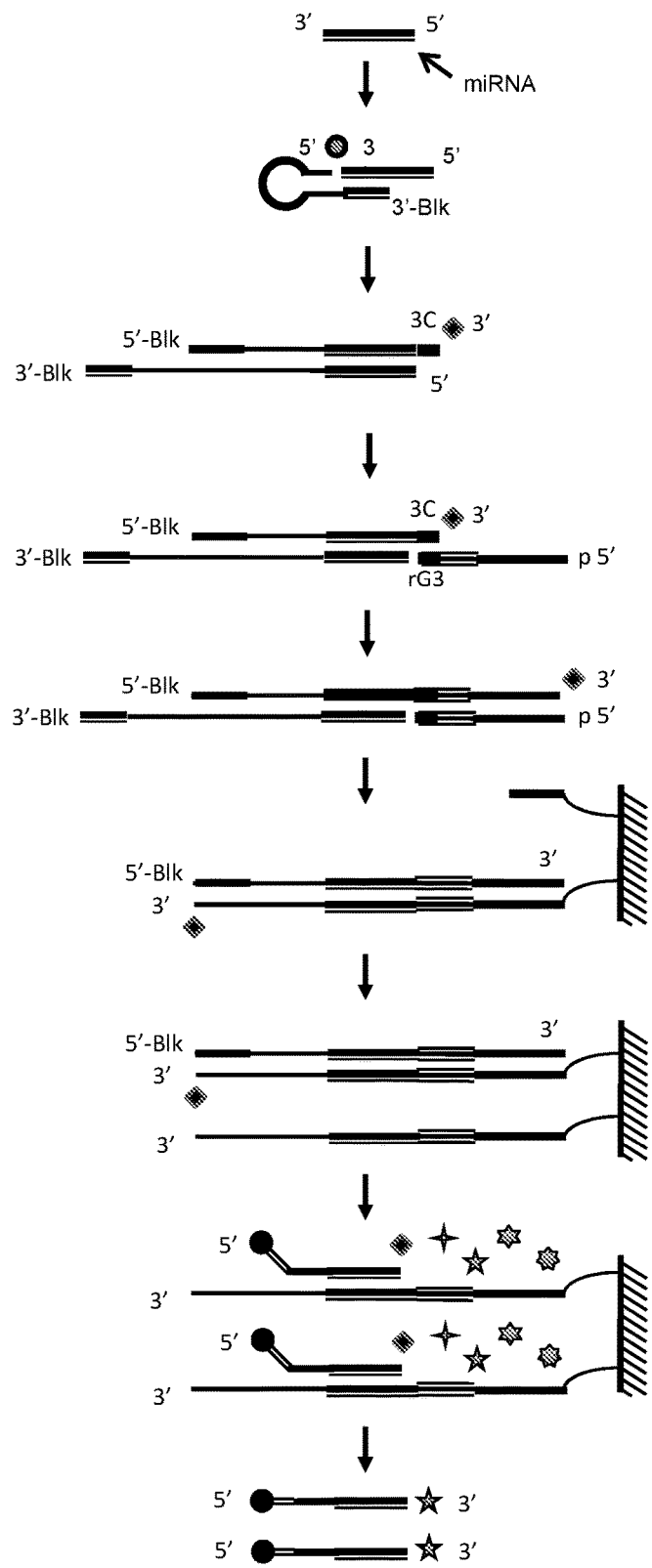

*FIG. 145*

A. Pixel-LDR to detect specific miRNA. Isolate miRNA from exosomes.

B. Ligate loop primer with specific hexamer complementary to 3' end of target miRNA, containing a stem-loop, an A rich primer binding sequence, and 3' blocking group.

C. Degrade unused loop primer with 5' nuclease. Use dU rich primer and reverse-transcriptase to make cDNA copy.

D. Cleave unused primer with UDG & EndoVIII, degrade RNA with RNaseI & RNaseH, and remove dNTPs and 1-3 base digestion products.

E. Tail 3' ends with Terminal deoxynucleotidyl transferase (TdT), using TTP to generate dT(100-150).

F. Distribute onto an addressable matrix array, such that the T(100) tail hybridizes to dA30 primers immobilized to pillars on a solid support. Extend hybridized primer with strand displacing Bst polymerase at 37oC, then raise the temperature to 55-60oC, allowing for an adjacent primer to hybridize and polymerase to displace primer strands to achieve a linear amplification of the original DNA.

G. miRNA sequence-specific ligation oligonucleotides contain 5' identifying signature modifiers for subsequent nanopore detection. Ligase covalently seals the two oligonucleotides together.

H. Wash away unligated probes. Denature product from target, then detect, and enumerate signal.

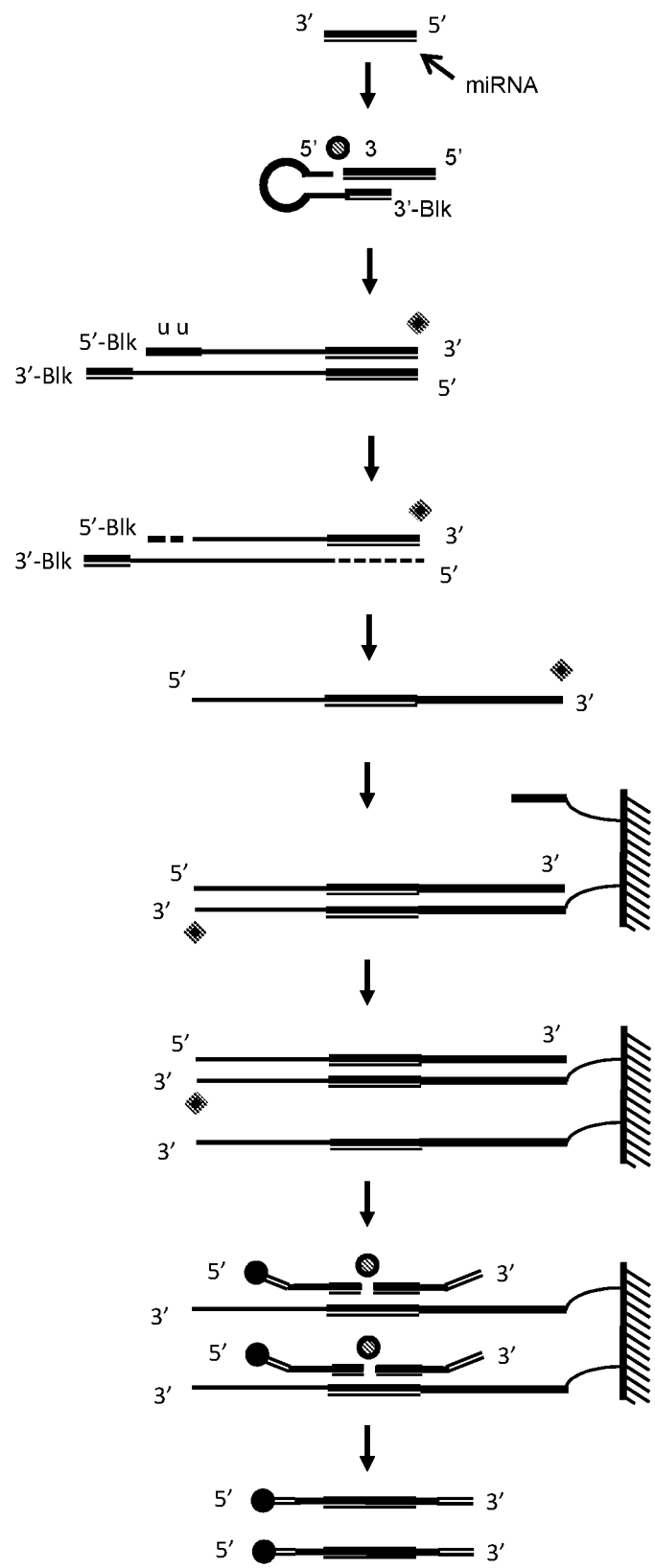

*FIG. 146*

A. Pixel-LDR to detect specific miRNA. Isolate miRNA from exosomes.

B. Ligate loop primer with specific hexamer complementary to 3' end of target miRNA, containing a stem-loop, a primer binding sequence, and 3' blocking group.

C. Degrade unused loop primer with 5' nuclease. Hybridize loop-specific primer and use reverse-transcriptase to make cDNA copy, which also appends C3 on 3' end of cDNA.

D. Hybridize second primer with 3' rG3, a second primer binding sequence, and dA30 tail.

E. Reverse transcriptase undergoes strand switching and copies second primer to generate a T30 tail on the cDNA. Optional: Degrade dA30 primer with 5' nuclease.

F. Distribute onto an addressable matrix array, such that the T(30) tail hybridizes to dA30 primers immobilized to pillars on a solid support. Extend hybridized primer with strand displacing Bst polymerase at 37oC, then raise the temperature to 55-60oC, allowing for an adjacent primer to hybridize and polymerase to displace primer strands to achieve a linear amplification of the original DNA.

G. miRNA sequence-specific ligation oligonucleotides contain 5' identifying signature modifiers for subsequent nanopore detection. Ligase covalently seals the two oligonucleotides together.

H. Wash away unligated probes. Denature product from target, then detect, and enumerate signal.

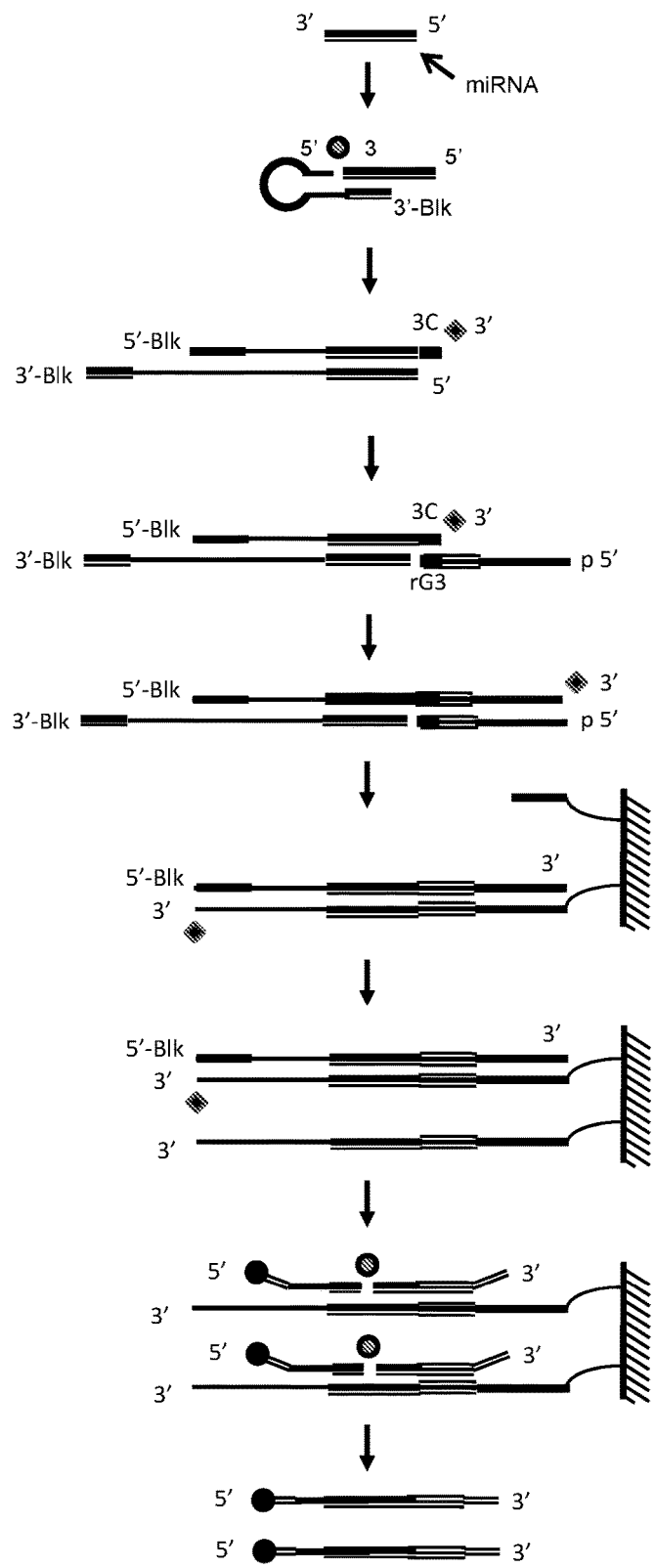

*FIG. 147*

A. Pixel-Cleavage to detect specific miRNA. Isolate miRNA from exosomes.

B. Ligate loop primer with specific hexamer complementary to 3' end of target miRNA, containing a stem-loop, a primer binding sequence, and 3' blocking group.

C. Degrade unused loop primer with 5' nuclease. Hybridize loop-specific primer and use reverse-transcriptase to make cDNA copy, which also appends C3 on 3' end of cDNA.

D. Hybridize second primer with 3' rG3, a second primer binding sequence, and dA30 tail.

E. Reverse transcriptase undergoes strand switching and copies second primer to generate a T30 tail on the cDNA. Optional: Degrade dA30 primer with 5' nuclease.

F. Distribute onto an addressable matrix array, such that the T(30) tail hybridizes to dA30 primers immobilized to pillars on a solid support. Extend hybridized primer with strand displacing Bst polymerase at 37oC, then raise the temperature to 55-60oC, allowing for an adjacent primer to hybridize and polymerase to displace primer strands to achieve a linear amplification of the original DNA.

G. Upstream and downstream oligonucleotides have miRNA-specific base, with the miRNA-specific flap oligonucleotides overlap at a miRNA base, and contain 5' identifying signature modifiers for subsequent nanopore detection. 5'-nuclease activity of polymerase or flap endonuclease cleaves off only matching 5'-overlapping base and additional flap; then detect, and enumerate signal.

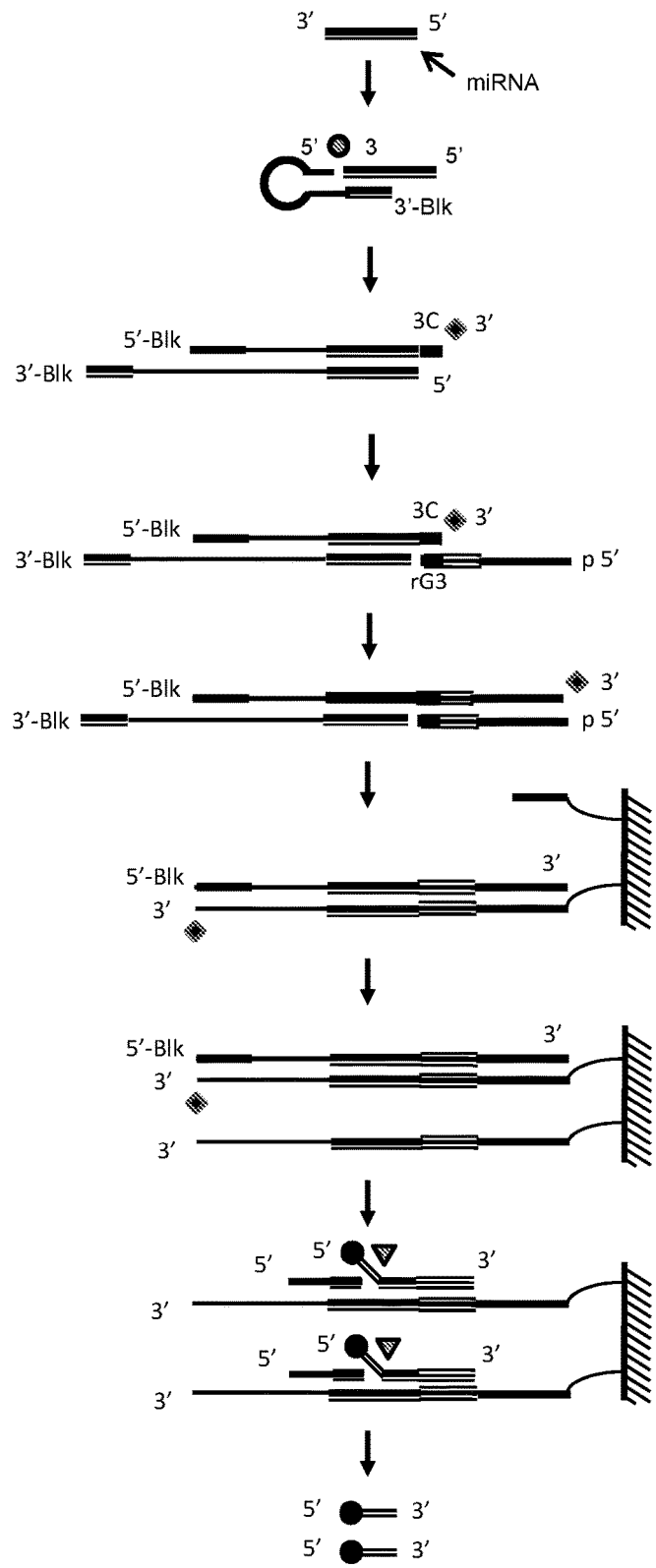

*FIG. 148*

A. Pixel-Nucleotide-Extension to detect specific miRNA. Isolate miRNA from exosomes.

B. Ligate loop primer with specific hexamer complementary to 3' end of target miRNA, containing a stem-loop, a primer binding sequence, and 3' blocking group.

C. Degrade unused loop primer with 5' nuclease. Hybridize loop-specific primer and use reverse-transcriptase to make cDNA copy, which also appends C3 on 3' end of cDNA.

D. Hybridize second primer with 3' rG3, a second primer binding sequence, and dA30 tail.

E. Reverse transcriptase undergoes strand switching and copies second primer to generate a T30 tail on the cDNA. Optional: Degrade dA30 primer with 5' nuclease.

F. Distribute onto an addressable matrix array, such that the T(30) tail hybridizes to dA30 primers immobilized to pillars on a solid support. Extend hybridized primer with strand displacing Bst polymerase at 37oC, then raise the temperature to 55-60oC, allowing for an adjacent primer to hybridize and polymerase to displace primer strands to achieve a linear amplification of the original DNA.

G. Wash away all dNTPs. Hybridize miRNA-specific oligonucleotides, which contain 5' identifying signature modifiers for subsequent nanopore detection.

H. Extend oligonucleotides with nucleotide analogue terminator dNTPs containing 3' encoding signature modifiers.

I. Wash away unhybridized probes and unincorporated analogues. Denature product from target, then detect, and enumerate signal.

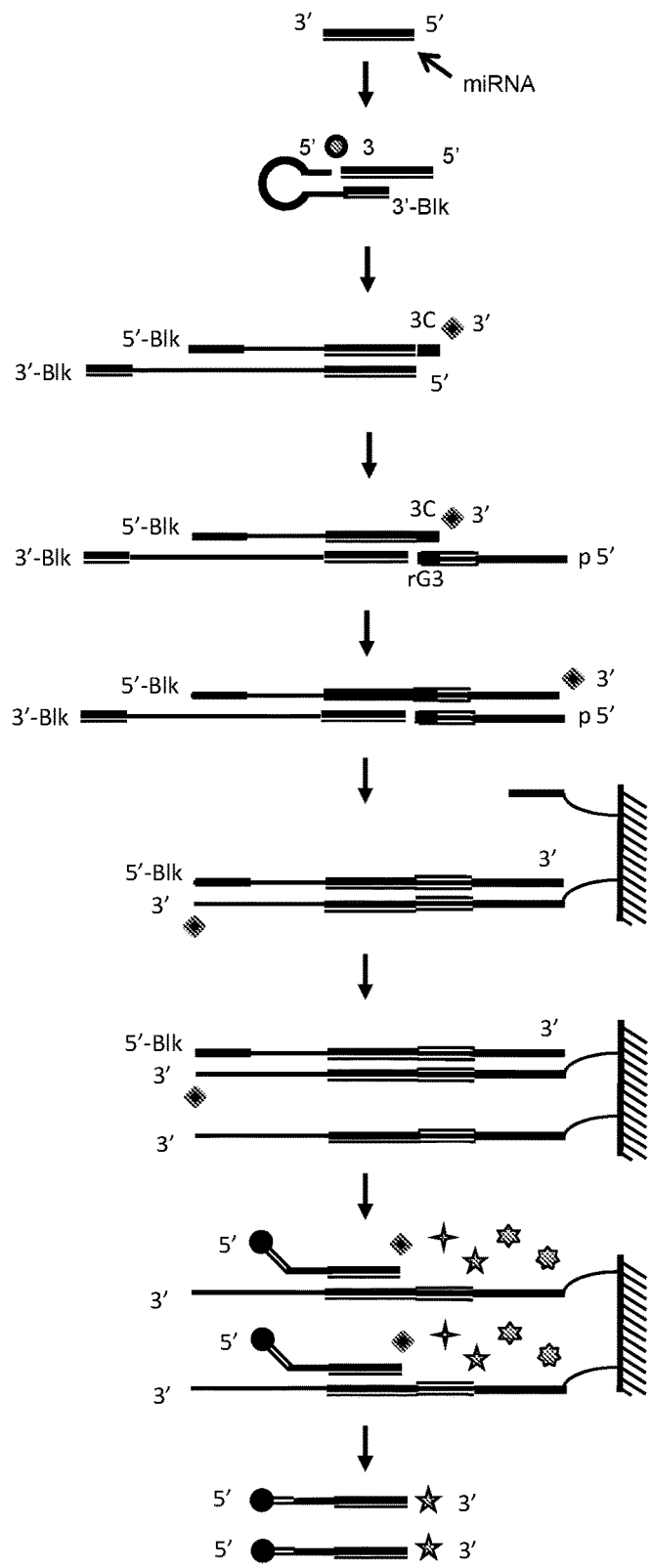

FIG. 149

A. Two sided general DNA amplification. Isolate genomic or cfDNA.

B. Blunt ends, extend 3'end with a single A base, and ligate on A:T rich linkers with single-base T overhang, 5' Universal primer(s) and 3'-T30 tails.

C. Distribute onto an addressable matrix array, such that the T30 tail hybridizes to dA30 primers immobilized to pillars on a solid support.

D. Extend hybridized primer with strand displacing Bst polymerase at 37oC. When raising the temperature to 55-60oC, the dA portion partially denatures, allowing for an adjacent primer to hybridize and polymerase displace the first primer strand. By this repetitive process, the original strand is "handed-off" to the next primer to achieve a linear amplification of the original DNA.

E. Meanwhile, Universal primer(s) in solution hybridizes to single-stranded extension product, and is extended by polymerase. As long as there are nearby dA30 primers, the process of handoff replication continues until primers are consumed.

F. Untethered extension products are melted off the solid support and removed.

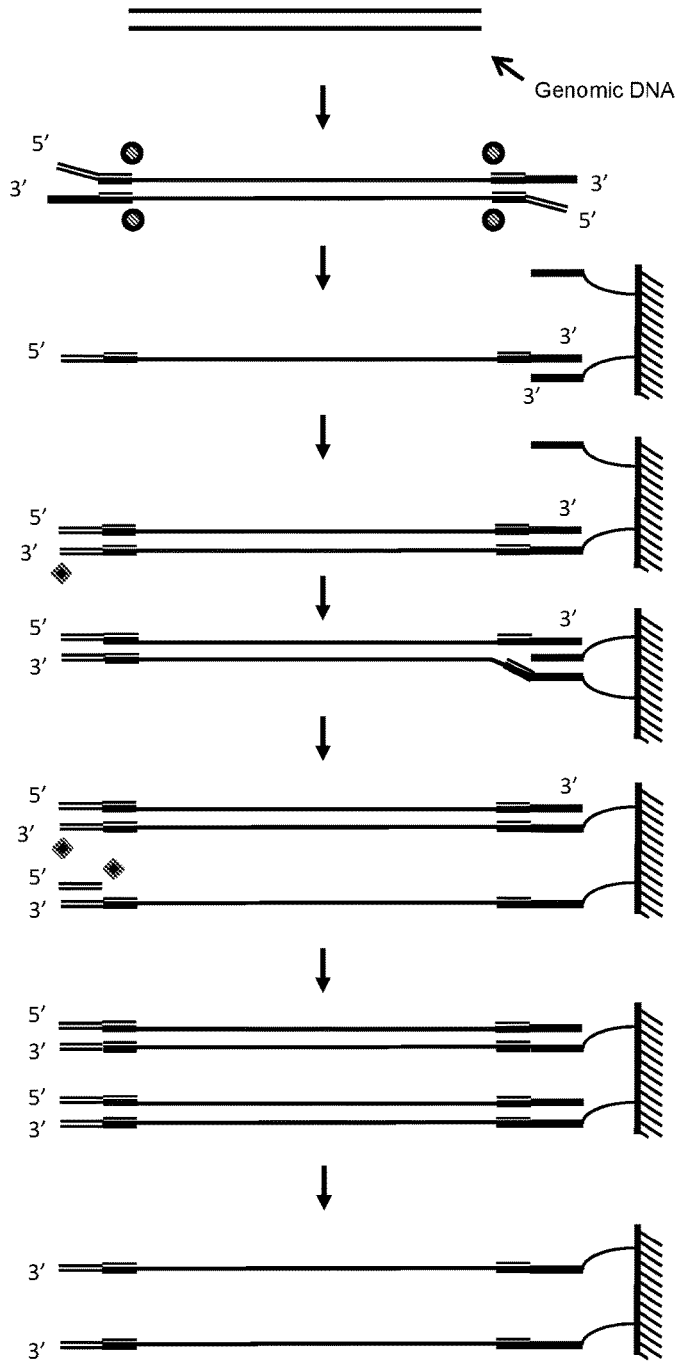

FIG. 150

A. Linker design for sequencing and identifying mutations in either target strand. cfDNA of average length of about 160 bp. Repair ends with T4 polymerase or DNA Polymerase I, Large (Klenow) Fragment.

B. Phosphorylate 5' ends with T4 kinase.

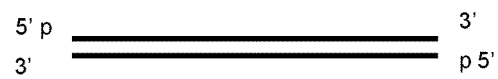

C. Add an A base to the 3' end using DNA Polymerase I, Large (Klenow) Fragment, lacking 3'->5' nuclease activity.

D. Ligate on 3' T overhang linkers with T30 sequence, primer binding site, 3' single-base T overhang and 5' phosphate on other end.

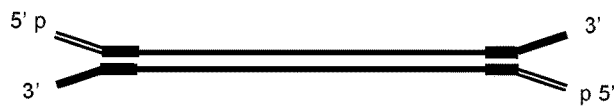

*FIG. 151*

A. Linker design for sequencing and identifying mutations in both target strands. cfDNA of average length of about 160 bp. Repair ends with T4 polymerase or DNA Polymerase I, Large (Klenow) Fragment.

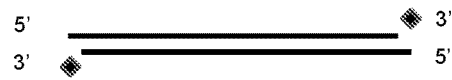

B. Phosphorylate 5' ends with T4 kinase.

C. Add an A base to the 3' end using DNA Polymerase I, Large (Klenow) Fragment, lacking 3'->5' nuclease activity.

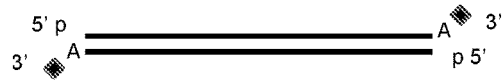

D. Ligate on 3' T overhang with "gap" linkers with T30 sequence, primer binding site, 3' single-base T overhang and 5' phosphate on other end.

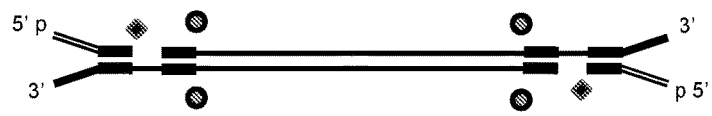

E. Polymerase copies unique identifier sequences to fill gaps, and ligase covalently seals the extended ends.

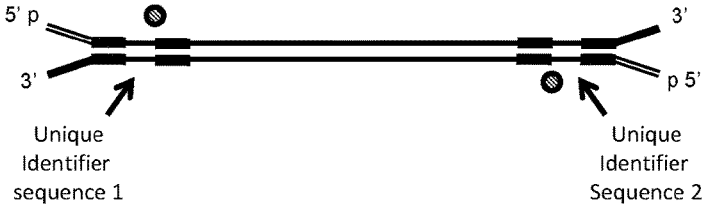

Unique Identifier sequence 1      Unique Identifier Sequence 2

*FIG. 152*

A. Linker design for sequencing and identifying mutations in both target strands. cfDNA of average length of about 160 bp. Repair ends with T4 polymerase or DNA Polymerase I, Large (Klenow) Fragment.

B. Phosphorylate 5' ends with T4 kinase.

C. Append C3 on 3' end using reverse transcriptase.

D. Hybridize primer pairs where the first has 3' rG3, a unique identifier sequence, and T30 tail, while the second is complementary to the first and has a primer binding site. Reverse transcriptase undergoes strand switching and copies unique identifier to fill gap.

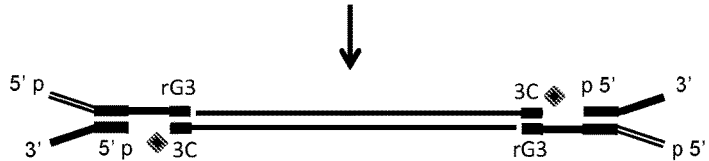

E. Ligase covalently seals extended target to second primer. RNaseH2 cleaves RNA bases, liberating 3'OH of rG3 in first primer

F. Polymerase fill gaps, and ligase covalently seals the extended ends.

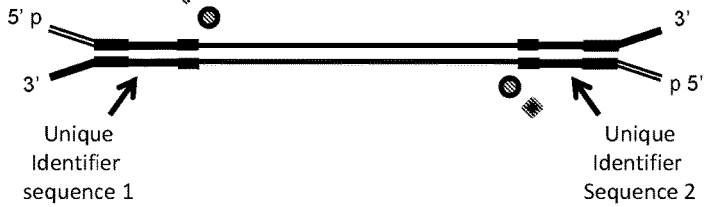

Unique Identifier sequence 1     Unique Identifier Sequence 2

*FIG. 153*

A. Two-sided targeted DNA amplification. Isolate DNA.

B. Tail 3' ends with Terminal deoxynucleotidyl transferase (TdT), using TTP to generate T(100-150).

C. Denature DNA and hybridize locus-specific primer with blocked 3' end. Primers are unblocked with RNaseH2 only when bound to target. Extend with polymerase to end to create single base (A) 3' overhang.

D. Ligate on linkers with single base T overhang and, 5' Blocked Universal primer(s). Optional: digest non-target genomic DNA with 5' nuclease.

E. Distribute onto an addressable matrix array, such that the T(100) tail hybridizes to dA30 primers immobilized to pillars on a solid support.

F. Extend hybridized primer with strand displacing Bst polymerase at 37oC. When raising the temperature to 55-60oC, the dA portion partially denatures, allowing for an adjacent primer to hybridize and polymerase displace the first primer strand. By this repetitive process, the original strand is "handed-off" to the next primer to achieve a linear amplification of the original DNA.

G. Meanwhile, Universal primer(s) in solution hybridizes to single-stranded extension product, and is extended by polymerase. As long as there are nearby dA30 primers, the process of handoff replication continues until primers are consumed. Untethered extension products are melted off the solid support and removed.

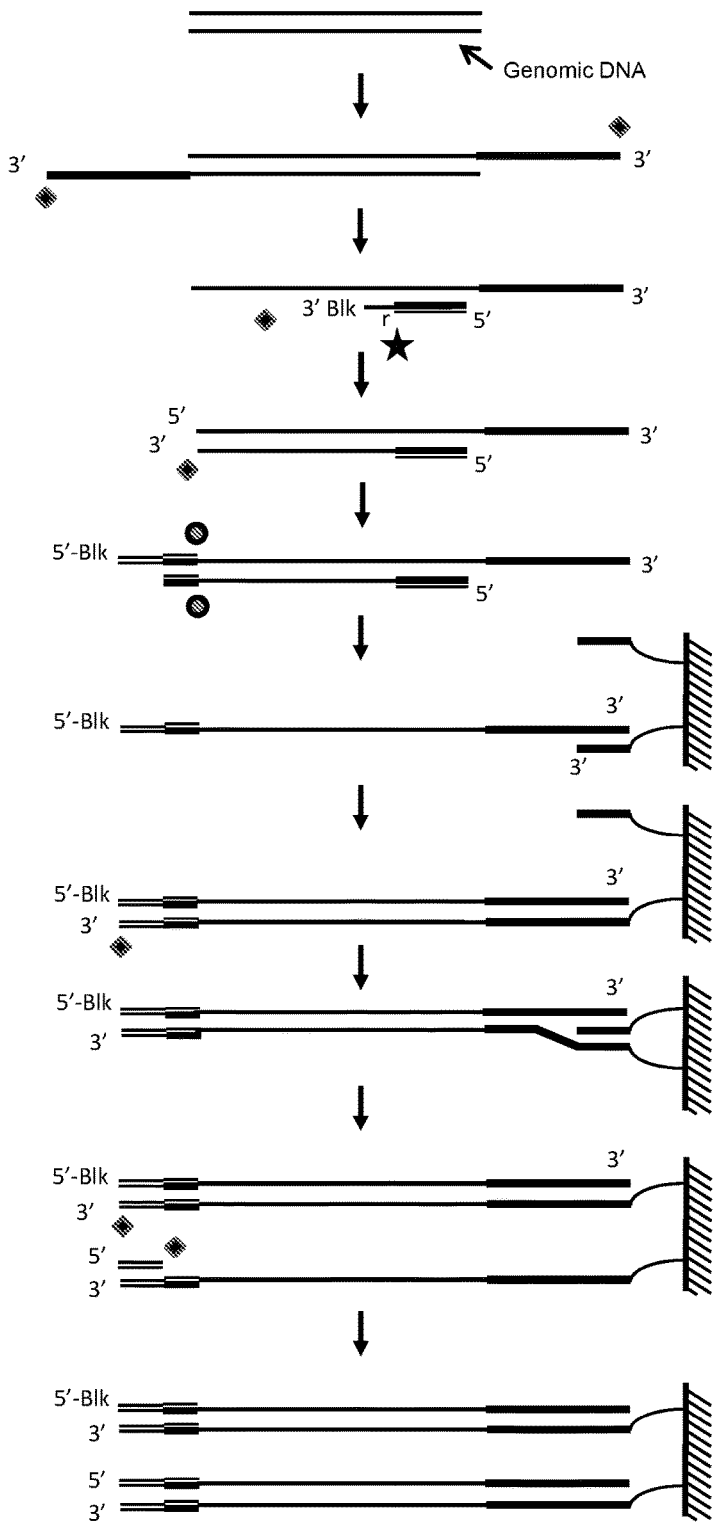

*FIG. 154*

A. Two-sided targeted DNA amplification. Isolate DNA.

B. Tail 3' ends with Terminal deoxynucleotidyl transferase (TdT), using TTP to generate T(100-150).

C. Denature DNA and hybridize locus-specific primer with blocked 3' end. Primers are unblocked with RNaseH2 only when bound to target. Extend with polymerase to end to create single base (A) 3' overhang.

D. Ligate on linkers with single base T overhang and, 5' Blocked Universal primer(s). Optional: digest non-target genomic DNA with 5' nuclease.

E. Distribute onto an addressable matrix array, such that the T(100) tail hybridizes to ss 3'-dA30 tail primers with AT rich dsDNA region, immobilized within hairpin to pillars on a solid support.

F. Extend hybridized primer with strand displacing Bst polymerase at 37oC. Polymerase also extends target T-tail through AT-hairpin. When raising the temperature to 55-60oC, the dA portion partially denatures, the partial hairpin reforms, allowing for an adjacent primer to hybridize and polymerase displace the first primer strand. By this repetitive process, the original strand is "handed-off" to the next primer to achieve a linear amplification of the original DNA.

G. Meanwhile, Universal primer(s) in solution hybridizes to single-stranded extension product, and is extended by polymerase. As long as there are nearby hairpin-ss-dA30 primers, the process of handoff replication continues until primers are consumed. Untethered extension products are melted off the solid support and removed.

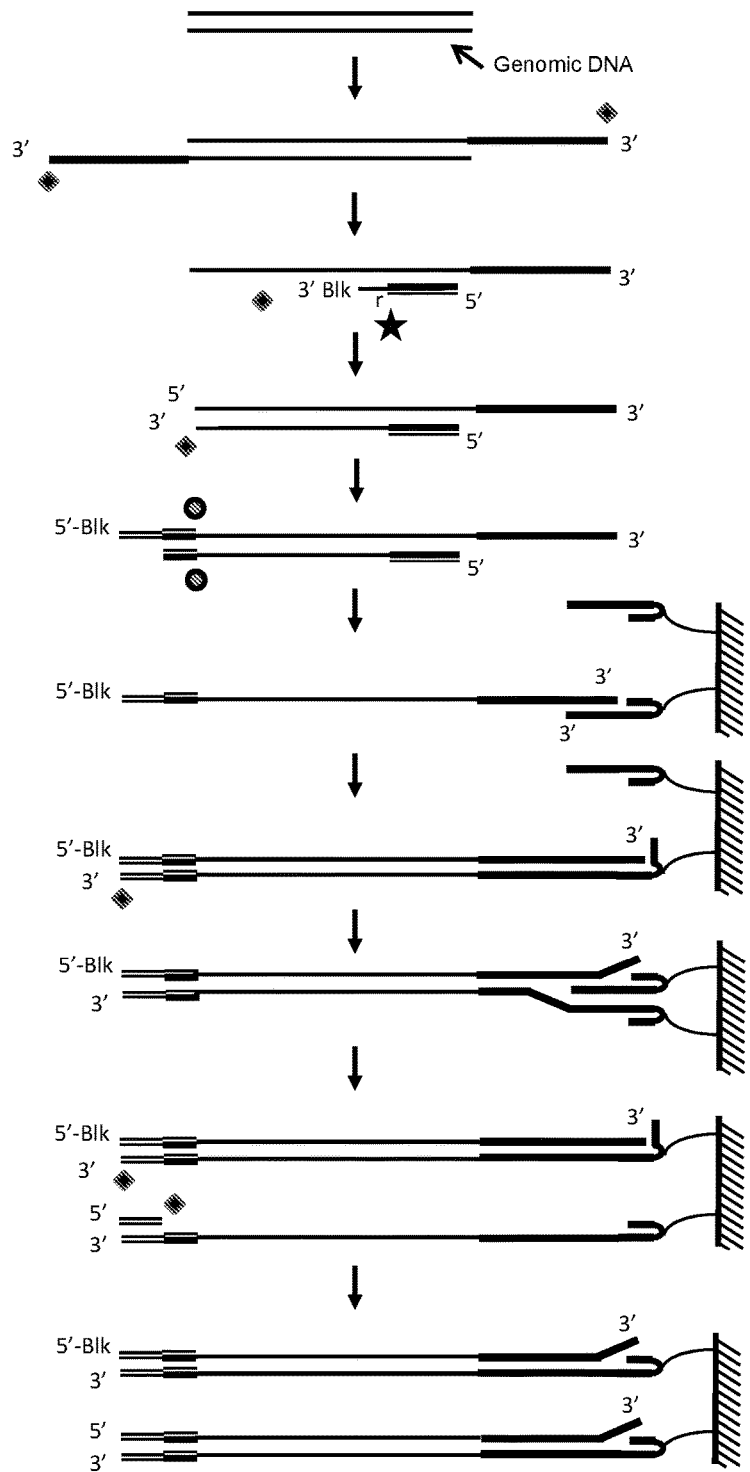

*FIG. 155*

A. Two-sided targeted DNA amplification. Isolate DNA.

B. Tail 3' ends with Terminal deoxynucleotidyl transferase (TdT), using TTP to generate T(100-150).

C. Denature DNA and hybridize locus-specific primer with optional blocked 3' end. Primers are unblocked with RNaseH2 only when bound to target. Hybridize target-specific primer and extend with reverse-transcriptase, which also appends C3 on 3' end of cDNA.

D. Hybridize second primer with 3' rG3, and universal primer(s) tail. Reverse transcriptase undergoes strand switching and copies second primer.

E. RNaseH2 cleaves RNA bases, liberating 3'OH adjacent to rG3 in second primer.

F. Polymerase with 5'-3' nuclease activity extends second primer and liberates 5' phosphate on target DNA. Ligase seals nick to ligate second primer to original target strand.

G. Distribute onto an addressable matrix array, such that the T(100) tail hybridizes to dA30 primers immobilized to pillars on a solid support.

H. Extend hybridized primer with strand displacing Bst polymerase at 37oC. When raising the temperature to 55-60oC, the dA portion partially denatures, allowing for an adjacent primer to hybridize and polymerase displace the first primer strand. By this repetitive process, the original strand is "handed-off" to the next primer to achieve a linear amplification of the original DNA.

I. Meanwhile, Universal primer(s) in solution hybridizes to single-stranded extension product, and is extended by polymerase. As long as there are nearby dA30 primers, the process of handoff replication continues until primers are consumed. Untethered extension products are melted off the solid support and removed.

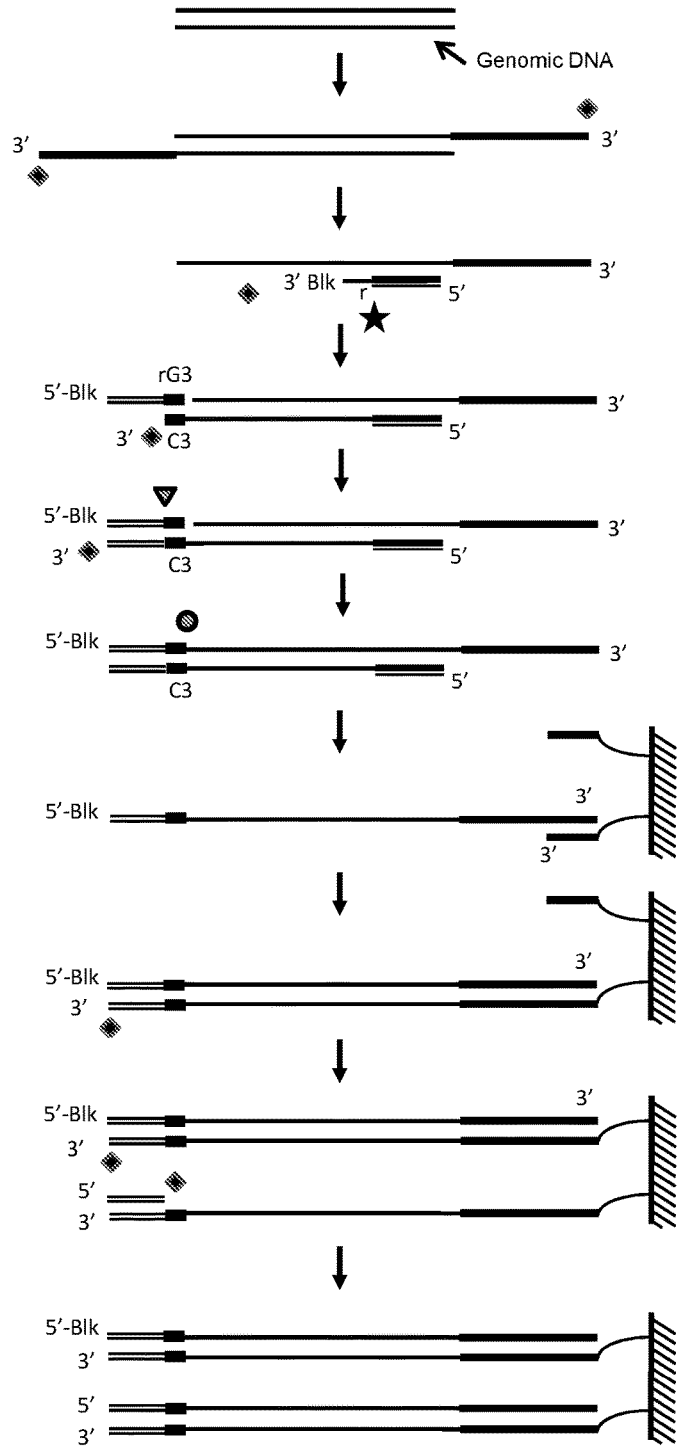

FIG. 156

A. Two-sided targeted DNA amplification. Isolate DNA.

B. Tail 3' ends with Terminal deoxynucleotidyl transferase (TdT), using TTP to generate T(100-150).

C. Denature DNA and hybridize locus-specific primer with optional blocked 3' end. Primers are unblocked with RNaseH2 only when bound to target. Hybridize target-specific primer and extend with reverse-transcriptase, which also appends C3 on 3' end of cDNA.

D. Hybridize second primer with 3' rG3, and universal primer(s) tail. Reverse transcriptase undergoes strand switching and copies second primer.

E. RNaseH2 cleaves RNA bases, liberating 3'OH adjacent to rG3 in second primer.

F. Polymerase with 5'-3' nuclease activity extends second primer and liberates 5' phosphate on target DNA. Ligase seals nick to ligate second primer to original target strand.

G. Distribute onto an addressable matrix array, such that the T(100) tail hybridizes to ss 3'-dA30 tail primers with AT rich dsDNA region, immobilized within hairpin to pillars on a solid support.

H. Extend hybridized primer with strand displacing Bst polymerase at 37oC. When raising the temperature to 55-60oC, the dA portion partially denatures, allowing for an adjacent primer to hybridize and polymerase displace the first primer strand. By this repetitive process, the original strand is "handed-off" to the next primer to achieve a linear amplification of the original DNA.

I. Meanwhile, Universal primer(s) in solution hybridizes to single-stranded extension product, and is extended by polymerase. As long as there are nearby hairpin-ss-dA30 primers, the process of handoff replication continues until primers are consumed. Untethered extension products are melted off the solid support and removed.

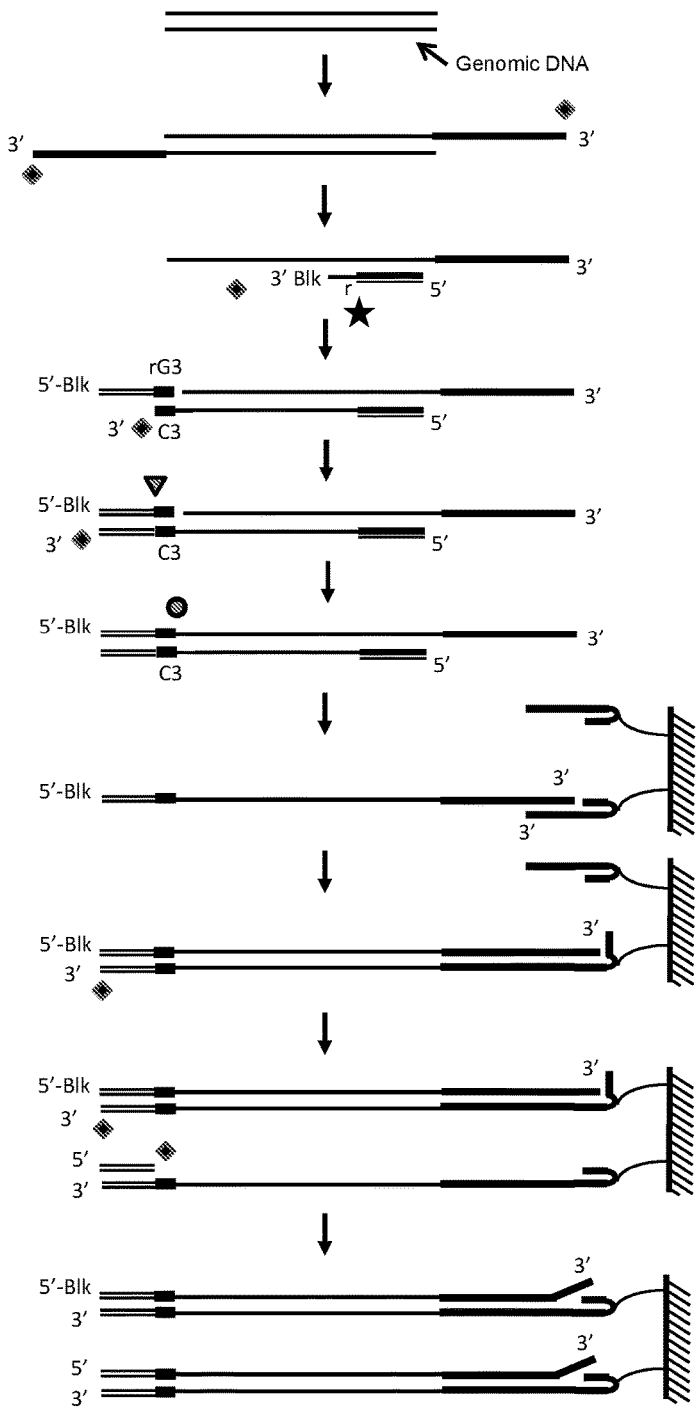

FIG. 157

A. Two-sided targeted DNA amplification, w/optional multiple Universal primers. Isolate DNA.

B. Denature DNA and hybridize locus-specific primer with 5'dA30 tails and blocked 3' end. Primers are unblocked with RNaseH2 only when bound to target. Extend with thermostable polymerase.

C. Denature DNA and hybridize locus-specific primer with 5'-blocked Universal primer(s) and blocked 3' end. Primers are unblocked with RNaseH2 only when bound to target. Extend with polymerase, and generate T30 on 3' end. Optional: Degrade dA30 primers with 5' nuclease.

D. Distribute onto an addressable matrix array, such that the T30 tail hybridizes to dA30 primers immobilized to pillars on a solid support.

E. Extend hybridized primer with strand displacing Bst polymerase at 37oC. When raising the temperature to 55-60oC, the dA portion partially denatures, allowing for an adjacent primer to hybridize and polymerase displace the first primer strand. By this repetitive process, the original strand is "handed-off" to the next primer to achieve a linear amplification of the original DNA.

F. Meanwhile, Universal primer(s) in solution hybridizes to single-stranded extension product, and is extended by polymerase. As long as there are nearby dA30 primers, the process of handoff replication continues until primers are consumed.

G. Untethered extension products are melted off the solid support and removed.

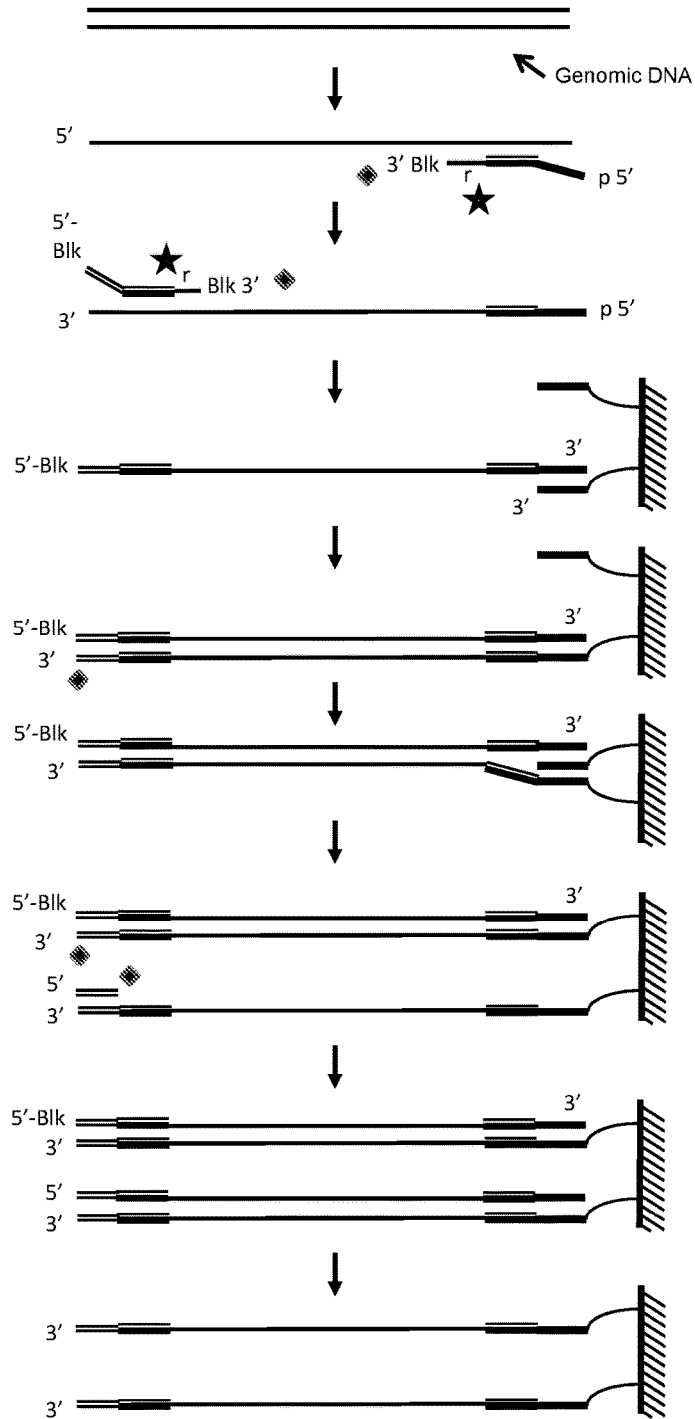

*FIG. 158*

A. Two-sided targeted DNA amplification, w/optional multiple Universal primers. Isolate DNA.

B. Denature DNA and hybridize locus-specific primer with 5'dA30 tails and blocked 3' end. Primers are unblocked with RNaseH2 only when bound to target. Extend with thermostable polymerase.

C. Denature DNA and hybridize locus-specific primer with 5'-blocked Universal primer(s) and blocked 3' end. Primers are unblocked with RNaseH2 only when bound to target. Extend with polymerase, and generate T30 on 3' end. Optional: Degrade dA30 primers with 5' nuclease.

D. Distribute onto an addressable matrix array, such that the T30 tail hybridizes to ss 3'-dA30 tail primers with AT rich dsDNA region, immobilized within hairpin to pillars on a solid support.

E. Extend hybridized primer with strand displacing Bst polymerase at 37oC. Polymerase also extends target T-tail through AT-hairpin. When raising the temperature to 55-60oC, the dA portion partially denatures, the partial hairpin reforms, allowing for an adjacent primer to hybridize and polymerase displace the first primer strand. By this repetitive process, the original strand is "handed-off" to the next primer to achieve a linear amplification of the original DNA.

F. Meanwhile, Universal primer(s) in solution hybridizes to single-stranded extension product, and is extended by polymerase. As long as there are nearby hairpin-ss-dA30 primers, the process of handoff replication continues until primers are consumed. Untethered extension products are melted off the solid support and removed.

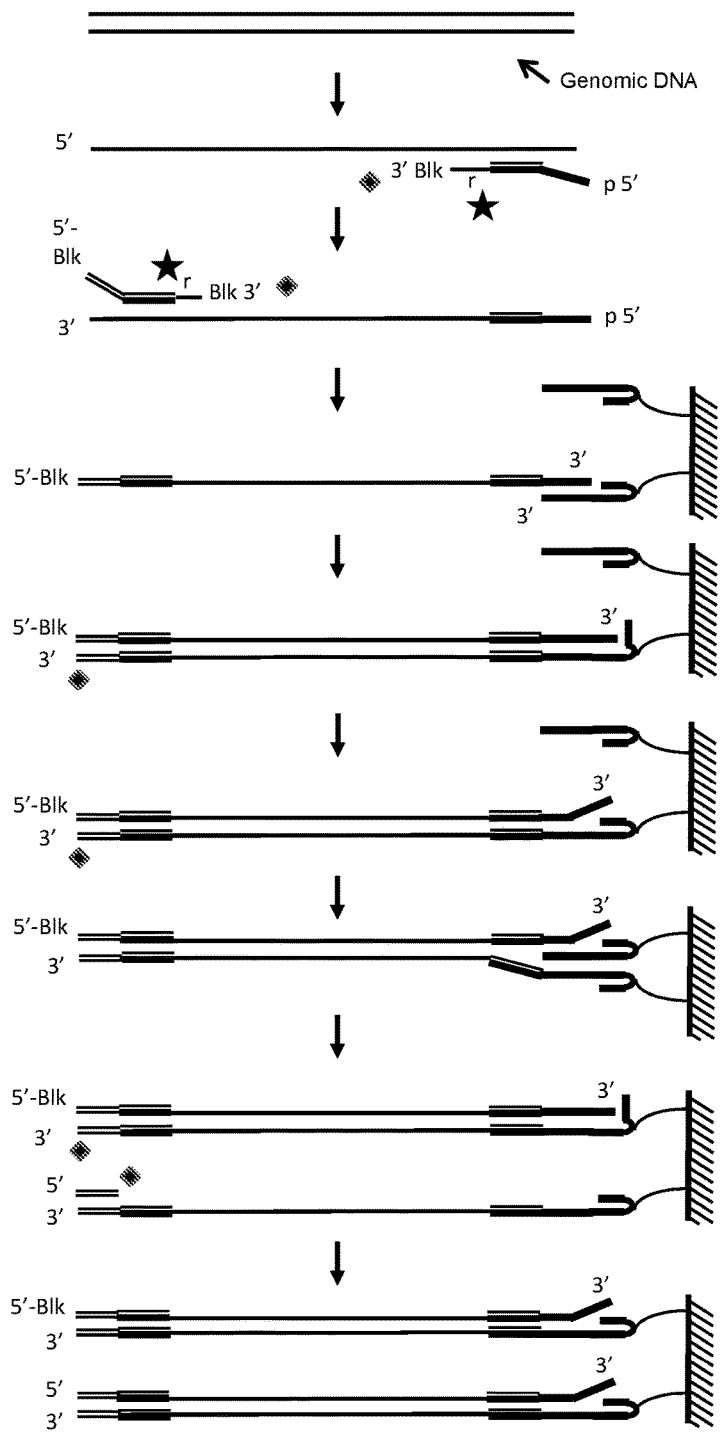

*FIG. 159*

A. Two-sided targeted DNA amplification, w/optional multiple Universal primers. Isolate DNA.

B. Tail 3' ends with Terminal deoxynucleotidyl transferase (TdT), using TTP to generate T(100-150).

C. Distribute onto an addressable matrix array, such that the T(100) tail hybridizes to dA30 primers immobilized to pillars on a solid support.

D. Extend hybridized primer with strand displacing Bst polymerase at 37oC. When raising the temperature to 55-60oC, the dA portion partially denatures, allowing for an adjacent primer to hybridize and polymerase displace the first primer strand. By this repetitive process, the original strand is "handed-off" to the next primer to achieve a linear amplification of the original DNA.

E. Meanwhile, locus-specific primer with 5' Universal primer(s) and blocked 3' end in solution hybridizes to single-stranded extension product. Primers are unblocked with RNaseH2 only when bound to target, and are extended by polymerase. As long as there are nearby dA30 primers, the process of handoff replication continues until primers are consumed. Extra Universal primer may also be added.

F. Untethered extension products are melted off the solid support and removed (not shown).

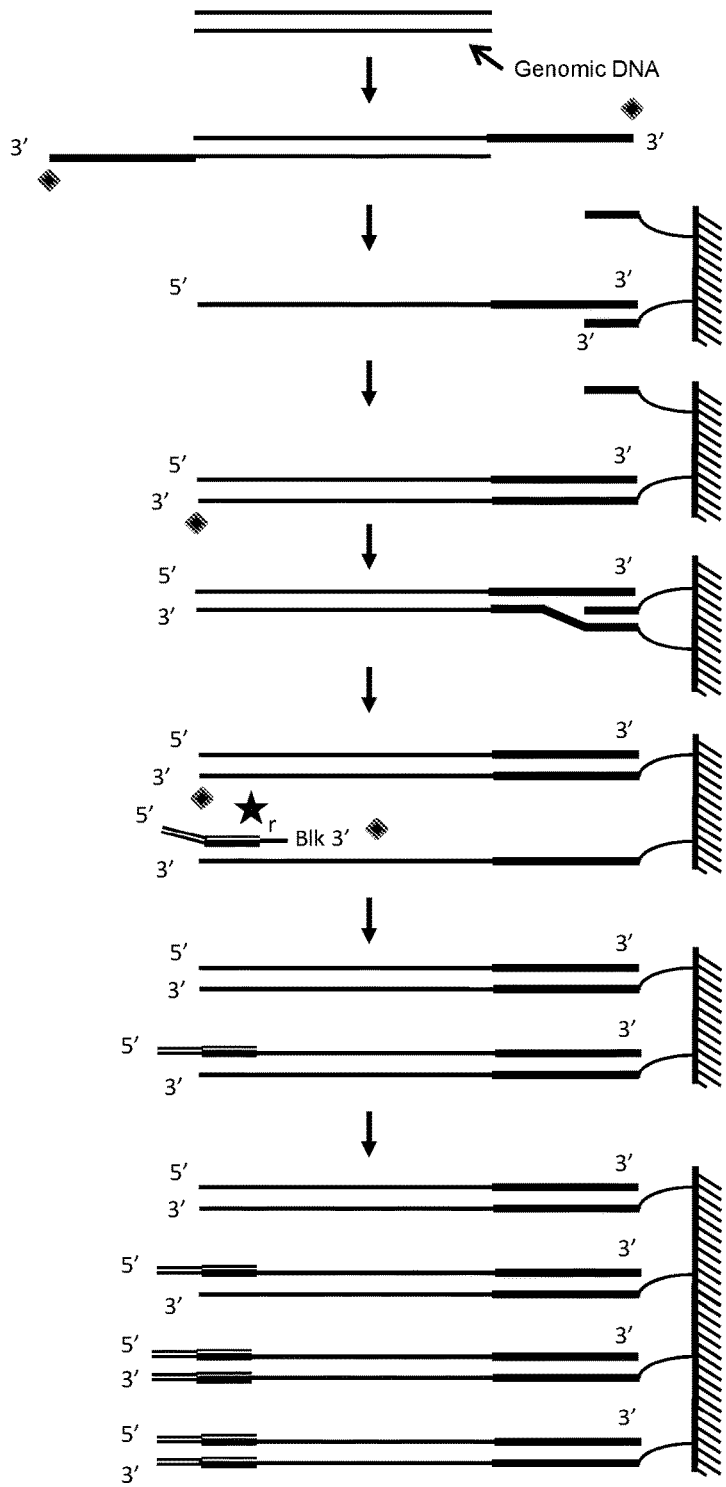

*FIG. 160*

A. Two-sided targeted DNA amplification, w/optional multiple Universal primers. Isolate DNA.

B. Tail 3' ends with Terminal deoxynucleotidyl transferase (TdT), using TTP to generate T(100-150).

C. Distribute onto an addressable matrix array, such that the T(100) tail hybridizes to ss 3'-dA30 tail primers with AT rich dsDNA region, immobilized within hairpin to pillars on a solid support.

D. Extend hybridized primer with strand displacing Bst polymerase at 37oC. Polymerase also extends target T-tail through AT-hairpin. When raising the temperature to 55-60oC, the dA portion partially denatures, the partial hairpin reforms, allowing for an adjacent primer to hybridize and polymerase displace the first primer strand. By this repetitive process, the original strand is "handed-off" to the next primer to achieve a linear amplification of the original DNA.

E. Meanwhile, locus-specific primer with 5' Universal primer(s) and blocked 3' end in solution hybridizes to single-stranded extension product. Primers are unblocked with RNaseH2 only when bound to target, and are extended by polymerase. As long as there are nearby hairpin-ss-dA30 primers, the process of handoff replication continues until primers are consumed. Extra Universal primer may also be added.

F. Untethered extension products are melted off the solid support and removed (not shown).

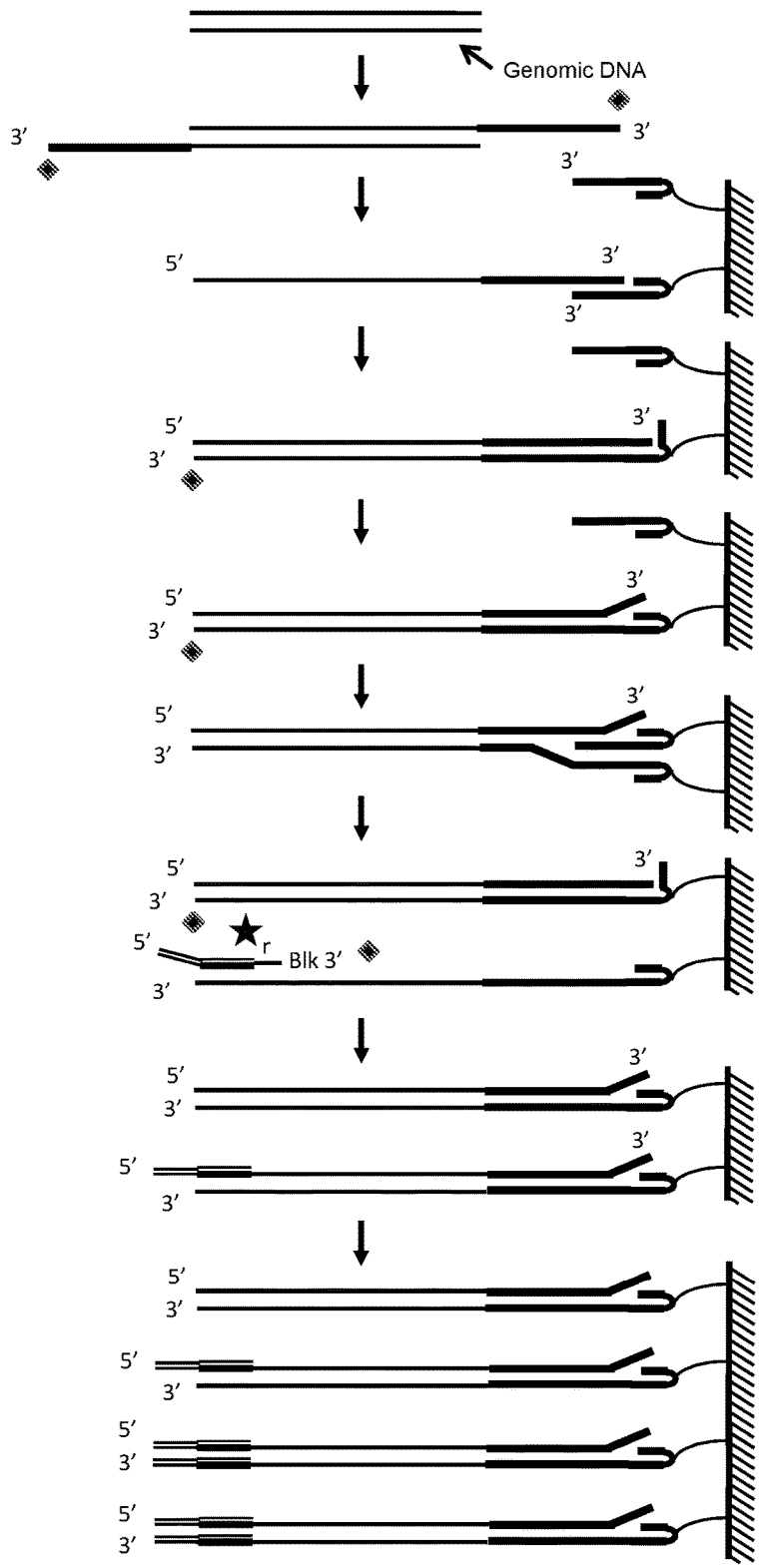

FIG. 161

A. Two-sided viral RNA targeted amplification, w/optional multiple Universal primers. Isolate DNA.

B. Denature DNA and hybridize tandem locus-specific primer with 5'-dA30 tails and extend with reverse transcriptase.

C. Denature DNA and hybridize tandem locus-specific primer with 5'-blocked Universal primer region(s). Extend with polymerase, and generate T30 on 3' end. Use of tandem primers improves detection even if sequence drifts. Optional: Degrade dA30 primers with 5' nuclease.

D. Distribute onto an addressable matrix array, such that the T30 tail hybridizes to ss 3'-dA30 tail primers with AT rich dsDNA region, immobilized within hairpin to pillars on a solid support.

E. Extend hybridized primer with strand displacing Bst polymerase at 37oC. Polymerase also extends target T-tail through AT-hairpin. When raising the temperature to 55-60oC, the dA portion partially denatures, the partial hairpin reforms, allowing for an adjacent primer to hybridize and polymerase displace the first primer strand. By this repetitive process, the original strand is "handed-off" to the next primer to achieve a linear amplification of the original DNA.

F. Meanwhile, Universal primer(s) in solution hybridizes to single-stranded extension product, and is extended by polymerase. As long as there are nearby hairpin-ss-dA30 primers, the process of handoff replication continues until primers are consumed. Untethered extension products are melted off the solid support and removed.

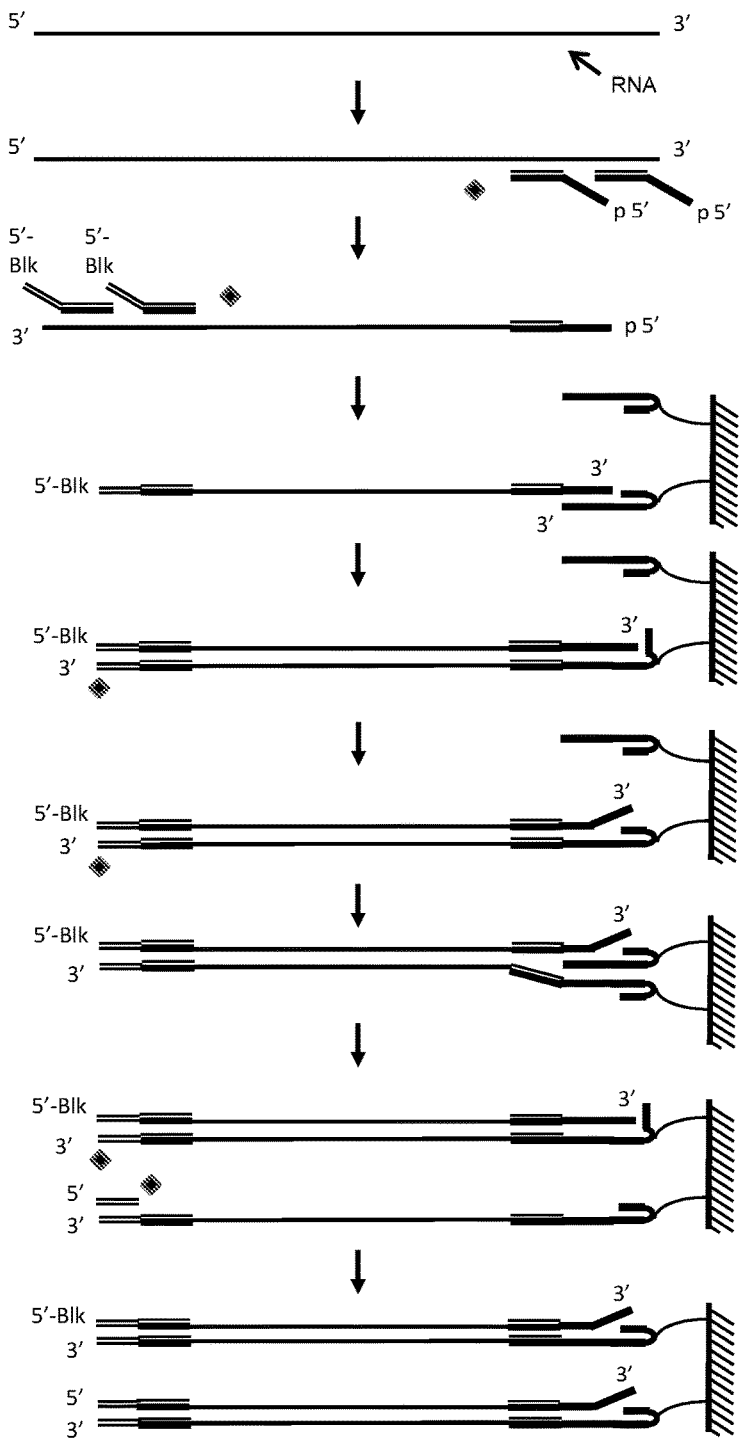

*FIG. 163*

A. cfDNA of average length of about 160 bp. Blunt ends, extend 3'end with a single A base, and ligate on linkers with T30 sequence, primer binding site, 3' single-base T overhang and optional 5' phosphate on other end.

B. Hybridize oligonucleotide containing sequences complementary to the 5' and 3' sides of the linkers. Oligonucleotide contains a primer-binding sequence, a dA30 sequence, an optional phosphate on 5' end, and a mismatched or blocked 3' end.

C. Polymerase with 5'-3' nuclease activity extends hybridized short linker 3' end and generates 5'-phospate on 5' linker.

D. Ligase covalently seals the adjacent ends of targets to create circular products.

E. Exonuclease(s) digest all unligated or nicked products leaving only desired single-stranded circular DNA comprising of original target DNA with T30 and a universal primer sequence. This product is suitable for optional additional steps and subsequent sequencing.

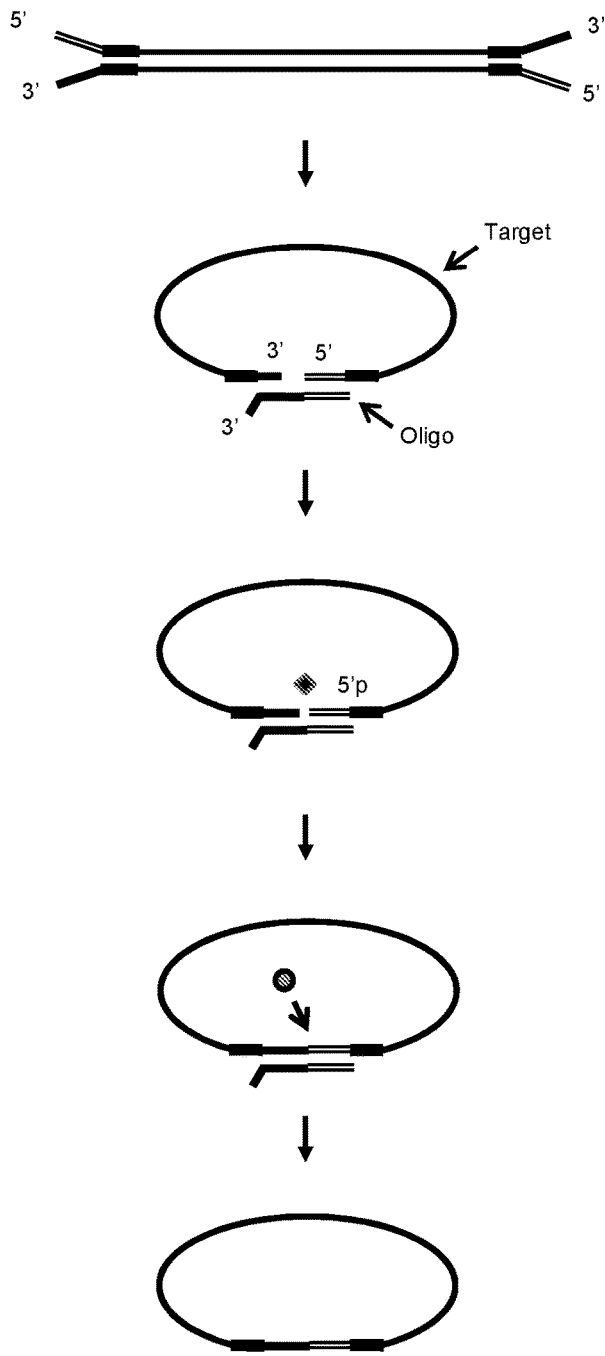

*FIG. 164*

A. cfDNA of average length of about 160 bp. Blunt ends, extend 3'end with a single A base, and ligate on A:T rich linkers with single-base T overhang and 5' phosphate on other end.

B. Hybridize oligonucleotides containing sequences complementary to a unique portion of the target, and the 5' and 3' sides of the linkers. Oligonucleotides contain a primer-binding sequence, a dA30 sequence, an optional phosphate on 5' end, a blocked 3' end, and a cleavable link (U).

C. Primers are unblocked with RNaseH2 only when bound to target. Polymerase extends hybridized 3' ends to copy the dA30 and Universal primer sequence. Extensions result in 3' ends directly adjacent to ligation competent 5' ends.

D. Ligase covalently seals the adjacent ends of both oligonucleotides and targets to create circular interlocked ligation products. Subsequently, a nick is introduced at the cleavable link of the oligonucleotide (e.g. UDG cleavage of U).

E. Exonuclease(s) digest all unligated or nicked products leaving only desired single-stranded circular DNA comprising of original target DNA with T30 and a universal primer sequence. This product is suitable for optional additional steps and subsequent sequencing.

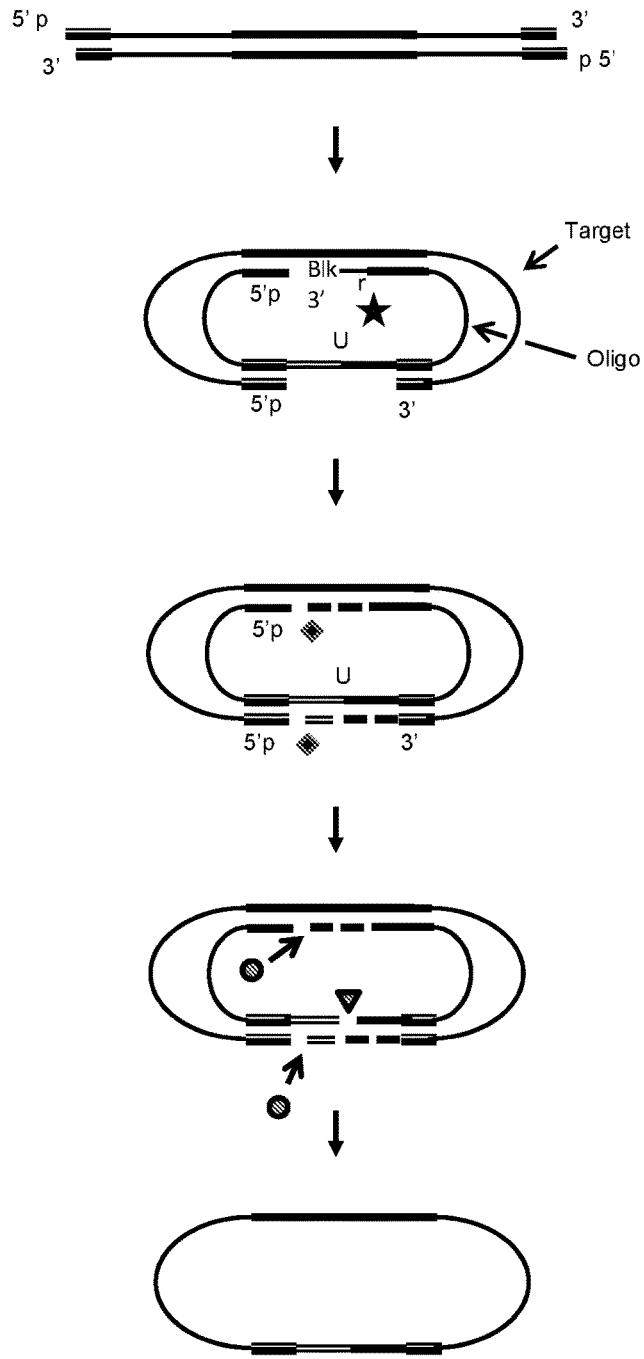

*FIG. 165*

A. cfDNA of average length of about 160 bp. Blunt ends, extend 3'end with a single A base, and ligate on linkers with T30 sequence, primer binding site, 3' single-base T overhang and 5' phosphate on other end.

B. Hybridize oligonucleotides containing sequences complementary to a unique portion of the target, and the 5' and 3' sides of the linkers. Oligonucleotides contain a primer-binding sequence, a dA30 sequence, an optional phosphate on 5' end, a blocked 3' end, and one or more cleavable links (U).

C. Primers are unblocked with RNaseH2 only when bound to target. Polymerase extends hybridized 3' end of linker as well as some target. Extensions result in 3' ends directly adjacent to ligation competent 5' ends.

D. Ligase covalently seals the adjacent ends of both oligonucleotides and targets to create circular interlocked ligation products. Subsequently, one or more nicks are introduced at the cleavable links of the oligonucleotide (e.g. UDG cleavage of U).

E. Exonuclease(s) digest all unligated or nicked products leaving only desired single-stranded circular DNA comprising of original target DNA with T30 and a universal primer sequence. This product is suitable for optional additional steps and subsequent sequencing.

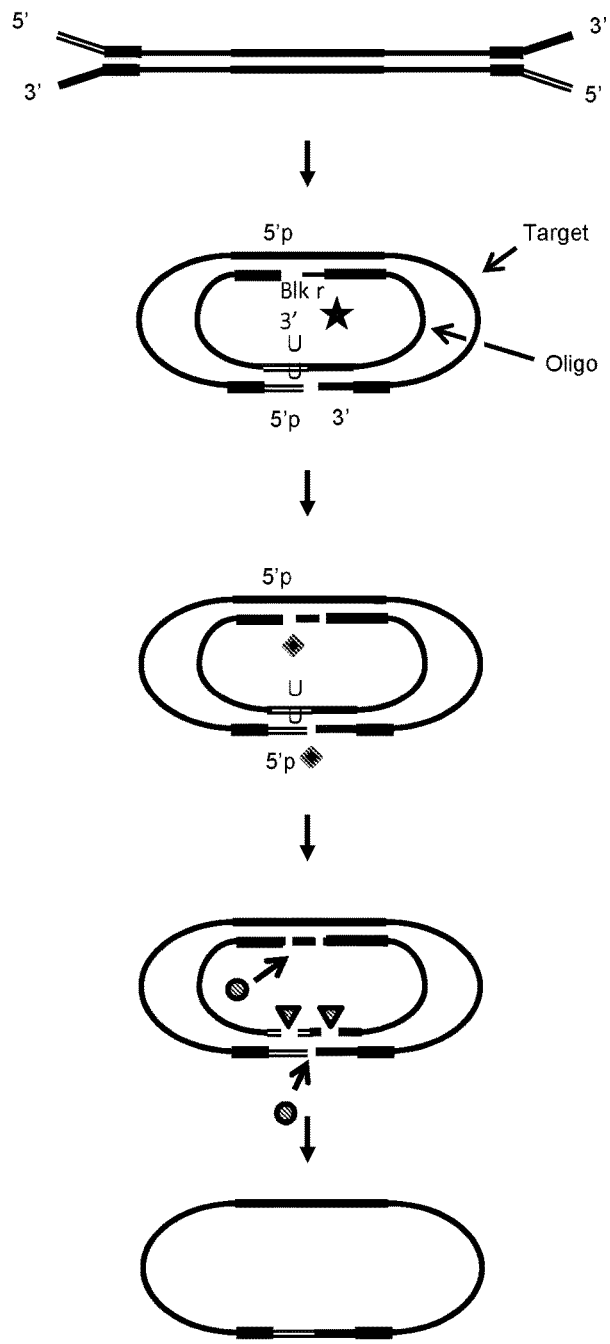

*FIG. 166*

A. cfDNA of average length of about 160 bp. Blunt ends, extend 3'end with a single A base, and ligate on A:T rich linkers with single-base T overhang and 5' phosphate on other end.

B. Hybridize oligonucleotides containing sequences complementary to a unique portion of the target, and the 5' and 3' sides of the linkers. Oligonucleotides contain a primer-binding sequence, a dA30 sequence, a phosphate on 5' end, a blocked 3' end, and a cleavable link (U).

C. Primers are unblocked with RNaseH2 only when bound to target. Ligase seals adjacent oligonucleotide ends. Polymerase extends hybridized 3' ends to copy the dA30 and Universal primer sequence. Extensions result in 3' ends directly adjacent to ligation competent 5' ends.

D. Ligase covalently seals the adjacent ends of extended targets to create circular interlocked ligation products. Subsequently, a nick is introduced at the cleavable link of the oligonucleotide (e.g. UDG cleavage of U).

E. Exonuclease(s) digest all unligated or nicked products leaving only desired single-stranded circular DNA comprising of original target DNA with T30 and a universal primer sequence. This product is suitable for optional additional steps and subsequent sequencing.

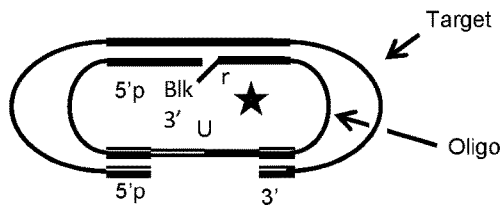
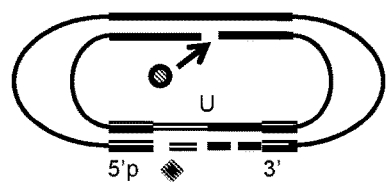
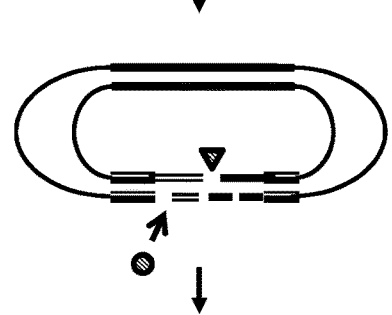

*FIG. 167*

A. cfDNA of average length of about 160 bp. Blunt ends, extend 3'end with a single A base, and ligate on linkers with T30 sequence, primer binding site, 3' single-base T overhang and 5' phosphate on other end.

B. Hybridize oligonucleotides containing sequences complementary to a unique portion of the target, and the 5' and 3' sides of the linkers. Oligonucleotides contain a primer-binding sequence, a dA30 sequence, an optional phosphate on 5' end, a blocked 3' end, and one or more cleavable links (U).

C. Primers are unblocked with RNaseH2 only when bound to target. Ligase seals adjacent target ends. Polymerase extends hybridized 3' end of linker. Extensions result in 3' ends directly adjacent to ligation competent 5' ends.

D. Ligase covalently seals the adjacent ends of oligonucleotides to create circular interlocked ligation products. Subsequently, one or more nicks are introduced at the cleavable links of the oligonucleotide (e.g. UDG cleavage of U).

E. Exonuclease(s) digest all unligated or nicked products leaving only desired single-stranded circular DNA comprising of original target DNA with T30 and a universal primer sequence. This product is suitable for optional additional steps and subsequent sequencing.

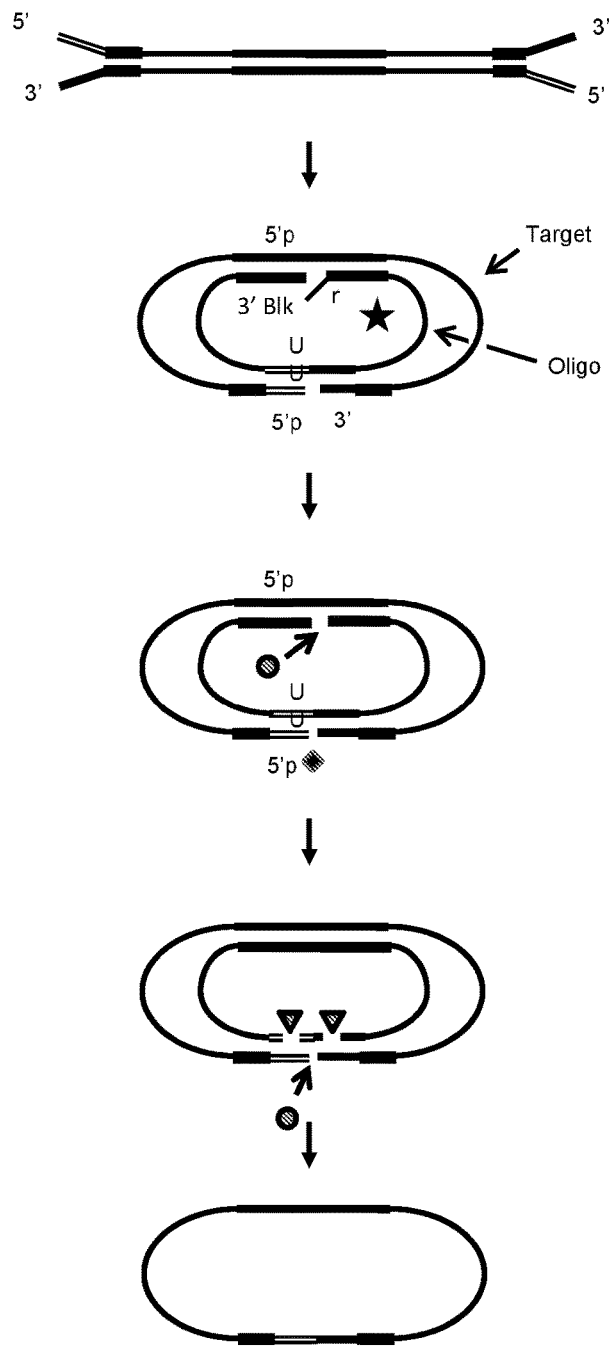

*FIG. 168*

A. cfDNA of average length of about 160 bp. Add T30-50 tails with terminal transferase.

B. Hybridize oligonucleotides containing sequences complementary to the 5' and 3' sides of the target, as well as complementary to the 3' tail. Oligonucleotides contain a primer-binding sequence, a dA50 sequence, and a cleavable link (U).

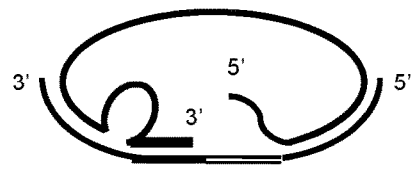

C. Polymerase extends hybridized T30-50 3' tail end to copy rest of dA50 and universal primer sequence, with 5'-nuclease cleavage of matching 5'-overlapping base of target, leaving ligation-competent 5'-phospate. Polymerase also extends 3' end of oligonucleotide on target.

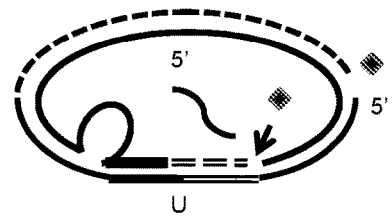

D. Ligase covalently seals the extended ends to create circular ligation products. Subsequently, a nick is introduced at the cleavable link of the oligonucleotide (e.g. UDG cleavage of U).

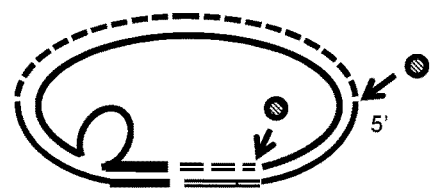

E. Exonuclease(s) digest all unligated or nicked products leaving only desired single-stranded circular DNA comprising of original target DNA with T30 and a universal primer sequence. This product is suitable for optional additional steps and subsequent sequencing.

*FIG. 169*

A. cfDNA of average length of about 160 bp. Blunt ends, extend 3'end with a single A base, and ligate on A:T rich linkers with single-base T overhang.

B. Hybridize oligonucleotides containing sequences complementary to the 5' and 3' sides of the target. Oligonucleotides contain a dA30 sequence, a primer-binding sequence, and a cleavable link (U).

C. Polymerase extends hybridized short linker 3' end to copy the dA30 and universal primer sequences, with 5'-nuclease cleavage of matching 5'-overlapping base of target, leaving ligation-competent 5'-phospate. Polymerase also extends 3' end of oligonucleotide on target.

D. Ligase covalently seals the extended ends to create circular ligation products. Subsequently, a nick is introduced at the cleavable link of the oligonucleotide (e.g. UDG cleavage of U).

E. Exonuclease(s) digest all unligated or nicked products leaving only desired single-stranded circular DNA comprising of original target DNA with T30 and a universal primer sequence. This product is suitable for optional additional steps and subsequent sequencing.

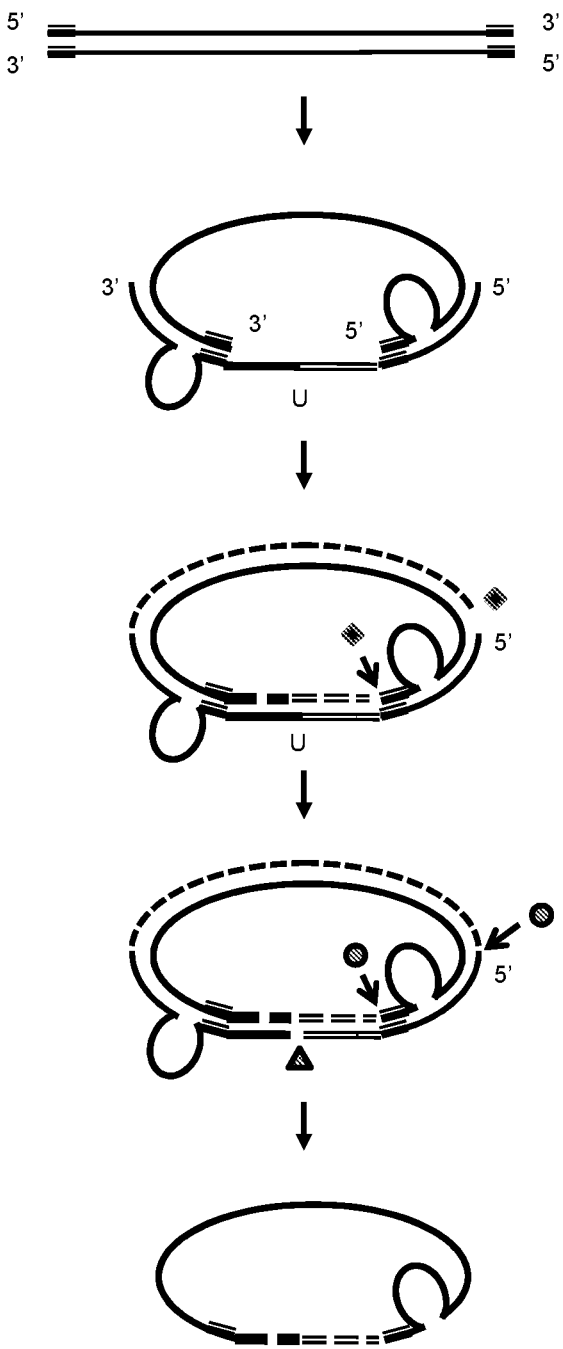

*FIG. 170*

A. cfDNA of average length of about 160 bp.

B. Hybridize oligonucleotides containing sequences complementary to the 5' and 3' sides of the target, with optional mismatches about every 12-15 bases. Oligonucleotides contain a primer-binding sequence, a dA30 sequence, and a cleavable link (U).

C. Polymerase with 3'-nuclease removes single stranded 3' end (if needed), then copies dA30 and universal primer sequence, with 5'-nuclease cleavage of matching 5'-overlapping base of target, leaving ligation-competent 5'-phospate. Polymerase also extends 3' end of oligonucleotide on target.

D. Ligase covalently seals the extended ends to create circular ligation products. Subsequently, a nick is introduced at the cleavable link of the oligonucleotide (e.g. UDG cleavage of U).

E. Exonuclease(s) digest all unligated or nicked products leaving only desired single-stranded circular DNA comprising of original target DNA with T30 and a universal primer sequence. This product is suitable for optional additional steps and subsequent sequencing.

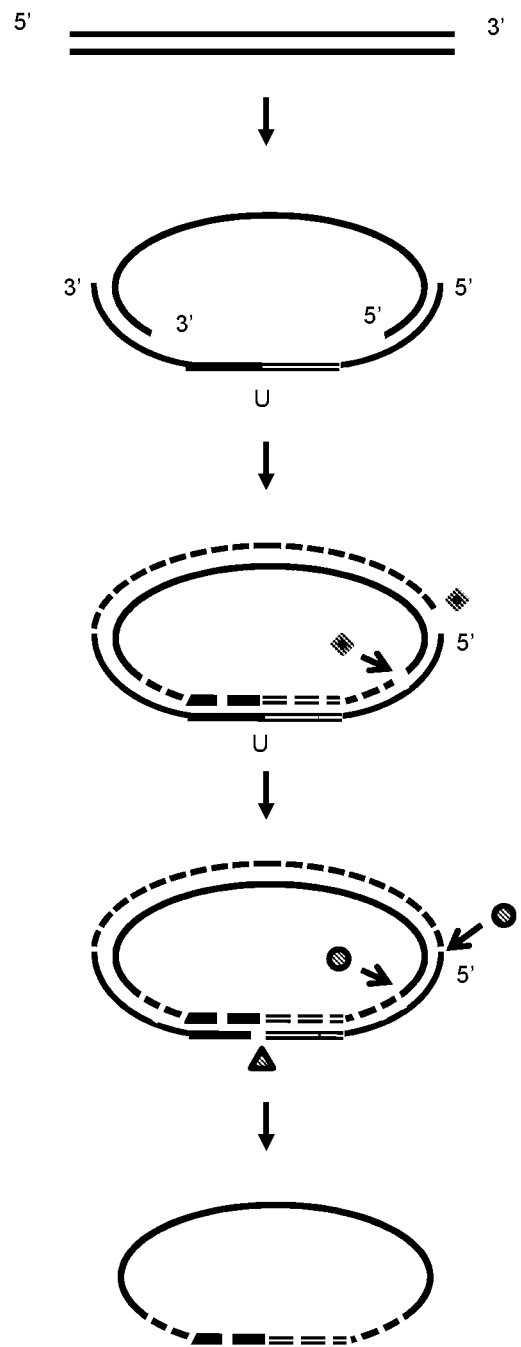

FIG. 171

A. Potentially methylated cfDNA of average length of about 160 bp. (Optional, cleave with methyl-sensitive restriction enzymes.)

B. Treat with bisulfite, which converts unmethylated dC to dU, and renders the strands non-complementary.

C. Hybridize oligonucleotides containing sequences complementary to the 5' and 3' sides of the target, with optional mismatches at CpG bases. Oligonucleotides contain a primer-binding sequence, a dA30 sequence, and a cleavable link (i.e. abasic site; Ab).

D. Polymerase with 3'-nuclease removes single stranded 3' end (if needed), then copies dA30 and universal primer sequence, with 5'-nuclease cleavage of matching 5'-overlapping base of target, leaving ligation-competent 5'-phospate. Polymerase also extends 3' end of oligonucleotide on target.

E. Ligase covalently seals the extended ends to create circular ligation products. Subsequently, a nick is introduced at the cleavable link of the oligonucleotide (e.g. AP endonuclease cleavage of Ab). Unmethylated DNA may also be cleaved with restriction endonucleases.

F. Exonuclease(s) digest all unligated or nicked products leaving only desired single-stranded circular DNA comprising of original target DNA with T30 and a universal primer sequence. This product is suitable for optional additional steps and subsequent sequencing.

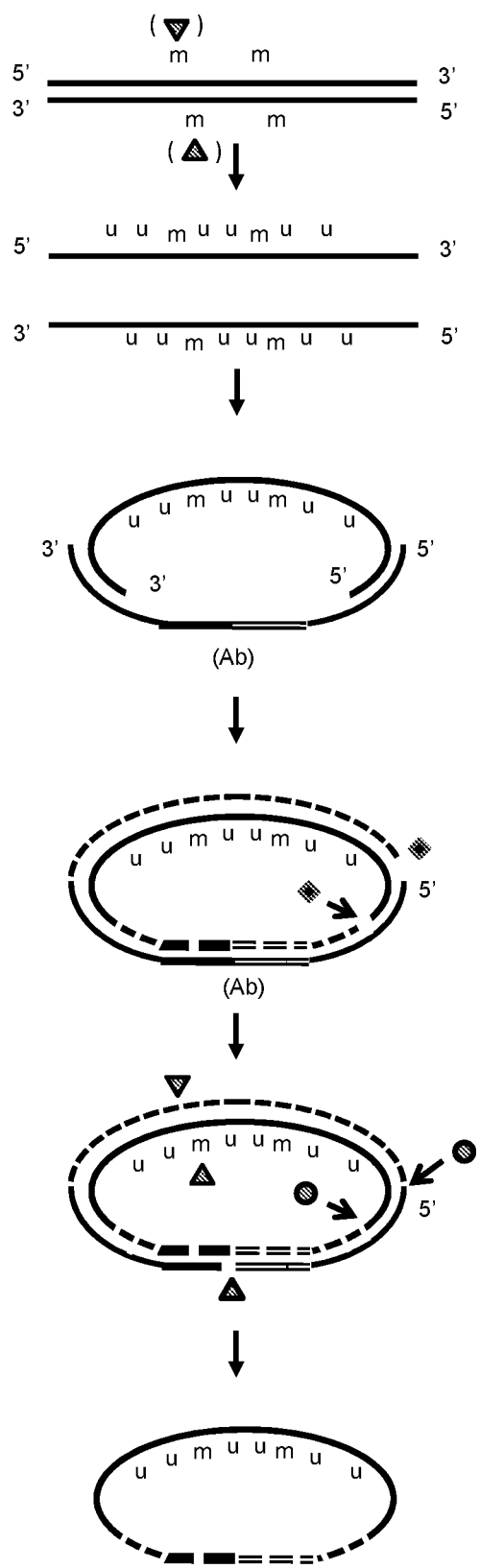

FIG. 172

A. Two-sided targeted DNA rolling circle amplification. Isolate DNA.

B. Generate circular DNA containing a T30 and one or more Universal Primer sequences. Distribute onto an addressable matrix array, such that the T30 region hybridizes to dA30 primers immobilized to pillars on a solid support.

C. Extend hybridized primer with strand displacing Bst polymerase at 37oC to initiate rolling circle amplification. Meanwhile, Universal primer(s) in solution hybridizes to single-stranded regions in rolling circle product, and is extended by polymerase.

D. When raising the temperature to 55-60oC, the dA portion partially denatures, allowing for an adjacent primer to hybridize and polymerase displace the first primer strand. By this repetitive process, each universal primer extension strand is "handed-off" to the next primer to achieve a linear amplification of the original DNA.

E. Even if a universal primer extension product is released in solution, it will bind to a fresh dA30 primer at the same or nearby pillar, and amplification continues. As long as there are nearby dA30 primers, the process of handoff replication continues until primers are consumed.

F. Untethered extension products are melted off the solid support and removed (Not shown).

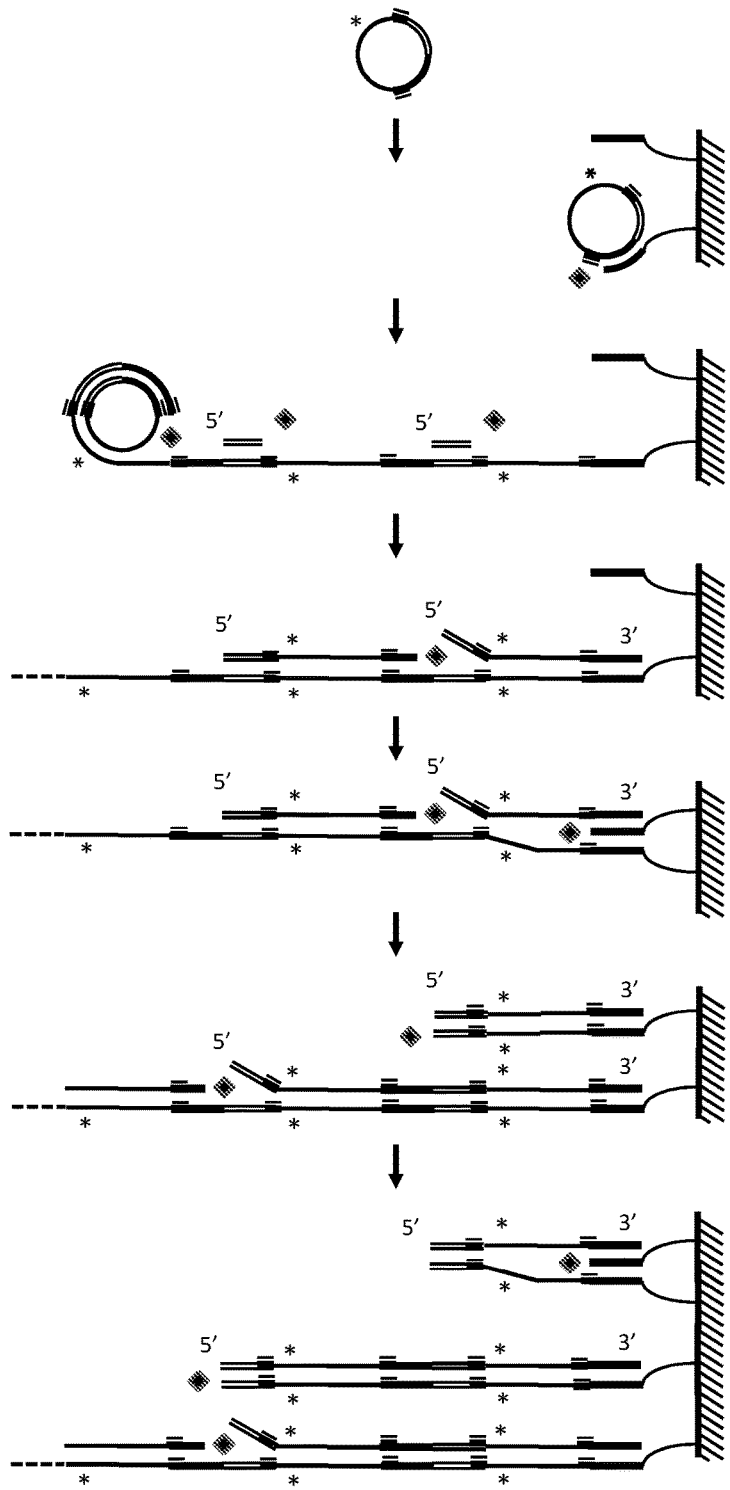

*FIG. 173*

A. Targeted DNA rolling circle amplification. Isolate DNA.

B. Generate circular DNA containing a T30 and one or more Universal Primer sequences. Distribute onto an addressable matrix array, such that the T30 region hybridizes to dA30 primers immobilized to pillars on a solid support.

C. Extend hybridized primer with strand displacing Bst polymerase at 37oC to initiate rolling circle amplification. Meanwhile, targeted primer(s) in solution hybridizes to single-stranded regions in rolling circle product, and is extended by polymerase.

D. When raising the temperature to 55-60oC, the dA portion partially denatures, allowing for an adjacent primer to hybridize and polymerase displace the first primer strand. By this repetitive process, each targeted primer extension strand is "handed-off" to the next primer to achieve a linear amplification of the original DNA.

E. Even if a targeted primer extension product is released in solution, it will bind to a fresh dA30 primer at the same or nearby pillar, and amplification continues. As long as there are nearby dA30 primers, the process of handoff replication continues until primers are consumed.

F. Untethered extension products are melted off the solid support and removed (Not shown).

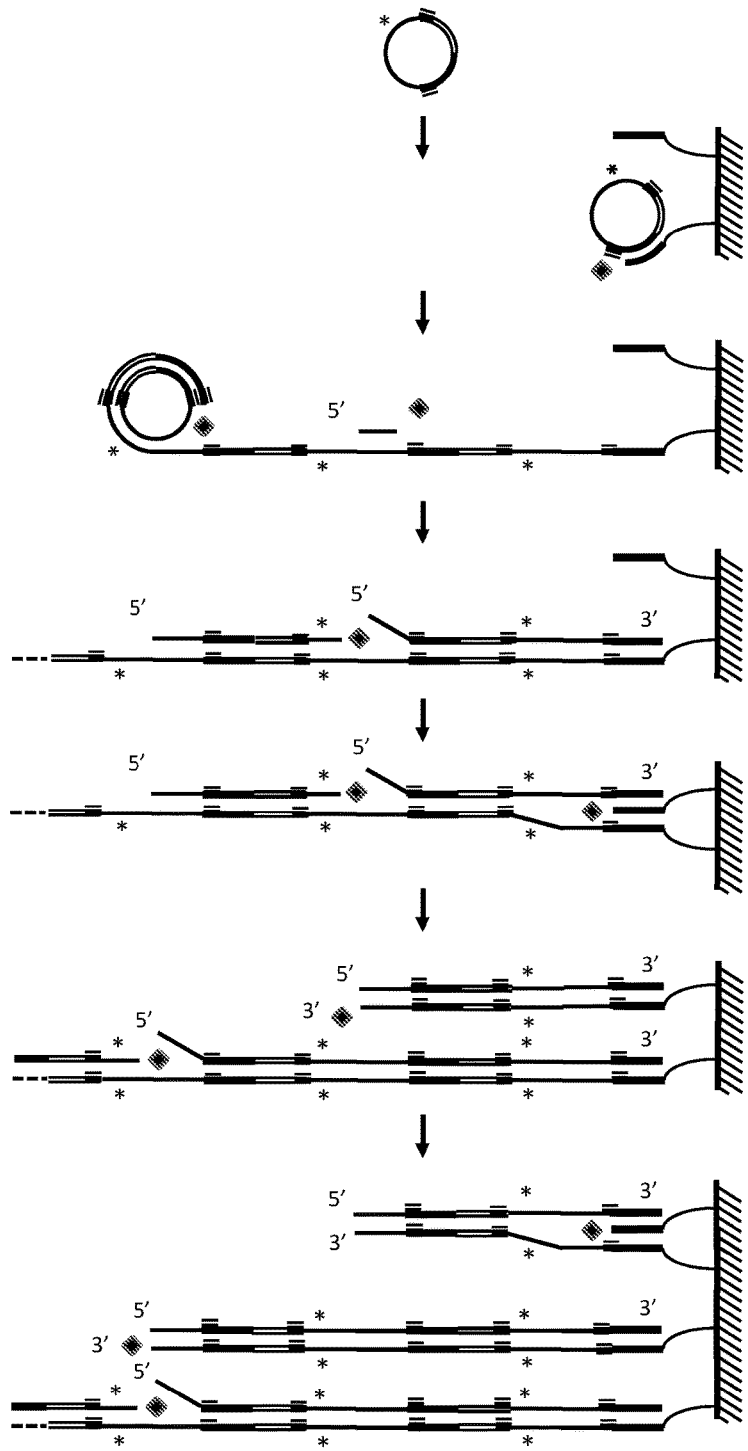

FIG. 174

A. Targeted DNA rolling circle amplification. Isolate DNA.

B. Generate circular DNA containing a T30 and one or more Universal Primer sequences. Distribute onto an addressable matrix array, such that the T30 region hybridizes to dA30 primers immobilized to pillars on a solid support.

C. Extend hybridized primer with strand displacing Phi 29 or Bst polymerase at 37oC to initiate rolling circle amplification. Denature and remove circular DNA.

D. Add targeted primer(s), which hybridizes to single-stranded regions in rolling circle product, and is extended by Bst polymerase.

E. When raising the temperature to 55-60oC, the dA portion partially denatures, allowing for an adjacent primer to hybridize and polymerase displace the first primer strand. By this repetitive process, each targeted primer extension strand is "handed-off" to the next primer to achieve a linear amplification of the original DNA.

F. Even if a targeted primer extension product is released in solution, it will bind to a fresh dA30 primer at the same or nearby pillar, and amplification continues. As long as there are nearby dA30 primers, the process of handoff replication continues until primers are consumed.

G. Untethered extension products are melted off the solid support and removed (Not shown).

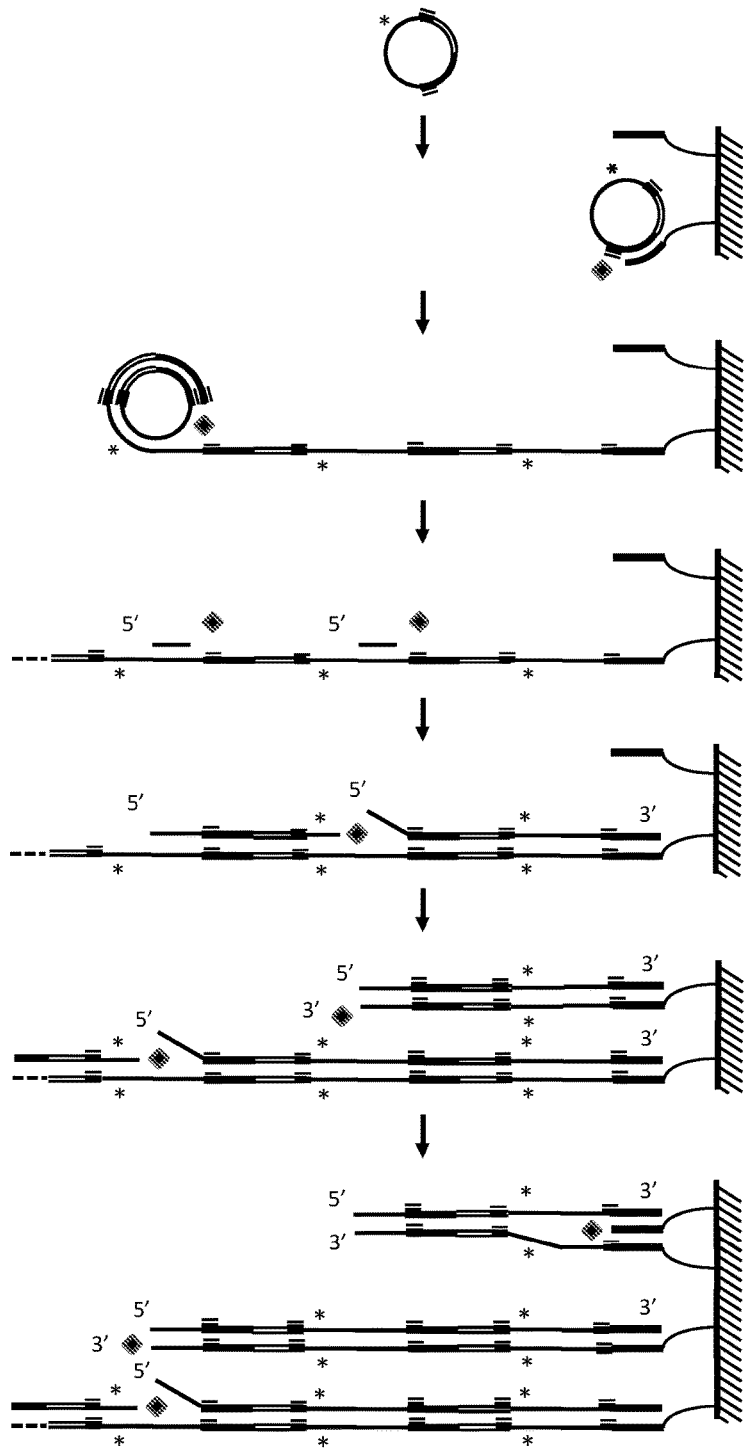

*FIG. 175*

A. Two-sided targeted DNA rolling circle amplification. Isolate DNA.

B. Generate circular DNA containing a T30 and one or more Universal Primer sequences. Distribute onto an addressable matrix array, such that the T30 region hybridizes to dA30 primers immobilized to pillars on a solid support.

C. Extend hybridized primer with strand displacing Bst polymerase at 37oC to initiate rolling circle amplification. Meanwhile, Universal primer(s) in solution hybridizes to single-stranded regions in rolling circle product, and is extended by polymerase.

D. When raising the temperature to 55-60oC, the dA portion partially denatures, allowing for an adjacent primer to hybridize and polymerase displace the first primer strand. By this repetitive process, each universal primer extension strand is "handed-off" to the next primer to achieve a linear amplification of the original DNA.

E. Even if a universal primer extension product is released in solution, it will bind to a fresh dA30 primer at the same or nearby pillar, and amplification continues. As long as there are nearby dA30 primers, the process of handoff replication continues until primers are consumed.

F. Untethered extension products are melted off the solid support and removed (Not shown).

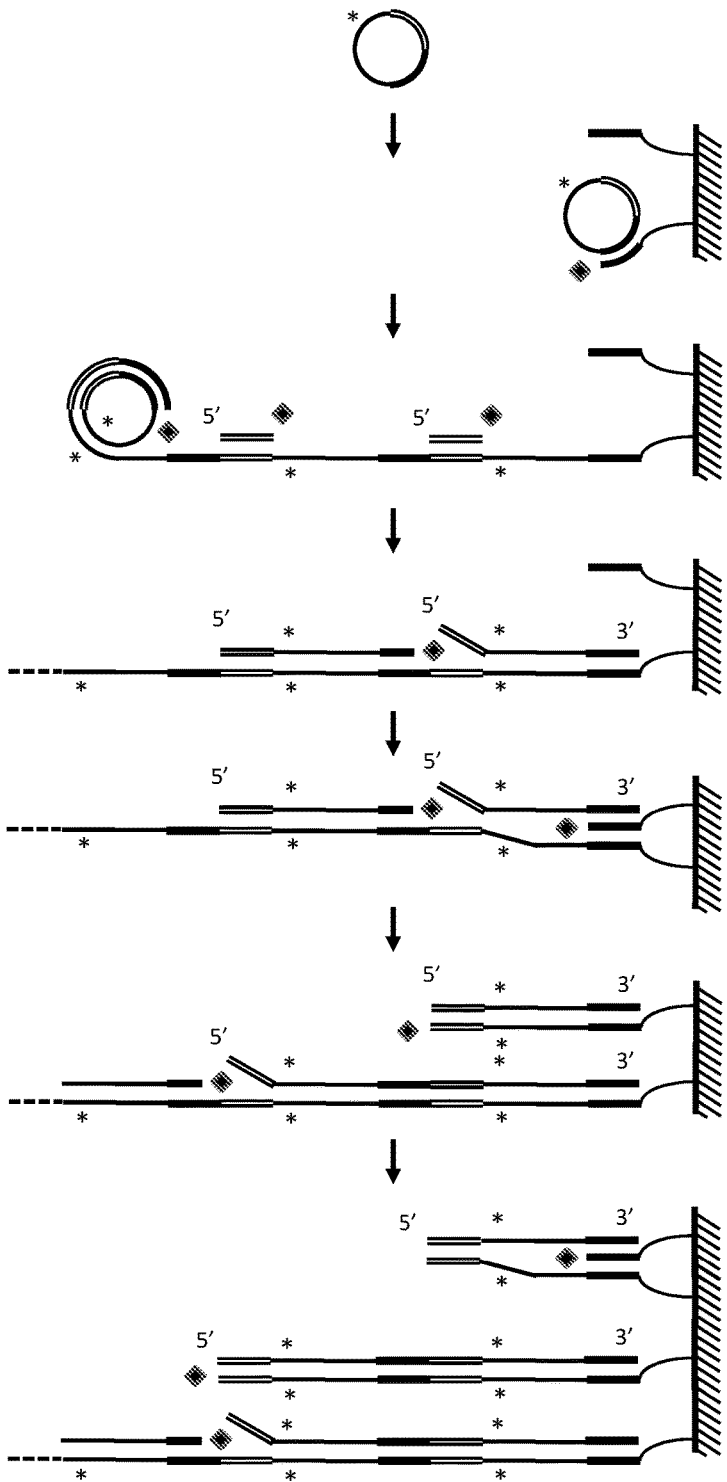

*FIG. 176*

A. Pixel-Sequencing, v01. Hybridize target-specific primers with blocked 3' end. Primers are unblocked with RNaseH2 only when bound to target.

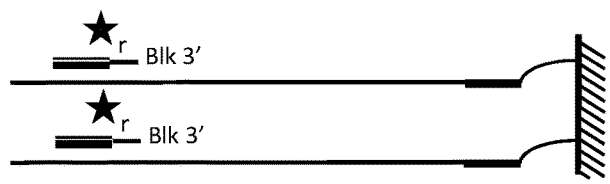

B. Extend primers with nucleotide analogue dNTPs containing different cleavable identifying signature modifier that prevent addition of the next dNTP.

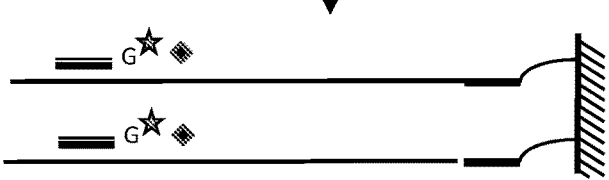

C. Wash away unincorporated analogue dNTPs. Add cleaving reagent, cleave, collect, and detect identifying signature modifiers using nanoscale flight tubes to identify base that was last incorporated.

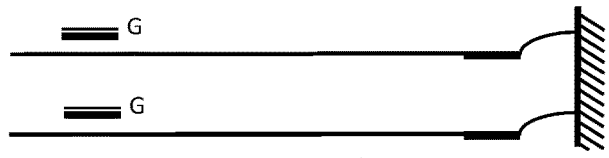

D. Wash away cleaving reagent. Add fresh set of nucleotide analogue dNTPs.

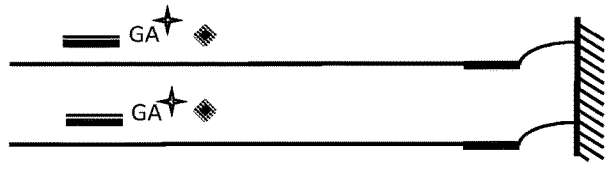

E. Wash. Cleave. Collect. Identify last incorporated base.

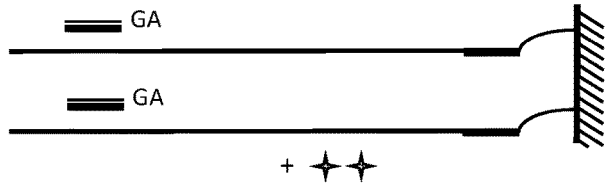

F. Repeat process to collect sequence information.

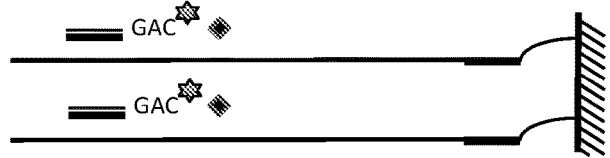

*FIG. 177*

A. Pixel-Sequencing, v02. Hybridize target-specific primers containing a 5' 15-20 base anchor sequence, 1-5 analogue, abasic, cleavable, or mismatched bases, and 6-10 matched bases on the 3' end.

B. Extend primers with dATP, dCTP, TTP, and a dG nucleotide analogue containing a cleavable identifying signature modifier that prevent addition of the next dNTP.

C. Wash away unincorporated analogue dNTPs. Add cleaving reagent, cleave, collect, and detect identifying signature modifiers using nanoscale flight tubes to identify base that was last incorporated.

D. Wash away cleaving reagent. Add fresh set of nucleotide analogue dNTPs containing different cleavable identifying signature modifiers, that prevent addition of the next dNTP.

E. Wash. Cleave. Collect. Identify last incorporated base.

F. Repeat process to collect sequence information.

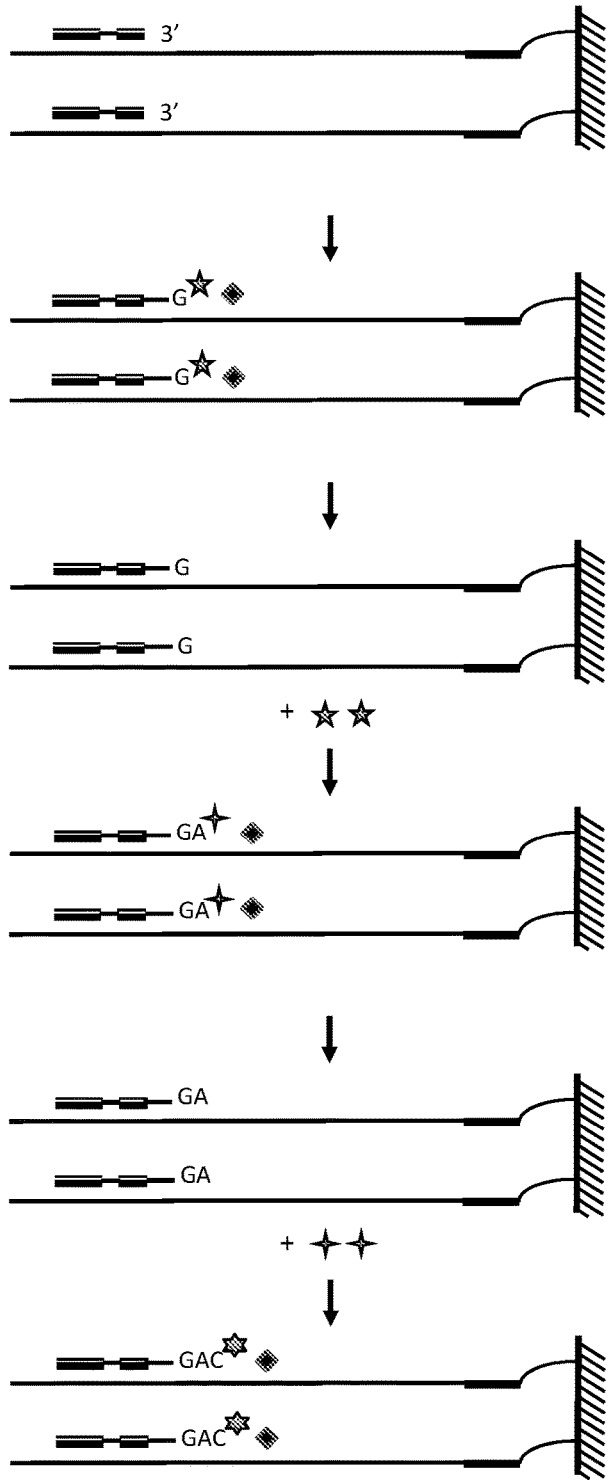

*FIG. 178*

A. Pixel-Sequencing, v06. Hybridize target-specific primers containing a 5' 15-20 base anchor sequence, 1-5 analogue, abasic, spacer, or mismatched bases, and 6-10 matched bases on the 3' end.

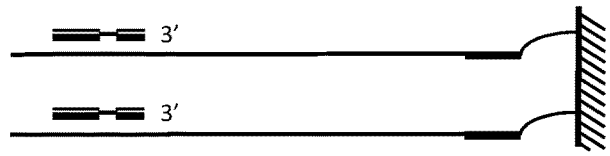

B. Extend primers with dATP, dCTP, dGTP, TTP, and a dA nucleotide analogue terminator containing a 3' identifying signature modifier.

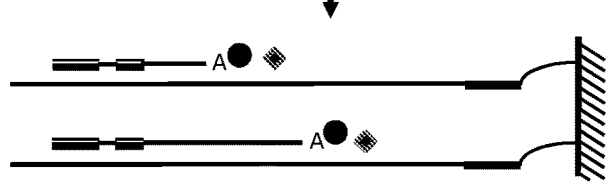

C. Wash away unincorporated analogue dNTPs.

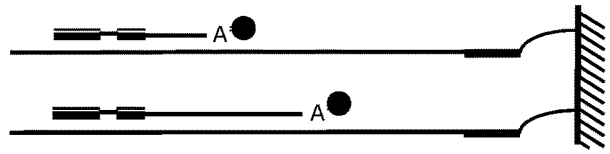

D. Denature products and detect identifying signature modifiers using nanoscale flight tubes to identify length of products terminating with A.

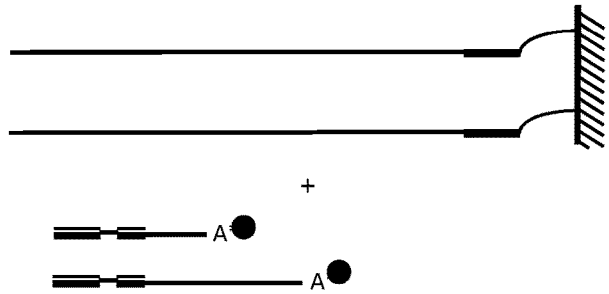

E. Repeat process, using dC nucleotide analogue terminator comprising a 3' identifying signature modifier, and then repeat again with dG analogue terminator, then repeat again with T analogue terminator to collect sequence information for all four bases.

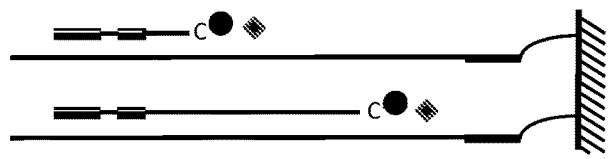

*FIG. 179*

A. Pixel-Sequencing, v07. Hybridize target-specific primers containing a 5' 15-20 base anchor sequence, 1-5 analogue, abasic, spacer, or mismatched bases, and 6-10 matched bases on the 3' end.

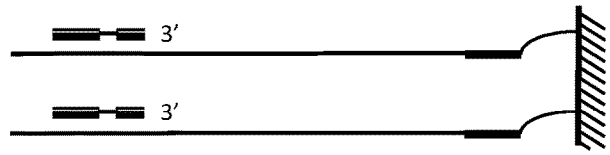

B. Extend primers with dATP, dCTP, dGTP, TTP, and a dA nucleotide analogue terminator containing a capture moiety (*) such as biotin.

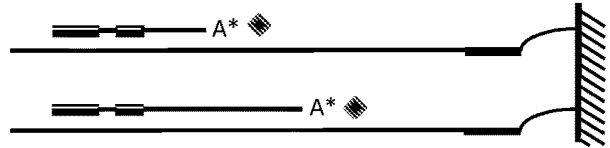

C. Wash away unincorporated analogue dNTPs. Add a 3' identifying signature modifier (i.e. streptavidin) that binds to the capture moiety.

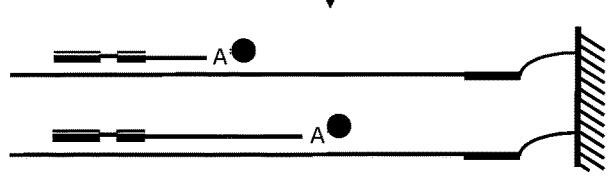

D. Denature products and detect identifying signature modifiers using nanoscale flight tubes to identify length of products terminating with A.

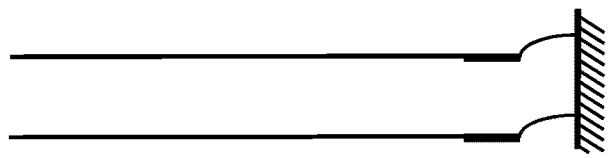

E. Repeat process, using dC nucleotide analogue terminator, and then repeat again with dG analogue terminator, then repeat again with T analogue terminator to collect sequence information for all four bases.

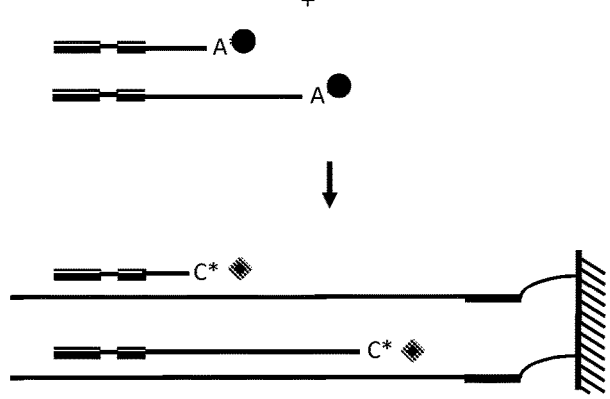

*FIG. 180*

A. Pixel-Sequencing, v08. Hybridize target-specific primers containing a 5' 15-20 base anchor sequence, 1-5 analogue or mismatched bases including a cleavable base or link, and 6-10 matched bases on the 3' end.

B. Extend primers with dATP, dCTP, dGTP, TTP, and a dA nucleotide analogue terminator containing a 3' identifying signature modifier.

C. Wash away unincorporated analogue dNTPs.

D. Cleave the products at the cleavable base or link and denature products and detect identifying signature modifiers using nanoscale flight tubes to identify length of products terminating with A.

E. Repeat process, using dC nucleotide analogue terminator comprising a 3' identifying signature modifier, and then repeat again with dG analogue terminator, then repeat again with T analogue terminator to collect sequence information for all four bases.

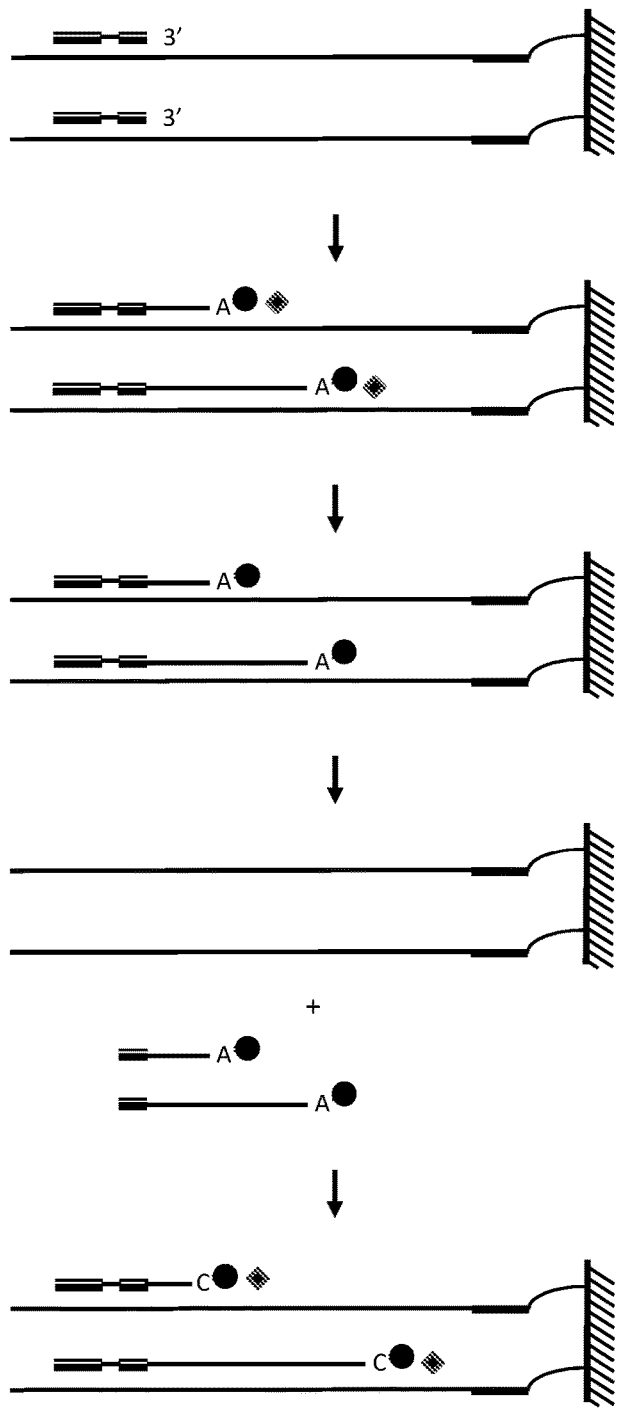

FIG. 181

A. Pixel-Sequencing, v09. Hybridize target-specific primers containing a 5' 15-20 base anchor sequence, 1-5 analogue or mismatched bases including a cleavable base or link, and 6-10 matched bases on the 3' end.

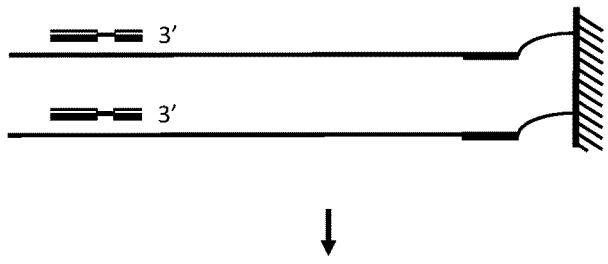

B. Extend primers with dATP, dCTP, dGTP, TTP, and a dA nucleotide analogue terminator containing a capture moiety (*) such as biotin.

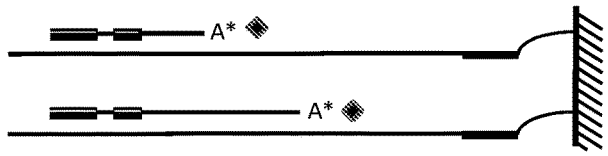

C. Wash away unincorporated analogue dNTPs. Add a 3' identifying signature modifier (i.e. streptavidin) that binds to the capture moiety.

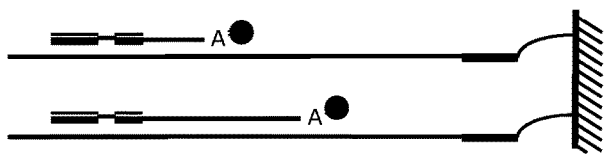

D. Cleave the products at the cleavable base or link and denature products and detect identifying signature modifiers using nanoscale flight tubes to identify length of products terminating with A.

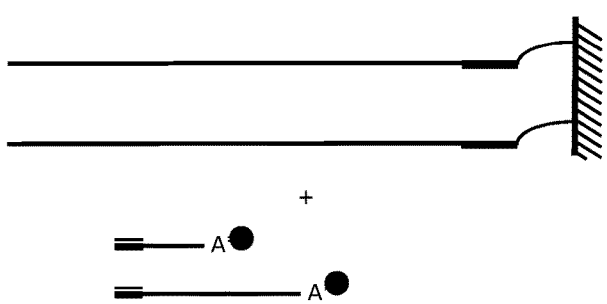

E. Repeat process, using dC nucleotide analogue terminator, and then repeat again with dG analogue terminator, then repeat again with T analogue terminator to collect sequence information for all four bases.

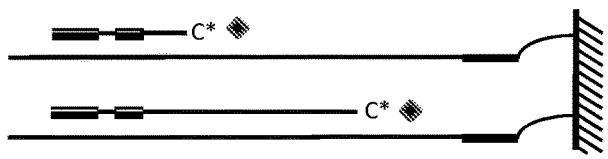

*FIG. 182*

A. Pixel-Sequencing, v10. Hybridize target-specific primers containing a 5' identifying signature modifier, a 5' 15-20 base anchor sequence, 1-5 analogue, abasic, spacer, or mismatched bases, and 6-10 matched bases on the 3' end.

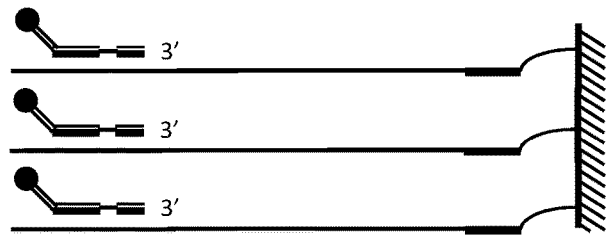

B. Extend primers with dATP, dCTP, dGTP, TTP, and a dA nucleotide analogue terminator containing a 3' identifying signature modifier.

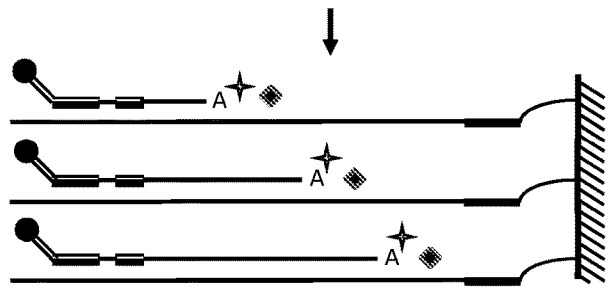

C. Wash away unincorporated analogue dNTPs. Denature products and detect identifying signature modifiers using nanoscale flight tubes to identify length of products terminating with A.

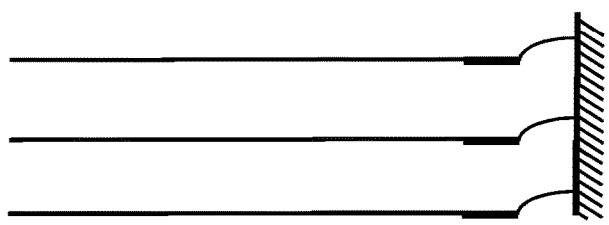

D. Repeat process, using dC nucleotide analogue terminator, and then repeat again with dG analogue terminator, then repeat again with T analogue terminator to collect sequence information for all four bases.

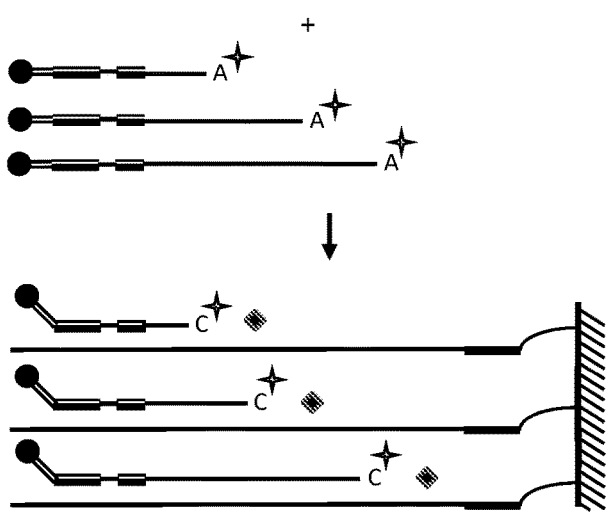

*FIG. 183*

A. Pixel-Sequencing, v11. Hybridize target-specific primers containing a 5' identifying signature modifier, a 5' 15-20 base anchor sequence, 1-5 analogue, abasic, spacer, or mismatched bases, and 6-10 matched bases on the 3' end.

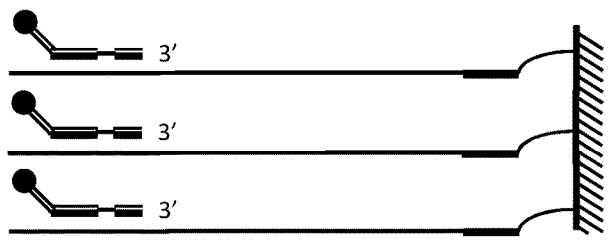

B. Extend primers with dATP, dCTP, dGTP, TTP, and both dA and dC nucleotide analogue terminators containing 3' encoding signature modifiers.

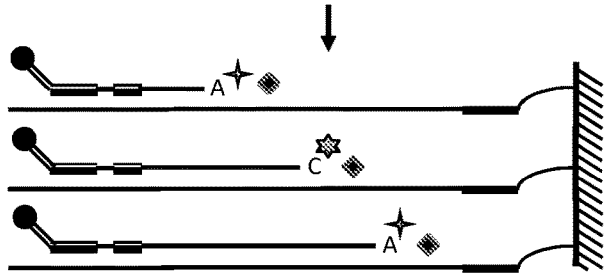

C. Wash away unincorporated analogue dNTPs. Denature products and detect identifying signature modifiers using nanoscale flight tubes to identify length of products terminating with A and C.

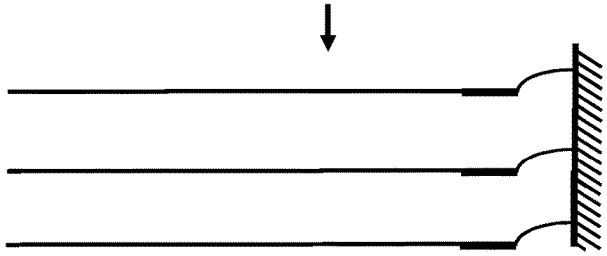

D. Repeat process, using both dC and dA nucleotide analogue terminators, but switch the 3' encoding signature modifiers on each terminator.

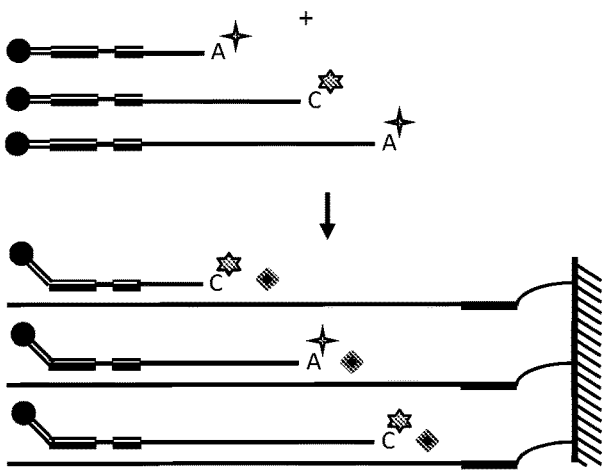

E. Repeat twice more using both dG and T nucleotide analogue terminators, and switch the 3' encoding signature modifiers, to collect sequence information for all four bases.

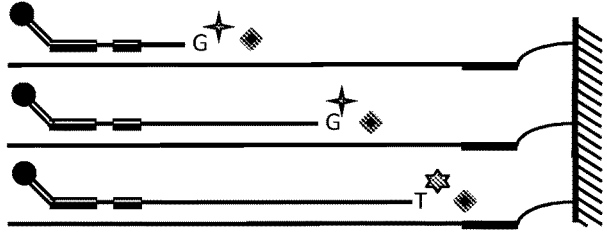

*FIG. 184*

A. Pixel-Sequencing, v12. Hybridize target-specific primers containing a 5' signature modifier, a 5' 15-20 base anchor sequence, 1-5 analogue, abasic, spacer, or mismatched bases, and 6-10 matched bases on the 3' end.

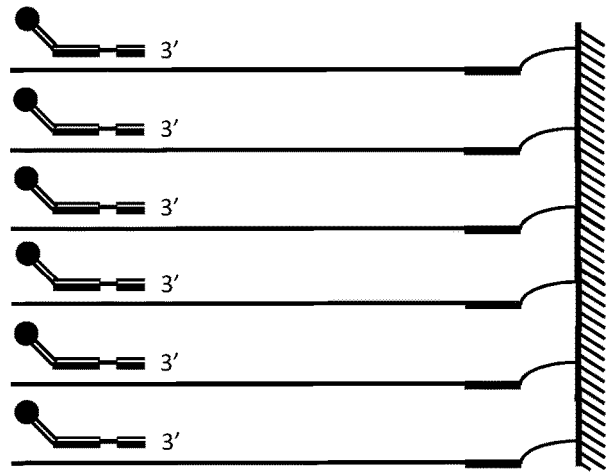

B. Extend primers with dATP, dCTP, dGTP, TTP, and dA, dC, dG, and T nucleotide analogue terminators containing 3' encoding signature modifiers. Wash away unincorporated analogue dNTPs.

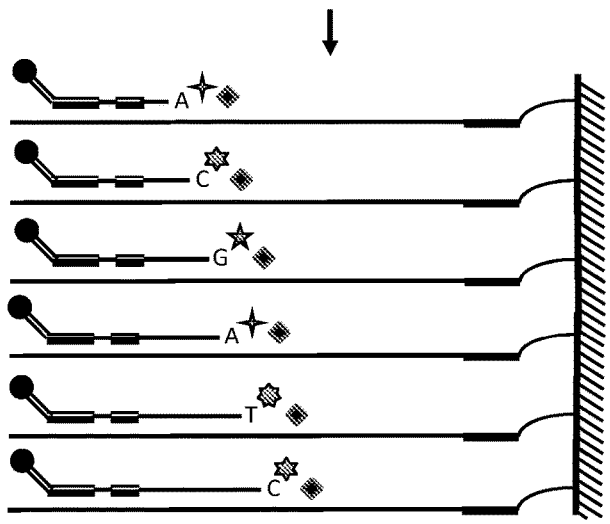

C. Denature products and detect moieties using nanoscale flight tubes to identify length of products. Repeat three more times using all 4 nucleotide analogue terminators, and switch the 3' encoding signature modifiers, to collect sequence information for all four bases.

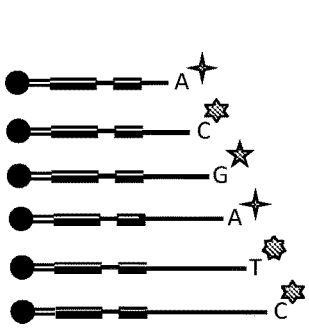

*FIG. 185*

A. Pixel-Sequencing, v03. Hybridize target-specific primers containing a 5' 15-20 base anchor sequence, 1-5 analogue, abasic, cleavable, or mismatched bases, 6-10 matched bases, with blocked 3' end. Primers are unblocked with RNaseH2 only when bound to target.

B. Extend primers with nucleotide analogue dNTPs containing different cleavable identifying signature modifiers that prevent addition of the next dNTP.

C. Wash away unincorporated analogue dNTPs. Add cleaving reagent, cleave, collect, and detect identifying signature modifiers using nanoscale flight tubes to identify base that was last incorporated.

D. Wash away cleaving reagent. Add fresh set of nucleotide analogue dNTPs.

E. Wash. Cleave. Collect. Identify last incorporated base.

F. Repeat process to collect sequence information.

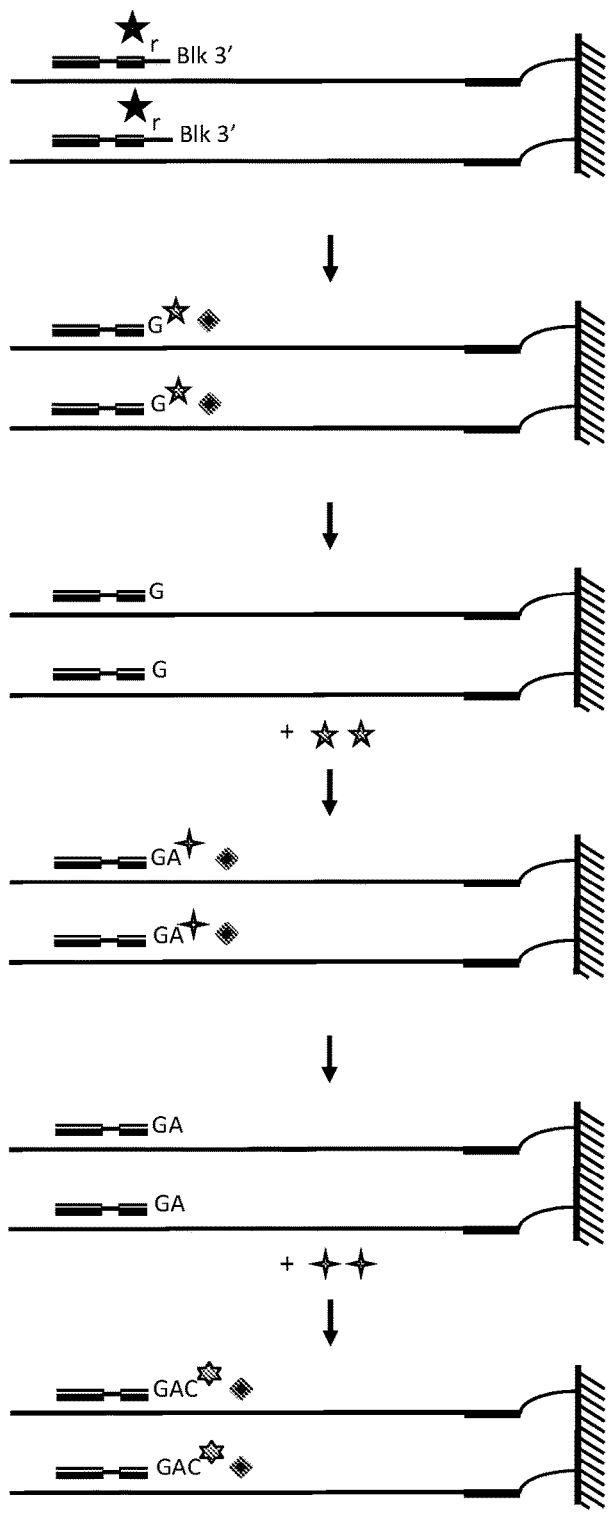

*FIG. 186*

A. Pixel-Sequencing of entire fragment. Hybridize target-specific primers to complementary sequences, and proceed with sequencing by synthesis.

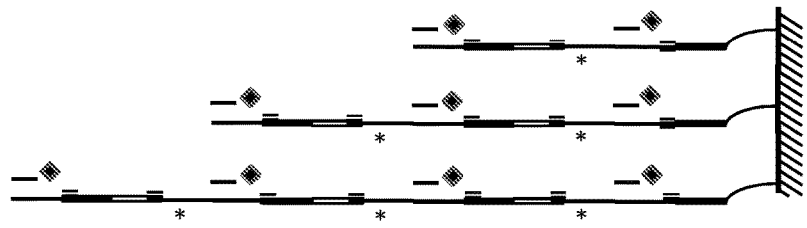

B. Sequence is generated for a portion of the target DNA, then the second linker / unique identifier sequence.

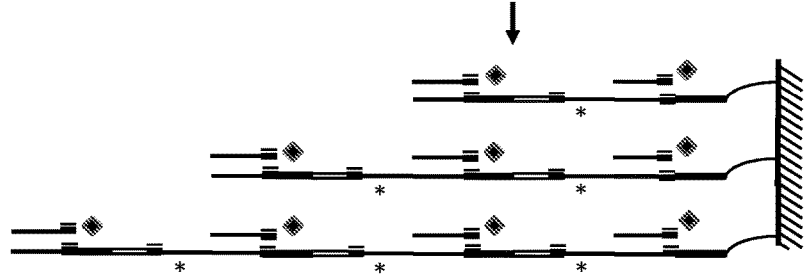

C. Sequence is generated through dA30 region. Some polymerases come to end of primer covalently linked to solid surface.

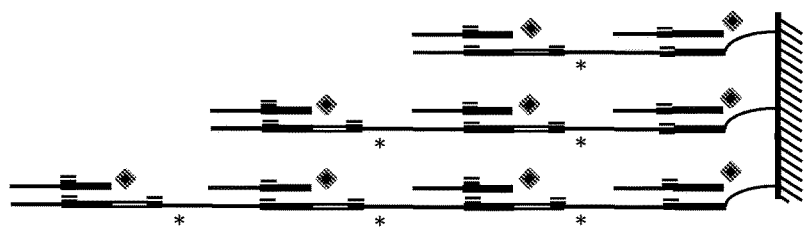

D. Sequence is generated through universal primer binding or other sequence, as well as the first linker / unique identifier sequence.

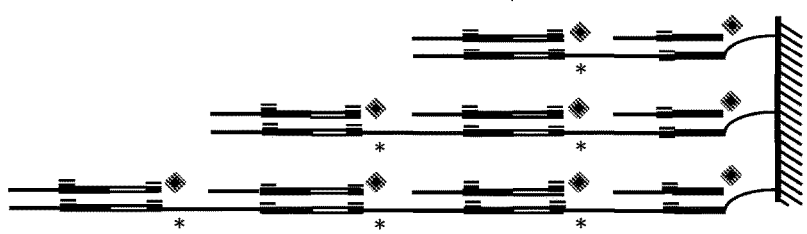

E. Sequence is generated through second portion of the target DNA, and polymerase can strand-displace target-specific primer to obtain sequence in that region.

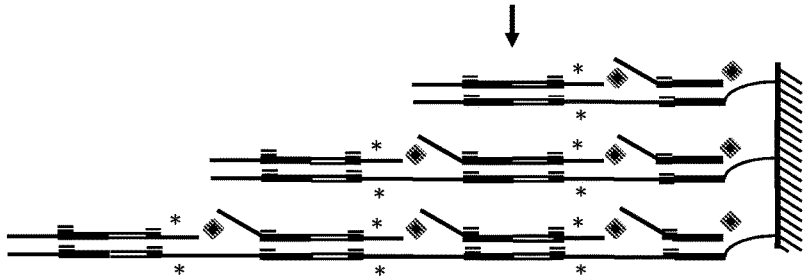

*FIG. 187*

A. Pixel-Sequencing, v04. Hybridize selected universal primers that correspond to the desired targets.

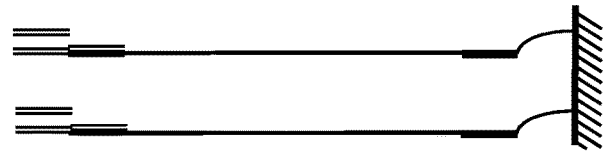

B. Extend primers with nucleotide analogue dNTPs containing different cleavable identifying signature modifiers that prevent addition of the next dNTP.

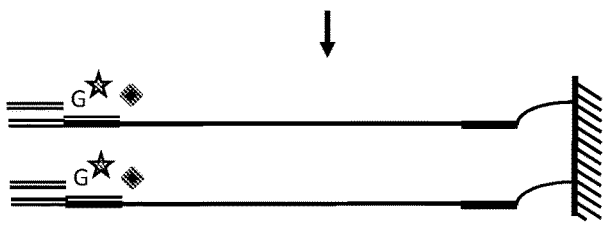

C. Wash away unincorporated analogue dNTPs. Add cleaving reagent, cleave, collect, and detect identifying signature modifiers using nanoscale flight tubes to identify base that was last incorporated.

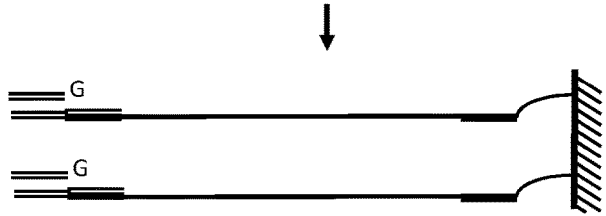

D. Wash away cleaving reagent. Add fresh set of nucleotide analogue dNTPs.

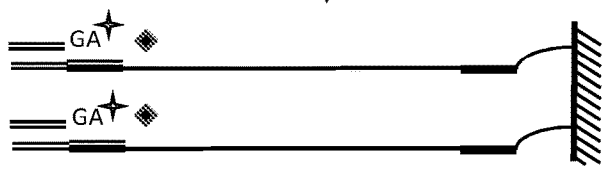

E. Wash. Cleave. Collect. Identify last incorporated base.

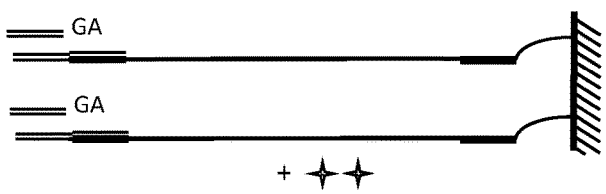

F. Repeat process to collect sequence information. Initially, target primer will be re-sequenced, followed by authentic target sequence.

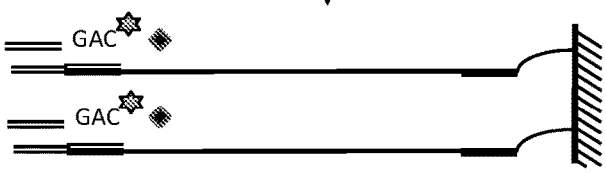

*FIG. 188*

A. Bi-directional Pixel-Sequencing, when using hairpin primer attached to solid support within hairpin. Hybridize selected universal or target-specific primers that are complementary to the immobilized extension products.

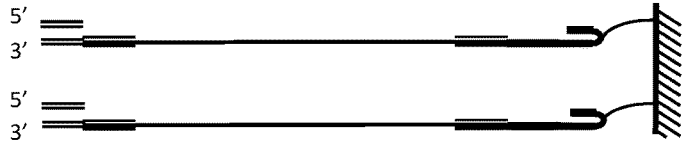

B. Determine sequence using either sequencing-by-synthesis (SBS) or sequencing-by-chain-terminators (Sanger).

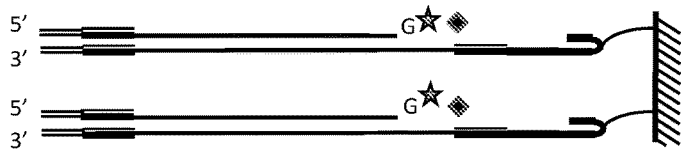

C. Denature sequencing products and hybridize selected universal or target-specific primers. Extend primers with polymerase lacking strand-displacement activity.

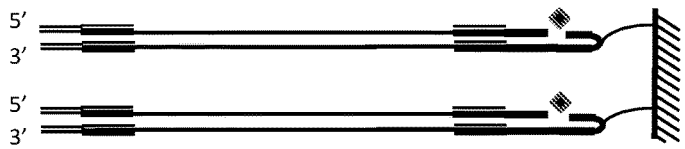

D. Phosphorylate 5' end of hairpin with T4 kinase, and seal nick with ligase. Alternatively, 5'-3' nuclease activity of polymerase or other nuclease(s) liberate 5' phosphate, which is sealed to extended target strands with ligase.

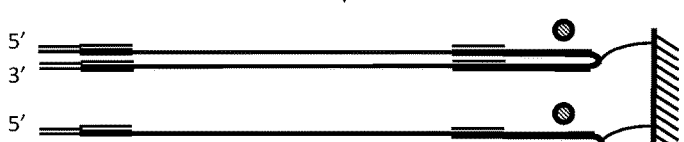

E. Degrade initial immobilized extension product strands using exonuclease with 3'-5' activity.

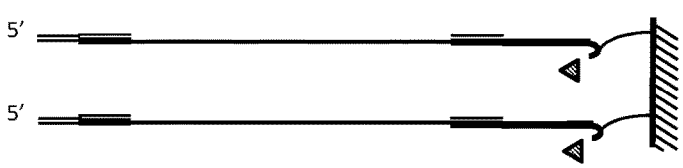

F. Hybridize universal dA30 or target-specific primers to the remaining strand, and determine the complementary sequence sequence using either sequencing-by-synthesis (SBS) or sequencing-by-chain-terminators (Sanger).

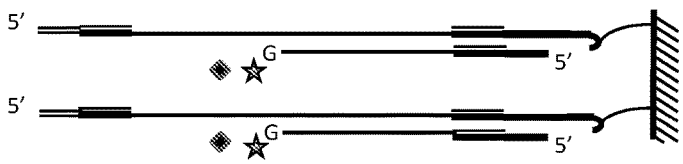

*FIG. 189*

A. Pixel-Sequencing, v05. Hybridize universal primers to complementary sequences.

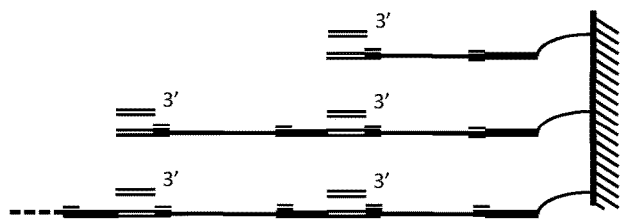

B. Extend primers past linker sequence with dATP, dCTP, TTP, and a dG nucleotide analogue containing a cleavable identifying signature modifier that prevent addition of the next dNTP.

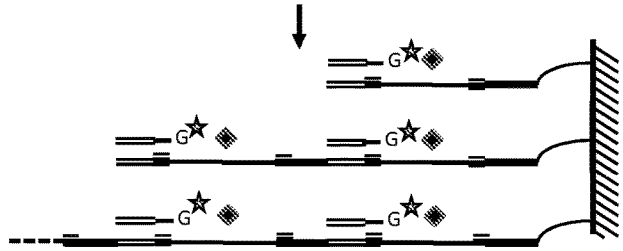

C. Wash away unincorporated analogue dNTPs. Add cleaving reagent, cleave, collect, and detect identifying signature modifiers using nanoscale flight tubes to identify base that was last incorporated.

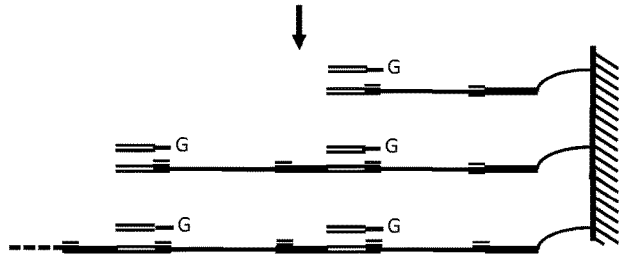

D. Wash away cleaving reagent. Add fresh set of nucleotide analogue dNTPs containing different cleavable identifying signature modifiers that prevent addition of the next dNTP.

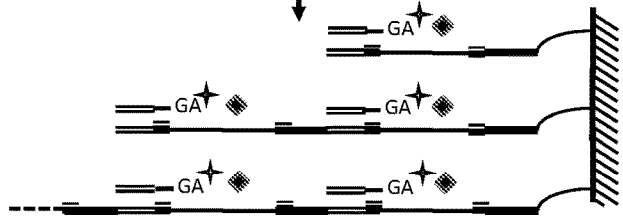

E. Wash. Cleave. Collect. Identify last incorporated base.

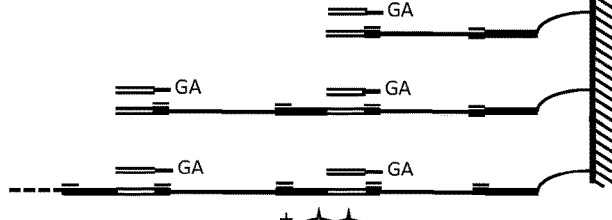

F. Repeat process to collect sequence information.

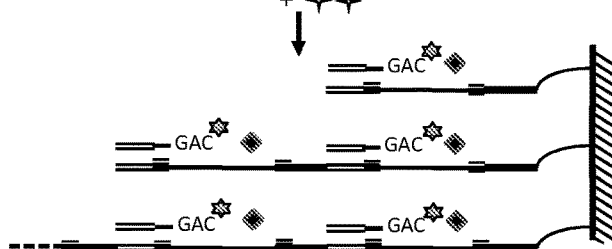

*FIG. 190*

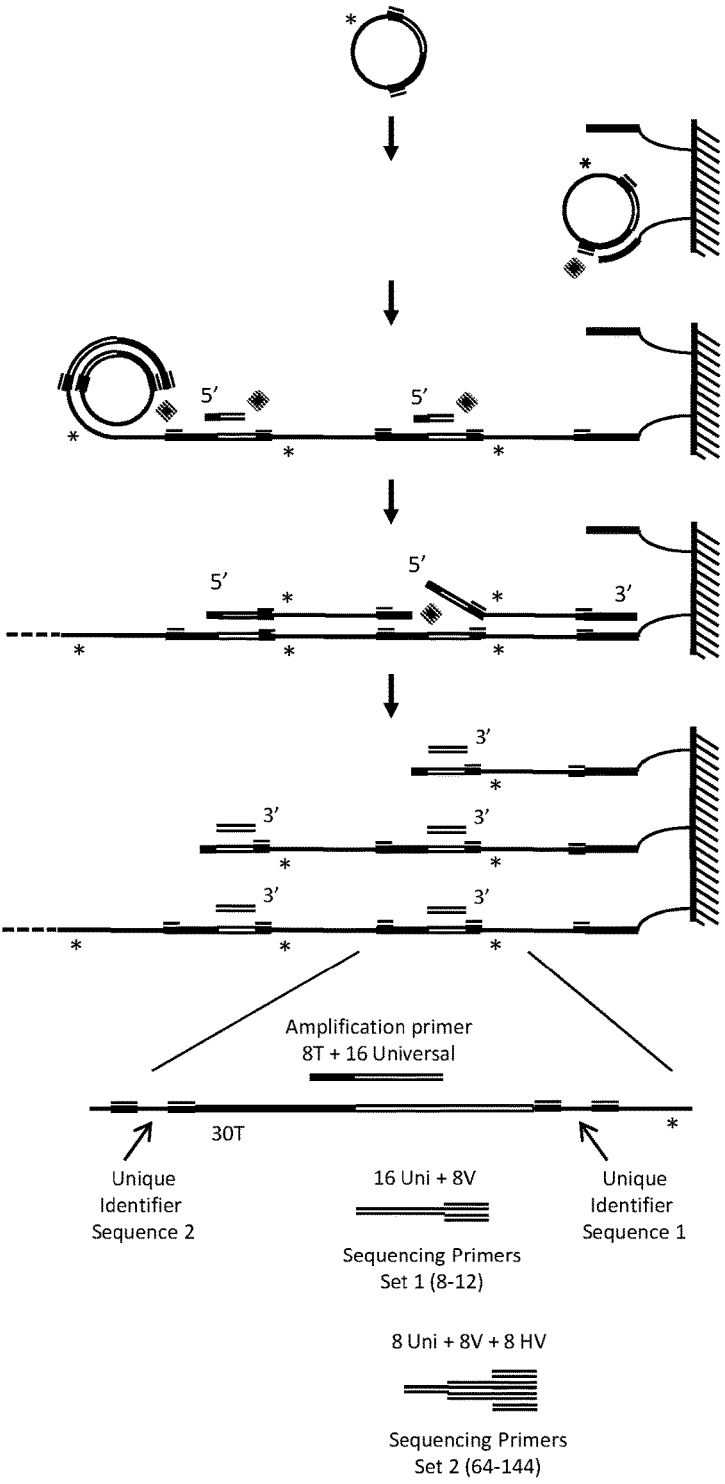

A. The top portion of this figure illustrates the standard approach to generate tethered tandem-repeat extension products starting with circularized templates and universal primers for amplification.

B. The bottom portion of this figure illustrates a close-up of different primers that may be used for extension and sequencing.

C. A universal amplification primer may comprise a portion of the T repeat region and universal primer sequence.

D. A first set of 8-12 sequencing primers may comprise a common 5' sequence (16 bases), and variable 3' sequences (8 bases).

E. A second set of 64-144 sequencing primers may comprise a common 5' sequence (8 bases), a variable middle sequence (8 bases, 8-12 variants) and hyper-variable 3' sequences (8 bases, 64-144 variants).

*FIG. 191*

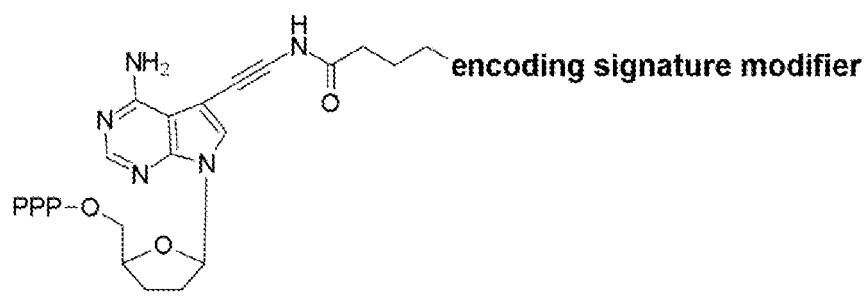
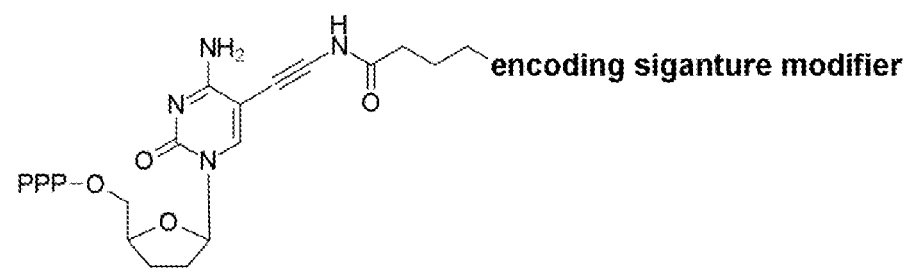
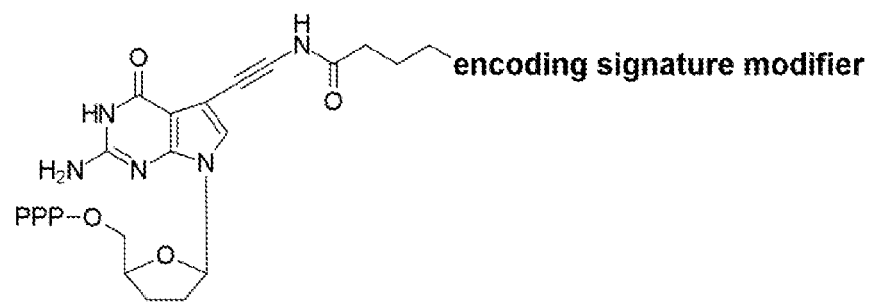
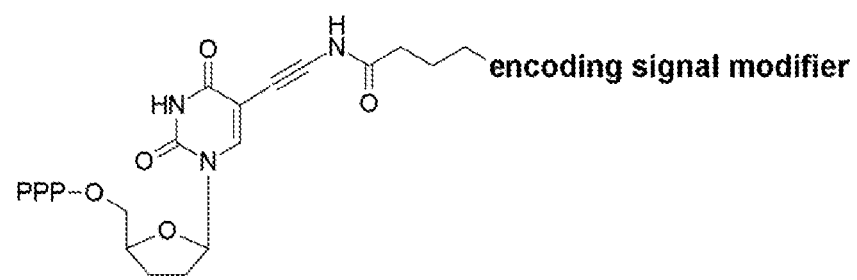
FIG. 194

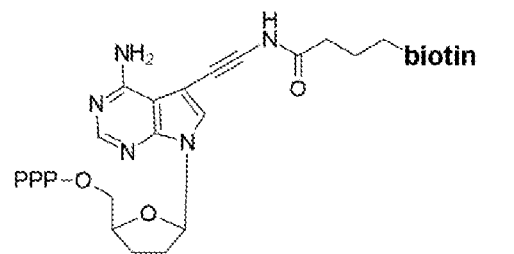
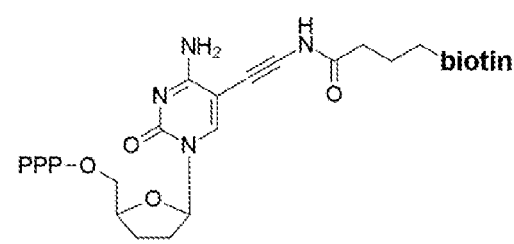
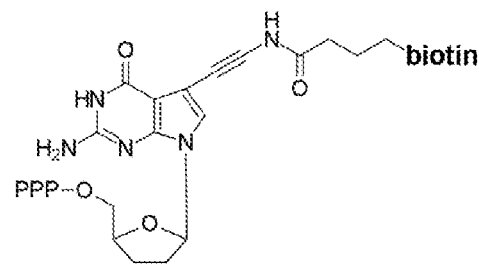
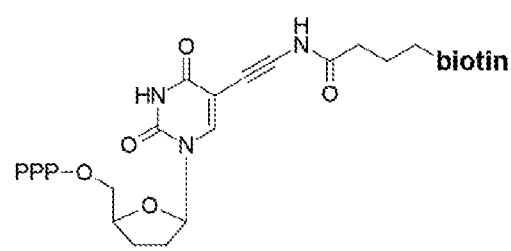
*FIG. 195*

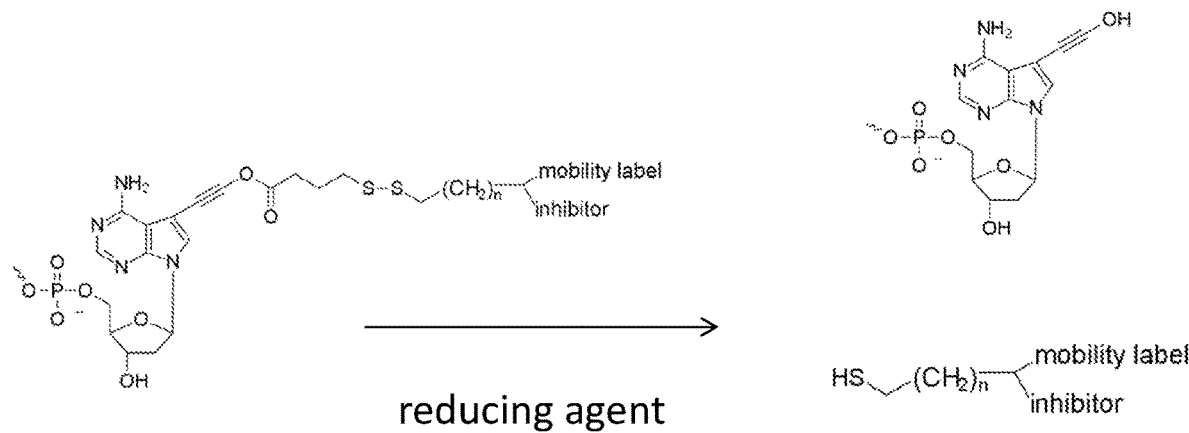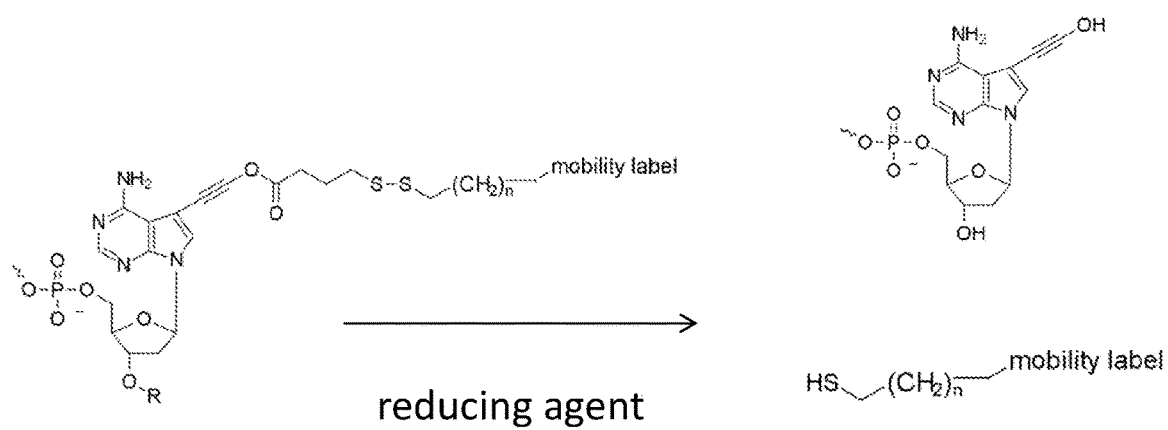
*FIG. 196*

| | | N | N | N | N | N | G | N | N | N | N | N |
|---|---|---|---|---|---|---|---|---|---|---|---|---|
| Minus | | -5 | -4 | -3 | -2 | -1 | 0 | 1 | 2 | 3 | 4 | 5 |
| 100 bases | | | | | | | 126 | 53 | 16 | 5 | | |
| 120 bases | | | | | | | 114 | 58 | 22 | 6 | | |
| 140 bases | | | | | | | 103 | 66 | 23 | 10 | | |
| 160 bases | | | | | | | 84 | 66 | 27 | 12 | 1 | |
| 180 bases | | | | | | | 84 | 71 | 31 | 10 | 3 | 1 |
| 200 bases | | | | | | | 78 | 75 | 38 | 10 | 1 | 3 |

| | | N | N | N | N | N | G | N | N | N | N | N |
|---|---|---|---|---|---|---|---|---|---|---|---|---|
| Plus-Minus | | -5 | -4 | -3 | -2 | -1 | 0 | 1 | 2 | 3 | 4 | 5 |
| 100 bases | | | | 2 | 12 | 39 | 90 | 47 | 8 | 2 | | |
| 120 bases | | | | 2 | 17 | 41 | 78 | 47 | 11 | 4 | | |
| 140 bases | | | | 6 | 15 | 39 | 76 | 46 | 16 | 3 | | |
| 160 bases | | | | 8 | 18 | 37 | 69 | 46 | 15 | 7 | | |
| 180 bases | | 1 | 1 | 7 | 20 | 35 | 63 | 48 | 18 | 7 | | |
| 200 bases | | 2 | 1 | 6 | 21 | 34 | 62 | 59 | 14 | 10 | | |

| Simplified Time of flight distribution per read length | | | | | | | |
|---|---|---|---|---|---|---|---|
| | -3 | -2 | -1 | 0 | 1 | 2 | 3 |
| 60 bases |  |  | 6 | 12 | 6 |  |  |
| 80 bases |  |  | 5 | 9 | 5 |  |  |
| 100 bases |  |  | 4 | 7 | 4 |  |  |
| 120 bases |  | 1 | 3 | 4 | 3 | 1 |  |
| 140 bases |  | 1 | 3 | 3 | 3 | 1 |  |
| 160 bases |  | 1 | 2 | 3 | 2 | 1 |  |

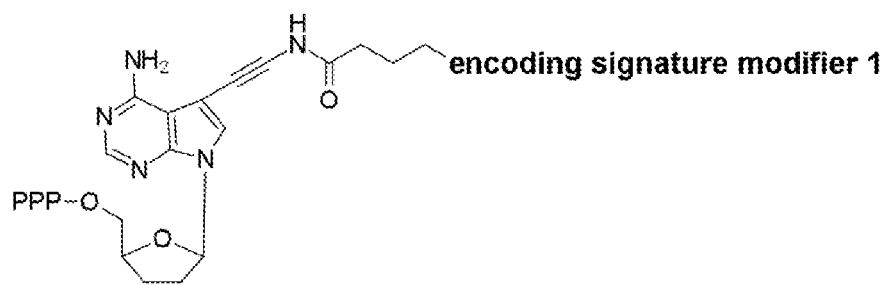
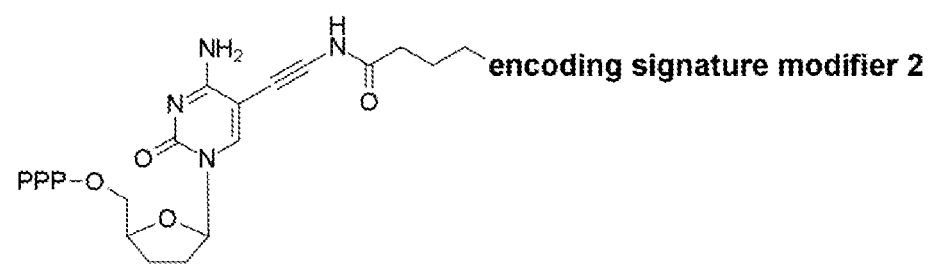
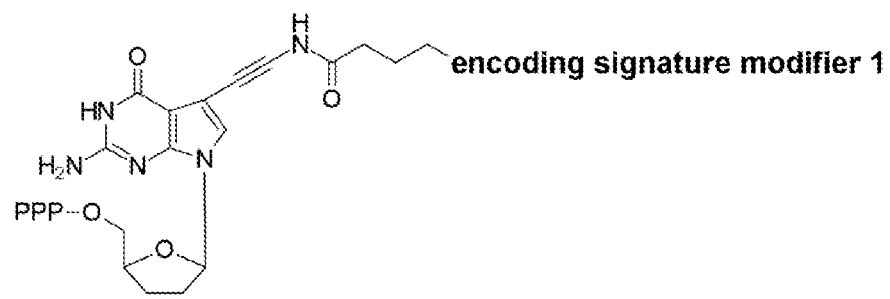
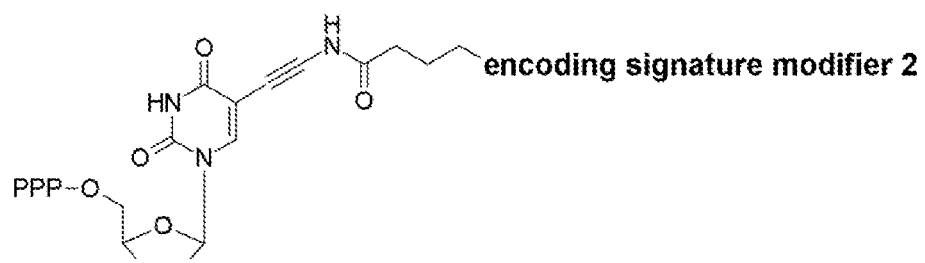
FIG. 219

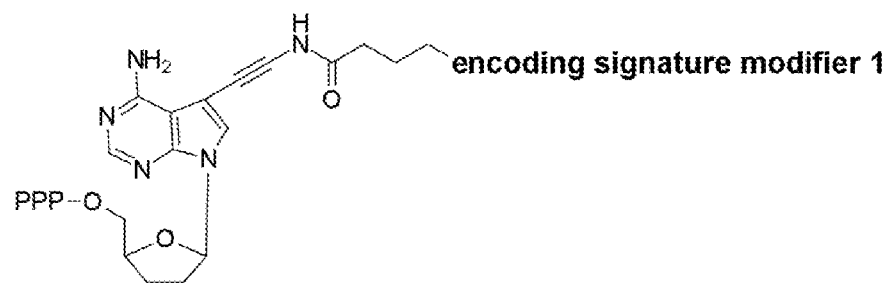
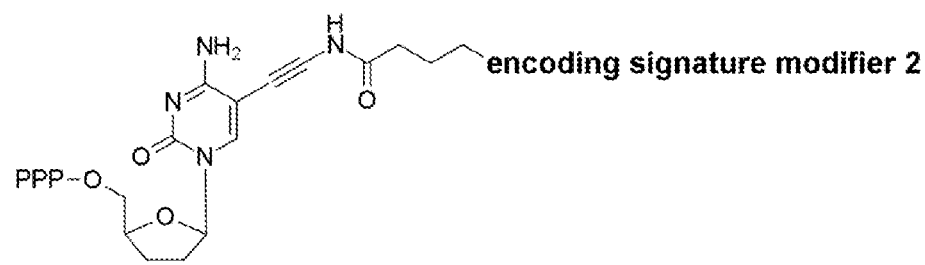
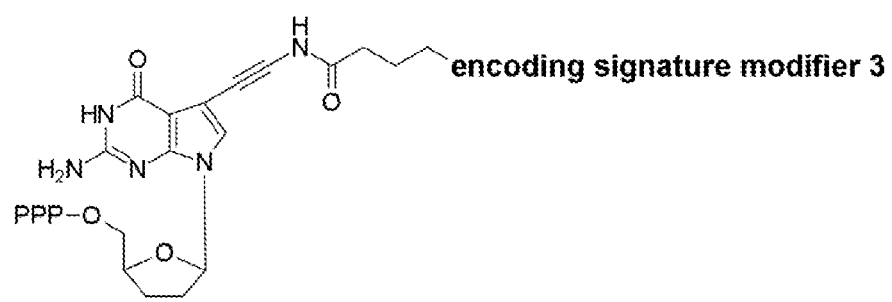
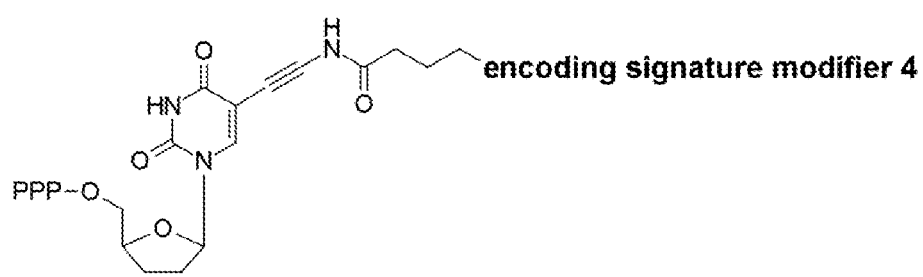
FIG. 220

```
                         SEQUENCE LISTING

<160> NUMBER OF SEQ ID NOS: 21

<210> SEQ ID NO 1
<211> LENGTH: 63
<212> TYPE: DNA
<213> ORGANISM: Artificial Sequence
<220> FEATURE:
<223> OTHER INFORMATION: hairpin primer
<220> FEATURE:
<221> NAME/KEY: misc_feature
<222> LOCATION: (19)..(19)
<223> OTHER INFORMATION: N at position 19 is any nucleotide analog

<400> SEQUENCE: 1
attattattt tttacaacnt aaaaaataat aataaaaaaa aaaaaaaaaa aaaaaaaaa         60 aaa                                                                     63

<210> SEQ ID NO 2
<211> LENGTH: 63
<212> TYPE: DNA
<213> ORGANISM: Artificial Sequence
<220> FEATURE:
<223> OTHER INFORMATION: hairpin primer
<220> FEATURE:
<221> NAME/KEY: misc_feature
<222> LOCATION: (19)..(19)
<223> OTHER INFORMATION: N at position 19 is any nucleotide analog

<400> SEQUENCE: 2
attattattt tttacaacnt aaaaaataat aataaaaaaa aaaaaaaaaa aaaaaaaaa         60 aaa                                                                     63

<210> SEQ ID NO 3
<211> LENGTH: 17
<212> TYPE: DNA
<213> ORGANISM: Artificial Sequence
<220> FEATURE:
<223> OTHER INFORMATION: k-ras codon 12 fragment

<400> SEQUENCE: 3
tggagctggt ggcgtag                                                      17

<210> SEQ ID NO 4
<211> LENGTH: 17
<212> TYPE: DNA
<213> ORGANISM: Artificial Sequence
<220> FEATURE:
<223> OTHER INFORMATION: k-ras codon 12 mutant fragment
```

-continued

```
<400> SEQUENCE: 4
tggagctgat ggcgtag                                                      17

<210> SEQ ID NO 5
<211> LENGTH: 17
<212> TYPE: DNA
<213> ORGANISM: Artificial Sequence
<220> FEATURE:
<223> OTHER INFORMATION: APC codon 1307 fragment
<220> FEATURE:
<221> NAME/KEY: misc_feature
<222> LOCATION: (9)..(9)
<223> OTHER INFORMATION: where N, when present, is T

<400> SEQUENCE: 5
agcagaaana aaagaaa                                                      17

<210> SEQ ID NO 6
<211> LENGTH: 17
<212> TYPE: DNA
<213> ORGANISM: Artificial Sequence
<220> FEATURE:
<223> OTHER INFORMATION: TP53 codon 248 fragment
<220> FEATURE:
<221> NAME/KEY: misc_feature
<222> LOCATION: (9)..(9)
<223> OTHER INFORMATION: N at position 9 is G or A

<400> SEQUENCE: 6
catgaaccng aggccca                                                      17

<210> SEQ ID NO 7
<211> LENGTH: 7
<212> TYPE: DNA
<213> ORGANISM: Artificial Sequence
<220> FEATURE:
<223> OTHER INFORMATION: synthetic A/G-rich sequence
<220> FEATURE:
<221> NAME/KEY: misc_feature
<222> LOCATION: (1)..(3)
<223> OTHER INFORMATION: N at positions 1-3 is A or G
<220> FEATURE:
<221> NAME/KEY: misc_feature
<222> LOCATION: (5)..(7)
<223> OTHER INFORMATION: N at positions 5-7 is A or G

<400> SEQUENCE: 7 nnngnnn                                                                  7

<210> SEQ ID NO 8
<211> LENGTH: 7
<212> TYPE: DNA
<213> ORGANISM: Artificial Sequence
<220> FEATURE:
<223> OTHER INFORMATION: synthetic A/G-rich sequence
<220> FEATURE:
<221> NAME/KEY: misc_feature
<222> LOCATION: (1)..(3)
<223> OTHER INFORMATION: N at positions 1-3 is A or G
<220> FEATURE:
<221> NAME/KEY: misc_feature
<222> LOCATION: (5)..(7)
<223> OTHER INFORMATION: N at positions 5-7 is A or G

<400> SEQUENCE: 8 nnnannn                                                                  7

<210> SEQ ID NO 9
```

```
<211> LENGTH: 9
<212> TYPE: DNA
<213> ORGANISM: Artificial Sequence
<220> FEATURE:
<223> OTHER INFORMATION: synthetic A/G-rich sequence
<220> FEATURE:
<221> NAME/KEY: misc_feature
<222> LOCATION: (2)..(8)
<223> OTHER INFORMATION: N at positions 2-8 is A or G

<400> SEQUENCE: 9 annnnnnng                                                                    9

<210> SEQ ID NO 10
<211> LENGTH: 13
<212> TYPE: DNA
<213> ORGANISM: Artificial Sequence
<220> FEATURE:
<223> OTHER INFORMATION: synthetic A/G-rich sequence
<220> FEATURE:
<221> NAME/KEY: misc_feature
<222> LOCATION: (4)..(6)
<223> OTHER INFORMATION: N at positions 4-6 is A or G
<220> FEATURE:
<221> NAME/KEY: misc_feature
<222> LOCATION: (8)..(10)
<223> OTHER INFORMATION: N at positions 8-10 is A or G

<400> SEQUENCE: 10 aaanngnnn ggg                                                               13

<210> SEQ ID NO 11
<211> LENGTH: 13
<212> TYPE: DNA
<213> ORGANISM: Artificial Sequence
<220> FEATURE:
<223> OTHER INFORMATION: synthetic A/G-rich sequence
<220> FEATURE:
<221> NAME/KEY: misc_feature
<222> LOCATION: (4)..(6)
<223> OTHER INFORMATION: N at positions 4-6 is A or G
<220> FEATURE:
<221> NAME/KEY: misc_feature
<222> LOCATION: (8)..(10)
<223> OTHER INFORMATION: N at positions 8-10  is A or G

<400> SEQUENCE: 11
aaannnannn ggg                                                              13

<210> SEQ ID NO 12
<211> LENGTH: 13
<212> TYPE: DNA
<213> ORGANISM: Artificial Sequence
<220> FEATURE:
<223> OTHER INFORMATION: synthetic A/G-rich sequence
<220> FEATURE:
<221> NAME/KEY: misc_feature
<222> LOCATION: (4)..(5)
<223> OTHER INFORMATION: N at positions 4-5 is A or G
<220> FEATURE:
<221> NAME/KEY: misc_feature
<222> LOCATION: (9)..(10)
<223> OTHER INFORMATION: N at positions 9-10 is A or G

<400> SEQUENCE: 12
aaannaagnn ggg                                                              13

<210> SEQ ID NO 13
<211> LENGTH: 13
<212> TYPE: DNA
<213> ORGANISM: Artificial Sequence
```

-continued

```
<220> FEATURE:
<223> OTHER INFORMATION: synthetic A/G-rich sequence
<220> FEATURE:
<221> NAME/KEY: misc_feature
<222> LOCATION: (4)..(5)
<223> OTHER INFORMATION: N at positions 4-5 is A or G
<220> FEATURE:
<221> NAME/KEY: misc_feature
<222> LOCATION: (9)..(10)
<223> OTHER INFORMATION: N at positions 9-10 is A or G

<400> SEQUENCE: 13
aaanngggnn ggg                                                              13

<210> SEQ ID NO 14
<211> LENGTH: 13
<212> TYPE: DNA
<213> ORGANISM: Artificial Sequence
<220> FEATURE:
<223> OTHER INFORMATION: synthetic A/G-rich sequence
<220> FEATURE:
<221> NAME/KEY: misc_feature
<222> LOCATION: (4)..(5)
<223> OTHER INFORMATION: N at positions 4-5 is A or G
<220> FEATURE:
<221> NAME/KEY: misc_feature
<222> LOCATION: (9)..(10)
<223> OTHER INFORMATION: N at positions 9-10 is A or G

<400> SEQUENCE: 14
aaanngaann ggg                                                              13

<210> SEQ ID NO 15
<211> LENGTH: 13
<212> TYPE: DNA
<213> ORGANISM: Artificial Sequence
<220> FEATURE:
<223> OTHER INFORMATION: synthetic A/G-rich sequence
<220> FEATURE:
<221> NAME/KEY: misc_feature
<222> LOCATION: (4)..(5)
<223> OTHER INFORMATION: N at positions 4-5 is A or G
<220> FEATURE:
<221> NAME/KEY: misc_feature
<222> LOCATION: (9)..(10)
<223> OTHER INFORMATION: N at positions 9-10 is A or G

<400> SEQUENCE: 15
aaannggann ggg                                                              13

<210> SEQ ID NO 16
<211> LENGTH: 39
<212> TYPE: DNA
<213> ORGANISM: Artificial Sequence
<220> FEATURE:
<223> OTHER INFORMATION: wildtype TP53 sequence fragment

<400> SEQUENCE: 16
aacagttcct gcatgggcgg catgaaccgg aggcccatc                                  39

<210> SEQ ID NO 17
<211> LENGTH: 39
<212> TYPE: DNA
<213> ORGANISM: Artificial Sequence
<220> FEATURE:
<223> OTHER INFORMATION: TP53-S241F sequence fragment

<400> SEQUENCE: 17
aacagtttct gcatgggcgg catgaaccgg aggcccatc                                  39
```

```
<210> SEQ ID NO 18
<211> LENGTH: 39
<212> TYPE: DNA
<213> ORGANISM: Artificial Sequence
<220> FEATURE:
<223> OTHER INFORMATION: TP53-G245S sequence fragment

<400> SEQUENCE: 18
aacagttcct gcatgggcag catgaaccgg aggcccatc                              39

<210> SEQ ID NO 19
<211> LENGTH: 39
<212> TYPE: DNA
<213> ORGANISM: Artificial Sequence
<220> FEATURE:
<223> OTHER INFORMATION: TP53-G245S sequence fragment

<400> SEQUENCE: 19
aacagttcct gcatgggcga catgaaccgg aggcccatc                              39

<210> SEQ ID NO 20
<211> LENGTH: 39
<212> TYPE: DNA
<213> ORGANISM: Artificial Sequence
<220> FEATURE:
<223> OTHER INFORMATION: TP53-R248W sequence fragment

<400> SEQUENCE: 20
aacagttcct gcatgggcgg catgaactgg aggcccatc                              39

<210> SEQ ID NO 21
<211> LENGTH: 39
<212> TYPE: DNA
<213> ORGANISM: Artificial Sequence
<220> FEATURE:
<223> OTHER INFORMATION: TP53-R248Q sequence fragment

<400> SEQUENCE: 21
aacagttcct gcatgggcgg catgaaccag aggcccatc                              39
```

METHOD FOR IDENTIFICATION AND ENUMERATION OF NUCLEIC ACID SEQUENCES, EXPRESSION, SPLICE VARIANT, TRANSLOCATION, COPY, OR DNA METHYLATION CHANGES USING COMBINED NUCLEASE, LIGASE, POLYMERASE, TERMINAL TRANSFERASE, AND SEQUENCING REACTIONS

RELATED APPLICATIONS

This application is a 35 U.S.C. § 371 national phase application of PCT Application PCT/US2016/023814 filed Mar. 23, 2016, which claims the benefit of U.S. Provisional Patent Application Ser. No. 62/137,009, filed Mar. 23, 2015, the entire contents of each of which are incorporated by reference herein.

STATEMENT OF FEDERAL SUPPORT

This invention was made with government support under Grant Numbers HG006278, EB010087 and EB020594 awarded by the National Institutes of Health and Grant Number CEBT-1067583 from the National Science Foundation. The government has certain rights in the invention.

STATEMENT REGARDING ELECTRONIC FILING OF A SEQUENCE LISTING

A Sequence Listing in ASCII text format, submitted under 37 C.F.R. § 1.821, entitled 5470-821 ST25.txt, 6,946 bytes in size, generated on Jun. 19, 2018 and filed via EFS-Web, is provided in lieu of a paper copy. This Sequence Listing is hereby incorporated by reference into the specification for its disclosures.

FIELD OF THE INVENTION

The present invention relates to a device and methods suitable for nucleic acid sequence detection and enumeration.

BACKGROUND OF THE INVENTION

Cancer is the leading cause of death in developed countries and the second leading cause of death in developing countries. Cancer has now become the biggest cause of mortality worldwide, with an estimated 8.2 million deaths from cancer in 2012. Cancer cases worldwide are forecast to rise by 75% and reach close to 25 million over the next two decades. A recent report by the world health organization concludes: "(The) Global battle against cancer won't be won with treatment alone. Effective prevention measures (are) urgently needed to prevent (a) cancer crisis". Detection of early cancer in the blood is the best means of effective prevention. It will save lives by enabling earlier and better treatment, as well as reduce the cost of cancer care.

Plasma or serum from a cancer patient contains nucleic acids released from cancers cells undergoing abnormal physiological processes. These nucleic acids have already demonstrated diagnostic utility (Diaz and Bardelli, *J Clin Oncol* 32: 579-586 (2014); Bettegowda et al., *Sci Transl Med* 6: 224 (2014); Newman et al., *Nat Med* 20: 548-554 (2014); Thierry et al., *Nat Med* 20: 430-435 (2014)). A further source of nucleic acids is within circulating tumor cells (CTCs), although early stage and a significant fraction of localized tumors send out very few to no CTC's per ml.

Normal plasma or serum contains nucleic acids released from normal cells undergoing normal physiological processes (i.e. exosome secretion, apoptosis). There may be additional release of nucleic acids under conditions of stress, inflammation, infection, or injury.

Further, exosomes are proving to contain an extraordinary diverse set of nucleic acid molecules, ranging from mRNA to lncRNA to miRNA, and in some cases, even nuclear DNA. In addition, even the whole cellular fraction contains both tumor cells and immune-response cells, each which may contain disease-specific nucleic acids (i.e. cancer-specific alternative splicing) that are not present in the vast majority of white-blood cells that co-purify with this fraction. As such blood presents a rich opportunity for disease detection.

The challenge to develop reliable diagnostic and screening tests is to distinguish those markers emanating from the tumor that are indicative of disease (e.g., early cancer) vs. presence of the same markers emanating from normal tissue (which would lead to a false-positive signal). There is also a need to balance the number of markers examined and the cost of the test, with the specificity and sensitivity of the assay. Comprehensive molecular profiling (mRNA, methylation, copy number, miRNA, mutations) of thousands of tumors by The Cancer Genome Atlas Consortium (TCGA), has revealed that colorectal tumors are as different from each other as they are from breast, prostrate, or other epithelial cancers (TCGA "Comprehensive Molecular Characterization of Human Colon and Rectal Cancer," *Nature* 487: 330-337 (2014)). Further, those few markers they share in common (i.e. K-ras mutations) are also present in multiple cancer types, hindering the ability to pinpoint the tissue of origin. For early cancer detection, the nucleic acid assay should serve primarily as a screening tool, requiring the availability of secondary diagnostic follow-up (e.g., colonoscopy for colorectal cancer).

Compounding the biological problem is the need to reliably quantify mutation, promoter methylation, or DNA or RNA copy number from either a very small number of initial cells (i.e. from CTCs), or when the cancer signal is from cell-free DNA (cfDNA) in the blood and diluted by an excess of nucleic acid arising from normal cells, or inadvertently released from normal blood cells during sample processing (Mateo et al., *Genome Biol* 15: 448 (2014)).

Likewise, an analogous problem of identifying rare target is encountered when using nucleic-acid-based techniques to detect infectious diseases directly in the blood. Briefly, either the pathogen may be present at 1 or less colony forming units (cfu)/ml, and/or there are many potential pathogens and sequence variations responsible for virulence or drug resistance. While these issues are exemplified with cancer, it is recognized that the solutions are equally applicable to infectious diseases Recently, a number of approaches have been developed to enumerate chromosomal regions to detect aneuploidy using cell-free DNA for non-invasive prenatal diagnosis. These approaches rely on counting the number of copies of DNA fragments arising from both the mother and fetus by either direct sequencing, using LDR to select certain sub-fractions and then using either sequencing or microarray readout, or by proportional PCR of SNP containing regions, and then enumerating these via sequencing.

The presence and absence of methylation in certain genetic regions has prenatal diagnostic and prognostic applications. For example, aberrant methylation on regions on chromosomes 13, 18, 21, X, and Y can be used to diagnose Down Syndrome (Patsalis et al., *Exp. Opin. Biol. Ther.*

12(Suppl. 1): S155-S161 (2012). Because fetal DNA and maternal DNA are differentially methylated, cell-free fetal DNA in maternal plasma can provide a source of fetal DNA, which can be obtained non-invasively and utilized to assess the methylation state of the aforementioned chromosomes. Since cell-free fetal DNA only accounts for 3-6% of total DNA in maternal circulation during the first trimester, a highly sensitive method of detection is warranted.

A Continuum of Diagnostic Needs Require a Continuum of Diagnostic Tests.

The majority of current molecular diagnostics efforts in cancer have centered on: (i) prognostic and predictive genomics, e.g., identifying inherited mutations in cancer predisposition genes, such as BrCA1, BrCA2, (Ford et al. *Am J Hum Genet* 62: 676-689 (1998)) (ii) individualized treatment, e.g., mutations in the EGFR gene guiding personalized medicine (Sequist and Lynch, *Ann Rev Med*, 59: 429-442 (2008), and (iii) recurrence monitoring, e.g., detecting emerging K-ras mutations in patients developing resistance to drug treatments (Hiley et al., *Genome Biol* 15: 453 (2014); Amado et al., *J Clin Oncol* 26: 1626-1634 (2008)). Yet, this misses major opportunities in the cancer molecular diagnostics continuum: (i) more frequent screening of those with a family history, (ii) screening for detection of early disease, and (iii) monitoring treatment efficacy. To address these three unmet needs, a new metric for blood-based detection termed "cancer marker load", analogous to viral load is needed.

DNA sequencing provides the ultimate ability to distinguish all nucleic acid changes associated with disease. However, the process still requires multiple up-front sample and template preparation, and is not always cost-effective. DNA microarrays can provide substantial information about multiple sequence variants, such as SNPs or different RNA expression levels, and are less costly then sequencing; however, they are less suited for obtaining highly quantitative results, nor for detecting low abundance mutations. On the other end of the spectrum is the TaqMan™ reaction, which provides real-time quantification of a known gene, but is less suitable for distinguishing multiple sequence variants or low abundance mutations.

It is critical to match each unmet diagnostic need with the appropriate diagnostic test—one that combines the divergent goals of achieving both high sensitivity (i.e., low false-negatives) and high specificity (i.e., low false-positives) at a low cost. For example, direct sequencing of EGFR exons from a tumor biopsy to determine treatment for non-small cell lung cancer (NSCLC) is significantly more accurate and cost effective than designing TaqMan™ probes for the over 180 known mutations whose drug response is already catalogued (Jia et al. *Genome Res* 23: 1434-1445 (2013)). The most sensitive technique for detecting point mutations, BEAMing (Dressman et al., *Proc Natl Acad Sci USA* 100: 8817-8822 (2003)), rely on prior knowledge of which mutations to look for, and thus are best suited for monitoring for disease recurrence, rather than for early detection. Likewise, to monitor blood levels of Bcr-Abl translocations when treating CML patients with Gleevec (Jabbour et al., *Cancer* 112: 2112-2118 (2008)), a simple quantitative reverse-transcription PCR assay is far preferable to sequencing the entire genomic DNA in 1 ml of blood (9 million cells×3 GB=27 million Gb of raw data).

Sequencing 2.1 Gb each of cell-free DNA (cfDNA) isolated from NSCLC patients was used to provide 10,000-fold coverage on 125 kb of targeted DNA (Kandoth et al. *Nature* 502: 333-339 (2013)). This approach correctly identified mutations present in matched tumors, although only 50% of stage 1 tumors were covered. The approach has promise for NSCLC, where samples average 5 to 20 mutations/Mb, however this approach is not be cost effective for other cancers such as breast and ovarian, that average less than 1 to 2 mutations per Mb. Current up-front ligation, amplification, and/or capture steps required for highly accurate targeted deep sequencing are still more complex than multiplexed PCR-TaqMan™ or PCR-LDR assays.

A comprehensive data analysis of over 600 colorectal cancer samples that takes into account tumor heterogeneity, tumor clusters, and biological/technical false-positives ranging from 3% to 10% per individual marker showed that the optimal early detection screen for colorectal cancer would require at least 5 to 6 positive markers out of 24 markers tested (Bacolod et al., *Cancer Res* 69:723-727 (2009); Tsafrir et al. *Cancer Res* 66: 2129-2137 (2006), Weinstein et al., *Nat Genet* 45: 1113-1120 (2013); Navin N. E. *Genome Biol* 15: 452 (2014); Hiley et al., *Genome Biol* 15: 453 (2014)); Esserman et al. *Lancet Oncol* 15: e234-242 (2014)). Further, marker distribution is biased into different tumor clades, e.g., some tumors are heavily methylated, while others are barely methylated, and indistinguishable from age-related methylation of adjacent tissue. Consequently, a multidimensional approach using combinations of 3-5 sets of mutation, methylation, miRNA, mRNA, copy-variation, alternative splicing, or translocation markers, is needed to obtain sufficient coverage of all different tumor clades. Analogous to non-invasive prenatal screening for trisomy (based on sequencing or performing ligation detection on random fragments of cfDNA Non-invasive prenatal testing for aneuploidy: current status and future prospects (Benn et al., *Ultrasound Obstet Gynecol.* 42(1):15-33 (2013); Chiu et al., *Proc Natl Acad Sci USA* 105: 20458-20463 (2008); Juneau et al., *Fetal Diagn Ther.* 36(4) (2014)) the actual markers scored in a cancer screen are secondary to accurate quantification of those positive markers in the plasma.

Technical Challenges of Cancer Diagnostic Test Development

Diagnostic tests that aim to find very rare or low-abundance mutant sequences face potential false-positive signal arising from: (i) polymerase error in replicating wild-type target, (ii) DNA sequencing error, (iii) mis-ligation on wild-type target, (iii) target independent PCR product, and (iv) carryover contamination of PCR products arising from a previous positive sample. The profound clinical implications of a positive test result when screening for cancer demand that such a test use all means possible to virtually eliminate false-positives.

Central to the concept of nucleic acid detection is the selective amplification or purification of the desired cancer-specific markers away from the same or closely similar markers from normal cells. These approaches include: (i) multiple primer binding regions for orthogonal amplification and detection, (ii) affinity selection of CTC's or exosomes, and (iii) spatial dilution of the sample.

The success of PCR-LDR, which uses 4 primer-binding regions to assure sensitivity and specificity, has previously has demonstrated exquisite specificity in distinguishing single-base mutations, and is compatible with high levels of multiplexing (Favis et al., *Nat Biotechnol*, 18, 561-564 (2000); Favis, R. and Barany, F., *Ann NY Acad Sci*, 906, 39-43 (2000); Favis et al., *Hum Mutat*, 24, 63-75 (2004); Gerry et al., *J Mol Biol*, 292, 251-262 (1999); Khanna, et al., *Oncogene*, 18, 27-38 (1999)). Desired regions are amplified using pairs or even tandem pairs of PCR primers, followed by orthogonal nested LDR primer pairs for detection. One advantage of using PCR-LDR is the ability to perform proportional PCR amplification of multiple fragments to enrich for low copy targets, and then use quantitative LDR to directly identify cancer-specific mutations. Single molecule detection (SMD) assay combined with reverse transcription and LDR to count and quantify mRNA transcripts using digital techniques (i.e. molecular counting) has also been demonstrated (Peng et al., *Anal Chem,* 85:7851-7858 (2013). A similar scheme has been adopted for detecting single nucleotide mutations in KRAS genes and strain-specific differentiation of bacterial pathogens (Peng et al., *Anal Chem* 82:9727-9735 (2010); Wabuyele et al., *J Am Chem Soc,* 125:6937-6945 (2003)). These assays use LDR primer pairs designed to identify the target sequence and following a successful ligation event, produces a molecular beacon that can be detected via single-pair fluorescence resonance energy transfer (spFRET).

Affinity purification of CTC's using antibody or aptamer capture has been demonstrated (Adams et al., *J Am Chem Soc* 130:8633-8641 (2008); Dharmasiri et al., *Electrophoresis* 30:3289-3300 (2009); Soper et al. *Biosens Bioelectron* 21:1932-1942 (2006)). Peptide affinity capture of exosomes has been reported in the literature. Enrichment of these tumor-specific fractions from the blood enables copy number quantification, as well as simplifying screening and verification assays.

The last approach, spatial dilution of the sample, is employed in digital PCR as well as its close cousin known as BEAMing (Vogelstein and Kinzler, *Proc Natl Acad Sci USA.* 96(16):9236-41 (1999); Dressman et al., *Proc Natl Acad Sci USA* 100:8817-8822 (2003)). The rational for digital PCR is to overcome the limit of enzymatic discrimination when the sample comprises very few target molecules containing a known mutation in a 1,000 to 10,000-fold excess of wild-type DNA. By diluting input DNA into 20,000 or more droplets or beads to distribute less than one molecule of target per droplet, the DNA may be amplified via PCR, and then detected via probe Finally, spatial localization is the cornerstone of next-generation sequencing technology, wherein random or enriched fragments are bar-coded and then clonally replicated on a solid support or beads at defined locations (Bennett et al., *Pharmacogenomics,* 6:373-382 (2005); Margulies et al., *Nature,* 437:376-380 (2005); Sandberg et al., *Sci Rep,* 1:108 (2011)). The four-orders of magnitude variability in mutations per 5 mL of plasma preclude practical use of sequencing as a first-line screening tool (Newman et al., *Nat Med,* 20:548-554 (2014); Kandoth et al., *Nature,* 502333-339 (2013)). Further, these PCR-based sequencing approaches were not designed for direct detection of DNA methylation at promoter regions, an important marker of tumor DNA.

The present invention is directed at overcoming these and other deficiencies of the art.

SUMMARY OF THE INVENTION

One aspect of the present invention is directed to a method for identifying, in a sample, one or more target nucleotide sequences differing from other nucleotide sequences in the sample by one or more nucleotides, one or more copy numbers, one or more transcript sequences, and/or one or more methylated residues. This method involves providing a sample containing one or more target nucleic acid molecules containing the target nucleotide sequence or complements thereof and providing a solid support comprising one or more immobilized capture molecules, said capture molecules suitable to bind to a portion of the one or more target nucleic acid molecules. The method further involves binding the one or more target nucleic acid molecules to the one or more immobilized capture molecules on the solid support thereby immobilizing the one or more target nucleic acid molecules on said solid support, and subjecting the immobilized target nucleic acid molecules or immobilized complementary target nucleic acid molecules thereof to a ligase detection reaction to produce ligation products hybridized to said immobilized target nucleic acid molecules or immobilized complementary target nucleic acid molecules thereof. The ligation products are denatured from the immobilized target nucleic acid molecules or immobilized complementary target nucleic acid molecules thereof to release the ligation products from the solid support, and the denatured ligation products are fed through one or more nanopores capable of detecting said ligation products. The method further involves detecting, as a result of said feeding, an identifying signature of each ligation product that is generated when each product passes through the one or more nanopores, and identifying, based on said detecting, the presence of one or more target nucleotide sequences differing from other nucleotide sequences in the sample by one or more nucleotides, one or more copy numbers, one or more transcript sequences, and/or one or more methylated residues.

Another aspect of the present invention is directed method for identifying, in a sample, one or more target nucleotide sequences differing from other nucleotide sequences in the sample by one or more nucleotides, one or more copy numbers, one or more transcript sequences, and/or one or, more methylated residues. This method comprises providing a sample containing one or more target nucleic acid molecules containing the target nucleotide sequence or complements thereof, and providing a solid support comprising one or more immobilized capture molecules, where the capture molecules are suitable to bind to a portion of the one or more target nucleic acid molecules. The method further involves binding the one or more target nucleic acid molecules to the one or more immobilized capture molecules on the solid support thereby immobilizing the one or more target nucleic acid molecules on said solid support. The immobilized target nucleic acid molecules or immobilized complementary target nucleic acid molecules thereof are contacted with (i) one or more oligonucleotide probes, wherein said one or more oligonucleotide probes are complementary to a portion of the immobilized target nucleic acid molecule or immobilized complementary target nucleic acid molecule thereof, and (ii) one or more nucleotide triphosphates or analogues thereof, where (i), (ii), or both comprise an identifying signature modifier or a group suitable for coupling an identifying signature modifier. The method further involves hybridizing the one or more oligonucleotide probes to their complementary immobilized target nucleic acid molecule or immobilized complementary target nucleic acid molecule thereof in a base specific manner and subjecting the one or more hybridized oligonucleotide probes to an extension reaction to produce extension products hybridized to the immobilized target nucleic acid molecules or immobilized complementary target nucleic acid molecules thereof. The extension products comprises a target specific portion or a complement thereof and (a) one or more identifying signature modifiers, (b) a group suitable for coupling to an identifying signature modifier, or both (a) and (b). The method further involves denaturing the extension products from the immobilized target nucleic acid molecules or immobilized complementary target nucleic acid molecules thereof to release the extension products from the solid support, and feeding the denatured extension products through one or more nanopores capable of detecting said extension products. The identifying signature of each extension product that is generated is detected, as a result of said feeding, when each extension product passes through the one or more nanopores, and the presence of one or more target nucleotide sequences differing from other nucleotide sequences in the sample by one or more nucleotides, one or more copy numbers, one or more transcript sequences, and/or one or more methylated residues is identified, based on said detecting.

Another aspect of the present invention is directed method for identifying, in a sample, one or more target nucleotide sequences differing from other nucleotide sequences in the sample by one or more nucleotides, one or more copy numbers, one or more transcript sequences, and/or one or more methylated residues. This method comprises providing a sample containing one or more target nucleic acid molecules containing the target nucleotide sequence or complements thereof, and providing a solid support comprising one or more immobilized capture molecules, where the capture molecules are suitable to bind to a portion of the one or more target nucleic acid molecules. The method further involves binding the one or more target nucleic acid molecules to the one or more immobilized capture molecules on the solid support thereby immobilizing the one or more target nucleic acid molecules on said solid support. The immobilized target nucleic acid molecules or immobilized complementary target nucleic acid molecules thereof are contacted with one or more oligonucleotide probes, where the one or more oligonucleotide probes are complementary to a portion of the immobilized target nucleic acid molecule or immobilized complementary target nucleic acid molecule thereof, and where at least one of said one or more oligonucleotide probes comprises an identifying signature modifier. The one or more oligonucleotide probes are hybridized to their complementary immobilized target nucleic acid molecule or immobilized complementary target nucleic acid molecule thereof in a base specific manner. The method further involves subjecting the one or more hybridized oligonucleotide probes to a cleavage reaction to produce a cleavage product, where the cleavage product comprising a portion of one of the one or more oligonucleotide probes and the identifying signature modifier. The cleavage products are fed through one or more nanopores capable of detecting the cleavage product, and the identifying signature of each cleavage product that is generated when each product passes through the one or more nanopore is detected, as a result of said feeding. The presence of one or more target nucleotide sequences differing from other nucleotide sequences in the sample by one or more nucleotides, one or more copy numbers, one or more transcript sequences, and/or one or more methylated residues is identified, based on said detecting.

Another aspect of the present invention is directed to a method for identifying, in a sample, one or more nucleotides in a target nucleotide sequence. This method involves providing a sample containing one or more target nucleic acid molecules containing the target nucleotide sequence or a complement thereof, and providing a solid support comprising one or more immobilized capture molecules, said capture molecules suitable to bind to a portion of the one or more target nucleic acid molecules. The method further involves binding the one or more target nucleic acid molecule to the one or more immobilized capture molecules on the solid support thereby immobilizing the one or more target nucleic acid molecules on said solid support, and contacting the immobilized target nucleic acid molecules or immobilized complementary target nucleic acid molecules thereof with a solution to form a nucleotide extension reaction mixture. The solution comprises one or more oligonucleotide primers, wherein said oligonucleotide primers are complementary to a portion of said immobilized target nucleic acid molecule or immobilized complementary target nucleic acid molecule thereof, a polymerase, and a collection of nucleotide triphosphates, each type of nucleotide triphosphate in the collection having (i) a different cleavable identifying signature-generating moiety, and (ii) a cleavable blocking moiety that inhibits addition of a subsequent nucleotide triphosphate. The nucleotide extension reaction mixture is subjected to a hybridization treatment wherein the one or more oligonucleotide primers hybridize in a base specific manner to their complementary immobilized target nucleic acid molecules or immobilized complementary target nucleic acid molecules thereof, and the hybridized oligonucleotide primers are extended by a single base-specific addition of a nucleotide triphosphate from the collection of nucleotide triphosphates to the 3' end of the hybridized oligonucleotide primers. The identifying signature-generating moiety and the blocking moiety are cleaved from each nucleotide added to the hybridized oligonucleotide primers after said extending, and the cleaved identifying signature-generating moiety is fed through one or more nanopores capable of detecting said identifying signature-generating moiety. The method further involves detecting, as a result of said feeding, an identifying signature generated by the cleaved identifying signature-generating moiety when said cleaved moiety passes through the one or more nanopores, and identifying, based on said detecting, the nucleotide triphosphate from the collection of nucleotide triphosphates that was added during said extending, thereby identifying one or more nucleotides in a target nucleotide sequence in the sample.

Circulating markers from blood represents an exciting in vitro diagnostic scenario because of the minimally invasive nature of securing these markers and the plethora of marker types found in blood, such as biological cells, cell-free molecules (proteins and cell-free DNA) and vesicles (nanometer assemblies such as exosomes). Unfortunately, many of these blood-borne markers have not been effectively utilized in clinical practice to manage challenging diseases such as cancer, infectious diseases and stroke to name a few. This deficiency has arisen primarily from the fact that disease associated blood markers are a vast minority in a mixed population making them difficult to find and analyze due to the lack of efficient platforms for their isolation and systems that can determine the molecular structural variations they may harbor. To address this pressing need, innovative diagnostic assays capable of selecting circulating markers from whole blood and processing disease-specific molecular signatures are needed and are described herein.

One family of assays described herein involves the detection of sequence variations in both DNA and RNA molecules using solid-phase ligase detection reactions (spLDR), polymerase mediated extension reactions, and/or enzymatic cleavage reactions. The oligonucleotide products formed during these reactions are electrokinetically swept into nanometer flight tubes with their identification based on molecular-dependent electrophoretic mobilities. A second family of assays described herein involves solid phase targeted amplification and sequencing of target nucleic acid molecule with time-of-flight based detection of sequencing information using a nanoscale flight tube containing one or more nanopores. Some advantages of these assays include, without limitation (i) elimination of PCR, improving quantification capabilities and reducing false-signal arising from PCR errors; (ii) digital counting of each target, which improves the analytical sensitivity of the measurement; (iii) universal platform for several different molecular assays (mutation, methylation, mRNA, miRNA, copy-variation, alternative splicing, or translocation markers); (iv) low-cost assays that do not require fluorescent labels and the associated optical hardware; (v) isothermal enzymatic reactions, obviating need for thermocycling hardware; (vi) rapid assay turn-around times with full process automation; and (vii) extremely high multiplexing power—screen for >20 mutations/methylation/expression in a single 5 min cycle, with the ability to run dozens of such cycles per sample.

BRIEF DESCRIPTION OF THE DRAWINGS

FIG. 1A is a perspective view of a nanosensor chamber 30 within a nanosensor module. In this embodiment, each nanosensor chamber 30 contains eight biomolecular processors 1, each coupled to a single nanotube 6. FIG. 1B is perspective view of the biomolecular processor 1 and nanotube 6. FIG. 1C is a top view of a nanopore 8 within the nanotube 6 shown in FIG. 1B.

FIG. 2A is a perspective view of a nanosensor chamber containing eight biomolecular processors 1 and eight nanotubes, where only the input end 12 of the nanotube is shown. FIG. 2B is a perspective view showing an isolated biomolecular processor and vertically positioned nanotube. FIG. 2C is a cross-sectional view through the vertically positioned nanotube.

FIGS. 7A-7B show a top view of a nanotube (FIG. 7A), and a circuit diagram of the nanotube with electrodes and measuring circuitry (FIG. 7B). The circuit diagram of FIG. 7B depicts one embodiment for measuring a biomolecule's identifying signature as it passes through a nanopore of the nanotube.

FIGS. 15A-15B are electronic system block diagrams showing two methods for detecting and processing biomolecular identifying signatures from a single nanotube.

FIGS. 18A-18B depict the cell isolation module of the uMPS. FIG. 18A is a perspective view of the cell isolation module comprising the cell capture bed. FIG. 18B (inset of FIG. 18A) is a perspective view of the sinusoidal channels that make up the capture bed of the cell isolation module.

FIGS. 20A-20D depict the plasma isolation module of the uMPS. FIG. 20A is a perspective view of the plasma isolation module. FIG. 20B is a cross-sectional perspective view (through line 20B-20B of FIG. 20A) showing the first main chamber, the first side chamber, and the passageway between the first main chamber and first side chamber of the plasma isolation module. FIG. 20C is a cross-sectional perspective view (through line 20C-20C of FIG. 20A) showing the second main chamber, the second side chamber, and the passageway between the second main chamber and second side chamber of the plasma isolation module. FIG. 20D is a cross-sectional view of the plasma isolation unit taken through line 20D-20D of FIG. 20A.

FIG. 21A is a perspective view of this plasma isolation unit. FIG. 21B is a cross-sectional view of this plasma isolation unit taken through line 21B-21B of FIG. 21A.

FIG. 23A is a perspective view of the impedance module, and FIG. 23B is an exploded perspective view showing the three layers of the impedance module.

FIG. 24 shows the process of making the impedance module depicted in FIGS. 23A-23B.

FIG. 26A is a perspective view of the diffusional purification module, and FIG. 26B is a top-view of the inset from FIG. 26A showing the spacing between obstacles within the diffusional purification bed.

FIG. 28B shows an assembled gasket-less seal. The alignment accuracy is ~10 μm. FIG. 28C shows that the superhydrophobic seals between mated pieces when aligned.

FIG. 29A shows the process of making the resin stamp that is used in the process of making the nanofluidic chambers and channels as depicted in FIG. 29B.

FIG. 30A is a schematic of the assembly of the hybrid-based fluidic devices and the thermal press instrument. FIG. 30B shows the temperature-pressure process profile showing the six stages for the thermal fusion bonding cycle.

FIG. 37A is a graph showing the change in current amplitude within the nanopore over time. FIG. 37B shows the statistics for the amplitude of the current peaks obtained from 156 translocation events through the differentially sized nanopores.

FIGS. 40A-40F show various aspects of the electrophoretic transport of silver nanoparticles (AgNP) through a nanotube. FIG. 40A is an intensity image of a single AgNP parked in a nanotube showing the intensity of the localized surface plasmon resonance of the single nanoparticle. FIG. 40B is representation of the electrophoretic transport for a single nanoparticle event (60 nm AgNP) in a nanotube. FIG. 40C shows a plot of the electrophoretic mobility and the theoretical plate number, which measures the variance of the mobility, as a function of field strength. FIGS. 40D-40F are histograms of time-of-flight events for silver nanoparticle in nanotube.

FIGS. 44A and 44B are diagrams illustrating the origin of higher than buffer-only resistance registered for intact cells (FIG. 44A) and drop in resistance for cells containing membranes that are compromised (FIG. 44B). $R_{cell}$ is the resistance of cell, and $R_{sol}$ is the resistance of volume of solution equal to volume of cell.

FIG. 45A shows a computational fluid dynamics simulation of plasma flow through a solid-phase extraction bed comprised of diamond micropillars with 15 μm side length and 5 μm spacing. FIG. 45B shows a Monte Carlo diffusion simulation. FIG. 45C represents results from the Monte Carlo diffusion simulation for the transport (pressure driven flow) through a 10 um wide channel whose walls are coated with an affinity agent specific for an exosome. The "X" marks the location where the exosome has become bound to the surface through the association between the surface attached affinity agent and the targeting antigen resident on the surface of the exosome.

FIG. 64 illustrates interrogation of support bound single molecule clusters of target DNA using polymerase extension assays of the present invention.

FIG. 65 illustrates interrogation of support bound single molecule clusters of target DNA using polymerase extension assays of the present invention.

FIG. 66 illustrates interrogation of support bound single molecule clusters of target DNA using polymerase extension assays of the present invention.

FIG. 74 shows a solid phase ligation reaction process utilized to detect mutations or copy number from genomic or cfDNA.

FIG. 75 shows a solid phase ligation reaction process utilized to detect mutations or copy number from genomic or cfDNA.

FIG. 76 illustrates a solid phase ligation reaction process with carryover protection to detect mutations or copy number from genomic or cfDNA.

FIG. 77 shows a solid phase ligation reaction process utilized to detect mutations or copy number from genomic or cfDNA.

FIG. 78 illustrates a solid phase cleavage reaction process suitable for detecting mutations or copy number from genomic or cfDNA.

FIG. 79 illustrates a solid phase primer extension process suitable for detecting mutations or copy number from genomic or cfDNA.

FIG. 80 illustrates a solid phase primer extension process suitable for detecting repeat polymorphisms of different length from genomic or cfDNA.

FIG. 81 shows a solid phase ligation reaction process utilized to detect mutations or copy number from genomic or cfDNA.

FIG. 82 illustrates a solid phase cleavage reaction process suitable for detecting mutations or copy number from genomic or cfDNA.

FIG. 83 illustrates a solid phase primer extension process suitable for detecting mutations or copy number from genomic or cfDNA.

FIG. 84 illustrates a solid phase primer extension process suitable for detecting repeat polymorphisms of different length from genomic or cfDNA.

FIG. 85 illustrates a solid phase ligation reaction process suitable for detecting locus-specific mutation or copy number from genomic or cfDNA.

FIG. 86 illustrates a solid phase cleavage reaction process suitable for detecting locus-specific mutation or copy number from genomic or cfDNA.

FIG. 87 illustrates a solid phase primer extension process suitable for detecting locus-specific mutation or copy number from genomic or cfDNA.

FIG. 88 illustrates another solid phase primer extension process suitable for detecting locus-specific mutation or copy number from genomic or cfDNA.

FIG. 89 illustrates a solid phase ligation reaction process suitable for detecting locus-specific mutation or copy number from genomic or cfDNA.

FIG. 90 illustrates a solid phase cleavage reaction process suitable for detecting locus-specific mutation or copy number from genomic or cfDNA.

FIG. 91 illustrates a solid phase primer extension process suitable for detecting locus-specific mutation or copy number from genomic or cfDNA.

FIG. 92 illustrates another solid phase primer extension process suitable for detecting locus-specific mutation or copy number from genomic or cfDNA.

FIG. 93 depicts a solid phase ligation reaction process suitable for enumerating copy number from a low input of genomic copies of DNA, such as from circulating tumor cell (CTC) DNA.

FIG. 94 depicts a solid phase cleavage reaction process suitable for enumerating copy number from a low input of genomic copies of DNA, such as from circulating tumor cell (CTC) DNA.

FIG. 95 depicts a solid phase primer extension process suitable for enumerating copy number from a low input of genomic copies of DNA, such as from circulating tumor cell (CTC) DNA.

FIG. 96 depicts another solid phase primer extension process suitable for enumerating copy number from a low input of genomic copies of DNA, such as from circulating tumor cell (CTC) DNA.

FIG. 97 illustrates a solid phase ligation reaction process suitable for enumerating low-abundance DNA in a sample.

FIG. 98 depicts a solid phase cleavage reaction process suitable for enumerating low-abundance DNA in a sample.

FIG. 99 depicts a solid phase primer extension process suitable for enumerating low-abundance DNA in a sample.

FIG. 100 depicts another solid phase primer extension process suitable for enumerating low-abundance DNA in a sample.

FIG. 101 illustrates a solid phase ligation reaction process suitable for detecting methylated residues in genomic or cfDNA.

FIG. 102 depicts a solid phase cleavage reaction process suitable for detecting methylated residues in genomic or cfDNA.

FIG. 103 depicts a solid phase primer extension process suitable for detecting methylated residues in genomic or cfDNA.

FIG. 104 depicts a solid phase primer extension process suitable for detecting methylated residues in genomic or cfDNA.

FIG. 105 illustrates a solid phase ligation reaction process suitable for detecting locus-specific methylation in a DNA sample.

FIG. 106 illustrates a solid phase ligation reaction process involving a bisulfite treatment that is suitable for detecting methylation in a genomic or cfDNA sample.

FIG. 107 illustrates a solid phase primer extension reaction process involving a bisulfite treatment that is suitable for detecting methylation in a genomic or cfDNA sample.

FIG. 108 illustrates a solid phase ligation reaction process involving a bisulfite treatment that is suitable for detecting methylation in a genomic or cfDNA sample.

FIG. 109 depicts a solid phase primer extension process involving a bisulfite treatment that is suitable for detecting methylation in a genomic or cfDNA sample.

FIG. 110 depicts a solid phase cleavage reaction process involving a bisulfite treatment that is suitable for detecting methylation in a genomic or cfDNA sample.

FIG. 111 depicts a solid phase primer extension process involving a bisulfite treatment that is suitable for detecting methylation in a genomic or cfDNA sample.

FIG. 112 depicts a solid phase ligation reaction process suitable for detecting mRNA in a sample.

FIG. 113 depicts a solid phase ligation reaction process suitable for detecting mRNA and/or long non-coding RNA (lncRNA) in a sample.

FIG. 114 depicts a solid phase ligation reaction process suitable for detecting mRNA and/or long non-coding RNA (lncRNA) in a sample.

FIG. 115 depicts a solid phase cleavage reaction process suitable for detecting mRNA and/or long non-coding RNA (lncRNA) in a sample.

FIG. 116 depicts a solid phase primer extension process suitable for detecting mRNA and/or long non-coding RNA (lncRNA) in a sample.

FIG. 117 depicts a solid phase ligation reaction process suitable for enumerating low-abundance specific mRNA transcript in a sample.

FIG. 118 depicts a solid phase ligation reaction process suitable for detecting mRNA and/or long non-coding RNA (lncRNA) in a sample.

FIG. 119 depicts a solid phase cleavage reaction process suitable for detecting mRNA and/or long non-coding RNA (lncRNA) in a sample.

FIG. 120 depicts a solid phase primer extension process suitable for detecting mRNA and/or long non-coding RNA (lncRNA) in a sample.

FIG. 121 depicts a solid phase ligation reaction process suitable for detecting mRNA and/or long non-coding RNA (lncRNA) in a sample.

FIG. 122 depicts a solid phase ligation reaction process suitable for detecting mRNA and/or long non-coding RNA (lncRNA) in a sample.

FIG. 123 depicts a solid phase cleavage reaction process suitable for detecting mRNA and/or long non-coding RNA (lncRNA) in a sample.

FIG. 124 depicts a solid phase primer extension process suitable for detecting mRNA and/or long non-coding RNA (lncRNA) in a sample.

FIG. 125 depicts a solid phase ligation reaction process suitable for detecting low abundance mRNA and/or long non-coding RNA (lncRNA) in a sample.

FIG. 126 depicts a solid phase cleavage reaction process suitable for detecting low abundance mRNA and/or long non-coding RNA (lncRNA) in a sample.

FIG. 127 depicts a solid phase primer extension process suitable for detecting low abundance mRNA and/or long non-coding RNA (lncRNA) in a sample.

FIG. 128 depicts a solid phase ligation reaction process suitable for detecting translocations at the mRNA level in a sample.

FIG. 129 depicts a solid phase ligation reaction process suitable for detecting translocations at the mRNA level in a sample.

FIG. 130 depicts a solid phase cleavage reaction process suitable for detecting translocations at the mRNA level in a sample.

FIG. 131 depicts a solid phase primer extension process suitable for detecting translocations at the mRNA level in a sample.

Figure 1A:
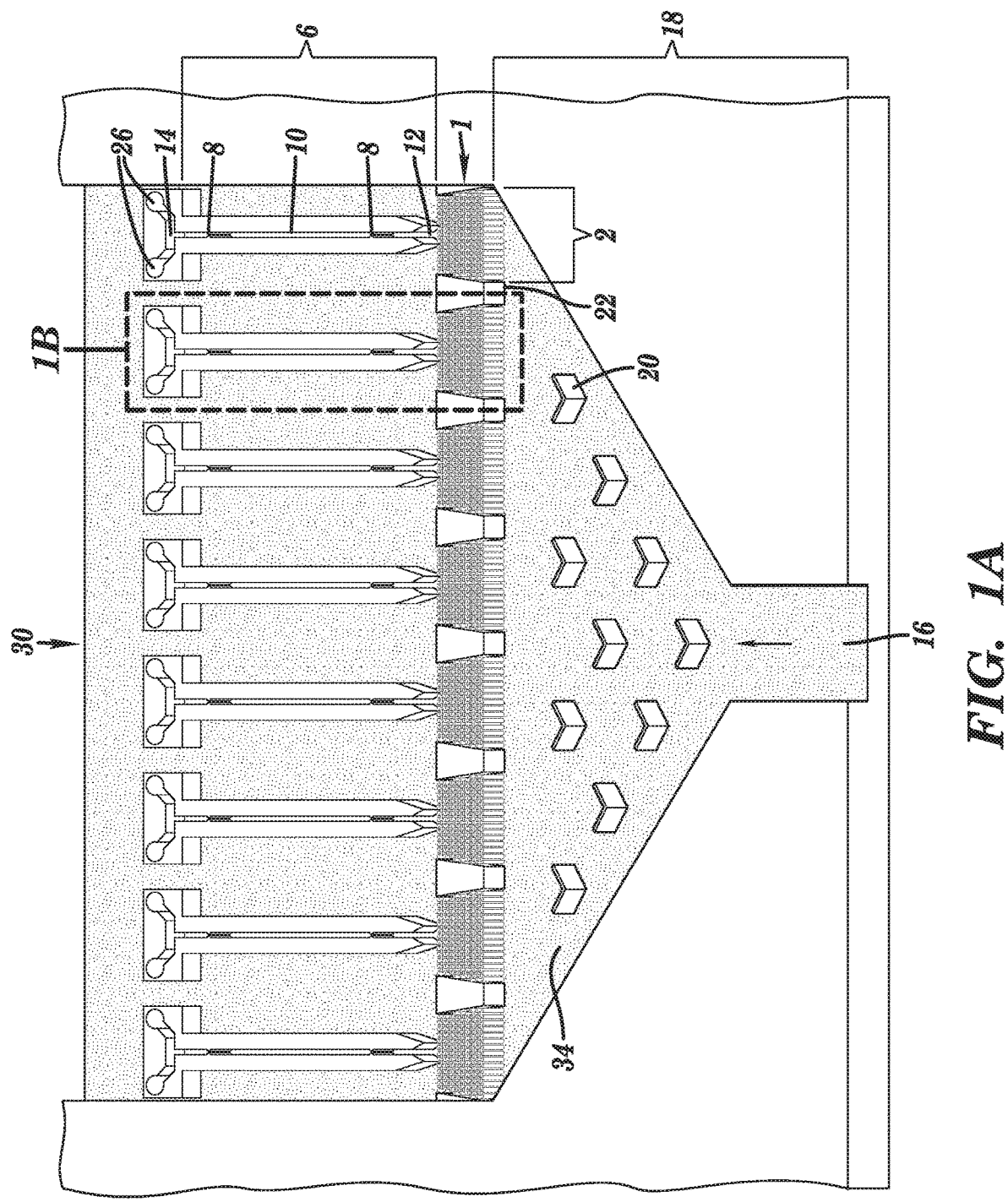
FIGS. 1A-1C are perspective views of the biomolecular processor and one or more nanotubes of a device as described herein.

FIG. 132 depicts a solid phase ligation reaction process suitable for detecting low abundance translocation events at the mRNA level in a sample.

FIG. 133 depicts a solid phase cleavage reaction process suitable for detecting low abundance translocations at the mRNA level in a sample.

FIG. 134 depicts a solid phase primer extension process suitable for detecting low abundance translocations at the mRNA level in a sample.

FIG. 135 depicts a solid phase ligation reaction process suitable for detecting and quantifying alternative splice variants in a mRNA transcript in a sample.

FIG. 136 depicts a solid phase ligation reaction process suitable for detecting and quantifying alternative splice variants in an mRNA transcript in a sample.

FIG. 137 depicts a solid phase cleavage reaction process suitable for detecting and quantifying alternative splice variants in an mRNA transcript in a sample.

FIG. 138 depicts a solid phase primer extension process suitable for detecting and quantifying alternative splice variants in an mRNA transcript in a sample.

FIG. 139 depicts a solid phase ligation reaction process suitable for detecting and quantifying low abundance alternative splice variants in an mRNA transcript in a sample.

FIG. 140 depicts a solid phase cleavage reaction process suitable for detecting and quantifying low abundance alternative splice variants in an mRNA transcript in a sample.

FIG. 141 depicts a solid phase primer extension process suitable for detecting and quantifying low abundance alternative splice variants in an mRNA transcript in a sample.

FIG. 142 shows a solid phase ligation reaction process suitable for detecting microRNA (miRNA) in a sample.

FIG. 143 shows a solid phase ligation reaction process suitable for detecting microRNA (miRNA) in a sample.

FIG. 144 depicts a solid phase cleavage reaction process suitable for detecting microRNA (miRNA) in a sample.

FIG. 145 depicts a solid phase primer extension process suitable for detecting microRNA (miRNA) in a sample.

FIG. 146 shows a solid phase ligation reaction process suitable for detecting microRNA (miRNA) in a sample.

FIG. 147 shows a solid phase ligation reaction process suitable for detecting specific microRNA (miRNA) in a sample.

FIG. 148 depicts a solid phase cleavage reaction process suitable for detecting specific microRNA (miRNA) in a sample.

FIG. 149 depicts a solid phase primer extension process suitable for detecting specific microRNA (miRNA) in a sample.

FIG. 150 illustrates two-sided general DNA amplification on a solid support.

FIG. 151 shows target nucleic acid molecule adapter design and method of appending adapter to target nucleic acid molecule.

FIG. 152 shows target nucleic acid molecule adapter design and method of appending adapter to target nucleic acid molecule.

FIG. 153 shows target nucleic acid molecule adapter design and method of appending adapter to target nucleic acid molecule.

FIG. 154 shows two-sided targeted DNA amplification on a solid support.

FIG. 155 shows two-sided targeted DNA amplification using a hairpin primer on a solid support.

FIG. 156 shows two-sided targeted DNA amplification on a solid support.

FIG. 157 shows two-sided targeted DNA amplification using a hairpin primer on a solid support.

FIG. 158 shows two-sided targeted DNA amplification on a solid support.

FIG. 159 shows two-sided targeted DNA amplification using a hairpin primer on a solid support.

FIG. 160 shows two-sided targeted DNA amplification on a solid support.

FIG. 161 shows two-sided targeted DNA amplification using a hairpin primer on a solid support.

Figure 162:
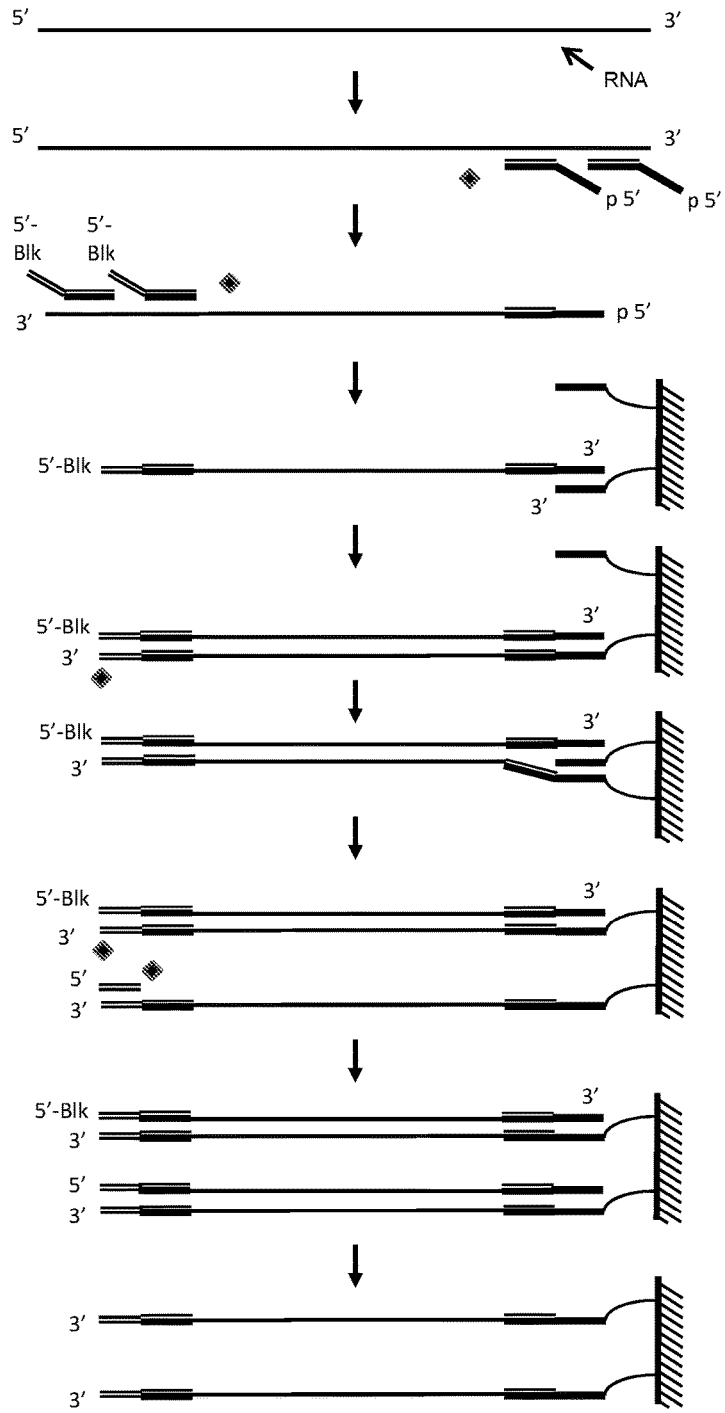

FIG. 162 shows two-sided targeted viral RNA amplification on a solid support.

FIG. 163 shows two-sided targeted viral RNA amplification on a solid support.

FIG. 164 depicts a process for circularizing a target nucleic acid molecule.

FIG. 165 depicts a process for circularizing a target nucleic acid molecule.

FIG. 166 depicts a process for circularizing a target nucleic acid molecule.

FIG. 167 depicts a process for circularizing a target nucleic acid molecule.

FIG. 168 depicts a process for circularizing a target nucleic acid molecule.

FIG. 169 depicts a process for circularizing a target nucleic acid molecule.

FIG. 170 depicts a process for circularizing a target nucleic acid molecule.

FIG. 171 depicts a process for circularizing a target nucleic acid molecule.

FIG. 172 depicts a process for circularizing a target nucleic acid molecule.

FIG. 173 illustrates a process for targeted DNA rolling circle amplification on a solid support.

FIG. 174 illustrates a process for targeted DNA rolling circle amplification on a solid support.

FIG. 175 illustrates a process for targeted DNA rolling circle amplification on a solid support.

FIG. 176 illustrates a process for targeted DNA rolling circle amplification on a solid support.

FIG. 177 shows a solid phase sequencing-by-synthesis process to obtain sequence information for a target nucleic acid molecule in a sample.

FIG. 178 shows a solid phase sequencing-by-synthesis process to obtain sequence information for a target nucleic acid molecule in a sample.

FIG. 179 shows a solid phase sequencing-by-chain-termination process to obtain sequence information for a target nucleic acid molecule in a sample.

FIG. 180 shows a solid phase sequencing-by-chain-termination process to obtain sequence information for a target nucleic acid molecule in a sample.

FIG. 181 shows a solid phase sequencing-by-chain-termination process to obtain sequence information for a target nucleic acid molecule in a sample.

FIG. 182 shows a solid phase sequencing-by-chain-termination process to obtain sequence information for a target nucleic acid molecule in a sample.

FIG. 183 shows a solid phase sequencing-by-chain-termination process to obtain sequence information for a target nucleic acid molecule in a sample.

FIG. 184 shows a solid phase sequencing-by-chain-termination process to obtain sequence information for a target nucleic acid molecule in a sample.

FIG. 185 shows a solid phase sequencing-by-chain-termination process to obtain sequence information for a target nucleic acid molecule in a sample.

FIG. 186 shows a solid phase sequencing-by-synthesis process to obtain sequence information for a target nucleic acid molecule in a sample.

FIG. 187 shows a solid phase sequencing-by-synthesis process to obtain sequence information for a target nucleic acid molecule in a sample.

FIG. 188 shows a solid phase sequencing-by-synthesis process to obtain sequence information for a target nucleic acid molecule in a sample.

FIG. 189 shows a bi-directional solid phase sequencing-by-chain-termination process to obtain sequence information for a target nucleic acid molecule in a sample.

FIG. 190 shows a solid phase sequencing-by-synthesis process to obtain sequence information for a target nucleic acid molecule in a sample.

FIG. 191 shows a solid phase sequencing-by-synthesis process to obtain sequence information for a target nucleic acid molecule in a sample.

Figure 192:
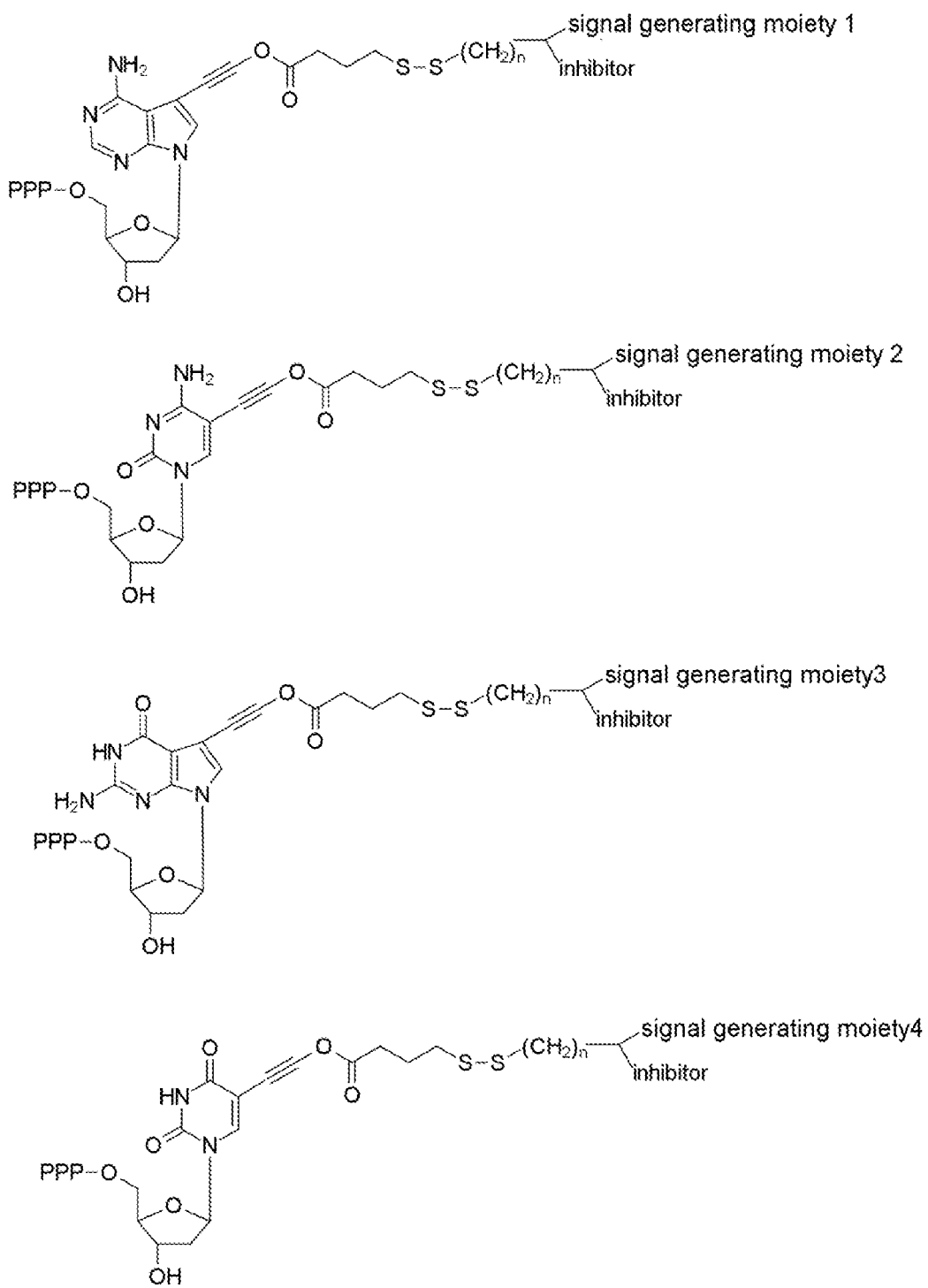

FIG. 192 shows the structures of reversible terminator dNTP analogs with unblocked 3'-OH that are suitable for use in the solid phase sequencing-by-synthesis process of the present invention.

Figure 193:
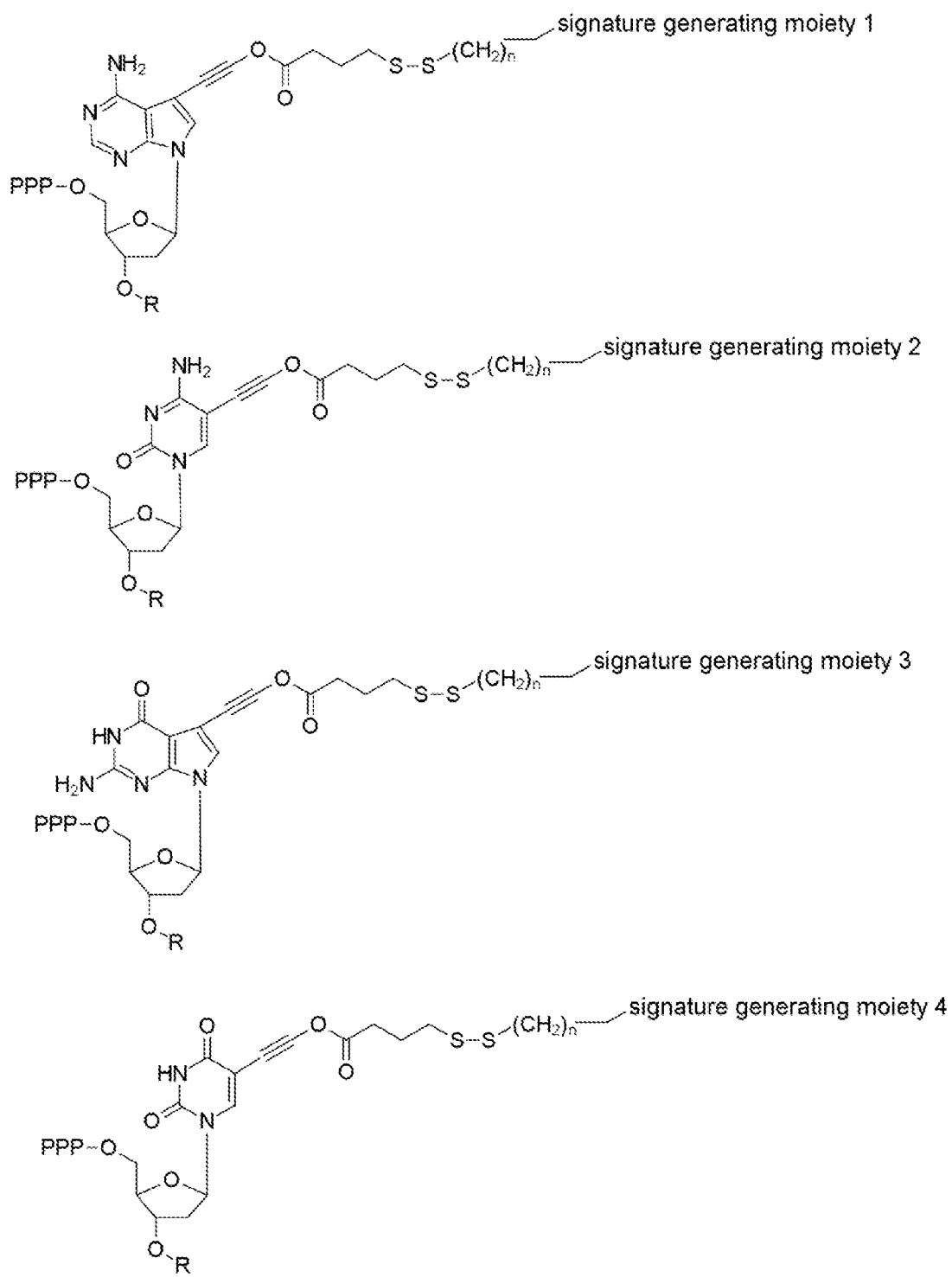

FIG. 193 illustrates the structures of reversible terminator dNTP analogs with blocked 3'-OH that are suitable for use in the solid phase sequencing-by-synthesis process of the present invention.

FIG. 194 illustrates the structures of dideoxy terminator dNTP analogs with 3' encoded identifying signature modifier groups that are suitable for use in the solid phase sequencing-by-chain-termination process of the present invention.

FIG. 195 illustrates the structures of dideoxy terminator dNTP analogs with biotin capture groups that are suitable for use in the solid phase sequencing-by-chain-termination process of the present invention.

FIG. 196 illustrates the cleavage mechanism for the two types of reversible terminator dNTP analogs described in FIGS. 192 and 193. The schematic of the top portion of FIG. 196 shows a reducing agent cleaving the disulfide linkage to simultaneously release the base extension inhibitor (i.e., the blocking moiety) and the identifying signature-generating moiety. The schematic at the bottom portion of FIG. 196 shows a reducing agent simultaneously removing the 3'-O-blocking group and cleaving the disulfide linkage to release the identifying signature-generating moiety.

FIG. 197 is a summary of the simulated effect of phase shift errors on the ability to interpret a sequencing-by-synthesis run on a universal molecular processor run.

Figure 198:
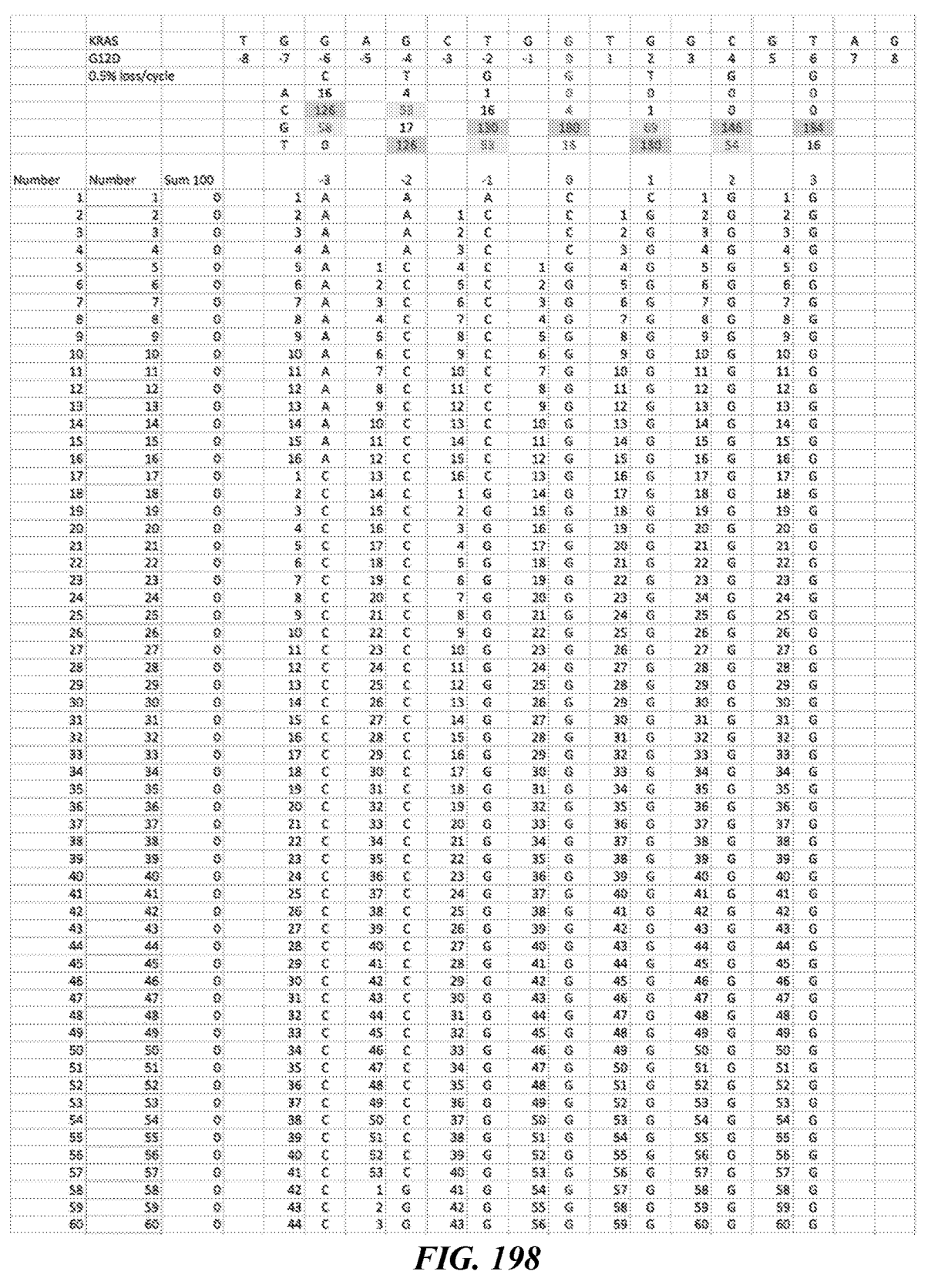

FIG. 198 is simulated raw data from universal molecular biomolecular processor sequencing to distinguish K-ras mutations with phase errors at 0.5% loss per cycles, and also at 0.5% loss and 0.5% gain per cycle after 100 cycles of simulated sequencing-by-synthesis. The wildtype K-ras sequence having a nucleotide sequence of TGGAGCTG-GTGGCGTAG (SEQ ID NO: 3) is depicted in this Figure.

Figure 199:
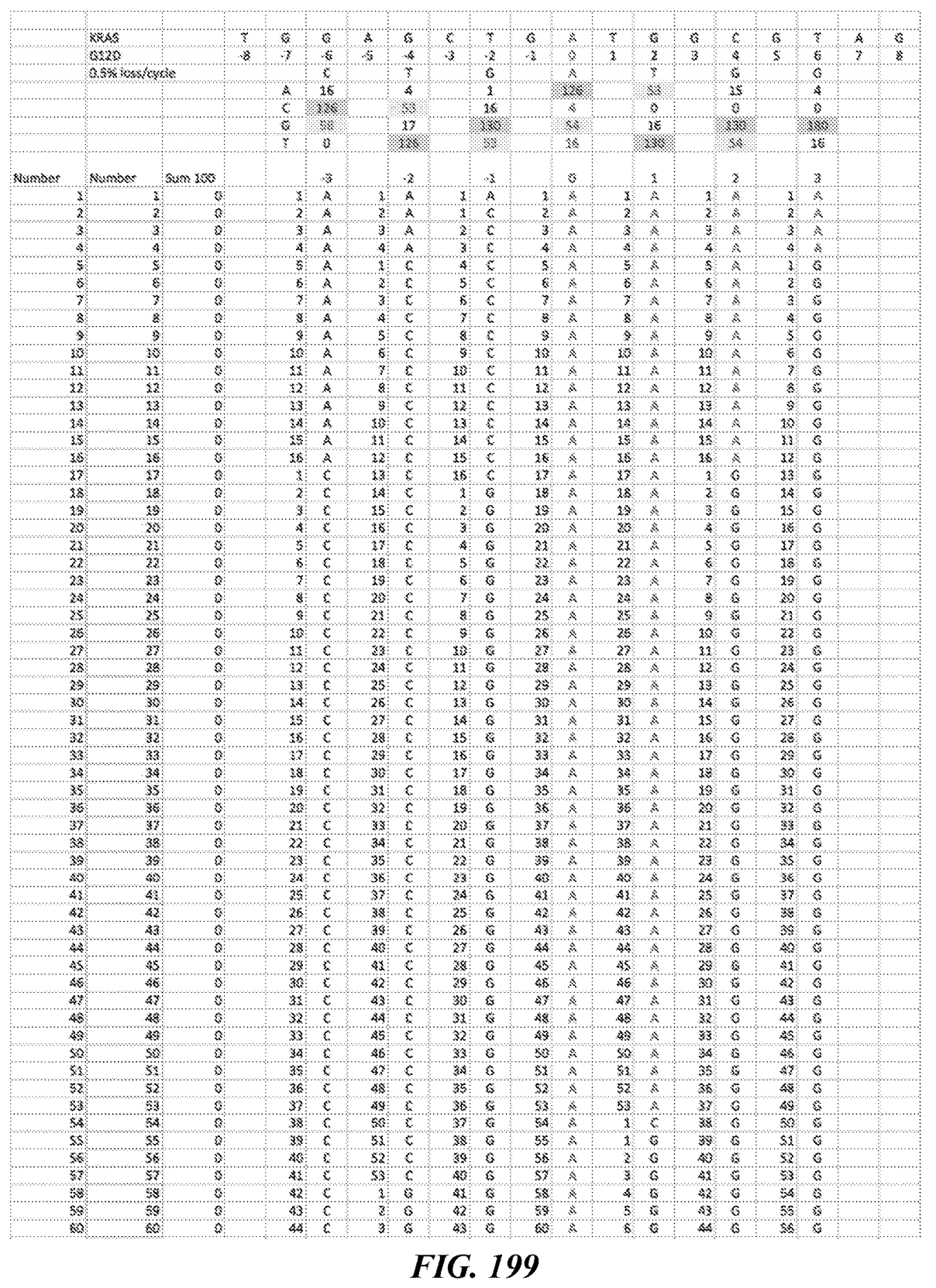

FIG. 199 is simulated raw data from universal molecular biomolecular processor sequencing to distinguish K-ras mutations with phase errors at 0.5% loss per cycles, and also at 0.5% loss and 0.5% gain per cycle after 100 cycles of simulated sequencing-by-synthesis. The mutant K-ras sequence having a nucleotide sequence of TGGAGCT-GATGGCGTAG (SEQ ID NO: 4) is depicted in this Figure.

Figure 200:
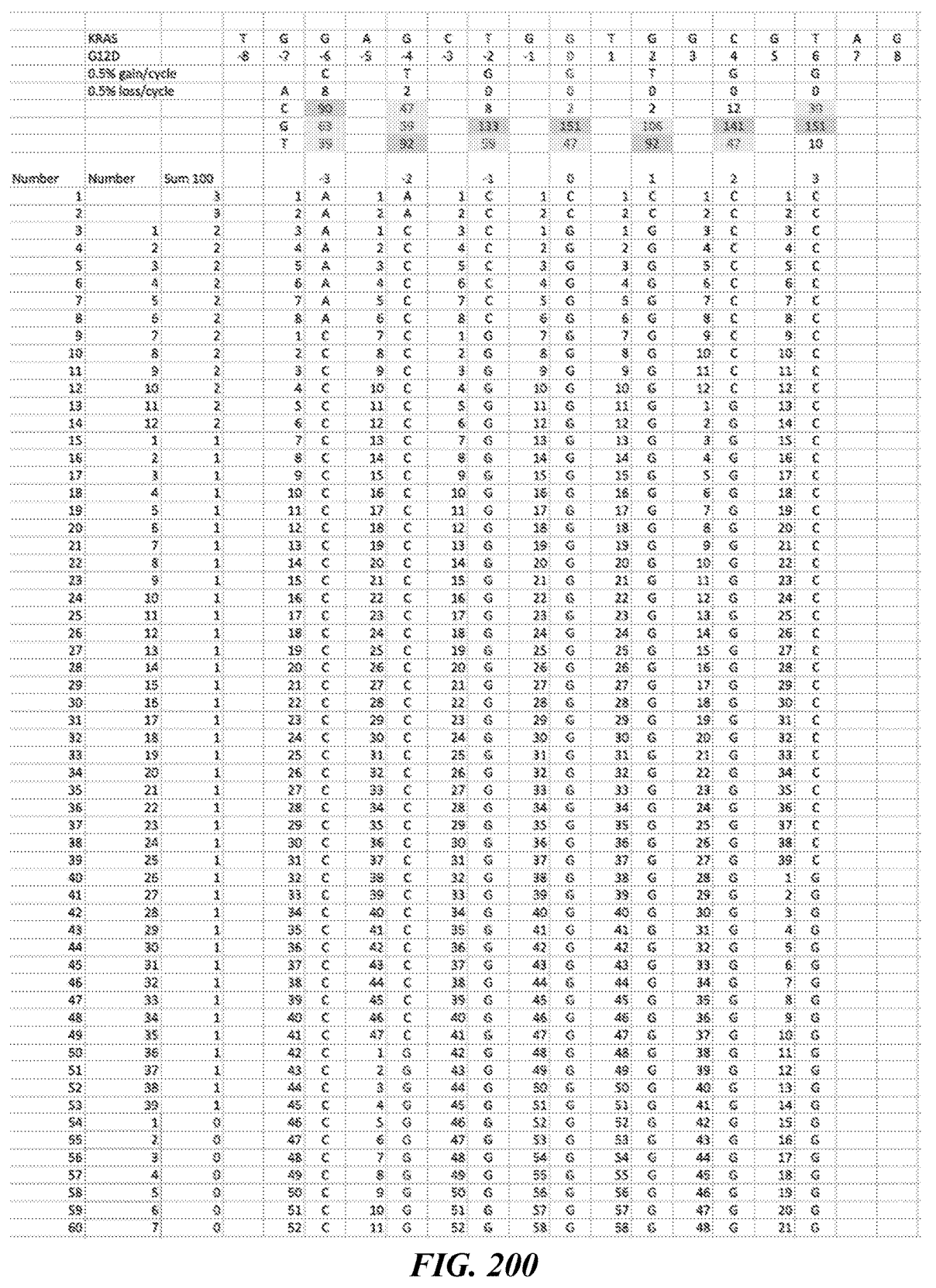

FIG. 200 is simulated raw data from universal molecular biomolecular processor sequencing to distinguish K-ras mutations with phase errors at 0.5% loss per cycles, and also at 0.5% loss and 0.5% gain per cycle after 100 cycles of simulated sequencing-by-synthesis. The wildtype K-ras sequence having a nucleotide sequence of TGGAGCTG-GTGGCGTAG (SEQ ID NO: 3) is depicted in this Figure.

Figure 201:
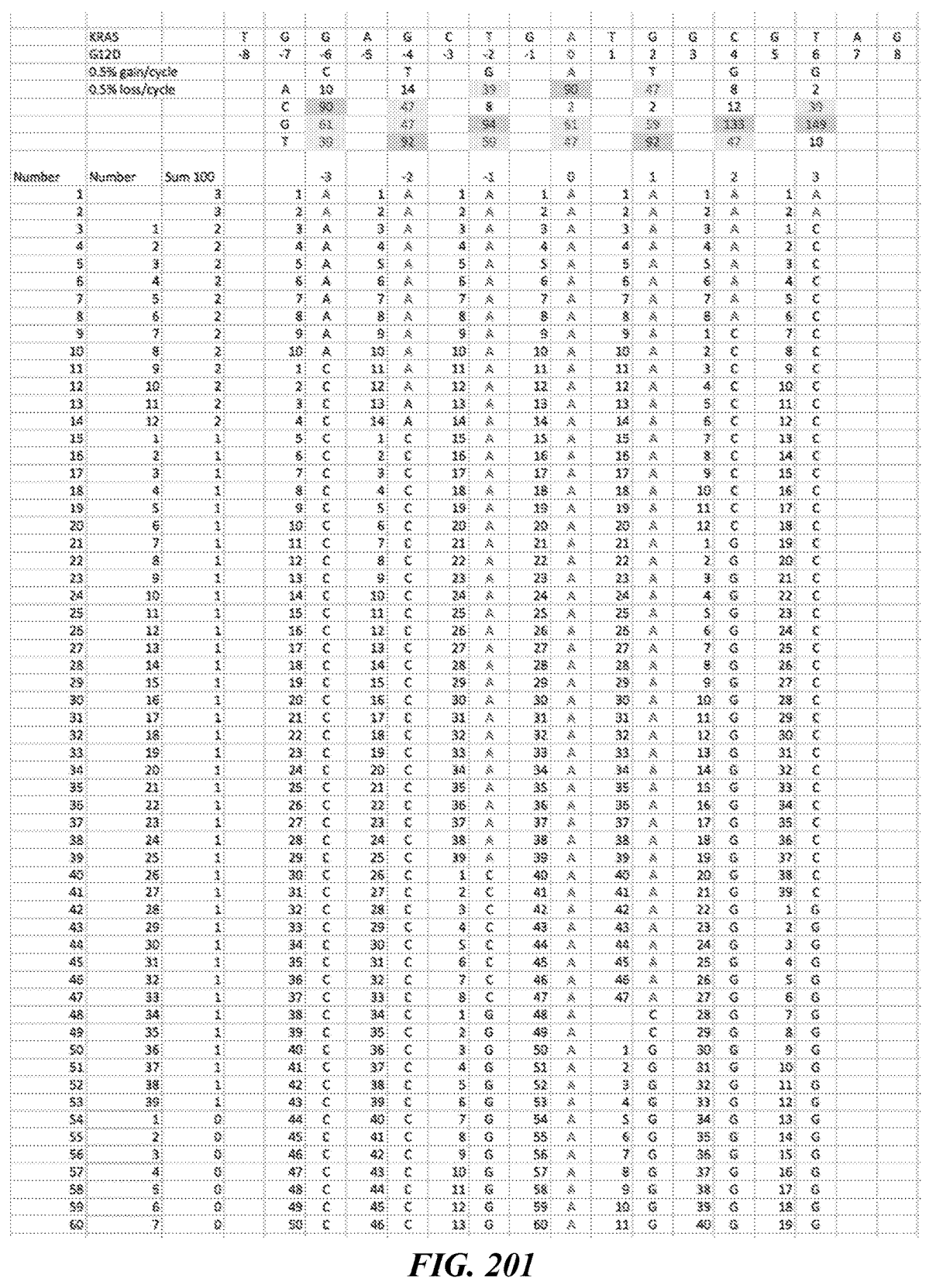

FIG. 201 is simulated raw data from universal molecular biomolecular processor sequencing to distinguish K-ras mutations with phase errors at 0.5% loss per cycles, and also at 0.5% loss and 0.5% gain per cycle after 100 cycles of simulated sequencing-by-synthesis. The mutant K-ras sequence having a nucleotide sequence of TGGAGCT-GATGGCGTAG (SEQ ID NO: 4) is depicted in this Figure.

Figure 202:
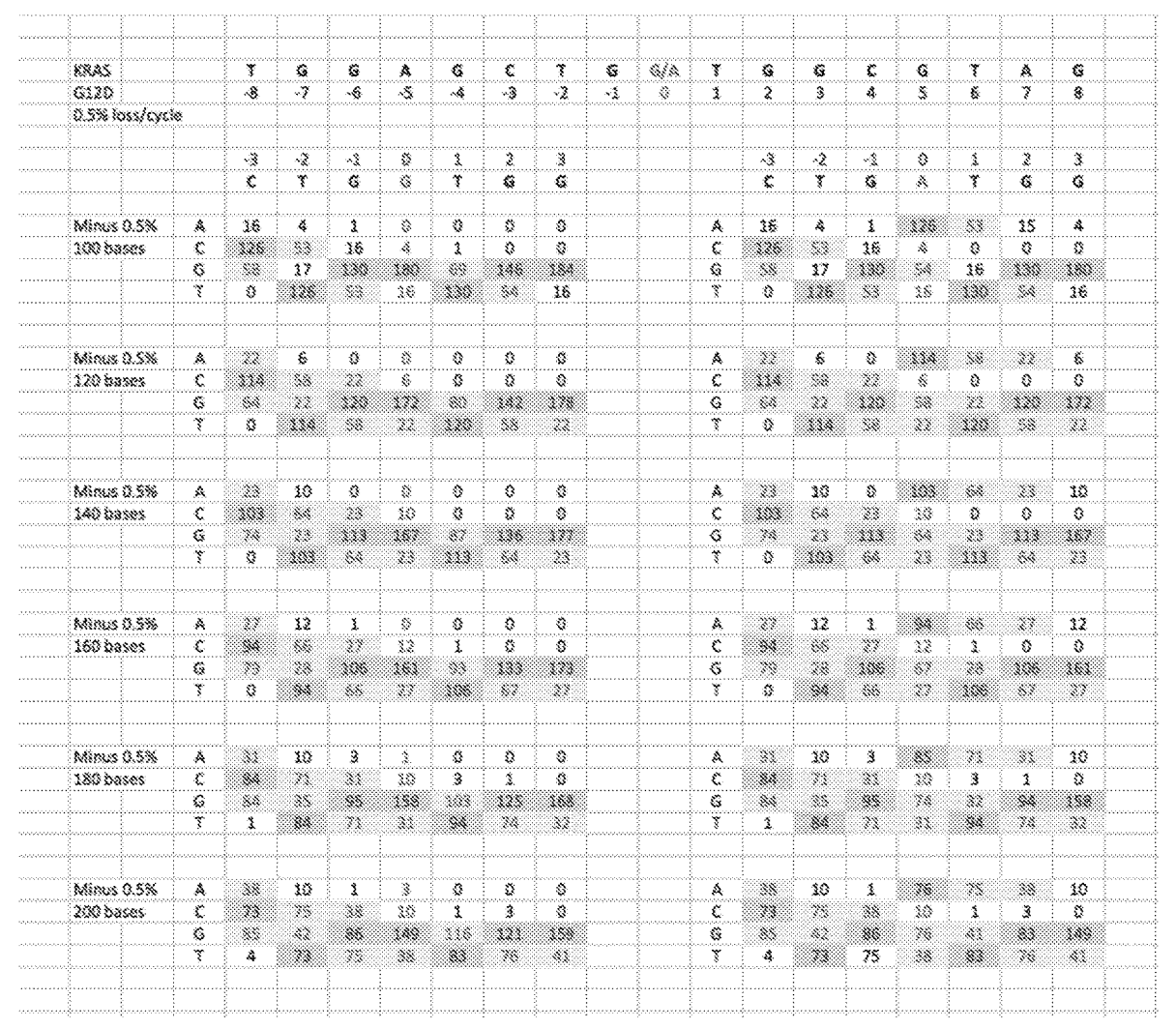

FIG. 202 provides a summary of the simulated calculations for base calls surrounding the wildtype (SEQ ID NO: 3)/mutant (SEQ ID NO: 4) base for a K-ras codon 12 mutation using universal molecular processor sequencing-by-synthesis.

Figure 203:
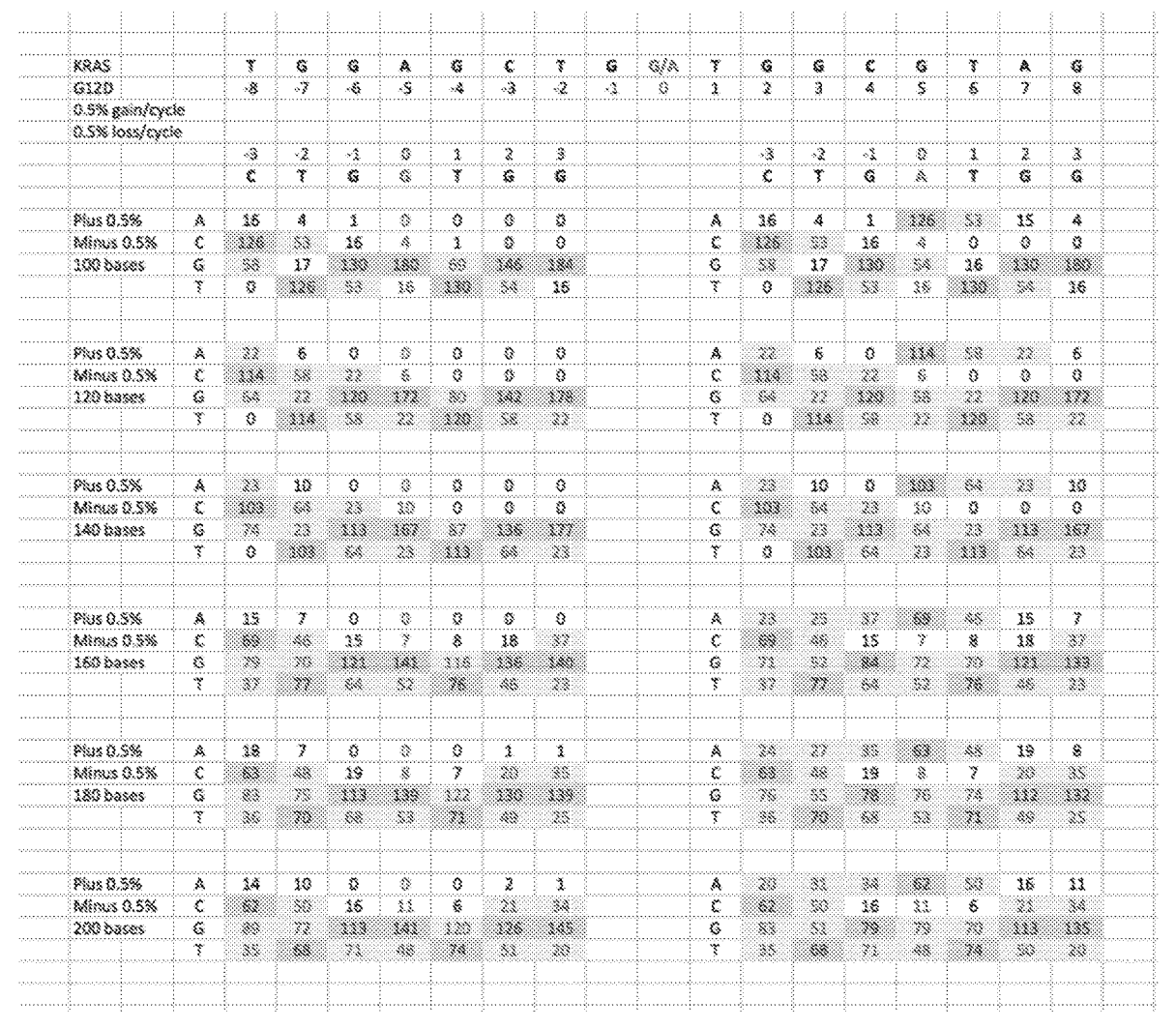

FIG. 203 provides a summary of the simulated calculations for base calls surrounding the wildtype (SEQ ID NO: 3)/mutant (SEQ ID NO: 4) base for a K-ras codon 12 mutation using universal molecular processor sequencing-by-synthesis.

Figure 204:
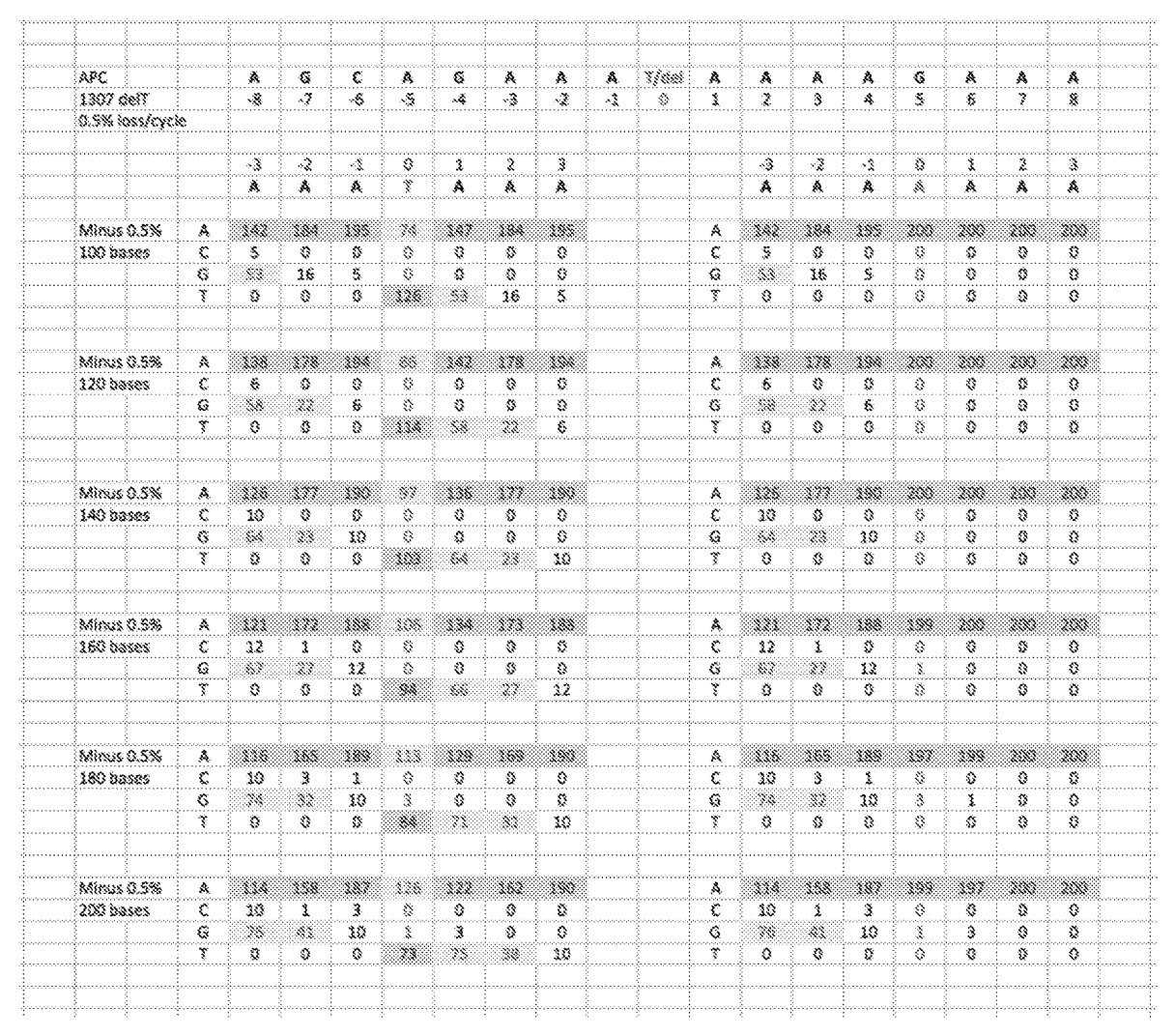

FIG. 204 provides a summary of the simulated calculations for base calls surrounding the wildtype/mutant base for a APC gene codon 1307 single-base deletion, i.e., AGCA-GAAA[T/del]AAAAGAAA (SEQ ID NO: 5), using universal molecular processor sequencing-by-synthesis.

Figure 205:
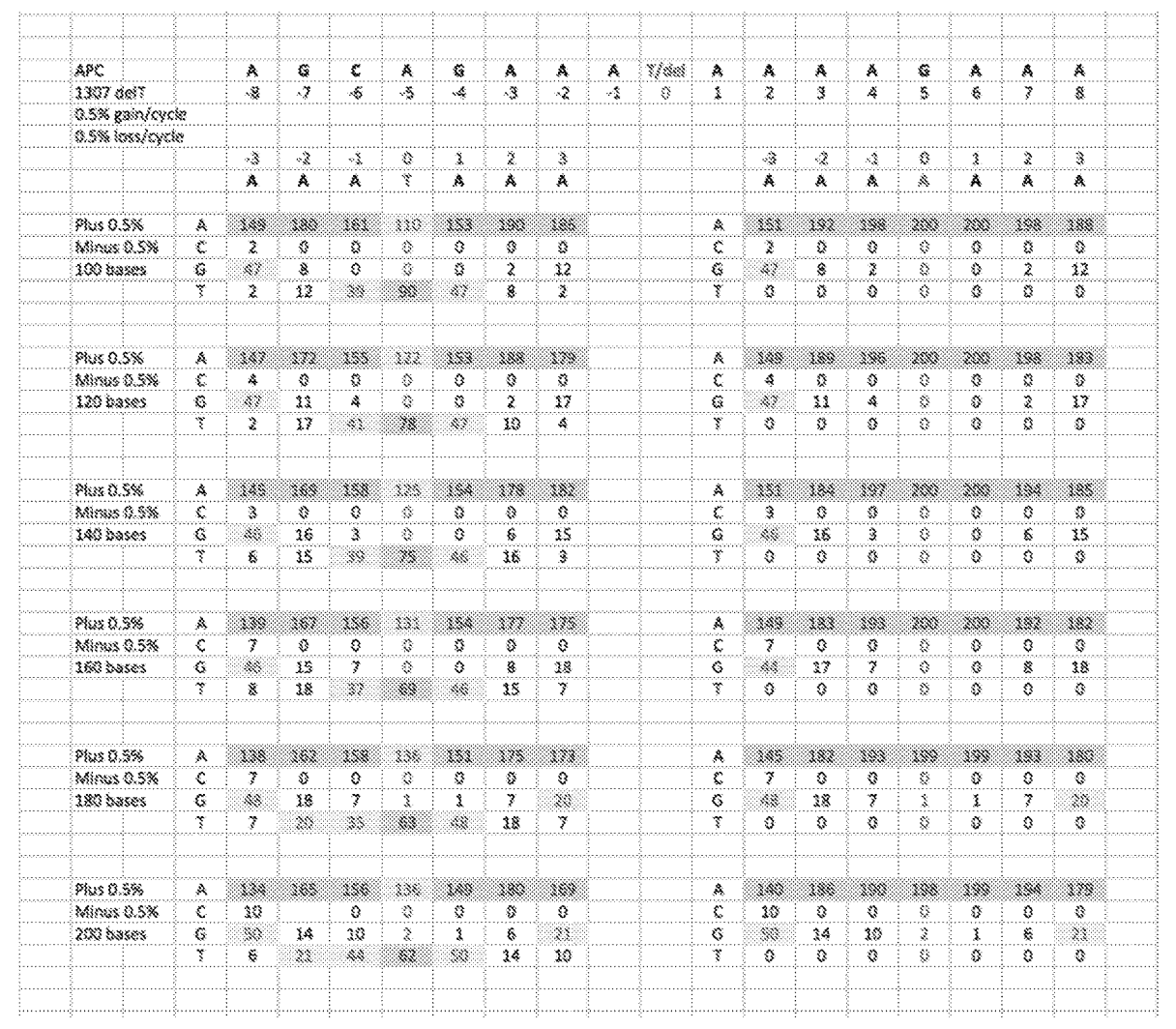

FIG. 205 provides a summary of the simulated calculations for base calls surrounding the wildtype/mutant base for a APC gene codon 1307 single-base deletion, i.e., AGCA-GAAA[T/del]AAAAGAAA (SEQ ID NO: 5), using universal molecular processor sequencing-by-synthesis.

Figure 206:
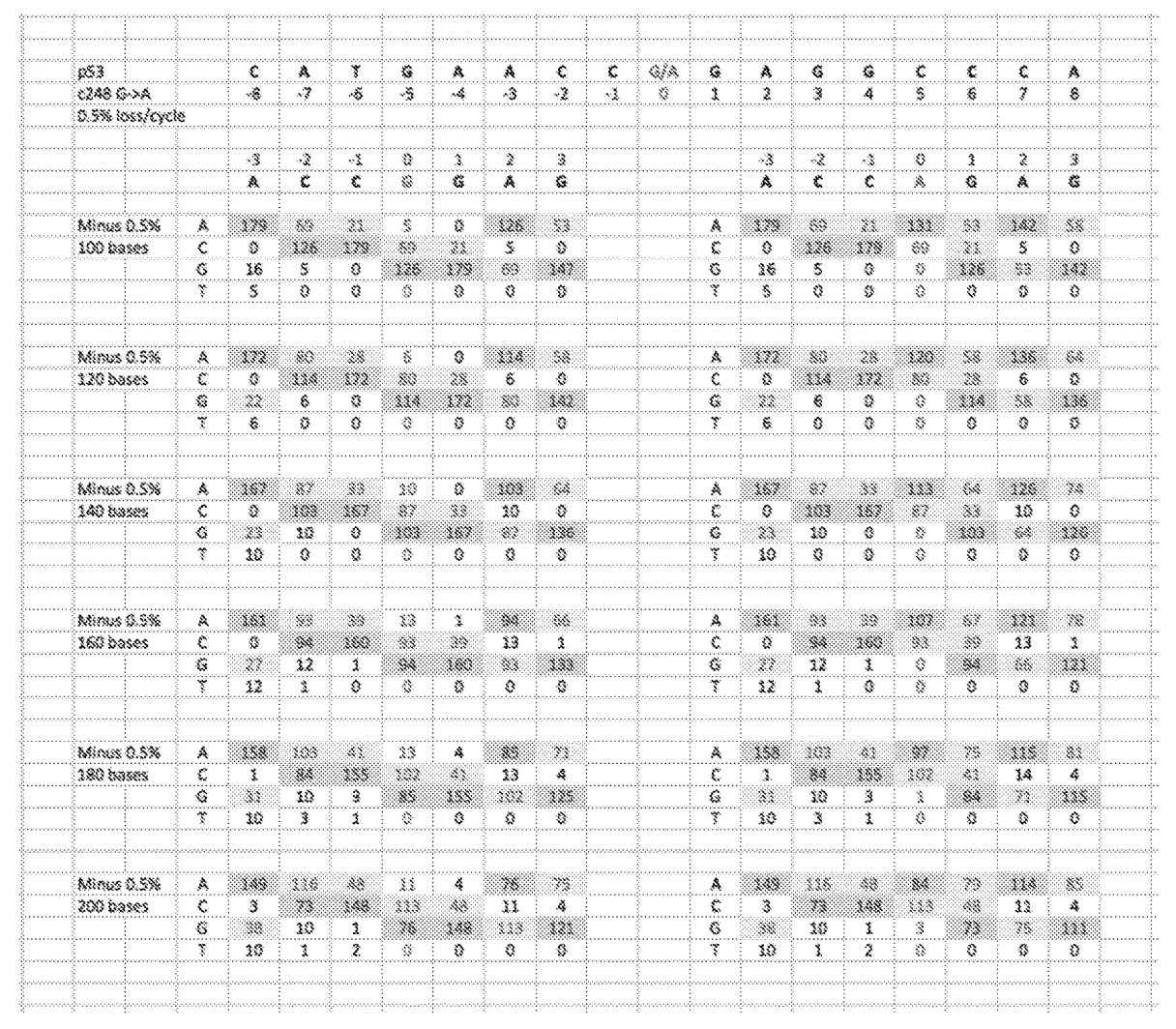

FIG. 206 provides a summary of the simulated calculations for base calls surrounding the wildtype/mutant base for a TP53 gene codon 248 mutation, i.e., CATGAACC[G/A] GAGGCCCA (SEQ ID NO: 6), using universal molecular processor sequencing-by-synthesis.

Figure 207:
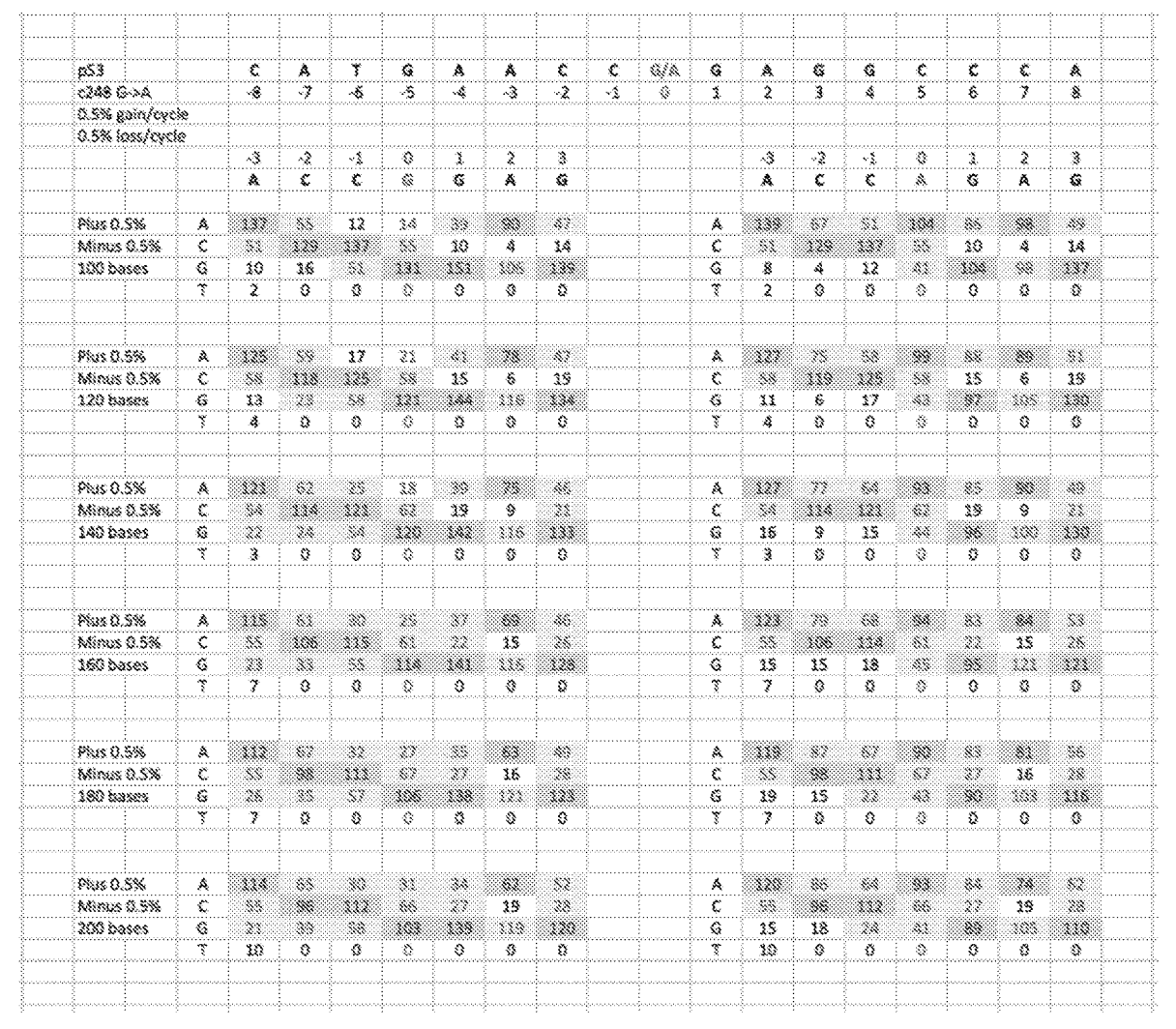

FIG. 207 provides a summary of the simulated calculations for base calls surrounding the wildtype/mutant base for a TP53 gene codon 248 mutation, i.e., CATGAACC[G/A] GAGGCCCA (SEQ ID NO: 6), using universal molecular processor sequencing-by-synthesis.

Figure 208:
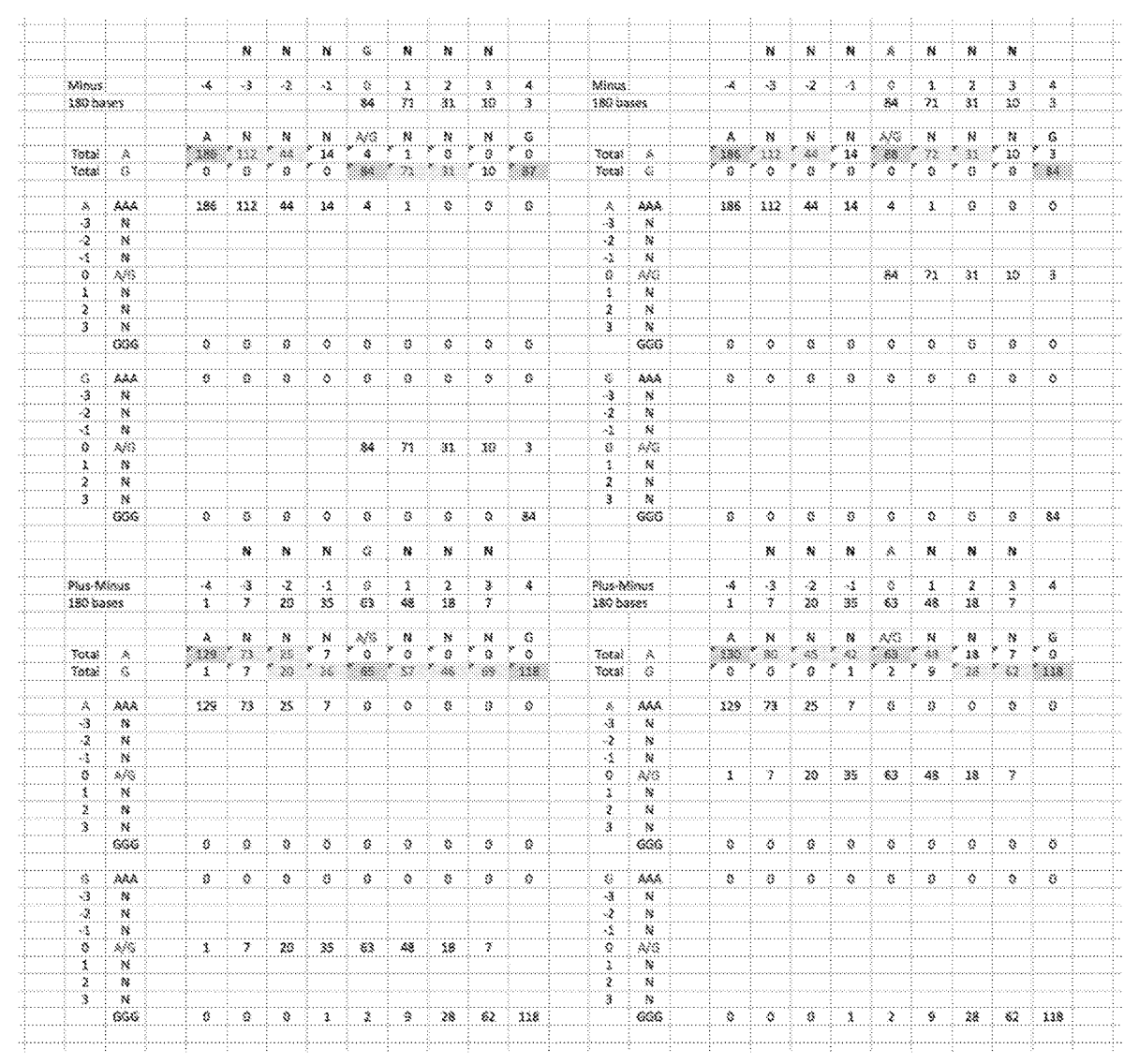

FIG. 208 provides an example of the simulated signal for any pattern of A and G sequence, i.e., NNNGNNN (SEQ ID NO: 7), NNNANNN (SEQ ID NO: 8), ANNN[A/G]NNNG (SEQ ID NO: 9), where "N" is A or G, using universal molecular biomolecular processor sequencing-by-synthesis.

Figure 209:
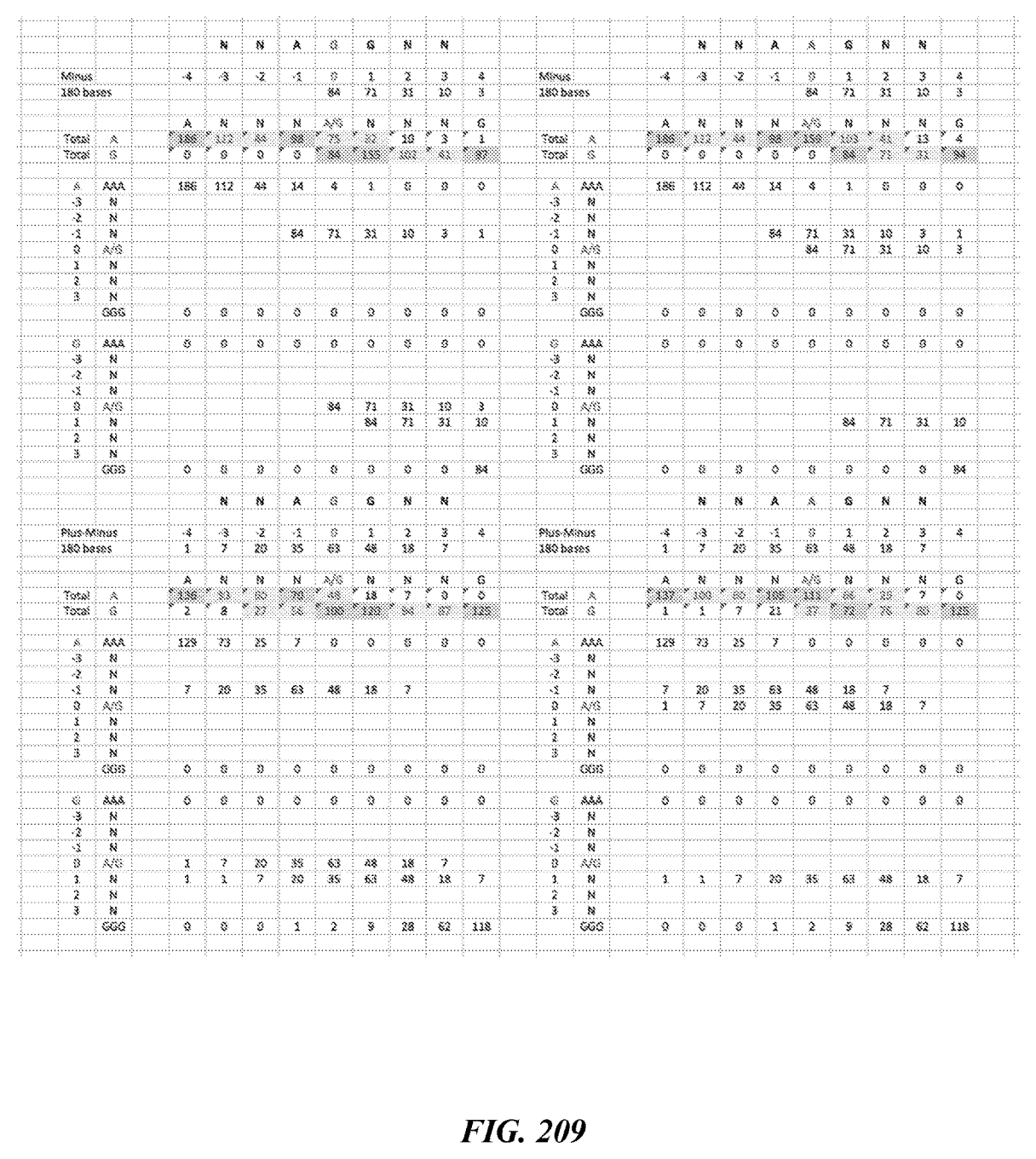

FIG. 209 provides an example of the simulated signal for any pattern of A and
G sequence, i.e., NNNGNNN (SEQ ID NO: 7), NNNANNN (SEQ ID NO: 8), ANNN[A/G]NNNG (SEQ ID NO: 9), where "N" is A or G, using universal molecular biomolecular processor sequencing-by-synthesis.

Figure 210:
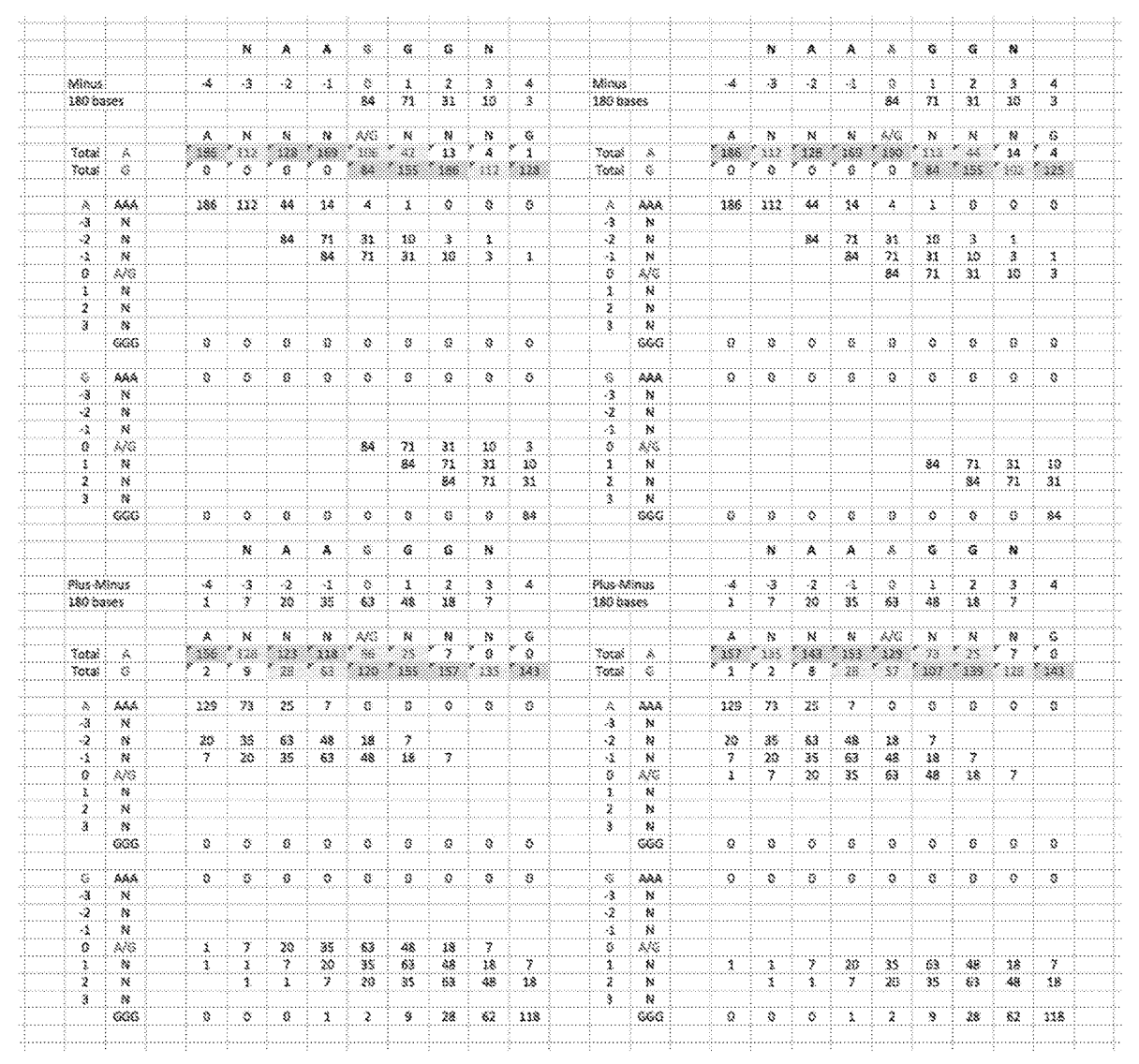

FIG. 210 provides an example of the simulated signal for any pattern of A and G sequence, i.e., NNNGNNN (SEQ ID NO: 7), NNNANNN (SEQ ID NO: 8), ANNN[A/G]NNNG (SEQ ID NO: 9), where "N" is A or G, using universal molecular biomolecular processor sequencing-by-synthesis.

Figure 211:
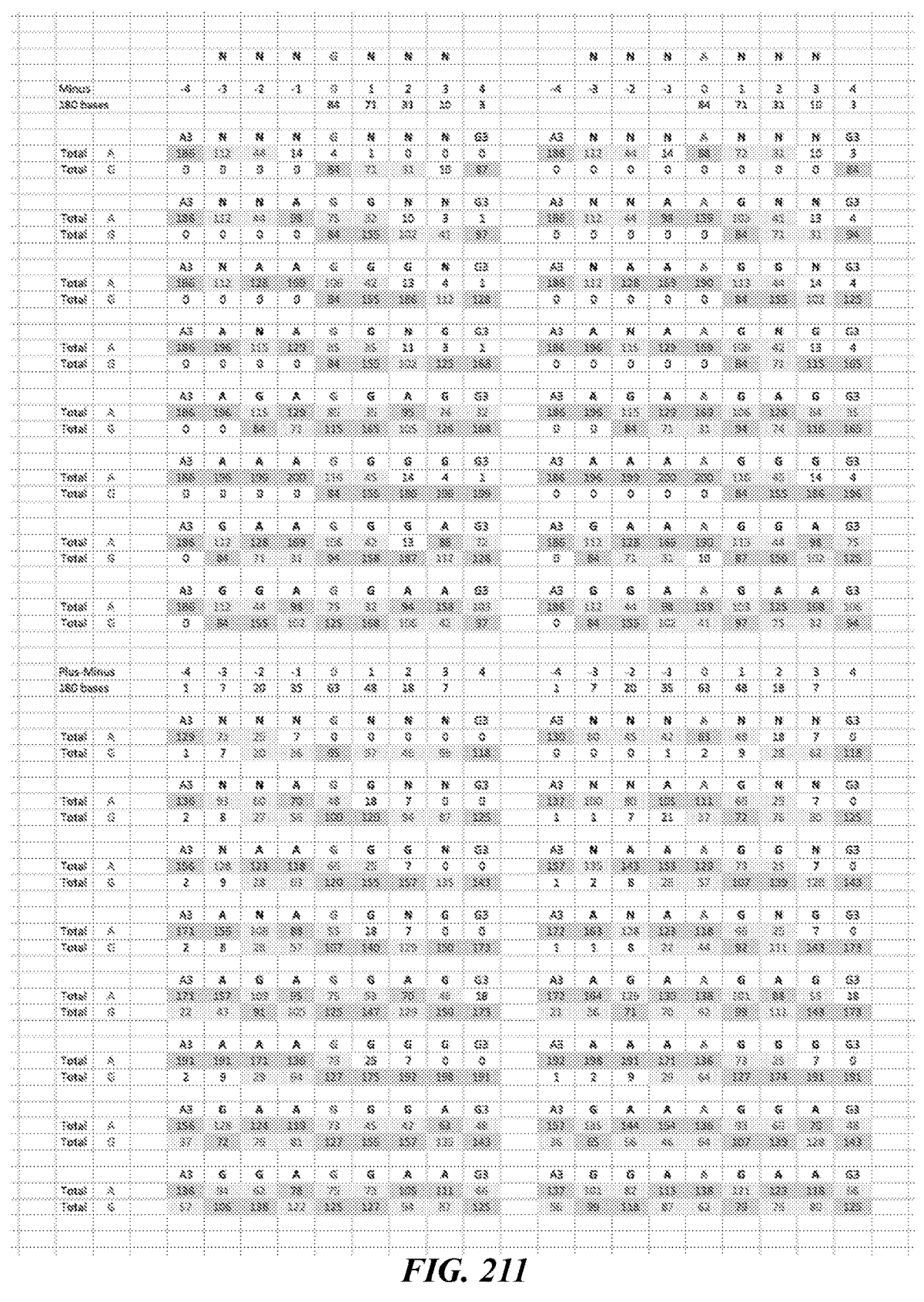

FIG. 211 provides simulated data from sequencing a pattern of A and G sequence, i.e., AAANNNGNNNGGG (SEQ ID NO: 10), AAANNNANNNGGG (SEQ ID NO: 11, where "N" is A or G, and various sequences encompassed by SEQ ID NOs: 10 and 11, using universal molecular biomolecular processor sequencing-by-synthesis.

Figure 212:
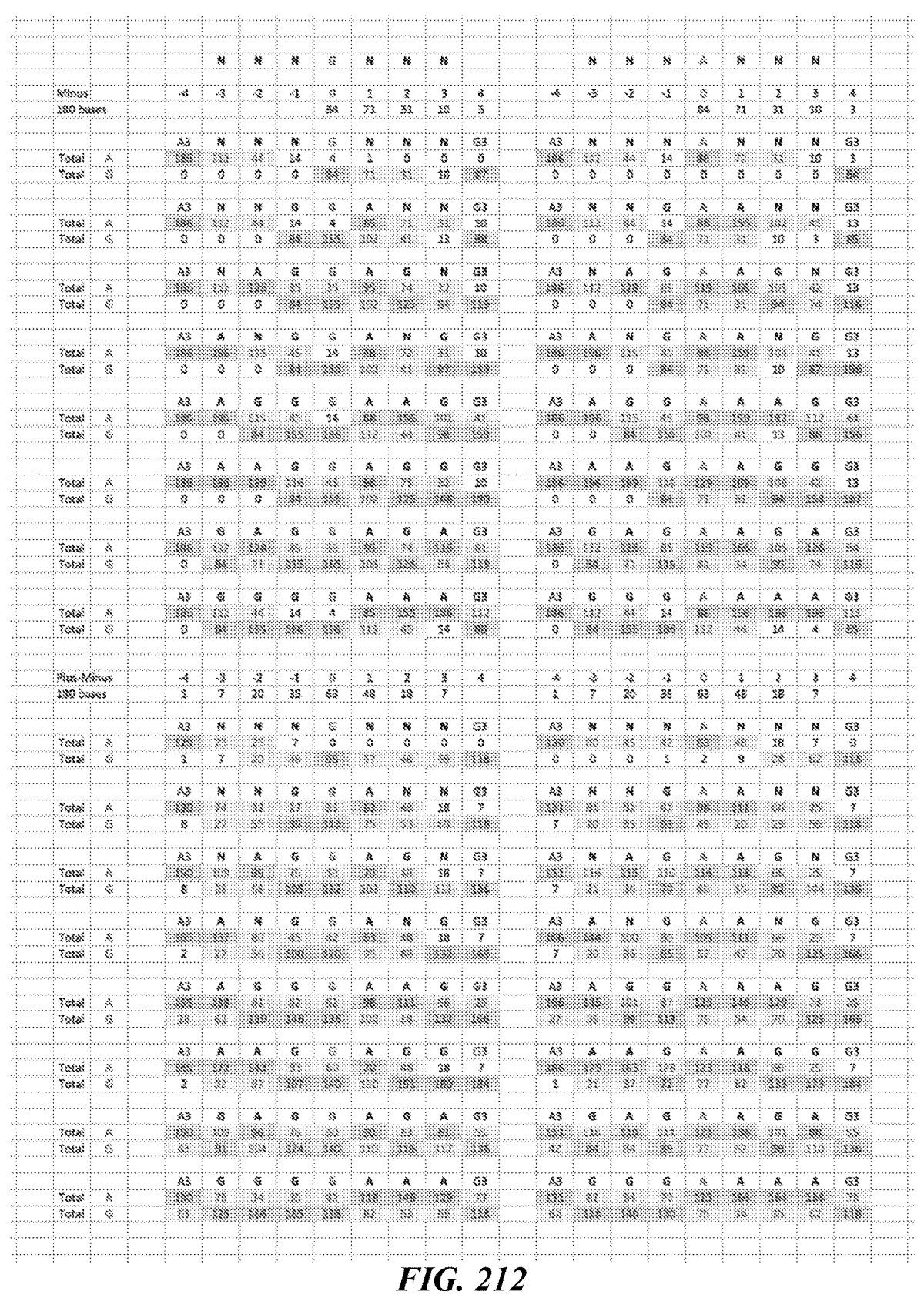

FIG. 212 provides simulated data from sequencing a pattern of A and G sequence, i.e., AAANNNGNNNGGG (SEQ ID NO: 10), AAANNNANNNGGG (SEQ ID NO: 11), where "N" is A or G, and various sequences encompassed by SEQ ID NOs: 10 and 11, using universal molecular biomolecular processor sequencing-by-synthesis.

Figure 213:
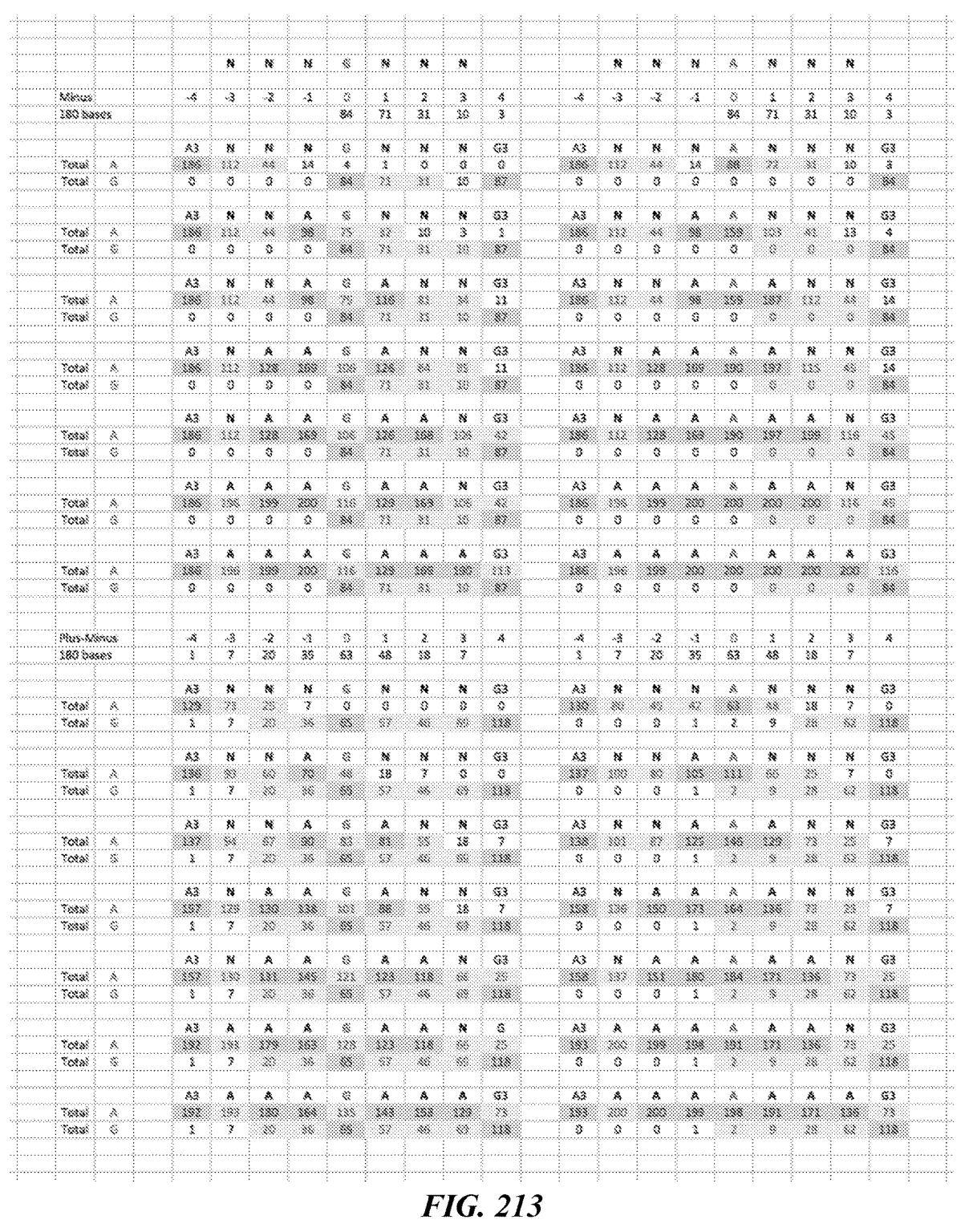

FIG. 213 provides simulated data from sequencing a pattern of A and G sequence, i.e., AAANNNGNNNGGG (SEQ ID NO: 10), AAANNNANNNGGG (SEQ ID NO: 11), where "N" is A or G, and various sequences encompassed by SEQ ID NOs: 10 and 11, using universal molecular biomolecular processor sequencing-by-synthesis.

FIG. 214 is a summary of the simulated effect of time of flight distribution per read length on the ability to interpret a sequencing-by-chain-termination run on a universal molecular processor.

Figure 215:
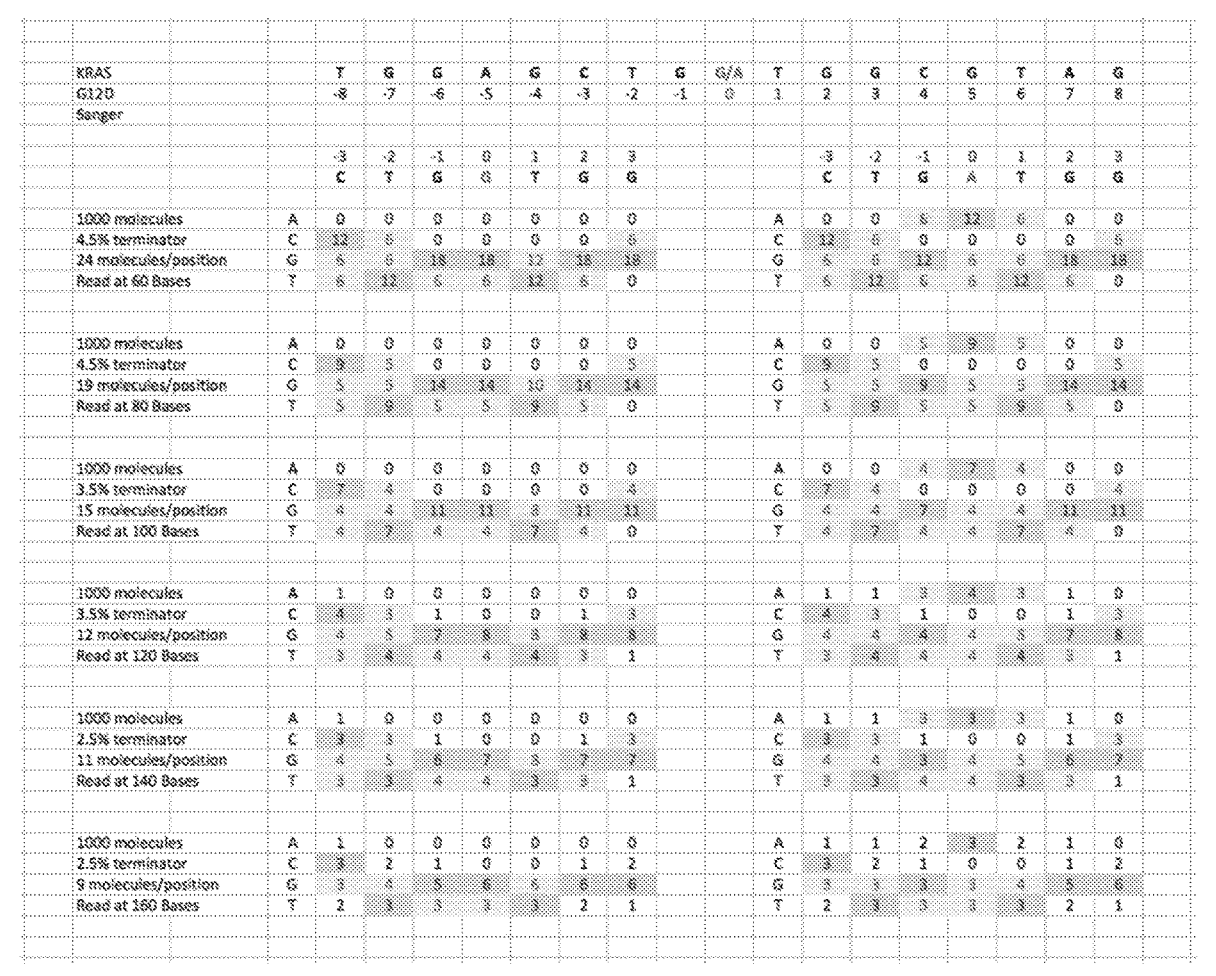

FIG. 215 provides a summary of the simulated calculations for base calls surrounding the wildtype/mutant base for a K-ras codon 12 mutation, (i.e., TGGAGCTGGTGGCGTAG (SEQ ID NO: 3) and TGGAGCTGATGGCGTAG (SEQ ID NO: 4)), using universal molecular processor sequencing-by-chain-termination.

Figure 216:
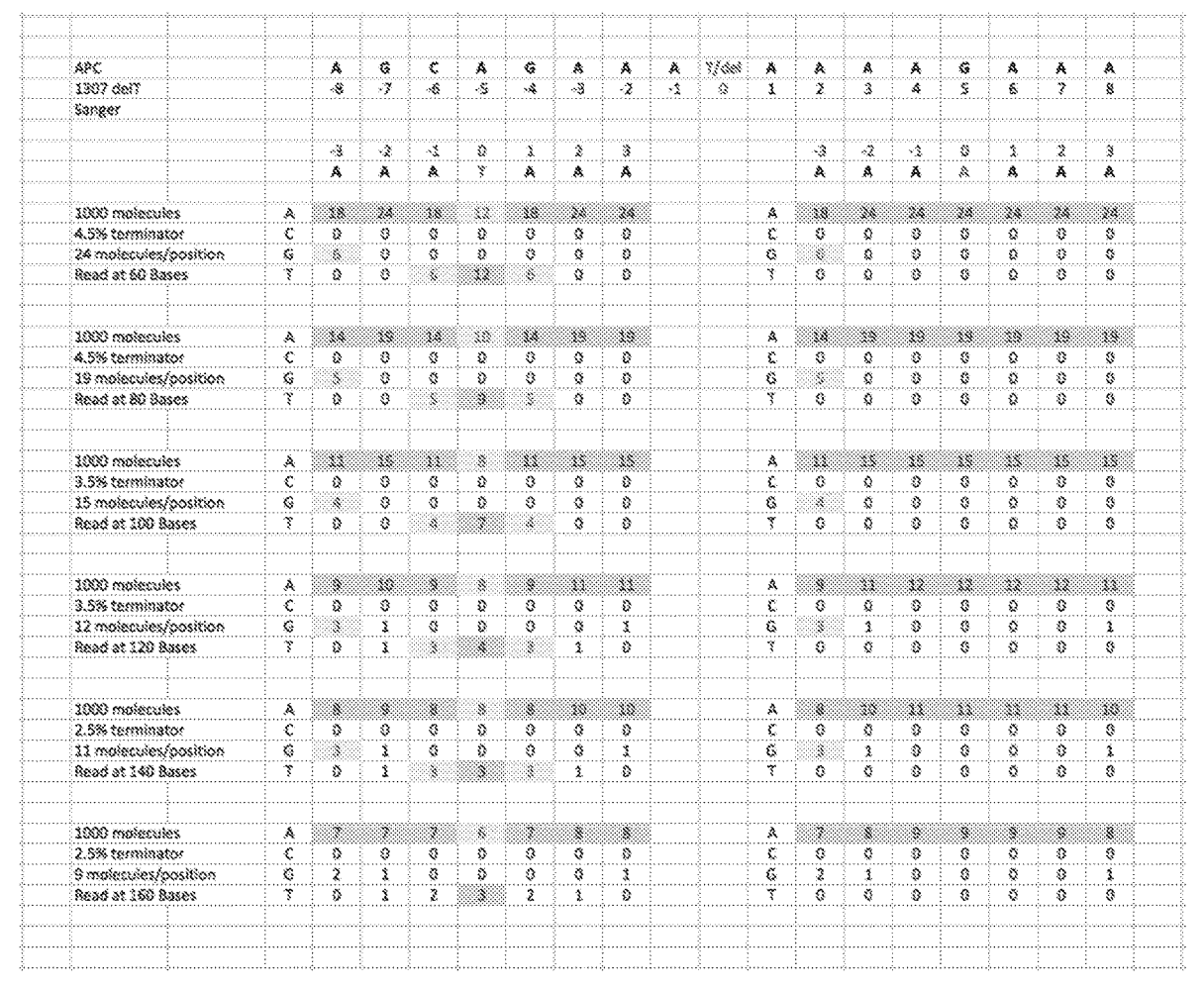

FIG. 216 provides a summary of the simulated calculations for base calls surrounding the wildtype/mutant base for an APC gene codon 1307 single-base deletion, i.e., AGCAGAAA[T/del]AAAAGAAA (SEQ ID NO: 5), using universal molecular processor sequencing-by-chain-termination.

Figure 217:
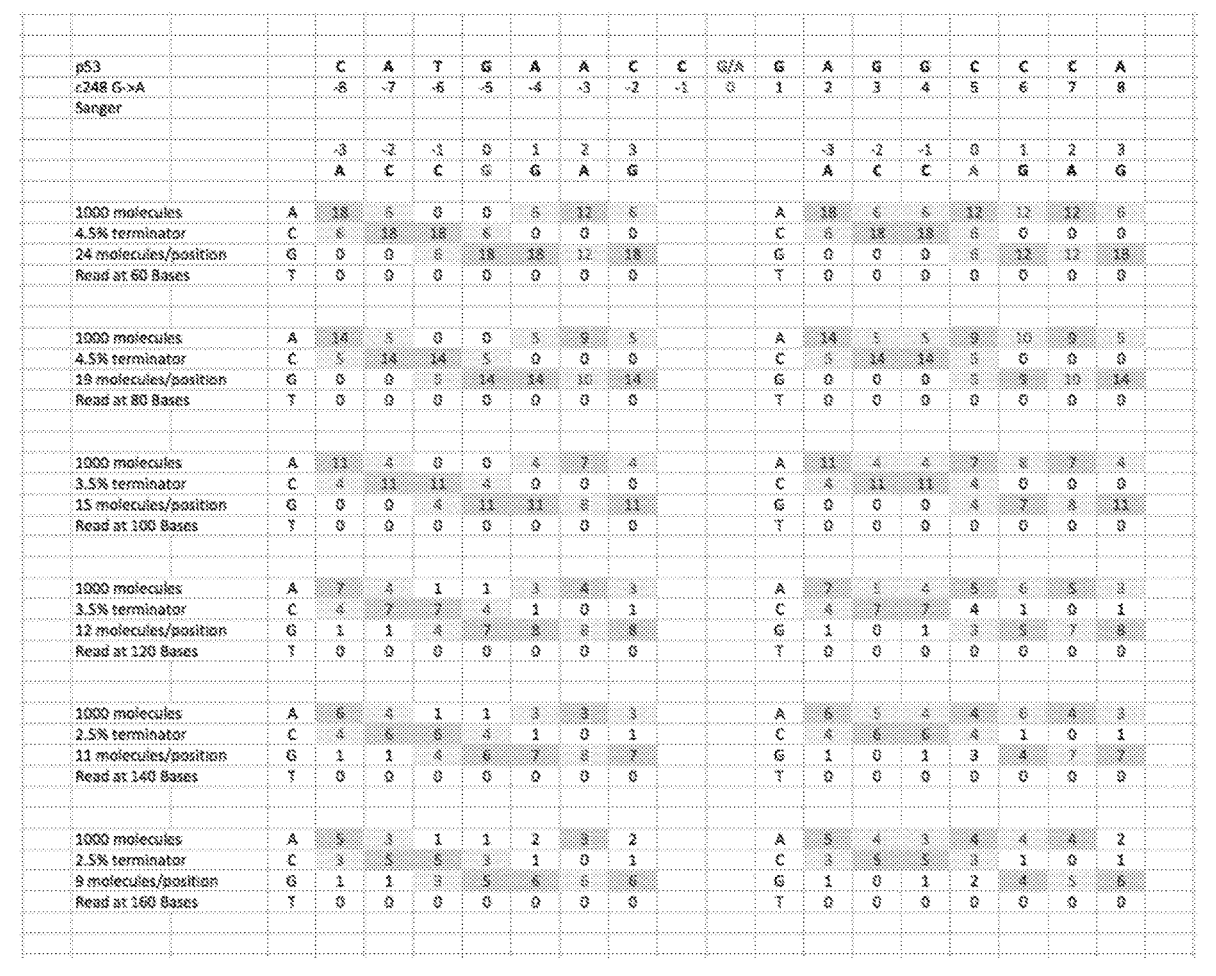

FIG. 217 provides a summary of the simulated calculations for base calls surrounding the wildtype/mutant base for a TP53 gene codon 248 mutation, i.e., CATGAACC [G/A] GAGGCCCA (SEQ ID NO: 6), using universal molecular processor sequencing-by-chain-termination.

Figure 218:
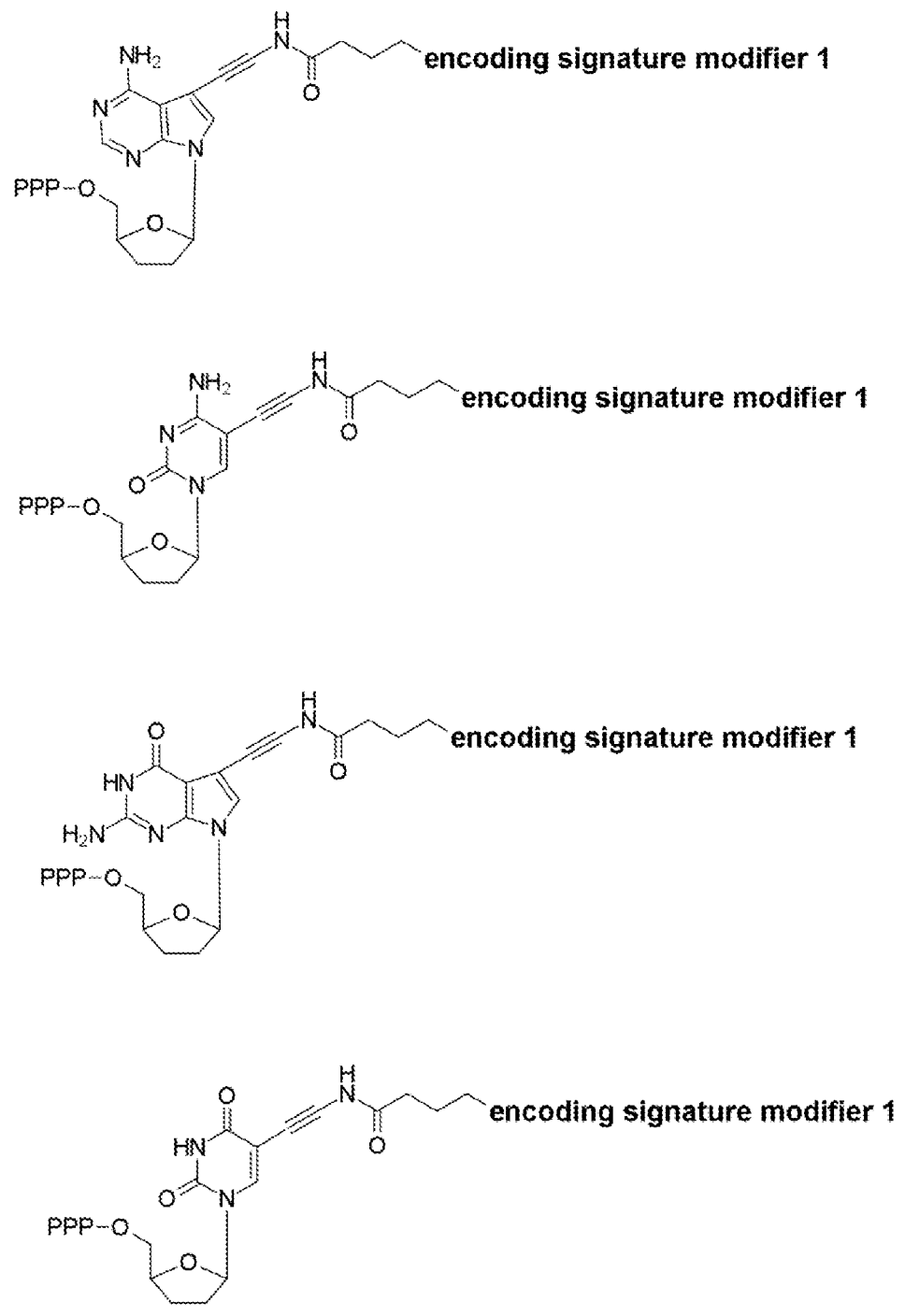

FIG. 218 illustrates the structures of dideoxy terminator dNTP analogs with the same 3' encoded identifying signature modifier group that is suitable for use in the solid phase sequencing-by-chain-termination process of the present invention.

FIG. 219 illustrates the structures of dideoxy terminator dNTP analogs with two 3' encoded identifying signature modifier groups that are suitable for use in the solid phase sequencing-by-chain-termination process of the present invention.

FIG. 220 illustrates the structures of dideoxy terminator dNTP analogs with four 3' encoded identifying signature modifier groups that are suitable for use in the solid phase sequencing-by-chain-termination process of the present invention.

Figure 221:
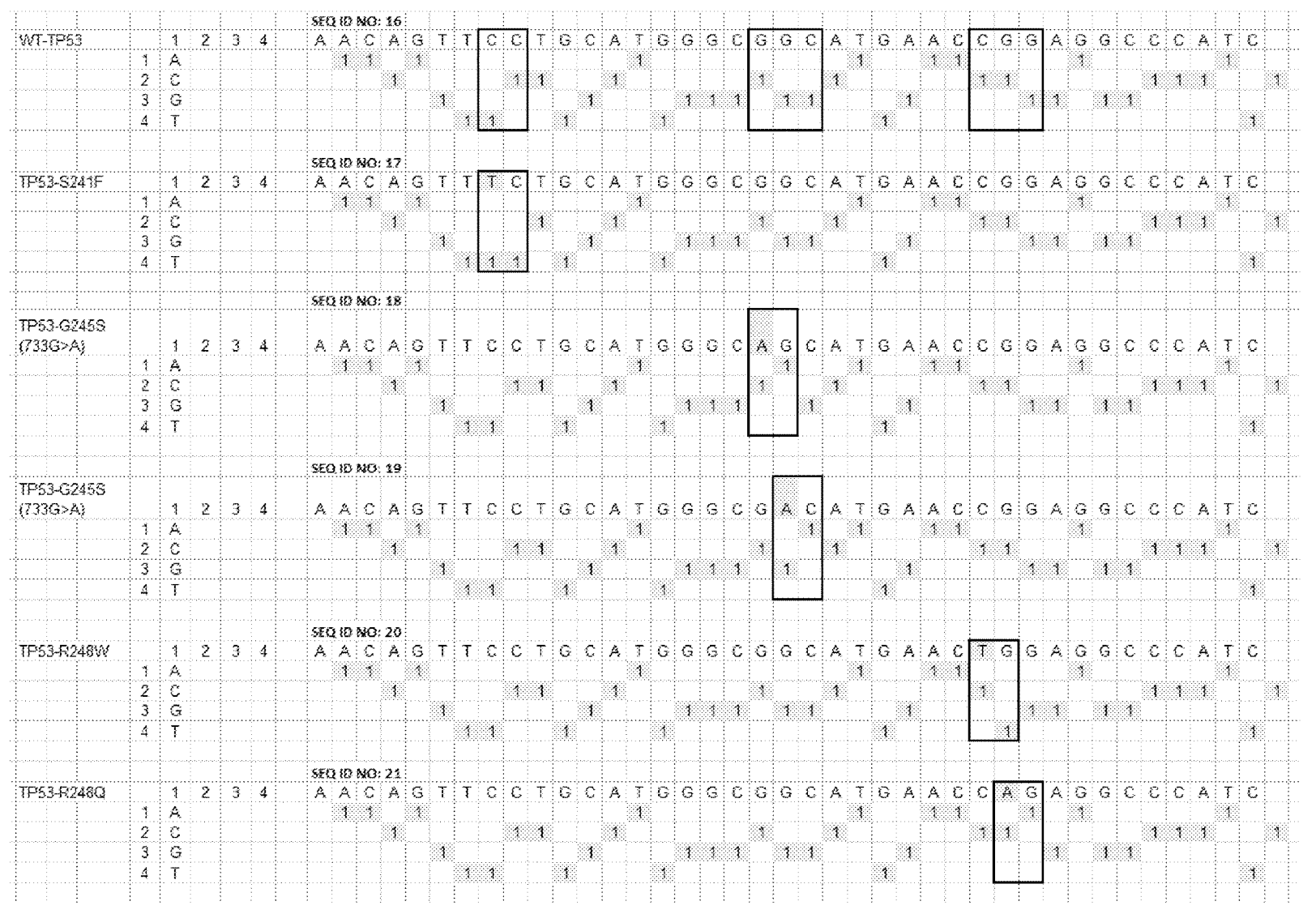

FIG. 221 illustrates a simulation of the pattern of time-of-flight distribution for various combinations of 3' encoded identifying signature modifiers, using the TP53 gene (SEQ ID NO: 16) and common mutations (SEQ ID NOs: 17-21) as examples.

Figure 222:
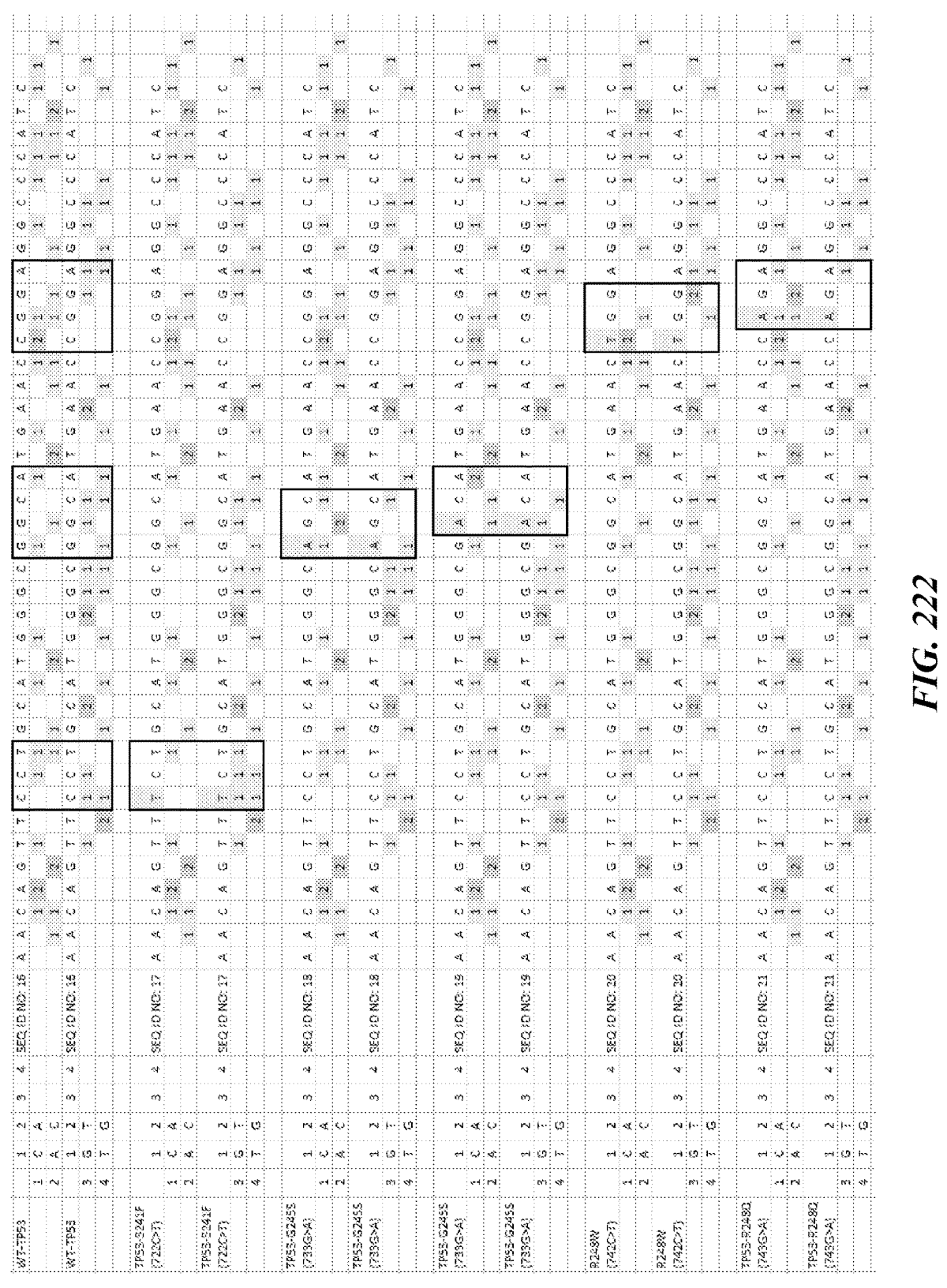

FIG. 222 illustrates a simulation of the pattern of time-of-flight distribution for various combinations of 3' encoded identifying signature modifiers, using the TP53 gene (SEQ ID NO: 16) and common mutations (SEQ ID NOs: 17-21) as examples.

Figure 223:
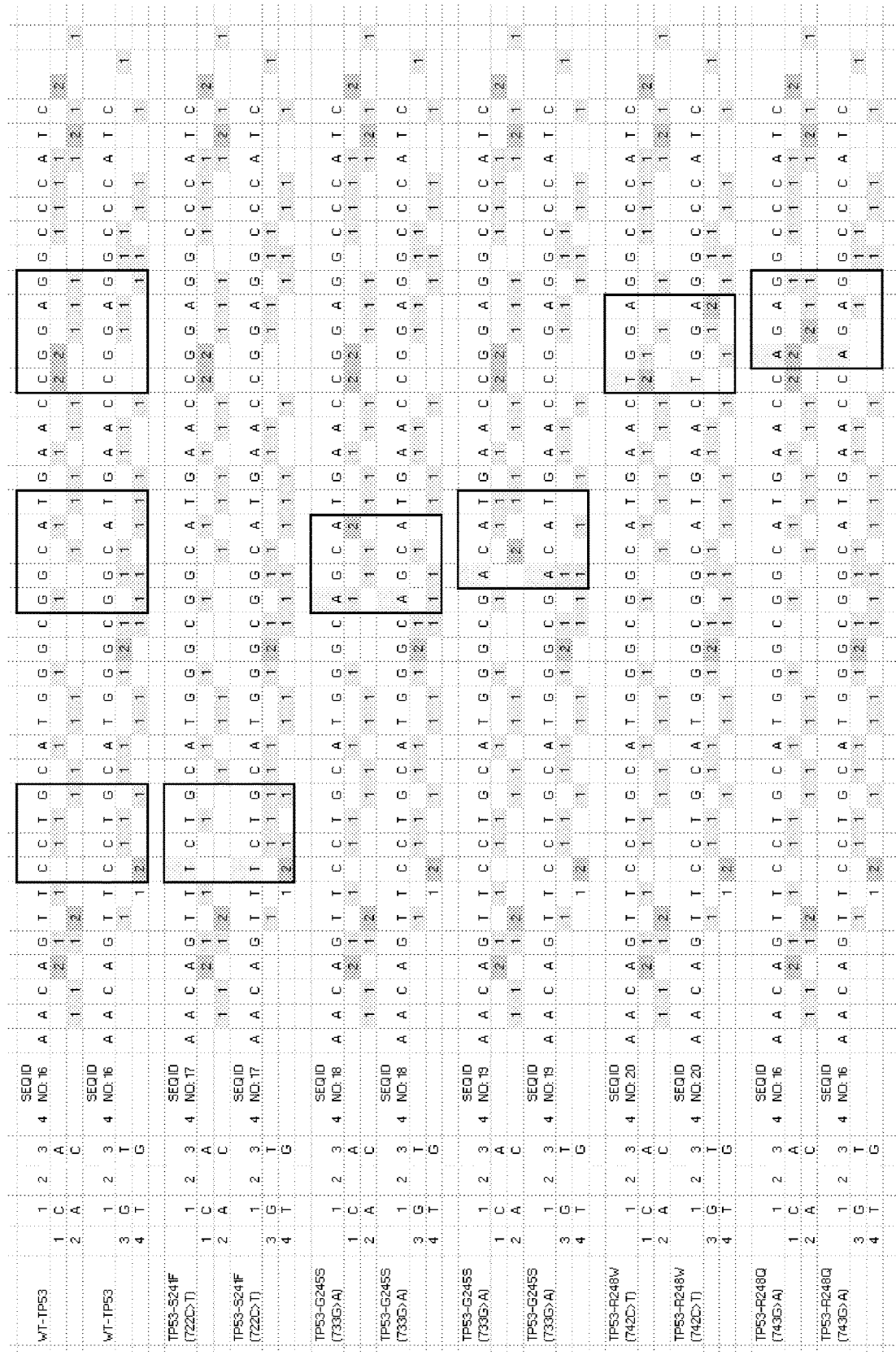

FIG. 223 illustrates a simulation of the pattern of time-of-flight distribution for various combinations of 3' encoded identifying signature modifiers, using the TP53 gene (SEQ ID NO: 16) and common mutations (SEQ ID NOs: 17-21) as examples.

Figure 224:
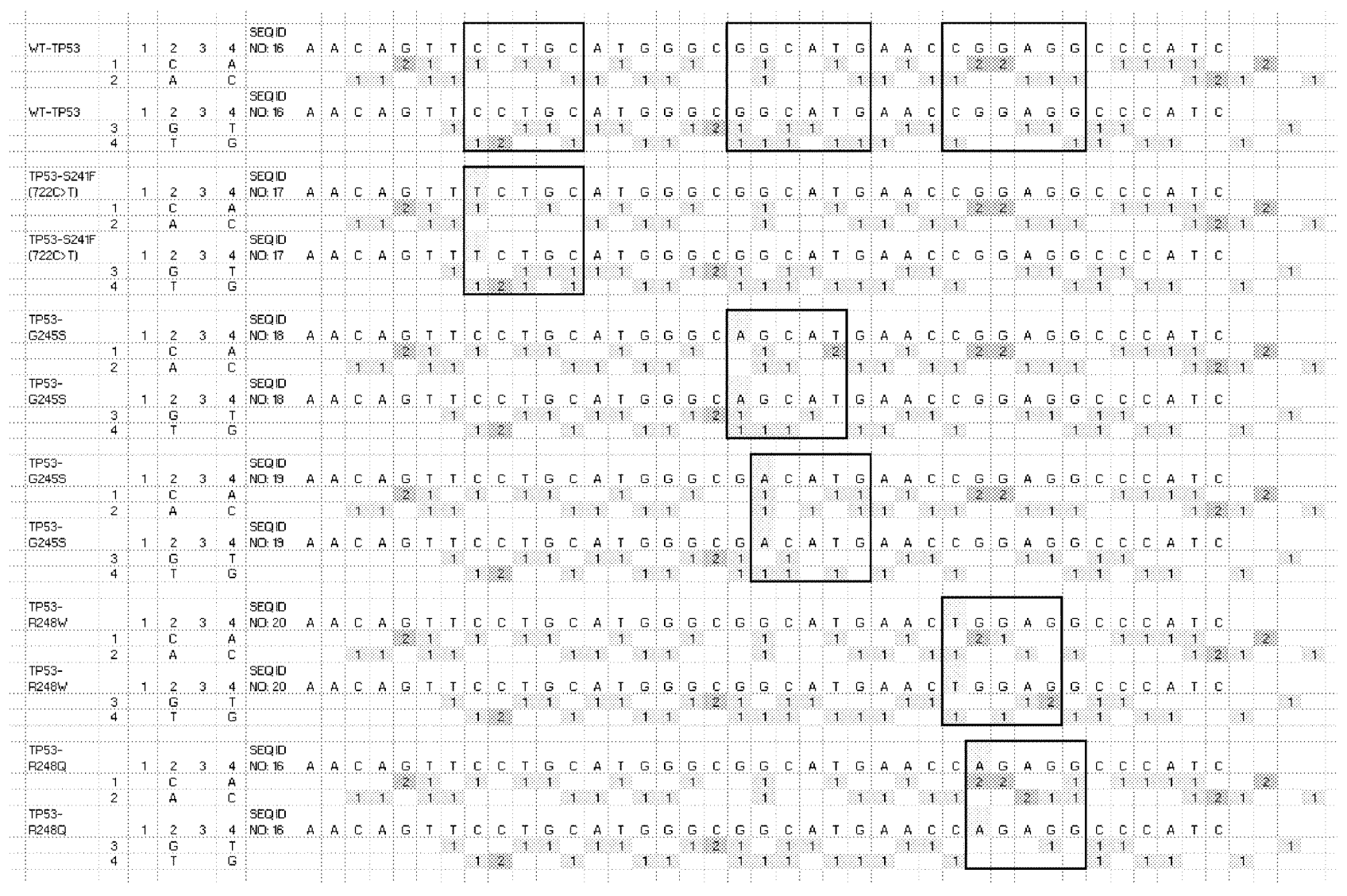

FIG. 224 illustrates a simulation of the pattern of time-of-flight distribution for various combinations of 3' encoded identifying signature modifiers, using the TP53 gene (SEQ ID NO: 16) and common mutations (SEQ ID NOs: 17-21) as examples.

Figure 225:
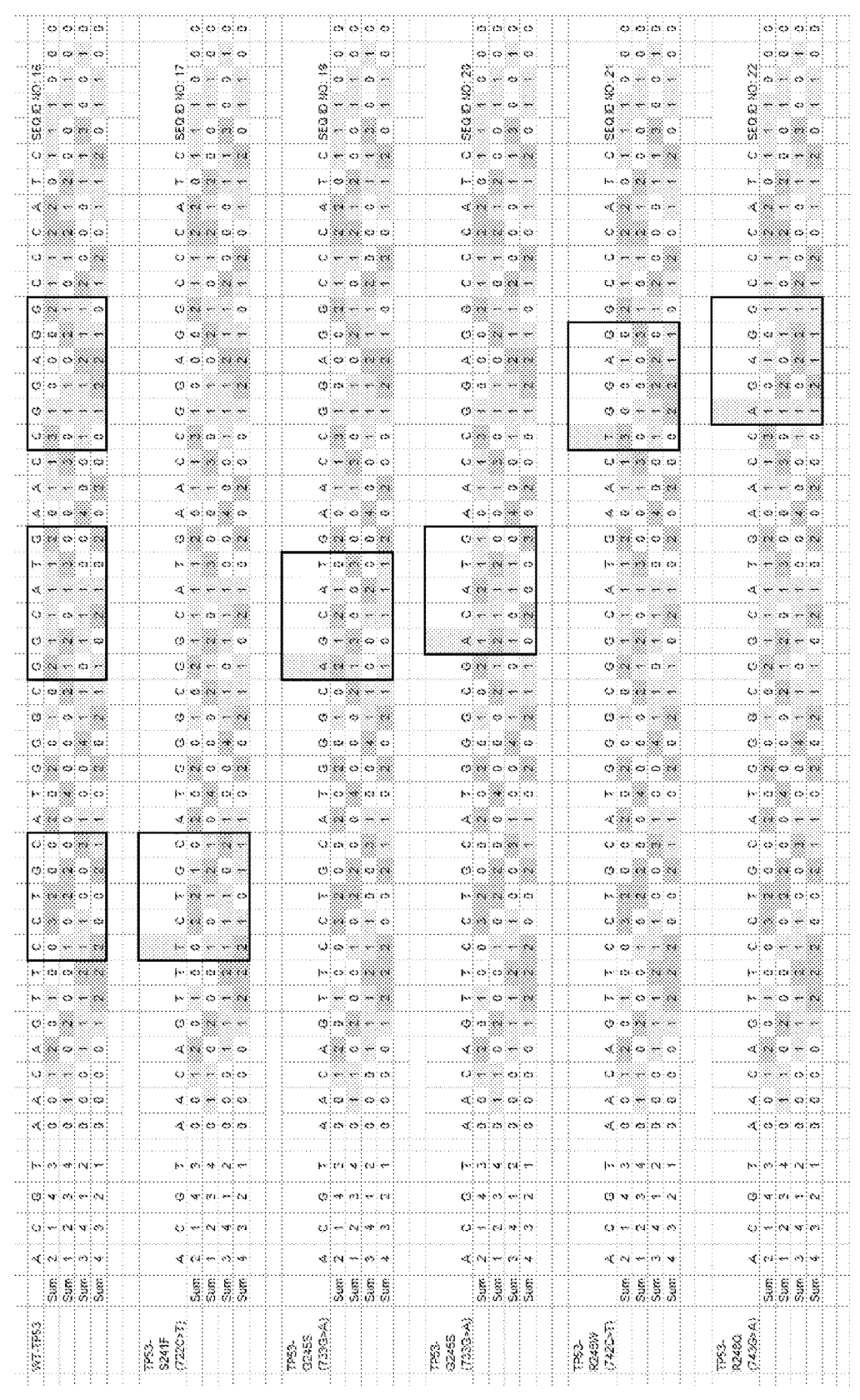

FIG. 225 illustrates a simulation of the pattern of time-of-flight distribution for various combinations of 3' encoded identifying signature modifiers, using

DETAILED DESCRIPTION OF THE INVENTION

One aspect of the present invention is directed to a device that comprises a biomolecular processor and one or more nanotubes. Each biomolecular processor comprises a bioreactor chamber defined by a solid substrate, a plurality of spaced support structures within said bioreactor chamber and attached to the solid substrate, and one or more capture molecules immobilized to some or all of said plurality of spaced support structures, said one or more capture molecules suitable to bind to a portion of a target nucleic acid molecule in a sample. The one or more nanotubes of the device are defined by the solid substrate and fluidically coupled to the bioreactor chamber of the biomolecular processor. Each of the one or more nanotubes has a passage extending between an input end proximate to the bioreactor chamber and an output end distal to the bioreactor chamber, and comprises one or more nanopores within the passage with each nanopore having a reduced diameter relative to the passage.

FIG. 1A is perspective view of a nanosensor chamber 30 containing a series of biomolecular processors 1 and nanotubes 6 as described herein. Each biomolecular processor 1 has a bioreactor chamber 2 that contains a plurality of spaced solid support structures 4 attached to the solid substrate. Two walls of each bioreactor chamber 2 are defined by separators 22 that help direct material within the bioreactor chamber 2 into the nanotube 6 that is coupled to the bioreactor chamber 2. The bioreactor chamber is further defined by a top cover plate, which is not shown in FIG. 1A. The nanosensor chamber also comprises a fluidic input port 16 and a feeder channel 18. The feeder channel 18 fluidically couples the input port 16 and the plurality of biomolecular processors 1 to deliver a sample from the input port 16 to the plurality of biomolecular processors 1. The feeder channel optionally contains one or more or a plurality of baffles 20 that function to disperse the sample entering the input port 16 to the plurality of biomolecular processors 1.

Figures 1B, 1C:
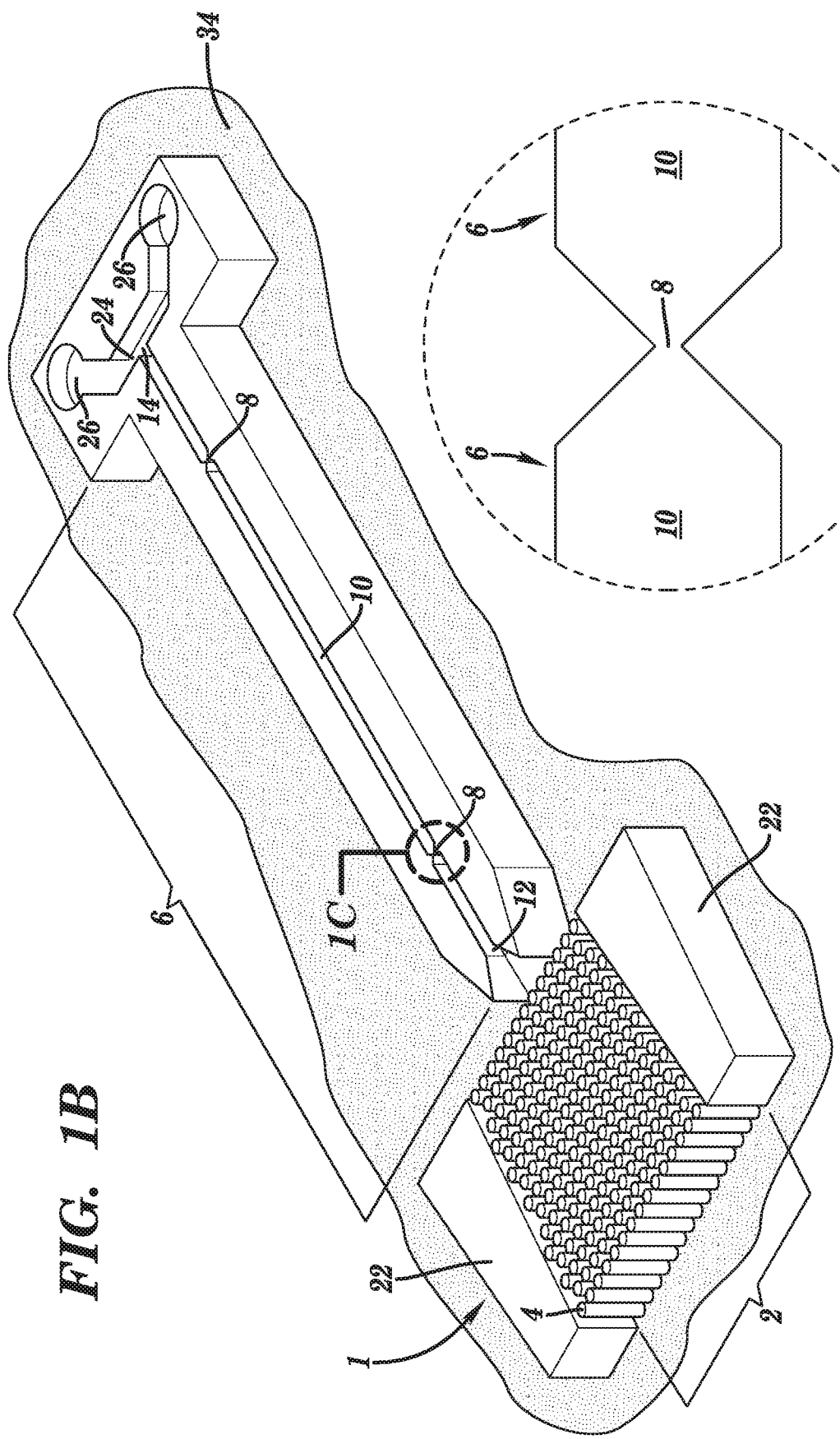

As depicted in FIG. 1A, each biomolecular processor is coupled to a nanotube. The perspective view of FIG. 1B shows a magnified view of nanotube 6 and biomolecular processor 1 containing bioreactor chamber 2. The nanotube 6 contains an input end 12 that is proximate to the bioreactor chamber 2 of the biomolecular processor 1, an output end 14 that is distal to bioreactor chamber 2, and a passage 10 that extends between the input 12 and output 14 ends. Input end 12 of nanotube 6 shown in FIG. 1B has a tapered inlet to help electrically load molecules into nanotube 6. The output end 14 of the nanotube 6 can be coupled to a microfluidic network 24 and microscale reservoirs 26 for inlet and outlet of fluids and bioreagents. Within the passage 10 of the nanotube 6 is one or more nanopores 8. The embodiment depicted in FIG. 1B shows a nanotube 6 having two nanopores 8; however as described herein and shown in FIG. 4, the nanotube can contain more than two nanopores. Each nanopore 8 has a reduced diameter relative to the remaining passage 10 of the nanotube 6 as shown in FIG. 1C.

In one embodiment, the biomolecular processors, one or more nanotubes, and any further units to which the biomolecular processors and nanotubes are, directly or indirectly, fluidically coupled to are positioned on a base plate. A cover plate is fitted on the base plate to form a compartment that seals the biomolecular processor, the nanotubes, and any further units.

Figure 2A:
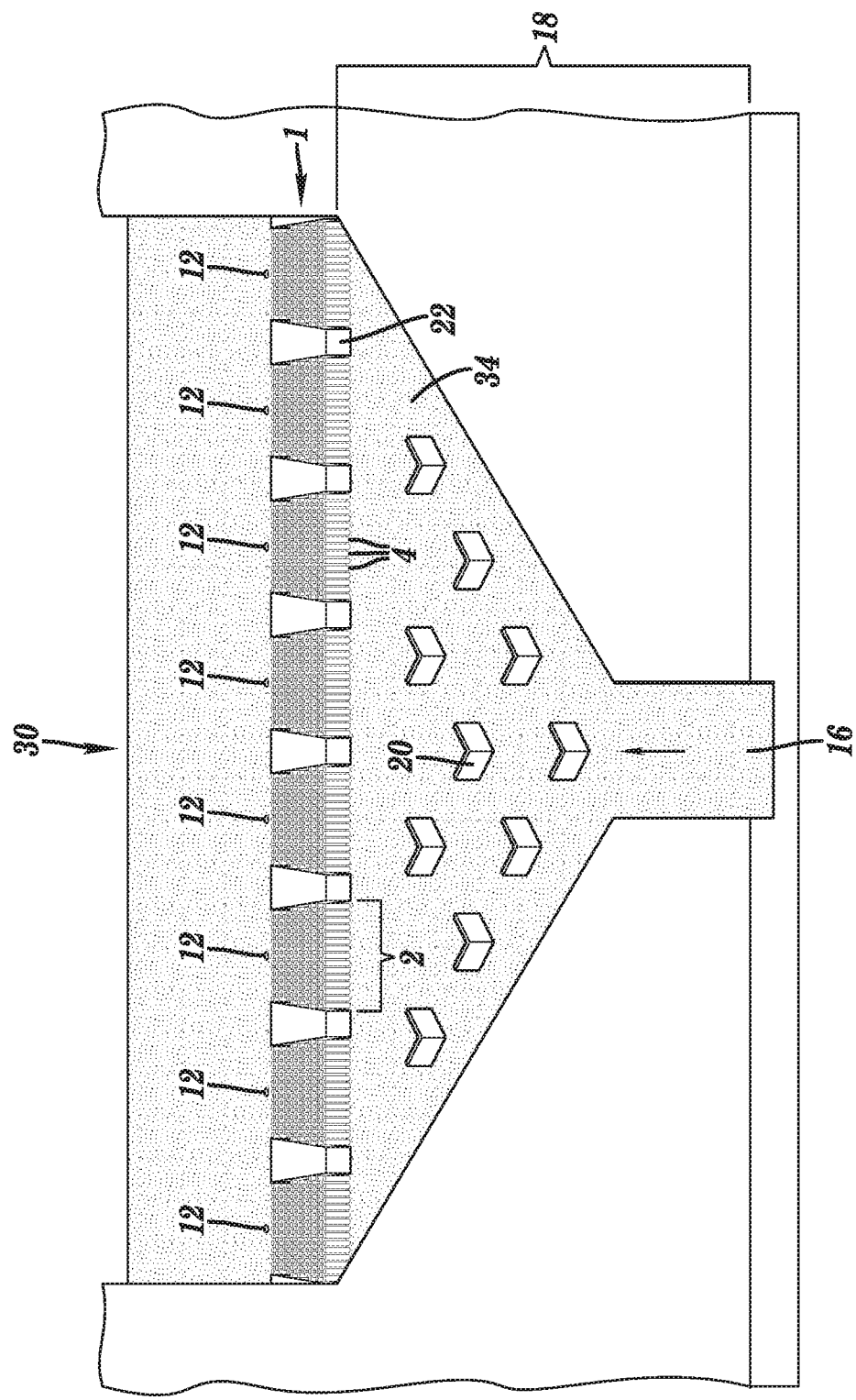
FIGS. 2A-2C are views of the biomolecular processor and one or more vertically orientated nanotubes of a device as described herein.
Figure 2B:
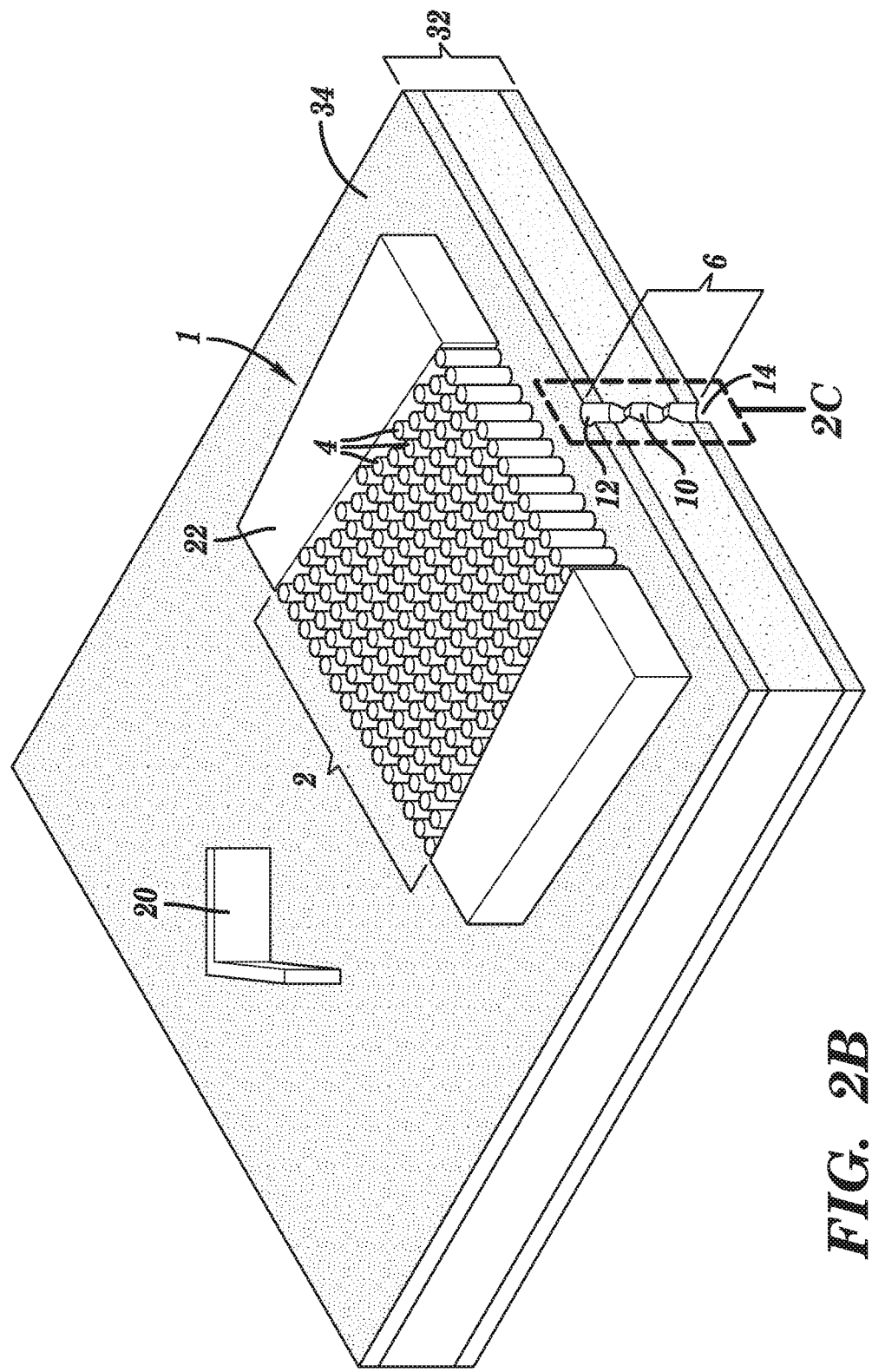
Figure 2C:
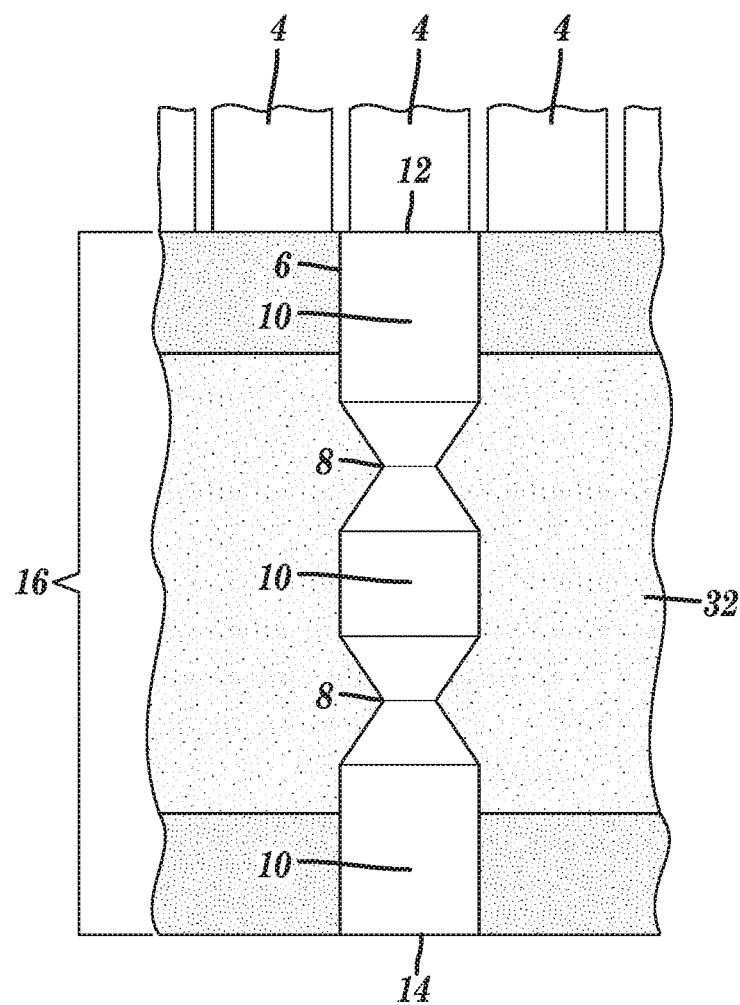

FIGS. 2A-2C show an alternative arrangement of the biomolecular processor and nanotube of a device of the present invention. FIG. 2A is a perspective view of a nanosensor chamber 30 containing eight biomolecular processors 1 and eight nanotubes, where only the input end 12 of the nanotube is visible in this perspective. In this embodiment, nanotube 6 is positioned vertically within solid substrate 32, while bioreactor chamber 2 of biomolecular processor 1 is located on the surface of solid substrate 34 adjacent to the input end 12 of the nanotube. Sample enters the bioreactor chamber 2 via the fluidic input 16, flows through the feeder channel 18 of the nanosensor chamber 30 where it is distributed among the bioreactor chambers 2 by the baffles 20 present in the feeder channel 18. The sample flows through the plurality of spaced support structures 4 within the bioreactor chamber 2, where target molecules are captured by capture molecules that are immobilized on the solid support structures 4. Upon release of the target molecules or other biomolecular products representative of the target molecules from the capture molecules, the target molecules or biomolecular products thereof are directed into the input end 12 of the nanotube for detection. FIG. 2B shows a magnified perspective view of one biomolecular processor 1 in nanosensor chamber on the surface 34 of substrate 32 and adjacent to nanotube 6 which is vertically positioned within the substrate 32. FIG. 2C is a cross-section of nanotube 6 vertically positioned in the substrate 32, showing the passageway 10 (also referred to as a nanochannel) and nanopores 8 of nanotube 6.

The solid substrate of the bioreactor chamber of the biomolecular processor can be made from a wide variety of materials. The solid substrate may be biological, nonbiological, organic, inorganic, or a combination of any of these. In one embodiment, the solid substrate is a polymeric material or other moldable material. Suitable polymeric materials include, without limitation, poly(methyl methacrylate) (PMMA), polycarbonates (PC), epoxy-based resins, copolymers, polysulfones, elastomers, cyclic olefin copolymer (COC), and polymeric organosilicons. The bioreactor chamber can be fabricated from thermoplastic via, for example, Nano-Imprint Lithography (NIL) as described herein and sits atop a heating element.

The spaced support structures 4 of the bioreactor chamber 2 encompass any raised structures, such as pillars as depicted in FIG. 1B. The space support structures 4 sit on top of the solid substrate surface 34 and have exposed top, bottom, and side surfaces. These spaced support structures 4 can be any geometrical three-dimensional shape, including, without limitation, spherical, cone, cylinder, triangular prism or tetrahedron, cube, rectangular prism, dodecahedron, hexagonal prism, octagonal prism, etc. Capture molecules are immobilized to the support structure surfaces (i.e., the top and side surfaces of the structures). In one embodiment, the capture molecules are oligonucleotides comprising a nucleotide sequence that is complementary to a nucleotide sequence that is a part of or is appended to a target molecule in a sample. For example, in one embodiment, the capture molecule is a poly-$dA_{30}$ oligonucleotide that is complementary to a poly-dT tail appended to a target nucleic acid molecule. The capture molecules are immobilized to the support structure surfaces via any suitable linker molecule.

The dimensions of the bioreactor chamber vary depending on a number of factors, including e.g., the device it is housed on and the type of sample being analyzed. The bioreactor chamber can be 5, 10, 15, 20, 25, 30, 35, 40, 45, 50 µm wide by 5, 10, 15, 20, 25, 30, 35, 40, 45, 50 µm deep, with a height of 1, 2, 3, 4, 5, 6, 7, 8, 10, 11, 12, 13, 14, 15, 16, 17, 18, 19, 20, 25, 30, 35, 40, 45, 50 µm. In one embodiment, the bioreactor chamber of the biomolecular processor is 20 µm×20 µm. The size of the bioreactor chamber dictates the number of solid support structures housed inside. Each bioreactor chamber may contain 100, 150, 200, 250, 300, 350, 400, 500, 550, 600, 650, 700, 750, 800, 850, 900, 950, 1000, or more spaced support structures, where each support structure is 0.1, 0.5, 1, 1.5, 2, 2.5, 3, 3.5, 4, 4.5, 5, 5.5, 6, 6.5, 7, 7.5 8, 8.5, 9, 9.5, or 10 µm in diameter and 0.5, 1, 2, 3, 4, 5, 6, 7, 8, 9, 10, 11, 12, 13, 14, 15, 16, 17, 18, 19, 20 µm tall. The support structures must be spaced apart from each other within the bioreactor chamber to allow flow through of a fluidic sample. In one embodiment, a bioreactor chamber of a biomolecular processor contains 250-300 spaced support structures that are 1 µm in diameter and 5 µm tall.

Design of the biomolecular processor is based on maximum loading capacity to accommodate the target nucleic acid molecules present in, e.g., a 1 mL of test sample, e.g., plasma. A pillar 1.0 µm in diameter and 5.0 µm in height (aspect ratio=5.0) has an available surface area of $1.57 \times 10^{-7}$ $cm^2$. With the known surface density of functional groups on UV-activated cyclic olefin copolymer (COC) ($19.0 \times 10^{-9}$ moles $cm^{-2}$) (Jackson et al., Lab Chip 14:106-117 (2014), which is hereby incorporated by reference in its entirety), there are $1.8 \times 10^9$ available sites on a pillar of these dimensions. When immobilizing $dA_{30}$ oligonucleotides (radius of gyration=3 nm) for capturing TdT tailed targets, the highest surface density that can be achieved for a hexagonally packed surface is $8 \times 10^{-12}$ moles $cm^2$, which is smaller than the density of surface carboxylates upon $UV/O_3$ activation. UV exposure (254 nm) of the polymer pillars generates surface-confined carboxylic acids only at sites exposed to the activating radiation, and suitable for attaching $NH_2$-$dA_{30}$ primers in the presence of EDC/NHS to generate a stable amide bond of the primer to the surface (Jackson et al., Lab Chip 14:106-117 (2014), which is hereby incorporated by reference in its entirety). However, not every capture molecule will capture a target. Based on literature reports of ~5,000 molecules per 1 $µm^2$, it is estimated that a given pillar can accommodate 78,500 molecules (Ma et al., Proc Natl Acad Sci USA 110:14320-14323 (2013), which is hereby incorporated by reference in its entirety). Thus, for a full load and no replication to accommodate capture of ~400 billion ssDNA molecules the array would have 5.1 million pillars. For a 20×20 µm bioreactor chamber that has pillars (each pillar being 1 µm in diameter) spaced by 0.25 µm with hexagonal packing, the number of pillars per bioreactor chamber is 288; the minimum number of bioreactor chambers required is 17,674. Thus, in one embodiment a nanosensor module has ~17,700 biomolecular processors.

Figure 3:
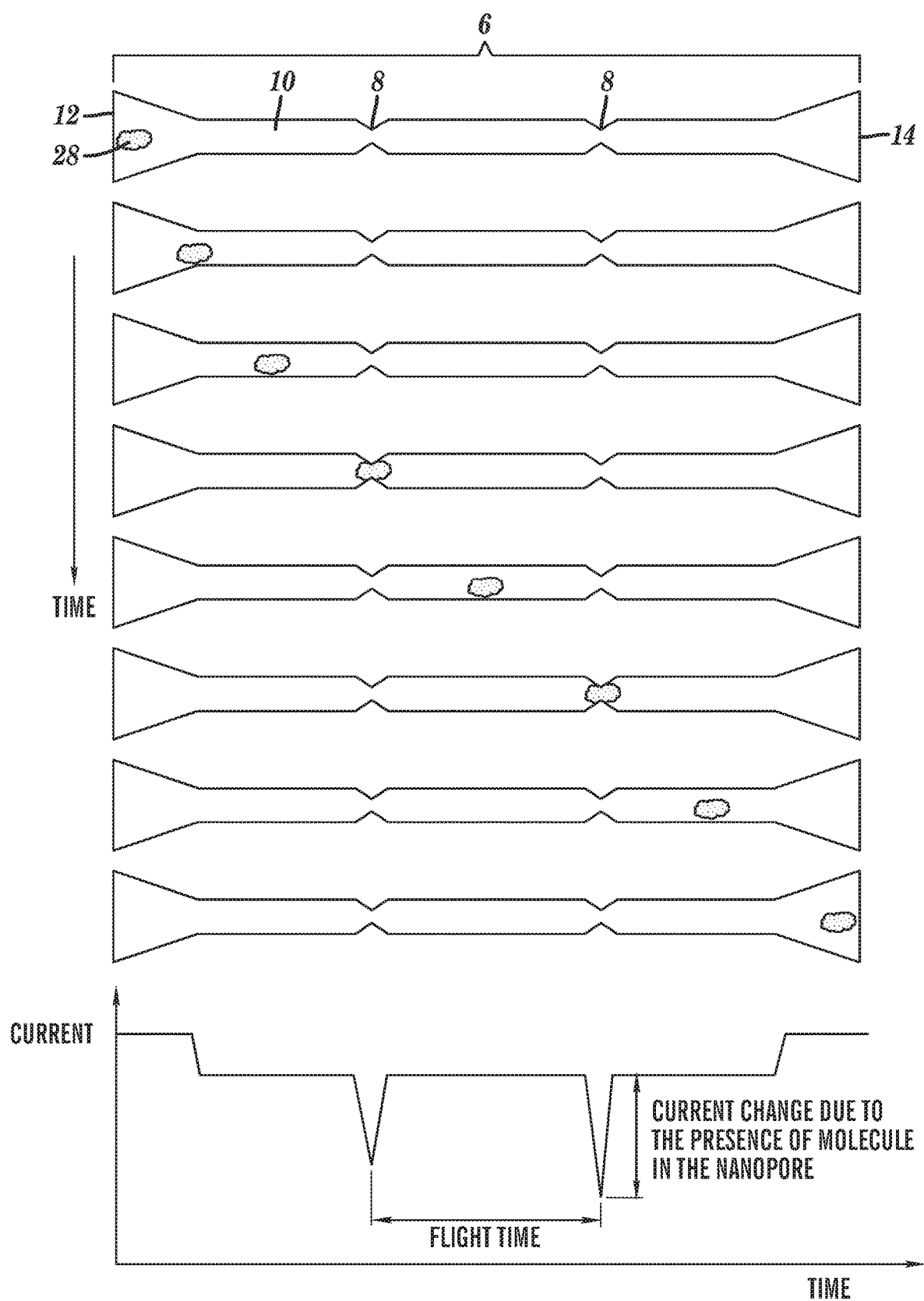
FIG. 3 is series of panels depicting the travel of a single molecule through a nanotube. Each panel shows a different position of the single molecule in the nanotube, with the graph at the bottom of the figure tracking the change in current as the molecule traverses the nanotube and nanopores within the nanotube.

As described in more detail herein, the nanotube functions to detect single molecules generated and/or processed within the bioreactor chamber of the biomolecular processor. Single molecules from the bioreactor chamber enter the nanotube at the input end and electrokinetically travel through the passageway of the nanotube containing the nanopores and exit at the output end. When the molecule passes through a nanopore, a current signature is generated depending on the ionic salt concentration and the size of the molecule that is detected. FIG. 3 is a schematic illustration of this process. The series of panels in FIG. 3 show the position of a biomolecule 28 in the nanotube 6 over time and the resulting current transient that is generated as the biomolecule 28 moves through the nanotube passage 10. The graph at the bottom of this figure tracks the change in current as a function of travel time of the single biomolecule through the flight tube. When a single biomolecule 28 enters into the nanotube 6 at the input end 12, there is a change in the transient current. When the single biomolecule 28 enters into a nanopore 8, there is additional change in the transient current, which will return to the previous value when the biomolecule 28 exits the nanopore 8, thus generating a drop in the current vs. time plot shown at the bottom of FIG. 3. Upon reaching the second in-plane synthetic pore, another current transient is generated and from the time difference between the first and second current transients, the flight time of the single molecule can be deduced and used to identify the single molecule traveling through the flight tube. The flight time depends on molecular structure and charge of the single molecule.

The nanotube may be 10-200 nm wide, 10-200 nm deep, and 5 to 250 μm long. In one embodiment, the nanotube is 10, 20, 30, 40, 50, 60, 70, 80, 90, 100, 110, 120, 130, 140, 150, 160, 170, 180, 190, or 200 nm wide. In another embodiment, the nanotube is 10, 20, 30, 40, 50, 60, 70, 80, 90, 100, 110, 120, 130, 140, 150, 160, 170, 180, 190, or 200 nm deep. In another embodiment the nanotube is 5, 10, 20, 30, 40, 50, 60, 70, 80, 90, 100, 110, 120, 130, 140, 150, 160, 170, 180, 190, 200, 210, 220, 230, 240, or 250 μm in length. In one embodiment, the dimensions of the nanotube passageway are less than or equal to 50 nm wide and less than or equal to 50 nm deep. In another embodiment of the present invention, the dimensions of the nanotube passageway are less than or equal to 25 nm wide and less than or equal to 25 nm deep. In another embodiment of the present invention, the dimensions of the nanotube passageway are less than or equal to 15 nm wide and less than or equal to 15 nm deep. In another embodiment of the present invention, the dimensions of the nanotube passageway are less than or equal to 10 nm wide and less than or equal to 10 nm deep. In another embodiment of the present invention, the dimensions of the nanotube passageway are less than or equal to 5 nm wide and less than or equal to 5 nm deep. The nanotube passageway can be 1 μm to >250 μm in length or 5 μm to 250 μm in length, and may have any desired geometrical cross-section, i.e., hemispherical, triangle, square, rectangle, pentagon, hexagon, heptagon, or octagon.

In one embodiment of the present invention, the nanotube channel comprises a polymeric material, e.g., PMMA, PC, epoxy-based resins, copolymers, polysulfones, elastomers, and polymeric organo silicons, or any combination of these materials. The polymeric material may be in its native state, or, alternatively, surface modified to enhance biomolecule discrimination and detection. For example, a polymeric passage wall may comprise a neutral, hydrophobic, hydrocarbon surface with different degrees of chain order. In another example, the nanotube passage wall surface may comprise a charge neutral, hydrophilic surface. In yet another example, the nanotube passage wall surface may comprise a charged, hydrophilic surface. As noted above, the composition of the nanotube passage wall will effect the time-of-flight of the biomolecule, and therefore helps define the identifying signature of a biomolecule.

The wall surface of the nanotube passageway comprising a neutral, hydrophobic, hydrocarbon surface with different degrees of chain order can be formed from monolayers of methyl-terminated alkane chains having various lengths that are built on the polymer nanochannel surfaces (Henry et al., "Surface Modification of Poly(methyl methacrylate) Used in the Fabrication of Microanalytical Devices," *Anal. Chem.* 72:5331-5337 (2000), which is hereby incorporated by reference in its entirety). The monolayers can be formed by attachment of amino-alkanes to carboxylic acid-terminated surfaces (McCarley et al., "Resist-Free Patterning of Surface Architectures in Polymer-Based Microanalytical Devices," *J. Am. Chem. Soc.* 127:842-843 (2005); Wei et al., "Photo-chemically Patterned Poly(methyl methacrylate) Surfaces Used in the Fabrication of Microanalytical Devices. *J. Phys. Chem. B* 109:16988-16996 (2005), which are hereby incorporated by reference in their entirety). Alternatively, the monolayers can be formed from urea-linked alkane layers on amine functionalities attached to the polymer via amide bonds (Henry, A. C., "Surface Modification and Characterization of PMMA Used in the Construction of Microelectromechanical Systems," In *Chemistry*, pp. 147, Louisiana State University, Baton Rouge (2001); Henry et al., "Surface Modification of Poly(methyl methacrylate) Used in the Fabrication of Microanalytical Devices," *Anal. Chem.* 72:5331-5337 (2000), which are hereby incorporated by reference in their entirety). For example, well-ordered octadecyl monolayers can be formed on PMMA surfaces by reaction of n-octadecylisocyanate with amine-terminated PMMA surfaces (Henry & McCarley, "Selective Deposition of Metals on Plastics Used in the Construction of Microanalytical Devices: Photo-Directed Formation of Metal Features on PMMA," *J. Phys. Chem. B* 105:8755-8761 (2001), which is hereby incorporated by reference in its entirety), and these $C_{18}$-PMMA surfaces are excellent for chromatographic separations in embossed channels (Galloway et al., "Contact Conductivity Detection in Poly(methyl methacylate)-Based Microfluidic Devices for Analysis of Mono- and Polyanionic Molecules," *Anal. Chem.* 74:2407-2415 (2002), which is hereby incorporated by reference in its entirety). Thus, various chain length n-alkylisocyanates can be used to make hydrophobic polymer surfaces possessing different degrees of order, which will affect the flight-time of passing molecules. Issues regarding non-zero electroosmotic flows (EOFs) can be addressed by capping unreacted foundation groups (Henry, A. C., "Surface Modification and Characterization of PMMA Used in the Construction of Microelectromechanical Systems," In *Chemistry*. Louisiana State University, Baton Rouge (2001); Wei et al., "Photochemically Patterned Poly(methyl methacrylate) Surfaces Used in the Fabrication of Microanalytical Devices. *J. Phys. Chem. B* 109:16988-16996 (2005), which are hereby incorporated by reference in their entirety).

One approach for creating hydrophilic, charge neutral surfaces, involves reacting properly activated carboxylic-acid terminated polymer surfaces with ethanolamine or amino-tri(ethyleneglycol) (Wei, S., "Multianalyte Detection of Breast Cancer by Fabrication of Hybridmicroarrays on Polymer-based Microanalytical Devices," In *Chemistry*. Louisiana State University, Baton Rouge (2005), which is hereby incorporated by reference in its entirety). As an alternative, amine-terminated PMMA and PC surfaces can be modified with glycols having surface generated carboxylic groups, such as glycolic acid or carboxyl-tri(ethyleneglycol). Cationic surfaces can be formed using well-established methods for production of amine-terminated polymers (Henry & McCarley, "Selective Deposition of Metals on Plastics Used in the Construction of Microanalytical Devices: Photo-Directed Formation of Metal Features on PMMA," *J. Phys. Chem: B* 105:8755-8761 (2001); Henry et al., "Surface Modification of Poly(methyl methacrylate) Used in the Fabrication of Microanalytical Devices," *Anal. Chem.* 72:5331-5337 (2000); McCarley et al., "Resist-Free Patterning of Surface Architectures in Polymer-Based Microanalytical Devices," *J. Am. Chem. Soc.* 127:842-843 (2005); Wei et al., "Photochemically Patterned Poly(methyl methacrylate) Surfaces Used in the Fabrication of Microanalytical Devices. *J. Phys. Chem. B* 109:16988-16996 (2005), which are hereby incorporated by reference in their entirety). Anionic surfaces will result from routes that lead to either carboxylic-acid terminated surfaces (McCarley et al., "Resist-Free Patterning of Surface Architectures in Polymer-Based Microanalytical Devices," *J. Am. Chem. Soc.* 127:842-843 (2005); Vaidya et al., "Surface Modification and Characterization of Microfabricated Poly(carbonate) Devices: Manipulation of Electroosmotic Flow," *Analyst* 127:1289-1292 (2002), which are hereby incorporated by reference in their entirety) or those bearing sulfonic acids, with the latter having an almost pH-independent surface charge (Henry, A. C., "Surface Modification and Characterization of PMMA Used in the Construction of Microelectromechanical Systems," In *Chemistry*, pp. 147, Louisiana State University, Baton Rouge (2001), which is hereby incorporated by reference in its entirety).

Figure 4:
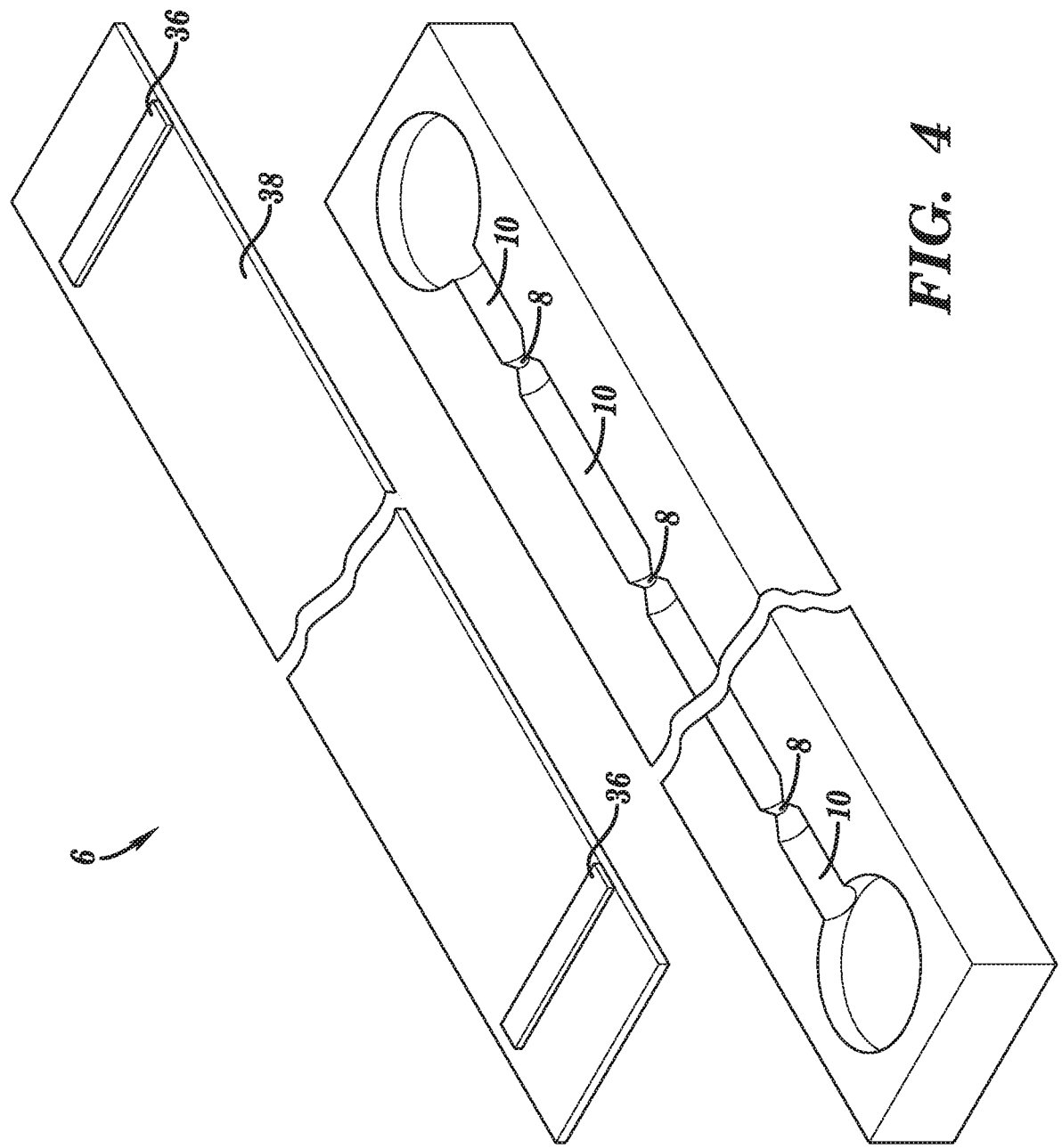
FIG. 4 is a perspective view of a nanotube showing the positioning of three or more (represented by the break in the nanotube) synthetic nanopores within a single nanotube. This figure also shows the nanotube cover and placement of the electrodes on the cover.

The nanotube as described herein may comprise one time-of-flight segment that is situated between two nanopores within a nanotube. Alternatively, as shown in FIG. 4, the nanotube may comprise multiple, i.e., three of more, time-of-flight segments coupled together, with each time-of-flight segment situated between two nanopores. In one embodiment, each time-of-flight segment is characterized by a passage wall having a unique chemistry that differentially interacts with the passing molecules and their identifying signature modifiers or generators. The time-of-flight segments can be the same length or different lengths, having the same or different surface chemistries. The time-of-flight channels have the same dimensional limitations as the nanotube with regard to the width and depth. In other words, the time-of-flight channel may be 10-200 nm wide and 10-200 nm deep. With regard to length, the time-of-flight channel is the length of the nanotube between two nanopores. Therefore, the length of the time-of-fight channel may be <5 µm and >200 µm or anywhere between 5-200 µm in length. These design formats allow for multidimensional separations to enhance identification and characterization of individual molecules moving through the nanotube.

The dimensions of the nanopores of the nanotube are significantly smaller than the passageway of the nanotube. For example the nanopore can be 1-150 nm in width or depth or both, and may be 5-500 nm long. The nanopore may be 1, 2, 3, 4, 5, 10, 20, 30, 40, 50, 60, 70, 80, 90, 100, 110, 120, 130, 140, or 150 nm in width or depth or both, and may be 5, 10, 20, 30, 40, 50, 60, 70, 80, 90, 100, 110, 120, 130, 140, 150, 160, 170, 180, 190, 200, 210, 220, 230, 240, 250 260, 270, 280, 290, 300, 310, 320, 330, 340, 350, 360, 370, 380, 390, 400, 410, 420, 430, 440, 450, 460, 470, 480, 490, 500 nm long. When two or more nanopores are present in a nanotube, each or some of the two or more nanopores may have the same or different dimensions. In one embodiment, two or more spaced nanopores are of different dimensions so that when the detector measures changes in current levels across the spaced two or more nanopores for a particular biomolecule, current change differences between the two or more spaced nanopores establish that that biomolecule is passing through the two or more spaced nanopores in a sequential manner and the time between those current changes.

As described herein, the nanopore is a small hole within the nanotube, having a diameter that is smaller than the diameter of passage extending through the nanotube on either side of the nanopore. As noted above, one nanotube may contain two or more nanopores, each nanopore being the same or different. The diameter of the nanopore is of a size such that when molecules of interest pass through the nanopore, the passage of the molecules is detected by a change in electrical signal, for example, current, though the nanopore. In one embodiment the nanopore comprises a protein, such as alpha-hemolysin or MspA, which can be modified or unmodified. In another embodiment, the nanopore is a synthetic nanopore, e.g., a solid state nanopore or graphene nanopore. Solid state nanopores can be produced as described herein or as described in U.S. Pat. No. 7,258,838 which are hereby incorporated by reference in their entirety. Exemplary solid state nanopores are disclosed by Storm et al., *Nature Mater.* 2:537-540 (2003); Venkatesan et al., *Adv. Mater.* 21:2771-2776 (2009); Kim et al., *Adv. Mater.* 18:3149-3153 (2006); Nam et al., *Nano Lett.* 9:2044-2048 (2009) and Healy et al., *Nanomedicine* 2:875-897 (2007) which are incorporated herein by reference in their entirety. In another embodiment, the nanopore comprises a hybrid protein/solid state nanopore in which a nanopore protein is incorporated into a solid state nanopore. Suitable nanopores are described, for example in Mager, M. D. & Melosh, N. A, *Adv. Mater.* 20:4423-4427 (2008); White, R. J. et al., *Langmuir* 22:10777-10783 (2006); Venkatesan, B. M. et al., *Biomed. Microdevices* 13:671-682 (2011); Iqbal et al., *Nature Nanotech.* 2:243-248 (2007); Wanunu et al., *Nano Lett.* 7:1580-1585 (2007); Siwy et al., *Chem. Soc. Rev.* 39:1115-1132 (2009); Kowalczy et al. *Nature Nanotech.* 6:433-438 (2011); and U.S. Patent Application Publ. No. US20100331194, which are hereby incorporated by reference in their entirety.

In another embodiment, the nanopore is a graphene nanopore. Suitable graphene nanopores are described in Geim, A. K., *Science* 324:1530-1534 (2009); Fischbein et al., *Appl. Phys. Lett.* 93:113107-113103 (2008); Girit et al. *Science* 323:1705-1708 (2009); Garaj et al., *Nature* 467:190-193 (2010); Merchant et al., *Nano Lett.* 10:2915-2921 (2010); Schneider et al., *Nano Lett.* 10:3163-3167 (2010), which are hereby incorporated by reference in their entirety.

In one embodiment, the device of the present invention comprises 1-100 biomolecular processors and nanotubes, 100-1,000 biomolecular processors and nanotubes, 1,000-10,000 biomolecular processors and nanotubes, 10,000-100,000 biomolecular processors and nanotubes, or 100,000-1,000,000 biomolecular processors and nanotubes. In another embodiment, the device of the present invention comprises more than 1,000,000 biomolecular processors and nanotubes. A series of biomolecular processors and nanotubes can be housed together in a nanosensor chamber, with a series of nanosensor chambers being housed together in a nanosensor unit or module on a device as described in more detail herein. For example, in one embodiment, 8 biomolecular processors and 8 nanotubes are housed together to form one nanosensor chamber, with the nanosensor unit comprising ~2,500 nanosensor chambers.

In accordance with this aspect of the present invention, the device further comprises electrodes positioned at locations upstream of the bioreactor chamber and downstream of the one or more nanotubes, and a voltage source is electrically coupled to the electrodes to establish a voltage gradient between the location upstream of the bioreactor chamber and downstream of the one or more nanotubes. This voltage gradient causes molecules to pass from said bioreactor chamber through the one or more nanotubes to the output end. A detector is positioned within the device to measure changes in current levels across the one or more nanopores as biomolecules pass through said one or more nanotubes.

The series of schematics shown in FIG. 3 represent the travel of a single molecule through a flight tube fitted with two nanopores and the change in current ($\Delta I_B$) as a function of travel time of the single molecule through the flight tube. As can be seen in the plot at the bottom of FIG. 3, current flow is at an open channel state before the molecule enters into the nanochannel. When the molecule enters the channel but before entering the pore in this example, $\Delta I_B$ begins to show a negative response, indicating that the ion flux is reduced when the particle enters this channel. At the in-plane pore, the value of $\Delta I_B$ drops to a lower value, but with a transient nature indicating that the particle is within the pore interstitial volume and drops to its nanochannel value as the molecule exists the first pore. Upon reaching the second in-plane nanopore, another current transient is generated. The time difference between the first and second current transients, the flight time of the single molecule can be deduced. The amplitude of $\Delta I_B$ is greater for the second in-plane nanopore with respect to the first, because the pore diameter is smaller; the difference in the $\Delta I_B$ for the first and second pore can be deduced by either making the pore longer or adjusting the pore diameter.

It is also possible to use a series of three or more nanopores within the flight tube. In FIG. 4, the break in the nanotube represents the presence of "n" pores placed in series, where "n" is any desired number. This can provide many benefits such as the ability to generate consensus between time-of-flight measurements to reduce error in the determination. In addition, different types of surface coatings can be imposed on the nanotube walls between a set of pores as described supra to improve single molecule identification by taking advantage of a technique called multi-dimensional chromatography. This multidimensional approach can also increase the peak capacity of the system to allow for higher multiplexing capabilities.

FIG. 4 also illustrates a top cover 38 of the nanotube 6, and placement of the two electrodes 36 on the top cover 38, where the electrodes are positioned near the input and output ends of the nanotube. In another embodiment, the cover plate may contain a third electrode that is positioned between the nanopores. In accordance with this embodiment, a nanotube containing "n" nanopores, may contain "n" electrodes positioned on the cover plate.

Figure 5:
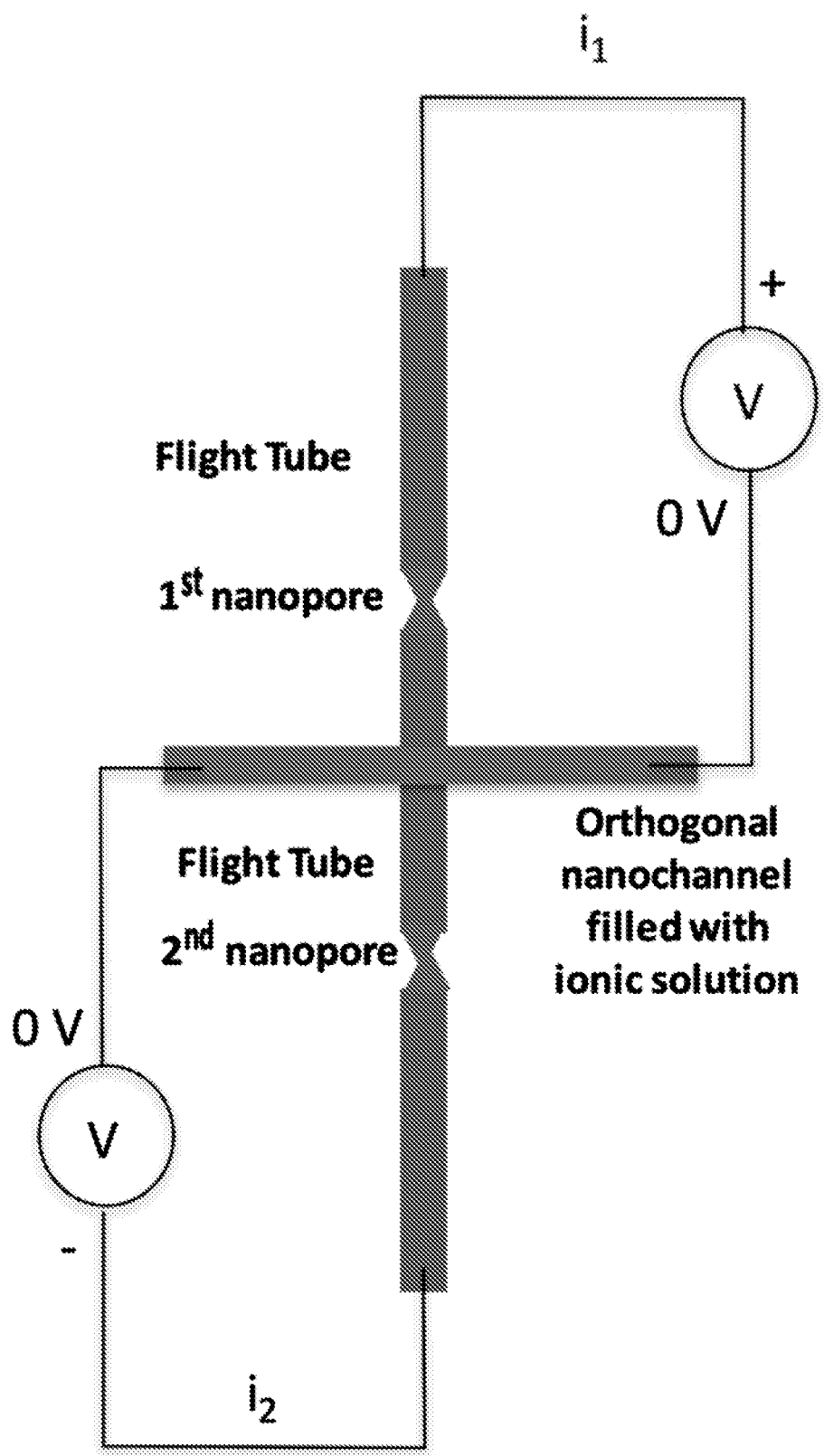
FIG. 5 shows a simplified electrical diagram of one embodiment of the nanotube described herein.
Figure 6:
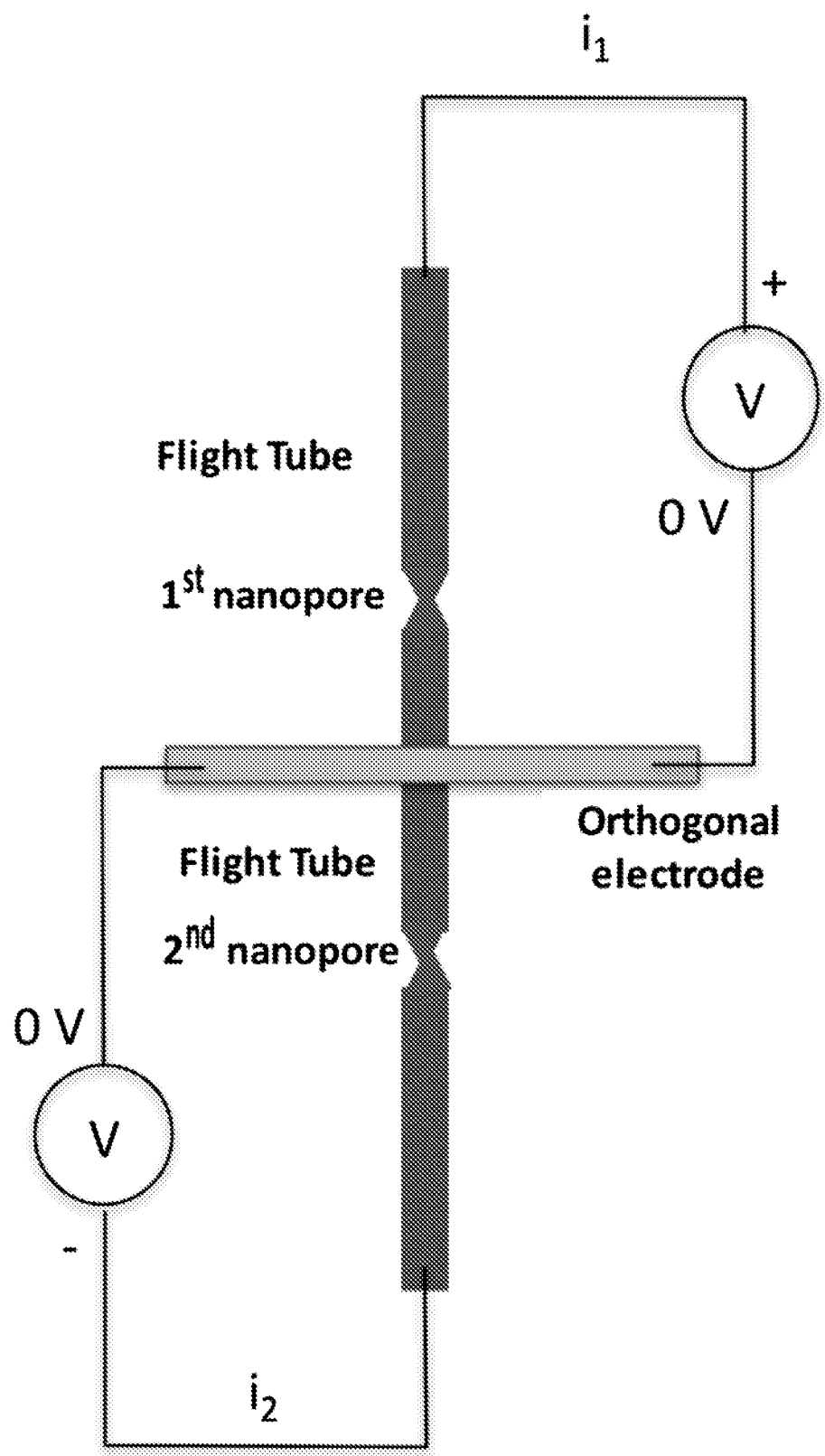
FIG. 6 shows a simplified electrical diagram of one embodiment of the nanotube described herein.

FIGS. 5 and 6 depict alternative single electrode arrangements for detecting current changes in the nanotubes.

In the embodiment depicted in FIG. 5, an additional nanochannel is placed orthogonal to the nanotube containing the nanopores and situated between the two nanopores. When the nanochannel is filled with an ionic solution and connected to an external electrode, the nanochannel filled with ionic solution serves as a common floating ground for separate transient current measurements at the two individual nanopores, which also allows for determining the time-of-flight of a molecule between the two nanopores. A similar structure has been disclosed by Menard et al., *ACS Nano* 6 (10): 9087-9094 (2012), which is hereby incorporated by reference in its entirety.

The embodiment depicted in FIG. 6 also shows an electrode built orthogonal to the nanotube between the two nanopores. In order not to hinder the movement of the molecules passing through passageway of the nanotube, the orthogonal electrode is situated to pass through the top or bottom surface of the flight tube. A thin insulating layer may be coated on the electrode surface. The orthogonal electrode serves as a common floating ground for separate transient current measurements at the two individual nanopores, which also allows for determining the time-of-flight of a molecule between the two nanopores.

Electronic amplification circuitry is necessary to detect changes in current as molecules pass through and occlude the nanopores of the nanotube. The circuit diagrams of FIGS. 7-14 show various alternative embodiments of the electronic circuitry suitable to detect current changes within the nanotube of the device as described herein.

FIG. 7A shows a top view of a nanotube with an entry pore (Pore 1) and an exit pore (Pore 2). Above the entry pore is a fluid chamber, or well, with conductive Electrode A in contact with the fluid contents of the well. In the same fashion, below the exit pore is another fluid chamber with an electrode in it. Biomolecules or nano-particles suspended in an ionic solution are driven from the top well to the bottom well iontophoretically. As the biomolecule moves through the pore and obstructs it, a change in current occurs (blockage current).

FIG. 7B is a circuit diagram of the nanotube with electrodes and measuring circuitry. The circuit diagram shows voltage (V1), which is the potential source for driving molecules or nano-particles through the nanotube. V1 is adjusted to provide the desired speed of transit of the molecules through the nanotube and its pores. The very small diameter of each of the nanopores causes a resistance to the flow of electrical current, represented by "Rpore1" and "Rpore2". Each of these resistances is indicated as a variable resistor, because, when the pore is blocked by a molecule or particle, the resistance increases proportionally to the percentage of the diameter of the pore that is blocked (or alternatively, proportionally to the size of the molecule or particle). This change in current is then measured by the current-to-voltage converter amplifier as shown, and its output is:

$$V_{out} = I * Rf$$

Where: $V_{out}$ is the output voltage of the amplifier

I is the current resulting from the drive voltage applied across the pores

Rf is the value of the feedback resistor

The output voltage is a pulse with a duration that is proportional to the speed of the molecule or particle and the pore length. The amplitude of the voltage pulse is proportional to the change in current due to the blockage event in each pore. Note that filtering or pulse shaping circuitry, whether in analog or digital form can be used with all of the circuits shown herein to improve the S/N ratio or to improve detectability of the blockage events.

Figures 8A, 8B:
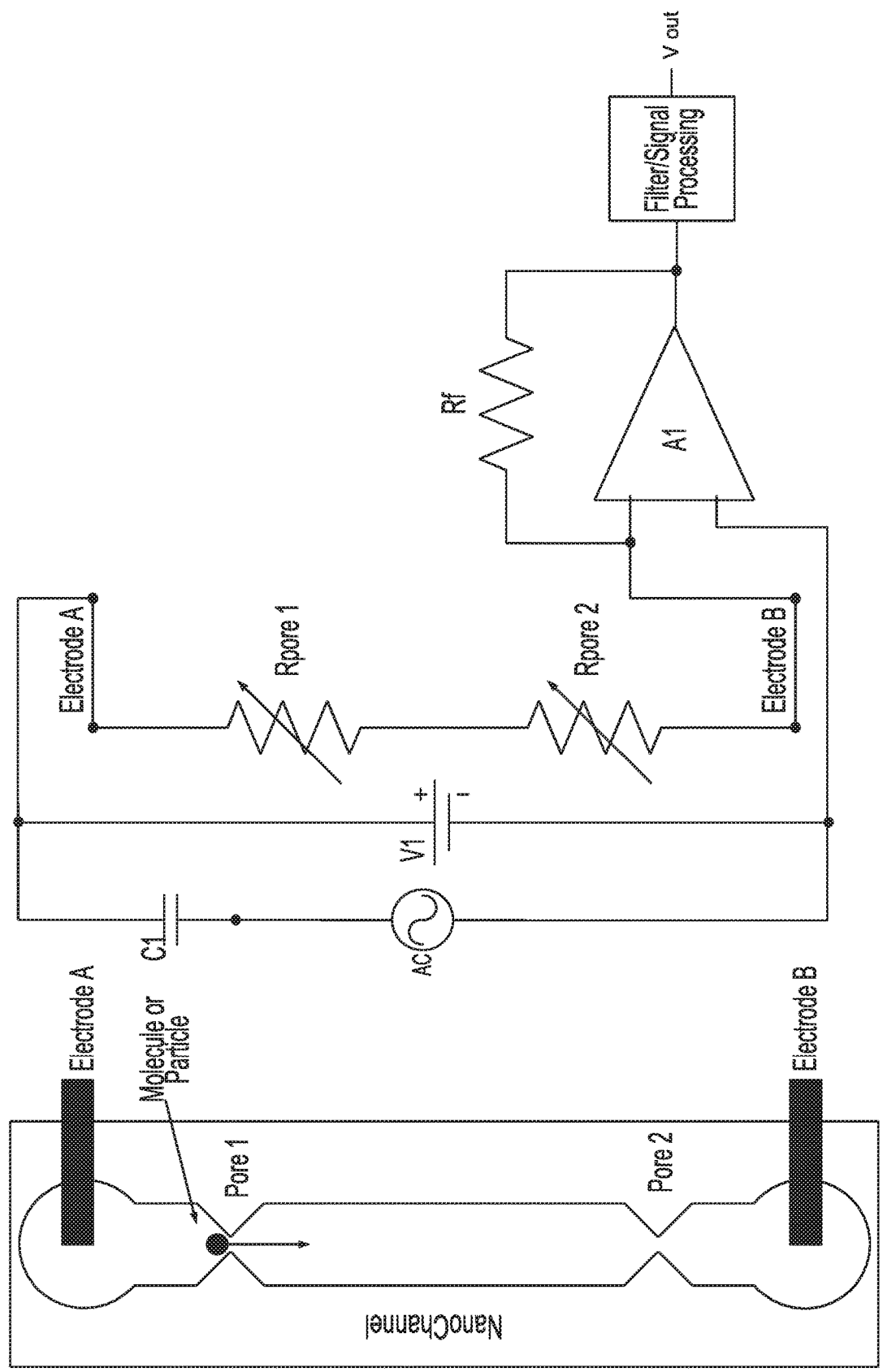
FIGS. 8A-8B show a top view of a nanotube (FIG. 8A) and a circuit diagram of the nanotube with electrodes and measuring circuitry (FIG. 8B). The circuit diagram of FIG. 8B depicts an alternative embodiment for measuring a biomolecule's identifying signature as it passes through a nanopore of the nanotube.

FIGS. 8A-B repeat many of the same features shown in FIGS. 7A-B; however, FIG. 8B shows the introduction of an AC source. In this case, the DC voltage source, V1, still supplies the voltage gradient required to transport the molecules or particles through the nanochannel and its pores, but now the blockage current measurements are not dependent on the DC current from V1. In this case, an AC signal source is capacitively coupled across the nanochannel superimposing an AC signal on top of the DC drive voltage. The changes in the AC current are now used to detect the blockage events instead of the DC current. This decouples the measurement of the blockage currents from the drive voltage and any changes that can occur in the drive voltage. In normal operation, the drive voltage, V1, must be kept at very low potentials to avoid any electrochemistry from occurring at the electrodes. This limits the amplitude of the current change that can be measured. With the AC source, however, the frequency will be chosen to be high enough to prevent electrochemistry from occurring. In addition, since the AC signal is symmetric around zero, no ion polarization will occur. This allows higher voltages to be applied across the nanotube without affecting the transit of the molecules or particles, thus increasing the resulting current which improves the measurability of the blockage event. In addition, filtering (i.e., low pass, bandpass, high pass, or any other filter topology) may be effectively applied to remove noise and drift. Also, signal processing can be implemented to measure the amplitude and phase of the blockage current changes, thus presenting additional correlated measurements that can be used to improve the signal-to-noise ratio for measuring the current blockage event (e.g. molecule resident within the nanopore). Note that in this embodiment, and all subsequent embodiments described below, the AC source can also be transformer-coupled and a secondary center tap can be used to establish the mid-point, or common, voltage.

Figures 9A, 9B:
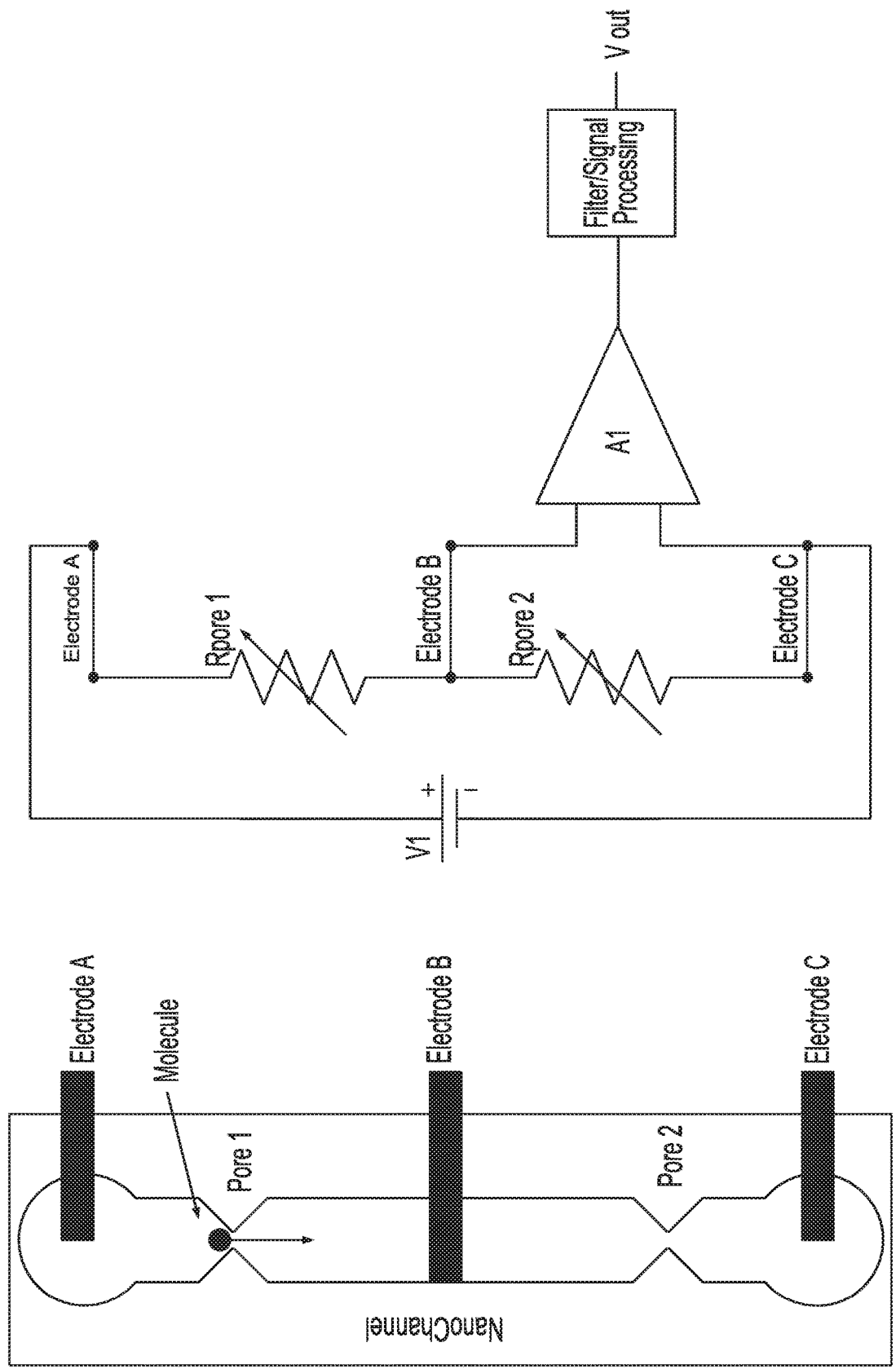
FIGS. 9A-9B show a top view of a nanotube (FIG. 9A) and a circuit diagram of the nanotube with electrodes and measuring circuitry (FIG. 9B). The circuit diagram of FIG. 9B depicts an alternative embodiment for measuring a biomolecule's identifying signature as it passes through a nanopore of the nanotube.

FIGS. 9A-B illustrate an alternative embodiment to measuring the blockage current as shown in FIGS. 7A-B and 8A-B. This method involves measuring voltage change instead of the current change directly. A similar method has been described in Fraikin et al., "A High-throughput Label-free Nanoparticle Analyser," *Nature Nanotechnology* 6: 308-313 (2011), which is hereby incorporated by reference in its entirety. In this embodiment, a third electrode is placed in the middle of the nanotube between the pores. FIGS. 9A-B show measuring the voltage change across the second pore; however, the voltage change can be measure across either pore (Rpore1 or Rpore2). A standard voltage amplifier with gain can be used to make this measurement as shown. In this embodiment, a blockage event in Pore 1 will cause the voltage measured across Rpore2 to increase. A blockage event in Pore 2 will cause the measured voltage to decrease. This arrangement works best when the resistances of the nanopores are identical in order to obtain the largest voltage change for a blockage event in each pore. However, when the resistances of the nanopores differ greatly, a physical resistor may be added in series with the lowest resistance pore to equalize the voltages. This measurement method offers certain advantages over the current measurement method of FIGS. 7A-B and 8A-B, because for certain values of Rpore, the signal-to-noise ratio and bandwidth of a pure voltage amplifier can be better than those of a current-to-voltage amplifier.

Figures 10A, 10B:
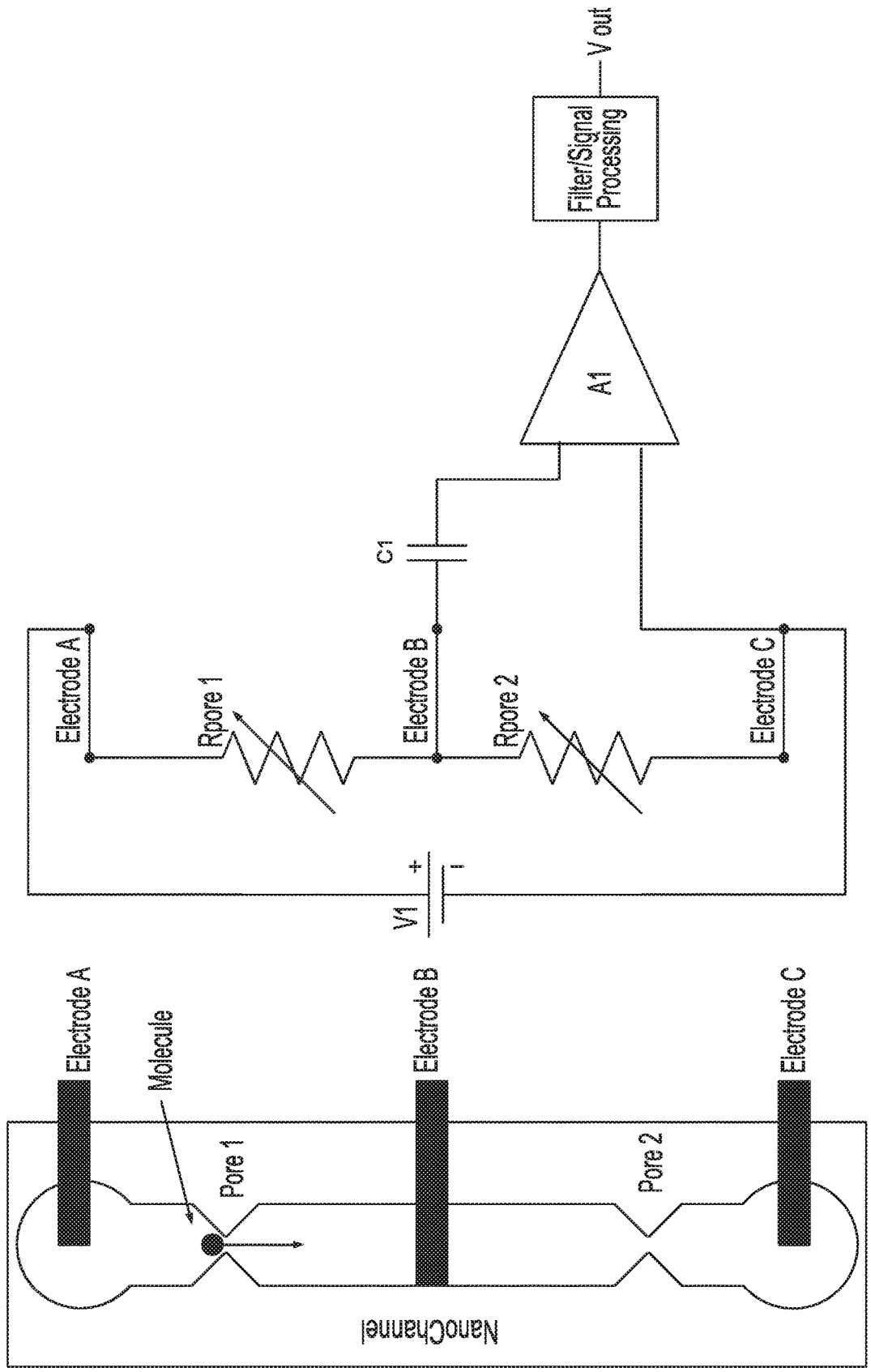
FIGS. 10A-10B show a top view of a nanotube (FIG. 10A) and a circuit diagram of the nanotube with electrodes and measuring circuitry (FIG. 10B). The circuit diagram of FIG. 10B depicts an alternative embodiment for measuring a biomolecule's identifying signature as it passes through a nanopore of the nanotube.

The embodiment depicted in FIGS. 10A-B shows all of the features of FIGS. 9A-B, except that the voltage amplifier is now capacitively coupled. This capacitive coupling can be created by the use of a physical capacitor in series with the electrode, or can be from a dielectric insulator applied to the middle electrode itself (or due to other physical properties of the electrode itself). The first method of capacitive coupling creates a high-pass filter which can be designed to remove low frequency noise and drift from the measurement. The second method of capacitive coupling due to the application of an insulator to the electrode can help to make the electrode chemically inert and thus reduce or eliminate its effect on the DC field potentials and on the molecules or particles as they traverse the nanotube. This capacitive coupling can be used because the voltage signature of a blockage event is theoretically a single square pulse that can be reproduced reasonably well by capturing only its high frequency content. The value of C1 can be adjusted to optimize the cutoff frequency of the high pass filter that is formed.

Figures 11A, 11B:
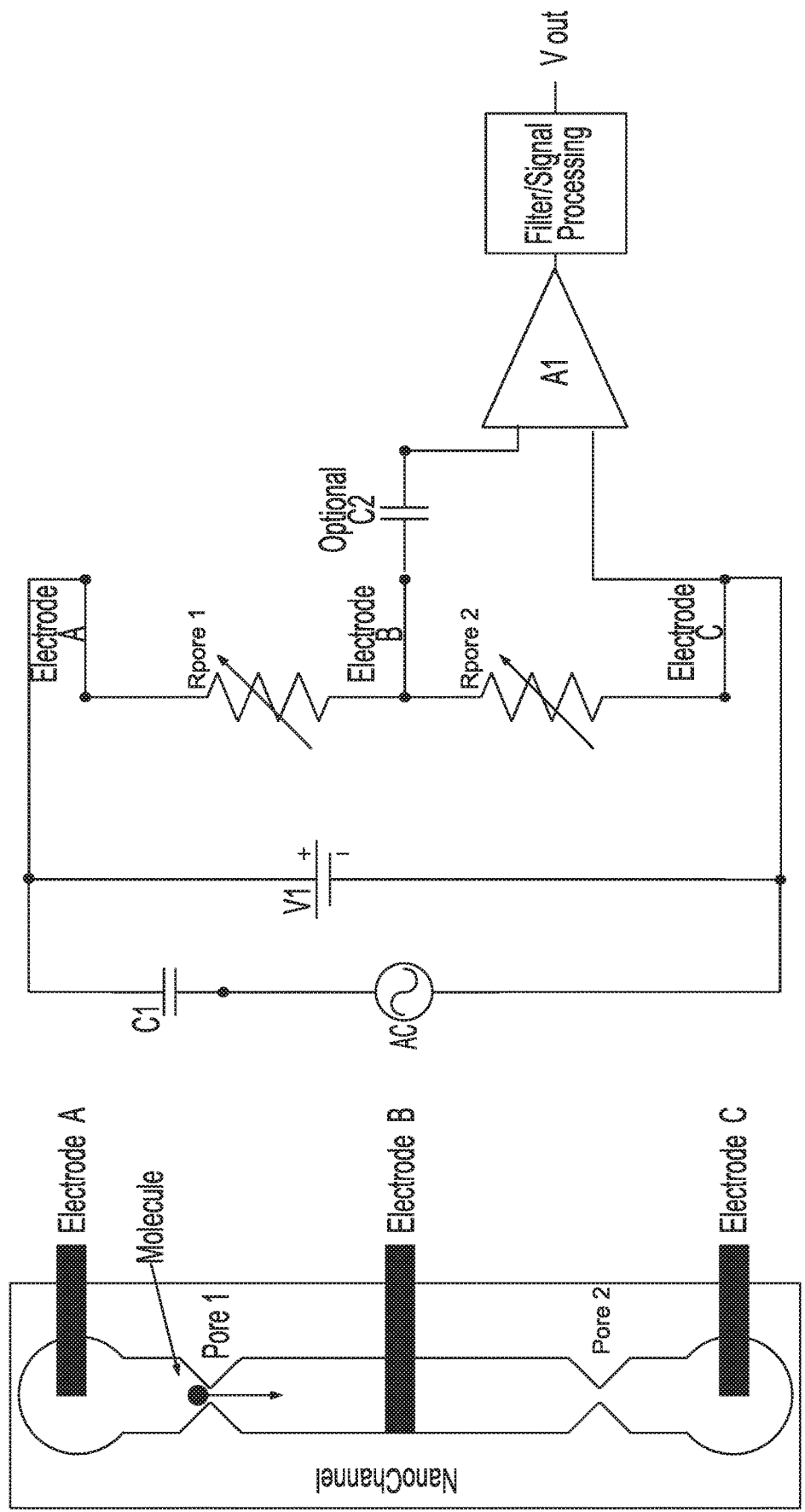
FIGS. 11A-11B show a top view of a nanotube (FIG. 11A) and a circuit diagram of the nanotube with electrodes and measuring circuitry (FIG. 11B). The circuit diagram of FIG. 11B depicts an alternative embodiment for measuring a biomolecule's identifying signature as it passes through a nanopore of the nanotube.

FIGS. 11A-B depict the use of an AC voltage signal superimposed on the DC drive voltage (V1) which, like FIGS. 8A-B above, separate the drive voltage source from the measurement source and has all of the same advantages as those described for FIGS. 8A-B. A1 can be AC or DC coupled through C2. C2 can either be a series capacitor, or as described above, can be a dielectric associated with the electrode itself.

Figures 12A, 12B:
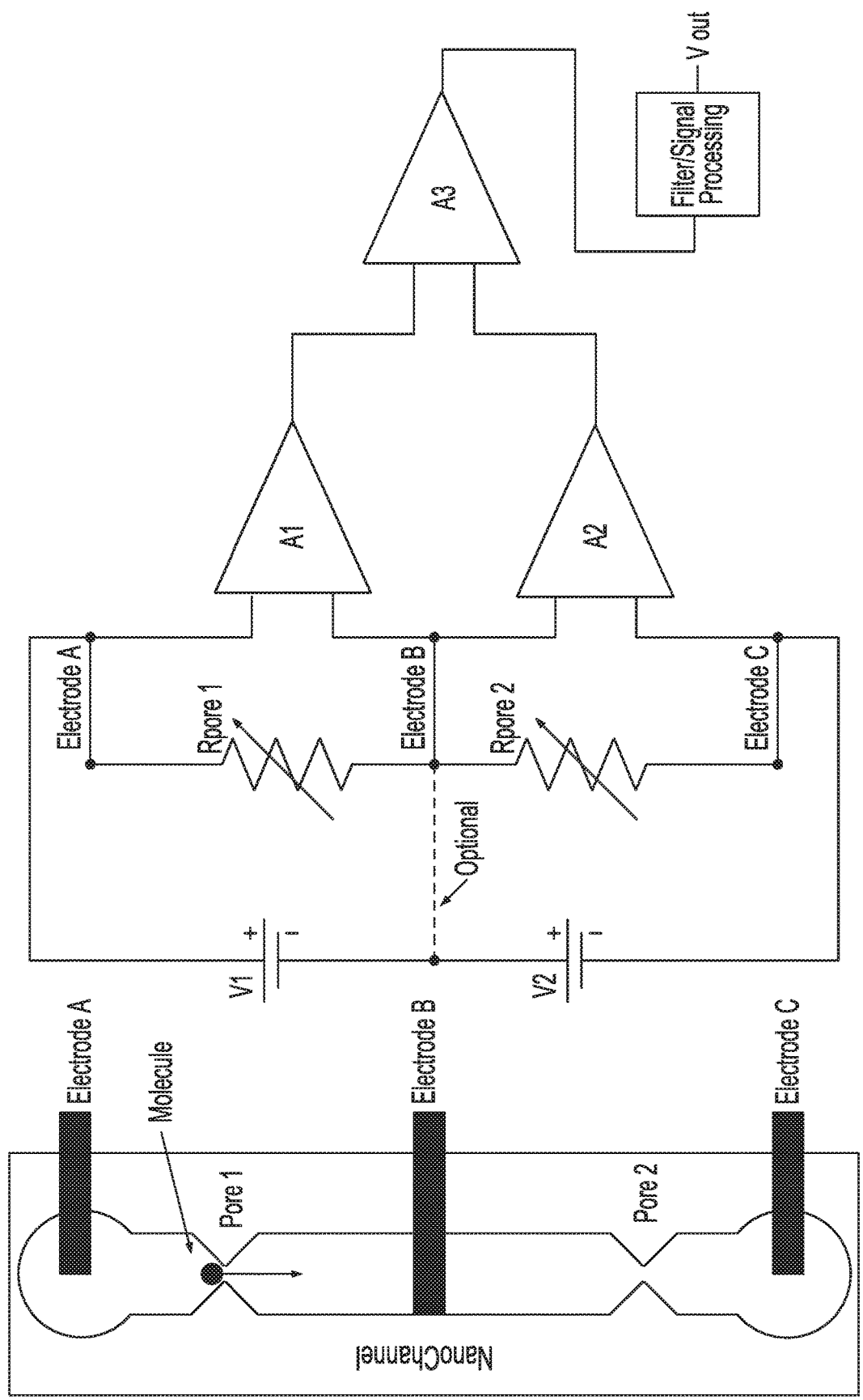
FIGS. 12A-12B show a top view of a nanotube (FIG. 12A) and a circuit diagram of the nanotube with electrodes and measuring circuitry (FIG. 12B). The circuit diagram of FIG. 12B depicts an alternative embodiment for measuring a biomolecule's identifying signature as it passes through a nanopore of the nanotube.

In FIGS. 12A-B, two DC voltage sources arranged in a bipolar fashion are used to drive molecules or particles through the nanotube. These voltage sources can be replaced by a single source, but having a bipolar source allows a mid-point connection to be used optionally as a common, or reference, in the circuitry when that may provide an advantage. This bipolar drive method also allows for different drive voltages to be applied across the two pores, allowing full differential control of speed through the individual pores. Amplifiers A1, A2, and A3 are arranged in a typical differential amplifier or instrumentation amplifier (InAmp) topology. This circuit topology can be fashioned from discrete components (transistors or OpAmps) or one of the many commercial implementations of instrumentation amplifiers can be used.

Figures 13A, 13B:
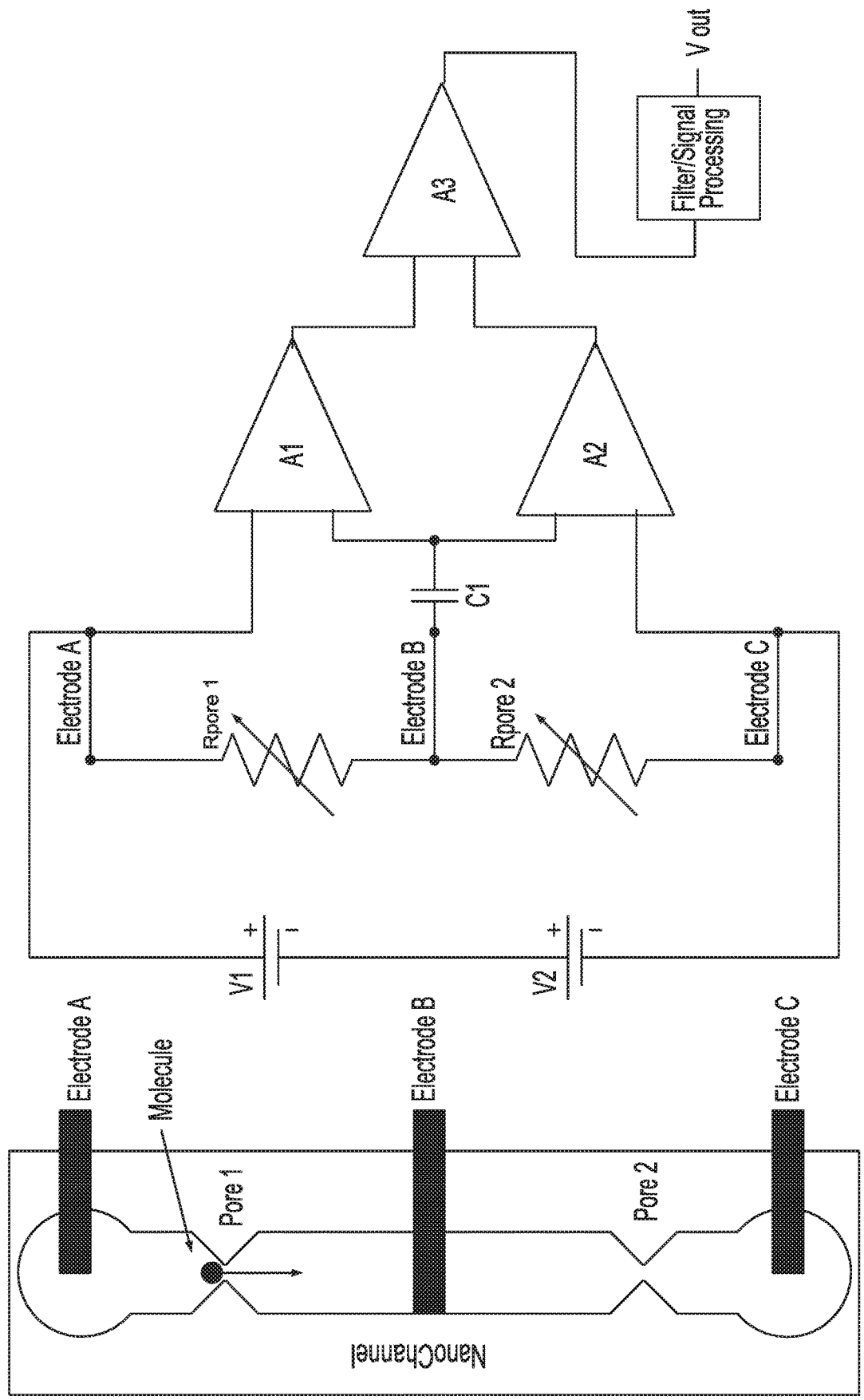
FIGS. 13A-13B show a top view of a nanotube (FIG. 13A) and a circuit diagram of the nanotube with electrodes and measuring circuitry (FIG. 13B). The circuit diagram of FIG. 13B depicts an alternative embodiment for measuring a biomolecule's identifying signature as it passes through a nanopore of the nanotube.

The embodiment depicted in FIGS. 13A-B are identical to that shown in FIGS. 12A-B, except that it shows AC coupling of the center electrode. As above, C1 can be a series coupling capacitor or it can be due to a dielectric associated with the electrode itself.

Figures 14A, 14B:
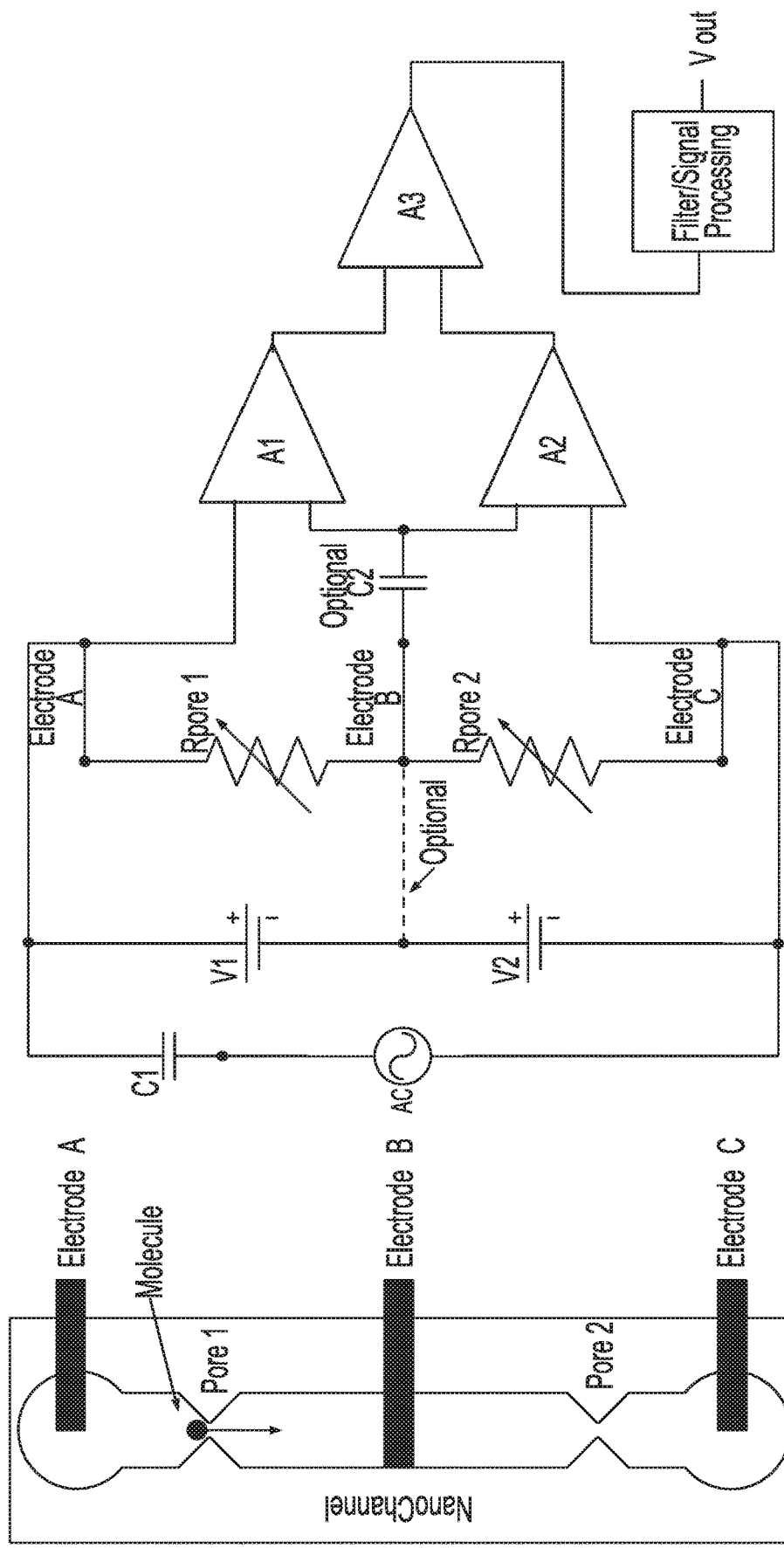
FIGS. 14A-14B show a top view of a nanotube (FIG. 14A) and a circuit diagram of the nanotube with electrodes and measuring circuitry (FIG. 14B). The circuit diagram of FIG. 14B depicts an alternative embodiment for measuring a biomolecule's identifying signature as it passes through a nanopore of the nanotube.

The embodiment shown in FIGS. 14A-B illustrates the use of a capacitively-coupled AC source superimposed on the DC drive voltage. The use of the AC source has the same advantages listed in the previous embodiments described above. The differential amplifier(s) can be either AC or DC coupled as described above through the use of C2. Filtering or signal processing can be used on the output.

FIG. 15 shows two methods for detecting and processing the blockage event signals generated by a biomolecule in a single nanotube. In both cases, amplifier A along with the filtering/signal processing can represent any of the measurement methods shown in FIGS. 7 to 14. In the method depicted in FIG. 15A, the pulse signals from blockage events at either pore are continuously converted in an Analog to Digital Convertor (ADC) and presented over a bus to the data processing/computing equipment. This requires a high conversion bandwidth for the ADC and it presents a significant amount of data to the processing equipment over time. In addition, this method collects data at the high conversion rate even when there are no blockage signals present. The data processing equipment must take this data and utilize algorithms to determine pulse height and time-of-flight. This method works well for research experiments or low-throughput analysis, but when the process is scaled up to thousands or millions of nanotubes, the data throughput becomes unsustainable. FIG. 15B shows an alternative method which allows the quantity of data required to be reduced. In embodiments where only time-of-flight data is gathered, the blockage signals can be routed to a constant fraction discriminator that provides a timing pulse for the entry blockage event and another timing pulse for the exit event. The entry pulse starts the Time Interval Counter while the exit pulse stops the counter. The Time Interval Counter then passes a single number to the data processing equipment that represents the time-of-flight. This reduces potentially millions of samples per second down to only one value for every pair of blockage events. In embodiments where the blockage event magnitude is measured, the constant fraction discriminator can be used to trigger a sample/hold and the ADC so that only a few values are converted for each blockage event. This reduces the quantity of data down to just a few points during each blockage event instead of running the ADC continuously.

Figure 16A:
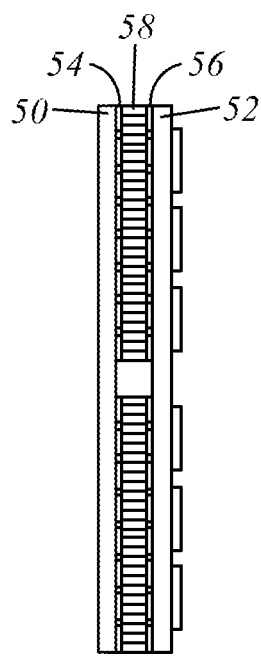
FIG. 16A is a side view and FIG. 16B is a top view of the high-density electrical connections between the nanosensor module and a printed circuit board (PCS).
Figure 16B:
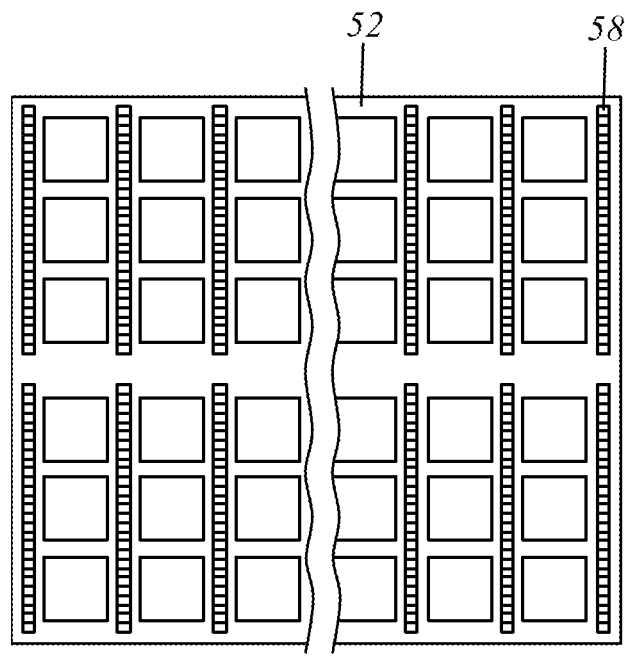

Electrical connections between the nanosensor unit and external electronic circuitry are required to measure the current transients generated when molecules travel through the in-plane synthetic nanopores. In addition, the drive voltage for producing the electrophoresis of the solid-phase generated products following release from the space solid supports of the bioreactor chamber must occur as well. FIG. 16 is a diagram showing a configuration allowing high-density electrical connections between the nanosensor unit 50 and a typical printed circuit board (PCB) 52. Gold contacts 54, 56 are plated onto the nanosensor 50 and on the PCB 52 as described below. Elastomeric ("Zebra") connectors 58 are used to make connection between the gold pads 54, 56. The elastomeric connectors 58 are commercially-available connectors comprising alternating conductive and insulating layers in a compressible elastomer. Gold pads 54, 56 with a width to accept at least two conductive layers in the elastomeric connector 58 are used to ease the alignment of the panels and the connector. The nanosensor 50 and the PCB 52 are then put under compression to make the connection. The nanosensor can be removed and replaced allowing the nanosensor to be a disposable component.

The electrical connections can be fabricated adopting the strategy described in Kong et al., *Electrophoresis* 27:2940-2950 (2006), which is hereby incorporated by reference in its entirety. In this case, the top cover plate is injection molded from the appropriate plastic to make the necessary through holes. The position of the electrical leads on the plastic plate are defined by exposing the plastic cover plate with $UV/O_3$ radiation through an optical mask that creates the carboxylic acid functional groups only at places where the plastic was exposed to the radiation. The photopatterned plate is immersed in a solution of ethylenediamine solution containing EDC for selective amination of the photolysed area. The selectively aminated substrate is sequentially immersed in an aqueous solutions of $HAuCl_4$, $NaBH_4$, and KSCN to prepare for electroless plating. Gold micro-contacts are electrolessly plated onto the selectively activated area of the plastic plate by placing the plate in a gold plating bath containing $Na_3Au(SO_3)_2$, $NaSO_3$, and formaldehyde.

To make a device of the present invention commercially useful, it is necessary that the nanosensor chambers are operated in large arrays. Accordingly, the electronics are integrated into chip form as integrated circuits (IC) with sufficient input and output channels to handle the array of nanosensor chambers. These ICs can be encapsulated using high-density technologies such as HyperBGA packaging and can be mounted on a printed circuit board (PCB).

The Universal Molecular Processor System (uMPS)

The device of the present invention may further comprise one or more units or modules defined by the solid substrate and upstream of said biomolecular processor and one or more nanotubes. The one or more additional modules are configured to carry out sample preparation and processing, i.e., isolation and preparation of target nucleic acid molecules within a sample to enter the biomolecular processor and the nanotube. An exemplary device as described herein containing a plurality of biomolecular processors and nanotubes housed together in a nanosensor unit together with a plurality of task-specific units designed to prepare a biological sample for processing and detection in the biomolecular processor and nanotube is depicted in FIGS. 17A and 17B and referred to herein as a Universal Molecular Processor System (uMPS).

Figure 17A:
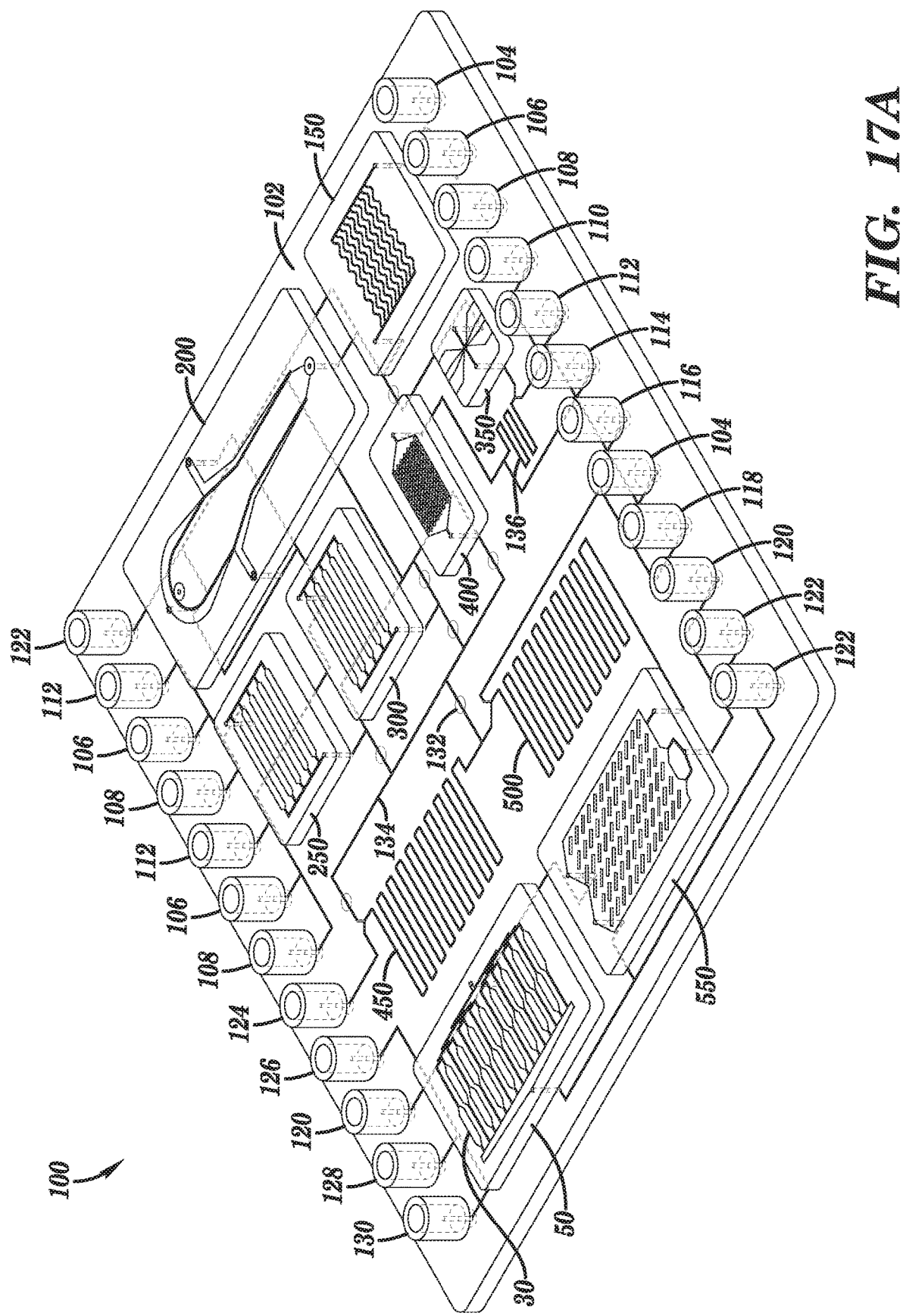
FIGS. 17A-17B are perspective and top views, respectively, of a device encompassed by the present invention. This device, which is referred to herein as a universal molecular processing system (uMPS), comprises several task specific modules that are interconnected via a fluidic motherboard.
Figure 17B:
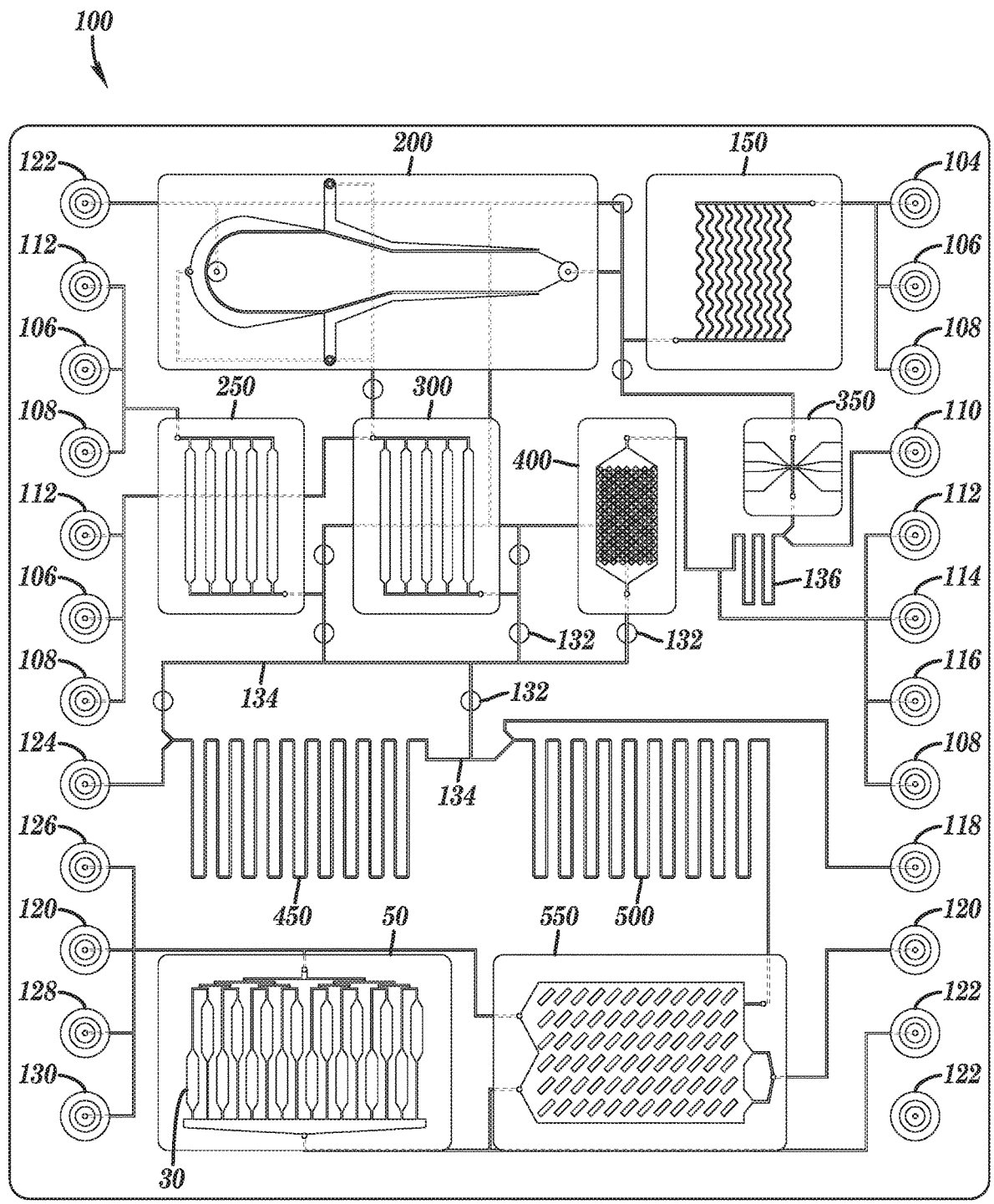

The uMPS 100 as depicted in FIGS. 17A (perspective view) and 17B (top-view) is comprised of 10 task-specific modules 150, 200, 250, 300, 350, 400, 450, 500, 550, and 50, that are connected to a fluidic motherboard 102 and organized into 3 sub-systems, which are described below. The modules are fabricated from plastics using technologies such as, but not limited to, hot embossing, injection molding, or imprinting. The particular plastic selected for each module is predicated on optimizing the task carried out on that module. These modules are connected to the fluidic motherboard using leak-free interconnects that also are engineered to minimize unswept volumes as well as degas solutions (remove air bubbles) as solutions move through the interconnects. The modules are aligned with respect to the motherboard using pins and v-grooves embossed into the substrates. The plastic surfaces are also modified using procedures to prevent non-specific adsorption artifacts.

The nanosensor module 50, depicted as the last module on the uMPS device 100 of FIG. 17A, houses the biomolecular processors and nanotubes as described supra. The nanosensor unit 50 of the uMPS houses 100-1,000,000 nanosensor chambers 30, where each nanosensor chamber houses 8 biomolecular processors and 8 nanotubes (see FIG. 1A, 30). In one embodiment, the nanosensor unit houses 2,500 nanosensor chambers, each nanosensor chamber having a dimension of ~200 µm×~410 µm.

Calculations for the footprint of 2,500 nanosensor chambers to accept 400 billion ssDNAs are shown below.

Square containing 2,500 chambers=20,000 biomolecular processors:

$2,500=XY=2.05Y^2$; therefore Y=34.9=35

Then X=71.6

2,500 chambers fits in a 14.3×14.3 mm array=1.4×1.4 cm size=0.6×0.6 in. sq.

Square containing 25,000 chambers=200,000 biomolecular processors:

$25,000=XY=2.05Y^2$; therefore Y=110.43

Then X=226.38

25,000 chambers fits in a 45×45 mm array, =4.5×4.5 cm size=1.8×1.8 in sq.

The calculated sizes of these numbers of nanosensor chambers poised on the nanosensor module 50 will allow this module to easily fit onto a 6" wafer comprising the uMPS 100 and provide sufficient space to accommodate the other processing modules 150, 200, 250, 300, 350, 400, 450, 500, 550 as depicted in FIGS. 17A-17B.

Depending on the application of the uMPS, it may be desirable to maximize the number of biomolecular processors per uMPS device. Thus, in one embodiment, the nanosensor chamber can be streamlined to exhibit dimensions of 175×175 µm, containing 8 biomolecular processors, each in a 25×16 µm footprint (each biomolecular processor with 288 pillars). With 5 µm spacing between 16 µm biomolecular processors×8+5 µm wall=175 µm wide. Input area 25 µm+Chevron baffles 50 µm+25 µm biomolecular processors+50 µm flight tube+20 µm space+5 µm for wall=175 µm.

A 4×4 inch wafer=101.6 mm×101.6 mm. That means 580×580=336,400 chambers×8 biomolecular processors=2,691,200 biomolecular processors. Therefore, in this embodiment, a 4×4 inch wafer contains about 336,000 chambers and 2,600,000 biomolecular processors.

A 6×6 inch wafer=152.4 mm×152.4 mm, but using only 135 mm (5.3 inches) per side=135 mm×135 mm. That means 771×771=594,441 chambers×8 biomolecular processors=4,755,528 biomolecular processors. Therefore, in this embodiment, a 6×6 inch wafer contains about 600,000 chambers and 4,700,000 biomolecular processors.

The device of the present invention may contain any one or more of the task-specific units (also referred to as modules) depicted on the uMPS device of FIGS. 17A and 17B in combination with the nanosenor unit housing the biomolecular processors and nanotubes. The particular combination of units depends on the desired function of the uMPS (i.e., the sample being analyzed (e.g., exosome vs. cfDNA vs. RNA) and the endpoint being analyzed (e.g., mutation detection, copy number enumeration, methylation detection, sequencing, etc)). In one embodiment of the present invention, the device contains all of the modules of the uMPS device as depicted in FIGS. 17A and 17B. Depending on the particular application of the device, only select modules are utilized when processing a particular sample, i.e., not all modules on the device need to be employed for sample analysis. For example, in one embodiment, 1, 2, 3, 4, 5, 6, 7, 8, or all 9 of the modules of the uMPS device can be utilized for any given application in combination with the nanosensor module 50. The flow of the sample to, through, and/or away from various modules of the device is conducted through the microfluidic network 134 of the motherboard 102, and controlled by a series of valves 132 located throughout the microfluidic network. Reagent 108-114, 118, 120, 124-130, wash 106, air 116, and waste 122 reservoirs line opposing outside edges of the motherboard facilitating the delivery and removal of reaction components to the various task-specific modules.

In reference to FIG. 17A, the first sub-system of the uMPS device is comprised of 6 modules, and is capable of manipulating a sample of blood entering the device at the sample input port 104 to isolate target biological cells (e.g., circulating tumor cells (CTCs), immune cells, etc.) or microbial pathogens, via the cell selection module 150, separate plasma from red and white blood cells via the plasma isolation unit 200, and extract cfDNA and/or select exosomes from the plasma via the solid-phase extraction modules 250 and 300, respectively. The other two modules for this sub-system consist of an impedance sensor 350 that is used to count individual cells released from the cell selection module, and a solid-phase extraction module 400 for capturing DNA/RNA released from lysed biological cells selected from whole blood.

Figure 18B:
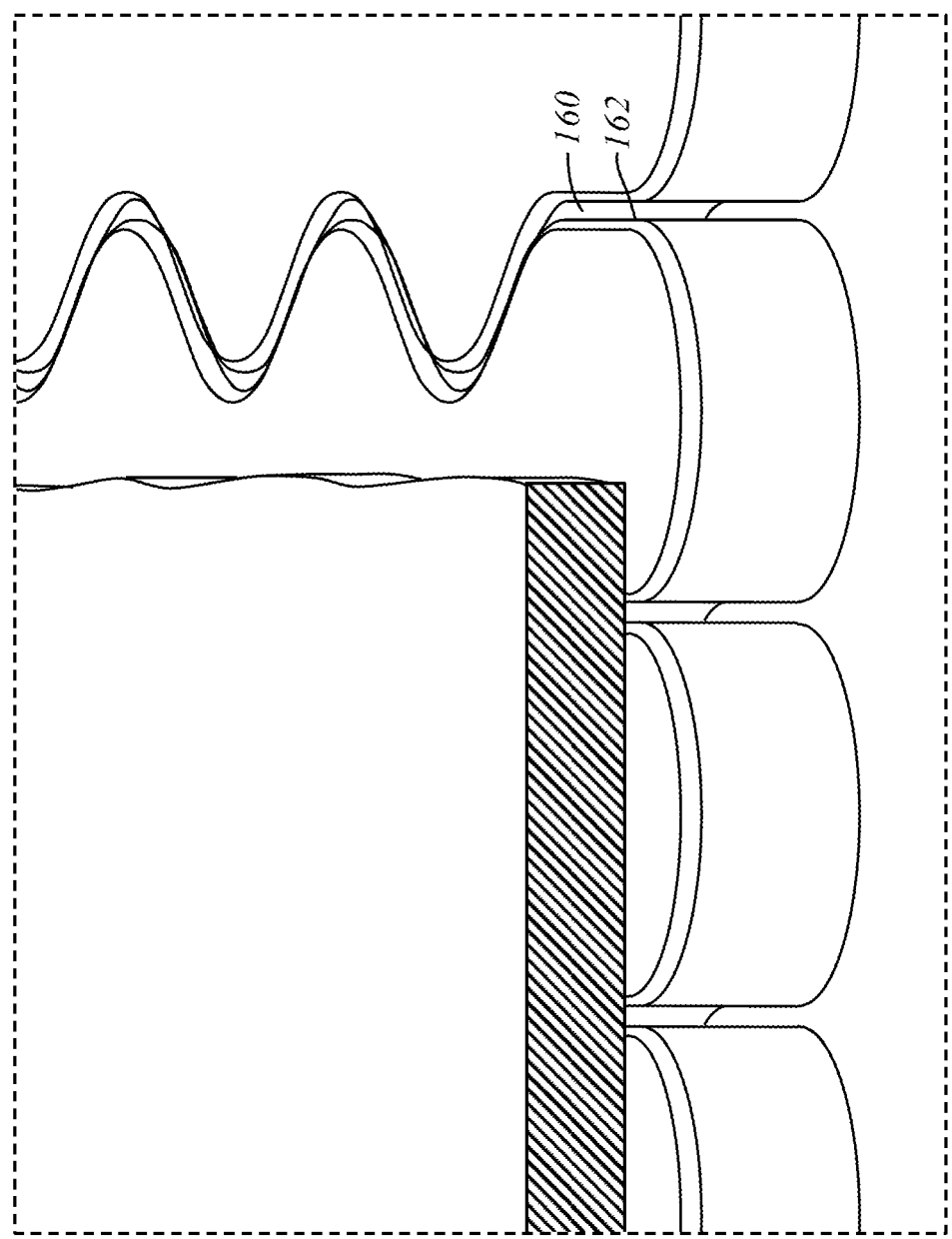

A perspective view of the cell selection module 150 is shown in FIG. 18A. The module consists of an input port 152, a capture bed 154, and an output port 156. A magnified perspective view of the capture bed 154 is shown in FIG. 18B. As shown in this figure, the capture bed comprises a multitude of parallel channels 160, where the channels have a sinusoidal, quasi-sinusoidal, or other meandering channel shape used to enhance contact between cells in the fluid sample and channel walls 162. The channels have a high aspect ratio (3:1 or more), with a width that is on the order of 1-2 times the target cell diameter. The channel walls are decorated with monoclonal antibodies, aptamers, or other binding molecules specific for a targeted cell type (Kamande et al., *Anal. Chem.* 85:9092-9100 (2013) and Pullagurla et al., *Anal. Chem.* 86:4058-4065 (2014), which are hereby incorporated by reference in their entirety). Following sample flow through, the target cells bound to the channel walls of the selection module 150 are washed via wash fluid from the wash reservoir 106 (see FIG. 17B).

Figure 19:
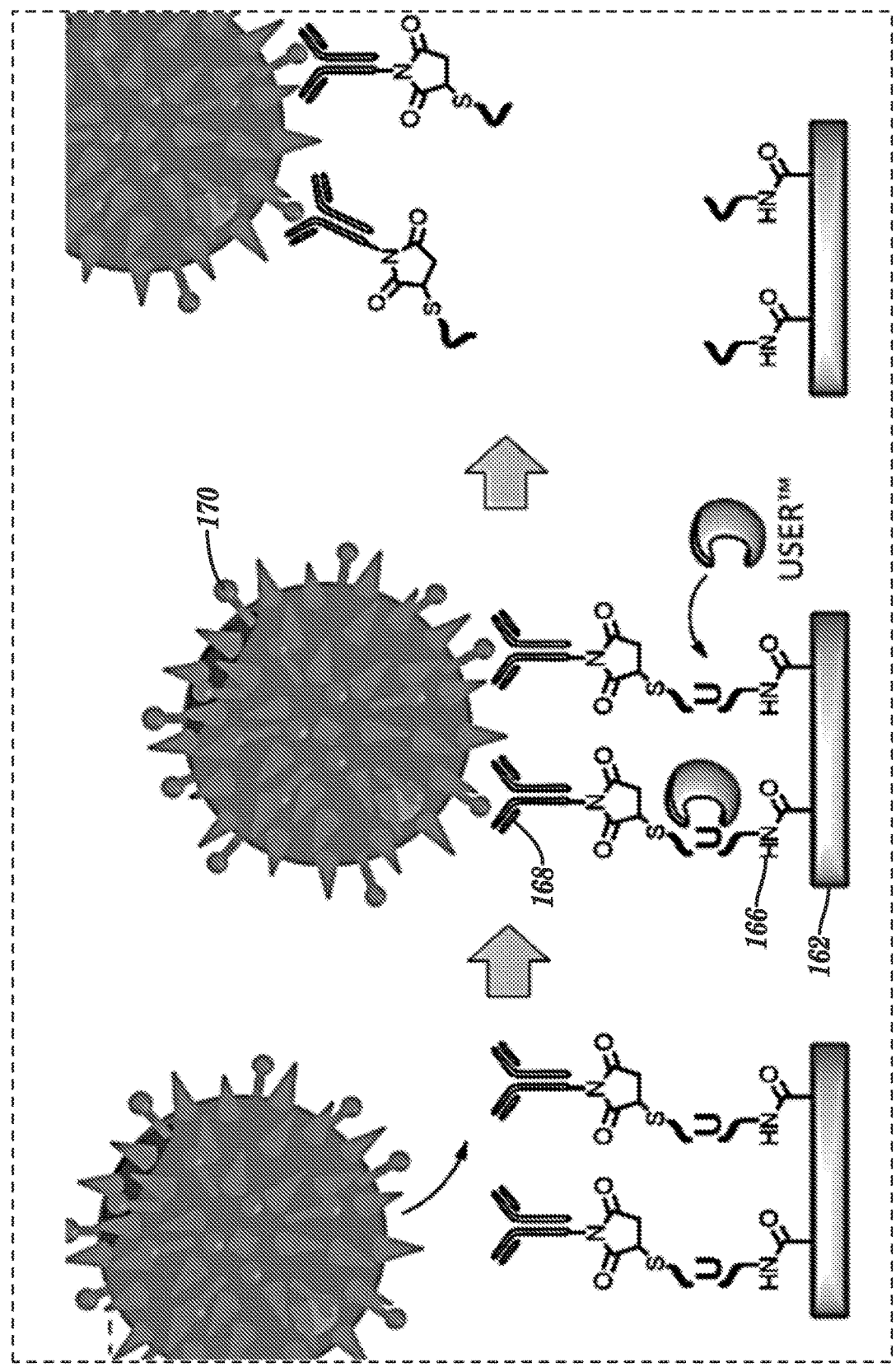
FIG. 19 is a schematic drawing of the capture antibodies immobilized to channel walls of the cell isolation module. The antibodies are immobilized using cleavable oligonucleotide linkers.

To selectively release target cells after capture and washing, the monoclonal antibody, aptamer, or other affinity agent utilized to capture the target cells is attached to the channel wall surface via an oligonucleotide with a hetero-bifunctional linker (SMCC) as depicted in FIG. 19. In one embodiment, oligonucleotide linkers contain a modified nucleotide, e.g., uridine or photocleavable residue, that is cleaved enzymatically to release target cells bound by the antibody or aptamer. The release buffer containing the cleaving enzyme is housed in the release reservoir 108 adjacent the cell isolation module 150 as depicted in FIGS. 17A and 17B. The use of oligonucleotide linkers is attractive because they are low-cost, release efficiency is >93%, and >90% of the released cells remain viable. In addition, due to the selective action of USER (Uracil-Specific Excision Reagent), cells that non-specifically attached to the channel wall surface are not released. The immobilization of affinity capture molecules, e.g., antibodies or aptamers, to the channel walls of the cell selection module involves UV/$O_3$ (254 nm) irradiation of a thermoplastic to produce surface-confined carboxylic acids for the covalent attachment of the oligonucleotide through a 5' amino group; the sulfhydryl on its 3' end reacts with the SMMC/affinity conjugate.

Other methods for releasing affinity-selected cell targets can alternatively be employed, for example release of CTCs from affinity agent-decorated solid surfaces can be achieved using trypsinization (Dharmasiri et al., *Anal. Chem.* 83:2301-2309 (2011); Kamande et al., *Anal. Chem.* 85:9092-9100 (2013); Adams et al., *J. Am. Chem. Soc.* 130:8633-8641 (2008); and Sheng et al., *Lab Chip.* 14:89-98 (2014)), hydrogels (Hatch et al., *Langmuir* 27:4257-4264 (2011); Yu et al., *Small* 9:3895-3901 (2013); and Shah et al., *Anal. Chem.* 84:3682-3688 (2012), which are hereby incorporated by reference in their entirety), mediated magnetic release (Yu et al., *Small* 9:3895-3901 (2013), which is hereby incorporated by reference in its entirety), exonuclease digestion of aptamers (Chen et al., *Adv. Materr* 23:4376-4380 (2011) and Shen et al., Adv. Mater. 25:2368-2373 (2013), which are hereby incorporated by reference in their entirety), or PGLA nanofibers with sections removed via laser-microdissection (Hou et al., *Angew Chem. Int. Ed. Engl.* 52:3379-3383 (2013), which is hereby incorporated by reference in its entirety).

The cell selection module is fabricated using a plastic and produced via micro-replication. Methods of making and using the cell selection module depicted in FIG. 18 are described further in U.S. Patent Publication No. 20120100521 to Soper et al., Dharmasiri et al., *Analytical Chem.* 83:2301-2309 (2011); and Jackson et al., *Lab Chip* 14(1): 106-107 (2014), which are hereby incorporated by reference in their entirety. Alternative nanostructured cell selection modules that are suitable for use on the uMPS device of FIG. 17 are known in the art, see e.g., (Lim et al., *Lab Chip.* 12:4388-4396 (2012); Wang et al., *Angew Chem. Int. Ed. Engl.* 50:3084-3088 (2011); Wang et al., *Angew Chem. Int. Ed. Engl.* 50:3084-3088 (2010); Stott et al., *Proc. Nat'l. Acad. Sci. U.S.A.* 107:18392-18397 (2010); Lin et al., *Clin. Cancer Res.* 16:5011-5018 (2010); Hosokawa et al., *Anal. Chem.* 82:6629-6635 (2010); Xu et al., *Anal. Chem.* 81:7436-7442 (2009); and Tan et al., *Biomed. Microdev.* 11:883-892 (2009), which are hereby incorporated by reference in their entirety).

The device of the present invention may further comprise a longitudinally-extending plasma isolation unit that is defined by the solid substrate and upstream of the biomolecular processor and one or more nanotubes. The longitudinally-extending plasma isolation unit comprises an entrance passage, a discharge passage which is wider than the entrance passage, and a transition passage connecting the entrance passage and the discharge passage. The transition passage becoming wider and shallower as the transition passage progresses from the entrance passage to the discharge passage. The plasma isolation unit also comprises primary side channels extending laterally away from the entrance passage, where a separator, positioned between the entrance passage and each primary side channel, is sized to permit plasma, but not cells, to pass from the entrance passage to the primary side channels. The plasma isolation unit also comprises secondary side channels extending laterally away from the discharge passage, where a separator, positioned between the discharge passage and each secondary side channel, is sized to permit plasma, but not cells, to pass from the entrance passage to the secondary side channels.

Figure 20D:
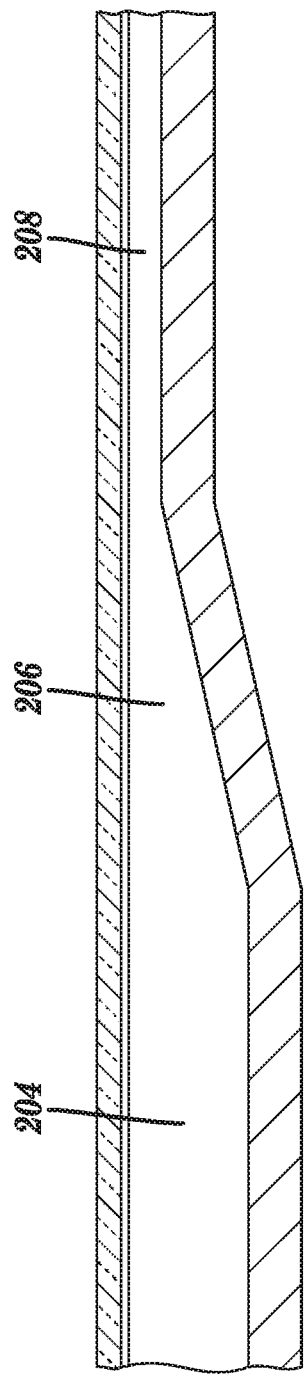

The plasma isolation unit 200 is located adjacent to the cell isolation unit 150 on the uMPS device of FIG. 17A. An exemplary plasma isolation unit is depicted in FIGS. 20A-20D. As shown in FIG. 20A, the plasma isolation unit comprises a primary tapered isolation channel (i.e., entrance passage) 204 that opens to a wider secondary isolation channel (i.e., discharge passage) 208. The cross-section of FIG. 20D, which is taken through line 20D-20D of FIG. 20A, shows that the primary isolation channel 204 having a depth of about 130 μm that allows for high flow rate plasma removal. A transition channel 206 which serves as size selection filter connects the deeper primary isolation channel 204 to the secondary channel 208 having a depth of only about 30 μm (see FIG. 20D). Primary side channels 210 are used to collect and transport plasma that are separated from the blood sample that enters the plasma isolation module via the input port 202. FIG. 20B, is a cross-section through line 20B-20B of FIG. 20A, showing the primary channel side port 228 (~2 μm tall), which runs the length of the primary channel 204 and transition channel 206, and opens into the primary side channel 210. In reference to FIG. 20B, the primary channel side port 228 is formed from a primary separator 212 that is positioned between the primary isolation channel 204 and the primary side channels 210. The primary separator 212 is sized to permit plasma, but not cells to exit the primary channel 204 via the primary channel side ports 228, into the primary side channels 210. The primary side channels 210 lead to the primary receiver ports 216 that collect the plasma and its constituents (e.g., exosomes, cfDNA and ions), while the cellular materials, such as erythrocytes and leukocytes, are transported along the filtration wall and toward the waste port 224. Plasma that has entered the secondary isolation channel (i.e., the discharge passage) 208, likewise exits the secondary isolation channel 208, via the secondary channel side ports 230 and flows into the secondary side channels 218 for collection in the secondary receiver port 226. The secondary channel side port 230 is formed from a secondary separator 220 that is positioned between the secondary isolation channel 208 and the secondary side channels 218. The secondary separator 220 is sized to permit plasma, but not cells to exit the secondary channel 208 via the secondary channel side ports 230, into the secondary side channels 218. The cellular material which does not pass through the secondary side channel ports 230 travels along the secondary channel wall toward the waste port 224. FIG. 20C is a cross-section through line 20C-20C of FIG. 20A showing the secondary channel 208, the secondary side channel port 230, the secondary separator 220, and the secondary side channel 218. Plasma collected in the primary and secondary receiver ports is sent onto other processing modules, e.g., the extractor units for exosome and cfDNA isolation. The removal efficiency and plasma recovery rate are affected by adjusting the flow rates at the receiver ports 216, 226.

The primary, secondary, and side channels are sealed with a cover plate 232 using thermal fusion bonding. Two syringe pumps operating in suction mode at the primary 216 and secondary 226 side receiver ports, and the waste outlet 224 fluidically controlled the system. Waste from the plasma isolation unit exits the unit and is collected in the waste reservoir 122 on the uMPS (FIG. 17A).

Figure 21A:
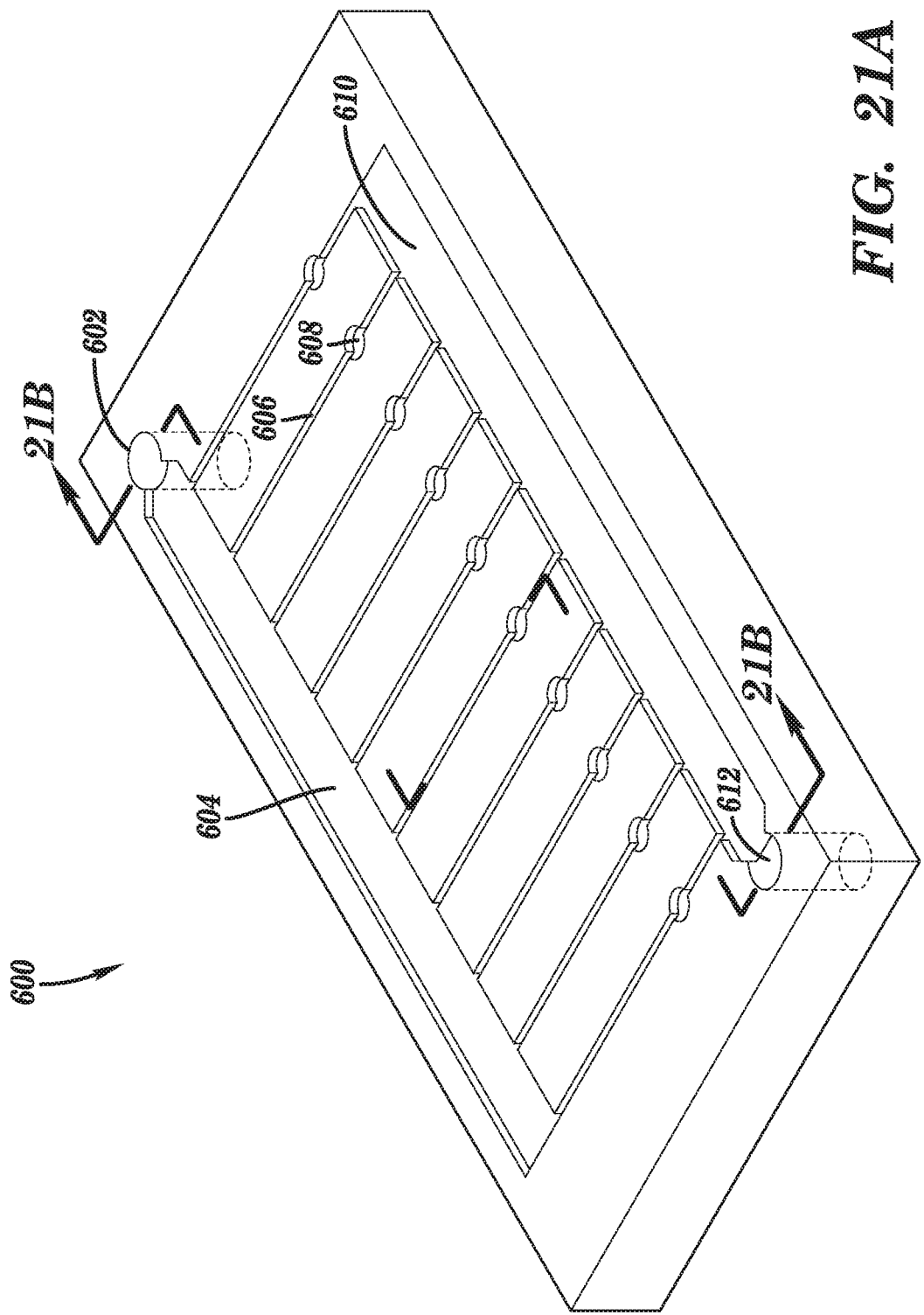
FIGS. 21A-21B depict an alternative plasma isolation module of the uMPS.
Figure 21B:
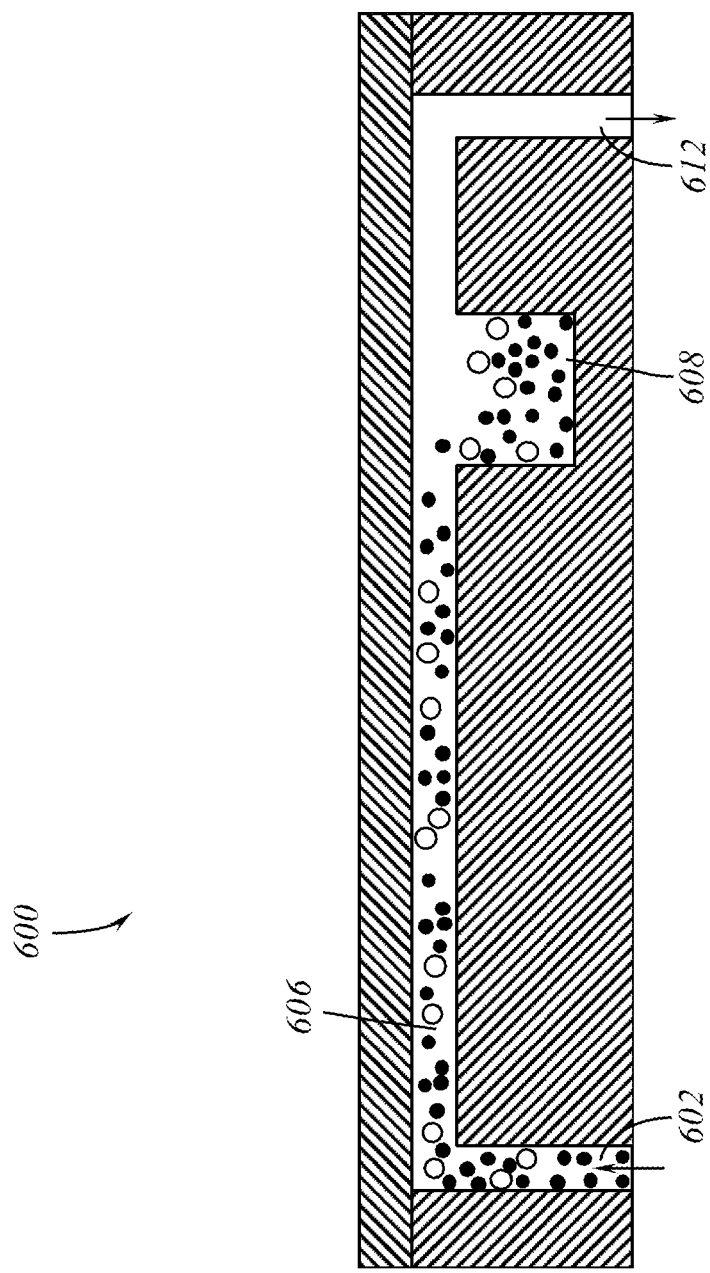

An alternative plasma isolation module is depicted in FIGS. 21A-21B. This device separates white blood cells and red blood cells from plasma containing exosomes and cell free DNA based on differences in sedimentation as previously described by Dimov et al., *Lab on a Chip*, 11: 845-850 (2011), which is hereby incorporated by reference in its entirety. The perspective view of FIG. 21A shows an exemplary alternative plasma isolation module 600 that consists of an input port 602 and feeder channel 604. The feeder channel 604 intersects with a series of parallel isolation channels 606, each isolation channel containing a blood cell trap 608. FIG. 21B, which is a cross-sectional view through from line 21B-21B of FIG. 21A, shows the input port 602, where a whole blood sample enters the module, and one of the parallel isolation channels 606 containing a trap 608. Each trap is ~1 cm in depth, has a diameter of ~0.24 cm, and a total volume of ~0.045 mL. As the sample travels through the isolation channel, the blood cells are retained in the cell trap 608, while the plasma and its constituents (e.g., exosomes, cfDNA and ions) exit the isolation channel flowing into the common exit channel 610 and out of the module via the output port 612.

To increase throughput and the amount of blood cells that can be collected, ten isolation channels 606, each containing a cell trap 608 are placed in a z-configuration, parallel arrangement as shown in FIG. 21A. The feeder channel 604 has a large cross-sectional area that fills with blood before the blood enters each isolation channel 606 containing the trap 608 due to the lower fluidic resistance in these larger channels. For a device that contains 10 traps, the volume throughput is 0.25 ml/s and the total volume of blood cells that can be contained in the traps is 0.45 mL.

In one embodiment, the device of the present invention further comprises one or more extractor units. Each extractor unit is defined by the solid substrate and located upstream of the biomolecular processor and one or more nanotubes. The extractor unit comprises solid supports with passages between them, where the solid supports are provided with a material suitable to immobilize nucleic acids or exosomes or vesicles.

Figure 22:
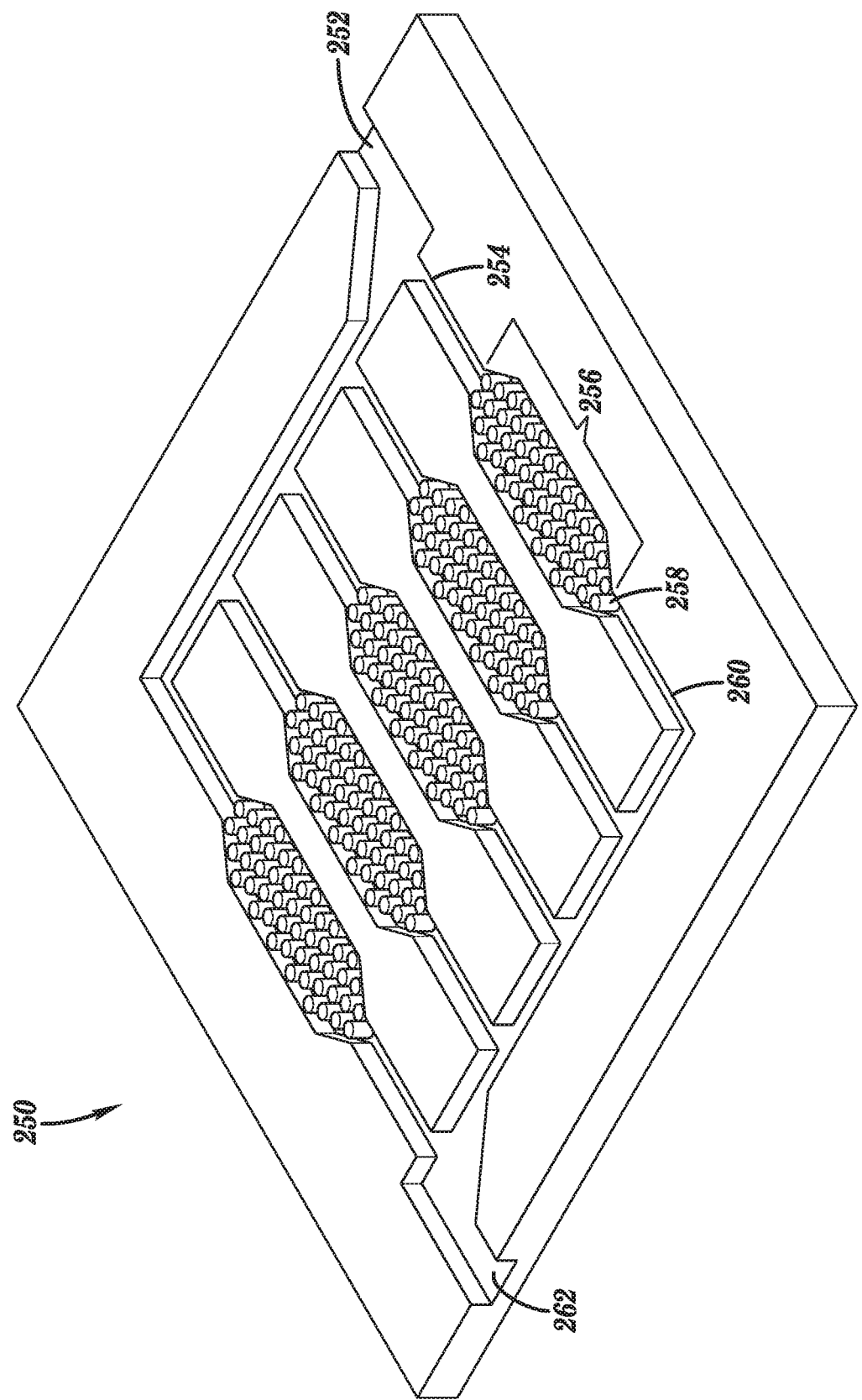
FIG. 22 is a perspective view of a solid phase extractor (SPE) module of the uMPS used for exosome or cfDNA isolation.

The extractor units are depicted as modules 250 and 300 of the uMPS shown in FIGS. 17A and 17B, where module 250 is suitable for exosome extraction and module 300 is suitable for nucleic acid extraction. Structurally, these modules are the same, and an exemplary extractor unit 250 is depicted in FIG. 22. These modules differ in the material on the solid supports that is used to immobilize the desired target (i.e., exosome or nucleic acid). With reference to the embodiment illustrated in FIG. 22, the extractor unit 250 comprises an input channel 252 that intersects with a series of parallel channels 254, each channel containing at least one extraction bed 256. While the extractor unit 250 of FIG. 22 is shown with a series of five extraction beds 256 arranged in parallel, the extractor unit 250 can readily be designed to hold more than ten extraction beds in the same parallel configuration. Arranging the extraction beds in parallel provides uniform addressing of all beds with a constant flow velocity when tapering the extractor bed feeder channel 254 and the extractor bed exit channels 260. In addition, within a single extraction bed 256, the entire circumference of the solid support 258 is uniformly accessible by the target (Battle et al., *Analyst* 139:1355-1363 (2014), which is hereby incorporated by reference in its entirety). The solid supports 258 of the extractor bed 256 can be, for example and without limitation, pillars (e.g., polycarbonate pillars), beads (e.g., silica beads) (Breadmore et al., *Anal. Chem*, 75:1880-1886 (2003), which is hereby incorporated by reference in its entirety), reactive ion etched silica pillars (Christel et al., *J. Biomech. Engin.* 121:22-27 (1999), which is hereby incorporated by reference in its entirety), or resins (Tian et al., *Anal. Biochem.* 283:175-191 (2000), which is hereby incorporated by reference in its entirety). The passages between the solid supports can have any desired configuration, e.g., a sinusoidal configuration. As sample flows through the extraction bed 256, target molecule, e.g., exosomes or cfDNA is captured on the solid support via the appropriate immobilized affinity agent. The remainder of the sample exits the extractor bed via the output channel 260, and the SPE module 250 via the common SPE module output channel 262. In reference to FIGS. 17A and 17B, the extractor units 250, 300 are fed immobilization buffer, wash, and release reagents from adjacent reservoirs 112, 106, and 108, respectively, on the motherboard of the device 100.

In one embodiment, the extractor unit is made from polycarbonate with extraction beds populated with micropillars as disclosed in U.S. Patent Application Publ. No. 20040191703 to Soper et al., which is hereby incorporated by reference in its entirety. Polycarbonate solid phase extraction (SPE) beds such as these can be fabricated using a single replication step with bed preparation requiring only $UV/O_3$ irradiation (Witek et al., *Nucl. Acids Res.* 34(10):e74 (2006), which is hereby incorporated by reference in its entirety). The pillar/bead diameters and spacing are varied to optimize target molecule recovery.

To selectively release target molecules (e.g., exosome or nucleic acids), affinity agents can be attached to support surfaces via an oligonucleotide and affinity agent modified with a hetero-bifunctional linker (SMCC) containing a cleavable nucleotides as described above with regard to the cell isolation unit and depicted in FIG. 19. As described supra, the immobilization of the affinity capture agents involves $UV/O_3$ (254 nm) irradiation of a thermoplastic to produce surface-confined carboxylic acids for the covalent attachment of the oligonucleotide through a 5' amino group; the sulfhydryl on its 3' end reacts with the SMMC/affinity conjugate.

An extractor unit suitable for extracting exosomes employs affinity selection reagents specific for circulating exosomes. In this module, the pillars are decorated with antibodies or aptamers specific for exosomes. For example, the pillars may be decorated with antibodies or aptamers specific for CD63 or RAPS proteins that are expressed on circulating exosome population (Clayton et al., *J. Immunol. Methods* 247:163-174 (2001); Zhou et al., *Methods* S1046-2023(15):30130-4 (2015), which are hereby incorporated by reference in their entirety). Alternatively, the pillars may be decorated with antibodies or aptamers specific for EpCAM, Her2/neu, or separase for selecting tumor-related exosomes from a sample. In one embodiment, the exosome extractor module is made from COC because this material can be efficiently UV-activated to provide high loads of functional groups in the form of surface-confined carboxylic acids even for high aspect ratio structures (Jackson et al., "UV Activation of Polymeric High Aspect Ratio Microstructures: Ramifications in Antibody Surface Loading for Circulating Tumor Cell Selection," *Lab on a Chip* 14:106-117 (2014), which is hereby incorporated by reference in its entirety).

An exemplary extractor unit suitable for extracting cfDNA may comprise a polycarbonate SPE bed that has been UV activated to isolate short DNAs, similar in size to cfDNA. The efficiency of cfDNA isolation is dependent on the composition of the immobilization buffer. In one embodiment, a suitable immobilization buffer comprises of Polyethylene Glycol (PEG), sodium chloride (NaCl), and ethanol (EtOH).

In one embodiment, the device of the present invention further comprises a sensor unit defined by the solid substrate and upstream of the biomolecular processor and the one or more nanotubes. The sensor unit comprises an inlet and an outlet and is configured to count cells passing through the sensor unit. The sensor unit also comprises a pair of electrodes and a fluidic channel. The fluidic channel is between the pair of electrodes and fluidically coupled to said separator unit.

Figure 23A:
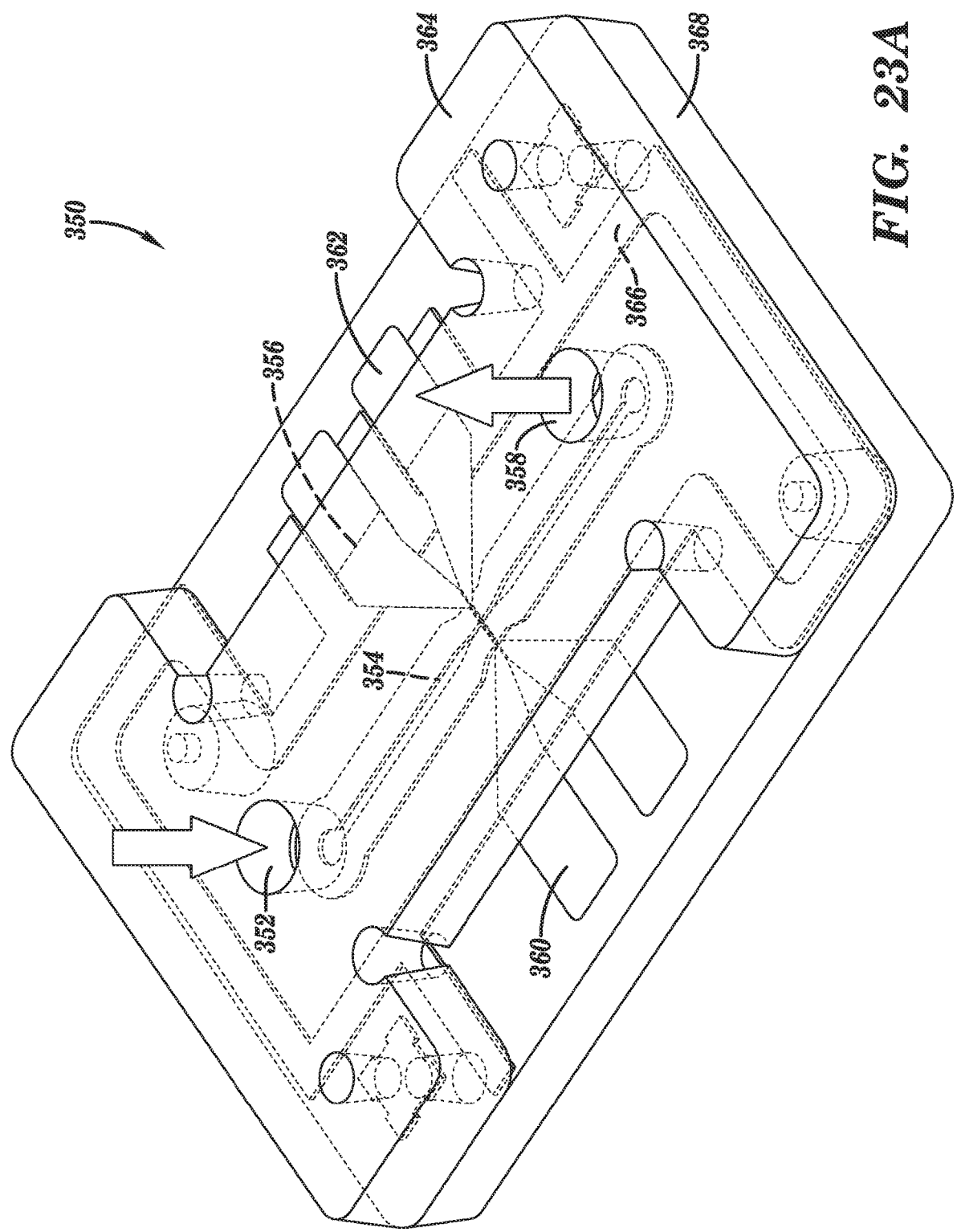
FIGS. 23A-23B depict the impedance module of the uMPS.
Figure 23B:
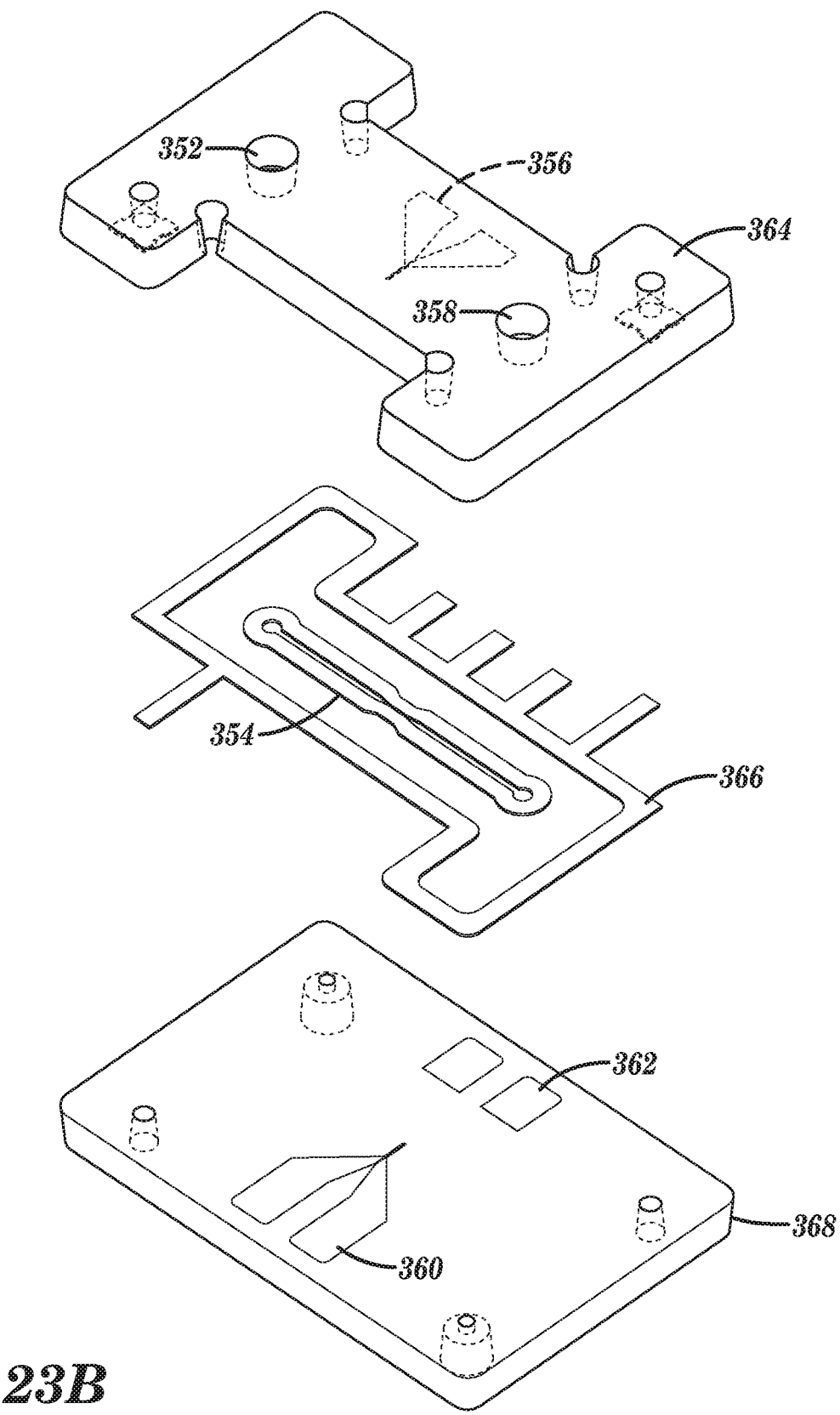

The sensor unit of the device is depicted as module 350 of the uMPS as shown in FIGS. 17A and 17B. An exemplary sensor unit, also referred to as an impedance unit, is depicted in FIGS. 23A and 23B. The impedance module is used to enumerate cells released from upstream units of the device and determine their viability.

An exemplary impedance module suitable for incorporation into the device as described herein or as a stand-alone module is a 3-layered module that consists of electrodes on the top and bottom face of a fluidic channel. A perspective view of this module is depicted in FIG. 23A, and the exploded view of FIG. 23B shows the individual layers of the device. As shown in these Figures, the first layer or top layer 364 has a top and bottom surface, where the inlet 352 and outlet 358 ports are located on the top surface of the first layer. The first layer 364 also has microelectrodes 356 on its bottom surface that intersect with the microfluidic channel 354 of the middle layer 366 in the assembled module. The second or bottom layer 368 of the impedance unit 350 also has top and bottom surface. The second layer 368 has microelectrodes 360 on its top surface that intersect with the microchannel 354 of the middle layer opposite the microelectrodes 356 located on the bottom surface of the first layer 364 in the assembled unit. The top surface of the second (bottom) layer also has contact pads 362 that contact the microelectrodes 356 on the bottom surface of the first (top) layer 364 in the assembled unit. The second layer also contains female, conical ports used for interconnecting the impedance module to the fluidic motherboard. The middle layer 366 of the module comprises a thin plastic layer containing the microfluidic channel 354. The middle layer sets the spacing between the microelectrodes 356, 360 of the first and second layers, respectively. A section of the microfluidic channel serving as the detection volume has a through-hole to allow for solution electrical contact with both the top 356 and bottom 360 electrodes.

In use, the impedance module enumerates cells released from the upstream capture surface of the cell separation module, and also determines their viability. A cell containing sample enters the impedance module 350 via the input port 352 and travels through the microchannel 354 passing between the microelectrodes 356, 360. The signal measured by the module is proportional to the resistance of the medium between the electrodes. When no cell is present between the electrodes the signal is proportional to the resistance of the buffer solution and this defines the baseline for the measurements. Every cell passing between the electrodes replaces a small volume of the buffer solution. Intact cells are considered non-conductive at the frequency of the electrical signal (40 kHz) applied between electrodes due to high cell membrane capacitance. Thus, the small volume of the solution replaced by the cell has higher resistance than the corresponding volume of the buffer alone. This leads to an increase in the overall resistance measured by impedance sensor, which presents itself as positive peaks recorded for a passing cell (see FIG. 44A). When the cells' membrane is compromised, the cell resistance can be approximated by the resistance of the cell interior, which is composed primarily by cytoplasmic components. If the resistance of cell cytoplasm is lower than that of the corresponding volume of buffer solution, the overall resistance measured by sensor drops, which results in a negative peak (see FIG. 44B).

FIG. 24 provides a schematic overview of an exemplary fabrication method employed to produce the impedance module depicted in FIGS. 23A and 23B. This fabrication modality does not require manual insertion of platinum wires into prefabricated channels (Adams et al., *J. Am. Chem. Soc.* 130:8633-8641 (2008) and Galloway et al., *Anal. Chem.* 74: 2407-2415 (2002), which are hereby incorporated by reference in their entirety). In steps 1 and 2, the top and bottom covers of the module comprising cyclic olefin copolymer (COC) are prepared using hot-embossing or injection molding. In steps 3 and 4, photolithography or electroless deposition is used to pattern the photoresist in preparation for thin film (200 nm) Au electrode deposition (Shadpour et al., *Anal. Chem.* 79:870-878 (2007) and Kong et al., *Electrophoresis* 27:2940-2950 (2006), which are hereby incorporated by reference in their entirety), which is carried out using e-beam evaporation (step 5) and lift-off (step 6). In step 7, lithography is employed to define a Su-8 photoresist the microchannel. The fluidic ports of the top cover are opened (step 8) and the top and bottom patterned covers are aligned for UV glue injection and cure (step 9).

Other microfluidic impedance units that are known in the art can alternatively be included on the uMPS device of the present invention as described herein. Suitable impedance modules include, without limitation, microfluidic coulter systems (see e.g., Zhang et al., *Microfluid. Nanofluid.* 7:739-749 (2009), which is hereby incorporated by reference in its entirety), microfluidic FACs systems (see e.g., Fu et al., *Nat. Biotech.* 17:1109-1111 (1999), which is hereby incorporated by reference in its entirety), and microfluidic impedance systems (see e.g., (Dharmasiri et al., *Anal. Chem.* 83:2301-2309 (2011); Adams et al., *J. Am. Chem. Soc.* 130:8633-8641 (2008); Aufforth et al., *Annals of Surg. Oncol.* 20:S129-S129 (2013); Spegel et al., *Electroanalysis* 20:680-702 (2008); and U.S. Pat. No. 8,390,304 to Patterson, which are hereby incorporated by reference in their entirety). Other impedance modules suitable for use in the device of the present invention are reviewed in Cheung et al., *Cytometry Part A* 77A:648-666 (2010), which is hereby incorporated by reference in its entirety.

In one embodiment, the alternative impedance module comprises an arrangement of a Coulter counter module that provides label-less cell enumeration and sizing. This module is composed of two fluid-filled chambers connected by a small orifice and two electrodes positioned at either side of the orifice. As a cell passes through the orifice, it displaces the conductive fluid and alters the resistance of the orifice. Each signal pulse corresponds to the movement of a single cell through the orifice, the magnitude of which is proportional to the amount of fluid displaced. The highest sensitivity of the measurement is achieved when the orifice size is similar to the measured cell size. For example an orifice size of 50×50 $\mu m^2$ would achieve sufficient sensitivity to detect cells in the size range of 6-30 $\mu m$. Measurement electrodes poised on both sides of the orifice have large dimensions (few $mm^2$) to reduce the effects of electrical double layer capacitance and can be produced by screen printing of conductive silver inks on the polymer surface negating the need for lithography (see Sun and Morgan, *Microfluid. Nanofluid.* 8: 423-443 (2010), which is hereby incorporated by reference in its entirety).

In one embodiment, the device of the present invention further comprises a separator unit defined by the solid substrate and upstream of the biomolecular processor and one or more nanotubes. The separator unit comprises a separation chamber including solid surfaces defining channels between them with cell specific capture agents attached to the solid surfaces, an inlet to the chamber, and an outlet from the chamber.

The separator unit is depicted as module 400 in the uMPS device of FIGS. 17A and 17B. As shown in these figures, separator unit 400 receives sample from sensor module 350. Once the enumerated cells exit the sensor module, they are introduced to lysis buffer coming from reservoir 110, and cell lysis occurs within the small serpentine microfluidic network 136 upstream of separator unit 400. The contents of the lysed cells enter separator unit 400 where isolation of the nucleic acid components occurs. Separator unit 400 is fed immobilization buffer, air, ethanol, and release reagents via respective reservoirs 112, 114, 116, and 108 located on the periphery of the motherboard of uMPS 100 as depicted in FIGS. 17A and 17B.

Figure 25:
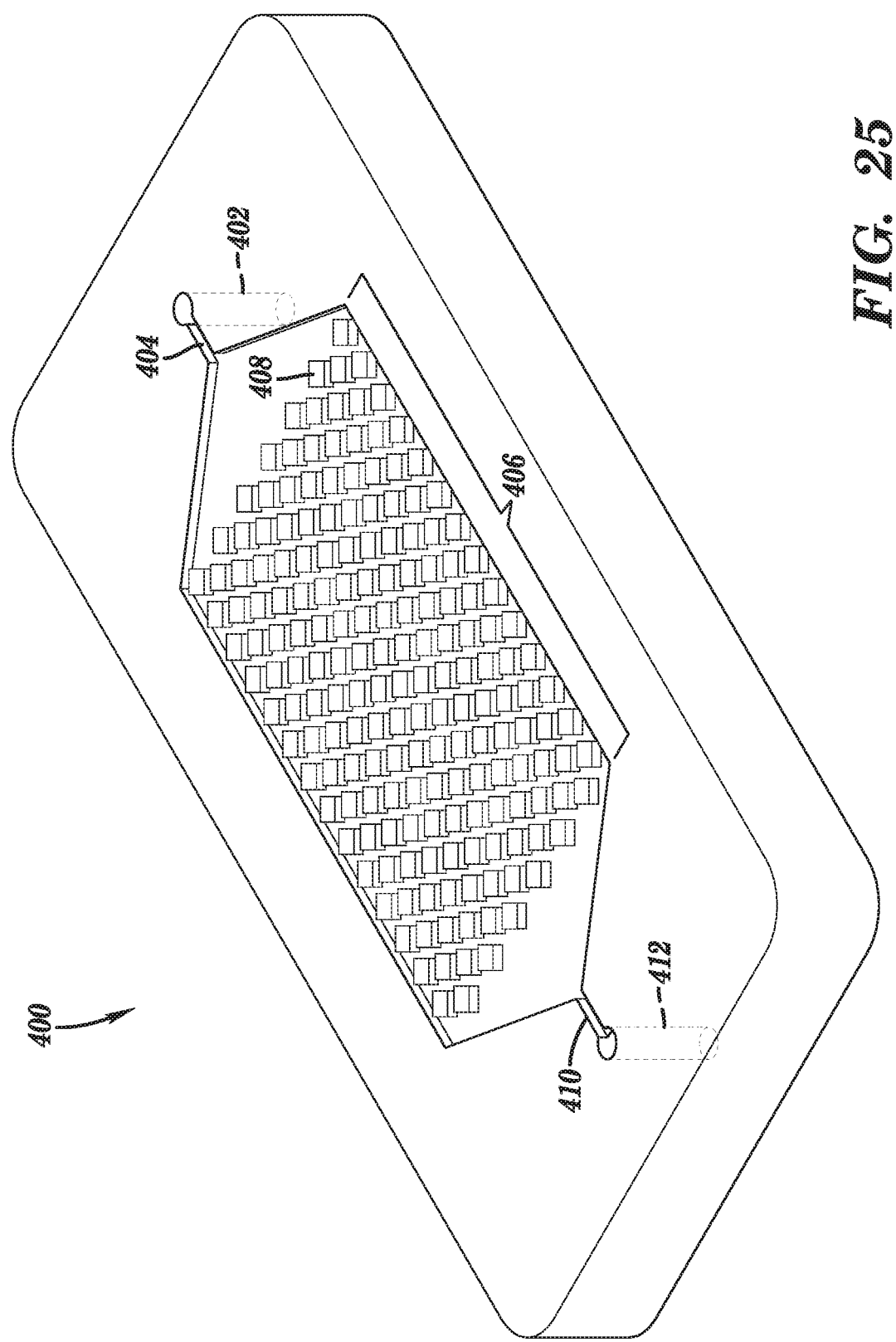
FIG. 25 is a perspective view of a SPE RNA/DNA isolation module of the uMPS.

A perspective view of the separator module is depicted in FIG. 25. As shown in this depiction, separator unit 400 is similar in structure and function to extractor units 250 and 300 described supra, differing in that it comprises single solid-phase extraction bed 406, containing a plurality of solid supports or surfaces 408. A single extraction bed is suitable, because the sample volume that requires processing is small (~10 μL) and the amount of target material to be extracted, e.g., DNA/RNA from a small number of cells isolated upstream, is low as well. The sample enters separator module 400 via input port 402 and flows through bed feeder channel 404 to ether extraction bed 406. Sample components that are not captured on solid supports 408 of extraction bed 406, move through the channels defined by solid supports 408 to extraction bed output channel 410, and exit the module via output port 412. Once the extracted sample material (e.g., the DNA/RNA) is released from solid supports 408 of extraction bed 406, it also flows out of the separation unit via output channel 410 and output port 412.

In one embodiment, the device of the present invention has one or more reactor units defined by the solid substrate and upstream of the biomolecular processor. The reactor units comprise a reaction channel with a heater. The one or more reactor units 450 and 500, which constitute the second subsystem of the uMPS device of FIGS. 17A and 17B, are continuous flow reactors used for molecular pre-processing reactions such as multiplexed reverse transcription of RNA to generate cDNA, and appending poly-dT to DNAs using terminal deoxynucleotidyl transferase (TdT). Alternative molecular pre-processing reactions that can be carried out in these units include, without limitation, enzymatic digestion reactions, e.g., digestion of input DNA with restriction endonuclease(s) for subsequent determination of methylation status, an initial reverse-transcription step, primer extension reaction, and/or appending a loop primer to miRNA, facilitating its accurate tailing, capture, and detection.

The continuous flow reactor units of the device used for the aforementioned biochemical thermal reactions are depicted as modules 450 and 500 of the uMPS device shown in FIGS. 17A and 17B. These reactors are based on a continuous flow format, in which a single meandering channel is fed the reaction reagents from adjacent reservoir 124 (e.g., RT reaction reagents), and the target material. Thermal heaters placed on the underside of the reaction zone generate the necessary temperature. This continuous flow thermal reactor consists of a serpentine channel with the linear velocity and length of the reactor channel determining the reaction time. These continuous flow thermal reactors have been used for a variety of reactions, including PCR, ligase detection reactions, and reverse transcription using thermoplastic substrates (see e.g., Hashimoto et al, *Lab on a Chip* 4:638-645 (2004); Hashimoto et al., *Analytical Chemistry* 77:3243-3255 (2005), Chen et al., *Assessment and Improvement of the Thermal Performance of a Polycarbonate Micro Continuous Flow Polymerase Chain Reactor (CFPCR)* (2007), Chen et al., *Biomedical Microdevices* 10:141-152 (2008), which are hereby incorporated by reference in their entirety). The reactor is built during the imprinting step used to produce the fluidic base plate. A thin film Kapton heater is placed underneath the reactor to generate the necessary temperature for the reaction.

In one embodiment, the device of the present invention has a flow purification unit that is upstream of the biomolecular processor and the one or more nanotubes. The flow purification unit comprises a housing defining a chamber, one or more inlets connected to the chamber, a product outlet connected to the chamber, a waste outlet connected to the chamber, and a plurality of obstacles positioned within the chamber and oriented to preferentially direct product, in the chamber, to the product outlet and to direct waste, in the chamber, to the waste outlet. Flow purification unit 550 and nanosensor unit 50 constitute the third subsystem of the uMPS device depicted in FIGS. 17A and 17B.

The flow purification unit is designed to purify the target nucleic acid molecules (e.g., cDNA) that are generated in other upstream units of the device from excess dNTPs and/or other non-target nucleic acid nucleotide components. Purification is required due to the limited number of binding sites available on the solid support structures of the bioreactor chambers of the biomolecular processor unit. While there are a variety of methods to accomplish the required removal of excess reagent(s) such as chromatographic or electrophoretic techniques, they use a "batch" operational mode in which samples are injected onto the column and the separation invoked with heart cutting used to isolate the desired material. The flow purification unit of the device described herein uses a continuous separation mode that does not require injection and heart cutting to simplify operation. It is particularly appealing to use a continuous flow format, because injection/run cycles are not required with the reaction products continuously inserted into the separation matrix with the ability to redirect the excess reagent(s) into a waste reservoir while at the same time, direct processed targets into another path.

Figure 26:
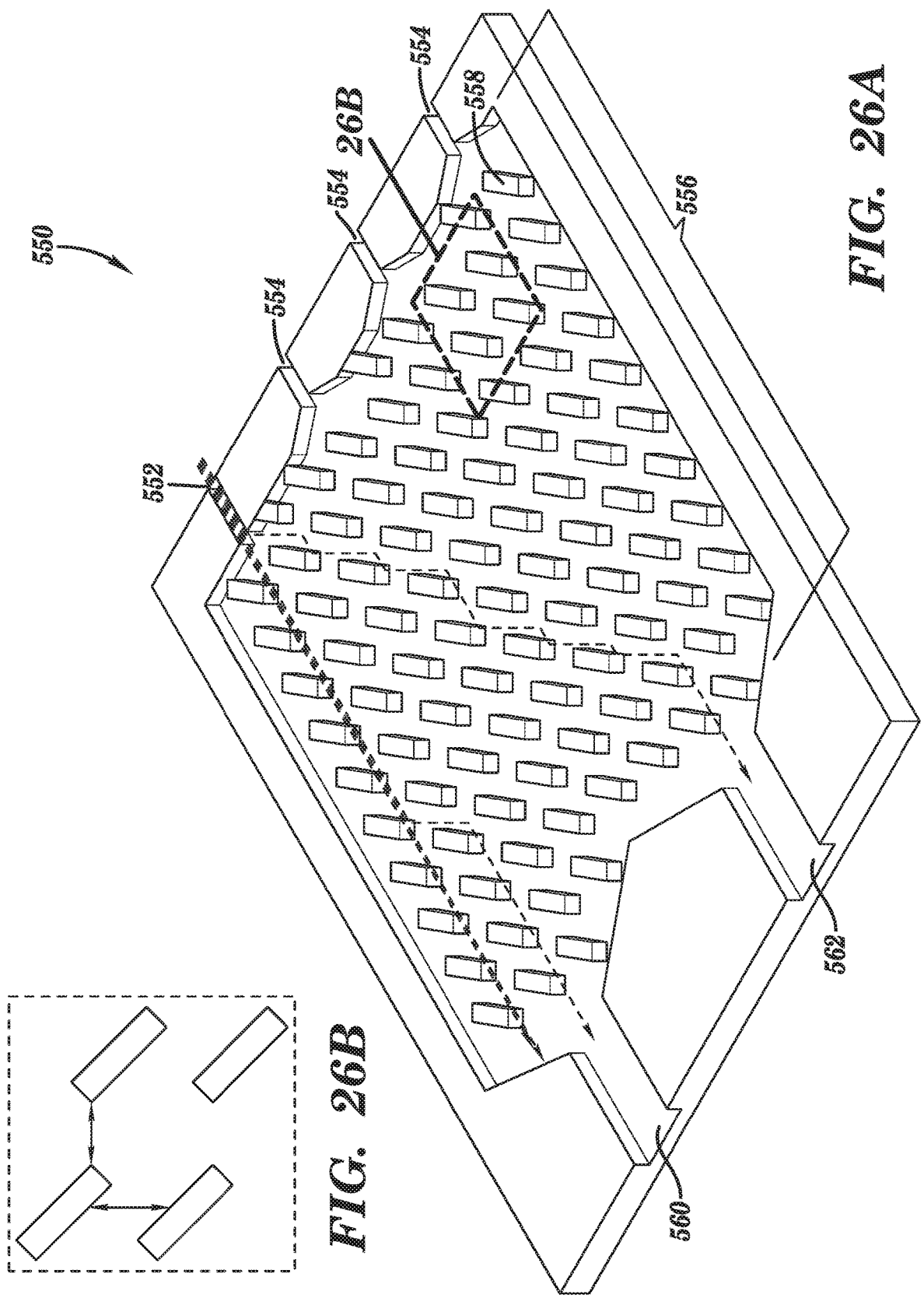
FIGS. 26A-26B show the diffusional purification module of the uMPS.

The architecture of diffusional flow purification unit 550 is shown in FIG. 26A. The module is fabricated in the appropriate substrate using micro-replication in the same step used to produce the fluidic network and thus, not requiring multi-step lithographic techniques. The basic concept is to employ the use of a regular lattice of asymmetric obstacles 558 to alter the lateral Brownian motion of the molecules so that molecules of different sizes follow different trajectories through the device. In one embodiment, obstacles 558 within flow purification bed 556 possess a length of ~5-7 μm, a width of ~0.5-2 μm, a gap spacing (G)~4-5 μm, and are situated at ~45° angle with respect to the flow path (Chou et al., *Proc. Nat'l. Acad. Sci. U.S.A.* 96:13762-13765 (1999), which is hereby incorporated by reference in its entirety). A mixture of molecules in a sample enters module 550 via sample input channel 552, buffer enters the module via buffer input channels 554, and the mixture is sorted continuously as it moves through the device. The output is divided into two channels 560, 562, one 562 for directing reagents (e.g., dNTPs) to waste and the other 560 for sending target molecules (e.g., cDNA) to the final module on the uMPS, i.e., the nanosensor module, for final processing and detection. The performance metrics of this module includes generating short development times (<60 s), removing >95% of excess reagent(s) and minimal loss of target (<1%).

Figure 27:
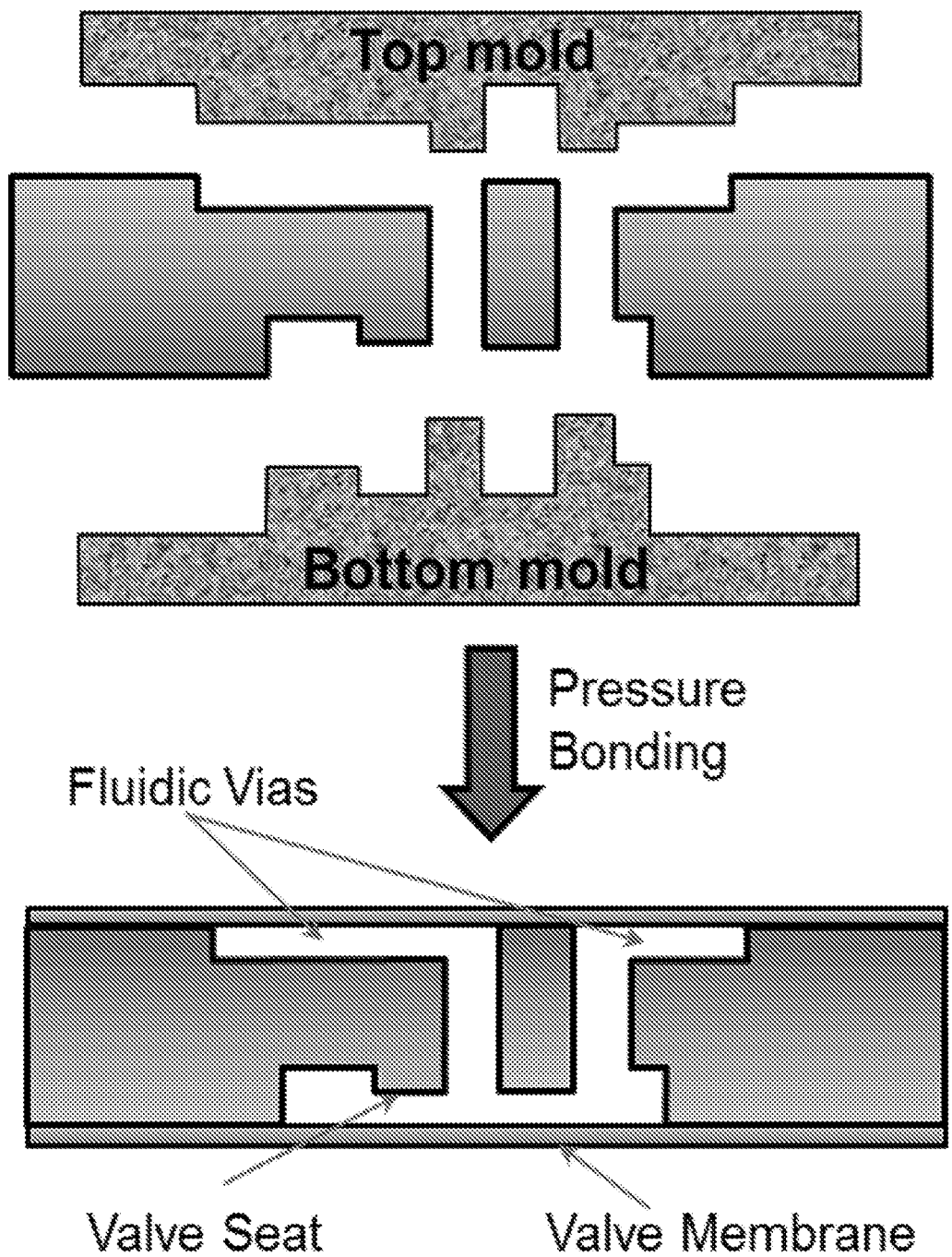
FIG. 27 illustrates the valves on a device of the present invention. The simultaneous front and backside molding of a valve and valve seat using embossing is shown.

Fluidic flow through the various units of the uMPS device of FIGS. 17A and 17B is controlled by plurality of valves 132 located throughout fluidic network 134 of device 100. The valves have a three-layer structure as depicted in FIG. 27. These three layers consist of cover plate, fluidic layer, and back cover plate. Valve seat and valve membrane are configured to be on the back side of the fluidic motherboard for the uMPS 100 along with mechanical solenoids to actuate the valves. This will allow for complete electrical connections poised on the top cover plate of the uMPS. FIG. 27 also shows simultaneous front and backside molding of the valve and valve seat using embossing. The fluidic network located on the top of the motherboard is made in the same embossing step.

Most microfluidic interconnects of the uMPS device of FIG. 17A rely on direct physical contact between the fluid port and the unit being connected. Each contact acts as a passive kinematic constraint on the assembly. If care is not taken, two or more interconnects in conjunction with other assembly features will lead to over-constrained systems and unpredictable dead volumes.

Figure 28A:
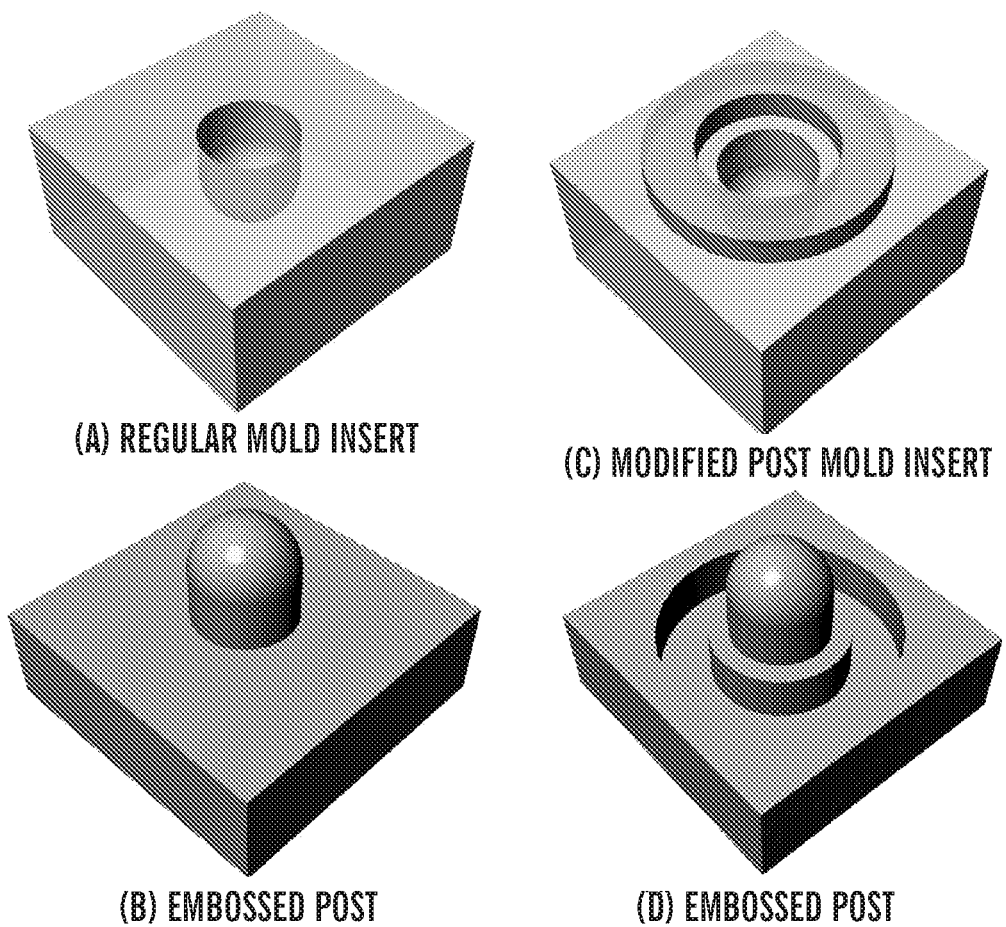
FIGS. 28A-28C show the kinematic alignment pins and grooves of the gasket-less seal. The alignment pins and grooves (FIG. 28A) can be fabricated into the fluidic substrate backside using double sided embossing with the pins and grooves poised on the two mating pieces.
Figure 28B:
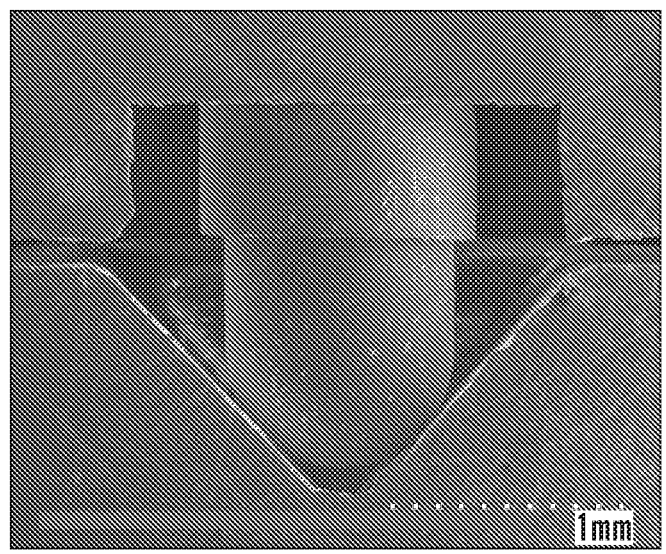
Figure 28C:
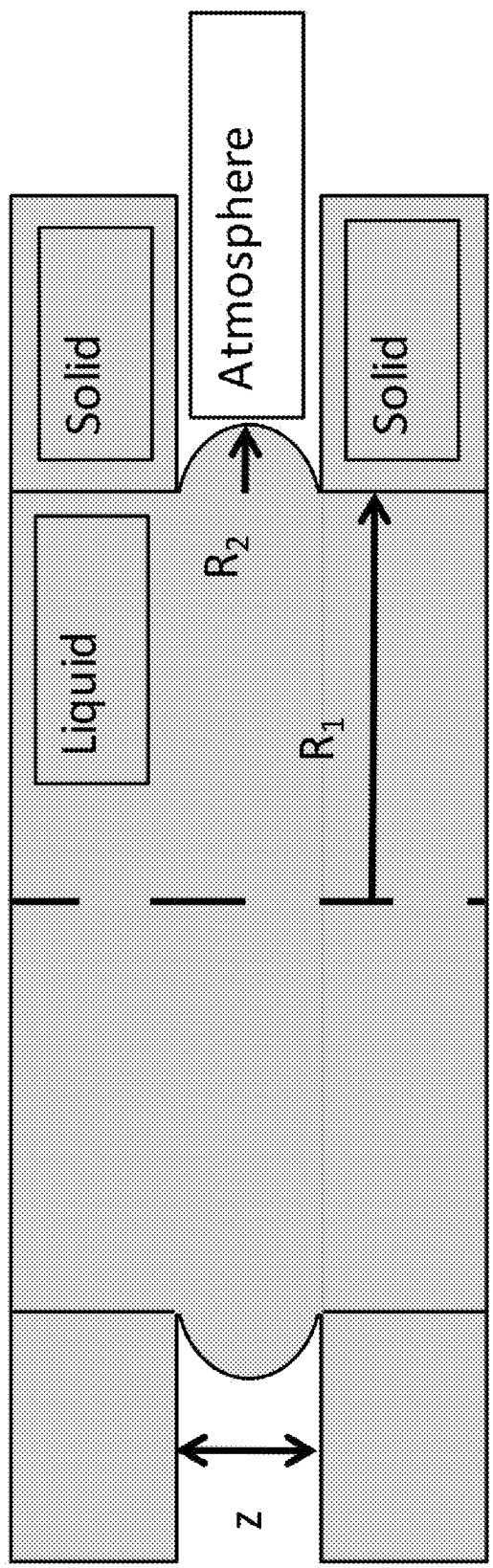

For microfluidic ports with micro-scale gaps between facing surfaces, capillary forces, as defined by the Young-Laplace equation, should resist leakage without any direct physical contact between the facing surfaces, forming a gasket-less seal as depicted FIG. 28B (Brown, et al., *IMECE* 2012, Nov. 9-15, 2012. ASME, Houston, Tex., pp. IMECE2012-89634 (2012), which is hereby incorporated by reference in its entirety). The kinematic pins and grooves of these gasket-less seals are depicted in FIG. 28A. The alignment pins and grooves can be fabricated into the fluidic substrate backside using double sided embossing with the pins and grooves poised on the two mating pieces. The alignment accuracy is ~10 μm. Superhydrophobic seals between mating pieces that can be perfectly aligned or slightly offset. The through holes on each mating piece is surrounded by a surface with a water contact angle ~150°; surface tension forces and capillary forces cause the solution to move into the opposite hole with no dead volume (see FIG. 28C).

The gasket-less seals require super-hydrophobic surfaces on the opposing surfaces around each inlet/outlet port. Different approaches can be used for obtaining the super hydrophobic surfaces including: (1) injection molding, (2) NIL, or (3) layer-by-layer deposition. Another approach involves mounting anodized aluminum oxide membranes (AAO) inside a conventional mold insert and filling the patterns with a polymer melt. These techniques supply the necessary super-hydrophobicity. The advantage of this approach is that super-hydrophobic surfaces could be molded in the same material as the device and at the same time, so there are no surface adhesion or adsorption concerns.

NIL with polymer stamps can be used to transfer a super-hydrophobic pattern into the inlet/outlet surfaces. This can be performed on injection molded or hot embossed substrates as a secondary process. Another approach is layer-by-layer (LBL) deposition, which can be used to build nanoscale thin films with high static contact angles (188). This can be performed using a mask to ensure that only the desired areas are covered. The LBL process can produce layers with much better control of the thickness. Successive dipping steps require additional time to obtain the desired layer properties, but may be comparable in duration to those necessary for moving to another machine as in the case of NIL.

Passive alignment structure: Passive alignment structures will be used to establish the height of the gap separating two modules (<20 µm) minimizing lateral offset so that dead volumes are not introduced in the inlets/outlets of modules and the relative angle between the two surfaces is minimized (see FIGS. 28A-28B). This requires selecting the type, size, and location of the alignment structures to use. These alignment structures are hemispherical pin in v-groove kinematic pairs that have been characterized (You et al., *J. Micromech. Microeng.* 19:125025 (2009) and You et al., *JMEMS* 24:634-650 (2015), which are hereby incorporated by reference in their entirety). Annular rings around the posts resulted in better pins, permitting better filling and less variation between the pins (Chen et al., *Replication of Reliable Assembly Features for Polymer Modular Microfluidic Systems* (2008), which is hereby incorporated by reference in its entirety.

Another aspect of the present invention is directed to a device comprising a longitudinally-extending plasma isolation unit as described supra and depicted in FIGS. 20A-20D. The longitudinally-extending plasma isolation unit is defined by the solid substrate and comprises an entrance passage, a discharge passage which is wider and shallower than the entrance passage, and a transition passage connecting the entrance passage and the discharge passage. The transition passage becomes wider and shallower as the transition passages progresses from the entrance passage to the discharge passage. The plasma isolation unit further comprises primary side channels extending laterally away from the entrance passage, where a separator, positioned between the entrance passage and each primary side channel, is sized to permit plasma, but not cells, to pass from the entrance passage to the primary side channels. The plasma isolation unit further comprises secondary side channels extending laterally away from the discharge passage, where a separator, positioned between the discharge passage and each secondary side channel, is sized to permit plasma, but not cells, to pass from the entrance passage to the secondary side channels.

Another aspect of the present invention is directed to a device comprising an extractor unit as described supra and depicted in FIG. 25. The extractor unit is defined by a solid substrate and comprises an inlet, an outlet, a plurality of separate chambers each extending between and sharing the inlet and said outlet. The device also comprises a plurality of solid pillars in each of the chambers, wherein the pillars have passages between them, and are provided with a material suitable to immobilize cells, nucleic acids, or exosomes from a sample.

Another aspect of the present invention is directed to a device comprising a sensor unit as described supra and depicted in FIGS. 23A-23B. The sensor unit is defined by the solid substrate and comprises: an inlet; an outlet; and a cell counter positioned to count cells passing from the inlet to the outlet of said sensor unit.

Surface Modification of Thermoplastic Surfaces on the uMPS

Surface properties are important for controlling the transport of molecules through the various microchannels, nanochannels, and other nano-structures of the modules on the uMPS, especially when the molecules bear charges and the transport is enabled by electrokinetics. The surfaces of the polymer nanostructures and microstructures are modified using a combination of an activation process to produce functional scaffolds followed by the surface modification to create new chemical species on the surface of the polymer substrates (Jackson et al., *Lab Chip.* 14:106-117(2014) and McCarley et al., *J. Am. Chem. Soc.* 127:842-843 (2005), which are hereby incorporated by reference in their entirety). In addition, where functional groups are required on the polymer surfaces in the micro- and nano-domains for the covalent attachment of various biological agents (e.g., antibodies or oligonucleotides), techniques for producing functional groups regio-specifically are utilized. Regio-specific activation, which is required, for example, to activate only pillared regions for the covalent attachment of various molecular targets within the nanosensor module, can be accomplished using UV/O$_3$ activation through a photomask.

Many thermoplastics do not contain surface functional groups and therefore, activation protocols can be employed to create the appropriate functional scaffolds. Suitable robust, yet simple surface modification chemistries for thermoplastics within the micro-scale regime, where the surface is activated with UV/O$_3$ or an O$_2$ plasma are know in the art (Jackson et al., *Lab Chip.* 14:106-117 (2014) and Situma et al., *Anal. Biochem.* 340:123-135 (2005), which are hereby incorporated by reference in their entirety). Exposure to plasma or UV/O$_3$ renders the surface hydrophilic due to the interactions of high energy radicals on the surface. At sufficiently high energy, both UV and oxidative stress can generate radicals within the polymer, which can form carboxylic acids or other O-containing species. The presence of these functional groups provides ionizable groups that, when in contact with solutions, can either alter the electroosmotic flow or serve as scaffolds for attachment of biologics.

Fabrication of the Nanotube

Figures 29A, 29B:
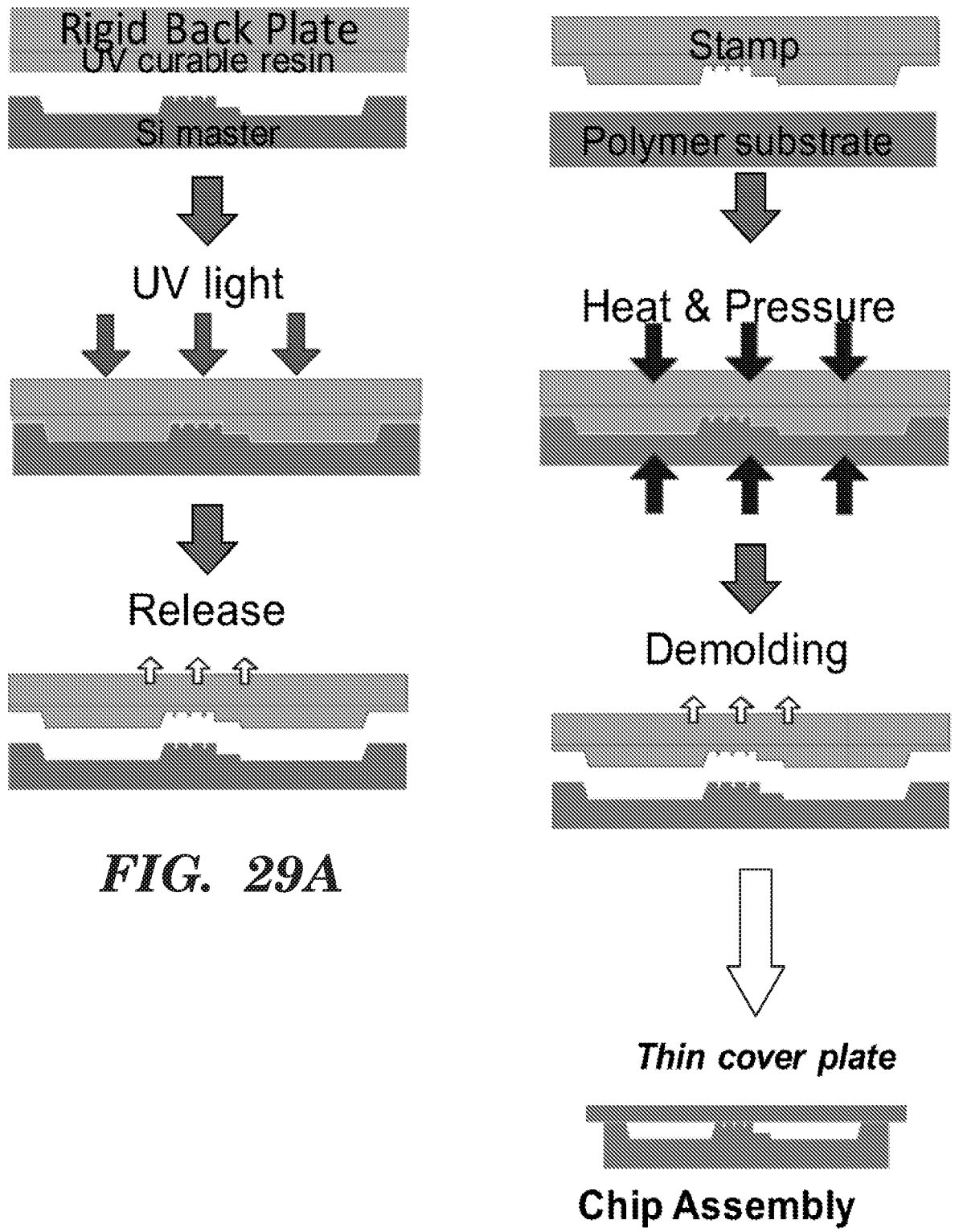
FIGS. 29A-29B illustrate the processing steps for making the nanofluidic chambers and channels of the device described herein using imprinting.
Figure 30A:
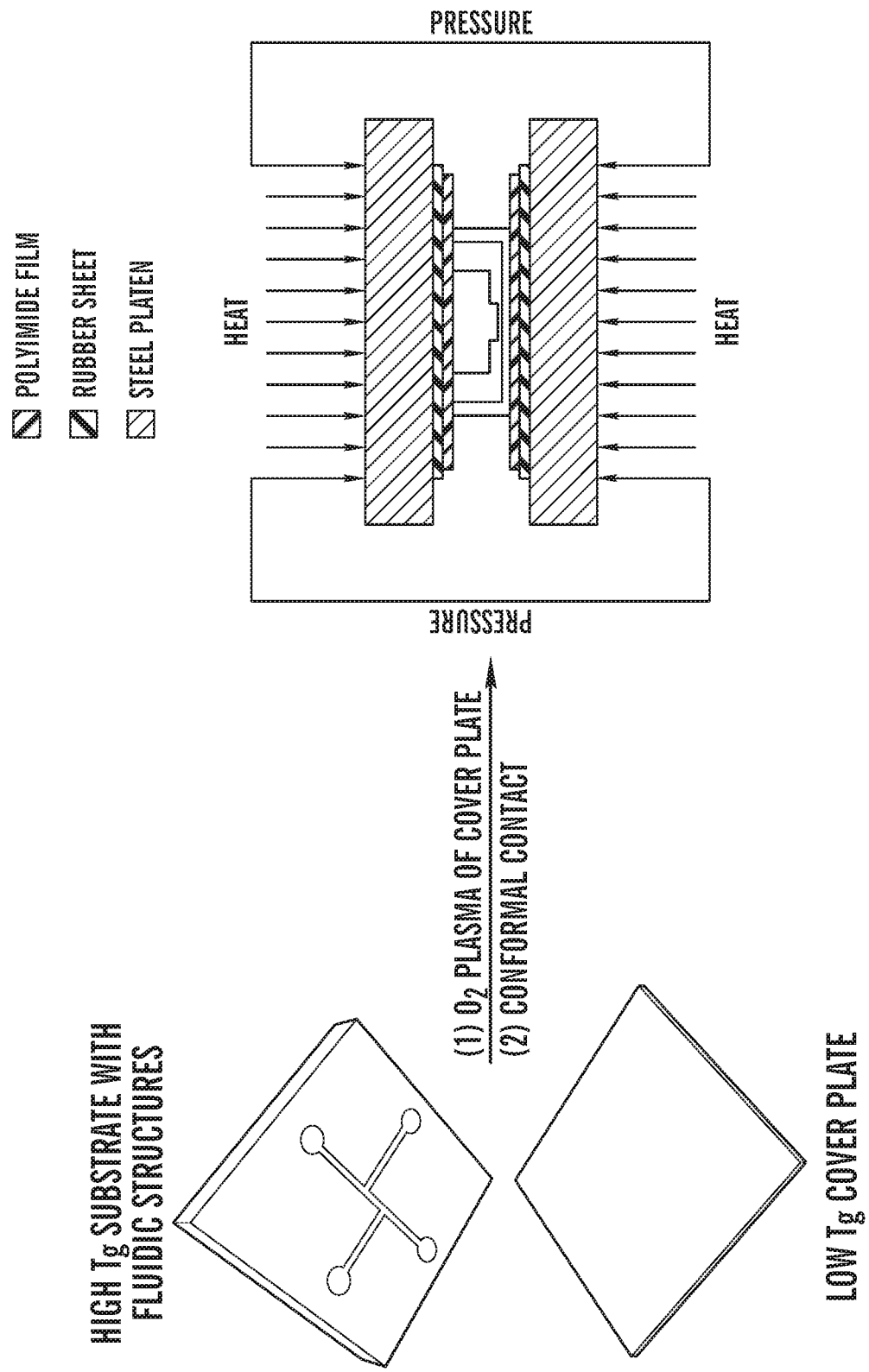
FIGS. 30A-30B show processes involved in assembling the device of the present invention.
Figure 30B:
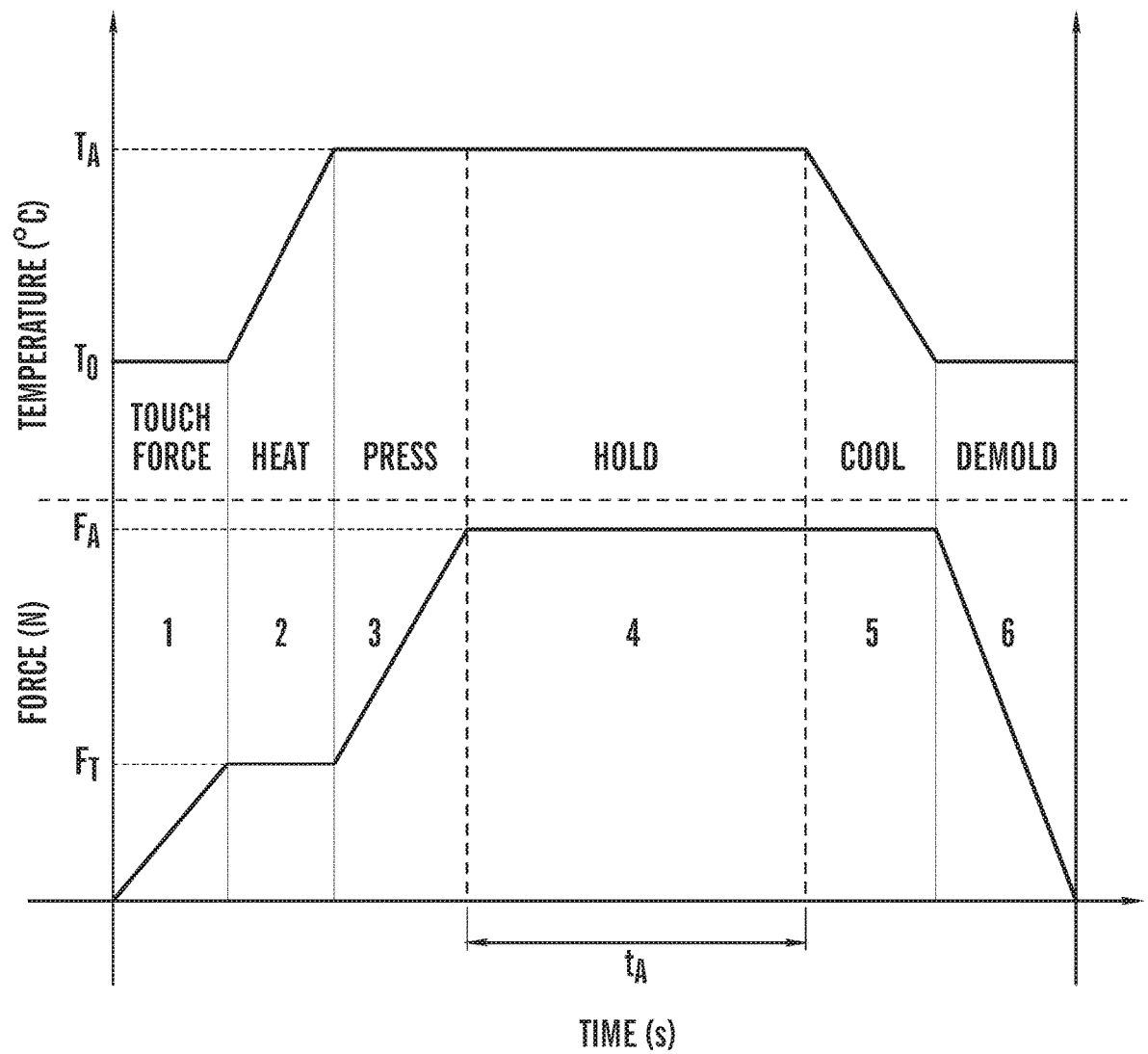

Three different strategies can be used to make the nanotubes comprising the in-plane synthetic nanopores and time-of-flight channels as described herein. A first approach involves a single step Nanoimprint lithography (NIL). A schematic of this procedure is depicted in FIGS. 29A-29B and FIG. 30. In short, because stamp structures <10 nm are required, one can use for master fabrication the Si substrate coated with a chromium layer (~300 Å) for focused ion beam (FIB) milling with varying exposure doses controlling both the width and depth for the nanochannels and in-plane synthetic nanopores (Menard & Ramsey, *Nano Letters* 11:512-517 (2010), which is hereby incorporated by reference in its entirety). As shown in FIG. 29A, the resin stamp can be fabricated via a UV-NIL process. The resin stamp is used to imprint the sensor structures into various polymer substrates as depicted in FIG. 29B. The S/N ratio of the current transients generated by the in-plane synthetic nanopores will depend on the size ratio of the nanochannel to the pores.

The second fabrication approach involves a combination of NIL and a size reduction process. It can be challenging to produce long nanochannels via single step NIL with the required in-plane synthetic nanopores, because the fabrication is affected by various factors such as a non-uniform deposition of the intermediate chromium layer, a non-uniform beam current for large area scanning in FIB and surface defects. Accordingly, in some embodiments it may be desirable to combine NIL with a size reduction process. Enlarged sensor structures can be produced in the polymer substrate with the scale ratio of 2-5, meaning that the width and depth of the nanochannels will be in the range of 100-200 nm and the size of the orifices in the range of 20-50 nm. Precise control over the polymer deformation at the nanometer scale is the key to the size reduction process to achieve sub-10 nm structures, which is difficult to achieve at a molding temperature during NIL.

Two suitable size reduction processes include (i) pressed self-perfection (PSP) process and (ii) polymer reflow process. In the PSP process, polymer nanostructures are pressed by a blank silica wafer at a temperature close to the glass transition temperature (Wang et al., *Nano Letters* 8:1986-1990 (2008), which is hereby incorporated by reference in its entirety). This process not only decreases the width and diameter of nanoscale trenches and holes, respectively, but also reduces sidewall roughness of those structures. PSP can be used in combination with NIL to generate nanopores in a freestanding polymer membrane (Choi et al., *J. Nanosci. Nanotechnol.* 13:4129-4133 (2013), which is hereby incorporated by reference in its entirety). Starting with micropores having 3 μm diameter, the pore size can be effectively reduced to ~300 nm. The second size reduction process, i.e., polymer reflow process, can generate free-standing SU-8 membranes with sub-10 nm pores. The shrinkage rate for uncured SU-8 by the polymer reflow process at 45° C. is ~3 nm/min (see FIG. 38C), which is comparable to the shrinkage rates of 6-16 nm/min and 1.2-15 nm/min used for fabricating silicon and glass-based nanopores via irradiation with a high-energy electron beam (Steinbock et al., *Nano Letters* 13:1717-1723 (2013), which is hereby incorporated by reference in its entirety). A low shrink rate makes the polymer reflow process extremely attractive to achieve nanoscale controllability for polymer nano-manufacturing.

The third fabrication approach involves integration of nanopore membranes with track-etched membranes. In this approach, the nanotubes are fabricated by vertically stacking prefabricated nanopore membranes with a track-etched membrane. In this process, free-standing nanopore membranes are produced with a well-defined pore diameter in the range of 10 nm by a single NIL step into a double resist layer. The pore size in the membrane can be further reduced by employing a post-NIL polymer reflow process to achieve sub-10 nm pores. For the nanochannels, track-etched polycarbonate membranes are used to generate low density nanopores. The pore diameter and membrane thickness is in the range of 100-200 nm and 60-100 respectively. The alignment of a nanopore in the free-standing SU-8 membrane and a nanopore in the track-etched membrane is done using optical microscopy. This is feasible, because the nanopore in the SU-8 membrane has a tapered structure along the membrane thickness and the micro-scale bottom pore of the track-etched membrane has a well-defined octagon shape. The stacked membranes (SU-8 membrane/track-etched membrane/SU-8 membrane) will contain the designed structures of nanochannel with two nanopores and the tapered inlet and exit for the nanopores in the SU-8 to reduce the error caused by the entropic barrier in the determination of the flight time. Finally, the stacked membrane is sandwiched between two thermoplastic (PMMA or others) chips with a microchannel in a cross configuration to complete an enclosed fluidic device for longitudinal transient current measurements. A single pore in the stacked membrane can be registered between upper and lower microchannels by controlling the width of the microchannels. FIG. 2A-2B show an example of a vertically positioned nanopore fabricated using this approach.

Methods for Detecting a Target Nucleic Acid Molecule

Another aspect of the present invention is directed to a method for identifying, in a sample, one or more target nucleotide sequences differing from other nucleotide sequences in the sample by one or more nucleotides, one or more copy numbers, one or more transcript sequences, and/or one or more methylated residues. This method involves providing a sample containing one or more target nucleic acid molecules containing the target nucleotide sequence or complements thereof and providing a solid support comprising one or more immobilized capture molecules, said capture molecules suitable to bind to a portion of the one or more target nucleic acid molecules. The method further involves binding the one or more target nucleic acid molecules to the one or more immobilized capture molecules on the solid support thereby immobilizing the one or more target nucleic acid molecules on said solid support, and subjecting the immobilized target nucleic acid molecules or immobilized complementary target nucleic acid molecules thereof to a ligase detection reaction to produce ligation products hybridized to said immobilized target nucleic acid molecules or immobilized complementary target nucleic acid molecules thereof. The ligation products are denatured from the immobilized target nucleic acid molecules or immobilized complementary target nucleic acid molecules thereof to release the ligation products from the solid support, and the denatured ligation products are fed through one or more nanopores capable of detecting said ligation products. The method further involves detecting, as a result of said feeding, an identifying signature of each ligation product that is generated when each product passes through the one or more nanopores, and identifying, based on said detecting, the presence of one or more target nucleotide sequences differing from other nucleotide sequences in the sample by one or more nucleotides, one or more copy numbers, one or more transcript sequences, and/or one or more methylated residues.

Another aspect of the present invention is directed method for identifying, in a sample, one or more target nucleotide sequences differing from other nucleotide sequences in the sample by one or more nucleotides, one or more copy numbers, one or more transcript sequences, and/or one or more methylated residues. This method comprises providing a sample containing one or more target nucleic acid molecules containing the target nucleotide sequence or complements thereof, and providing a solid support comprising one or more immobilized capture molecules, where the capture molecules are suitable to bind to a portion of the one or more target nucleic acid molecules. The method further involves binding the one or more target nucleic acid molecules to the one or more immobilized capture molecules on the solid support thereby immobilizing the one or more target nucleic acid molecules on said solid support. The immobilized target nucleic acid molecules or immobilized complementary target nucleic acid molecules thereof are contacted with (i) one or more oligonucleotide probes, wherein said one or more oligonucleotide probes are complementary to a portion of the immobilized target nucleic acid molecule or immobilized complementary target nucleic acid molecule thereof, and (ii) one or more nucleotide triphosphates or analogues thereof, where (i), (ii), or both comprise an identifying signature modifier or a moiety suitable for coupling an identifying signature modifier. The method further involves hybridizing the one or more oligonucleotide probes to their complementary immobilized target nucleic acid molecule or immobilized complementary target nucleic acid molecules thereof in a base specific manner and subjecting the one or more hybridized oligonucleotide probes to an extension reaction to produce extension products hybridized to said immobilized target nucleic acid molecules or immobilized complementary target nucleic acid molecules thereof. The extension products comprises a target specific portion or a complement thereof and (a) one or more identifying signature modifiers, (b) a moiety suitable for coupling to an identifying signature modifier, or both (a) and (b). The method further involves denaturing the extension products from the immobilized target nucleic acid molecules or immobilized complementary target nucleic acid molecule thereof to release the extension products from the solid support, and feeding the denatured extension products through one or more nanopores capable of detecting said extension products. The identifying signature of each extension product that is generated is detected, as a result of said feeding, when each extension product passes through the one or more nanopores, and the presence of one or more target nucleotide sequences differing from other nucleotide sequences in the sample by one or more nucleotides, one or more copy numbers, one or more transcript sequences, and/or one or more methylated residues is identified, based on said detecting.

Another aspect of the present invention is directed method for identifying, in a sample, one or more target nucleotide sequences differing from other nucleotide sequences in the sample by one or more nucleotides, one or more copy numbers, one or more transcript sequences, and/or one or more methylated residues. This method comprises providing a sample containing one or more target nucleic acid molecules containing the target nucleotide sequence or complements thereof, and providing a solid support comprising one or more immobilized capture molecules, where the capture molecules are suitable to bind to a portion of the one or more target nucleic acid molecules. The method further involves binding the one or more target nucleic acid molecules to the one or more immobilized capture molecules on the solid support thereby immobilizing the one or more target nucleic acid molecules on said solid support. The immobilized target nucleic acid molecules or immobilized complementary target nucleic acid molecules thereof are contacted with one or more oligonucleotide probes, where the one or more oligonucleotide probes are complementary to a portion of the immobilized target nucleic acid molecule or immobilized complementary target nucleic acid molecule thereof, and where at least one of said one or more oligonucleotide probes comprises an identifying signature modifier. The one or more oligonucleotide probes are hybridized to their complementary immobilized target nucleic acid molecule or complementary target nucleic acid molecule thereof in a base specific manner. The method further involves subjecting the one or more hybridized oligonucleotide probes to a cleavage reaction to produce a cleavage product, where the cleavage product comprising a portion of one of the one or more oligonucleotide probes and the identifying signature modifier. The cleavage products are fed through one or more nanopores capable of detecting the cleavage product, and the identifying signature of each cleavage product that is generated when each product passes through the one or more nanopore is detected, as a result of said feeding. The presence of one or more target nucleotide sequences differing from other nucleotide sequences in the sample by one or more nucleotides, one or more copy numbers, one or more transcript sequences, and/or one or more methylated residues is identified, based on said detecting.

In one embodiment, this method is carried out using a device as described supra, where the solid support comprising the one or more immobilized capture molecules comprises the biomolecular processor as described supra, and the one or more nanopores are within the nanotube coupled to the biomolecular processor as described supra. This device comprising the biomolecular processor and one or more nanotubes may contain one or more task-specific units upstream of the biomolecular processor that are configured to prepare the sample for analysis in the biomolecular processor and one or more nanotubes. These units are described supra and include, a cell separator unit for separating or enriching for target biological cells (e.g., circulating tumor cells), a longitudinally-extending plasma isolation unit to separate plasma from red blood cells and white blood cells, a first extractor unit for affinity purifying exosomes, a second extractor unit) for purification of cfDNA, a sensor unit for counting cells and determining viability, a second extractor unit for DNA and/or RNA isolation, one or more reactor modules for reverse transcriptase reactions and TdT reactions, and a flow purification module to remove excess dNTPs and other non-target nucleic acid molecule components from the sample prior to entering the nanosensor chamber and biological processor.

This method of the present invention can alternatively be carried out using other nanopore detection systems know in the prior art, for example, and without limitation, plastic nanopores, protein nanopores, and DNA oragami nanopores (see e.g., Hernandez-Aina et al., *ACS Nano* 7(7):6024-30 (2013), Langecker et al., *Nano Letters* 11:5002-5007 (2011), Kant et al., *Sensors*, 14:21316-21328 (2014), Saleh and Sohn, *Nano Letters* 3(1): 37-38 (2003), Quick et al., *Nature* 530(7589): 228-32 (2016), Ashton et al., *Nature Biotech.* 33(3): 296-300 (2015), Steinbock and Radenovic, *Nanotechnology* 26(7): 074003 (2015), which are hereby incorporated by reference in their entirety).

In accordance with this and all aspects of the present invention, the samples containing nucleic acid molecules of interest for analysis using the methods described herein include, without limitation, tissue, cells, serum, blood, plasma, amniotic fluid, sputum, urine, bodily fluids, bodily secretions, bodily excretions, cell-free circulating nucleic acids, cell-free circulating tumor nucleic acids, cell-free circulating fetal nucleic acids in pregnant woman, circulating tumor cells, tumor, tumor biopsy, and exosomes.

The target nucleic acid molecules within the sample to be detected can be double stranded deoxyribonucleic acid molecules (DNA), single stranded DNA molecules, DNA molecules comprising one or more methylated nucleotide bases, DNA molecules comprising one or more modified or damaged nucleotide bases, ribonucleic acid (RNA) molecules, i.e., long non-coding RNA (lncRNA), ribosomal RNA (rRNA), small nuclear RNA (snoRNA), microRNA (miRNA), transfer RNA (tRNA), and small interfering RNA (siRNA), RNA molecules comprising one or more modified or damaged nucleotide bases, and RNA/DNA hybrid molecules.

In accordance with this and all aspects of the present invention, the immobilized capture molecule is a binding partner to a portion of the target nucleic acid molecule or a portion appended to the target nucleic acid molecule. Suitable capture molecules and their respective binding partners present on the nucleic acid molecule include, without limitation, biotin and streptavidin, maltose and maltose binding protein, chitin and chitin binding protein, amylase and MBP, glutathione transferase and glutathione-S-transferase, histag and NTA matrix, integrin and integrin binding peptides. In another embodiment, the capture molecule is a polynucleotide sequence that is complementary to a portion of the nucleic acid sequence of the target nucleic acid molecule. For example, in one embodiment, the capture molecule is a homopolymer sequence of a mononucleotide triphosphate, e.g., a poly-dA or poly-T primer, and the target nucleic acid molecules of the sample contain the complementary homopolymer sequence of mononucleotide triphosphate, i.e., a poly-T or poly-dA tail.

In one embodiment of the present invention, the binding partner of the immobilized capture molecule is appended to the target nucleic acid molecule to facilitate immobilization. The nucleic acid molecules in the sample may be randomly fragmented and treated so as to append the adaptor portions containing a suitable binding partner, and optionally, one or more further portions, e.g., a primer binding portion, to each end of the fragmented nucleic acid molecules. For example, the ends of a DNA molecule, either blunt ended or made flush using a variety of enzymes, such as T4 polymerase or E. coli polymerase, can be phosphorylated using T4 Kinase. A polymerase without 3' to 5' proofreading activity (such as Klenow (exo)) is used to add an extra "A" to the 3' end, creating a single base 3'A overhang suitable for adapter ligation using linkers containing single base 3'T overhangs. Appending adaptor portions to a nucleic acid molecule and complement thereof can also be achieved using anyone of a variety of enzymatic reactions known in the art. Suitable enzymes include, without limitation, ligases (e.g., E. coli ligase or T4 DNA ligase), polymerases (e.g., Taq polymerase, T4 polymerase, or E. coli polymerase), recombinases, terminal transferases, endonucleases, DNA repair enzymes, and reverse transcriptases. Exemplary approaches for appending adapter portions to various target nucleic acid molecules (e.g., DNA, mRNA, miRNA) are well known in the art.

In one embodiment, the adapter portions are added using a terminal transferase to append a homopolymer sequence of mononucleotide triphosphate, i.e., a poly-T or poly-dA tail to the 3' end of the target nucleic acid molecule. In another embodiment, the adapter portions are appended to the target nucleic acid molecule using locus specific set of oligonucleotide primers and a polymerase. In this embodiment, a first oligonucleotide primer of the primer set comprises a 5' nucleotide adapter sequence that serves as a binding partner to the capture molecule, e.g., a poly-dA, poly-T sequence tail, and a 3' target nucleotide sequence that is complementary to a portion of the target nucleic acid molecule. The second oligonucleotide primer of the primer set comprises an optional 5' primer-specific portion and a 3' nucleotide sequence that is complementary to a portion of an extension product formed from the first primer. To enhance specificity of adapter appending polymerase reaction, one or both oligonucleotide primers of the oligonucleotide primer set have a 3' cleavable nucleotide or nucleotide analogue and a blocking group that block polymerase mediated extension of one or both primers. Suitable blocking groups include for example, without limitation, a propanol group (3' SpC3), a dideoxy ribose base (3'ddC), a phosphate (3' phosphate), or a phosphorothioate group (Nikiforow, et al., "The Use of Phosphorothioate Primers and Exonuclease Hydrolysis for the Preparation of Single-stranded PCR Products and their Detection by Solid-phase Hybridization," *PCR Methods and Applications*, 3:p. 285-291 (1994), which is hereby incorporated by reference). Cleavage of the 3' blocking group of the oligonucleotide primer to liberates a 3'OH suitable for polymerase can be achieved using RNaseH when the primer is designed to contain an internal ribonucleotide base (see Dobosy et. al. "RNase H-Dependent PCR (rhPCR): Improved Specificity and Single Nucleotide Polymorphism Detection Using Blocked Cleavable Primers," *BMC Biotechnology* 11(80): 1011 (2011), which is hereby incorporated by reference in its entirety), using Tth Endo IV or E. coli Endo IV when the primer is designed to contain an internal abasic site (e.g., tetrahydrofuran), or using Tth Endo V or E. coli Endo V when the primer is designed to contain an internal U paired to a G on the template (cleavage will liberate the 2nd or 3rd phosphodiester bond 3' to the U-G mismatch).

Target nucleic acid molecules may optionally be enriched prior to immobilization to the solid support via binding to their respective capture molecule. Target nucleic acid molecule enrichment can be carried out using methods known in the art and as described herein.

Once the target nucleic acid molecules are immobilized to the solid support via binding to their respective immobilized capture molecules, the immobilized target nucleic acid molecules or immobilized complementary target nucleic acid molecules thereof are subject to a ligation reaction process, extension reaction process, cleavage reaction process, or other enzymatic reaction.

In one embodiment, terminal transferase appends biotinylated nucleotide triphosphates to the end of the nucleic acid molecule, and the biotinylated target nucleic acid molecule is immobilized on the solid support via binding to streptavidin coated to the surface of the solid support. Although biotin-streptavidin is not a covalent binding interaction, tailing with biotin generally allows capture of 2-3 biotins from the same molecule on the streptavidin tetramer, and immobilization in this manner can withstand denaturing conditions (high formamide, and/or heating to 90° C.) of the ligation reaction process and other enzymatic reaction processes. Such a denaturation is required to release the ligation and extension products generated by the ligation reaction process from the immobilized target on the solid surface for the subsequent distinguishing and detection step.

In another embodiment, terminal transferase appends dCTP to a target nucleic acid end, and the labeled target nucleic acid molecule is immobilized on the solid support via binding to $dG_{50}$ oligonucleotide capture molecules on the solid support. Similar to the biotin-streptavidin binding interaction, homo-polymer dC:dG binding is strong enough to withstand the denaturing conditions described above. Such a denaturation is required to release the ligation products and extension products generated by the ligation and extension reaction processes, respectively, from the immobilized target on the solid surface for the subsequent distinguishing and detection step. This allows the target nucleic acid molecule to serve as the template for the ligation and extension reaction processes.

In another embodiment, immobilized complementary target nucleic acid molecules that are complementary to the immobilized target nucleic acid molecule are generated on the spaced support structures of the bioreactor chamber, and used as the template for the various reaction processes Immobilized complementary target nucleic acid molecule are generated using solid phase amplification reactions known to those of skill art and/or as described herein.

In one embodiment, the capture molecule is a capture oligonucleotide that also serves as a primer to facilitate linear solid phase amplification of bound target nucleic acid molecules. In accordance with this embodiment, a capture oligonucleotide, e.g., a poly-dA capture primer, hybridized to a complementary portion of the target nucleic acid molecule, e.g., an adapter portion of the target nucleic acid molecule containing poly-T tail, is extended using polymerase and pool of dNTPs to make a full-length complementary copy of the immobilized target nucleic acid molecule. Using a polymerase having strand-displacement activity, such as Bst polymerase, allows for linear amplification of the target nucleic acid molecule. Following primer extension to form an immobilized extension product that is complementary to the target nucleic acid molecule, the temperature is increased such that the poly-T portions of target nucleic acid molecule and its extension product denature, allowing for an adjacent, non-hybridized capture oligonucleotide to bind to the target nucleic acid molecule and be extended. This linear amplification faithfully produces complementary copies the original template strand of the nucleic acid molecule as it is "handed-off" to the next primer. This process continues until non-hybridized capture oligonucleotide primers on the solid support are exhausted (see e.g., step D in FIGS. 74-84).

In another embodiment, the target nucleic acid molecule with appended adapter portions is circularized, and solid phase amplification is achieved via a rolling circle amplification reaction (Lizardi et al., "Mutation Detection and Single-molecule Counting Using Isothermal Rolling-circle Amplification," *Nat Genet* 19:225-232 (1998), which is hereby incorporated by reference in its entirety). Methods of circularizing the adapter appending nucleic acid molecule are described herein and illustrated in FIGS. 164-173. In accordance with this embodiment, the immobilized capture oligonucleotide serves as a primer to prime the solid phase rolling circle amplification. The circularized nucleic acid molecule hybridizes to the immobilized capture oligonucleotide via its complementary adapter portion (e.g., the poly-T sequence of the circularized nucleic acid molecule hybridizes to the immobilized poly-dA capture oligonucleotide). In the presence of polymerase having strand displacing activity and a pool of dNTPs, the immobilized primer is continually extended around the circularized nucleic acid molecule to generate immobilized extension products (i.e., complementary target nucleic acid molecules) that comprise multimeric tandem linear repeating sequences that are complementary to the sequence of the circularized adapter appended target nucleic acid molecule.

To further enhance solid phase amplification and immobilization of extension products that are complementary to the target nucleic acid molecule (i.e., complementary target nucleic acid molecules), the adapter portion of the target nucleic acid molecule is designed to contain one or more universal primer-specific portions. In accordance with this embodiment, one or more primers having a 3' portion having the same sequence of the universal primer-specific portion of the adapter portion of the target nucleic acid molecule is provided to hybridize to its complementary universal primer specific portion of the immobilized complementary target nucleic acid molecule formed from extension of the capture oligonucleotide. Extension of the hybridized primer on the immobilized extension products forms a secondary extension product. The secondary extension product is denatured and captured at an adjacent or nearby capture oligonucleotide primer on the solid support, which primer subsequently extends to form additional immobilized extension products that are complementary to the target nucleic acid molecule. This process continues until non-hybridized capture oligonucleotide primers on the solid support are exhausted (see e.g., FIG. 173).

Another suitable approach for carrying out solid phase amplification in accordance with the methods of the present invention is described in WO2013/012440 to Barany et al., which is hereby incorporated by reference in its entirety. Isothermal approaches for carrying our solid phase amplification in accordance with the methods of the present invention are described in Ma et al., *Proc Natl Acad Sci USA* 110(35):14320-3 (2013), which is hereby incorporated by reference in its entirety.

In accordance with one aspect of the present invention, the immobilized target nucleic acid molecules or immobilized complementary target nucleic acid molecules thereof are subjected to a ligation reaction to produce ligation products. In one embodiment of the present invention, the ligation reaction is a ligation detection reaction. The ligation detection reaction mixture comprises a ligase and one or more oligonucleotide probe sets, each probe set having a first oligonucleotide probe having a target nucleotide sequence-specific portion, and a second oligonucleotide probe having a target nucleotide sequence-specific portion. The first and second oligonucleotide probes of a probe set are configured to hybridize, in a base specific manner, on a complementary region of the immobilized target nucleic acid molecules or immobilized complementary target nucleic acid molecules thereof. In one embodiment, the first and second oligonucleotide probes of a probe set hybridize immediately adjacent to each other, with a junction between them, on their complementary region of the immobilized target nucleic acid or complementary target nucleic acid molecules thereof and are ligated together to form a ligation product. In another embodiment, the first and second oligonucleotide probes of a probe set hybridize to their complementary regions on the target nucleic acid molecule or complementary target nucleic acid molecules thereof with a space or gap between them. In this embodiment, a polymerase is utilized to extend the 3' end of the first oligonucleotide probe to create a junction with the second oligonucleotide probe, and then ligase ligates the two probes together to form a ligation product.

Several variations of the above described ligation reaction can be employed to enhance the specificity of ligation product generation, and therefore, target nucleic acid detection. In one embodiment, the first oligonucleotide probe bears a ligation competent 3' OH group while the second oligonucleotide probe bears a ligation incompetent 5' end (i.e., an oligonucleotide probe without a 5' phosphate). In accordance with the method of the present invention the oligonucleotide probes of a probe set are designed such that the terminal 3' base of the first oligonucleotide probe is overlapped by the immediately flanking 5'-most base of the second oligonucleotide probe that is complementary to the target nucleic acid molecule. The overlapping nucleotide is referred to as a "flap". When the overlapping flap nucleotide of the second oligonucleotide probe is complementary to the target nucleic acid molecule sequence and the same sequence as the terminating 3' nucleotide of the first oligonucleotide probe, the phosphodiester bond immediately upstream of the flap nucleotide of the second oligonucleotide probe is discriminatingly cleaved by an enzyme having flap endonuclease (FEN) or 5' nuclease activity. That specific FEN activity produces a novel ligation competent 5' phosphate end on the second oligonucleotide probe that is precisely positioned alongside the adjacent 3' OH of the first oligonucleotide probe. This method and variations thereof that are suitable for use in accordance with this aspect of the present invention are described in U.S. Patent Application Publication No. 2015/0038336 to Barany et al., which is hereby incorporated by reference in its entirety.

Detection or identification of a low-abundance mutation using a ligase detection reaction may be improved by employing various probe design features. For example, an intentional mismatch or nucleotide analogue (e.g., inosine, nitroindole, or nitropyrrole) can be incorporated into the first oligonucleotide probe at the $2^{nd}$ or $3^{rd}$ base from the 3' junction end to slightly destabilize hybridization of the 3' end if it is perfectly matched at the 3' end, but significantly destabilize hybridization of the 3' end if it is mis-matched at the 3' end. This design reduces inappropriate misligations when mutant probes hybridize to wild-type target. Alternatively, RNA bases that can be cleaved by RNAses can be incorporated into the oligonucleotide probes to ensure template-dependent product formation. For example, Dobosy et. al. "RNase H-Dependent PCR (rhPCR): Improved Specificity and Single Nucleotide Polymorphism Detection Using Blocked Cleavable Primers," *BMC Biotechnology* 11(80): 1011 (2011), which is hereby incorporated by reference in its entirety, describes using an RNA-base close to the 3' end of an oligonucleotide probe with 3'-blocked end, and cutting it with RNAse $H_2$ generating a PCR-extendable and ligatable 3'-OH. This approach can be used to generate either ligation-competent 3' OH or 5'-P, or both, provided a ligase that can ligate 5'-RNA base is utilized.

For insertions or deletions, incorporation of a matched base or nucleotide analogues (e.g., -amino-dA or 5-propynyl-dC) in the first oligonucleotide probe at the $2^{nd}$ or $3^{rd}$ position from the junction improves stability and may improve discrimination of such frameshift mutations from wild-type sequences. For insertions, use of one or more thiophosphate-modified nucleotides downstream from the desired scissile phosphate bond of the second oligonucleotide probe will prevent inappropriate cleavage by the 5' nuclease enzyme when the probes are hybridized to wild-type DNA, and thus reduce false-positive ligation on wild-type target. Likewise, for deletions, use of one or more thiophosphate-modified nucleotides upstream from the desired scissile phosphate bond of the second oligonucleotide probe will prevent inappropriate cleavage by the 5' nuclease enzyme when the probes are hybridized to wild-type DNA, and thus reduce false-positive ligation on wild-type target.

Other possible modifications include abasic sites, e.g., dSpacer (aka, THF tetrahydrofuran) or oxo-G. These abnormal "bases" have specific enzymes that remove abnormal base and generate ligation-competent 3'-OH or 5'P sites. Endonuclease IV, Tth EndolV (NEB) will remove abasic residues after the ligation oligonucleotides anneal to the target nucleic acid, but not from a single-stranded DNA. Similarly, one can use oxo-G with Fpg or inosine/uracil with EndoV or Thimine glycol with EndoVIII.

In another embodiment, a probe set for the ligation reaction can further comprise a third oligonucleotide probe also having a target-specific portion that is complementary to a region of the immobilized target nucleic acid molecule or complementary target nucleic acid molecules thereof. In this embodiment, the second and third oligonucleotide probes of a probe set are configured to hybridize adjacent to one another on the target nucleotide sequence with a junction between them. The target specific portion of the third oligonucleotide probe has an overlapping identical nucleotide flap at the junction with the second oligonucleotide probe in a probe set that is removed by an enzyme having FEN activity when it is complementary to the target nucleotide sequence and is the same sequence as the terminating 3' nucleotide of the second oligonucleotide probe. Cleavage of the flap liberates a ligation competent 5'phosphate on the third oligonucleotide probe that allows ligation between the second and third oligonucleotide probes at the junction to form a ligated product sequence The utilization of three probes in a primer set allows for detection of longer target regions with increased specificity The ligation reaction utilized in the method of the present invention is well known in the art. Ligases suitable for ligating oligonucleotide probes of a probe set together following cleavage of the 5' flap on the second oligonucleotide probe include, without limitation *Thermus aquaticus* ligase, *Thermus* sp. AK16D ligase, *E. coli* ligase, T4 DNA ligase, T4 RNA ligase, Taq ligase, 9 N° ligase, and *Pyrococcus* ligase, or any other thermostable ligase known in the art. In accordance with the present invention, the nuclease-ligation process of the present invention can be carried out by employing an oligonucleotide ligation assay (OLA) reaction (see Landegren, et al., "A Ligase-Mediated Gene Detection Technique," *Science* 241:1077-80 (1988); Landegren, et al., "DNA Diagnostics—Molecular Techniques and Automation," *Science* 242:229-37 (1988); and U.S. Pat. No. 4,988,617 to Landegren, et al., which are hereby incorporated by reference in their entirety), a ligation detection reaction (LDR) that utilizes one set of complementary oligonucleotide probes (see e.g., WO 90/17239 to Barany et al, which is hereby incorporated by reference in their entirety), or a ligation chain reaction (LCR) that utilizes two sets of complementary oligonucleotide probes see e.g., WO 90/17239 to Barany et al, which is hereby incorporated by reference in their entirety).

In accordance with another aspect of the present invention, the immobilized target nucleic acid molecules or immobilized complementary target nucleic acid molecules thereof are subjected to a cleavage reaction to produce cleavage products. Suitable cleavage reactions include, without limitation, a flap endonuclease reaction using a flap endonuclease, a restriction endonuclease cleavage reaction using a restriction endonuclease, a target-dependent ribonucleotide cleavage reaction using an RNase, or a target-dependent probe cleavage reaction using an apurinic/apyrimidinic endonuclease, an 8-oxoguanine DNA glycosylase, a uracil-DNA glycosylase, an endonuclease, and/or an exonuclease.

In one embodiment, the cleavage reaction is a flap endonuclease cleavage reaction. As described above, a modification of the ligation reaction involves the first oligonucleotide probe bearing a ligation competent 3' OH group and a second oligonucleotide probe bearing a ligation incompetent 5' end (i.e., an oligonucleotide probe without a 5' phosphate). The oligonucleotide probes are designed such that the terminal 3' base of the first oligonucleotide probe is overlapped by the immediately flanking 5'-most base of the second oligonucleotide probe that is complementary to the target nucleic acid molecule. The overlapping nucleotide is referred to as a "flap". In accordance with this embodiment, the 5' end of the flap comprises an identifying signature modifier. When the overlapping flap nucleotide of the second oligonucleotide probe is complementary to the target nucleic acid molecule sequence and the same sequence as the terminating 3' nucleotide of the first oligonucleotide probe, the phosphodiester bond immediately upstream of the flap nucleotide of the second oligonucleotide probe is discriminatingly cleaved by an enzyme having flap endonuclease (FEN) or 5' nuclease activity. That specific FEN activity produces a cleavage product having a unique identifying signature that can be detected as it passes through one or more nanopores as described herein.

Flap endonucleases or 5' nucleases that are suitable for cleaving the 5' flap of the second oligonucleotide probe prior to ligation include, without limitation, polymerases that bear 5' nuclease activity such as *E. coli* DNA polymerase and polymerases from Taq and *T. thermophilus*, as well as T4 RNase H and TaqExo.

In accordance with another aspect of the present invention, the immobilized target nucleic acid molecules or immobilized complementary target nucleic acid molecules thereof are subjected to an extension reaction to produce extension reaction products. In one embodiment the extension reaction is a polymerase extension reaction mediated by a DNA polymerase, a DNA polymerase lacking 5'-3' nuclease and/or strand displacing activity, or any other DNA polymerase known in the art. The extension reaction may comprise, for example and without limitation, a primer extension reaction, a single-nucleotide primer extension reaction, or a sequencing reaction. Various examples of extension reactions are illustrated herein.

The oligonucleotide probes of a probe sets and primers can be in the form of ribonucleotides, deoxynucleotides, modified ribonucleotides, modified deoxyribonucleotides, peptide nucleotide analogues, modified peptide nucleotide analogues, modified phosphate-sugar-backbone oligonucleotides, nucleotide analogs, and mixtures thereof.

Once formed, the ligation products, extension products, or cleavage products, collectively referred to herein as an "oligonucleotide products" are fed through one or more nanopores capable of detecting and distinguishing the identifying signature of the oligonucleotide product as it passes through it. In one embodiment, the identifying signature of an oligonucleotide product is the change in current through one or more nanopores that occurs when the oligonucleotide product passes through it. The change in current can be an increase (i.e., current augmentation) or a decrease in current (i.e., a current blockade) through the nanopore or nanopores. The magnitude and duration of current change through a nanopore is detected and measured to identify and distinguish one oligonucleotide product from another. In accordance with this embodiment, the identifying signature of an oligonucleotide product is influenced by the size (i.e., length), shape or conformation (e.g., folded vs. linear), charge, and conductivity of the oligonucleotide product.

In another embodiment, the identifying signature of the oligonucleotide product is its time of flight in a nano-scale time-of-flight channel. In this embodiment, the oligonucleotide product is fed through at least a first and second nanopore, where the first and second nanopores are positioned on opposing ends of a nano-scale time-of-flight channel. The time it takes for the oligonucleotide product to pass through the first nanopore, the time-of-flight channel and the second nanopore are measured and used as the identifying signature of the ligation product. In accordance with this embodiment, the identifying signature of the oligonucleotide product is influenced by the size (i.e., length), shape or conformation (e.g., folded vs. linear), charge, and conductivity of the oligonucleotide product.

In another embodiment, the identifying signature of the oligonucleotide product is the change in current through at least two nanopores that occurs when the oligonucleotide product passes through the two nanopores in combination with the time-of-flight measurement between the two nanopores. The identifying signature of the oligonucleotide product is influenced by the size (i.e., length), shape or conformation (e.g., folded vs. linear), charge, and conductivity of the oligonucleotide product.

Figure 57:
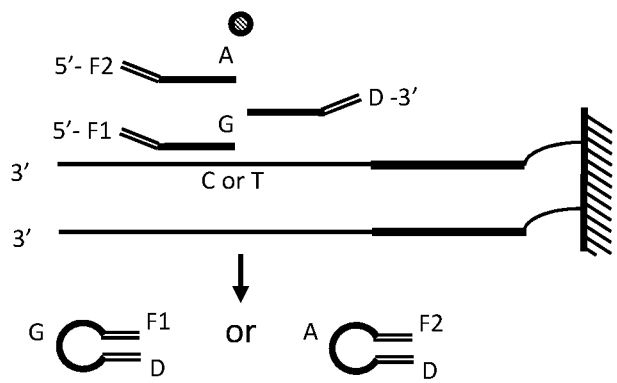
FIG. 57 illustrates interrogation of support bound single molecule clusters of target DNA using the ligation methods of the present invention.

The identifying signature of an oligonucleotide product is an inherent property of the oligonucleotide product itself that can be further modified by the incorporation or appendage of one or more identifying signature modifiers. For example, the first and second oligonucleotide probes of a ligation probe set are designed to each contain a further portion on their 5' and 3' end, respectively, that function as an identifying signature modifier. In one embodiment, the further portions are nucleotide sequences that are complementary to each other to allow hairpin formation or molecular beacon formation of the ligation product once denatured from the immobilized target nucleic acid molecule or an extension product thereof as shown in FIG. 57. The hairpin or molecular beacon act as identifying signature modifiers, because, when passing through the one or more nanopores, the hairpin or molecular beacon of the ligation product changes the magnitude of current flow through the pore to a different extent than non-ligated ligation probes. In addition, different ligation products can be distinguished by using different length hairpin structures, or imperfect hairpins (which bend), or other 3-dimensional structures that form only as a ligation product, but can be distinguished from each other or the starting probes due to differences in mobility through the nanopore.

Figure 58:
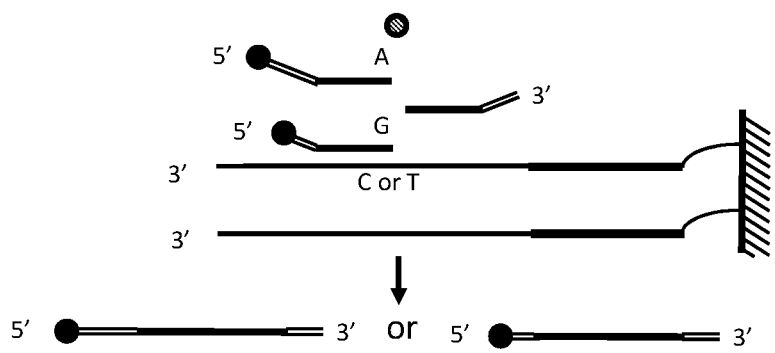
FIG. 58 illustrates interrogation of support bound single molecule clusters of target DNA using the ligation methods of the present invention.
Figure 59:
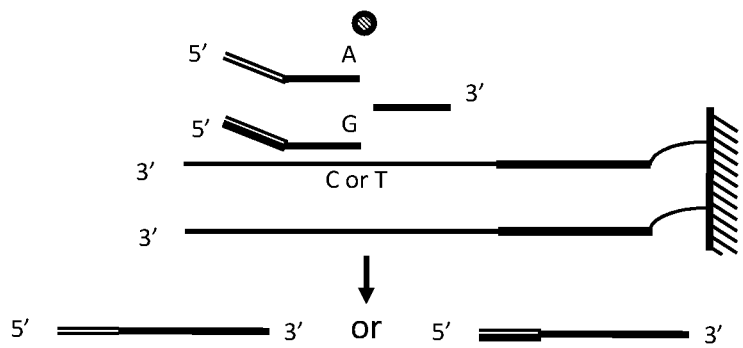
FIG. 59 illustrates interrogation of support bound single molecule clusters of target DNA using the ligation methods of the present invention.
Figure 60:
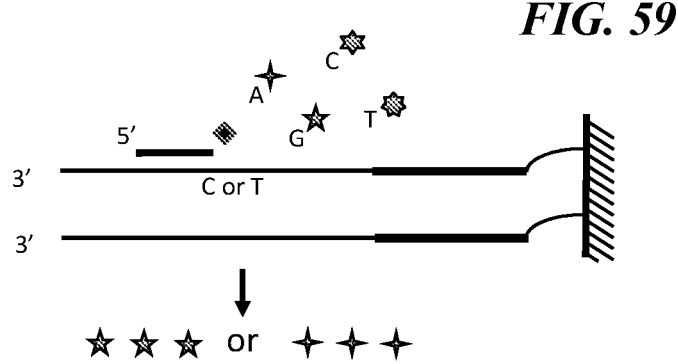
FIG. 60 illustrates interrogation of support bound single molecule clusters of target DNA using single nucleotide extension methods of the present invention.

In another embodiment, any one or more of various "identifying signature modifiers" which influence the change in current produced as a oligonucleotide product passes through a nanopore or the time-of-flight of the oligonucleotide product through the time-of-flight channel are appended to the oligonucleotide product. Identifying signature modifiers are water soluble, neutral, or charged molecules that modify the mobility of the oligonucleotide product, e.g., drag-tags. Exemplary identifying signature modifiers include, without limitation, polypeptides, polynucleotides, peptide nucleotide analogue (PNA) multimers, peptoids, polyethers (polyethylene oxide and polypropylene oxide), nanospheres, nanocrystals, oligosaccharides, dendrimers, polyesters (polyglycolic acid, polylactic acid), polyurethanes, polyamides, polysulfonamides, polysulfoxides, polyphosphates, polyphosphonates, and combinations thereof. Accordingly, in one embodiment, identifying signature modifiers are appended to the discriminating oligonucleotide probes used in a ligation reaction to generate ligation products that can be readily discriminated from each other based on their identifying signature (see FIGS. 58 and 59). Likewise, an identifying signature modifier can be appended to an oligonucleotide probe of an extension reaction to generate extension products that are distinguished from each other based on their identifying signature (see FIGS. 64 and 66). In another embodiment, an identifying signature modifier is appended to an oligonucleotide probe utilized in a cleavage reaction, and cleavage of the oligonucleotide probe generates a cleavage product that can be discriminated from other cleavage products based on its identifying signature (see FIGS. 61-63). This approach is based on free solution conjugate electrophoresis (FSCE), also known as end-labeled free-solution electrophoresis (ELFSE) (Ren et al., "Separating DNA Sequencing Fragment without a Sieving Matrix," *Electrophoresis* 20(12): 2501-9 (1999), which is hereby incorporated by reference in its entirety). In this embodiment, single-base differences of oligonucleotide products generated via ligation, extension or cleavage reactions are distinguished by use of different identifying signature modifiers (Albrecht et al., "Simultaneous Detection of 19 K-ras Mutations by Free Solution Conjugate Electrophoresis of Ligase Detection Reaction Products on Glass Microchips," *Electrophoresis* 34(4):590-7 (2013); Sinville et al., "Ligase Detection Reaction for the Analysis of Point Mutations using Free-solution Conjugate Electrophoresis in a Polymer Microfluidic Device," *Electrophoresis* 29(23):4751-60 (2008), which are hereby incorporated by reference in their entirety). The resultant oligonucleotide products differ in length and/or mass/charge ratio, and thus they migrate differently from each other and the initial probes, and may be distinguished by their influence on current through a nanopore.

In another embodiment, the identifying signature modifier is a molecular sequence barcode (FIG. 59), i.e., a nucleotide sequence that can be distinguished through a nanopore based on sequence specific current modification through one or more nanopores (Manrao et al., "Reading DNA at Single-nucleotide Resolution with a Mutant MspA Nanopore and phi29 DNA Polymerase," *Nat Biotechnol.* 30(4):349-53 (2012), which is hereby incorporated by reference in its entirety). In this example, single-base differences at the ligation junction are distinguished by use of different sequence bar-codes on the upstream probes, which serve as markers for the individual base that is being interrogated. The short ligation products generated can either be distinguished by their innate sequences as they pass through a nanopore or by the use of sequence bar-codes which have been designed to compensate for the high error rates of existing nanopore sequencing systems. By way of example, consider two different solutions for detecting and distinguishing 100 different hot-spot mutations in the TP53 gene using sequencing via passing the ssDNA product through a nanopore, wherein the error rate per base call is 15%. In the first solution, the 100 different upstream probes have appended on them 100 different DNA bar-codes of 24 bases each, where each bar-code differs from every other bar-code by at least 6 bases (see U.S. Pat. No. 7,803,233 to Barany et al., which is hereby incorporated by reference in its entirety). In this solution, the 100 different LDR products are distinguishable by their bar-code sequence alone. In the second solution, only a handful of bar-codes are used for distinguishing mutations on the same or closely located codons. Overall, it is the sequence of the bar-code plus the sequence of the appended TP53-specific DNA ligation product that allows for distinction of each unique ligation product for each mutation.

Alternatively, the bar-codes can be composed of non-nucleotidic polymers which enhance their detection and discrimination as they pass through a nanopore (Kumar et al. "PEG-Labeled Nucleotides and Nanopore Detection for Single Molecule DNA Sequencing by Synthesis," *Sci. Reports* 2:684 (2012), which is hereby incorporated by reference in its entirety). Since the mobility of ss DNA molecules through nanopores is too high for accurate sequence determination, it is sometimes necessary to append a molecular motor directly to the nanopore or alternatively to a sequence motif covalently appended to the oligonucleotide product to allow the controlled stepwise ratcheting of the oligonucleotide product through the nanopore (Lieberman et al., "Dynamics of the translocation step measured in individual DNA polymerase complexes," *J Am Chem Soc.* 134(45):18816-23 (2012), which is hereby incorporated by reference in its entirety).

In another embodiment, the identifying signature modifier is an encoded identifying signature modifier. An "encoded identifying signature modifiers" is a molecule that is coupled to a nucleotide via a non-cleavable linkage and is capable of measurably modifying or modulating (i.e., augmenting or blocking) current through the one or more nanopores. Suitable encoded identifying signature modifiers include, without limitation, water soluble, charged molecules, for example and without limitation, acidic polypeptides, basic polypeptides, dinucleotides, trinucleotides, peptide nucleotide analogues, charged polymers (e.g., polyethylene glycol polymers), nanospheres, nanocrystals, charged oligosaccharides, dendrimers, fluorescent dyes, infrared dyes, chromophores, quinolones, coumarin, porphyrins, porphyrin-metal complexes, water soluble aromatic polycyclic molecules, water soluble aromatic heterocyclic molecules, transition-metal complexes, metal chelates, metal chelate polymers, 2-nitrobenzyl derivatives, or any combination of these moieties. The encoded identifying signature modifier is appended to each nucleotide triphosphate at its nucleoside C5 position or its nucleoside C7 position.

Figure 61:
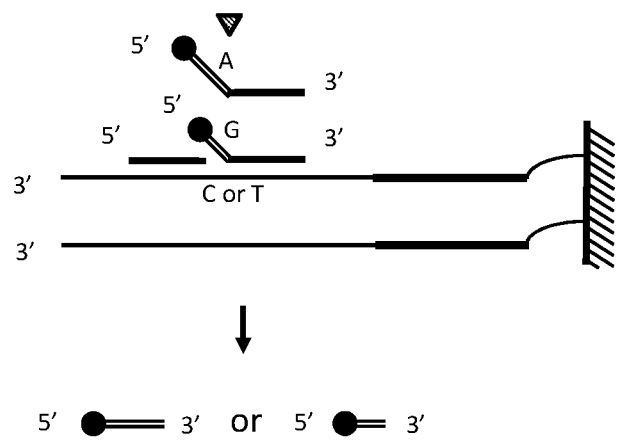
FIG. 61 illustrates interrogation of support bound single molecule clusters of target DNA using enzymatic cleavage methods of the present invention.
Figure 62:
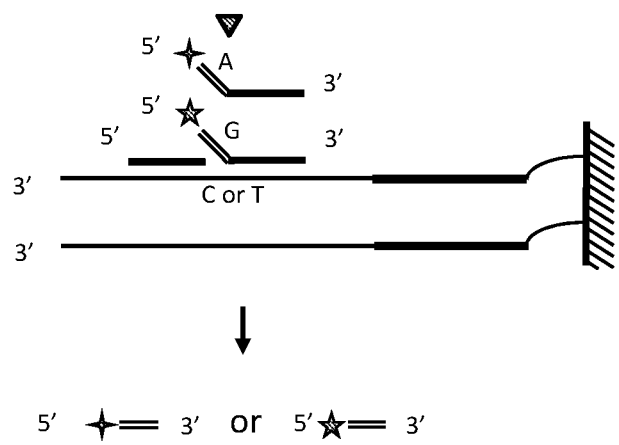
FIG. 62 illustrates interrogation of support bound single molecule clusters of target DNA using enzymatic cleavage methods of the present invention.
Figure 63:
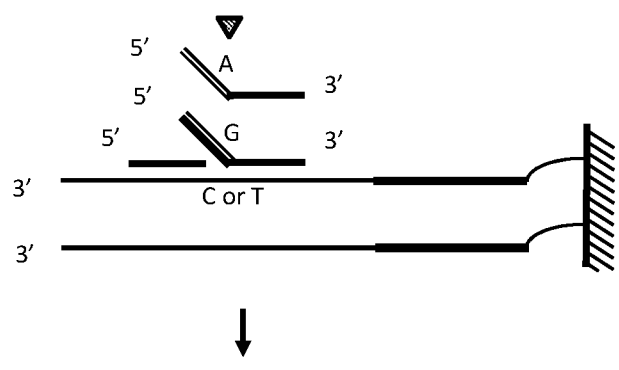
FIG. 63 illustrates interrogation of support bound single molecule clusters of target DNA using enzymatic cleavage methods of the present invention.

FIGS. 61-63 illustrate interrogation of support bound single molecule clusters of target DNA using three different modes of detecting a cleavage reaction product. In all of these approaches, upstream and downstream oligonucleotides overlap at the mutation base forming a "flap". Addition of flap endonuclease—or the 5'-3' exonuclease activity of polymerase—and $Mg^{2+}$ initiates cleavage of the flap when the upstream and downstream oligonucleotides are hybridized to their complementary target nucleotide sequences. In one embodiment, the enzyme is added first to allow for binding of the upstream primer, and cleavage is initiated by the addition of $Mg^{2+}$. In the approach shown in FIG. 61, the flap contains a 5' identifying signature modifier, and different mutations or alleles are distinguished by the mobility of the 5' identifying signature modifier in a time-of-flight channel. The cleaved flap is fed through at least a first and second nanopore that are positioned on opposing ends of a nano-scale time-of-flight channel. The time it takes for the cleavage product to pass through the first nanopore, the time-of-flight channel and the second nanopore are measured and used as the identifying signature of the cleavage product. In the approach shown in FIG. 62, the flap contains a 5' encoded identifying signature modifier, and different products distinguished by the mobility of the 5' encoded identifying signature modifier in a time-of-flight channel. In the approach illustrated in FIG. 63, the cleavage product is a bar-code that is distinguished from other bar-codes based on its sequence when passing through a nanopore.

FIGS. 64-66 illustrate interrogation of support bound single molecule clusters of target DNA using polymerase extension assays. These assays are designed for easily distinguishing insertions or deletions, repeat polymorphisms, copy enumeration, as well as for distinguishing methylation status of a target after bisulfite conversion. Upstream and downstream oligonucleotides flank the area of potential length or sequence variation. A DNA polymerase lacking 5'-3' exonuclease activity and strand displacement activity extends the 3' end first primer until it cannot extend further due to the presence of the second oligonucleotide. In one embodiment, the upstream primer has a mutation or SNP-specific base at its 3' terminus, and will only extend if it is perfectly matched to the complementary base of the target. In a variation of this embodiment, the upstream primer comprises a nucleotide analogue or mismatched base at the second or third position from the 3' end to enhance the discrimination in extending on a matched base on the 3' end. In another embodiment, the upstream and downstream oligonucleotides flank a region containing a di-, tri-, or tetranucleotide repeat region, and the different polymorphisms are distinguished by different length products. In a variation of this embodiment, polymerase incorporates one or more nucleotide analogues into the extension product, which act as identifying signature modifiers. The products are subsequently distinguished by the combination of length and the identifying signature modifiers. In another embodiment, the target DNA is converted with bisulfite, such that methylated CpG dinucleotides retain a CpG sequence, while unmethylated CpG dinucleotides are converted to a TpG sequence. Polymerase incorporates one or more dCTP analogues comprising an encoded identifying signature modifier into the extension product, and products are subsequently distinguished by the combination of length and encoded identifying signature modifiers, which enumerate the number of original methylated CpG dinucleotides in the target. In these assays, the second oligonucleotide primer contains either mismatched bases or a blocking group on the 3' end so that it does not extend to create a confounding signal.

In FIG. 64, the upstream primer contains a 5' identifying signature modifier, and different mutations, alleles, insertions, deletions, sequence, or length polymorphisms are distinguished by mobility of the extension product containing the 5'identifying signature modifier in a time-of-flight channel. As described above, the product is fed through at least a first and second nanopore that are positioned on opposing ends of a nano-scale time-of-flight channel. The time it takes for the extension product to pass through the first nanopore, the time-of-flight channel and the second nanopore is measured and used as the identifying signature of the extension product.

In FIG. 65, the polymerase extension incorporates nucleotide analogues, such that the resulting extension product contains an encoded identifying signature modifier. The extension products are fed through at least first and second nanopore that are positioned on opposing ends of a nanoscale time-of-flight channel. The time-of-flight of the product through the channel is measured and used to distinguish different extension products corresponding to different alleles. In FIG. 66, the extension product comprises both a 5' identifying signature modifier on the 5' end as well as 3' encoded identifying signature modifiers. The combined signature differences are distinguished when passing the extension products through a nano-pore.

Figure 67:
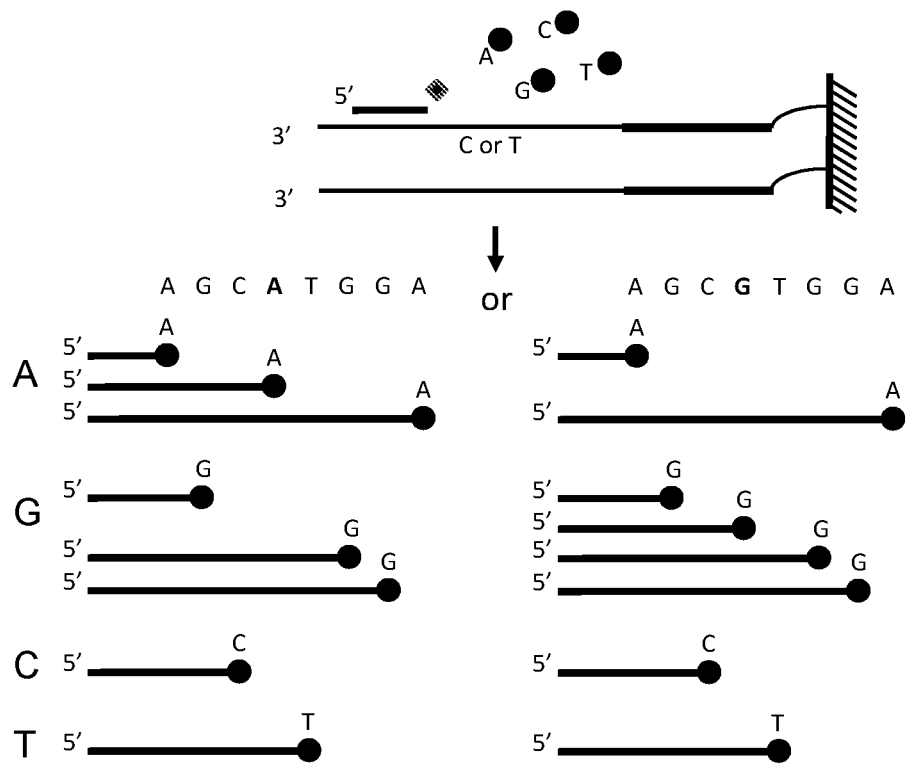
FIG. 67 illustrates interrogation of support bound single molecule clusters of target DNA by dideoxy sequencing based methods.
Figure 68:
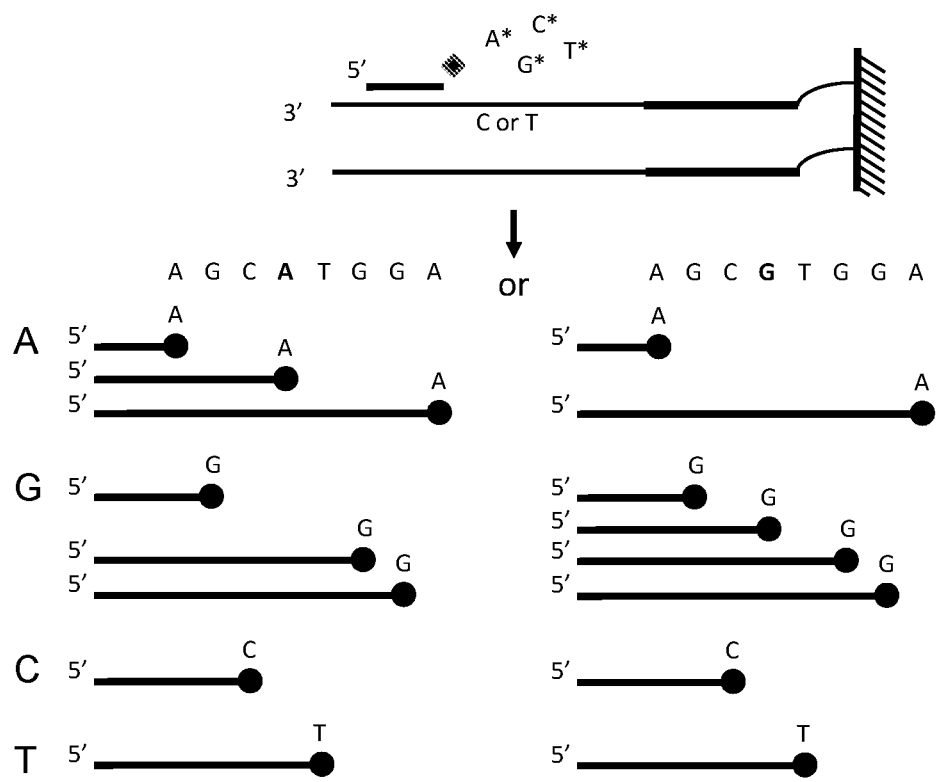
FIG. 68 illustrates interrogation of support bound single molecule clusters of target DNA by dideoxy sequencing based methods.

FIGS. 67 and 68 illustrate a version of Sanger sequencing using polymerase to extend a target-specific primer using a mix of dNTPs and base-specific modified terminators in four separate reactions. In FIG. 67, nucleotide terminators comprise an encoded identifying signature modifier. Polymerase extends a primer with dNTPs, and appends the nucleotide analogue terminators to the 3'-end of each extension product in a base-specific manner. The extension products are fed through at least a first and a second nanopore positioned on opposing ends of a nano-scale time-of-flight channel, and the time-of-flight of the extension product through the channel is measured as described supra. Aligning all of the products for each of the 4 terminating bases in ascending order of time-of-flight provides the sequence information for the target. In FIG. 68, the nucleotide terminators comprise a capture group, such as biotin. After extension of primer with polymerase incorporates terminators at different positions in a base-specific manner, a thermostable version of streptavidin is appended as an identifying signature modifier to all terminated products. These extension products are subsequently denatured from target, and are fed through at least a first and a second nanopore positioned on opposing ends of a nano-scale time-of-flight channel for a time-of-flight measurement as described supra. Aligning all the products for each of the 4 terminating bases in ascending order of time-of-flight provides the sequence information for the target.

Figure 69:
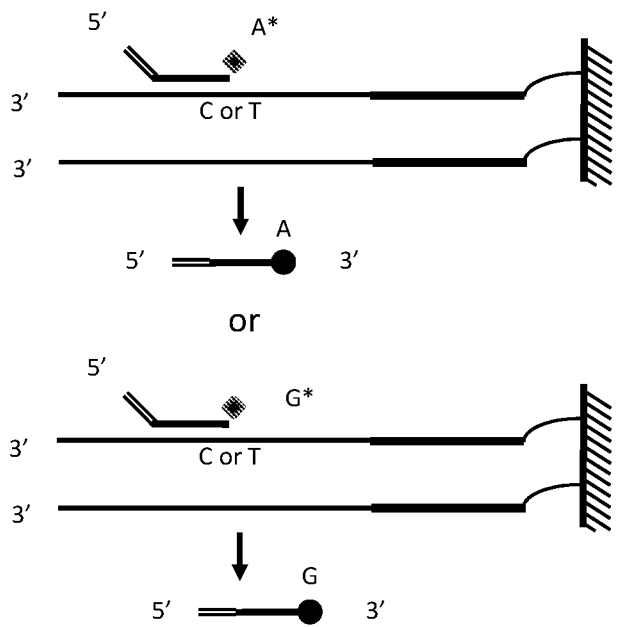
FIG. 69 illustrates interrogation of support bound single molecule clusters of target DNA using one variation of a single nucleotide extension assay.

FIG. 69. illustrates a version of primer extension (mini-sequencing) using a tailed target-specific primer with biotinylated terminators in four separate reactions (two of these reactions are shown). A thermostable version of streptavidin binds to the terminated extension product, thus appending an identifying signature modifier. Subsequently, the products are denatured from the target and are fed through at least a first and a second nanopore positioned on opposing ends of a nano-scale time-of-flight channel for a time-of-flight measurement as described supra. Different length tails allow for the primer extension assay to assay 20 to 40 alleles in a single run, with the process repeated for all 4 bases to distinguish all single-base mutations or polymorphisms.

Figure 70A:
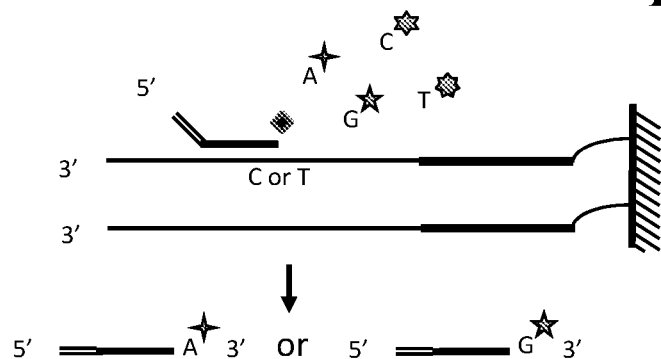
FIGS. 70A-70B illustrate interrogation of support bound single molecule clusters of target DNA using two different variations of a single nucleotide extension assay.

FIG. 70A illustrates a version of primer extension using a tailed target-specific primer with terminators containing four different encoded identifying signature modifiers, in a single reaction. The single-base extension products are fed through at least a first and second nanopore, where the first and second nanopores are positioned on opposing ends of a nano-scale time-of-flight channel. The time it takes for the extension products to pass through the first nanopore, the time-of-flight channel and the second nanopore are measured and used as the identifying signature of the extension products. Different length tails on target-specific primers containing 5' identifying signature modifiers, allows for primer extension assays to assay 10 to 20 targets in a single run.

Figure 70B:
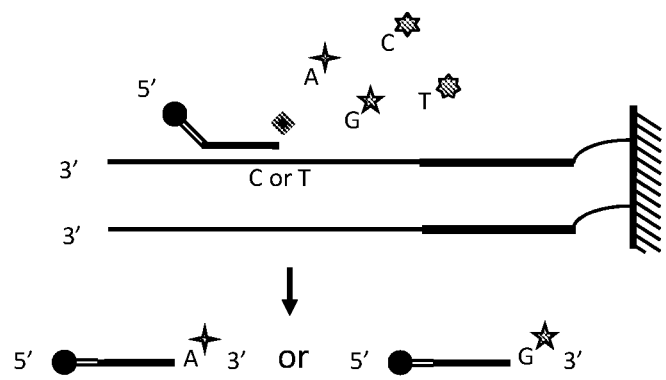

FIG. 70B illustrates a version of primer extension assay using polymerase to extend target-specific primer bearing common 5'-identifying signature modifiers with terminators containing 4 different encoded identifying signature modifiers, in a single or multiple reaction. The extension products and are fed through at least a first and a second nanopore positioned on opposing ends of a nano-scale time-of-flight channel for a time-of-flight measurement as described supra. Target-specific primers contain encoded identifying signature modifiers, providing unique combinations of time-of-flight signatures. Repeating these reactions with different 3' encoded identifying signature modifiers on different bases will provide different signatures, where the distribution of products from each run, in combination, provides the sequence information for the target.

Figure 71:
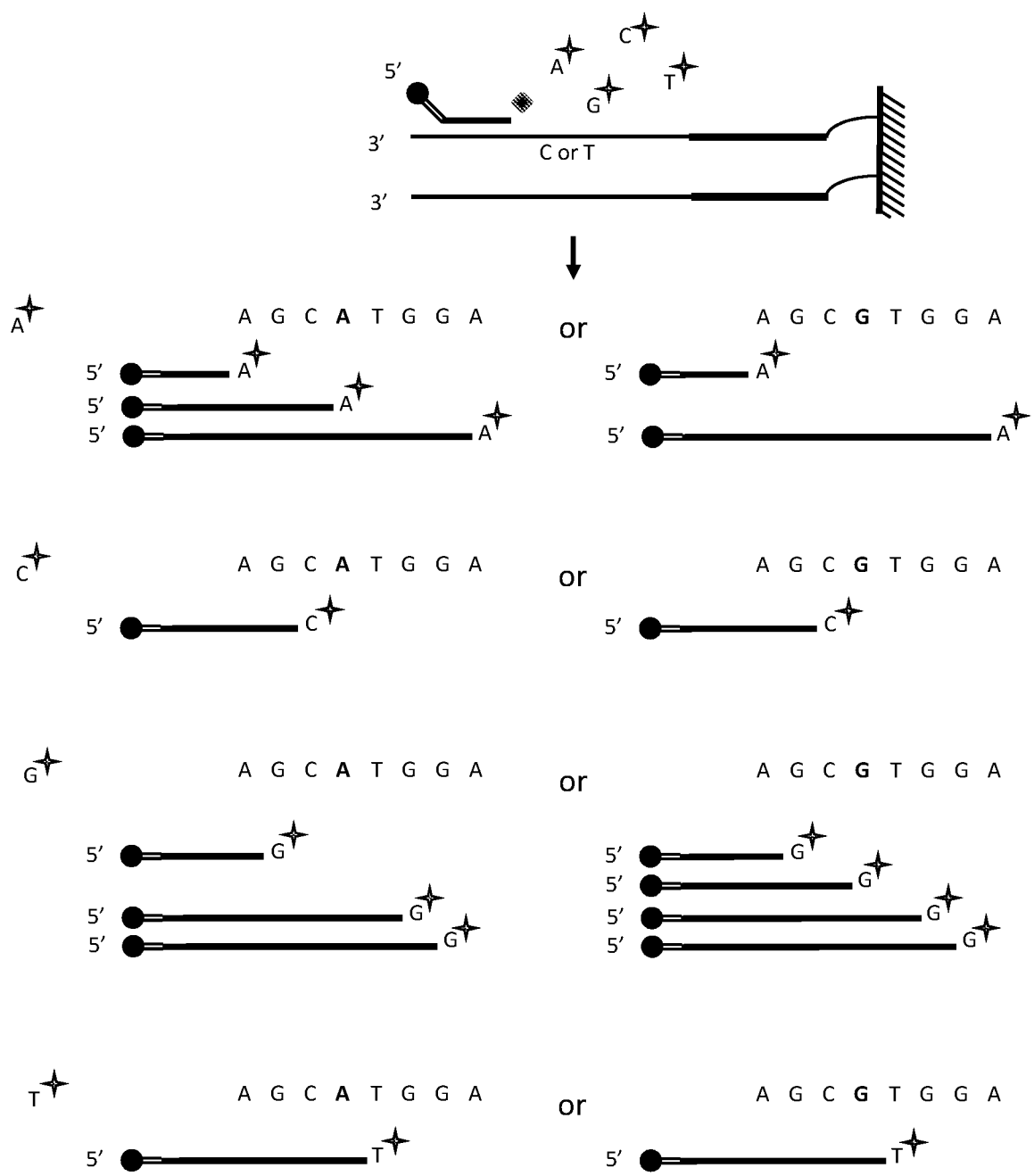
FIG. 71 illustrates interrogation of support bound single molecule clusters of target DNA by a serial four-reaction dideoxy-sequencing based method.

FIG. 71 illustrates interrogation of support bound single molecule clusters of target DNA by a serial four-reaction dideoxy-sequencing based method. A sequencing-by-chain-termination procedure is employed to generated extension products that are distinguished by their identifying signature when passing through one or more nanopores. The identifying signature of each extension product is a function of one or more identifying signature modifiers (e.g., a 5' identifying signature modifier illustrated as a black circle on the 5' end of the extension product; 3' encoded identifying signature modifiers illustrated as a star on the 3' end of the extension product), and the length of the extension products. In this illustration, only one base terminator has a 3' encoded identifying signature modifier per extension, and extension products from four separate reactions (ddA, ddC, ddG, and ddT) are detected and distinguished.

Figure 72:
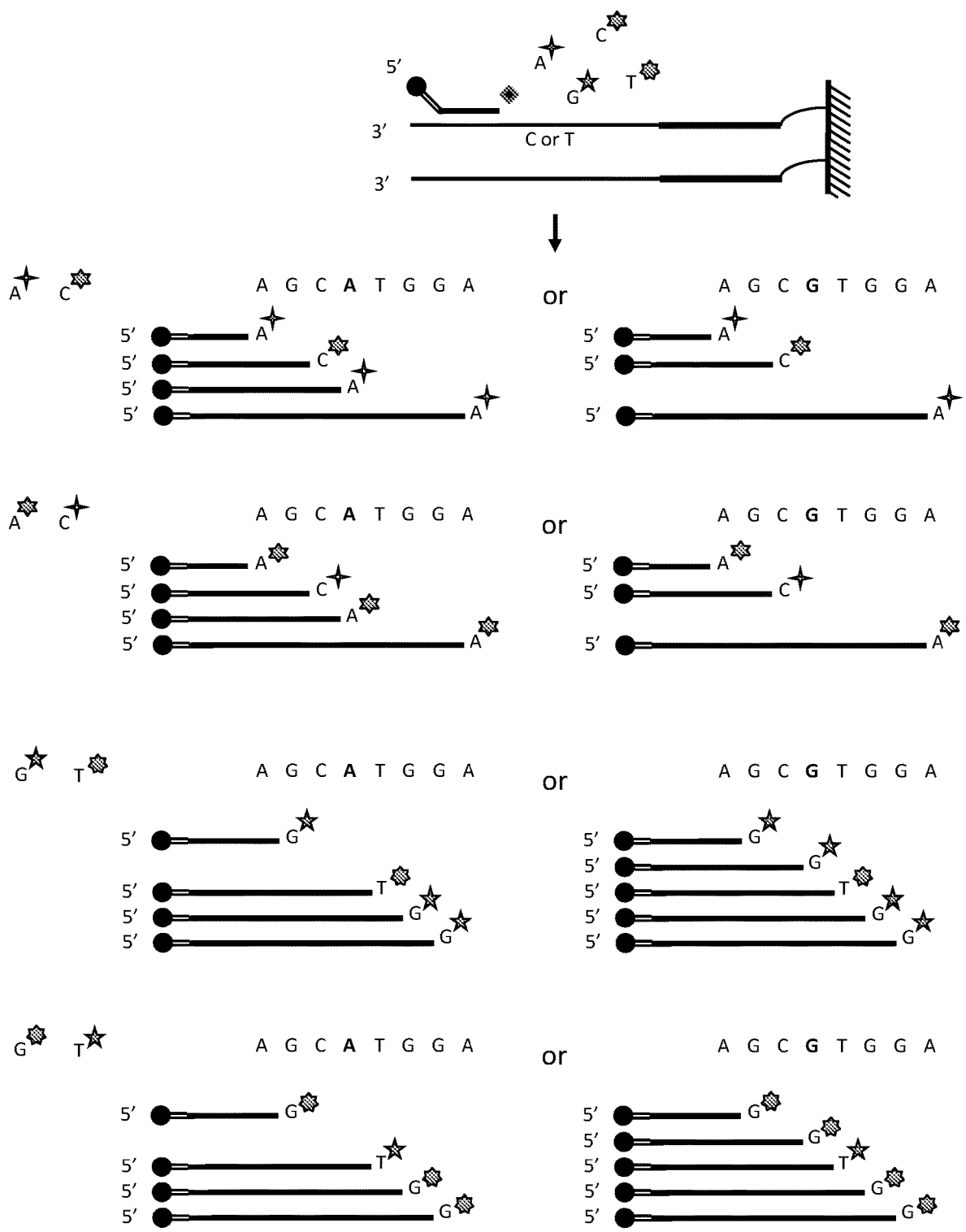
FIG. 72 illustrates interrogation of support bound single molecule clusters of target DNA by serial two-base encoded dideoxy sequencing based methods.

FIG. 72 illustrates interrogation of support bound single molecule clusters of target DNA by serial two-base encoded dideoxy sequencing based methods. Extension products that are generated in a sequencing-by-chain-termination procedure are distinguished by their identifying signature when passing through one or more nano-pores. Their identifying signature is a function of one or more identifying signature modifiers (e.g., a 5' identifying signature modifier illustrated as a black circle on the 5' end of the extension product; 3' encoded identifying signature modifiers, illustrated as a star on the 3' end of the extension product), and the length of the extension products. In this illustration, two base terminators have different 3' encoded identifying signature modifiers per extension, and extension products from four separate reactions (ddA+ddC, ddC+ddA; ddG+ddT; and ddT+ddG) are detected and distinguished.

Figure 73A:
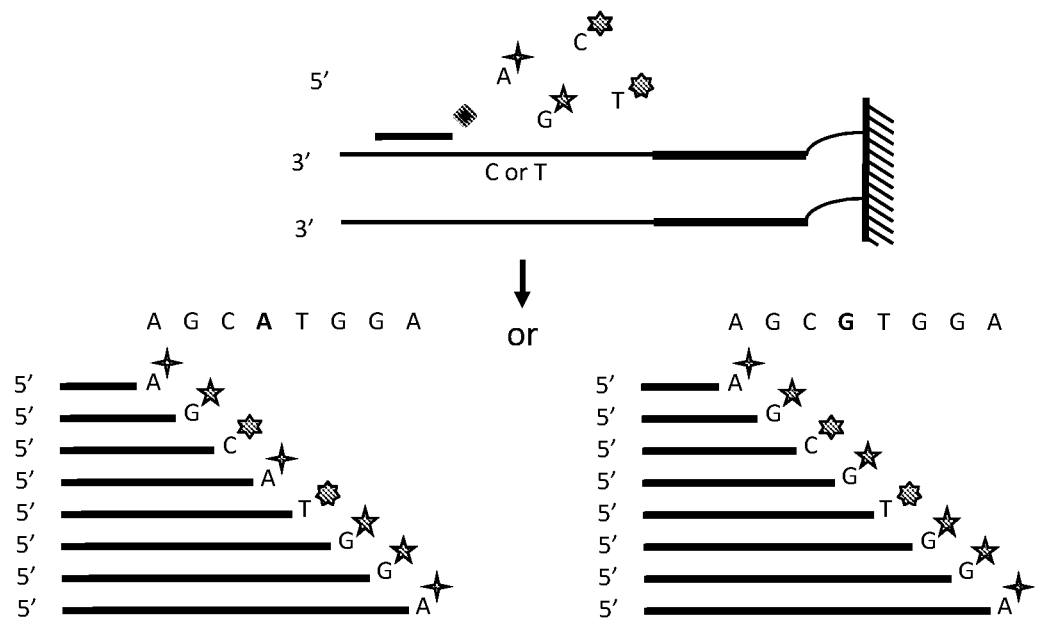
FIGS. 73A-73B illustrates interrogation of support bound single molecule clusters of target DNA using detection methods of the present invention in combination with two different parallel reaction dideoxy sequencing based methods.
Figure 73B:
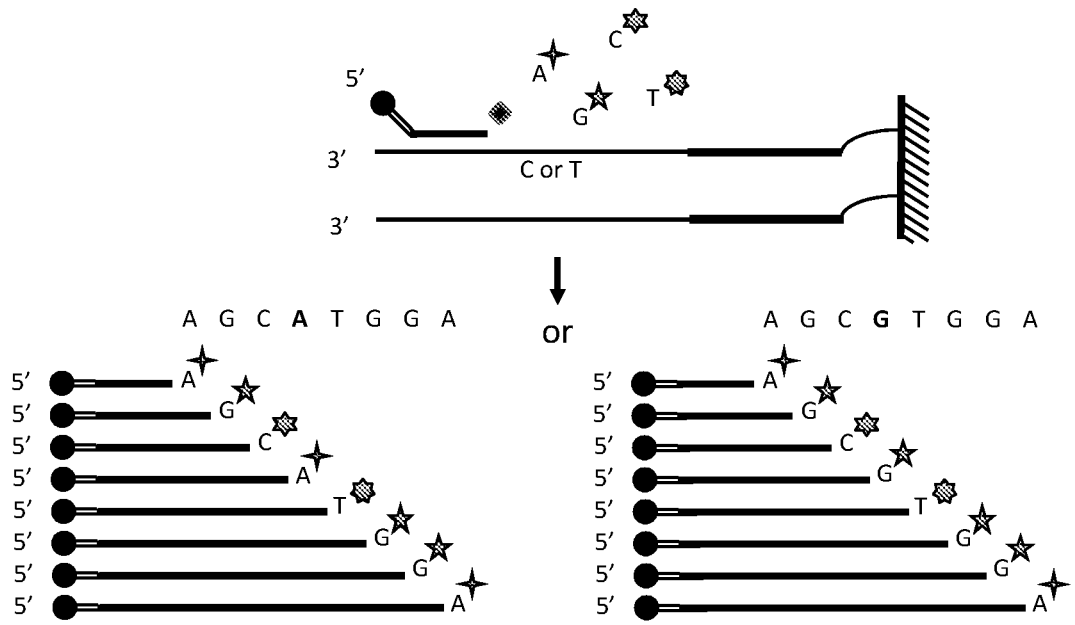

FIGS. 73A-73B illustrate interrogation of support bound single molecule clusters of target DNA using two different parallel reaction dideoxy sequencing based methods. FIG. 73A illustrates extension products in a sequencing-by-chain-termination procedure that are distinguished by an identifying signature when passing through one or more nano-pores. The identifying signature is a function of one or more identifying signature modifiers (e.g., 3' encoded identifying signature modifiers, illustrated as a star on the 3' end of the extension product), and the length of the extension products. In this illustration, all four base terminators have different 3' encoded identifying signature modifiers per extension, and extension products from four separate reactions (containing different permutations of 3' encoded identifying signature modifiers on ddA, ddC, ddG, and ddT) are detected and distinguished. FIG. 73B illustrates extension products in a sequencing-by-chain-termination procedure that are distinguished by an identifying signature that is a function of one or more identifying signature modifiers (e.g., 5' identifying signature modifier illustrated as a black circle on the 5' end of the extension product; 3' encoded identifying signature modifiers, illustrated as a star on the 3' end of the extension product), and the length of the extension products. In this illustration, all four base terminators have different 3' encoded identifying signature modifiers per extension, and extension products from four separate reactions (containing different permutations of 3' encoded identifying signature modifiers on ddA, ddC, ddG, and ddT) are detected and distinguished.

FIGS. 74-97 illustrate various embodiments of the above described methods of the present invention for detecting target nucleic acid molecules.

FIG. 74 illustrates one approach for detecting mutations or copy number of a target genomic DNA or cfDNA sequence. In this embodiment, a 3' poly-T tail is appended to the 3' ends of the target genomic DNA or cfDNA using terminal deoxynucleotidyl transferase (TdT) (FIG. 74, Steps A-B). The poly-T tail is approximately ~100-150 nucleotides in length. The 3' tailed target nucleic acid molecules are distributed on a solid support containing immobilized capture oligonucleotides having a complementary poly-dA sequence (containing a stretch of approximately 30 or more adenine bases, dA30). The poly-T tail of the target nucleic acid molecule hybridizes to the dA30 primer (FIG. 74, Step C), and the primer is extended using a strand displacing polymerase, such as Bst. Following extension at ~37° C., the temperature is raised to ~55-60° C. to partially denature the dT tail of the target nucleic acid molecule from the dA30 primer. This allows an adjacent dA30 primer to hybridize and polymerase to displace the first primer extension strand (FIG. 74, Step D). By this repetitive process, the original strand is "handed-off" to the next primer to achieve a linear amplification of the original DNA. As shown in FIG. 74, Step E, oligonucleotide ligation probes containing an identifying signature modifier are introduced to carry out the ligation reaction on the plurality of hybridized complementary target nucleic acid molecule extension products. The unligated probes are washed away, and the ligation products are denatured from the immobilized complementary target nucleic acid extension products and fed through the one or more nanopores for detection of their identifying signature.

FIG. 75 illustrates a similar process as shown in FIG. 74. However, in this embodiment, the specificity of the ligation process is enhanced by using first oligonucleotide probes (i.e., discriminating oligonucleotide probes) having a blocking moiety on their 3'end which prevent ligation. As shown in FIG. 75, step E, the mutation specific ligation probe contains a cleavable blocking moiety, i.e., the moiety is removed by cleaving a ribose base located a couple of bases in from the 3' end using RNaseH2. RNaseH2 cleavage only occurs when the oligonucleotide probe is hybridized to its complementary target nucleic acid molecule. The oligonucleotide probe designed to detect the non-mutant (wild-type) target nucleic acid molecule contains a blocking group that is not cleavable. The mutation specific ligation probe in this embodiment is also designed to contain an identifying signature modifier that enhances its detection and discrimination from unligated probes and other ligation products.

The embodiment illustrated in FIG. 76 is similar to the embodiment illustrated in FIG. 75. However, in this embodiment, the genomic DNA or cfDNA is treated with uracil DNA glycosylase and EndoVII prior to appending an adapter portion and immobilizing to a solid support to prevent carryover contamination and prepare DNA or cfDNA for appending a 3' poly-dU tail (approximately 100-150 dU) (FIG. 76, steps A-B). In this embodiment, the poly-dU tail of the target nucleic acid molecule hybridizes to its complementary capture oligonucleotide sequence (dA30 primer) immobilized to the solid support (FIG. 76, step C). Linear amplification and generation of extension products complementary to the target nucleic acid molecules are carried out as described supra (FIG. 76, step D). The upstream, discriminating ligation probes contain a cleavable (mutation specific oligonucleotide probe) or non-cleavable (wildtype specific oligonucleotide probe) blocking moiety and the downstream probe contains a dU at the penultimate 3' position for extra protection (FIG. 76, steps E, F).

The embodiment depicted in FIG. 77 highlights the use of an enhanced ligation reaction process. Steps A-D of FIG. 77 are the same as steps A-D of FIG. 75, however, oligonucleotide probes of a probe set are designed such that the terminal 3' base of the first oligonucleotide probe is overlapped by the immediately flanking 5'-most base of the second oligonucleotide probe that is complementary to the target nucleic acid molecule. The overlapping nucleotide is referred to as a "flap". When the overlapping flap nucleotide of the second oligonucleotide probe is complementary to the target nucleic acid molecule extension sequence and the same sequence as the terminating 3' nucleotide of the first oligonucleotide probe, the phosphodiester bond immediately upstream of the flap nucleotide of the second oligonucleotide probe is discriminatingly cleaved by an enzyme having flap endonuclease (FEN) or 5' nuclease activity (such as the 5'-3' exonuclease activity of a polymerase). That specific FEN activity produces a novel ligation competent 5' phosphate end on the second oligonucleotide probe that is precisely positioned alongside the adjacent 3' OH of the first oligonucleotide probe. The ligase covalently seals the upstream and unblocked downstream oligonucleotides together to generate ligation products containing an identifying signature moiety suitable for detection (FIG. 77, steps F-G)

FIG. 78 illustrates a method of detecting a target nucleotide sequence using a cleavage assay. FIG. 78 is similar to FIG. 77 but uses a downstream primer with a flap bearing a 5' identifying signature modifier to allow detection as described in FIG. 61. Oligonucleotide probes of a probe set are designed such that the 3'-most base of the first oligonucleotide probe is overlapped by an immediately flanking 5'-base of the second oligonucleotide probe that is complementary to the target nucleic acid molecule. The overlapping nucleotide has additional bases on the 5' side (referred to as a flap), and an identifying signature moiety. When the overlapping flap nucleotide of the second oligonucleotide probe is complementary to the target nucleic acid molecule extension sequence and the same sequence as the terminating 3' nucleotide of the first oligonucleotide probe, the phosphodiester bond immediately upstream of the flap nucleotide of the second oligonucleotide probe is discriminatingly cleaved by an enzyme having flap endonuclease (FEN) or 5' nuclease activity (such as the 5'-3' exonuclease activity of a polymerase). The cleaved products contain an identifying signature moiety suitable for detection (FIG. 78, step E). Since the product is released during the enzymatic reaction, one embodiment involves adding reagents and enzymes to the solid support in the absence of a metal co-factor, washing away unhybridized primers and other reagents/enzymes, and then initiating the cleavage reaction by addition of the metal cofactor (i.e. Mg2+). Alternatively, the flap can bear different 5' identifying signature modifiers, or a sequence bar-code to allow detection as described in FIGS. 62 and 63 respectively.

FIG. 79 illustrates a method of detecting a target nucleotide sequence using a primer extension assay. FIG. 79 is similar to FIG. 77 but uses nucleotide terminators bearing 3' encoded identifying signature modifiers to allow detection of the next nucleotide base as described in FIG. 70B. Oligonucleotide probes are designed to hybridize to the target such that the 3' base is upstream of the potential SNP or mutation. Polymerase extends the probes using dideoxyterminators containing different 3' encoded identifying signature modifiers for each base. Single-nucleotide extension products that may be distinguished by an identifying signature when passing through one or more nanopores, that is a function of one or more identifying signature modifiers (5' identifying signature modifier—illustrated as a black circle on the 5' end of the extension product; 3' encoded identifying signature modifier, illustrated as a star on the 3' end of the extension product), and the time-of-flight of the single-nucleotide extension products (FIG. 79, steps F & G). Alternatively, the 5' end of the probe can bear a sequence bar-code to allow detection as described in FIG. 70A.

FIG. 80 (Primer extension assay) is similar to FIG. 77 but uses an upstream probe comprising a 5' identifying signature modifier and a downstream probe comprising a 3' end to block primer extension, to allow detection of potential nucleotide length variation as described in FIG. 64. Oligonucleotide probes are designed to hybridize to the target such that the upstream and downstream probes flank the potential repeat polymorphism. A DNA polymerase lacking 5'-3' exonuclease activity and strand displacement activity extends the upstream probe until it cannot extend further due to the presence of the downstream probe. Different length extension products that may be distinguished by an identifying signature when passing through one or more nanopores, that is a function of the 5' identifying signature modifier (illustrated as a black circle on the 5' end of the extension product), and the time-of-flight of the extension products (FIG. 80, steps F & G). Alternatively, polymerase incorporates one or more nucleotide analogues comprising an encoded identifying signature modifier into the extension product, and products are subsequently distinguished by the combination of identifying signature modifier, encoded identifying signature modifiers, and/or length to allow detection as described in FIGS. 65 and 66.

The embodiment illustrated in FIG. 81 is also similar to the embodiment shown in FIG. 75. However, in step 2 of FIG. 81 the poly-T tails are appended to the target nucleic acid molecules via ligation of linkers having single-base poly-T tails (i.e., 3'-T30 tails). In one version, genomic DNA or cfDNA ends are made blunt using polymerase with proofreading activity in the presence of dNTPs, 5' end phosphorylated with T4 kinase, followed by 3' end extension with a single adenine base, and ligation of A:T rich linkers having single-base poly-T tails (i.e., 3'-T30 tails). All subsequent steps of FIG. 81 are the same as those shown and described in relation to FIG. 75.

FIG. 82 (Cleavage Assay) is similar to FIG. 81 but uses a downstream primer with a flap bearing a 5' identifying signature modifier to allow detection as described in FIG. 61. Alternatively, the flap can bear different 5' identifying signature modifiers, or a sequence bar-code to allow detection as described in FIGS. 62 and 63, respectively.

FIG. 83 (Primer extension assay) is similar to FIG. 81 but uses nucleotide terminators bearing 3' encoded identifying signature modifiers to allow detection of the next nucleotide base as described in FIG. 70B. Alternatively, the 5' end of the probe can bear a sequence bar-code to allow detection as described in FIG. 70A.

FIG. 84 (Primer extension assay) is similar to FIG. 81 but uses an upstream probe comprising a 5' identifying signature modifier and a downstream probe comprising a 3' end to block primer extension, to allow detection of potential nucleotide length variation as described in FIG. 64. Alternatively, polymerase incorporates one or more nucleotide analogues comprising an encoded identifying signature modifier into the extension product, and products are subsequently distinguished by the combination of identifying signature modifier, encoded identifying signature modifiers, and/or length to allow detection as described in FIGS. 65 and 66.

FIG. 85 shows an approach for target nucleic acid molecule enrichment prior to immobilization on the solid support. In this embodiment, a poly-T tail is appended to the 3'end of genomic or cell-free DNA using TdT as shown in steps A-B. Tailed double stranded DNA is denatured to allow a locus specific primer to hybridize. As shown in step C of FIG. 85, this primer can contain a 3' cleavable blocking moiety that prevents polymerase extension in the absence of target nucleic acid molecule hybridization. Once the blocking moiety is cleaved, in this case via RNaseH2 cleavage at an internal ribose base, the hybridized primer is extended using polymerase and biotin d-CTP. The biotinylated extension product is captured on a streptavidin coated solid support and non-captured non-target nucleic acid molecules are removed from the sample. The biotinylated target nucleic acid molecules are released from the streptavidin coated solid, support to produce a target nucleic acid molecule enriched sample that is suitable for further analysis as shown in steps E-H of FIG. 85 (i.e., immobilization of the target nucleic acid molecule to the solid support via hybridization to complementary capture oligonucleotide (step E), polymerase mediated extension of hybridized capture oligonucleotide to form immobilized complementary target nucleic acid molecule extension products (step F), and ligation reaction to produce detectable ligation products (steps G-H).

FIG. 86 (Cleavage Assay) is similar to FIG. 85 but uses a downstream primer with a flap bearing a 5' identifying signature modifier to allow detection as described in FIG. 61. Alternatively, the flap can bear different 5' identifying signature modifiers, or a sequence bar-code to allow detection as described in FIGS. 62 and 63, respectively.

FIG. 87 (Primer extension assay) is similar to FIG. 85 but uses nucleotide terminators bearing 3' encoded identifying signature modifiers to allow detection of the next nucleotide base as described in FIG. 70B. Alternatively, the 5' end of the probe can bear a sequence bar-code to allow detection as described in FIG. 70A.

FIG. 88 (Primer extension assay) is similar to FIG. 85 but uses an upstream probe comprising a 5' identifying signature modifier and a downstream probe comprising a 3' end to block primer extension, to allow detection as described in FIG. 64. Alternatively, polymerase incorporates one or more nucleotide analogues comprising an encoded identifying signature modifier into the extension product, and products are subsequently distinguished by the combination of identifying signature modifier, encoded identifying signature modifiers, and/or length to allow detection as described in FIGS. 65 and 66.

The embodiment illustrated in FIG. 89 involves appending poly-T tails to the 3' ends of genomic DNA or cfDNA using blunt end digestion, 3' end single base extension, and ligation of linkers containing the poly-T tails as described above in reference in FIG. 81 (FIG. 89, step B). Additionally, this embodiment utilizes the target nucleic acid enrichment step described in reference to FIG. 85, where 3' tailed double stranded DNA is denatured to allow a locus specific primer to hybridize. As shown in step C of FIG. 89, this primer can contain a 3' cleavable blocking moiety that prevents polymerase extension in the absence of target nucleic acid molecule hybridization. Once the blocking moiety is cleaved, in this case via RNaseH2 cleavage at an internal ribose base, the hybridized primer is extended using polymerase and biotin d-CTP. The biotinylated extension product is captured on a streptavidin coated solid support and non-captured non-target nucleic acid molecules are removed from the sample. The biotinylated target nucleic acid molecules are released from the streptavidin coated solid support to produce a target nucleic acid molecule enriched sample that is suitable for further analysis as described supra.

FIG. 90 (Cleavage Assay) is similar to FIG. 89 but uses a downstream primer with a flap bearing a 5' identifying signature modifier to allow detection as described in FIG. 61. Alternatively, the flap can bear different 5' identifying signature modifiers, or a sequence bar-code to allow detection as described in FIGS. 62 and 63, respectively.

FIG. 91 (Primer extension assay) is similar to FIG. 89 but uses nucleotide terminators bearing 3' encoded identifying signature modifiers to allow detection of the next nucleotide base as described in FIG. 70B. Alternatively, the 5' end of the probe can bear a sequence bar-code to allow detection as described in FIG. 70A.

FIG. 92 (Primer extension assay) is similar to FIG. 89 but uses an upstream probe comprising a 5' identifying signature modifier and a downstream probe comprising a 3' end to block primer extension, to allow detection as described in FIG. 64. Alternatively, polymerase incorporates one or more nucleotide analogues comprising an encoded identifying signature modifier into the extension product, and products are subsequently distinguished by the combination of identifying signature modifier, encoded identifying signature modifiers, and/or length to allow detection as described in FIGS. 65 and 66.

FIG. 93 shows another approach for appending adapters containing poly-T tails to the target nucleic acid molecules. In this embodiment, the genomic DNA is blunt end digested, and the 3' ends are extended with a single adenine base to form ends suitable A:T rich linker ligation (FIG. 93, step B). The ligated linkers contain single-base T overhangs and 5' polyA tails. The double stranded DNA is denatured to allow a locus primer containing cleavable blocking moieties on its 3' and 5' ends to hybridize to its complementary region on the target nucleic acid molecule. The blocking moieties are cleaved only when the primer hybridizes to its target nucleic acid molecule and is extended to form an extension product of the target nucleic acid molecule containing a poly-T tail on its 3'end (FIG. 93, step C). The poly-dA linkers can optionally be removed using a 5' nuclease. The extension products containing the 3' poly-T tails are then suitable for immobilization on the solid support via hybridization to their complementary capture poly-dA oligonucleotide primers on the support.

FIG. 94 (Cleavage Assay) is similar to FIG. 93 but uses a downstream primer with a flap bearing a 5' identifying signature modifier to allow detection as described in FIG. 61. Alternatively, the flap can bear different 5' identifying signature modifiers, or a sequence bar-code to allow detection as described in FIGS. 62 and 63 respectively.

FIG. 95 (Primer extension assay) is similar to FIG. 93 but uses nucleotide terminators bearing 3' encoded identifying signature modifiers to allow detection of the next nucleotide base as described in FIG. 70B. Alternatively, the 5' end of the probe can bear a sequence bar-code to allow detection as described in FIG. 70A.

FIG. 96 (Primer extension assay) is similar to FIG. 93 but uses an upstream probe comprising a 5' identifying signature modifier and a downstream probe comprising a 3' end to block primer extension, to allow detection as described in FIG. 64. Alternatively, polymerase incorporates one or more nucleotide analogues comprising an encoded identifying signature modifier into the extension product, and products are subsequently distinguished by the combination of identifying signature modifier, encoded identifying signature modifiers, and/or length to allow detection as described in FIGS. 65 and 66.

FIG. 97 shows another approach for appending adapters containing poly-T tails to the target nucleic acid molecules. In this embodiment, genomic DNA is denatured and a locus specific primer containing a 5' poly-dA tail and 3' cleavable blocking moiety is hybridized. Once hybridized, the cleavable blocking moiety is removed and the primer extends in the presence of a thermostable polymerase to form an extension product containing a 5' poly-dA tail. A second primer that is complementary to the formed extension product is provided. As shown in FIG. 97, step C, this primer can contain a 5' and 3' blocking moiety, where at least the 3' blocking moiety is cleavable when the primer is hybridized to its complementary sequence of the extension product. Following cleavage of the 3' blocking moiety of the hybridized second primer, the primer is extended to form a secondary extension product having a 3' poly-T tail. The poly-dA linkers can optionally be removed using a 5' nuclease. The extension products containing the poly-T tails are then suitable for immobilization on the solid support via hybridization to their complementary capture poly-dA oligonucleotide primers on the support.

FIG. 98 (Cleavage Assay) is similar to FIG. 97 but uses a downstream primer with a flap bearing a 5' identifying signature modifier to allow detection as described in FIG. 61. Alternatively, the flap can bear different 5' identifying signature modifiers, or a sequence bar-code to allow detection as described in FIGS. 62 and 63 respectively.

FIG. 99 (Primer extension assay) is similar to FIG. 97 but uses nucleotide terminators bearing 3' encoded identifying signature modifiers to allow detection of the next nucleotide base as described in FIG. 70B. Alternatively, the 5' end of the probe can bear a sequence bar-code to allow detection as described in FIG. 70A.

FIG. 100 (Primer extension assay) is similar to FIG. 97 but uses an upstream probe comprising a 5' identifying signature modifier and a downstream probe comprising a 3' end to block primer extension, to allow detection as described in FIG. 64. Alternatively, polymerase incorporates one or more nucleotide analogues comprising an encoded identifying signature modifier into the extension product, and products are subsequently distinguished by the combination of identifying signature modifier, encoded identifying signature modifiers, and/or length to allow detection as described in FIGS. 65 and 66.

Another embodiment of the invention relates to the detection of one or more target nucleotide sequences that originally contained one or more methylated resides. In accordance with this embodiment, one or more approaches can be utilized to enrich the sample for the methylated target nucleic acid molecules to enhance detection and discrimination from unmethylated target nucleic acid molecules. A first approach is to contact the sample with at least a first methylation sensitive enzyme to form a restriction enzyme reaction mixture prior to immobilizing the target nucleic acid molecule on the solid support (see e.g., FIGS. 101-105). In accordance with this and all aspects of the present invention, a "methylation sensitive enzyme" is an endonuclease that will not cleave its cognate recognition sequence in a nucleic acid molecule when it contains a methylated residue (i.e., it is sensitive to the presence of a methylated residue within its recognition sequence). A "methylation sensitive enzyme recognition sequence" is the cognate recognition sequence for a methylation sensitive restriction enzyme. A non-limiting list of methylation sensitive restriction endonuclease enzymes that are suitable for use in the methods of the present invention include, without limitation, AciI, HinP1I, Hpy99I, HpyCH4IV, BstUI, Bsh1236I, HpaII, HhaI, TaiI, or any combination thereof. Alternatively, or in combination with the above described approach, the sample may be subject to a bisulfite treatment, which converts unmethylated cytosine residues to uracil residues (see e.g., FIGS. 106-108). Yet another approach that can be used alone or in combination with the above approaches when applicable, is to include one or more methylation sensitive enzymes that cleave double stranded nucleic acid molecules containing unmethylated residues within a methylation sensitive enzyme recognition sequence in the polymerase replication reaction where immobilized extension products complementary to the target nucleic acid molecule are formed. In accordance with this approach, the methylation sensitive enzyme will cleave double stranded DNA (i.e., the immobilized target nucleic acid molecule hybridized to its complementary extension product formed from extension of the immobilized capture molecule) if unmethylated, but not if the double stranded complex is a hybrid containing methylated and unmethylated resides at corresponding positions (see e.g., FIG. 101).

FIGS. 101-108 illustrate various embodiments of the present invention suitable for detecting the presence of methylated target nucleic acid molecules in the sample. In FIG. 101, the genomic DNA or cfDNA containing methylated residues is optionally enriched for methylated DNA using methylation specific antibodies. As shown in FIG. 101, step B, a poly-T tail is appended to the 3'end of genomic or cell-free DNA using TdT. The tailed DNA is treated with methyl sensitive restriction endonuclease Bsh1236I which cleaves DNA at a recognition sequence consisting of CG^CG, when unmethylated. The uncleaved DNA is immobilized on a solid support via hybridization between the poly-T tails of the target nucleic acid molecule and poly-dA primers of the solid support (FIG. 101, step D). The immobilized capture oligonucleotides are extended to form immobilized extension products complementary to the target nucleic acid molecules in the presence of BstU1, methylation sensitive enzymes that cleave double stranded nucleic acid molecules containing unmethylated residues. BstU1 cleaves dsDNA if unmethylated, but does not digest hybrid methylated/unmethylated DNA or unmethylated ssDNA (FIG. 101, step E). Accordingly, extension products of originally methylated target nucleic acid molecules remain immobilized to the solid support and are subject tor the ligation reaction to form detectable ligation products.

FIG. 102 (Cleavage Assay) is similar to FIG. 101 but uses a downstream primer with a flap bearing a 5' identifying signature modifier to allow detection as described in FIG. 61. Alternatively, the flap can bear different 5' identifying signature modifiers, or a sequence bar-code to allow detection as described in FIGS. 62 and 63, respectively.

FIG. 103 (Primer extension assay) is similar to FIG. 101 but uses nucleotide terminators bearing 3' encoded identifying signature modifiers to allow detection of the next nucleotide base as described in FIG. 70B. Alternatively, the 5' end of the probe can bear a sequence bar-code to allow detection as described in FIG. 70A.

FIG. 104 (Primer extension assay) is similar to FIG. 101 but uses an upstream probe comprising a 5' identifying signature modifier and a downstream probe comprising a 3' end to block primer extension, to allow methylation detection as described in FIG. 64. Alternatively, polymerase incorporates one or more nucleotide analogues comprising an encoded identifying signature modifier into the extension product, and products are subsequently distinguished by the combination of identifying signature modifier, encoded identifying signature modifiers, and/or length to allow detection as described in FIGS. 65 and 66.

The embodiment of FIG. 105 is similar to that shown in FIG. 101, but includes an additional target nucleic acid enrichment step (i.e., FIG. 105, step C) using biotin/streptavidin capture as described supra. Specifically, the tailed double stranded DNA is denatured to allow a locus specific primer to hybridize. As shown in step C of FIG. 105, this primer can contain a 3' cleavable blocking moiety that prevents polymerase extension in the absence of target nucleic acid molecule hybridization. Once the blocking moiety is cleaved, in this case via RNaseH$_2$ cleavage at an internal ribose base, the hybridized primer is extended using polymerase and biotin d-CTP. The biotinylated extension product is captured on a streptavidin coated solid support and non-captured non-target nucleic acid molecules are removed from the sample. The biotinylated target nucleic acid molecules are released from the streptavidin coated solid support to produce a target nucleic acid molecule enriched sample that is suitable for further analysis as shown in steps E-H of FIG. 101, i.e., immobilization of the target nucleic acid molecule to the solid support via hybridization to complementary capture oligonucleotide (FIG. 105, step E), polymerase mediated extension of hybridized capture oligonucleotide to form immobilized complementary target nucleic acid molecule extension products (step F), methylation sensitive enzymatic digestion of unmethylated dsDNA (step F), and ligation reaction to produce detectable ligation products (steps G-H).

The embodiments illustrated in FIGS. 106, 107, and 108 show approaches for enriching methylated target nucleic acid molecules using a bisulfite treatment. In these embodiments, poly-T tails are appended to the 3' ends of genomic DNA or cfDNA using TdT (FIGS. 106 and 107, step B) or by blunt end digestion, single nucleotide extension, and ligation of A:T rich linkers containing 5'dA$_{30}$ tails (FIG. 108, step B). As shown in step C of FIGS. 106, 107, and 108, the adapter appended target nucleic acid molecules are subject to a bisulfite treatment which converts unmethylated dC to dU and renders the strands of DNA non-complementary to each other. The bisulfite treated target nucleic acid molecules is ready for immobilization to the solid support (FIGS. 106 and 107, step D), or for locus specific primer hybridization and extension to create an extension product having a 3' poly-T tail suitable for capture and immobilization to the solid support (FIG. 108, steps D-E). The process of generating immobilized complementary target nucleic acid molecules extension products and ligation products indicative of target nucleic acid molecules originally containing methylated residues is carried out as described supra.

FIG. 107 (Primer extension assay) is similar to FIG. 106 but uses an upstream probe comprising a 5' identifying signature modifier and a downstream probe comprising a 3' end to block primer extension, to allow detection of a methylation product as described in FIG. 66. A polymerase incorporates one or more dCTP nucleotide analogues comprising an encoded identifying signature modifier into the extension product, and products are subsequently distinguished by the combination of identifying signature modifier, encoded identifying signature modifiers, and length to allow quantification of the number of methylated CpG dinucleotides in the original target region.

FIG. 109 (Primer extension assay) is similar to FIG. 107 and uses an upstream probe comprising a 5' identifying signature modifier, a downstream probe comprising a 3' end to block primer extension, and incorporation of one or more dCTP nucleotide analogues comprising an encoded identifying signature modifier into the extension product to allow methylation detection as described supra.

FIG. 110 (Cleavage Assay) is similar to FIG. 108 but uses a downstream primer with a flap bearing a 5' identifying signature modifier to allow detection as described in FIG. 61. Alternatively, the flap can bear different 5' identifying signature modifiers, or a sequence bar-code to allow detection as described in FIGS. 62 and 63, respectively FIG. 111 (Primer extension assay) is similar to FIG. 108 but uses nucleotide terminators bearing 3' encoded identifying signature modifiers to allow detection of the next nucleotide base as described in FIG. 70B. Alternatively, the 5' end of the probe can bear a sequence bar-code to allow detection as described in FIG. 70A.

In some embodiments of the present invention, the one or more target nucleic acid molecules containing a target nucleotide sequence of interest is a ribonucleic acid (RNA) molecule. Detection of mRNA requires conversion into cDNA. This approach depends on the fidelity of four enzymes: (i) reverse Transcriptase to faithfully copy low-level copies of mRNA, lncRNA, or aberrant RNA transcripts in the initial sample, (ii) terminal transferase to generate T tails on all or selected cDNA fragments (iii) polymerase to replicate the tailed cDNA, and (iv) thermostable ligase in discriminating probes hybridized adjacent to each other. Once a ligation event has taken place, those products will be uniquely identified and distinguished using one or more nanopores alone or in combination with a time-of-flight nanotube based on their identifying signature.

Recently, an approach for appending primer sequences based on strand-switching of reverse transcriptase has been developed (Picelli et al., "Full-length RNA-seq from Single Cells using Smart-seq2," Nat Protoc. 9(1):171-81 (2014), which is hereby incorporated by reference in its entirety). This may be modified for use with the methods described herein, and depends on the fidelity of three enzymes: (i) reverse Transcriptase to faithfully copy low-level copies of mRNA, lncRNA, or aberrant RNA transcripts in the initial sample, as well as to append T tails onto the cDNA (ii) polymerase to replicate the tailed cDNA, and (iii) thermostable ligase in discriminating primers hybridized adjacent to each other. Once a ligation event has taken place, those products will be uniquely identified and distinguished based on their identifying signature.

Yet another alternative approach is dependent on directly capturing the 3' poly-A tail of mRNA and lncRNA. In this embodiment, instead of using a dA$_{30}$ primer, the solid support contains a T$_{60}$ primer. A T$_{60}$ DNA-RNA hybrid has sufficient binding affinity to work for this protocol, however the preferred temperature for replication will be in the range of 45-55° C. Strand displacing M-MuLV reverse transcriptase or Pyrophage 3173 DNA polymerase, which have reverse-transcriptase activity, are used instead of Bst polymerase.

One advantage of using a ligation reaction, e.g., ligation detection reaction (LDR), is that it can discriminate a translocation event independent of the precise breakpoints. Further, when a translocation or alternative splicing creates new exon-exon junctions, LDR is ideally suited to precisely distinguish these junctions, down to the exact bases at the junctions.

There are at least two sources of aberrantly spliced transcripts in tumors. Tumors may undergo global deregulation of gene expression through overall hypo-methylation. One consequence of hypo-methylation is the degradation of control of transcription start sites in promoter regions, allowing for alternative sequences in the 5' end of transcripts. Such alternatively spliced leader sequences may then be accurately identified and quantified using LDR-based assays. A second source of aberrantly spliced transcripts arises from deregulation of the splicing machinery. Some such transcripts are translated into proteins that facilitate or even drive tumor growth. Again, these alternatively spliced transcripts may then be accurately identified and quantified using LDR-based assays, including providing relative levels of both the aberrant and wild-type transcript in the same LDR reaction.

FIGS. 112-142 illustrate various embodiments of the present invention where mRNA is the starting target nucleic acid molecule.

As shown in FIG. 112, one approach for analyzing mRNA in accordance with the method of the present invention is to generate cDNA from the mRNA using a poly-dUV or T$_{30}$dUV primer (V is dC, dG, or dA) and reverse transcriptase as shown in FIG. 112, step 2. To ensure that neither DNA primer nor other nucleic acids in the sample are tailed, unused primer is cleaved using UDG and EndoVIII digestion, and RNA is cleaved with RNaseI and RNAseH digestion. The sample is further cleaned up to remove the digestion products and dNTPS. The remaining cDNA is suitable for appendage of poly-T containing adapter tails using TdT as described supra and shown in FIG. 112, step D. The process of target nucleic acid immobilization, extension product formation and ligation product formation continues as described supra and shown in FIG. 112, steps E-G).

The embodiment of FIG. 113 shows how target mRNA or lncRNA molecules having polyA 3' ends can be immobilized directly to the solid support via hybridization to complementary $T_{60}$ capture oligonucleotide primers on the solid support (FIG. 113, step B). Once immobilized, the hybridized capture oligonucleotide primers are extended using a suitable reverse transcriptase having strand displacement activity (e.g., M-MuLV) or polymerase having reverse transcriptase and strand displacement activity (e.g., Pyrophage 3173) to generate immobilized complementary cDNA. Raising the temperature after initial extension allows the $T_{60}$ primer to partially denature from the polyA RNA tail, which allows and adjacent primer to hybridize to the polyA tail of the RNA to generate additional immobilized cDNA molecules. By repeating this process, the original RNA strand is "handed-off" to the next primer to achieve a linear amplification of the original RNA molecule. RNA-sequence specific ligation probes are introduced to form ligation products indicative of the presence of the target mRNA or lncRNA in the sample FIG. 114 illustrates another approach for preparing mRNA or lncRNA for immobilization on solid support and solid phase ligation reaction. In this embodiment, total RNA or 3' polyA tail RNA is isolated (FIG. 114, step A). A polyT or polyU primer (e.g., T, $dU_{30}VN$ (where V is dA, dC, or dG and N is dA, dC, dG, or dT) is hybridized to the polyA tail of the RNA to generate cDNA of the 3' regions of polyadenylated mRNA targets (FIG. 114, step B). A reverse transcriptase such as Moloney Murine Leukemia Virus Reverse Transcriptase, or Superscript II or III Reverse Transcriptase that appends three C bases to the 3' end of each cDNA extension product is utilized to generate a first strand of cDNA. A second primer with (optional 5' phosphate), 5' $dA_{30}$ and three ribose G bases on the 3' end is hybridized to the $C_3$ overhang (FIG. 114, step C). Preferably, the 3' end G is an LNA base. The reverse transcriptase undergoes strand switching and copies the $dA_{30}$ tail to generate a $T_{30}$ tail on the 3' end of the first strand cDNA (FIG. 114, step D). Degrade the original $(dU,T)_{30}VN$ primer with UDG. Optionally, the second primer with 5' $dA_{30}$ portion is degraded with a 5' nuclease (such as lambda exonuclease). The first strand cDNA containing the 3' poly-T tail is suitable for immobilization to the solid support via hybridization to complementary poly-dA capture oligonucleotide primers, immobilized extension product formation and solid phase ligation reaction to generate detectable ligation products.

FIG. 115 (Cleavage Assay) is similar to FIG. 114 but uses a downstream primer with a flap bearing a 5' identifying signature modifier to allow detection as described in FIG. 61. Alternatively, the flap can bear different 5' identifying signature modifiers, or a sequence bar-code to allow detection as described in FIGS. 62 and 63, respectively.

FIG. 116 (Primer extension assay) is similar to FIG. 114 but uses nucleotide terminators bearing 3' encoded identifying signature modifiers to allow detection of the next nucleotide base as described in FIG. 70B. Alternatively, the 5' end of the probe can bear a sequence bar-code to allow detection as described in FIG. 70A.

FIG. 117 illustrates a variation of the embodiment illustrated in FIG. 112, where the technique is expanded to detect lncRNA & mRNA, for example, isolated from exosomes. In this variation, random hexamers are used as primers for reverse transcriptase reaction, containing a dU in either the $2^{nd}$ or $3^{rd}$ position from the 3' end (FIG. 117, step B). Alternatively, the primers contain an abasic site and an extra base appended to the 3' end. After random priming and extension using MMLV reverse transcriptase (or an engineered version such as Superscript 3) to form cDNA copies of both lncRNA & mRNA, the unreacted hexameric primers are digested with UDP & EndoVIII, such that digestion products are either shorter than 3 bases, or contain a 3' phosphate, and thus are not substrates for terminal transferase (FIG. 117, step C). After tailing with terminal transferase (FIG. 117, step D), the cDNA products are captured on the solid support, replicated by polymerase mediated extension of the immobilized capture oligonucleotide primer, and subjected to the solid phase ligation reaction as described supra.

FIG. 118 illustrates a variation of FIG. 114 where the approach is expanded to detect lncRNA & mRNA, for example, isolated from exosomes. In this variation, random hexamers are used as primers, with reverse transcriptase appending three C bases at the 3' end of the cDNA (FIG. 118, step B). After strand-switching to provide a $T_{30}$ tail (FIG. 118, step C), the cDNA products are captured on the solid support, replicated by polymerase mediated extension of the immobilized capture oligonucleotide primer, and subjected to the solid phase ligation reaction as described in supra.

FIG. 119 (Cleavage Assay) is similar to FIG. 118 but uses a downstream primer with a flap bearing a 5' identifying signature modifier to allow detection as described in FIG. 61. Alternatively, the flap can bear different 5' identifying signature modifiers, or a sequence bar-code to allow detection as described in FIGS. 62 and 63, respectively.

FIG. 120 (Primer extension assay) is similar to FIG. 118 but uses nucleotide terminators bearing 3' encoded identifying signature modifiers to allow detection of the next nucleotide base as described in FIG. 70B. Alternatively, the 5' end of the probe can bear a sequence bar-code to allow detection as described in FIG. 70A.

FIG. 121 illustrates a variation of FIG. 112, where the approach has been focused to detect and enumerate specific mRNA or other RNA transcripts. In this variation, MMLV reverse transcriptase is used to extend transcript-specific primers, containing dU in either the 2nd or 3rd position from the 3' end, which generates cDNA to the desired targets (FIG. 121, step B). Digestion of both unused primers with UDP & EndoVIII, generates products that are either shorter than 3 bases, or contain a 3' phosphate, and thus are not substrates for terminal transferase (FIG. 121, step C). In contrast, digestion of the primer extension products (i.e. cDNA) generates a primer fragment that cannot be extended, but the cDNA fragment can be tailed by terminal transferase. Remaining RNA is degraded with RNaseI and RNaseH, and dNTPs and 1-3 base digestion products are removed (FIG. 121, step C). After tailing with terminal transferase (FIG. 121, step D), the cDNA products are captured on the solid support, replicated by polymerase mediated extension of the immobilized capture oligonucleotide primer, and subjected to the solid phase ligation reaction as described supra.

FIG. 122 illustrates a variation of FIG. 114, where the technique has been focused to detect and enumerate specific mRNA or other RNA transcripts. In this variation, transcript-specific primers are used as primers with a reverse transcriptase that appends three C bases at the 3' end of the cDNA (FIG. 122, step B). After strand-switching to provide a $T_{30}$ tail (FIG. 122, step C-D), the cDNA products are captured on the solid support, replicated by polymerase mediated extension of the immobilized capture oligonucleotide primer, and subjected to the solid phase ligation reaction as described supra.

FIG. 123 (Cleavage Assay) is similar to FIG. 122 but uses a downstream primer with a flap bearing a 5' identifying signature modifier to allow detection as described in FIG. 61. Alternatively, the flap can bear different 5' identifying signature modifiers, or a sequence bar-code to allow detection as described in FIGS. 62 and 63, respectively.

FIG. 124 (Primer extension assay) is similar to FIG. 122 but uses nucleotide terminators bearing 3' encoded identifying signature modifiers to allow detection of the next nucleotide base as described in FIG. 70B. Alternatively, the 5' end of the probe can bear a sequence bar-code to allow detection as described in FIG. 70A.

FIG. 125 illustrates a variation of FIG. 121. In this embodiment, the technique has been focused to detect and enumerate low abundance specific mRNA transcript. In this variation, MMLV reverse transcriptase is used to extend transcript-specific primers, containing a $dA_{30}$ at the 5' end, which generates cDNA to the desired targets (FIG. 125, step B). cDNA is denatured, and locus-specific primers with blocked 3' ends hybridize to their complementary sequences (FIG. 125, step C). Primers are unblocked with RNaseH2 only when bound to target. The liberated 3' ends are extended with polymerase through the 5'-$dA_{30}$ tail to generate a 3'-$T_{30}$ tail (FIG. 125, step C). The desired enriched target copy is distributed onto the solid support such that the $T_{30}$ tail hybridizes to $dA_{30}$ capture oligonucleotide primers immobilized to pillars. An optional variation, not shown, would have a 5' blocking group on a second set of locus-specific primers that lack the 5'-$dA_{30}$ tails. After extension steps are complete, the extension products and primers containing the 5'-$dA_{30}$ tails, the original target strands, and other non-target DNA are removed by digestion with (lambda) 5' exonuclease. The copy of the cDNA (hybridized to $dA_{30}$ primers on the solid support) is replicated by polymerase-mediated extension of the immobilized capture oligonucleotide primer, and subjected to the solid phase ligation reaction as described supra.

FIG. 126 (Cleavage Assay) is similar to FIG. 125 but uses a downstream primer with a flap bearing a 5' identifying signature modifier to allow detection as described in FIG. 61. Alternatively, the flap can bear different 5' identifying signature modifiers, or a sequence bar-code to allow detection as described in FIGS. 62 and 63, respectively.

FIG. 127 (Primer extension assay) is similar to FIG. 125 but uses nucleotide terminators bearing 3' encoded identifying signature modifiers to allow detection of the next nucleotide base as described in FIG. 70B. Alternatively, the 5' end of the probe can bear a sequence bar-code to allow detection as described in FIG. 70A.

FIG. 128 illustrates detection and enumeration of specific translocations at the mRNA level translocation using a variation of the embodiment illustrated in FIG. 121. In this variation, MMLV reverse transcriptase is used to extend target-specific primers, containing dU in either the 2nd or 3rd position from the 3' end, which generates cDNA that cover the desired translocation(s) (FIG. 128, step B). Unused primers are digested with UDP & EndoVIII, remaining RNA is degraded with RNaseI and RNaseH, and dNTPs and 1-3 base digestion products are removed (FIG. 128, step C). After tailing with terminal transferase (FIG. 128, step D), the cDNA products are captured on the solid support, replicated by polymerase mediated extension of the immobilized capture oligonucleotide primer, and subjected to the solid phase ligation reaction as described supra. This approach allows for enumeration of both wild-type downstream mRNA sequence, as well as mRNA sequences comprising the translocation transcripts.

FIG. 129 illustrates detection and enumeration of specific translocations at the mRNA level using a variation of the embodiment shown in FIG. 122. In this variation, transcript-specific primers are used as primers, with a reverse transcriptase that appends three C bases at the 3' end of the cDNA (FIG. 129, step B). After strand-switching to provide a $T_{30}$ tail (FIG. 129, step C-D), the cDNA products are captured on the solid support, replicated by polymerase mediated extension of the immobilized capture oligonucleotide primer, and subjected to the solid phase ligation reaction as described supra. This approach allows for enumeration of both wild-type downstream mRNA sequence, as well as mRNA sequences comprising the translocation transcripts.

FIG. 130 (Cleavage Assay) is similar to FIG. 129 but uses a downstream primer with a flap bearing a 5' identifying signature modifier to allow detection as described in FIG. 61. Alternatively, the flap can bear different 5' identifying signature modifiers, or a sequence bar-code to allow detection as described in FIGS. 62 and 63, respectively.

FIG. 131 (Primer extension assay) is similar to FIG. 129 but uses nucleotide terminators bearing 3' encoded identifying signature modifiers to allow detection of the next nucleotide base as described in FIG. 70B. Alternatively, the 5' end of the probe can bear a sequence bar-code to allow detection as described in FIG. 70A.

FIG. 132 illustrates an embodiment that achieves detection of low-abundance translocations at the mRNA level using a variation of the method shown in FIG. 125. In this variation, MMLV reverse transcriptase is used to extend transcript-specific primers, containing a $dA_{30}$ at the 5' end, which generates cDNA to the desired targets (FIG. 132, step B). cDNA is denatured, and locus-specific primers with blocked 3' ends hybridize to their complementary sequences (FIG. 132, step C). Primers are unblocked with RNaseH2 only when bound to complementary target. The liberated 3' ends are extended with polymerase through the 5'-$dA_{30}$ tail to generate a 3'-$T_{30}$ tail (FIG. 132, step C). The desired enriched target copy is distributed onto the solid support such that the $T_{30}$ tail hybridizes to $dA_{30}$ primers immobilized on the solid support, replicated by polymerase mediated extension of the immobilized capture oligonucleotide primer, and subjected to the solid phase ligation reaction as described supra. This approach allows for enumeration of low-abundance mRNA sequences comprising the translocation transcripts, and is especially useful for identifying low-abundance cancer cells in an excess of normal cells.

FIG. 133 (Cleavage Assay) is similar to FIG. 132 but uses a downstream primer with a flap bearing a 5' identifying signature modifier to allow detection as described in FIG. 61. Alternatively, the flap can bear different 5' identifying signature modifiers, or a sequence bar-code to allow detection as described in FIGS. 62 and 63, respectively.

FIG. 134 (Primer extension assay) is similar to FIG. 132 but uses nucleotide terminators bearing 3' encoded identifying signature modifiers to allow detection of the next nucleotide base as described in FIG. 70B. Alternatively, the 5' end of the probe can bear a sequence bar-code to allow detection as described in FIG. 70A.

FIG. 135 illustrates detection and enumeration of specific splice variants at the mRNA level using a variation of the method illustrated in FIG. 121. A hypothetical example of wild-type (1-2a-3) and alternative splice variant (1-2b-3)

mRNA's are illustrated in FIG. 135, step A. In this embodiment, MMLV reverse transcriptase is used to extend target-specific primer (to exon 3 in this example) that contains dU in either the 2nd or 3rd position from the 3' end (FIG. 135, step B). This process generates cDNA that cover the desired splice variants. While only extension of the 2b exon-containing product is illustrated, the same primer will also extend to generate the 2a exon-containing product. Unused primers are digested with UDP & EndoVIII, remaining RNA is degraded with RNaseI and RNaseH, and dNTPs and 1-3 base digestion products are removed (FIG. 135, step C). After tailing with terminal transferase (FIG. 135, step D), the cDNA products are captured on the solid support, replicated by polymerase mediated extension of the immobilized capture oligonucleotide primer, and subjected to the solid phase ligation reaction as described supra. Ligation probes are designed to detect both the normal and/or the alternative splice variant (2a-1, and 2b-1; shown) across the splice junctions, using a common downstream ligation probe. This approach allows for enumeration of both wild-type mRNA sequence (2a-1), as well as mRNA sequences comprising the alternative splice site (2b-1).

FIG. 136 illustrates detection and enumeration of specific splice variants at the mRNA level using a variation of the method illustrated in FIG. 122. A hypothetical example of wild-type (1-2a-3) and alternative splice variant (1-2b-3) mRNAs are illustrated in FIG. 136, step A. In this variation, transcript-specific primers are used with a reverse transcriptase capable of appending three C bases at the 3' end of the cDNA (FIG. 136, step B). After strand-switching to provide a $T_{30}$ tail (FIG. 136, steps C-D), the cDNA products are captured on the solid support, replicated by polymerase mediated extension of the immobilized capture oligonucleotide primer, and subjected to the solid phase ligation reaction as described supra. Ligation probes are designed to detect both the normal and/or the alternative splice variant (2a-1, and 2b-1; shown) across the splice junctions, using a common downstream ligation probe. This approach allows for enumeration of both wild-type mRNA sequence (2a-1), as well as mRNA sequences comprising the alternative splice site (2b-1).

FIG. 137 (Cleavage Assay) is similar to FIG. 136 but uses a downstream primer with a flap bearing a 5' identifying signature modifier to allow detection as described in FIG. 61. Alternatively, the flap can bear different 5' identifying signature modifiers, or a sequence bar-code to allow detection as described in FIGS. 62 and 63, respectively.

FIG. 138 (Primer extension assay) is similar to FIG. 136 but uses nucleotide terminators bearing 3' encoded identifying signature modifiers to allow detection of the next nucleotide base as described in FIG. 70B. Alternatively, the 5' end of the probe can bear a sequence bar-code to allow detection as described in FIG. 70A.

FIG. 139 illustrates detection and enumeration of specific low-abundance splice variants at the mRNA level using a variation of the method shown in FIG. 125. A hypothetical example of wild-type (1-2-3a-4) and alternative splice variant (1-2-3b-4) mRNA's are illustrated in FIG. 139, step A. In this variation, MMLV reverse transcriptase is used to extend transcript-specific primers (to exon 4 in this example), containing a $dA_{30}$ at the 5' end to generate cDNA of the desired targets (FIG. 139, step B). The cDNA is denatured, and splice-variant-specific primers (in this example, across the 2-3b junction) with blocked 3' ends hybridize to their complementary sequences (FIG. 139, step C). Primers are unblocked with $RNaseH_2$ only when bound to complementary target. The liberated 3' ends are extended with polymerase through the 5'-$dA_{30}$ tail to generate a 3'-$T_{30}$ tail (FIG. 139, step C). The desired enriched target copy is distributed onto the solid support such that the $T_{30}$ tail hybridizes to $dA_{30}$ primers immobilized on the solid support, replicated by polymerase mediated extension of the immobilized capture oligonucleotide primer, and subjected to the solid phase ligation reaction as described supra. Ligation probes are designed to detect both the low-abundance alternative splice variant (3b-4) across the splice junction. This approach allows for enumeration of low-abundance mRNA sequences comprising the alternatively spliced transcripts, and is especially useful for identifying low-abundance cancer cells in an excess of normal cells.

FIG. 140 (Cleavage Assay) is similar to FIG. 139 but uses a downstream primer with a flap bearing a 5' identifying signature modifier to allow detection as described in FIG. 61. Alternatively, the flap can bear different 5' identifying signature modifiers, or a sequence bar-code to allow detection as described in FIGS. 62 and 63, respectively.

FIG. 141 (Primer extension assay) is similar to FIG. 139 but uses nucleotide terminators bearing 3' encoded identifying signature modifiers to allow detection of the next nucleotide base as described in FIG. 70B. Alternatively, the 5' end of the probe can bear a sequence bar-code to allow detection as described in FIG. 70A.

The methods of the present invention are also suitable to achieve accurate quantification of miRNA changes from isolated exosomes or from circulating tumor cells. Micro-RNA (miRNA) have been identified as potential tissue-specific markers of the presence of tumors, their classification and prognostication. miRNA exist in serum and plasma either as complexes with Ago2 proteins or by encapsulation as exosomes.

Detection of miRNA requires conversion into cDNA, and depends on the fidelity of five enzymes: (i) T4 ligase to append a loop primer to mRNA (ii) reverse transcriptase to faithfully copy low-level copies of miRNA transcripts in the initial sample, (iii) terminal transferase to generate T tails on all or selected cDNA fragments (iv) polymerase to replicate the tailed cDNA, and (v) thermostable ligase in discriminating primers hybridized adjacent to each other. Alternatively, the strand-switching activity of reverse transcriptase can be utilized as described supra to append the adapter portions. Once a ligation event has taken place, those products will be uniquely identified and distinguished based on their identifying signature as detected by one or more nanopores.

Detection of miRNA presents a unique challenge because such fragments are too small (19-25 bases) for traditional reverse-transcript priming, and are smaller than the footprint required for solid phase ligation reactions (about 50-60 bases). To address this challenge, a 3'-blocked loop primer is appended to the miRNA. The 3' terminal six random bases are complementary, such that the phosphorylated 5' end of the primer ligates to the 3' end of the miRNA (see FIGS. 142-149 described in more detail below). The product now has 5' RNA sequence, but the original loop primer has a 5' phosphorylated DNA end, and is now a substrate for degradation using lambda exonuclease. The DNA-RNA chimeric product is copied using a 5'-blocked dU-rich primer, complementary to the A-rich region of the loop primer. The stem region is double-stranded during the ligation step (using T4 ligase) at 16° C., but opens during the subsequent reverse transcription step to allow for a full copy of the loop sequence as well as the miRNA to be generated. miRNA and other sample RNA is destroyed with RNaseI and RNaseH, unused primer is destroyed with UDG, and surviving cDNA is purified using a ratchet array or electrophoresis. Enzymes are inactivated by heat denaturation.

FIG. 142 illustrates one embodiment of detecting miRNA using the methods of the present invention. In this embodiment, a loop primer is ligated to the 3' end of miRNA (FIG. 142, step B). The loop primer has a random hexamer sequence that is complementary to the 3' end of target miRNA, a stem-loop having an adenine rich primer sequence, and a 3' blocking group. The unused loop primer is degraded with lambda exonuclease (FIG. 142, step C). MMLV reverse transcriptase is used to extend a 5' blocked, uracil rich primer, which generates cDNA of the ligated miRNA. To assure that neither DNA primer, nor other nucleic acids are tailed, the reactants are digested with UDP & EndoVIII, while the RNA is degraded by RNaseI & RNaseH (FIG. 142, step D). To assure that tailing only adds TTP, both digestion products and initial dNTPs are removed. After tailing with terminal transferase (FIG. 142, step E), the cDNA products are captured on the solid support, replicated by polymerase mediated extension of the immobilized capture oligonucleotide primer, and subjected to the solid phase ligation reaction as described supra. Ligation probes are hybridized to target and only form product when there is perfect complementarity at the ligation junction. Unreacted ligation probes or target-independent ligation products are then washed away. Ligation probes are designed to contain identifying signature modifiers, and additional sequences such that products may be uniquely identified and distinguished based on their identifying signature as they pass through one or more nanopores.

FIG. 143 illustrates a variation of the embodiment shown in FIG. 142, for 3' miRNA sequence detection and enumeration on isolated miRNA. In this embodiment, a loop primer is ligated to the 3' end of miRNA (FIG. 143, step B). The loop primer has a random hexamer sequence that is complementary to the 3' end of target miRNA, a stem-loop having an adenine rich primer sequence, and a 3' blocking group. The unused loop primer is degraded with lambda exonuclease (FIG. 143, step C). MMLV reverse transcriptase is used to extend a 5' blocked, loop-specific primer, which generates cDNA of the ligated miRNA, as well as appending three C bases at the 3' end of the cDNA (FIG. 143, step C). After strand-switching to provide a $T_{30}$ tail (FIG. 143, step D), the cDNA products are captured on the solid support, replicated by polymerase mediated extension of the immobilized capture oligonucleotide primer, and subjected to the solid phase ligation reaction as described supra.

FIG. 144 (Cleavage Assay) is similar to FIG. 143 but uses a downstream primer with a flap bearing a 5' identifying signature modifier to allow detection as described in FIG. 61. Alternatively, the flap can bear different 5' identifying signature modifiers, or a sequence bar-code to allow detection as described in FIGS. 62 and 63, respectively.

FIG. 145 (Primer extension assay) is similar to FIG. 143 but uses nucleotide terminators bearing 3' encoded identifying signature modifiers to allow detection of the next nucleotide base as described in FIG. 70B. Alternatively, the 5' end of the probe can bear a sequence bar-code to allow detection as described in FIG. 70A.

FIGS. 146 and 147 illustrate further variations of FIGS. 142 and 143 respectively, where the technique is adjusted to detect specific miRNAs. In these figures, the 3' end of the loop primer is specifically designed to be complementary to the desired miRNA targets. The use of random bases in the loop primer provides both the opportunity and risk of ligating promiscuously to all RNA present in exosomes. The problem may be addressed by designing loop primers whose six bases on the 3' end are complementary to known miRNA species. Although a given loop primer may still amplify multiple lncRNA and closely related miRNA sequences, the desired miRNA may be distinguished by the subsequent solid phase ligation reaction step, which can discriminate down to single-nucleotide differences.

FIG. 148 (Cleavage Assay) is similar to FIG. 147 but uses a downstream primer with a flap bearing a 5' identifying signature modifier to allow detection as described in FIG. 61. Alternatively, the flap can bear different 5' identifying signature modifiers, or a sequence bar-code to allow detection as described in FIGS. 62 and 63, respectively.

FIG. 149 (Primer extension assay) is similar to FIG. 147 but uses nucleotide terminators bearing 3' encoded identifying signature modifiers to allow detection of the next nucleotide base as described in FIG. 70B. Alternatively, the 5' end of the probe can bear a sequence bar-code to allow detection as described in FIG. 70A.

The methods of the present invention are also suitable for carrying out two-sided target replication and targeted cell-free DNA replication for detection of mutations via ligation reaction or sequencing reactions.

An advantage of using DNA replication from original target DNA is the ability to distinguish true mutations (which are replicated in each step) from polymerase error "mutations", (which occur randomly due to polymerase error) (Ma et al., "Isothermal Amplification Method for Next-generation Sequencing," *Proc Natl Acad Sci USA* 110:14320-14323 (2013), which is hereby incorporated by reference in its entirety). This feature becomes critical in distinguishing low-abundance mutations that need to be detected via sequencing. One advantage of using spaced solid support structures within defined bioreactor chamber is that the sequencing strands can be present anywhere within the chamber. Thus, only one strand needs to be tethered to the solid support, while the second one may either be hybridized to the tethered strand during replication, or alternatively denatured, and replicated elsewhere within the same bioreactor area.

Further, there is a need to accurately capture and replicate desired sequences from a sample. A number of approaches to address this challenge are based on circular chimeric single-stranded nucleic acid constructs comprising of original genomic DNA and a synthetic segment. Some examples for constructing such chimeric single-stranded nucleic acid molecules are presented below (see FIGS. 164-172). Additional detail is also available in U.S. Provisional Patent Application Ser. No. 61/009,047 to Barany and Efcavitch, which is hereby incorporated by reference in its entirety. Other approaches for capturing and replicating the desired sequence are presented below (see FIGS. 150-162).

FIG. 150 illustrates two-sided amplification of genomic or cfDNA for subsequent targeted sequencing or spLDR detection. This approach allows for sequencing both the Watson and Crick strand of a given target. If generalized sequencing is desired, multiple 5' universal sequences may be used, such that on average, a given bioreactor has captured and replicated only one target with that universal primer. Each sequencing run would then use a different set of universal primers. If targeted sequencing is desired, then target-specific primers would be used (as described in more detail below).

FIGS. 151-153 illustrates in a bit more detail various embodiments of the initial steps from FIG. 150. In these embodiments, the original genomic segments comprise segments of cfDNA (~160 bp) or segments of sheared genomic DNA (~160 bp) containing, e.g., tumor specific mutations, SNPs, or polymorphic repetitive sequences. In FIG. 151, the ends of fragmented DNA are repaired using a polymerase with 3'-5' exonuclease activity such as T4 polymerase or DNA Polymerase I, Large (Klenow) Fragment, which extends recessed 3' ends or degrades 3' overhang ends till they are flush with the 5' end. The 5' ends are phosphorylated with T4 kinase, and an additional A base appended to the 3' end using DNA Polymerase I, Large (Klenow) Fragment, lacking 3'→5' nuclease activity. Linkers with 3' T overhangs are ligated on using T4 ligase. In this figure, the double stranded region of the linker is illustrated as two thick black lines, the single stranded 3' end of the linker comprises a $T_{30}$ sequence (for capture on a solid support by $dA_{30}$ primers, medium black line), and the 5' end with an optional phosphate comprises a further sequence, such as a universal primer binding sequence or a set of universal primer sequences. Such a set may comprise from 1 to 10 universal primer sequences, from 10 to 100 universal primer sequences, or from 100 to 1,000 universal primer sequences. This product is suitable for circularization of top or bottom original target strand as illustrated in FIGS. 164-172.

While the standard approach illustrated in FIG. 151 also provides the opportunity for introducing unique sequences on the single-stranded portions of the linkers, these sequences do not allow for unambiguous matching of a top strand sequence with a bottom strand sequence. To achieve this type of construct, the standard approach is modified as illustrated in FIG. 152. The ends of fragmented DNA are repaired using a polymerase with 3'-5' nuclease activity such as T4 polymerase or DNA Polymerase I, Large (Klenow) Fragment, which extends recessed 3' ends, or degrades 3' overhang ends until they are flush with the 5' end. The 5' ends are phosphorylated with T4 kinase, and an additional A base appended to the 3' end using DNA Polymerase I, Large (Klenow) Fragment, lacking 3'→5' nuclease activity. Linkers with 3' T overhangs are ligated on using T4 ligase. Here, the linker is comprised of 3 pieces comprising a single-stranded gap of unique sequence in the double-stranded portion. This allows for use of polymerase to fill the gap, and in the presence of ligase, seal the nick. If the shorter linker is not phosphorylated, the polymerase should have 5'-3' nuclease activity to liberate a 5'phosphate suitable for ligation. If the shorter linker is phosphorylated on the 5' end, the polymerase should lack 5'-3' nuclease activity, allowing it to extend up to the linker, followed by ligase sealing the nick. In this figure, the double stranded regions of the linker are illustrated as two thick black lines, the single stranded 3' end of the linker comprises a $T_{30}$ sequence (for capture on a solid support by $dA_{30}$ primers, medium black line), and the 5' end with an optional phosphate comprises a further sequence, such as a universal primer binding sequence or a set of universal primer sequences. Such a set may comprise from 1 to 10 universal primer sequences, from 10 to 100 universal primer sequences, or from 100 to 1,000 universal primer sequences. This product is suitable for circularization of top or bottom original target strand as illustrated in FIGS. 164-172. Upon determining the sequences of these strands the unique identifier sequences 1 & 2 will enable unambiguous matching of a top strand sequence with a bottom strand sequence, thus allowing for independent verification of low-abundance mutation on both strands of the original target molecule.

FIG. 153 exemplifies another approach for appending adapter portions containing primer sequences to the ends of target DNA, such that it is suitable for producing chimeric circular single stranded nucleic acid target constructs, and allow for unambiguous matching of a top strand sequence with a bottom strand sequence. The ends of fragmented DNA are repaired using a polymerase with 3'-5' nuclease activity, which extends recessed 3' ends, or degrades 3' overhang ends till they are flush with the 5' end. The 5' ends are optionally phosphorylated with T4 kinase (See below). A reverse transcriptase such as Moloney Murine Leukemia Virus Reverse Transcriptase (M-MLV RT) or Superscript II or III Reverse Transcriptases are used to append three C bases to the 3' end of each target. A primer pair comprising both single-stranded (thinner black and double lines) and double stranded portions (thick black bars), a unique identifier sequence and three ribose G bases on the 3' end hybridizes to the $C_3$ overhang. Optionally, the 3' G base is an LNA base as described supra. The reverse transcriptase undergoes strand switching and copies the unique identifier to fill the gap. T4 ligase covalently seals the extended target to the second primer. RNaseH2 cleaves the RNA bases, liberating the 3' OH by removing the $rG_3$ of the first primer. This allows for use of polymerase to fill the gap, and in the presence of ligase, seal the nick. If the second primer or target DNA is not phosphorylated on the 5' end, the polymerase should have 5'-3' nuclease activity to liberate a 5'phosphate suitable for ligation. If the second primer and target are phosphorylated, the polymerase should lack 5'-3' nuclease activity, allowing it to extend up to the 5' end of the second primer or target respectively, followed by ligase sealing the nick. In this figure, the double stranded region of the linker are illustrated as two thick black lines, the single stranded 3' end of the linker comprises a $T_{30}$ sequence (for capture on a solid support by $dA_{30}$ primers, medium black line), and the 5' end with an optional phosphate comprises a further sequence, such as a universal primer binding sequence or a set of universal primer sequences. Such a set may comprise from 1 to 10 universal primer sequences, from 10 to 100 universal primer sequences, or from 100 to 1,000 universal primer sequences. This product is suitable for circularization of top or bottom original target strand as illustrated in FIGS. 164-172. Upon determining the sequences of these strands, the unique identifier sequences 1 & 2 will enable unambiguous matching of a top strand sequence with a bottom strand sequence, thus allowing for independent verification of low-abundance mutation on both strands of the original target molecule.

FIG. 154 illustrates two-sided amplification of genomic or cfDNA, with one-directional target-specific primers used to achieve selection of the desired targets. This approach may be used, for example, to sequence all exons of targeted genes. By appending multiple universal primers, such that on average a given bioreactor has captured and replicated only one target with that universal primer, then the entire captured fragment may be sequenced. Alternatively, target-specific primers may also be used, again provided that on average a given bioreactor has captured and replicated only one target with that primer.

The methods of the present invention are also suitable for carrying out two-sided target replication and targeted cell-free DNA replication for detection of mutations via paired-end sequencing reactions. There are a number of approaches for preparing first one strand of the target, and then its complement for paired-end sequencing of DNA on a solid surface or beads (see U.S. Patent Application Publication No. 20150099642 to Barany et al., and U.S. Patent Application Publication 20150361489 to Barany et al.; Holt R A, Jones S J., *Genome Res*. 18(6):839-46 (2008), Ma et al. *Proc Natl Acad Sci USA* 110:14320-14323 (2013), which are hereby incorporated by reference in their entirety). Herein a simpler approach is presented that enables the error-reduction replication approach for both strands to minimize the chances of incorrectly scoring a replication error as a mutation. The principle is to use a primer comprising of a 3' single-stranded $dA_{30}$ tail, an A:T-rich region that hairpins and forms a double-stranded sequence, and a free 5' end. The hairpin primer is coupled to the solid support at or near the hairpin region, allowing for target replication identical to the strand displacement approaches illustrated with standard $dA_{30}$ primers in FIGS. 154, 156, 158, 160, and 162, as recapitulated with the hairpin primer in FIGS. 155, 157, 159, 161, and 163, respectively. After sequencing on the first strand, the complement is sequenced as described in FIG. 189.

One embodiment of replicating DNA with a hairpin primer is to use a primer of the sequence:

```
                                            (SEQ ID NO: 1)
5'-ATTATTATTTTTTACAAC-x-TAAAAAATAATAAT-
AAAAAAAAAAAAAAAAAAAAAAAAAAAAAA-3'
```

(Illustrated below in Hairpin form)

```
                                            (SEQ ID NO: 2)
5'-AATTTTTTATTATTCAAC-x-
TAAAAAATAATAATAAAAAAAAAAAAAAAAAAAAAAAAAAAAAA-3'
```

This primer contains a dA30 tail, with a calculated Tm value of about 57.9° C. (Using IDT OligoAnalyzer 3.1). It also contains a 14-bp hairpin with a calculated Tm value of about 57.4° C. The "x" indicates the position for coupling the primer to the solid support. The "x" also inhibits polymerase extension across this portion of the oligonucleotide primer. Hairpin probes with free 3' and 5' ends for covalent attachment to a surface can be made by direct chemical synthesis wherein one or more modified nucleotides are included in the hairpin region, such modified nucleotides comprise a reactive species which facilitates covalent attachment to a suitable modified surface. Typically, amine modified nucleotide analogs are used for attachment to activated surfaces but other reactive nucleotide analog-activated surface combinations are equally valid. Examples of such hairpin probes have been described by Wang J, et al., *Molecules* 8:153-68 (2003); Zhoa X et al, *Nuc Acids Res* 29(4):955-9 (2001); and U.S. Pat. No. 5,770,365 to Lane et al., which are hereby incorporated by reference in their entirety. In one embodiment, the "x" is a nucleotide analogue comprising a biotin group attached to a base. This biotin is suitable for capture on a solid surface coated with streptavidin. In other embodiments, the primer is covalently attached to the solid surface using internal nucleotide analogues comprising dibenzocyclooctyl (DBCO) for copper-free click chemistry (to an azide); 5-Octadiynyl dU for click chemistry (to an azide); amino modifier C6 dT (for peptide linkage); or azide, for click chemistry to an alkene or DBCO. Other approaches to capture the hairpin primer to the solid surface include hybridization. The capture step may be enhanced by use of PNA, LNA, or other nucleotide analogues within the primer, capture probe sequence or both, provided they do not interfere with the replication process. The hybridized strands may be cross-linked to each other to enable covalent coupling to the solid support.

When capturing target DNA containing a $T_{30}$ tail with the above hairpin primer coupled to the solid support, polymerase will extend the single-stranded dA tail from the solid support to replicate the target DNA. Strand-displacing polymerase will also extend the target T-tail through the A:T rich double-stranded region up to the hairpin. When raising the temperature to 55-60° C., the dA portion partially denatures, the partial hairpin reforms, allowing for an adjacent primer on the solid support to hybridize, and polymerase displaces the first primer strand. By this repetitive process, the original strand is "handed-off" to the next hairpin primer to achieve a linear amplification of the original target DNA. Meanwhile, universal primer(s) in solution hybridizes to single-stranded extension product, and are extended by polymerase. As long as there are nearby hairpin-ss-dA30 primers, the process of handoff replication continues until primers are consumed. Untethered extension products are melted off the solid support (or alternatively may be digested with 5'→3' exonuclease) and removed prior to sequencing.

FIG. 155 (Hairpin primer on solid support) illustrates a variation of FIG. 154, wherein the primers on the solid support comprise a 3' single-stranded $dA_{30}$ tail, an A:T-rich region that hairpins and forms a double-stranded sequence, and a free 5' end. The enzymatic steps are identical to those described in FIG. 154.

FIG. 156 illustrates a variation of FIG. 154, wherein the universal primer(s) are appended using reverse transcriptase. Genomic DNA is tailed with terminal transferase as shown in FIG. 156, step B. The DNA is denatured, and a set of first primers (target-specific, with optional blocked 3' ends), are hybridized to their complementary sequences (FIG. 156, step C). Primers are unblocked with $RNaseH_2$ only when bound to target, and extended using a reverse transcriptase which appends three C bases to the 3' end of each target (FIG. 156, step C). A set of universal primers containing three ribose G bases on the 3' end hybridizes to the $C_3$ overhang. Optionally, the 3' G base is an LNA base. The reverse transcriptase undergoes strand switching and copies the unique identifier to fill the gap (FIG. 156, step D). T4 ligase covalently seals the extended target to the second primer. RNaseH2 cleaves the RNA bases, liberating the 3' OH by removing the $rG_3$ of the second primer (FIG. 156, step E). This allows for use of polymerase to fill the gap, and in the presence of ligase, seal the nick (FIG. 156, step F). If the second primer is not phosphorylated on the 5' end, the polymerase should have 5'-3' nuclease activity to liberate a 5'phosphate suitable for ligation. If the second primer is phosphorylated, the polymerase should lack 5'-3' nuclease activity, allowing it to extend up to the 5' end of the second primer or target respectively, followed by ligase sealing the nick. The tailed products now have universal sequences on their 5' sides and the $T_{100-150}$ tails on their 3' side suitable for capture on the solid support (FIG. 156, step G). Bst polymerase (large fragment), which lacks both 3' and 5' exonuclease activity, but has strand displacement activity, will make full-length copies of each captured template (FIG. 156, step H). By raising the temperature to 55-60° C., the poly dA-T portions will partially denature, allowing for new primers to bind and be extended (FIG. 156, step H). This linear replication process faithfully copies the original template strand as it is "handed-off" to the next primer. Meanwhile, universal primer(s) in solution hybridize to single-stranded extension product, and are extended by polymerase (FIG. 156, step I). The process of handoff replication continues until unhindered primers are exhausted. Untethered extension products are melted off the solid support, which now has dozens to hundreds of single strands with identical sequence within a given bioreactor, suitable for sequencing-by-synthesis.

FIG. 157 (Hairpin primer on solid support) illustrates a variation of FIG. 156, wherein the primers on the solid support comprise a 3' single-stranded $dA_{30}$ tail, an A:T-rich region that hairpins and forms a double-stranded sequence, and a free 5' end. The enzymatic steps are identical to those described in FIG. 156.

FIG. 158 illustrates two-sided amplification of genomic or cfDNA, with two-directional target-specific primers used to achieve selection of the desired targets. This approach may be used for example to sequence all exons of targeted genes. A standard "set" of universal primers are appended to desired target-specific primers (FIG. 158, steps B-C). Thus, the same "set" of universal primers may be used for each sequencing run, provided that on average a given bioreactor has captured and replicated only one target with that primer.

FIG. 159 (Hairpin primer on solid support) illustrates a variation of FIG. 158, wherein the primers on the solid support comprise a 3' single-stranded $dA_{30}$ tail, an A:T-rich region that hairpins and forms a double-stranded sequence, and a free 5' end. The enzymatic steps are identical to those described in FIG. 158.

FIG. 160 illustrates two-sided amplification of genomic or cfDNA, with one-directional target-specific primers used to achieve extra amplification of the desired targets. In this scheme, the selective primers are added after generic capture of all DNA, but since only they have the universal primers appended, only those amplified products will be sequenced. A standard "set" of universal primers are appended to desired target-specific primers, allowing the standard "set" of universal primers to be used for each sequencing run.

FIG. 161 (Hairpin primer on solid support) illustrates a variation of FIG. 160, wherein the primers on the solid support comprise a 3' single-stranded $dA_{30}$ tail, an A:T-rich region that hairpins and forms a double-stranded sequence, and a free 5' end. The enzymatic steps are identical to those described in FIG. 160.

FIG. 162 illustrates a variation of two-sided amplification as described in FIG. 74, with two-directional tandem target-specific primers used to achieve selection of the desired targets. This design is optimized for detection of viral RNA, and includes an initial reverse transcription step using tandem target-specific primers with 5' $dA_{30}$ tails (FIG. 162, steps B-C). Use of tandem primers improves detection even if viral sequence drifts. The approach is ideal for using dozens to hundreds of viral-specific primers followed by solid phase ligation reaction to identify which (if any) viruses are present in the clinical sample. Since the fragments are already captured on a solid support, the universal primers for that virus may then be used to provide accurate sequence information for that isolate.

FIG. 163 (Hairpin primer on solid support) illustrates a variation of FIG. 162, wherein the primers on the solid support comprise a 3' single-stranded $dA_{30}$ tail, an A:T-rich region that hairpins and forms a double-stranded sequence, and a free 5' end. The enzymatic steps are identical to those described in FIG. 162.

FIGS. 164-172 illustrate variations for creating circular templates comprised of the original starting DNA that are suitable for undergoing a variation of strand-displacement amplification directly on the solid support to generate both tandem copies and monomeric replicates of the original target (see FIGS. 173-176). Additional detailed protocol information regarding the production of circularized templates is provided herein in the Example section.

FIG. 164 illustrates an approach for generating circular templates of generic DNA isolated from circulating tumor cells or cfDNA. cfDNA or genomic DNA isolated from CTC (sheared to about 150 bp) is blunt end digested and extended at 3' end with a single A nucleotide base to facilitate adapter ligation. The adapters contain a poly-T ($T_{30}$) sequence, primer binding site, 3' single base T overhang and optional 5' phosphate. The adapter appended DNA or efDNA is denatured and hybridized to oligonucleotide probe sequences containing sequences that are complementary to the 5' and 3' sides of the adapters (FIG. 164, step B). The oligonucleotide probes contain a primer-binding sequence, a $dA_{30}$ sequence, an optional phosphate on the 5' end and a mismatched or blocked 3' end. As shown in FIG. 164, step C, a polymerase extends the hybridized adapter end of the DNA and ligase seals adjacent ends of the target nucleic acid molecule to create a circularized product (FIG. 164, step D). Exonuclease digests all unligated or nicked products, leaving only desired single-stranded circular DNA comprising of original target DNA with $T_{30}$ and universal primer sequences. This product is suitable solid phase amplification and sequencing applications.

FIG. 165 illustrates an approach for generating circular templates for accurate quantification of tumor-specific copy changes or detection of mutations in known genes (e.g. Braf, K-ras, p53) in DNA isolated from circulating tumor cells or cfDNA. In this embodiment, cfDNA or genomic DNA is blunt end digested and extended at 3' end with a single A nucleotide base to facilitate A:T rich adapter ligation. The adapters contain 3' single base T overhang and optional 5' phosphate. The adapter appended DNA or cfDNA is denatured and hybridized to oligonucleotide probes containing sequences that are complementary to the 5' and 3' sides of the adapters (FIG. 165, step B). The oligonucleotide probes contain: (i) a primer-binding sequence, (ii) a dA30 sequence, (iii) an optional phosphate on the 5' end, (iv) a blocked 3' end, and (v) a cleavable link (U). The blocking moiety on the 3' end of the oligonucleotide probe is cleaved once hybridized to the target DNA, and polymerase extends the hybridized 3' ends of both the target DNA and the oligonucleotide probe to bring the 3' ends directly adjacent to ligation competent 5' ends as shown in FIG. 165, step C. By extending the 3' end of the target DNA, a copy the $dA_{30}$ and universal primer sequence is appended to the target DNA molecule. As shown in FIG. 165, step D, ligase seals the adjacent ends of both the oligonucleotide probe and the target DNA molecule to create circular interlocked ligation products. Subsequently, the oligonucleotide probe is nicked at the cleavable link using UDG or other suitable enzyme. Exonuclease(s) are introduced to digest all unligated or nicked products leaving only desired single stranded circular DNA comprising the original target nucleotide sequence with $T_{30}$ and universal primer sequence as shown in FIG. 165, step E.

FIG. 166 illustrates a variation of FIG. 165, where the oligonucleotide probe is complementary to the single-stranded portions of the adapter regions. The starting fragments are generated as described for FIGS. 151-153. The remaining steps are as described in FIG. 165.

FIG. 167 illustrates another variation of FIG. 165, where after cleavage of the blocking group with $RNasH_2$, the 5' and 3' ends of the oligonucleotide probe are directly adjacent to each other and suitable for direct ligation without polymerase extension. The $RNaseH_2$ and ligation step may be performed prior to, or in the same reaction with the polymerase extension of the target DNA molecule. The polymerase extension is still needed to extend across the $dA_{30}$ sequence and the primer-binding sequence to generate the covalently closed circle containing the original target strand that is suitable for capture on the solid support, subsequent replication and ligation reaction or sequencing steps.

FIG. 168 illustrates a variation of FIG. 167, where the oligonucleotide probe is complementary to the single-stranded portions of the adapter regions. The starting fragments are generated as described for FIGS. 151-153. The remaining steps are as described in FIG. 167.

FIGS. 169 and 170 illustrate variations where either $T_{30}$-$T_{50}$ tails or short adapters are appended to the DNA target (cfDNA of average length of about 160 bases). To capture the desired regions, an oligonucleotide probe comprising (i) a 5' region that is complementary to a 5' region of the target DNA, (ii) a connecting sequence comprising a primer-binding sequence and a $dA_{30-50}$ sequence, and (iii) a 3' region that is complementary to a 3' region of the target is hybridized to the target (FIG. 169, step B). Depending on the probe design and the starting and ending bases of the target fragment, a portion of the target may loop out as a single stranded region between the 3' adapter or tail and the portion of the target complementary to the 3' probe as shown in FIG. 169, step B. Alternatively, a portion of the 5' end of the target sequence may not hybridize, or a portion of the 3' oligonucleotide probe sequence may loop out as shown in FIG. 170, step B. Addition of a polymerase allows extension of the 3' end of the oligonucleotide probe around the target, as well as extension of the 3' adapter of the target DNA to incorporate the $T_{30-50}$ and the primer-binding sequence (FIGS. 169 and 170, step C).

The hybridization conditions are chosen such that hybridization of the 3' probe region complementary to a portion of the 3' end of the target DNA brings the local concentration of the 3' adapter end of the target to its complement on oligonucleotide probe, (or the $T_{30-50}$ tail to the $dA_{50}$ sequence) such that it hybridizes correctly and is readily extended by polymerase. However, if there is less than sufficient complementarity between the oligonucleotide probe and the target DNA, then the 3' end of the target adapter will not hybridize to the oligonucleotide probe and rarely be extended by polymerase. Extension of the 3' end of the oligonucleotide probe on the target enhances association of the probe to the target, and thus increases the ability of the 3' adapter end to hybridize correctly to its complement and be extended by polymerase. The 5'→3' nuclease cleavage activity of polymerase (or Fen nuclease) cleaves a matching 5'-overlapping base of target at or near the position where the 5' side of the target is complementary to the 5' portion of the probe, leaving ligation-competent 5'-phosphate from the authentic target. Polymerase also extends oligonucleotide on target, and either generates a ligation-competent 5'-phosphate (shown) (FIGS. 169 and 170, step C), or does not cleave the blocking group on the 5' end of the oligonucleotide.

Ligase covalently seals the extended 3' ends to the ligation-competent 5'-phosphate to create circular ligation products as depicted in FIGS. 169 and 170, step D. A nick is introduced at the cleavable link (e.g. UDG cleavage of U, followed by cleavage of the apurinic backbone with AP endonuclease, left side). Optional addition of Uracil-DNA glycosylase (UDG) and Formamidopyrimidine-DNA glycosylase (Fpg, also known as 8-oxoguanine DNA glycosylase, which acts both as a N-glycosylase and an AP-lyase) may be used to nick targets containing damaged bases. Exonuclease(s) are then added to digest all unligated or nicked products leaving only desired single-stranded circular DNA comprising of original target DNA with $T_{30}$ and primer-binding sequence (FIGS. 169 and 170, step E). This product is suitable for capture on the solid support and replicative rolling circle amplification.

FIGS. 171 and 172 illustrate variations where nothing is appended to the DNA target (cfDNA of average length of about 160 bases) prior to circularization. To capture the desired regions, oligonucleotide probes comprising (i) a 5' region complementary to a portion of the 5' end of the target DNA molecule, (ii) a connecting sequence comprising a primer-binding sequence and a $dA_{30}$ sequence, and (iii) a 3' region complementary to a portion of the 3' end of the target DNA molecule are hybridized to the target DNA molecule. The 5' and 3' regions of the oligonucleotide probe contain optional mismatches at regular intervals (i.e. 10, 12, or 15 bases). The oligonucleotide probe may contain an optional blocking group on one end, or an optional cleavable linker.

The hybridization conditions are chosen such that hybridization of the 3' region of the oligonucleotide probe that is complementary to a portion of the 3' end of the target and hybridization of the 5' region of the oligonucleotide probe that is complementary to a portion of the 5' end of the target are enriched over targets that hybridize to only one side (and would form an unproductive extension product that would not circularize) (FIGS. 171 and 172, step C). Extension of the 3' end of the target molecule enhances association of the target and probe. The 5'→3' nuclease cleavage activity of polymerase (or Fen nuclease) cleaves a matching 5'-overlapping base of target at or near the position where the 5' end of the target is complementary to the 5' portion of the probe, leaving ligation-competent 5'-phosphate from the authentic target (FIGS. 171 and 172, step D). Polymerase also extends oligonucleotide probe on target, and either generates a ligation-competent 5'-phosphate (FIGS. 171 and 172, step D), or does not cleave the blocking group on the 5' end of the oligonucleotide.

Ligase covalently seals the extended 3' ends to the ligation-competent 5'-phosphate to create circular ligation products (FIGS. 171 and 172, step E). A blocking group prevents circularization of oligonucleotide probe strand, or alternatively, a nick is introduced at the cleavable link (e.g. UDG cleavage of uracil, followed by cleavage of the apurinic backbone with AP endonuclease, left side). Optional addition of Uracil-DNA glycosylase (UDG) and Formamidopyrimidine-DNA glycosylase (Fpg, also known as 8-oxoguanine DNA glycosylase, which acts both as a N-glycosylase and an AP-lyase) may be used to nick targets containing damaged bases. Exonuclease(s) are then added to digest all unligated or nicked products leaving only desired single-stranded circular DNA comprising of original target DNA with $T_{30}$ and primer-binding sequence (FIGS. 171 and 172, step E). This product is suitable for capture on the solid support and replicative rolling circle amplification.

FIG. 172 illustrates a variation of FIG. 171 where optional methyl sensitive restriction enzymes are used to enrich for targets methylated in promoter regions. A bisulfite treatment converts unmethylated dC to dU, and renders the strands non-complementary. After forming covalently closed circles, targets receive an additional treatment with methyl sensitive restriction enzymes. The oligonucleotide contains an abasic site that is cleaved by AP endonuclease, or EndoVIII. This assures only methyl containing strands are left intact for subsequent evaluation via sequencing.

FIGS. 173-176 illustrate amplification of circular templates, preferably generated as described in FIGS. 166-172, but not limited to those approaches. In each of those examples, the circle comprises the original target DNA, the $T_{30}$ sequence, one or more optional universal primer binding sequence(s) (FIG. 176), and optionally, 2 linker sequences with or without unique identifier sequences (FIGS. 173-17493).

In the embodiment illustrated in FIG. 173, the circular DNA containing a $T_{30}$ sequence and one or more universal primer sequences is hybridized via its $T_{30}$ region to $dA_{30}$ capture oligonucleotide primers immobilized on the solid support (FIG. 173, step B). The immobilized capture oligonucleotide is extended using a strand displacing polymerase (e.g., Bst polymerase) to initiate rolling circle amplification. At the same time, universal primers in solution hybridize to the immobilized single stranded regions of the rolling circle extension product and are also extended by polymerase as shown in FIG. 173, step B to form universal primer extension strands. Raising the temperature allows the capture oligonucleotide primers ($dA_{30}$ primers) to partially denature allowing for an adjacent primer to hybridize to a universal primer extension strand as shown in FIG. 173, step D. By this repetitive process, each universal primer extension strand is handed-off to the next primer to achieve a linear amplification of the original DNA.

FIG. 174 shows a variation of the embodiment illustrated in FIG. 173. In this embodiment, targeted primers in solution are added while rolling circle amplification is initiated (FIG. 174, step C) to form target specific primer extension strands.

FIG. 175 shows another variation of the embodiment illustrated in FIG. 173. In this embodiment, the circular DNA containing a $T_{30}$ sequence and one or more universal primer sequences is hybridized via its $T_{30}$ region to $dA_{30}$ capture oligonucleotide primers immobilized on the solid support (FIG. 175, step B). The immobilized capture oligonucleotide is extended using a strand displacing polymerase (e.g., Phi29 or Bst polymerase) to initiate rolling circle amplification. In this embodiment, the circular DNA is denatured and removed (FIG. 175, step C), and targeted primers, which hybridize to the single-stranded regions of the rolling circle extension product are hybridized and extended to formed target specific primer extension strands (FIG. 175, step D). Raising the temperature allows the capture oligonucleotide primers ($dA_{30}$ primers) to partially denature allowing for an adjacent primer to hybridize to a universal primer extension strand as shown in FIG. 175, step E. By this repetitive process, each universal primer extension strand is handed-off to the next primer to achieve a linear amplification of the original DNA.

FIG. 176 shows a variation of the embodiment illustrated in FIG. 173. In this embodiment, the starting circle was generated without the use of linkers, for example, as described in FIGS. 171 and 172. Similar to FIG. 173, this scheme uses both the $dA_{30}$ immobilized primer and in solution universal primer(s) to achieve amplification of the circular template.

Another aspect of the present invention is directed to a method for identifying, in a sample, one or more nucleotides in a target nucleotide sequence. This method involves providing a sample containing one or more target nucleic acid molecules containing the target nucleotide sequence or a complement thereof, and providing a solid support comprising one or more immobilized capture molecules, said capture molecules suitable to bind to a portion of the one or more target nucleic acid molecules. The method further involves binding the one or more target nucleic acid molecule to the one or more immobilized capture molecules on the solid support thereby immobilizing the one or more target nucleic acid molecules on said solid support, and contacting the immobilized target nucleic acid molecules or immobilized complementary target nucleic acid molecules that are complementary to the target nucleic acid molecule with a solution to form a nucleotide extension reaction mixture. The solution comprises one or more oligonucleotide primers, wherein said oligonucleotide primers are complementary to a portion of said immobilized target nucleic acid molecule or immobilized complementary target nucleic acid molecule thereof, a polymerase, and a collection of nucleotide triphosphates, each type of nucleotide triphosphate in the collection having (i) a different cleavable identifying signature-generating moiety, and (ii) a cleavable blocking moiety that inhibits addition of a subsequent nucleotide triphosphate. The nucleotide extension reaction mixture is subjected to a hybridization treatment wherein the one or more oligonucleotide primers hybridize in a base specific manner to their complementary immobilized target nucleic acid molecules or immobilized complementary target nucleic acid molecules thereof, and the hybridized oligonucleotide primers are extended by a single base-specific addition of a nucleotide triphosphate from the collection of nucleotide triphosphates to the 3' end of the hybridized oligonucleotide primers. The identifying signature-generating moiety and the blocking moiety are cleaved from each nucleotide added to the hybridized oligonucleotide primers after said extending, and the cleaved identifying signature-generating moiety is fed through one or more nanopores capable of detecting said identifying signature-generating moiety. The method further involves detecting, as a result of said feeding, an identifying signature generated by the cleaved identifying signature-generating moiety when said cleaved moiety passes through the one or more nanopores, and identifying, based on said detecting, the nucleotide triphosphate from the collection of nucleotide triphosphates that was added during said extending, thereby identifying one or more nucleotides in a target nucleotide sequence in the sample.

The sequence of the target nucleotide sequence can be obtained by repeating the extending, the cleaving, the feeding, the detecting, and the identifying steps as described above.

In accordance with this aspect of the present invention, the method can be carried out using the device comprising the biomolecular processor and one or more nanotubes as described herein or an alternative nanopore detection system known in the art as described supra.

In accordance with this aspect of the present invention, suitable capture molecules and methods for immobilizing target nucleic acid molecules on the solid support are described supra. Similarly, methods of generating immobilized complementary target nucleic acid molecules using solid phase amplification are also described supra.

In accordance with this aspect of the present invention, the immobilized target nucleic acid molecule or immobilized complementary target nucleic acid molecule thereof is subject to a nucleotide extension reaction process. The nucleotide extension reaction mixture comprises a collection of nucleotide triphosphates where each type of nucleotide triphosphate in the collection has (i) a different cleavable identifying signature-generating moiety, and (ii) a cleavable blocking moiety that inhibits addition of a subsequent nucleotide triphosphate.

The blocking moiety of the nucleotide triphosphate may directly block the addition of a subsequent nucleotide triphosphate at its 3'OH group. In this embodiment, the blocking moiety is appended to the nucleoside triphosphate at the 2'-O of a ribose, or the 3'-O of a deoxyribose (see FIG. 193). These nucleotide triphosphates are analogous to fluorescent sequencing-by-synthesis. (Ju et al., "Four-color DNA Sequencing by Synthesis Using Cleavable Fluorescent Nucleotide Reversible Terminators," *Proc Natl Acad Sci USA*. 103(52):19635-40 (2006), which is hereby incorporated by reference in its entirety). In the case of 3'-O blocking groups, there are several well-demonstrated examples in the literature such as but not limited to amino, azidomethyl, and cyanoethyl groups. The specific nature of the group should be chosen for a combination of efficiency of enzymatic incorporation and ease of removal during the deblocking step. Removal of the blocking group is specific to the chemical nature of the blocking group but examples would be the use of mild aqueous reagents (i.e., reducing agents) at temperatures that preserve the primer-template duplex and do not cause loss of signal due to melting of the primer-template duplex.

Alternatively, the blocking moiety of the nucleotide triphosphate reversibly inhibits the addition of a subsequent nucleotide triphosphate at its 3'OH group. These blocking moieties can be appended to a nucleotide triphosphate at the C5 or C7 position of the nucleoside, i.e., the pyrimidine or purine, respectively (see FIG. 192). These nucleotide triphosphates are similar to Lightning Terminators™ (Laser-Gen, Inc.) (see Gardner et al., "Rapid Incorporation Kinetics and Improved Fidelity of a Novel Class of 3'OH Unblocked Reversible Terminators," *Nucleic Acids Research* 40(15): 7404-15 (2012) and Litosh et al., "Improved Nucleotide Selectivity and Termination of 3'-OH Unblocked Reversible Terminators by Molecular Tuning of 2 nitrobenzyl Alkylated HOMedU Triphosphates," *Nucleic Acids Research* 39(6): e39 (2011), which are hereby incorporated by reference in their entirety) and Virtual Terminator™ (Helicos BioSciences) (Bowers et al., "Virtual Terminator Nucleotides for Next-Generation DNA Sequencing," *Nat. Methods* 6:593-595 (2003), U.S. Pat. No. 8,071,755 to Efcavitch et al, U.S. Pat. No. 8,114,973 to Siddiqi et al, WO 2008/0169077 to Siddiqi et al, which are hereby incorporated by reference in their entire). Chemical moieties which interfere with incorporation of dNTPs by a template dependent DNA polymerase that utilize steric bulk or charged inhibition or combinations of both can be used. Examples of inhibitory moieties are dipeptides of Glu-Glu or Asp-Asp.

In accordance with this aspect of the present invention, a suitable identifying signature-generating moiety is molecule that is coupled to a nucleotide triphosphate and produces a measurably modifying or modulating (i.e., augmenting or blocking) current through one or more nanopores.

Suitable identifying signature-generating moieties include water soluble, charged molecules, for example and without limitation, acidic polypeptides, basic polypeptides, dinucleotides, trinucleotides, peptide nucleotide analogues, charged polymers (e.g., polyethylene glycol polymers), nanospheres, nanocrystals, charged oligosaccharides, dendrimers, fluorescent dyes, infrared dyes, chromophores, quinolones, coumarin, porphyrins, porphyrin-metal complexes, water soluble aromatic polycyclic molecules, water soluble aromatic heterocyclic molecules, transition-metal complexes, metal chelates, metal chelate polymers, 2-nitrobenzyl derivatives, or any combination of these moieties. The cleavable identifying signature-generating moiety is appended to each nucleotide triphosphates at its nucleoside C5 position or its nucleoside C7 position. In one embodiment, the identifying signature-generating moiety is appended to its nucleotide triphosphate via a cleavable linkage.

In one embodiment, the blocking moiety and the identifying signature-generating moiety are covalently attached through a linker at the C5 or C7 position of modified dNTP analogs as separate and distinct species. Joined through a linker, each moiety is optimized for its function of preventing multiple incorporations during a polymerase extension step and providing differential mobility in an electric field, respectively. In another embodiment, the blocking moiety and the identifying signature-generating moiety covalently attached through a linker at the C5 or C7 position of modified dNTP analogs are the same species.

The last functional element of the modified dNTPs is a cleavable linker between the nucleobases and either the identifying signature-generating moiety-blocking moiety combination or the identifying signature-generating moiety. The former is used with 3'-O-unblocked analogs while the latter is used with 3'-O-blocked analogs. Cleavage of the linker is specific to the chemical nature of the linker but examples would be the use of mild aqueous reagents (i.e., reducing agents) at temperatures that preserve the primer-template duplex and do not cause loss of signal due to melting of the primer-template duplex. FIG. 196 shows the results of treating an incorporated nucleoside with a reducing agent; the top panel shows a nucleoside with an unblocked 3'-OH while the lower panel shows a nucleoside with a blocked 3'-OH.

The process is also compatible with combining enzymatic and chemical methods for removing blocking moieties and/or identifying signature-generating moieties. For example, the nucleotide bases may be modified with a phosphate group at either the 3'-OH position when using modified deoxyribonucleotides, or the 2'OH position when using modified ribonucleotides, which inhibit incorporation of the next nucleotide unless removed by the phosphatase activity of T4 kinase or shrimp phosphatase, respectfully.

Once the identifying signature-generating moiety is cleaved, it is fed through one or more nanopores for detection. The identifying signature-generating moiety is detected as it passes through one or more nanopores based on a measurable change in current through each nanopore that is generated as the moiety passes through each nanopore. As noted supra, the change in current can be an increase (i.e., current augmentation) or a decrease in current (i.e., a current blockade) through the nanopore or nanopores. The magnitude, duration, and direction of current change through a nanopore is detected and measured to identify and distinguish each of the nucleotide triphosphates. The identifying signature generated by the identifying signature-generating moiety is influenced by the size, shape, charge, and conductivity of the moiety. It is also influenced by the length, diameter, and molecular properties of the nanopore (e.g., composition and/or surface coating of the nanopore).

In another embodiment, the identifying signature-generating moiety is detected and distinguished based on its time of flight in a nano-scale time-of-flight channel. In this embodiment, the cleaved electronic generating moiety is fed through at least a first and second nanopore, where the first and second nanopores are positioned on opposing ends of a nano-scale time-of-flight channel. The time it takes for moiety to pass through the first nanopore, the time-of-flight channel, and the second nanopore are measured and used as the identifying signature of the identifying signature-generating moiety. The identifying signature generated by the identifying signature-generating moiety is influenced by the size, shape, charge, and conductivity of the moiety. It is also influenced by the length, diameter, and molecular properties of the nanopores and the time-of-flight nanochannel (e.g., composition and/or surface coating of the nanopore and nanochannel).

In another embodiment, the identifying signature-generating moiety is detected and distinguished based on both the change in current through at least two nanopores that occurs when the ligation product passes through the two nanopores in combination with the time-of-flight measurement between the two nanopores.

FIGS. 177-190 illustrate different configurations of sequencing in which immobilized target nucleic acid molecules templates are subjected to sequential rounds of DNA polymerase mediated sequencing-by-synthesis where target-specific primers are extended with individually labeled, reversible terminator modified deoxynucleotide triphosphates (dNTPs) of each of the four bases. Each cycle of sequencing-by-synthesis is composed of at least the following four steps: 1) extension of each primer-target nucleic acid template pair by a suitable template dependent DNA polymerase in the presence of four reversible terminator modified dATP, dGTP, dCTP and dUTP, each containing a different identifying signature-generating moiety, 2) removal of unincorporated labeled dNTPs and DNA polymerase after each extension step, 3) cleavage of the incorporated identifying signature-generating moieties and terminator moieties with subsequent detection and 4) washing out of the cleavage reagent and preparation for the next cycle of incorporation reactions.

FIGS. 177-190 illustrate a generalized approach to sequencing target nucleic acid molecules using target-specific primers in accordance with the methods of the present invention. When considering a sequencing reaction, there is a probability that a primer specific for the target nucleic acid molecule sequence will extend off an incorrect sequence. If mis-priming is uncommon and occurs as a minority event compared to correct priming, then residual incorrect signal may be removed during data processing. However, such low-level background signal may degrade overall signal quality, especially as read length increases. The primers described below are designed to maximize binding to the desired target sequences, while minimizing off-target results.

The embodiment illustrated in FIG. 177 is based on using target-specific sequencing primers containing a cleavable base that are blocked at the 3' end. For example, as shown in FIG. 177, step A, the primers may contain an RNA base a few bases from the 3' end, and the authentic 3' OH is liberated by cleavage with RNaseH2 only when the primer hybridizes to its correct target. Alternative cleavable groups are abasic sites, which are cleaved by Exonuclease III when bound to the target. Once the 3' OH is liberated, the primers are extended with a single modified nucleotide triphosphate (dNTP) (i.e., each dNTP contains a blocking moiety that prevents subsequent incorporation of another nucleotide triphosphate and an identifying signature-generating moiety) (FIG. 177, step B). Unincorporated dNTPs are washed away, and the incorporated dNTP is cleaved with reducing reagent such as mercaptoethanol or DTT (FIG. 177, step C). The cleavable moieties are distinct from each other, such that when cleaved they may be distinguished based on their identifying signature detected by one or more nanopores as described supra. The process of single-base primer extension, cleavage, and detection is repeated as shown in FIG. 177, steps D-F to collect sequence information for the target nucleic acid.

FIG. 178 shows a variation of the embodiment depicted in FIG. 177. That utilizes a dual priming oligonucleotide (Chun et al., "Dual priming oligonucleotide system for the multiplex detection of respiratory viruses and SNP genotyping of CYP2C19 gene," *Nucleic Acids Res.* 35(6):e40 (2007), which is hereby incorporated by reference in its entirety). The dual priming oligonucleotide consists of a 5' target-specific sequence portion of about 15-20 matched bases as an anchor sequence, a spacer region of 3-5 nucleotide analogues such as inosine or nitroindole (or mismatched bases), and a 3' target-specific sequence portion of about 6-10 bases. The primer binds its correct target at two regions, with a bubble in-between (FIG. 178, step A). This structure provides the requisite specificity when bound to the correct target, but does not extend when there are mismatches either in the anchor sequence portion or in the 3' binding portion. When using these primers, the 3' binding portion can be anchored in place by choosing a region of the target sequence where extension would add several bases prior to the first "G" nucleotide. Thus extending the primers with dATP, dCTP, TTP, and a dG nucleotide analogue containing a cleavable moiety that prevents addition of the next dNTP should anchor dual priming oligonucleotide primers to their correct target sequence but not to closely related, but incorrect sequences.

Another aspect of the present invention is directed to a method for identifying, in a sample, one or more nucleotides in a target nucleotide sequence. This method involves providing a sample containing one or more target nucleic acid molecules containing the target nucleotide sequence or a complement thereof, and providing a solid support comprising one or more immobilized capture molecules, said capture molecules suitable to bind to a portion of the one or more target nucleic acid molecules. The method further involves binding the one or more target nucleic acid molecule to the one or more immobilized capture molecules on the solid support thereby immobilizing the one or more target nucleic acid molecules on said solid support, and contacting the immobilized target nucleic acid molecules or immobilized complementary target nucleic acid molecules thereof with a solution to form a nucleotide extension reaction mixture. The solution comprises one or more oligonucleotide primers, wherein said oligonucleotide primers are complementary to a portion of said immobilized target nucleic acid molecule or immobilized complementary target nucleic acid molecule thereof, a polymerase, natural nucleotide triphosphates (dNTPs), and one or more nucleotide triphosphate terminators comprising (i) a capture moiety, or (ii) an identifying signature-generating moiety. The nucleotide extension reaction mixture is subjected to a hybridization treatment wherein the one or more oligonucleotide primers hybridize in a base specific manner to their complementary immobilized target nucleic acid molecules or immobilized complementary target nucleic acid molecules thereof, and the hybridized oligonucleotide primers are extended by addition of (a) zero, one, or more dNTPs and (b) a nucleotide triphosphate terminator to the 3' end of the hybridized oligonucleotide primers. Unincorporated dNTPs are removed by washing. An identifying signature-generating moiety may be permanently linked to extension products either at the 5' or 3' end or linked to extension products comprising a capture moiety, by capturing the identifying signature-generating moiety. Extension products comprising the identifying signature-generating moiety are denatured from the immobilized target nucleic acid molecule or immobilized complementary target nucleic acid molecule thereof, and fed through one or more nanopores capable of detecting said identifying signature-generating moiety. The method further involves detecting, as a result of said feeding, an identifying signature generated by the extension product containing the identifying signature-generating moiety when said extension product passes through the one or more nanopores, and identifying, based on said detecting, the extension products generated for one or more of the 4 terminating bases, aligning them in ascending order of time-of-flight, thereby identifying one or more nucleotides in a target nucleotide sequence in the sample.

The concept of resolving a Sanger sequencing-like ladder of extension products by Free Solution Electrophoresis by attaching a hydrodynamic drag inducing species to a polyanion like ssDNA has been demonstrated by Ren et al., *Electrophoresis* 20(12):2501-9 (1999), Vreeland et al., *Bioconjug Chem.* 13(3):663-70 (2002), Vreeland et al., *Anal Chem.* 73(8):1795-803 (2001), Meagher et al., *Electrophoresis* 26(1):82-90 (2005), Meagher et al., *Electrophoresis* 27(9):1702-12 (2006), Meagher et al., *Anal Chem.* 80(8): 2842-8 (2008), Albrecht et al., *Anal Chem.* 83(2):509-15 (2011), which are hereby incorporated by reference in their entirety. The principle is based on altering the monotonic charge-to-mass ratio of a nucleic acid by attaching a nucleic acid to an monodisperse macromolecule that provides sufficient hydrodynamic drag to the complex such that the molecular weight of the nucleic acid is essentially negligible while the charge of the extension product supplies a differential charge which is proportional to the length of the nucleic acid and thus allows single nucleotide resolution of the extension products. Macromolecules with sufficiently high hydrodynamic drag to enable free solution electrophoresis of single stranded nucleic acids are typically appended to the 5' end of either common, universal, or target-specific primers used in sequencing reactions. Any suitable covalent mode of attachment to an oligonucleotide primer can be used, such a 5'-thiol or 5'-amino modified synthetic oligonucleotide with a heterofunctional linker to link the primer to a suitable identifying signature modifier. As described supra, suitable identifying signature modifiers include, without limitation, as polypeptides, polynucleotides, peptide nucleotide analogue (PNA) multimers, peptoids, polyethers (polyethylene oxide and polypropylene oxide), nanospheres, nanocrystals, oligosaccharides, dendrimers, polyesters (polyglycolic acid, polylactic acid), polyurethanes, polyamides, polysulfonamides, polysulfoxides, polyphosphates, polyphosphonates, and combinations thereof. Alternatively, a homofunctional linker can be used to mediate covalent attachment of the identifying signature modifier to a 5' modified oligonucleotide primer. Identifying signature modifiers can also be introduced to sequencing extension products through incorporation by a polymerase in the presence of a nucleotide analogue terminator comprising a covalently bound identifying signature modifier. Nucleotide triphosphate analogs modified at the C5 or C7 with a propargyl amine can be further modified with a suitable identifying signature modifier via a heterofunctional linker. Alternatively, an identifying signature modifier can be introduced to extension products through incorporation by a polymerase in the presence of a nucleotide analog terminator comprising a capture moiety, followed by exposure to an appropriately activated identifying signature modifier. Nucleotide analog terminators can be modified at the C5/C7 position with an appropriate linker, which is additionally modified with a capture moiety. Typical capture moieties include, without limitation, biotin, maltose, chitin, azide, alkynyl, dibenzocyclooctyl (DBCO) for the capture of thermostable streptavidin, alkynyl-modified identifying signature modifier for copper(I) catalyzed [3+2] azide-alkyne cycloaddition (CuAAC), azide-modified identifying signature modifier for copper(I) catalyzed [3+2] azide-alkyne cycloaddition (CuAAC), or azide-modified identifying signature modifier for copper-free click conjugation, respectively. Alternatively, when the 5' end of the extension product has been modified with an identifying signature modifier, the 3' end of the extension products can be appended with an additional encoded identifying signature modifier through incorporation by a polymerase in the presence of one or more nucleotide analog terminator comprising one or more different covalently bound encoded identifying signature modifiers. These species, which serve to provide a distinct signal upon passage through one or more nanopores include water soluble, charged molecules, for example and without limitation, acidic polypeptides, basic polypeptides, dinucleotides, trinucleotides, peptide nucleotide analogues, charged polymers (e.g., polyethylene glycol polymers), nanospheres, nanocrystals, charged oligosaccharides, dendrimers, fluorescent dyes, infrared dyes, chromophores, quinolones, coumarin, porphyrins, porphyrin-metal complexes, water soluble aromatic polycyclic molecules, water soluble aromatic heterocyclic molecules, transition-metal complexes, metal chelates, metal chelate polymers, 2-nitrobenzyl derivatives, or any combination of these moieties.

FIG. 179 shows the above embodiment for sequencing a template that is analogous to Sanger sequencing. Similar to the method depicted in FIG. 178, this embodiment starts with a dual priming oligonucleotide, which comprises a 5' target-specific sequence portion of about 15-20 matched bases as an anchor sequence, a spacer region of 1-5 nucleotide analogues, abasic, cleavable, or mismatched bases, and a 3' target-specific sequence portion of about 6-10 matched bases. The primer binds its complementary target at two regions, with a bubble in-between (FIG. 179, step A). This structure provides the requisite specificity when bound to the correct target, but does not extend when there are mismatches either in the anchor sequence portion or in the 3' binding portion. Once the primers are hybridized to their respective template, polymerase is added in the presence of dATP, dCTP, dGTP, TTP, and a dA nucleotide analogue terminator comprising a covalently bound identifying signature modifier (FIG. 179, step B.). Examples of nucleotide analogue terminators containing a covalently bound identifying signature modifier are illustrated in FIG. 194. Unincorporated dNTP and analogue nucleotides are washed away, and a 3' identifying signature modifier (i.e. streptavidin) is added to bind to the capture moiety (i.e. biotin). In one embodiment, a thermostable version of streptavidin binds the biotin of all extension products containing a biotinylated terminator. This allows for subsequent release of extension products from their targets on the solid support by thermal or other denaturation, while retaining the 3' identifying signature modifier on the extension product. Alternative capture moieties include, without limitation, maltose, chitin, dibenzocyclooctyl (DBCO) for the capture of thermostable streptavidin, alkynyl-modified identifying signature modifier for copper(I) catalyzed [3+2] azide-alkyne cycloaddition (CuAAC), azide-modified identifying signature modifier for copper(I) catalyzed [3+2] azide-alkyne cycloaddition (CuAAC), or azide-modified identifying signature modifier for copper-free click conjugation, respectively. The extension products are fed through at least a first and second nano-pore, where the first and second nano-pores are positioned on opposing ends of a nano-scale time-of-flight channel. The time it takes for the extension products to pass through the first nano-pore, the time-of-flight channel and the second nano-pore are measured and used as the identifying signature of the extension products. The process is repeated three more times, using dC, dG, and dU biotinylated terminators, as above. Aligning all the products for each of the 4 terminating bases in ascending order of time-of-flight provides the sequence information for the target.

FIG. 180 shows a dual-specificity primer that binds its complementary target at two regions, with a bubble in-between (FIG. 180, step A). This structure provides the requisite specificity when bound to the correct target, but does not extend when there are mismatches either in the anchor sequence portion or in the 3' binding portion. Once the primers are hybridized to their respective template, polymerase is added in the presence of dATP, dCTP, dGTP, TTP, and a dA nucleotide analogue terminator comprising a capture moiety, such as biotin (FIG. 180, step B.). Examples of nucleotide analogue terminators containing a biotin capture group are illustrated in FIG. 195. Unincorporated dNTP and analogue nucleotides are washed away, and a 3' identifying signature modifier (e.g., streptavidin) is added to bind to the capture moiety (e.g., biotin). In one embodiment, a thermostable version of streptavidin binds the biotin of all extension products containing a biotinylated terminator. This allows for subsequent release of extension products from their targets on the solid support by thermal and/or other denaturation, while retaining the 3' identifying signature modifier on the extension product. Alternative capture and 3' identifying signature modifiers that may be used are described supra.

The extension products are fed through at least a first and a second nanopore positioned on opposing ends of a nano-scale time-of-flight channel. The time it takes for an extension product to pass through the first nanopore, the time-of-flight channel and the second nanopore is measured and used as the identifying signature of the extension product. The process is repeated 3 more times using dC, dG, and dU biotinylated terminators as described above. Aligning all the products for each of the 4 terminating bases in ascending order of time-of-flight provides the sequence information for the target nucleic acid molecule.

FIGS. 181 and 182 show another variation of this method. In this version, the dual priming oligonucleotide comprises a 5' target-specific sequence portion of about 15-20 matched bases as an anchor sequence, a spacer region of 1-5 nucleotide analogues or mismatched bases including a cleavable base or link, and a 3' target-specific sequence portion of about 6-10 matched bases. FIG. 181, step B illustrates that after extension with dATP, dCTP, dGTP, TTP, and a dA nucleotide analogue terminator comprising a covalently bound identifying signature moiety, the extension products are cleaved at the cleavable base or link, and the shorter products are denatured from the target, separated, and distinguished in a time-of-flight nanoscale channel as described supra. The process is repeated three more times, using dC, dG, and dU biotinylated terminators as described above. Aligning all the products for each of the 4 terminating bases in ascending order of time-of-flight provides the sequence information for the target. FIG. 182, step B illustrates that after extension with dATP, dCTP, dGTP, TTP, and a dA nucleotide analogue terminator comprising a capture moiety, and binding the identifying signature generating moiety, the extension products are cleaved at the cleavable base or link. The shorter products are denatured from the target, separated, and distinguished in a time-of-flight nanoscale channel as described supra. The process is repeated three more times using dC, dG, and dU biotinylated terminators as above. Aligning all the products for each of the 4 terminating bases in ascending order of time-of-flight provides the sequence information for the target.

FIG. 183 shows a different variation for sequencing a template that is analogous to Sanger sequencing. As in FIG. 178, this embodiment starts with a dual priming oligonucleotide, which comprises an identifying signature modifier on the 5' portion of the oligonucleotide, a 5' target-specific sequence portion of about 15-20 matched bases as an anchor sequence, a spacer region of 1-5 nucleotide analogue, abasic, spacer, or mismatched bases, and a 3' target-specific sequence portion of about 6-10 matched bases. The primer binds its correct target at two complementary regions with a bubble in-between (FIG. 183, step A). This structure provides the requisite specificity when bound to the correct target, but does not extend when there are mismatches between the template and primer either in the anchor sequence portion or in the 3' binding portion. Once the primers are hybridized to their respective template, polymerase is added in the presence of dATP, dCTP, dGTP, TTP, and a dA nucleotide analogue terminator comprising a covalently attached identifying signature generating moiety (FIG. 183, step B). Examples of nucleotide analogue terminators comprising an identifying signature modifier are illustrated in FIG. 218. Unincorporated nucleotides and nucleotide analogues are washed away and the products containing an identifying signature modifier on the 5' end and an identifying signature modifier on the 3' end are denatured from the target. The extension products are fed through at least a first and a second nanopore positioned on opposing ends of a nano-scale time-of-flight channel, and the time-of-flight of the extension products are measured and used as the identifying signature of the extension products. The process is repeated three more times, using dC, dG, and dU terminators, with the same identifying signature modifier as above. Aligning all the extension products for each of the 4 terminating bases in ascending order of time-of-flight provides the sequence information for the target, in a manner similar to classical four lane Sanger sequencing using radioactive labeled extension products.

FIG. 184 shows a variation of the embodiment of FIG. 183. In this variation, after hybridizing the primers to their respective targets, polymerase is added in the presence of dATP, dCTP, dGTP, TTP, as well as a dA nucleotide analogue terminator comprising a first encoded identifying signature modifier and a dC nucleotide analogue terminator comprising a second encoded identifying signature modifier (FIG. 184, step B). Examples of nucleotide analogue terminators comprising a first and a second encoded identifying signature modifier are illustrated in FIG. 220: After washing away unincorporated nucleotides and nucleotide analogues, the extension products are denatured from the target, separated, and distinguished on a time-of-flight nanoscale channel as described supra. Repeating these reactions with different 3' encoded identifying signature modifiers on different bases will provide different signatures, where the distribution of products from each run, in combination, provides the sequence information for the target. In this example, the first run uses 3' encoded identifying signature modifier 1 on dA, and 3' encoded identifying signature modifier 2 on dC. The second run reverses the 3' encoded identifying signature modifiers by using 3' encoded identifying signature modifier 2 on dA, and 3' encoded identifying signature modifier 1 on dC, The third run uses 3' encoded identifying signature modifier 1 on dG, and 3' encoded identifying signature modifier 2 on T, while the fourth run uses 3' encoded identifying signature modifier 2 on dG, and 3' encoded identifying signature modifier 1 on T. The use of two different encoded identifying signature modifiers in one reaction increases the number of fragments passing through the time-of-flight nanoscale channel which has the advantage of increasing the data collection density and decreasing the differential mobility between successive signals by interleaving two base specific extension ladders. Subjecting each of the templates to two rounds of interrogation by switching the different encoded identifying signature modifiers reduces the error rate of the base calling thus allowing a higher confidence sequence identification.

FIG. 185 shows a variation of the embodiment of FIG. 184. In this variation, after hybridizing the primers to their respective targets, polymerase is added in the presence of dATP, dCTP, dGTP, TTP, as well as a dA nucleotide analogue terminator comprising a first encoded identifying signature modifier, a dC nucleotide analogue terminator comprising a second encoded identifying signature modifier, a dG nucleotide analogue terminator comprising a third encoded identifying signature modifier, and a T nucleotide analogue terminator comprising a fourth encoded identifying signature modifier (FIG. 185, step B). Examples of nucleotide analogue terminators comprising four different encoded identifying signature modifiers are illustrated in FIG. 220. The modified terminators are present at a concentration ratio relative to the four non-terminating nucleotides to generate a roughly equimolar set of nested extension products that are within the resolution space of the time-of-flight separation mechanism. After washing away unincorporated nucleotides and nucleotide analogues, the extension products are denatured from the target, separated, and distinguished on a time-of-flight nanoscale channel as described supra.

FIG. 186 shows another variation of the embodiments depicted in FIGS. 177 and 178 where a dual priming oligonucleotide containing a cleavable 3' blocking group is utilized. Under these conditions, both the cleavable group and the 3' binding portion provide extra selectivity, such that sequencing can commence directly off the 3' end, as shown in FIG. 186, steps B-F.

FIG. 187 is another variation of the embodiments shown in FIGS. 177-186 that illustrates how an entire nucleic acid fragment may be sequenced even when the target-specific primer is located in the middle of the captured target nucleic acid molecule template. The process depicted in FIG. 187 involves sequencing of immobilized extension products that comprise multimeric tandem linear repeating sequences that are complementary to the target nucleic acid molecule and arise from the circular replication methods described herein and illustrated in FIGS. 173-176. Sequencing-by-synthesis is carried out essentially as described in relation to the process shown in FIG. 177, where the initial sequence generated will cover a portion of the target DNA and a second linker/unique identifier sequence (if present) (FIG. 187, step B). The polymerase will then read through the $dA_{30}$ region, and those reads at the end of the fragment will cease generating sequence information. However, the remaining polymerase will continue generating sequence though the universal primer binding or other artificial sequence and the first linker/unique identifier sequence (if present) (FIG. 187, step D). Sequence is then generated through the second portion of the target DNA, and since the polymerase can strand-displace, through the target specific primer (FIG. 187, step E). This allows one to obtain original sequence under the sequencing primer-binding region.

FIGS. 188-191 illustrate a generalized approach to sequencing target nucleic acid molecules using universal primers in accordance with the methods of the present invention. Under these conditions, there has already been some selection for the specific target, using either one or two target-specific primers to significantly enrich for the desired sequences. Thus, universal primers will be sufficient for obtaining direct sequence information.

The process depicted in FIG. 188 starts with replication products that arise from the enrichment methods described in FIGS. 150-162. The sequencing-by-synthesis process is carried out essentially as described in FIG. 177, with the first 15-25 bases sequenced corresponding to either a known linker sequence (if starting with products as per FIGS. 150-156 or known target sequences (if starting with products as per FIGS. 158-162. Reagents can be added for the requisite cycles with no data collection if desired.

FIG. 189 illustrates a generalized approach to paired-end sequencing a target strand. FIG. 189, step A illustrates target replicated when using solid support primer with a hairpin. Such replicates may be generated as illustrated in FIGS. 155, 157, 159, 161, and 163. After hybridizing either universal or target-specific primers, the target strand is sequenced using either sequencing by synthesis (SBS, as illustrated in FIGS. 177, 178, 186, 187, 188, and 190), or sequencing using terminators (Sanger, as illustrated in FIGS. 179-185). After the first strand is sequenced, extension products are denatured from the target (in SBS), and selected universal primers or target-specific primers are hybridized to the target and extended with polymerase lacking strand displacement activity. After phosphorylation of the 5' end of the hairpin using T4 kinase, the nick is sealed with ligase. Alternatively, the 5'-3' nuclease activity of polymerase or other nuclease(s) liberates the 5' phosphate, which is sealed to the extended target complement strand using ligase (FIG. 189, step D). This generates double stranded DNA bearing a covalently attached hairpin at one end. The initial target strands may now be degraded using an exonuclease with 3'-5' activity on dsDNA, such as Exonuclease III. Thus, now the complementary single strand is remaining, and suitable for sequencing by hybridizing universal dA30 or target-specific primer, and using the procedures illustrated in FIGS. 177-190.

The process depicted in FIG. 190 starts with replication products that would arise from the enrichment methods described in FIGS. 164-172. In this example, the linker may be designed such that it does not contain a "G" in the sequence. Thus extending the primers with dATP, dCTP, TTP, and a dG nucleotide analogue containing a cleavable moiety that prevents addition of the next dNTP will anchor the universal oligonucleotide primers to their correct sequences. Subsequent sequencing-by-synthesis commences past the linker sequence, immediately providing useful sequence information. Alternatively, the universal primer-binding site is more sophisticated as illustrated in FIG. 191. This design enables use of one type of universal amplification primer, comprising of a 5' T repeat sequence and a universal sequence on the 5' side. Sequencing primers may be used at different levels of diversity, depending on the complexity of sequence replicated, the number of fragments replicated, and the number of bioreactors in the instrument—such that on average, less than one replicated product is sequenced per bioreactor. For example, use of a first set of 8-12 sequencing primers may comprise of a common 5' sequence (16 bases), and variable 3' sequences (8 bases). Alternatively, a second set of 64-144 sequencing primers may comprise a common 5' sequence (8 bases), a variable middle sequence (8 bases, 12-12 variants) and hyper-variable 3' sequences (8 bases, 64-144 variants).

As described herein the device and methods of the present invention are designed to detect, identify, quantify (i.e., copy number), and distinguish low-abundance nucleic acid molecules comprising one or more nucleotide base mutations, insertions, deletions, translocations, splice variants, miRNA variant, alternative transcript, alternative start site, alternative coding sequence, alternative non-coding sequence, alternative splicing, exon insertion, exon deletion, intron insertion, translocation, mutation, or other rearrangement at the genome level, and/or methylated nucleotide bases. The low-abundance nucleic acid molecules with one or more nucleotide base mutations, insertions, deletions, translocations, splice variants, miRNA variant, alternative transcript, alternative start site, alternative coding sequence, alternative non-coding sequence, alternative splicing, exon insertion, exon deletion, intron insertion, translocation, mutation, or other rearrangement at the genome level, and/or methylated nucleotide bases are identified and distinguished using the methods of the present invention from a high-abundance of nucleic acid molecules in the sample having a similar nucleotide sequence as the low-abundance nucleic acid molecules but without the one or more nucleotide base mutations, insertions, deletions, translocations, splice variants, miRNA variant, alternative transcript, alternative start site, alternative coding sequence, alternative non-coding sequence, alternative splicing, exon insertion, exon deletion, intron insertion, translocation, mutation, or other rearrangement at the genome level, and/or methylated nucleotide bases.

The ability to detect, identify, quantify (i.e., copy number), and distinguish low-abundance nucleic acid molecules in a sample allows for early diagnosis and prognosis of a disease state. In another embodiment, the ability to detect, identify, quantify and distinguish low-abundance nucleic acid molecules in a sample allows for the determination of a genotypes or disease predisposition.

The target nucleic acid molecules that are detected, identified and distinguished can be isolated from any suitable sample, including without limitation, tissue, cells, serum, blood, plasma, amniotic fluid, sputum, urine, bodily fluids, bodily secretions, bodily excretions, cell-free circulating nucleic acids, cell-free circulating tumor nucleic acids, cell-free circulating fetal nucleic acids in pregnant woman, circulating tumor cells, tumor, tumor biopsy, and exosomes.

EXAMPLES

The following examples are provided to illustrate embodiments of the present invention but are by no means intended to limit its scope.

Example 1—Detecting and Distinguishing Single Molecules in the Nanosensor Chambers of the uMPS Simulation Data:

Preliminary simulations generated using COMSOL® simulation software have been performed on a nanosensor chamber comprised of 8 biomolecular processors each processor measuring 20×20 µm and containing 288 pillars (1 µm×5 µm with a 250 nm spacing). For these simulations, three operational questions were addressed: (1) can all biomolecular processors of a single chamber be uniformly addressed from a common input (reduces chamber footprint) hydrodynamically with no fluid moving into the nanotube; (2) what is the capture efficiency of the TdT-tailed DNA products to the surface immobilized $dA_{30}$ primers; and (3) following thermal denaturation, could the products be efficiently directed into the nanotube sensors electrokinetically.

Figure 31:
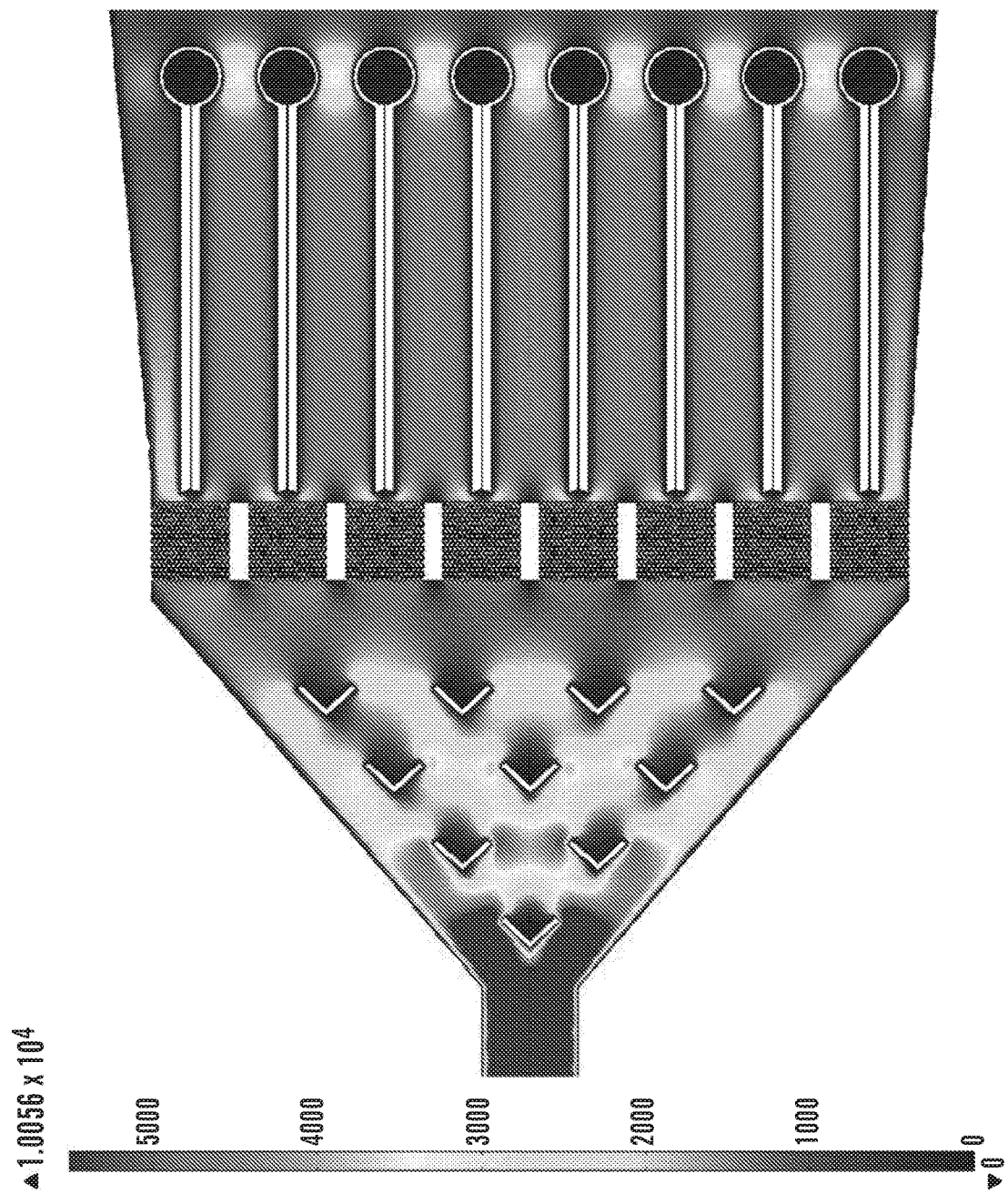
FIG. 31 shows a simulation of the fluid path through a nanosensor chamber containing eight biomolecular processors and eight nanotubes when flow is actuated via hydrodynamic pumping. The simulation shows uniform addressing of all biomolecular processors within a nanosensor chamber of a device.

For pressure driven flow (see FIG. 31), inclusion of Chevron baffles into the pre-biomolecular processor area of the chamber distributes input fluid across the entire biomolecular processor array in a substantially less amount of time then longitudinal diffusion only. In addition, due to, the high fluidic resistance in the nanotube during hydrodynamic operation, arising from its small cross-section (less than 50×50 nm, with a length greater than 100 µm length), very little if any fluid enters the nanotubes due to the extraordinarily high fluidic resistance. This is convenient because during the loading and reaction phases of the assay, which will use pressure driven flow to pump in sample/reagents, all material will travel around the flight tubes as shown in FIG. 31.

Figure 32A:
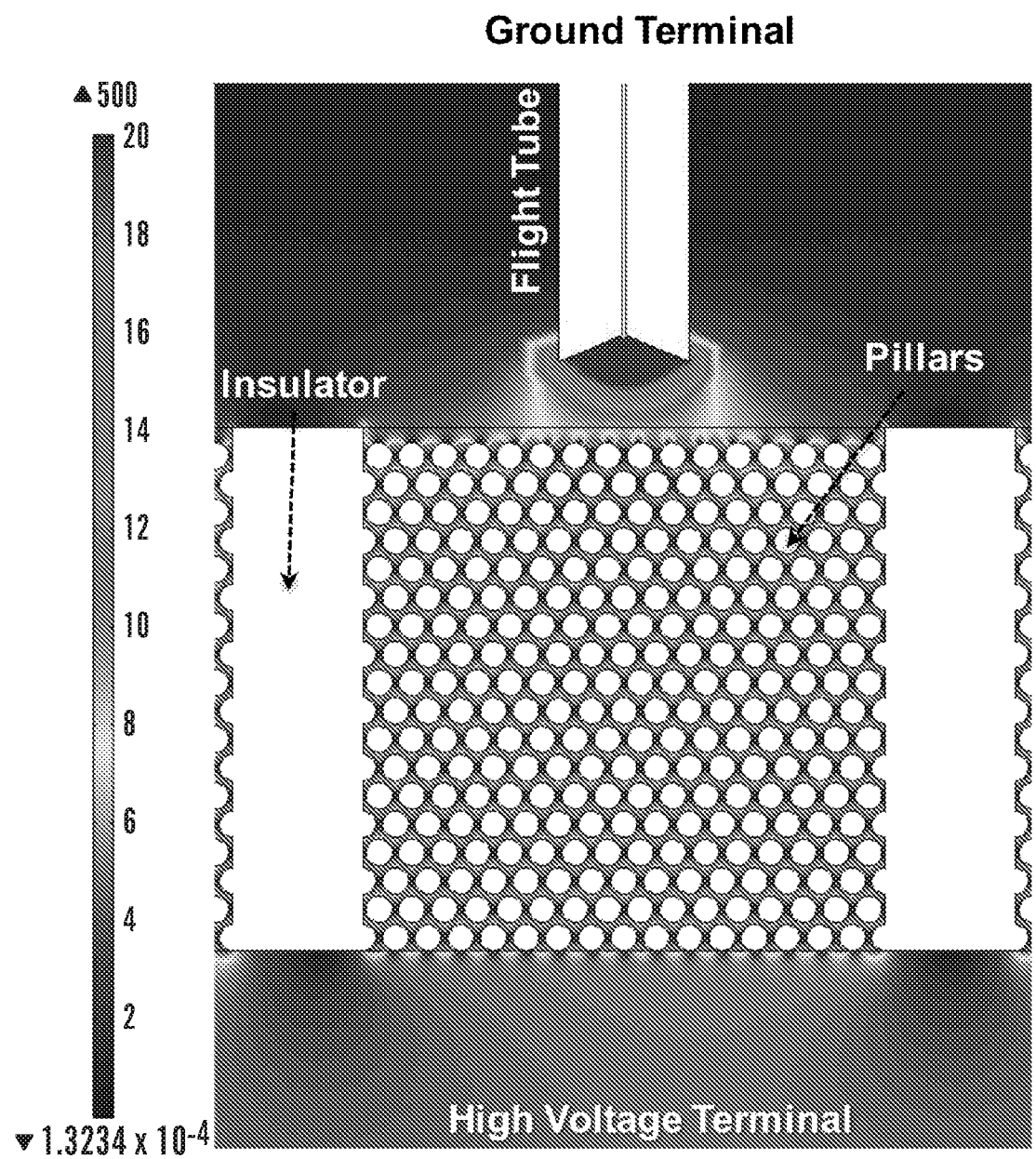
FIG. 32A shows a simulation of the fluid path through the plurality of spaced solid support structures within the bioreactor chamber of a biomolecular processor when flow is actuated via electrokinetic pumping.
Figure 32B:
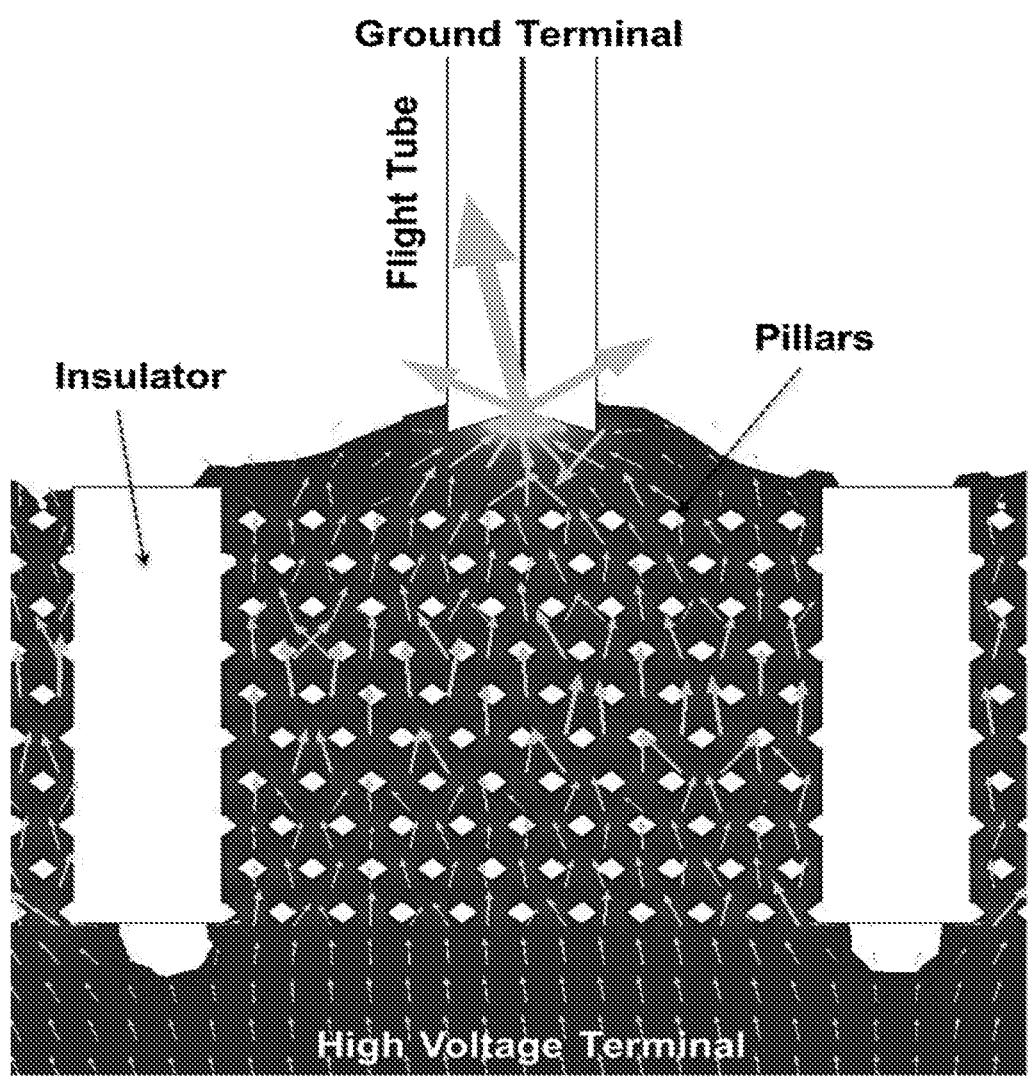
FIG. 32B shows the corresponding electric field lines through the bioreactor chamber of the biomolecular processor depicted in FIG. 32A.

However, when the chamber is actuated electrokinetically, which occurs after the solid-phase products are thermally melted from the immobilized target that are attached to the pillars of the bioreactor chamber, the thermally melted products are preferentially directed into the flight tube (FIG. 32A). As can be seen from FIG. 32A, the negatively charged products (oligonucleotides which may carry a drag tag label, but are polyanionic) are drawn preferentially into the flight tube because the majority of the electric potential drop (>95%) occurs within the nanometer flight tube. This allows for using virtual boundaries generated by the application of the electric field and the strong field lines that funnel the desired products into the flight tube (FIG. 32B). Thus, there is no need to fabricate via imprinting solid walls that would require valving operations to direct the flow of fluid in the proper direction.

Figure 33:
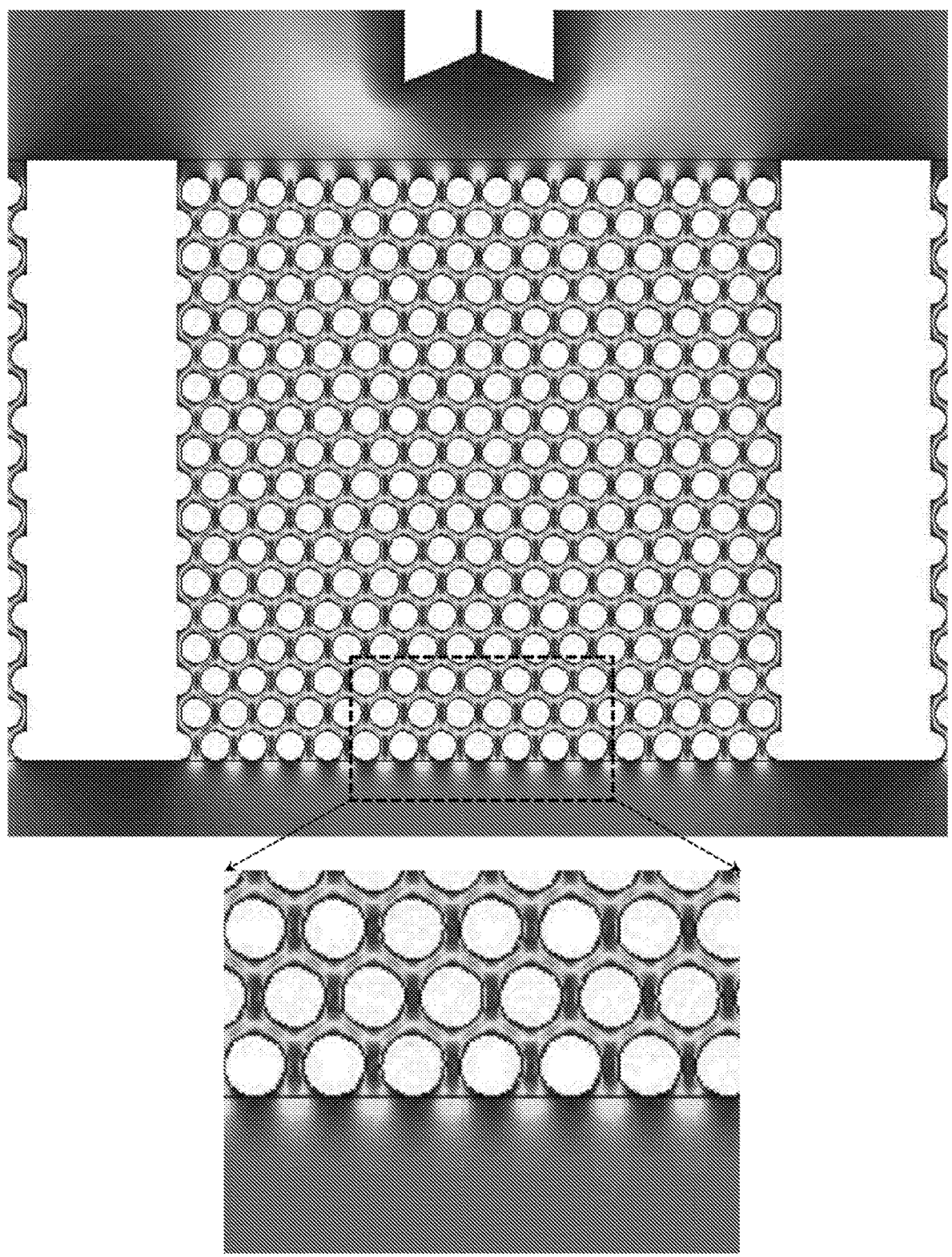
FIG. 33 shows a simulation to determine the capture efficiency of nucleic acid molecules as they move through the plurality of support structures in a single bioreactor chamber of a biomolecular processor.

Finally, using the pillar-based diffusional mode developed for predicting the recovery of pillared extraction beds and the pillar size and spacing that will be employed, the capture efficiency of the tailed DNA is >80% with equal loading onto all of the pillars (FIG. 33). This recovery is calculated for the input pillars of the single chamber component when the flow is driven hydrodynamically. Due to the use of the Chevron baffles and the uniform addressing of all biomolecular processors of a single chamber, i.e., eight biomolecule processors per nanosensor chamber (FIG. 31), there is an equal probability of capture by each pillar in the chamber. The pillars here can be of any size and shape to accommodate the given application to accommodate the load of target material required for the measurement. The pillars can be round, as shown in FIG. 31, or they can be square, diamond, rectangular shaped, etc., as described supra.

Unique to this application is a strategy that allows for the detection of single molecules traveling though nanotubes that consist of a long nanochannel and two or more in-plane synthetic nanopores. The nanopores have openings ranging from 5-50 nm and are located near the entrance and exit ends of the nanochannel, which serves as the flight tube (see FIG. 1B). When a molecule passes a nanopore, a current signature is generated depending on the ionic salt concentration and the size of the molecule, similar to what is seen in vertical nanopores, which consist of small openings in pores that are suspended on silicon nitride membranes. The nanopores can be naturally occurring pores, such as alpha-hemolysin or nanopores made via focused ion beam milling or electron beam milling in the silicon nitride membranes. Unique to this application is that the pores are in-plane with respect to the nanometer flight tube and fabricated in the same imprinting step used to create the nanofluidic network. In addition, a number of pores can be placed in series along the same path and those molecules entering/exiting the first pore and traveling into subsequent pores are sampled with 100% efficiency.

The two nanopores formed in a nanochannel will generate two current signatures, where the separation in time between the two peaks corresponds to the flight time of the thermally melted solid-phase product released from the pillars of the bioreactor chamber.

Figure 34:
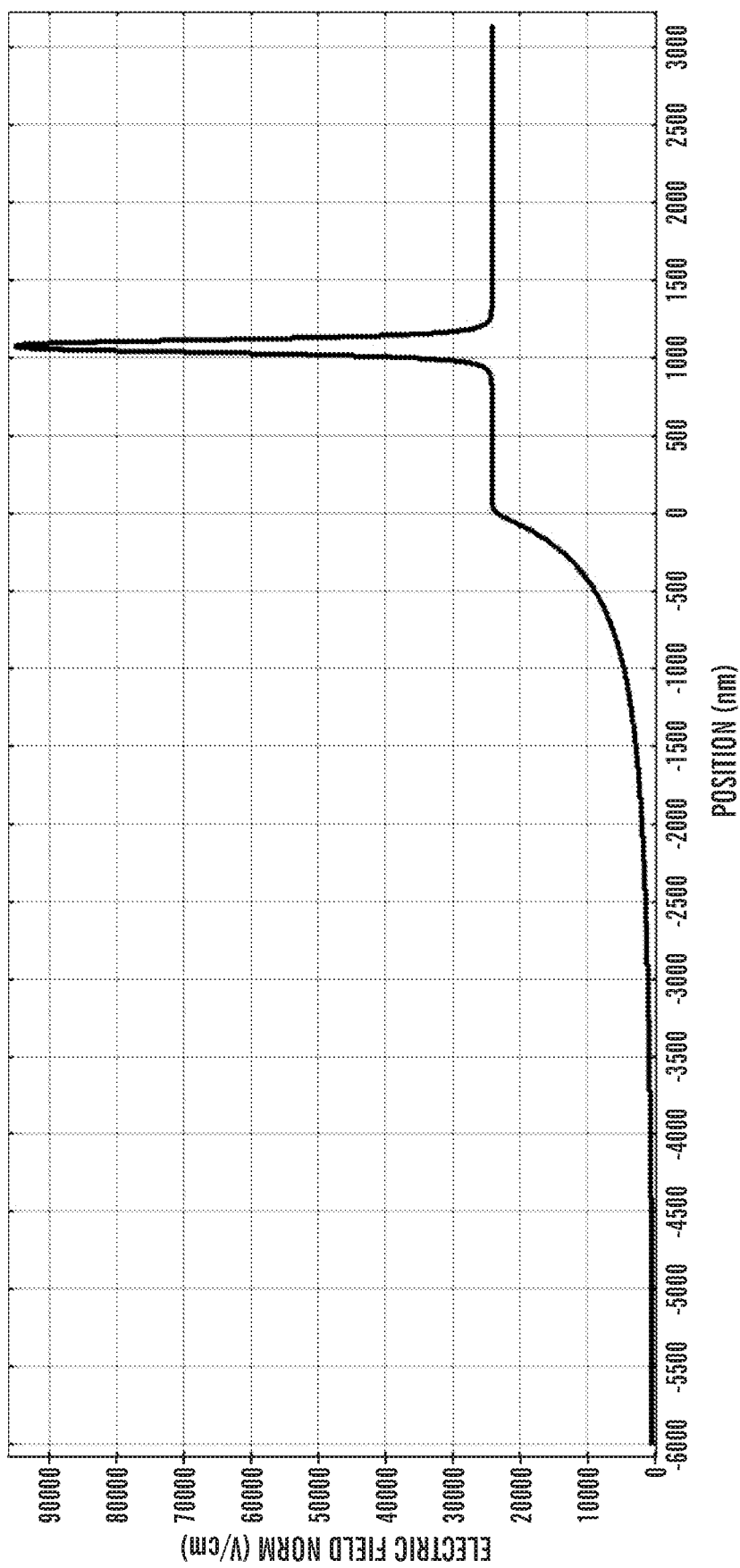
FIG. 34 is a graph showing simulated electric field distribution in a nanotube of the nanosensor module of the device of the present invention.

Extensive simulations have been carried out to demonstrate the feasibility of the in-plane synthetic nanopore strategy for detecting single molecules. FIG. 34 is a graph showing the simulated electric field distribution as a function of position within a nanotube containing a nanopore. In this example, the flight tube is 100×100 nm (w×d) and 100 µm in length with the pore being 50×50×50 nm, and the applied voltage across the tube is 10 V. However, the length of the flight tube can be 10's of microns in length to accommodate the given application. Longer flight tubes provide better electrophoretic resolution improving the identification efficiency of the single molecules. As shown in the graph of FIG. 34, when a longitudinal electric field is applied down the length of the nanometer flight tube, there is a large enhancement in the electric field across the in-plane pore due to its reduced size with respect to the flight tube. This indicates that the single molecule will speed up when traveling in this region of the flight tube.

Figure 35A:
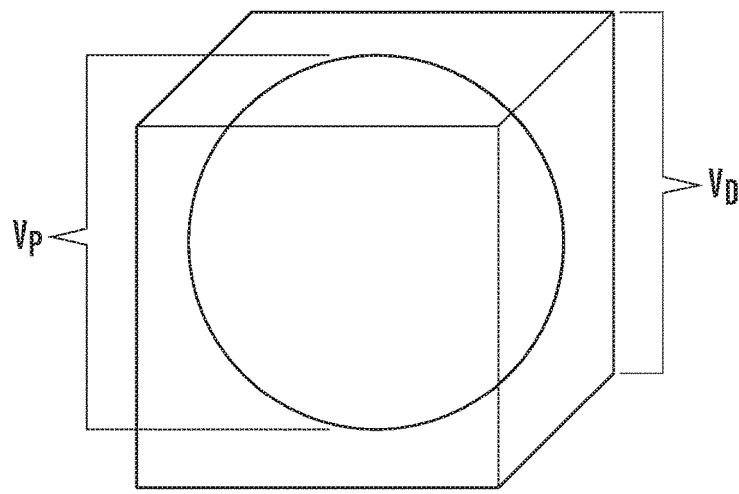
FIG. 35A is a schematic showing a spherical analyte in a nanopore, where Vp=volume of particle (analyte) and Vd=detection volume.
Figure 35B:
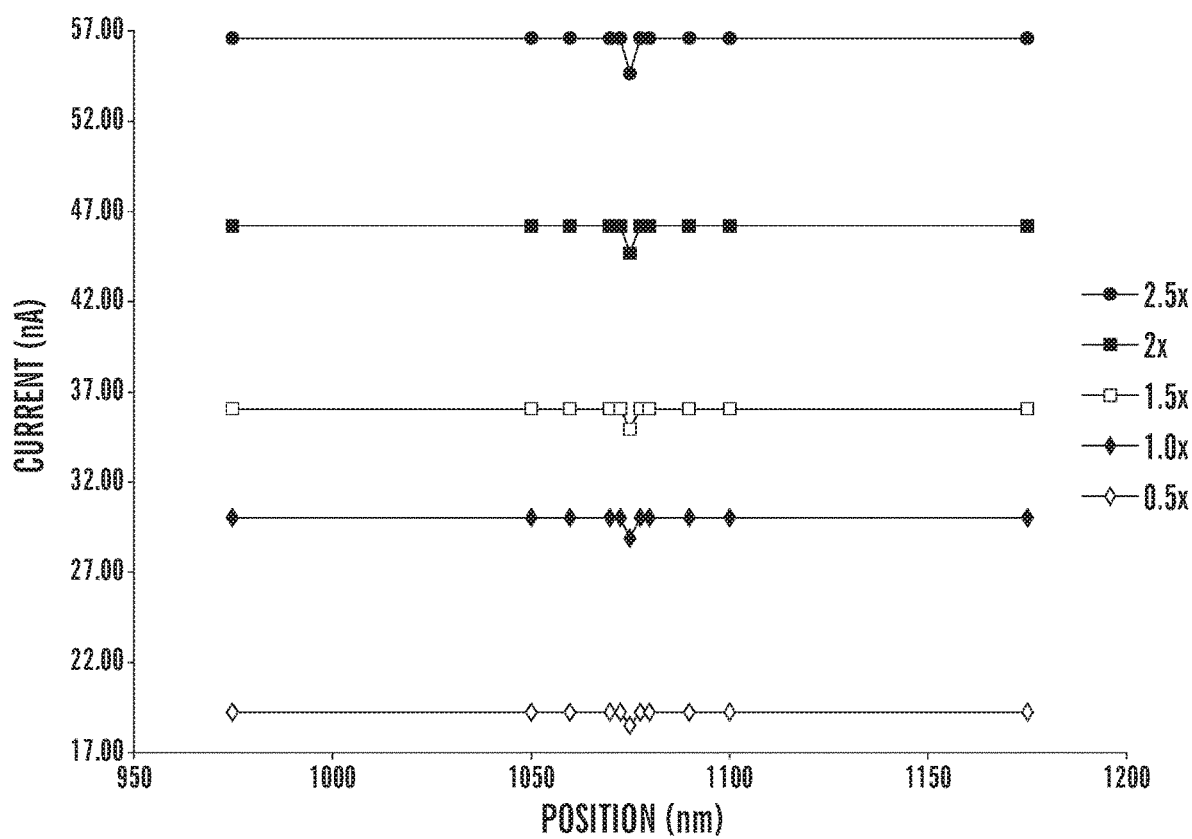
FIG. 35B is a graph showing the simulation results for a charged particle moving through a synthetic nanopore as a function of buffer electrolyte concentration. The magnitude of the blockage current depends on the carrier electrolyte concentration (TRIS/borate/EDTA buffer for 0.5×, 1.0×, 1.5×, 2× and 2.5×).

FIG. 35A shows a model of a spherically shaped particle residing within the in-plane synthetic nanopore. In this example, the spherical particle possesses a diameter of ~40 nm and the pore is 50×50 nm with a thickness of 50 nm. The current response that is generated ($\Delta I_B$) when the spherical particle is resident within the pore is predicted by $\Delta I_B \approx I(V_P/V_D)$. In this case, $\Delta I_B$ is equal to the unblocked current (I) multiplied by the ratio of the volume of the particle ($V_P$) to the interstitial volume between the pores ($V_D$). As can be seen in FIG. 35B, distinct current blockage events are generated when the particle is resident with the pore volume, $V_D$, irrespective of the ionic strength of the carrier electrolyte.

Figure 36A:
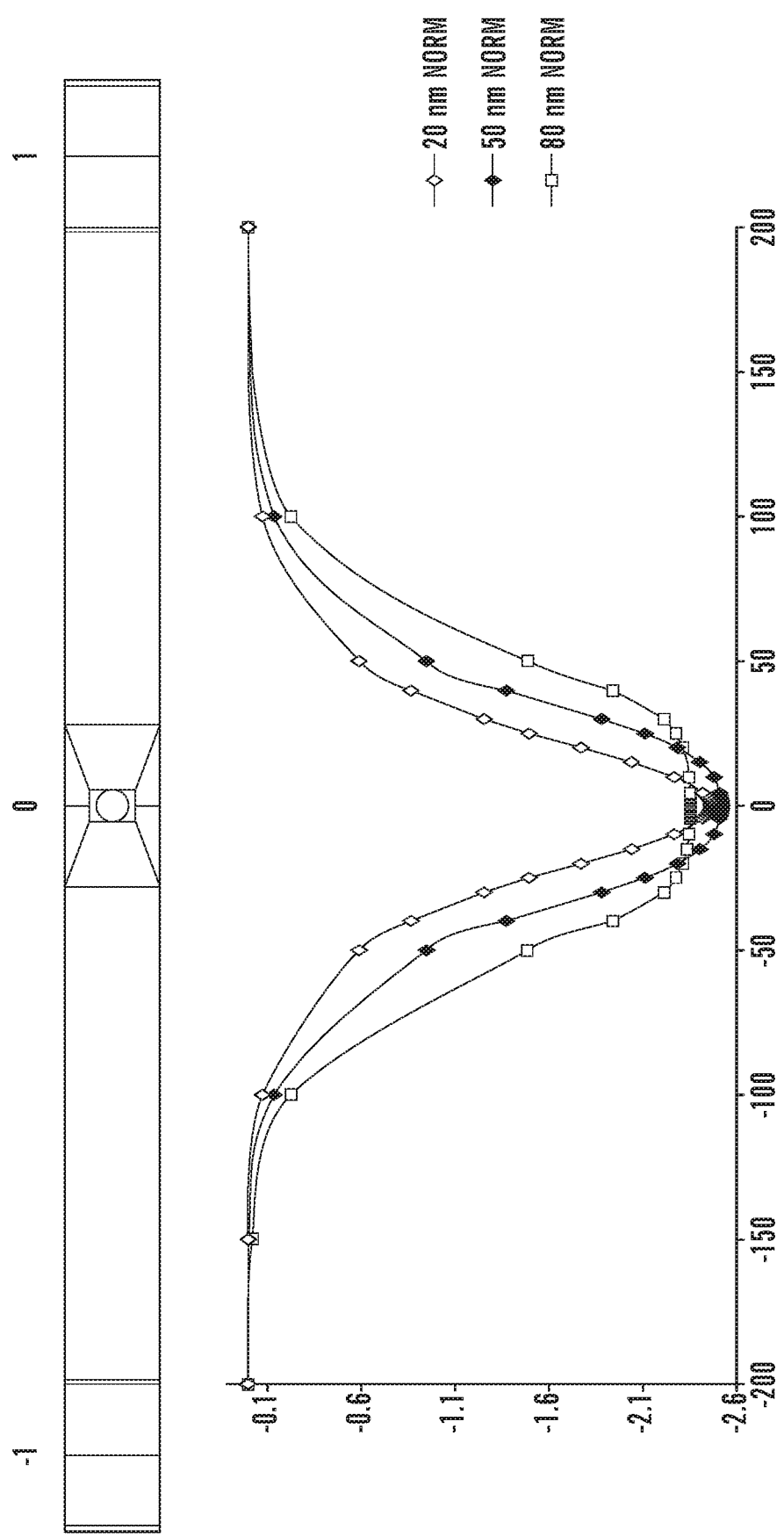
FIG. 36A is a simulation of the current blockage produced by a single DNA molecule moving through a nanopore of various lengths.
Figure 36B:
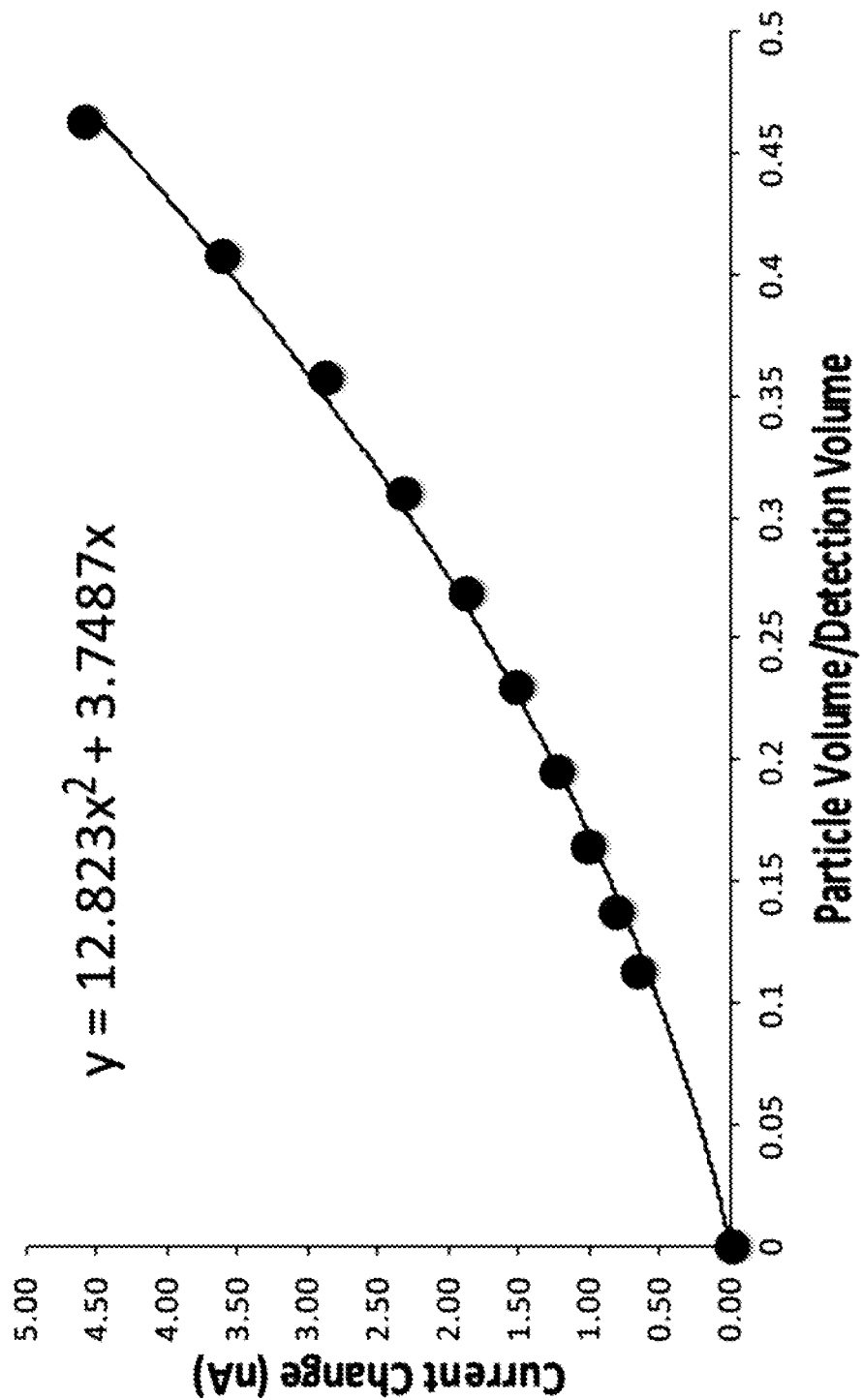
FIG. 36B is a graph depicting the magnitude of the current blockage event (nA) as a function of the spherical object/detection volume. The detection volume represents the pore volume.

FIGS. 36A and 36B show the results of a simulated current blockage produced by a single spherical DNA molecule having a 40 nM diameter moving through an in-plane synthetic nanopore of various lengths, but a constant cross section (50×50 nm). In this case, the pore length was altered at the following steps, 20 nm, 50 nm and 80 nm. As can be seen from the graph of FIG. 36A, the width of the current transient ($\Delta I_B$) peak was altered as a function of the pore length with longer pores producing wider signals. FIG. 36B shows a plot of the ratio of $V_P/V_D$ as a function of the amplitude of $\Delta I_B$. The plot was non-linear with the functional relationship shown in the accompanying graph.

These simulations demonstrate that a molecule's identifying signature, which in this case is a blockage current event, can be shaped by the pore length, i.e., larger pore length generates a broader current transient. As such, identifying signatures from different pores in the nanotube can be discerned by adjusting the length of the pore as these simulations show. Another way to change the shape of the identifying signature, i.e., current blockage event, is to change the pore diameter. Larger pores produce smaller current blockage events in terms of their amplitude.

Figure 38A:
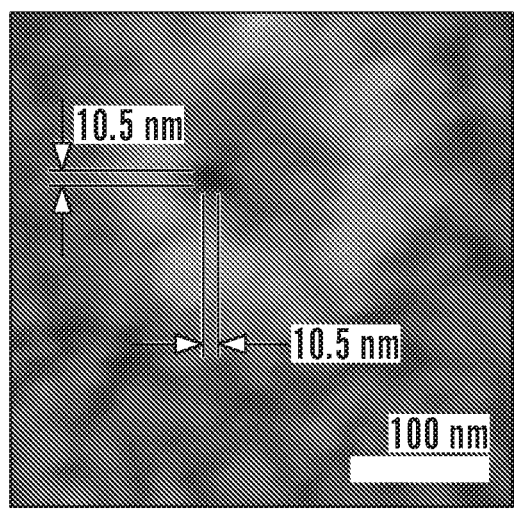
FIGS. 38A and 38B are SEM images for SU-8 membranes with perforated conical nanopores having differing diameters.
Figure 38B:
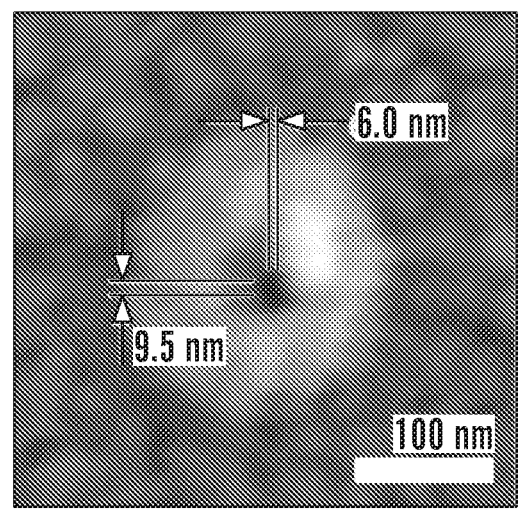
Figure 38C:
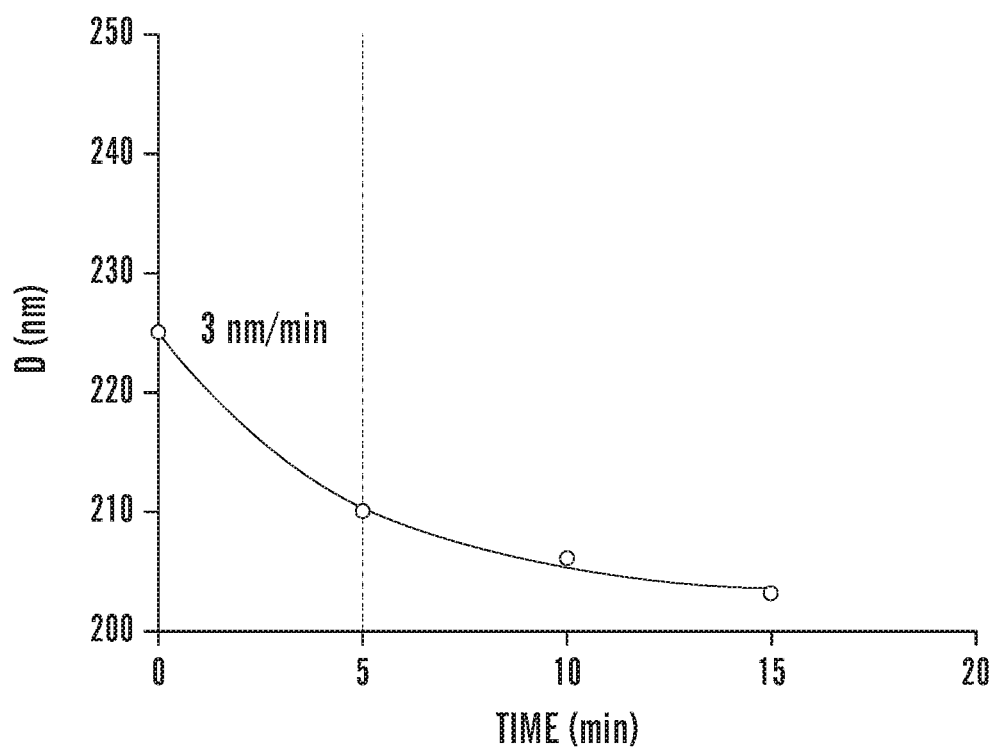
FIG. 38C is graph plotting the reduction of pore size as a function of reflow time.

Experimental Data:

A simple, high yield process for producing free-standing polymer membranes in SU-8 with perforated nanopores has been developed. The key feature of the process is to use a double resist layer for NIL, which is spin-coated sequentially. First, a lift-off resist (LOR) is used as a sacrificial layer, and then a negative photoresist SU-8 is used as the active layer. The micro/nanostructures are defined using NIL with Si stamps produced via lithography and wet chemical etching or deep reactive ion etching. The smallest pore achieved via a single step NIL process was ~10 nm diameter. The pore size was further reduced to ~6 nm by employing a polymer reflow process where the nanopores were placed between two plates and the polymer was heated above its respective glass transition temperature to 45° C. for 1 min. FIGS. 38A and 38B are SEM images of these SU-8 membrane conical nanopores having a diameter of 10 nm (FIG. 38A) or 6 nm (FIG. 38B). FIG. 38C is graph plotting the reduction of pore size as a function of reflow time. The size reduction rate was estimated to be 3 nm/min.

Figure 39B:
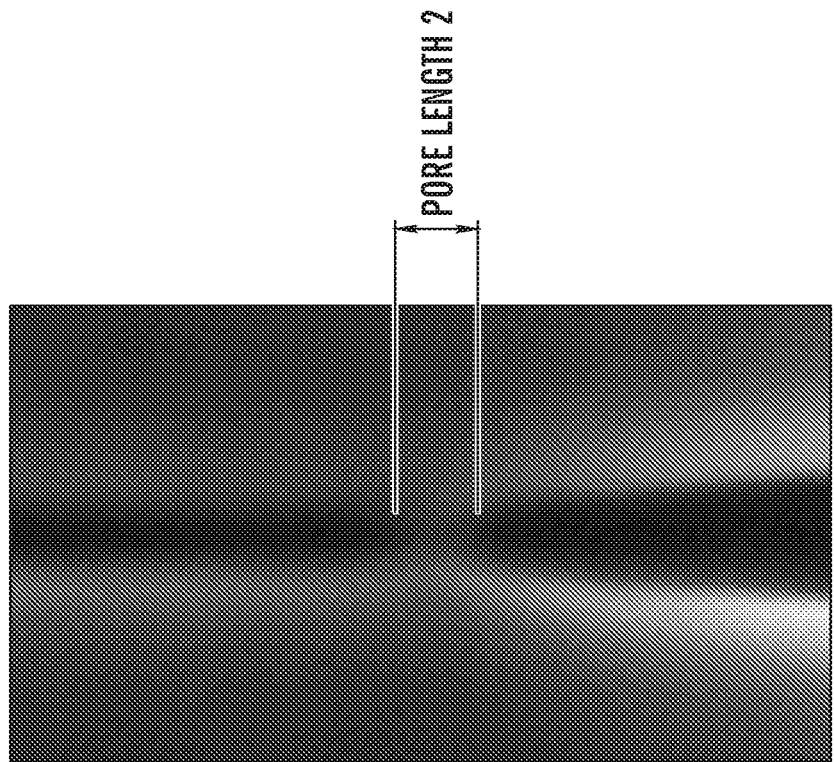
FIGS. 39A-39B are SEM images of nanopores having different pore lengths.
Figure 39A:
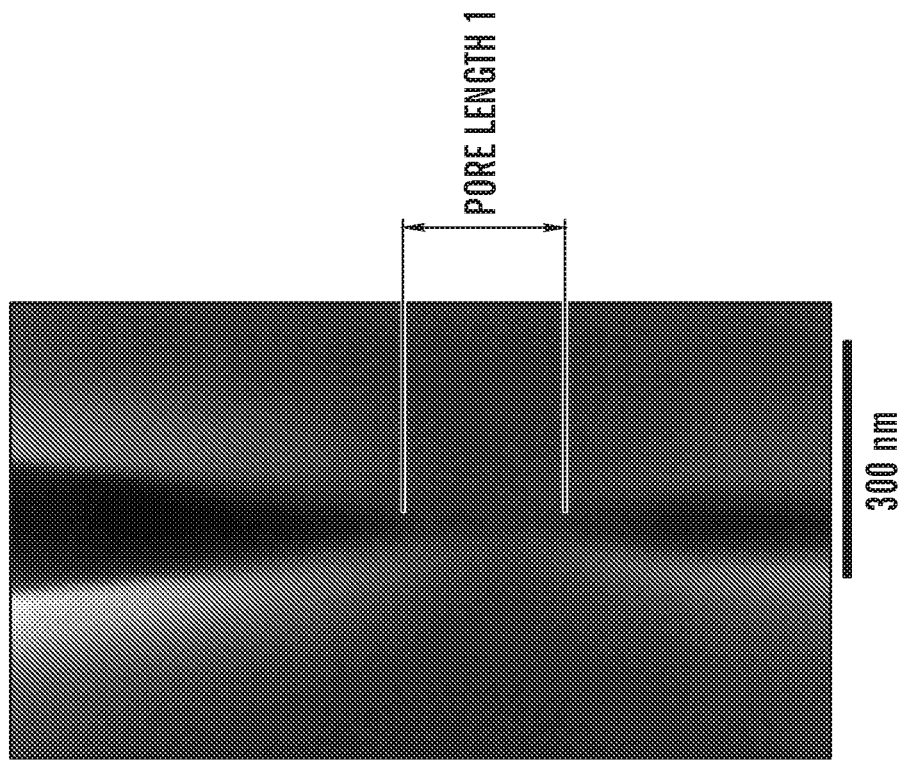

FIGS. 39A and 39B show fabricated nanotubes having nanopores of differing length.

Figure 37A:
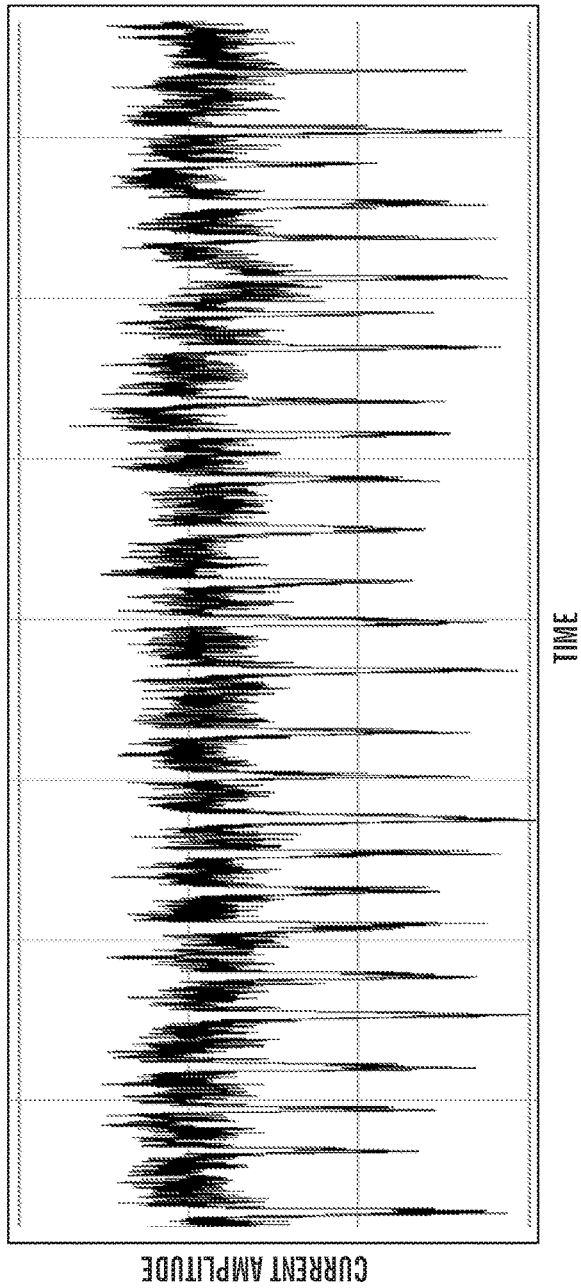
FIGS. 37A-37B show current blockage events for 500 base pair single DNA molecules electrokinetically travelling through polymer-based nanopores of two different sizes.
Figure 37B:
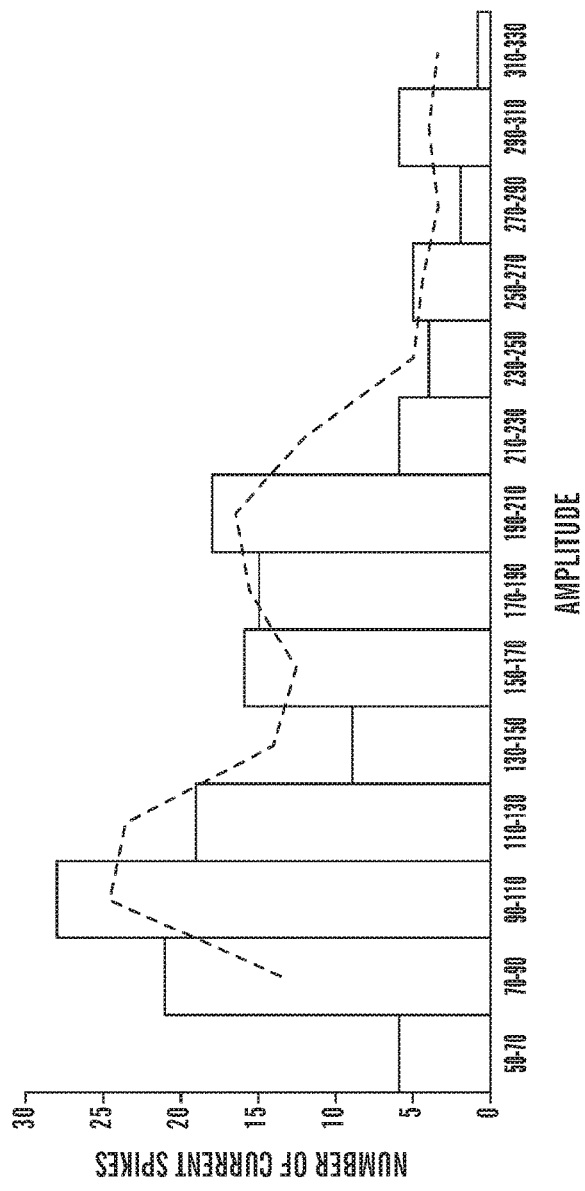

Preliminary experimental studies with the fabricated nanotubes have confirmed the simulation data. FIG. 37A shows an exemplary graph of the transient current versus time in a fabricated nanotube containing with two different size nanopores (50 nm×50 nm for the first pore and 80 nm×80 nm for the second pore). In this experiment, the nanotube was first filled with a buffer electrolyte. Then, a λ-DNA solution of the same ionic strength as the buffer electrolyte was added to the reservoir. A driving voltage was applied to electrophoretically drive the DNA molecules through the nanotube. The transient current was measured during the DNA translocation. The resulting graph of FIG. 37A shows multiple current peaks with different amplitudes. FIG. 37B shows the statistics for the amplitude of the current peaks obtained from 156 translocation events. The diagram shows a bimodal distribution with two amplitude peaks centered at 110 pA and 200 pA resulting from the two different nanopores. The result confirms that the amplitude and width of the current peak can be used as complementary molecular signatures.

Example 2—Electrophoresis for Multiplexing

The identification of the solid phase LDR (spLDR) products and other oligonucleotide products produced as a result of the solid-phase reactions being carried out on the pillars of the bioreactor chamber is based on their length (bp), which will be accomplished using electrophoretic mobility matching. This allows for mobility multiplexing with the multiplexing power determined by the peak capacity (P) of the system (multiplexing here is defined as the number of mutations that can be identified in a single analysis cycle by using different LDR primer pairs).

To test the sensitivity of the darkfield microscope to visualize single silver nanoparticles (AgNPs) in a nanochannel, a stationary AgNP (60 nm) was imaged and its localized surface plasmon resonance (LSPR) was monitored. FIG. 40A shows a three-dimensional image of the resulting signal demonstrating high sensitivity. The intensity profile was constant over time, indicating a lack of bleaching. Time-lapse images of the single AgNP (60 nm) moving through a PMMA nanochannel flight tube at an external field strength of 200 V/cm were obtained. FIG. 40B shows still LSPR images of the single AgNP moving electrophoretically through a PMMA nanochannel flight tube. The particle movement was in the direction from anode to cathode (same direction as EOF) with a transport time for this event of 1.3 s. Dimensions of the nanoslits were 100 µm in length and 150 nm in deep/width. In this case, the particle moved with a constant velocity with the absence of any intermittent motion due to stick/slip behavior.

FIG. 40C shows the electrophoretic mobility and variance in the mobilities of the single AgNPs as indicated by the plate number, N, as a function of the electric field strength. The electrophoretic mobility was found to be relatively constant irrespective of the electric field strength except at the lower field strengths (<200 V/cm) due to stick/slip motion. However, at high electric fields (>200 V/cm), the plate numbers dramatically increased.

Figure 40D:
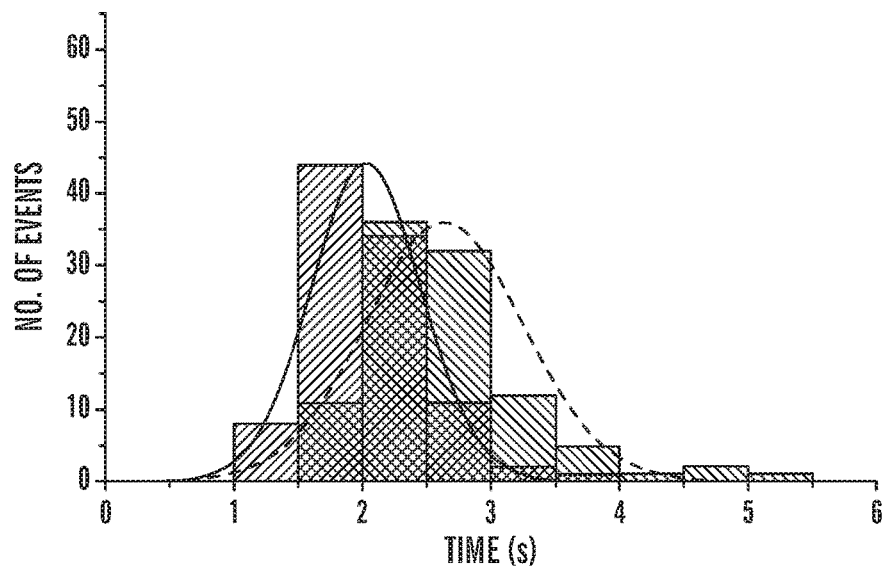
Figure 40E:
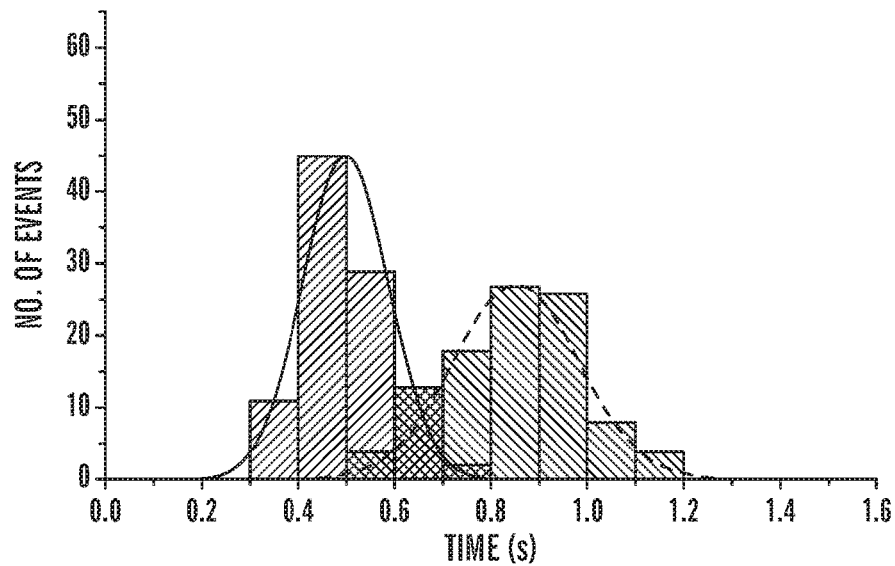
Figure 40F:
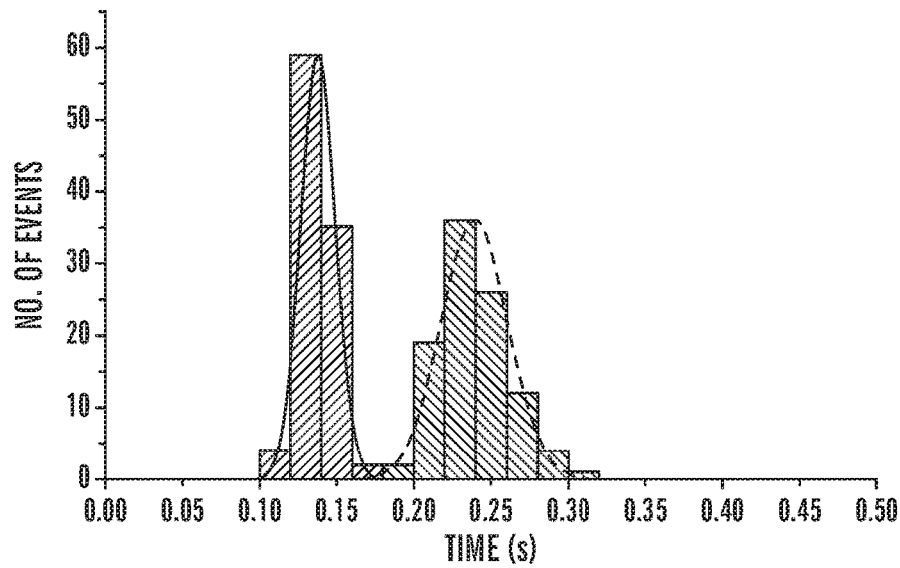

FIG. 40D-F shows histograms (100 events) of the electrophoretic flight times for 60 nm (▨) and 100 nm (▨) AgNPs transported electrokinetically through a 150 nm flight tube in 0.05 mM citrate buffer using applied electric fields of 100 V/cm (FIG. 40D), 500 V/cm (FIG. 40E), 1500 V/cm (FIG. 40F). "Stick/slip" motion of the AgNPs was observed at electric field strengths of 100 V/cm, which resulted in the broad nature of the single particle flight times. At the higher electric fields (500 and 1500 V/cm), this effect was not observed, which resulted in much narrower peak widths improving the separation of the Gaussian distributions.

Figure 41:
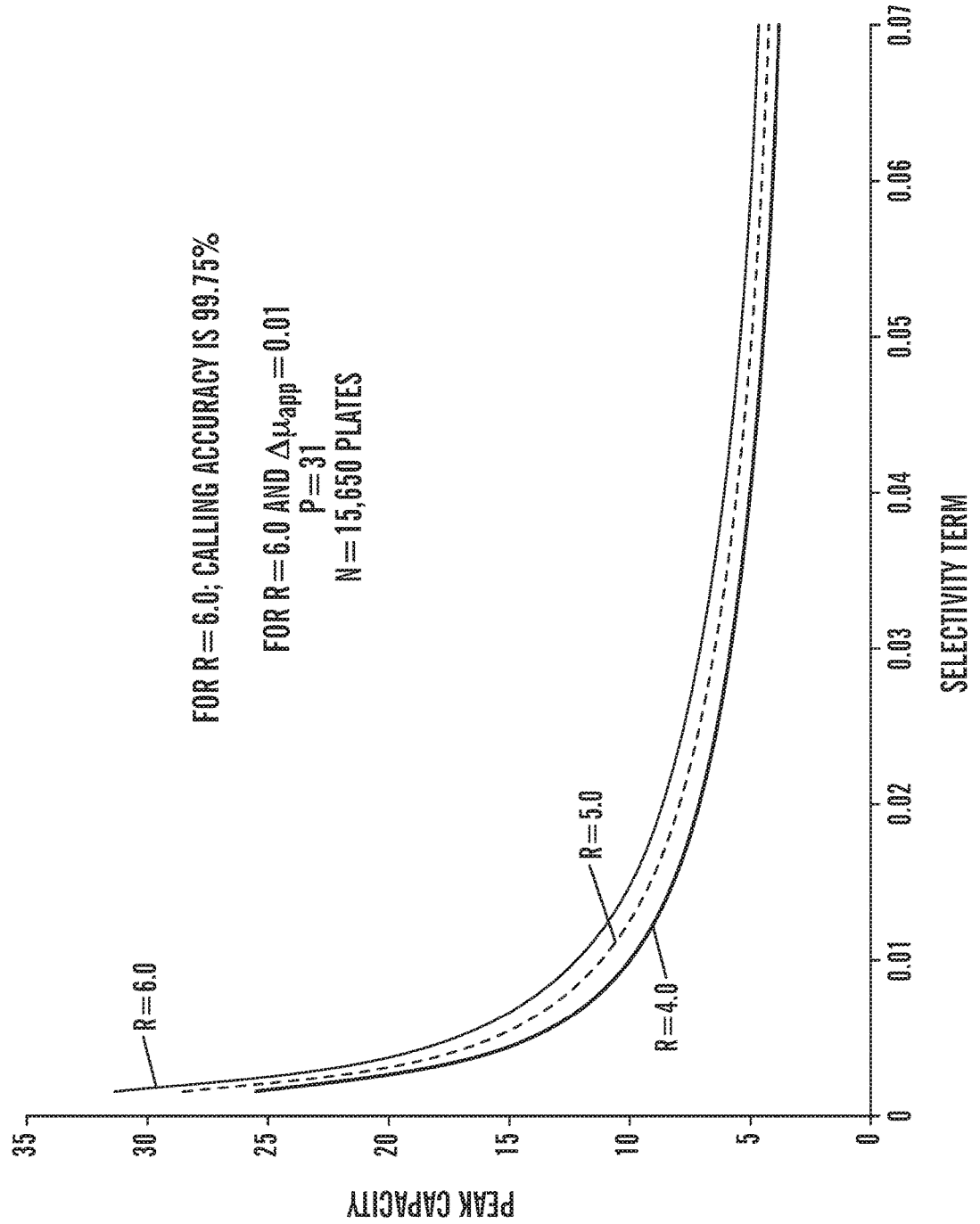
FIG. 41 is a graph showing the peak capacity as a function of the selectivity term, which is determined by the difference in the electrophoretic mobility of two components divided by the average electrophoretic mobility. For R=6.0 and 15,650 plates with a mobility difference of 0.01 the peak capacity is 31, which represents the number of biomolecules the nanotube can distinguish.

Multiplexing power is improved by using higher electric fields and/or lengthening the column. For example, increasing the field strength to 4000 V/cm and the nano-column length to 200 µm resulted in P≈31 (FIG. 41). This was calculated by assuming an electrophoretic resolution of 6, which describes a classification accuracy (i.e., molecule identification accuracy based on time-of-flight) of 99.75%. The data generated in FIG. 41 were collected assuming an electrophoretic mobility difference of 0.01 ($\Delta\mu_{app}$) between two analytes with an electrophoretic plate number (N) of 15,650. The results indicate that 31 different molecular species can be identified with an accuracy of 99.75%. The peak capacity and identification accuracy are enhanced by improving the selectivity by increasing differences in the electrophoretic mobility of the spLDR products. This is accomplished, for example, by using molecular drag tags to enhance the free solution mobility differences of the oligonucleotides (Albrecht et al., *Anal. Chem.* 83:509-515 (2011); Chubynsky & Slater, *Electrophoresis* 35:596-604 (2014); Forster et al., *Electrophoresis* 30:2014-2024 (2009); McCormick & Slater, *Electrophoresis* 27:1693-1701 (2006); Meagher et al., *Anal. Chem.* 80:2842-2848 (2008); Sinville et al., *Electrophoresis* 29:4751-4760 (2008); and Albrecht et al., *Electrophoresis* 34:590-597 (2013), which are hereby incorporated by reference in their entirety). As noted in FIG. 41, when the electrophoretic resolution is 6.0 between two molecules with different flight times, the calling accuracy is 99.75%. Changing the resolution will have an effect on $N_e$, for a certain selectivity term and different plate numbers generated for the separation.

Understanding the effects of concentration polarization that can occur at polymer microchannel/nanochannel interfaces is critical, which can prevent the ssDNA products from entering the nano-scale electrophoresis flight tubes. Concentration polarization is not only determined by $d/\lambda_D$, but more importantly by the inverse Dukhin number given by $G_{bulk}/G_o=(Fdzc_o/\sigma)$, where $G_{bulk}$ is the bulk conductance, $G_o$ is the surface conductance, F is the Faraday constant, d is the channel critical dimension (width and depth in our case, aspect ratio=1), z is the charge, $c_o$ is the ion concentration outside of the EDL and $\sigma$ is the surface charge.

For conventional capillary electrophoresis, operational characteristics are optimized to provide maximum component resolution in short times with high peak capacity. To maximize resolution, zonal dispersion is minimized and selectivity is maximized (i.e., differences in electrophoretic mobility). For zonal dispersion, there are several parameters that affect the dispersion including diffusion, injection and detection lengths, Joule heating, sample/buffer conductivity differences, and solute wall interactions. The resolution (Res) for two components (i,j) can be determined from the expression;

$$Res_{ij} = \frac{1}{4} \frac{\Delta\mu_{app}}{\mu_{app,avg}} N^{1/2} \tag{1}$$

where N is the plate number and $\Delta\mu_{app}$ is the difference in the apparent mobility (cm$^2$V$^{-1}$s$^{-1}$) for the two components for which $Res_{ij}$ is being determined and $\mu_{app,avg}$ is the average mobility of the two components. For a well-designed system, longitudinal diffusion is the predominate dispersion effect and N can be calculated from;

$$N = \frac{\mu_{avg}V}{2D} \tag{2}$$

where D is the molecular diffusion coefficient and V is the applied voltage; therefore, $Res_{ij}$ is proportional to $V^{1/2}$. The relation shown in equation (2) is similar to the formalism provided by Xuan in which ion separations in nanochannels were evaluated (Xuan, X. *Electrophoresis* 29:3737-3743 (2008), which is hereby incorporated by reference in its entirety).

The reduced plate height ($h_i=H_i/d$; where $H_i=L/N$) is given by;

$$h_i=2D'_i/dv_i \tag{3}$$

where $v_i$ is the average ion velocity for ion i, d is the channel critical dimension, and $D'_i$ is the effective diffusion coefficient, which includes hydrodynamic dispersion and molecular diffusion.

As evident from equations (2) and (3), increasing the applied voltage can increase plate numbers or decrease the value of $h_i$ due to increasing the average molecular velocity. As noted from FIG. 40D-40F, extremely high electric field strengths can be used without deleterious effects on N when using nano-columns.

Theory and experimental studies for electrokinetic separations in nanochannels has appeared in recent reviews (Baldessari & Santiago, *J. Nanobiotechnol.* 4:12 (2006) and Yuan et al., *Electrophoresis* 28:595-610 (2007), which are hereby incorporated by reference in their entirety). For ion transport with $d/\lambda_d$ ratios ranging from 1-10, anomalous transport behavior has been observed, such as charge-dependent ion speeds due to transverse electromigration (TEM) resulting from wall/solute electrostatic effects (Pennathur & Santiago, *Anal. Chem.* 77:6782-6789 (2005); Pennathur & Santiago, *Anal. Chem.*, 77:6772-6781 (2005); and Xuan & Li, *Electrophoresis* 27:5020-5031 (2006), which are hereby incorporated by reference in their entirety); ion maximum resolution occurs when the column diameter is 1-10 times $\lambda_D$ (Xuan, X. *Electrophoresis* 29:3737-3743 (2008), which is hereby incorporate by reference in its entirety). Pennathur and Santiago determined that electrokinetic separations in nanochannels were dependent on ion valence, $\zeta$ (zeta potential), ion mobility and $\lambda_D$ (Pennathur & Santiago, *Anal. Chem.* 77:6782-6789 (2005) and Pennathur & Santiago, *Anal. Chem.*, 77:6772-6781 (2005), which are hereby incorporated by reference in their entirety). For example, Garcia et al. illustrated the electrokinetic separation of the fluorescent dyes Alexa 488 (negatively charged) and rhodamine B (neutral) in nanochannels of various widths ranging from 35 to 200 nm (Garcia et al., *Lab Chip.* 5:1271-1276 (2005), which is hereby incorporated by reference in its entirety). The mobility of the fluorescent dyes was based on their charge and interaction(s) with channel walls. Therefore, unique effects produced from nanoscale electrophoresis can be used to affect electrophoretic separations that are not possible using conventional microscale separations.

One can also use drag tags to enhance the mobility differences between the oligonucleotide products using nano-scale electrophoresis (175,176). In this case, the mobility of DNA in free solution has a constant value irrespective of the length of the DNA molecule. However, when the drag tag is attached to the DNA molecule, it relieves its free draining behavior and causes the DNA to migrate in free solution at a rate that depends on its size (longer DNAs move faster than shorter DNAs). A variety of different drag tags, such as peptides and/or proteins consisting of repeating amino acid units of unique sequence (Albrecht et al., *Electrophoresis* 34:590-597 (2013), which is hereby incorporated by reference in its entirety) or even streptavidin (Heller et al., *J. Chromatog. A* 806:113-121 (1998), which is hereby incorporated by reference in its entirety) can be used. The drag tag can be covalently anchored to one of the LDR primers. To enhance resolution by increasing mobility differences, drag tags can also be attached to the end of each primer (Meagher et al., *Electrophoresis* 27:1702-1712 (2006), which is hereby incorporated by reference in its entirety).

Figure 42:
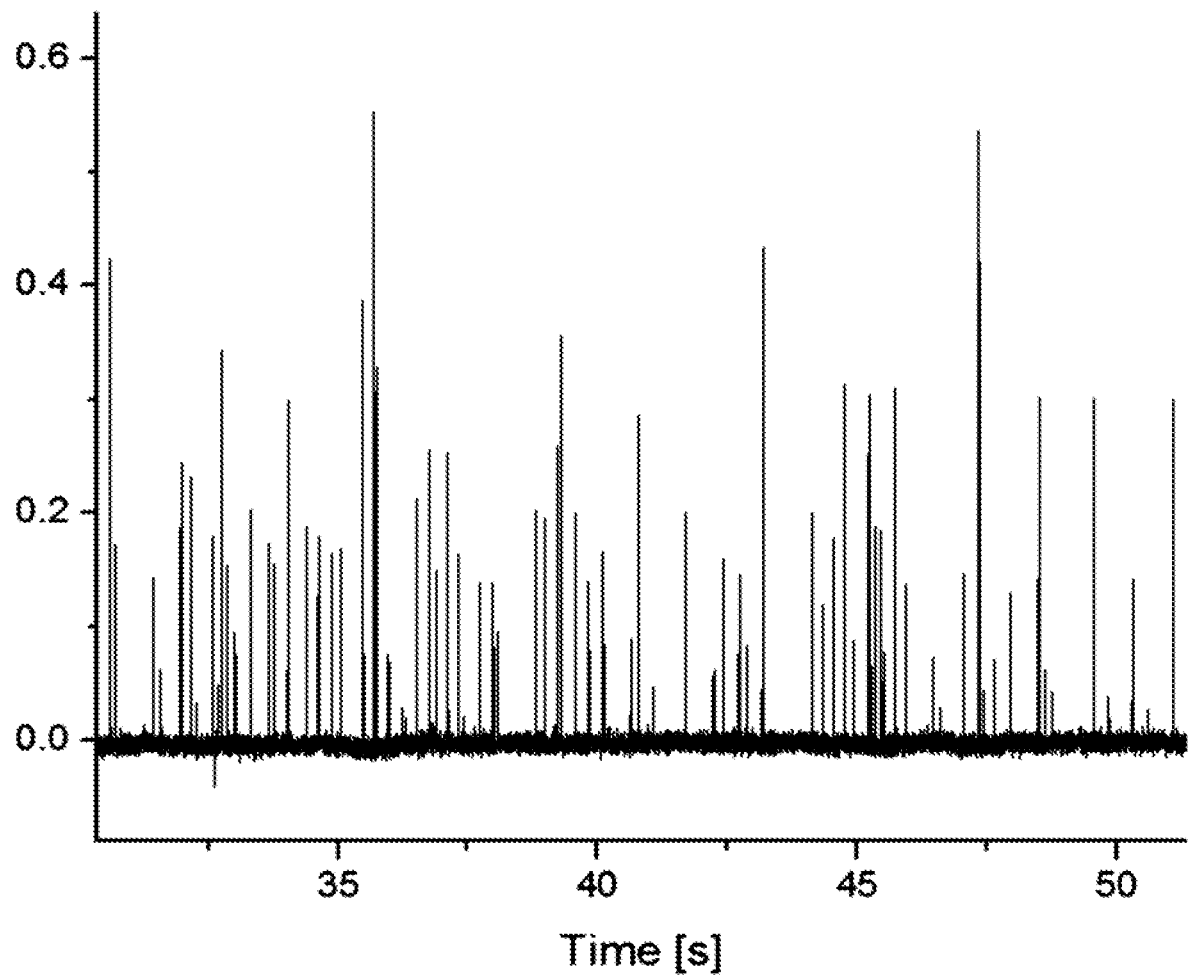
FIG. 42 shows single cell impedance measurements of breast cancer cells (MCF-7) using the sensor module of the device as described here.

Example 3—Single Cell Enumeration and Viability Assessment Using the Impedance Module As described supra, the impedance module (also referred to as the sensor module) is used to count single cells, as well as determine cell viability and cell size. FIG. 42 shows single cell impedance measurements of breast cancer cells (MCF-7) using the three-layered impedance module as described herein (shown in FIGS. 23A-23B). MCF-7 cells were introduced to the microchannel of the impedance module via the input port and were measured as they individually passed through the pair of electrodes that intersect with opposing sides of the microchannel. Each peak in the graph of FIG. 42 represents a signature from a single cell with the amplitude related to the size of the cell. The impedance measurement was made at a frequency of 40 KHz.

Figure 43:
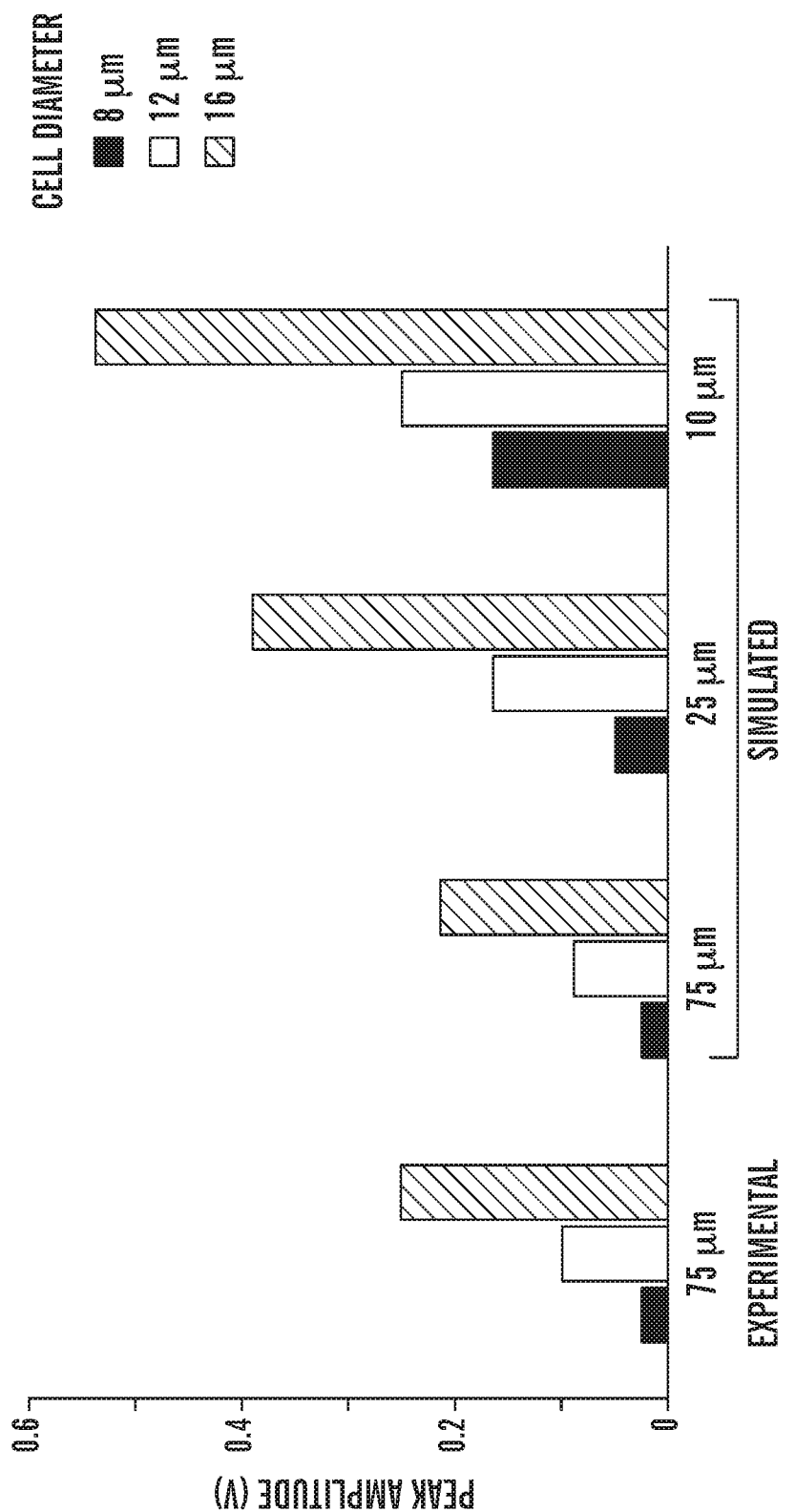
FIG. 43 is a graph of simulations showing the impedance response of different diameter cells for electrodes of different sizes (i.e., 20, 25 and 75 μm). Also shown is experimental data for the impedance peak amplitude for cells of 3 different average sizes for an electrode pair that is 75 μm wide.

Simulations, generated using COMSOL® software, were used to determine the effects of electrode size in the impedance module as a function of particle diameter to show that the relative difference in signal amplitude with particle size was not terribly affected by electrode size, but the signal-to-noise ratio was. Smaller electrodes provided better signal-to-noise ratio compared to larger electrodes. FIG. 43 is a graph of the simulation data showing the impedance response of different diameter cells for electrodes of different sizes (i.e., 20, 25 and 75 μm). Also shown is experimental data for the impedance peak amplitude for cells of three different average sizes (i.e., 8, 12 and 16 μm) for an electrode pair that is 75 μm wide.

Unique to the three-layered impedance module described herein is its ability to determine cell viability. The signal measured by the impedance sensor is proportional to the resistance of the medium between the electrodes and can be used to determine cell viability. When no cell is present between the electrodes the signal is proportional to the resistance of the buffer solution and this defines the baseline for the measurements. Every cell passing between the electrodes replaces a small volume of the buffer solution. Intact cells are considered non-conductive at the frequency of the electrical signal (40 kHz) applied between electrodes due to high cell membrane capacitance. Thus, the small volume of the solution replaced by the cell has higher resistance than the corresponding volume of the buffer alone. This leads to an increase in the overall resistance measured by impedance sensor, which presents itself as positive peaks recorded for a passing cell as demonstrated in FIG. 44A. When the cells' membrane is compromised, the cell resistance can be approximated by the resistance of the cell interior, which is composed primarily by cytoplasmic components. If the resistance of cell cytoplasm is lower than that of the corresponding volume of buffer solution, the overall resistance measured by sensor drops, which results in a negative peak (FIG. 44B).

Figure 44C:
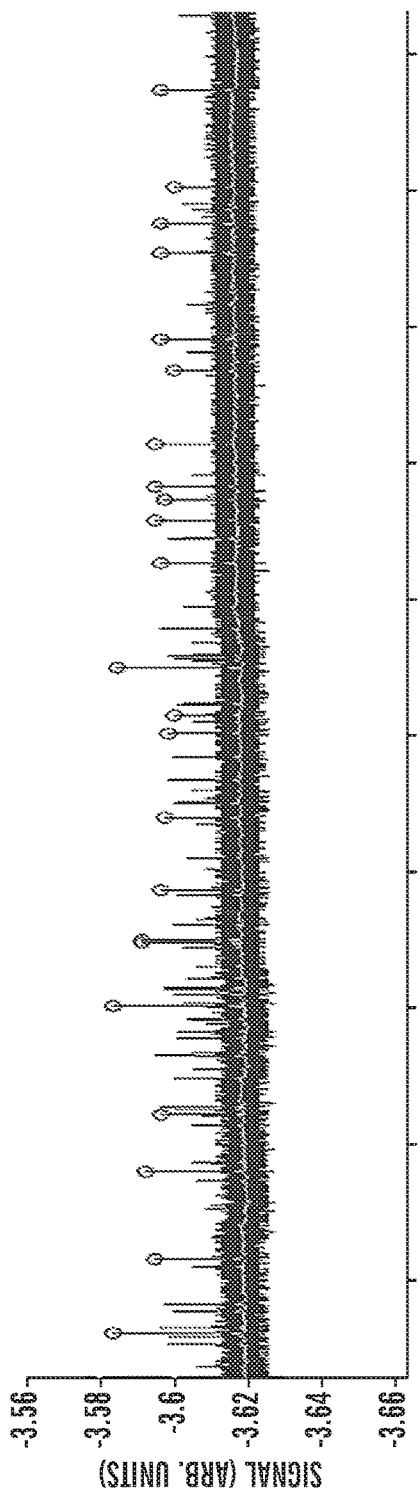
FIGS. 44C and 44D are impedance traces for Hs578T live cells in 1×TG buffer (FIG. 44C), and paraformaldehyde and Triton X-100 treated cells in 1×TG buffer (FIG. 44D).
Figure 44D:
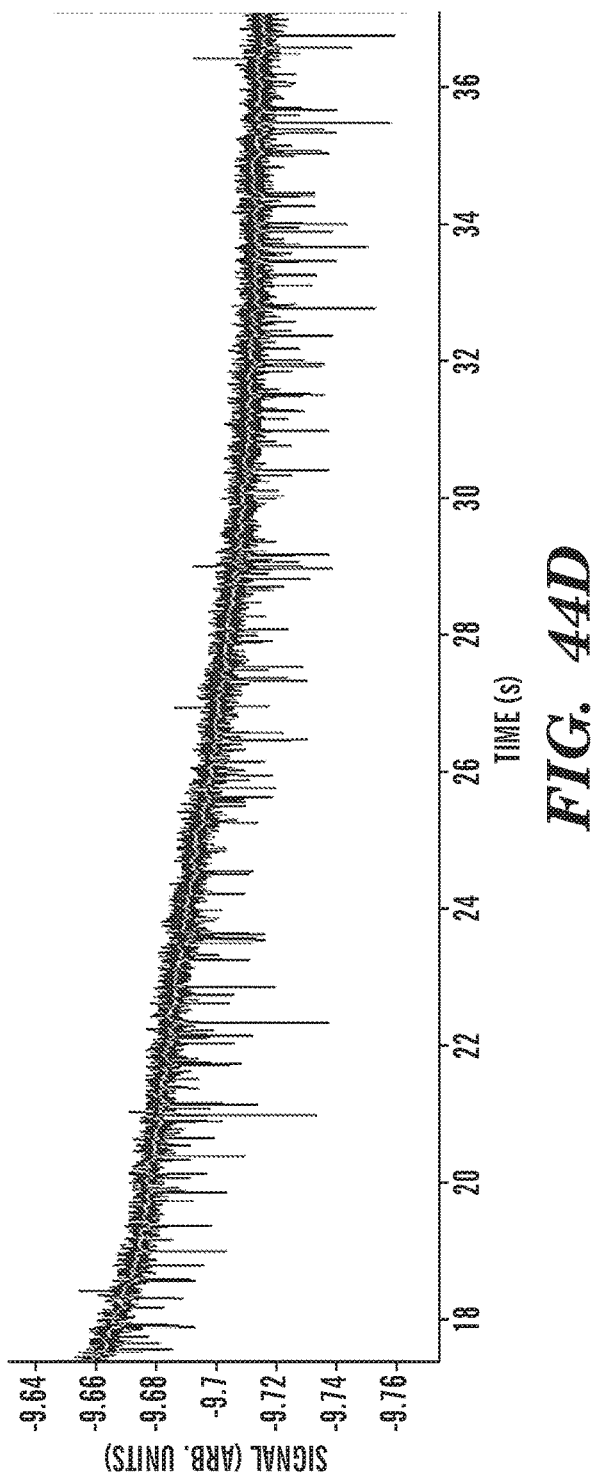

To demonstrate the functionality of the impedance module to distinguish viable and non-viable cells, live and fixed Hs578T cells that were gentle permeabilized were re-suspended in 1× TG buffer introduced into the impedance sensor. FIGS. 44C and 44D show traces for live cells and fixed cells, respectively. For live cell suspensions, only positive peaks consistent with intact membranes were observed. For fixed and slightly permeabilized cells, positive and negative peaks were observed. Clearly, cells having compromised membranes (i.e., permeabilized) provide electrical sensing of the cell interior thus generating a resistance or impedance lower than in the absence of the cell for the solution volume between the electrode pair creating negative polarity peaks in the trace with respect to the carrier electrolyte. These conclusions are also supported by other experiments showing that cells treated with formaldehyde only produced predominantly positive peaks (cross-linking of the cell membrane), while cells exposed to prolonged incubation with Triton X-100 after fixation showed only negative peaks (compromised cell membrane).

Example 4—Exosome Extraction on the uMPS

Computational fluid dynamic simulation experiments have been carried out to investigate plasma flow through a solid-phase extraction bed for exosomes isolation. The SPE bed in these simulations is comprised of diamond micropillars with 15 μm side length and 5 μm spacing (see FIG. 45A). Besides regions near the corners of the micropillars, the flow dynamics in the SPE bed can be approximated using a simplified parabolic velocity profile that is typical of Poiseuille flow, which greatly reduces the computational cost for simulating exosome dynamics in the moving fluid. Here, the effective microchannel width is given by the micropillar spacing and the length of the channel by the SPE bed's end-to-end length that is then amplified by a path correction factor, which adjusts for the distance spanned around the pillar. The physical properties of the exosome used for the Monte Carlo simulations are summarized in Table 1 below.

Both convective and diffusive transfer of exosomes is then simulated via Monte Carlo methods. The position of an exosome is propagated over incremental time steps ($\Delta t$). The exosome's position is first convectively moved using the Poiseuille flow profile with the exosome's axial and longitudinal position perturbed by diffusive dynamics, which are approximated with a pseudo-random number generator that is normally distributed about the exosome's position with a given by $\sqrt{2D\Delta t}$, where D is the exosome's diffusion coefficient (see FIG. 45B).

Each encounter with a micropillar surface may or may not lead to successful SPE of the exosome to the surface that is decorated with an antibody associated with an antigen found in the membrane of the exosome, and these reaction dynamics are assessed by comparing the probability of antibody/antigen association according to Chang-Hammer dynamics with a pseudo-random number generator with uniform distribution. Note that the simulations are repeated until the resultant recovery converges with respect to the number of exosome trajectories simulated and the time discretization.

Additionally, for every simulation, the recoveries from 41 different axial starting positions were averaged to represent an initially homogenous exosome solution.

TABLE 1

Physical Properties of the Exosome Used for the Monte Carlo Simulations.

| Exosome Property | Value |
| --- | --- |
| Size | 50-150 nm |
| Diffusion Coefficient | 5-15 µm²/s |
| Exosome Antigen | CD63 |

Figure 46:
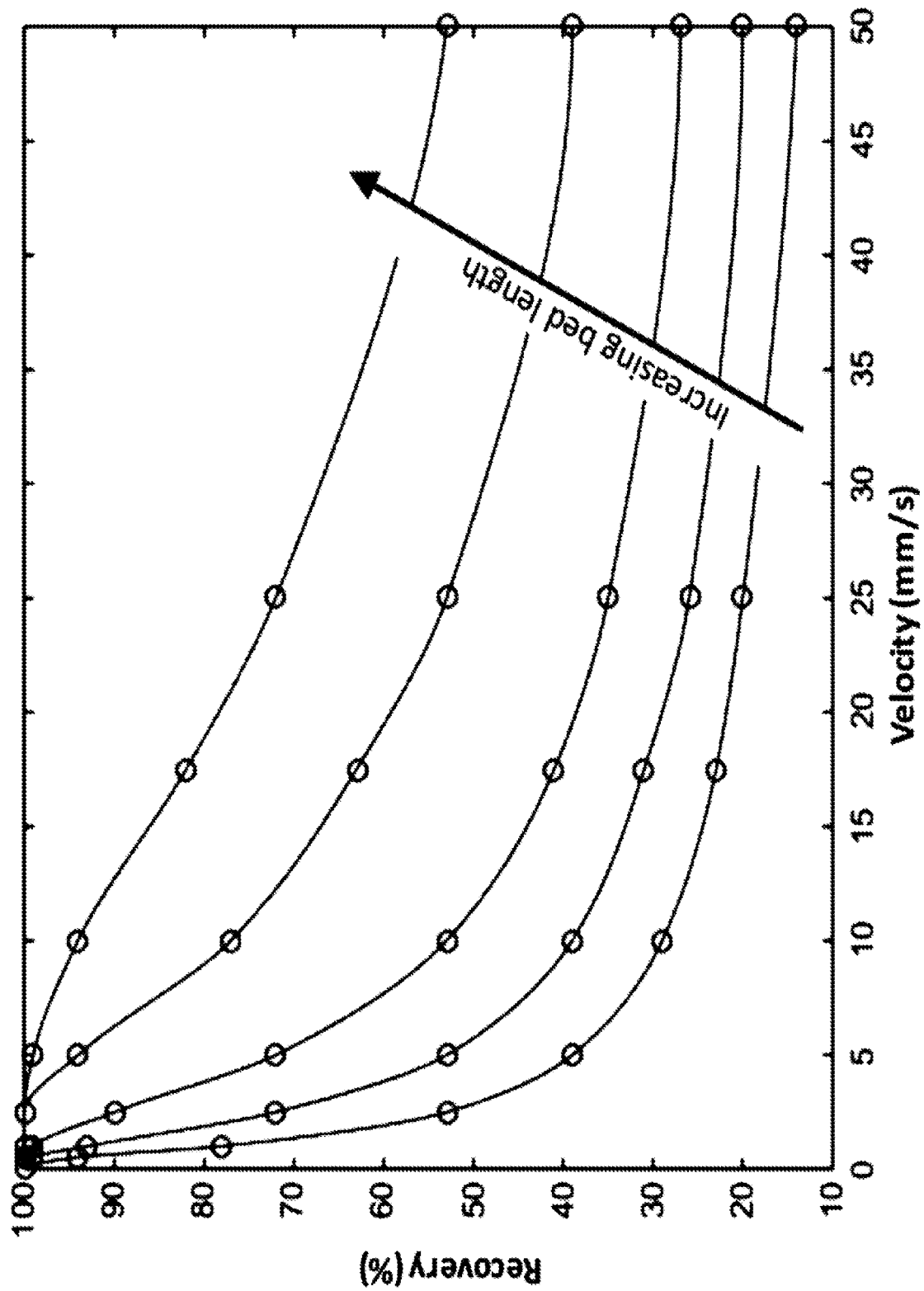
FIG. 46 is a graph showing the effects of velocity and SPE bed length on exosome recovery using the simulation depicted in FIG. 45A.

FIG. 46 is a graph showing the effect of velocity and extraction bed length on exosome recovery in the simulation experiments. For each pillar spacing and bed length, velocity was varied and recovery was assessed. The bed lengths used here were 2.5 mm, 5 mm, 10 mm, 25 mm, and 50 mm. The pillars were 15 µm in size with a spacing of 5 µm. As shown in FIG. 46, exosome recovery is maximized at lower velocities through longer extraction beds.

Figure 47:
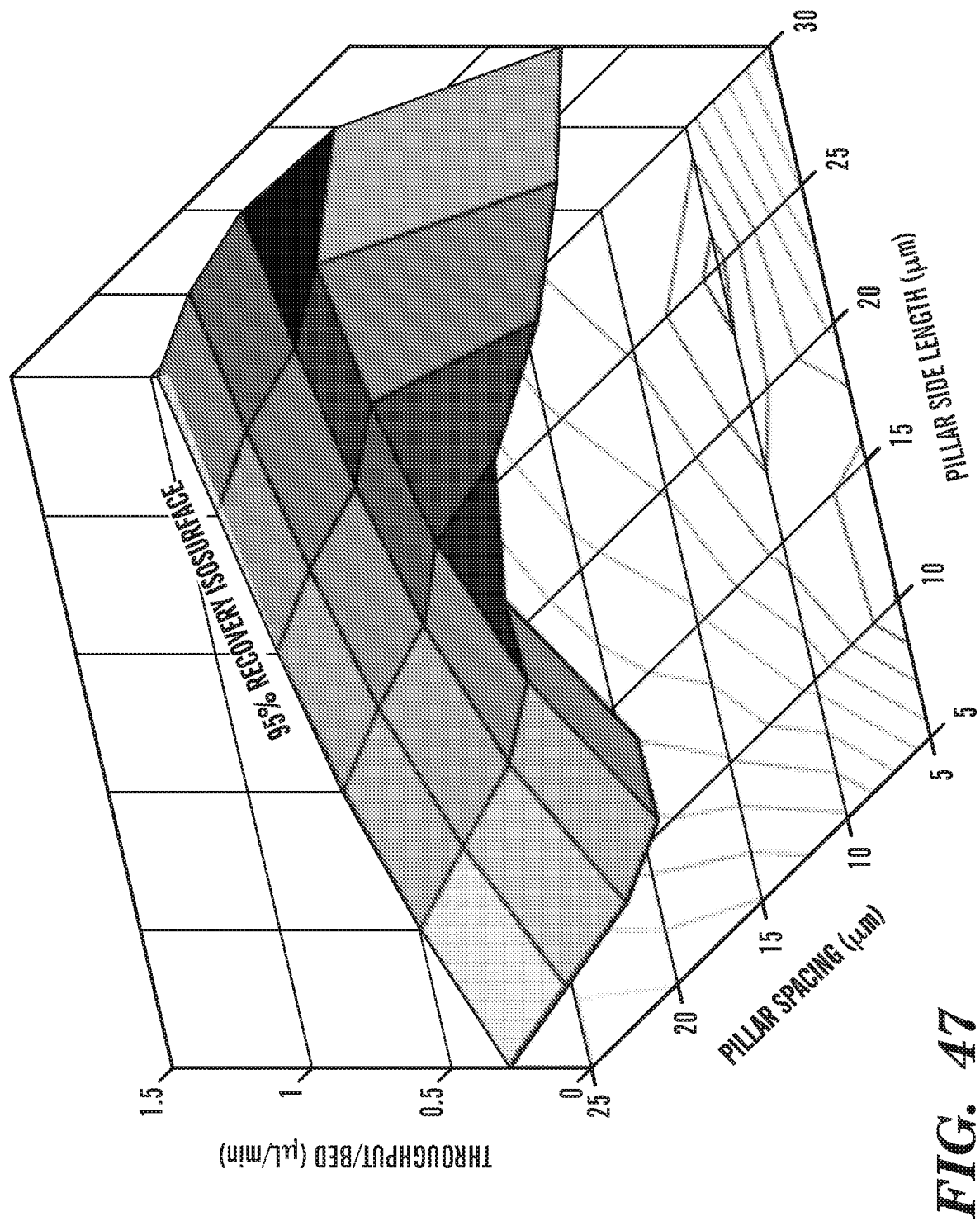
FIG. 47 is a 3D isosurface and underlying contour plot for conditions which exosome recovery is predicted to be 95% by the Monte Carlo/Chang-Hammer simulations of FIG. 45B.

FIG. 47 is a 3D isosurface and underlying contour plot for conditions at which exosome recovery is predicted to be 95% by the Monte Carlo/Chang-Hammer simulations. Note that SPE bed length is kept constant at 50 mm for this graph. Throughput is derived from the velocities output by the simulations. Bed width was constrained to 2 mm to provide longitudinal pressures that reduce the probability of air bubbles in the SPE device, which affected the number of pillar and open conduits between pillars that affect throughput. Two conditions are noted which provide both high recovery and a maximal throughput of 1.4 µL/min per SPE bed: Pillar dimensions of 10 µm×5 µm×20 µm and of 25 µm×10 µm×100 µm (side length×spacing×height). Also noted is that the large pillar dimensions require over an order of magnitude lower pressure for plasma infusion, which lends to simpler incorporation of multiple SPE beds in serial connection (for extracting exosomes with orthogonal markers) and incorporation of the SPE system into more complex, integrated microfluidic networks that can perform further assays on the same blood sample.

Figure 48:
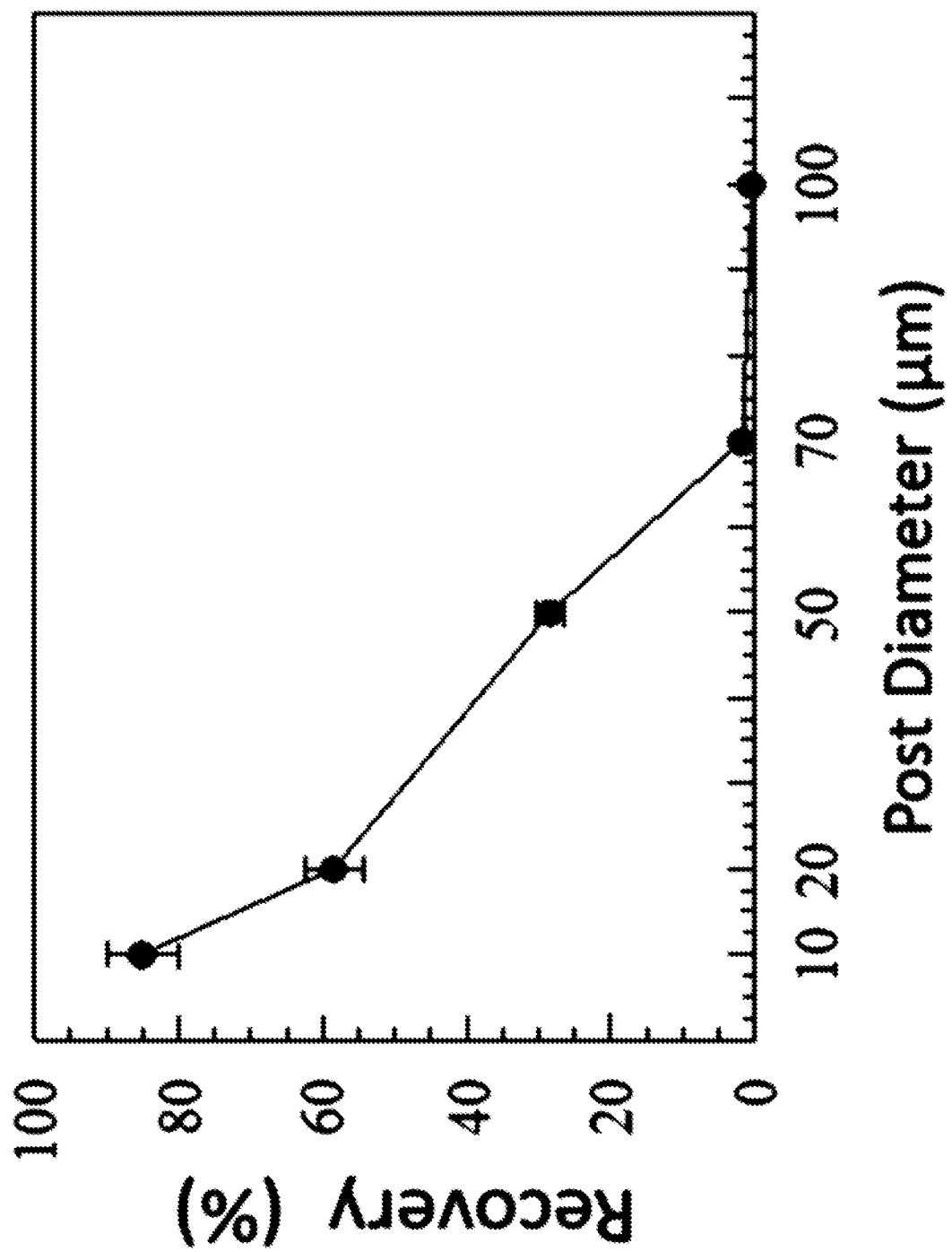
FIG. 48 is a graph showing the recovery of DNA molecules from plasma in the SPE DNA/RNA isolation module of the uMPS device as a function of the pillar diameter. The recovery increases when the pillar diameter is <70 μm in diameter.

Example 5—Nucleic Acid Extraction Via the Solid Phase Extractor Module of the uMPS A solid phase extractor (SPE) unit was fabricated using injection molding of a plastic. The unit consists of a bed of micropillars having a gradient of sizes from input to output that allows some filtering of particulates from entering the SPE bed. The graph of FIG. 48 shows that the recovery of DNA/RNA is highly dependent on the pillar diameter with a similar spacing. For example, using 10 µm pillars that are spaced by 10 µm can provide a DNA recovery that is >80%. Table 2 below shows the effect of pillar size and spacing on the bed volume and genomic DNA load. For a 10 µm pillar size and 10 µm spacing, a single SPE bed can accommodate 190 ng of genomic DNA with a volume of 120 nL.

TABLE 2

Effect of Pillar Size and Spacing on SPE Bed Volume and Genomic DNA Load

| Post Diameter (µm) | Post Spacing (µm) | Bed Volume (nL) | gDNA load (ng) |
| --- | --- | --- | --- |
| 10 | 10 | 120 | 190 |
| 50 | 40 | 230 | 94 |
| 70 | 100 | 390 | 5.6 |
| 100 | 150 | 590 | 1.3 |

Figure 49:
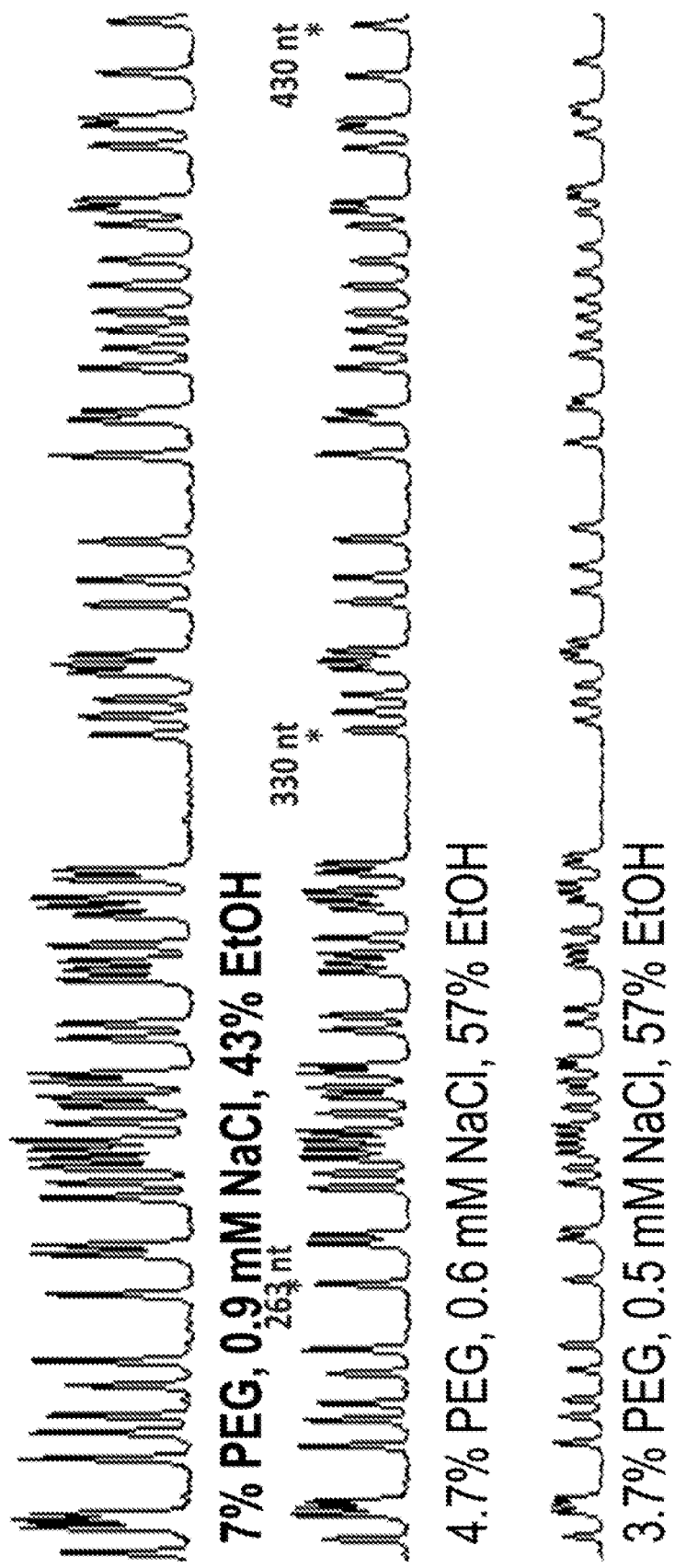
FIG. 49 shows capillary gel electrophoresis of DNA fragments recovered using the SPE module of the uMPS. Recovery was as a function of the PEG/NaCl/EtOH content, with maximum recovery observed at 7% PEG, 0.9 mM NaCl and 43% EtOH.

The polycarbonate SPE bed that has been UV activated can be used to isolate short DNAs, similar in size to cfDNA and the efficiency of isolation is dependent on the composition of the immobilization buffer, which is comprised of polyethylene glycol (PEG), sodium chloride (NaCl) and ethanol (EtOH). As seen in FIG. 49, the maximum recovery of the DNA occurs for an immobilization buffer composition of 7% PEG, 0.9 mM NaCl and 43% EtOH. The SPE module can also be used to pre-concentrate the cfDNA as well. The DNA can be enriched from an initial starting volume of 1 mL plasma to a final volume of 10 µL ($10^2$ enrichment factor).

Figure 50:
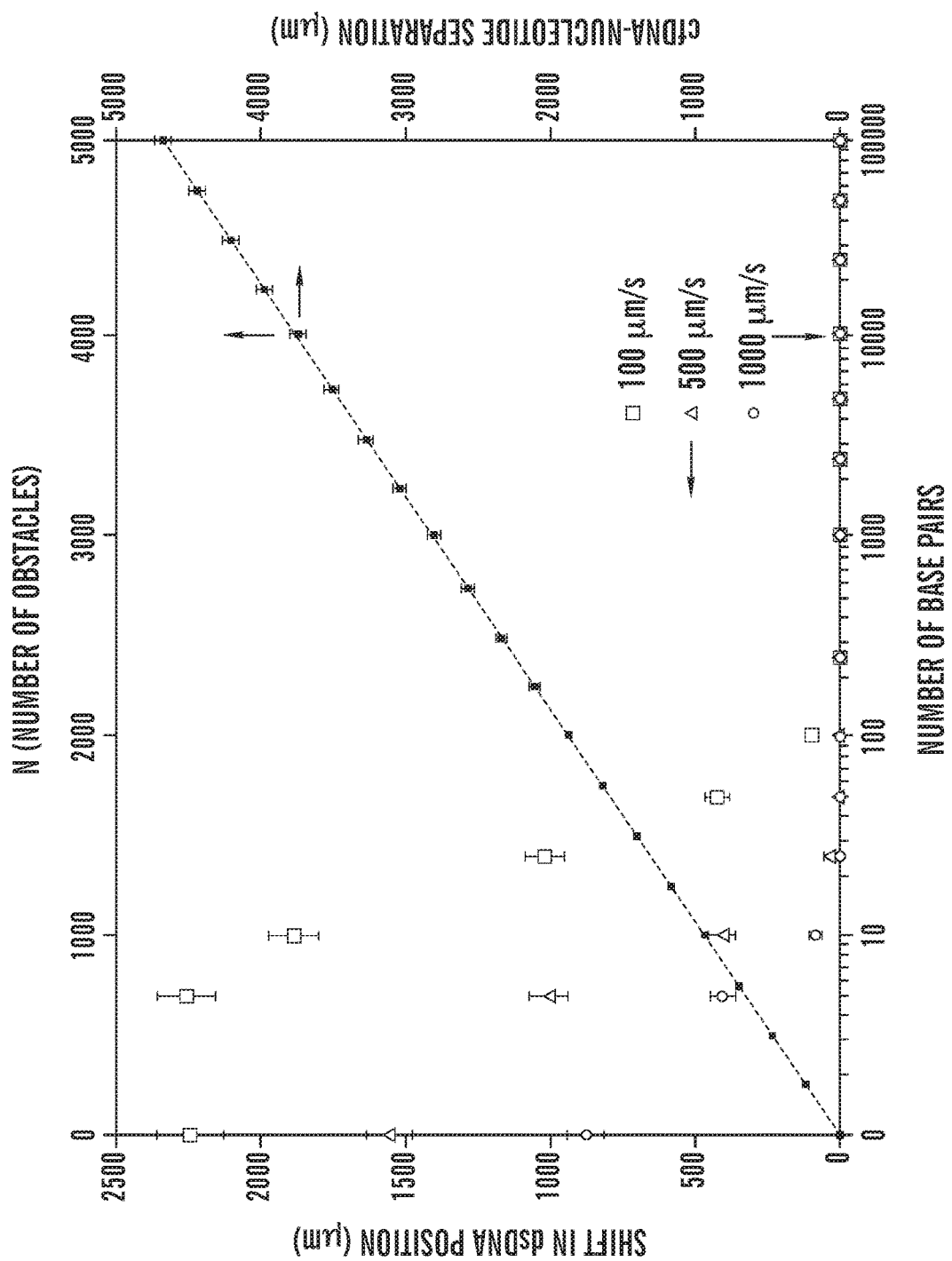
FIG. 50 is a graph showing the diffusional displacement of DNAs with different base numbers in the diffusional purification module. Also shown in the cfDNA to dNTP displacement as a function of the number of obstacles.

Example 6—Purification of Target Nucleic Acid Molecule Via the Diffusional Purification Module The diffusional flow purification module of the uMPS device is designed to purify the target nucleic acid molecules that are generated in other upstream units of the device from excess dNTPs and/or other non-target nucleic acid nucleotide components. FIG. 50 displays the displacement of DNAs with different base numbers associated with the cfDNA. The data for this graph is based on calculations using double stranded DNA and dNTP diffusion coefficients. The length of the array necessary to remove the majority of dNTPs from the cfDNA (resolution is proportional to $N^{1/2}$, where N is the number of obstacles; the lateral displacement is proportional to N) can be determined by taking into account the differences in diffusional coefficient between the dNTP and the double stranded cell free DNA molecule length. As can be seen in FIG. 50, as the number of obstacles increases, the separation distance between a cell free DNA molecule and the dNTP increases in a linear fashion. For example, an array comprising 4000 obstacles produces a separation distance of ~3,750 µm between the dNTP and cfDNA after traveling through the array. Also shown in FIG. 50 is that the shift in cell free DNA travel due to the obstacles is less when the flow rate is higher. Finally, FIG. 50 shows the shift distance for a cell free DNA molecule gets significantly smaller as the length the DNA molecule gets larger primarily due to the fact that the diffusion coefficient gets smaller for the larger DNA molecules. For DNA molecules containing >100 bases, no shift in the motion is observed irrespective of flow rate.

Example 7—Assembly of Modules to Fluidic Motherboards to Build the uMPS

Figure 51:
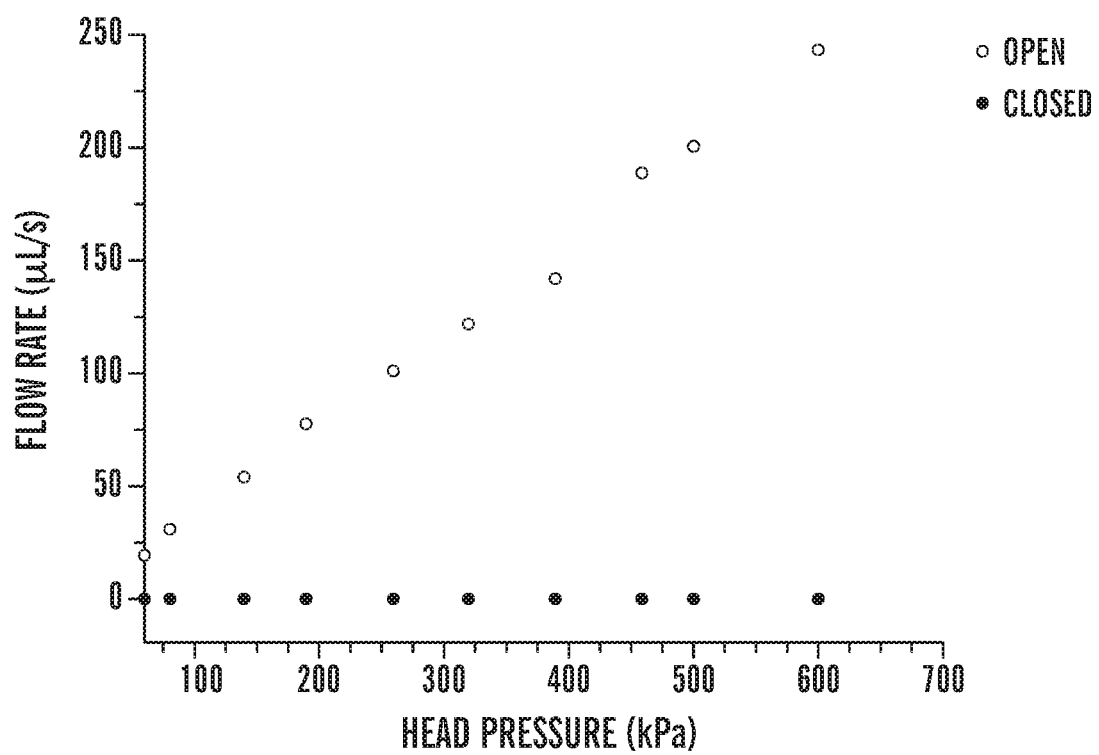
FIG. 51 is a graph showing the volume flow rate versus valve head pressure in a valve of the uMPS.

The valves on the uMPS require a three-layer structure, the cover plate, the fluidic layer and the back cover plate. The valve seats and membrane valves are configured to be on the back side of the fluidic motherboard for the uMPS along with the mechanical solenoids to actuate the valves. Therefore, a unique strategy for producing these thermoplastic valves was employed, which did not only provide higher rates of producing successful valves, but did not require thermal processing for assembly (Jackson et al., *Lab Chip.* 14:106-117 (2014), which is hereby incorporated by reference in its entirety). Laminates coated with a pressure sensitive adhesive are used as the membrane so that no thermal bonding is required. A polyolefin laminate possessing a favorable tensile strength (25-40 mPa), high elongation at break (150-300%), ~100 μm thick, and coated with a silicone acrylate pressure sensitive adhesive (50 μm thick) was utilized. A test device was built by pressure sealing the aforementioned laminate to a thermoplastic microchannel. It was found that one can "deactivate" the adhesive by UV/$O_3$ treatment; the laminate poised directly above the valve seat can be deactivated to prevent the membrane from sticking to the valve seat. This laminate can withstand pressures >600 kPa without failure (FIG. 51), sufficient for the processing steps carried out by the uMPS.

Gasket-less seals: Most microfluidic interconnects rely on direct physical contact between the fluid port and the device being connected. Each contact acts as a passive kinematic constraint on the assembly. If care is not taken, two or more interconnects in conjunction with other assembly features will lead to over-constrained systems and unpredictable dead volumes.

Figure 52:
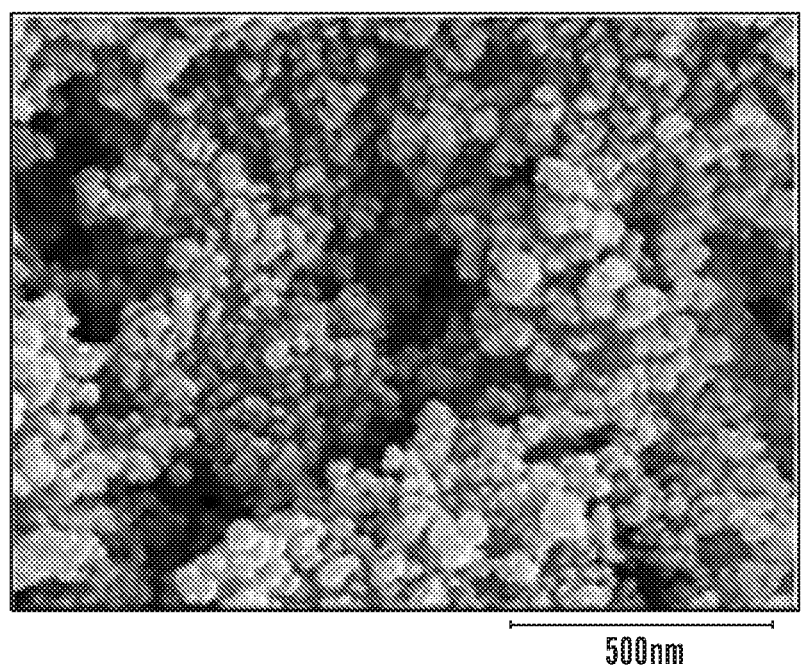
FIG. 52 is a SEM of the super-hydrophobic surface spin coated around the microfluidic through-hole for each gasket-less seal assembly to create the seal.
Figure 53:
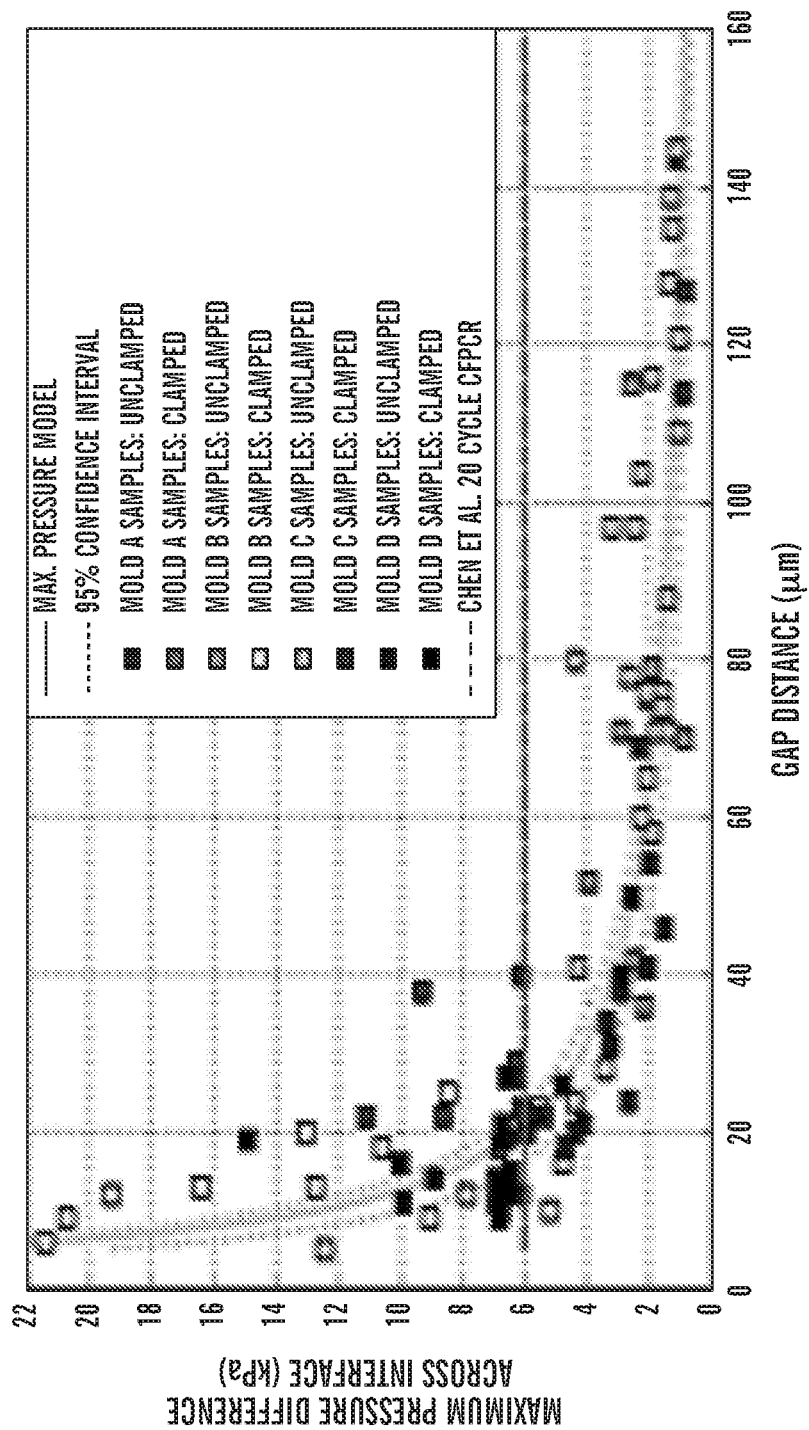
FIG. 53 is a graph showing that the measured maximum pressures the gasket-less seals could withstand were consistent with those estimated using the Young-Laplace equation.
Figure 54:
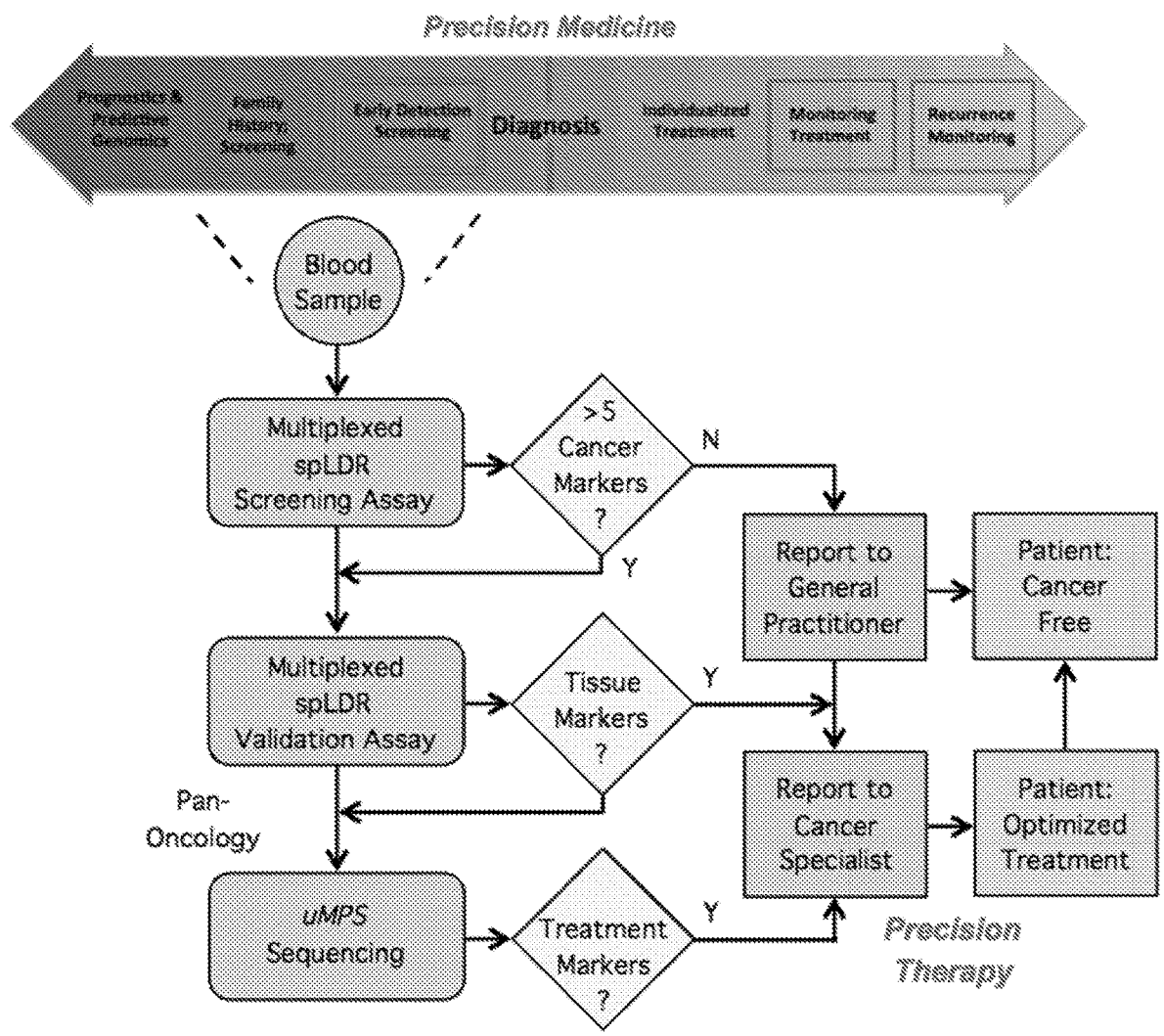
FIG. 54 is a flow chart outlining the multi-tiered strategy for the screening and detection of blood based markers for cancer.
Figure 55:
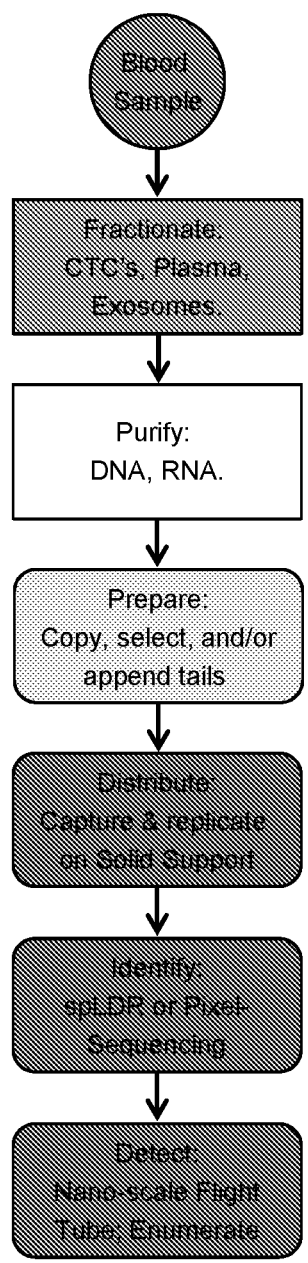
FIG. 55 shows a high level overview of the general protocol associated with the molecular analysis of mutations by the device of the present invention for both DNA and RNA isolated from CTC's, plasma or exosomes.
Figure 56:
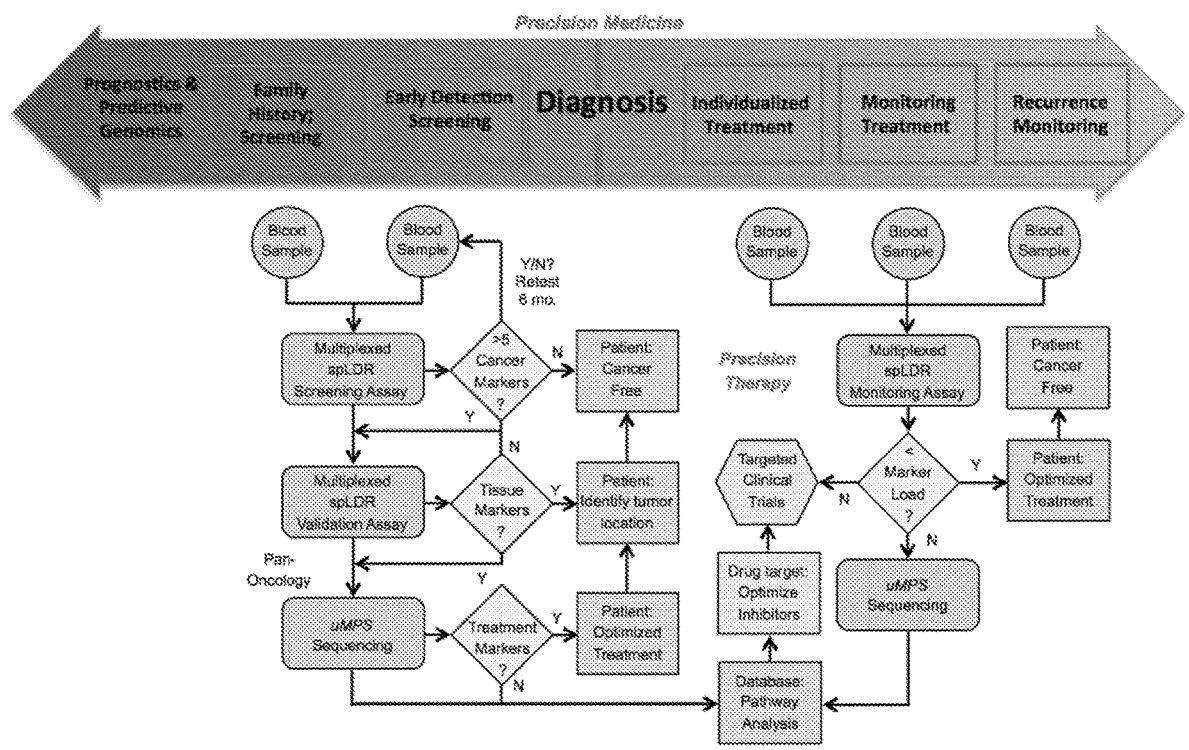
FIG. 56 illustrates a decision tree based on the use of multiplexed PCR/LDR across the diagnostic spectrum for cancer thus enabling Precision Medicine.

For microfluidic ports with micro-scale gaps between facing surfaces, capillary forces, as defined by the Young-Laplace equation, should resist leakage without any direct physical contact between the facing surfaces, forming a gasket-less seal, see FIG. 33B (Brown, et al., *IMECE* 2012, Nov. 9-15, 2012. ASME, Houston, Tex., pp. IMECE2012-89634 (2012), which is hereby incorporated by reference in its entirety). This concept was tested and it was found that if the facing surfaces are super-hydrophobic (water contact angles)>130°), the capillary forces are sufficient to withstand the pressure drop in a typical microfluidic channel. Test parts were created by double-sided injection molding cyclic olefin copolymer parts with microfluidic through holes near an edge to permit observation through a microscope, alignment standards for measuring the relative offset of the mating parts and v-grooves to act as ball bearing seats (see FIG. 28B). Different gaps were created using different diameter precision ceramic ball bearings as the kinematic constraints. Super-hydrophobic surfaces were generated by spin coating the polymer surfaces around the through holes with a commercial coating (see FIG. 52). FIG. 53 is a graph showing that the measured maximum pressures the seals could withstand were consistent with those estimated using the Young-Laplace equation.

Example 8—Prophetic Example: Highly Sensitive Detection of Low Abundance Mutation Marker or Copy Number Enumeration Prophetic Example Overview of approach: This approach depends on the fidelity of four enzymes: (i) Terminal transferase to generate T tails on all or selected fragments (i) Bst polymerase to faithfully replicate DNA in the initial sample, (ii) RNase H2 enzyme removing a blocking group on the upstream LDR primer, and (iii) Ligase in discriminating a match from mismatch on the 3' side of the upstream primer. The later is enhanced further by using an intentional mismatch or nucleotide analogue in the $2^{nd}$ or $3^{rd}$ base from the 3' end that slightly destabilizes hybridization of the 3' end if it is perfectly matched at the 3' end, but significantly destabilizes hybridization of the 3' end if it is mis-matched at the 3' end.

The most difficult case is for K-ras mutations, where 6 changes on codon 12 and 1 change on codon 13 are all spaced together. In general, for highest fidelity, the mismatch between mutant probe and wild-type sequence should at least be C:A for the last base, not G:T. Thus, one needs to use both upper-strand and lower-strand primers, or 2 ligation sets per detection reaction.

Since the different probes will compete with each other in binding the (rare) mutant sequence, it is important to allow for all the probes to hybridize to the correct sequence. There will be 3 upstream and 1 downstream probe for the K-ras codon 12 $1^{st}$ position mutations. False ligation of mutant LDR probes on wild-type target sequence may be further suppressed by using blocked upstream LDR probe with the wild-type sequence at the discriminating base, but lacking the appropriate tag sequence The aim is to avoid false ligation/false signal of mutant primers to normal sequence, but also for correct ligations to occur in the presence of the mutant sequence.

Terminal deoxynucleotidyl Transferase (TdT) is a template independent polymerase that adds deoxynucleotides in a distributive fashion to the free 3' ends of both DNA and RNA substrates (Michelson et al., "Characterization of the homopolymer tailing reaction catalyzed by terminal deoxynucleotidyl transferase. Implications for the cloning of cDNA" *J Biol Chem*, 257, 14773-14782 (1982), which is hereby incorporated by reference in its entirety). It will exhaust the mononucleotide-triphosphate in solution, and thus by controlling the ratio of free ends/TTP, one can achieve relatively narrow Poisson distribution of tail lengths of those ends (Yarranton et al., "A DNA Polymerase from Ustilago maydis," *Eur J Biochem*, 77, 521-527 (1977), which is hereby incorporated by reference in its entirety).

Optimal conditions for TdT addition are established in solution using spiked fluorescently labeled TTP, with fragment lengths verified by capillary electrophoresis (Medintz, et al., "Fluorescence labeling methods for microchannel plate capillary electrophoresis DNA sizing," *J Capill Electrophor Microchip Technol*, 7, 43-49 (2002), which is hereby incorporated by reference in its entirety).

Optimal conditions for hybridization are experimentally determined to: (i) Maximize recovery of targets; and (ii) provide uniform addressing of all pillars as molecules are transported through the biomolecular processor array. Bst polymerase, a strand-displacing enzyme, will extend poly-$dA_{30}$ primers hybridized to a poly-T tailed target, and after raising the temperature to 55-60° C., will generate identical and adjacent copies that are covalently attached to the pillar.

Detailed Protocol: Append $T_{(100-150)}$ tails to ends of input cfDNA. A range of incubation conditions and TTP concentrations are tested to determine conditions to achieve relatively uniform addition of about 100-150 T bases to the 3' ends of each DNA molecule in the sample. In this example, T tails should be of sufficient length, such that one or more $dA_{30}$ primers will capture all fragments in the subsequent solid-phase step.

Capture of tailed targets on the solid support. Distribution of tailed single-stranded DNA among pillars within a given bioreactor chamber of a biomolecular processor is a function of the target's diffusion constant, the spacing of the pillars and the fluid velocity. These are adjusted to capture >80% of input targets, where one or more primers should hybridize to the $T_{100-150}$ tail. Bst polymerase (large fragment), which lacks both 3' and 5' exonuclease activity, but has strand displacement activity, will make full-length copies of each captured template. By raising the temperature to 55-60° C., the poly dA-T portions will partially denature, allowing for new primers to bind and be extended. This linear replication process faithfully copies the original template strand as it is "handed-off" to the next primer, until unhindered primers are exhausted.

Add thermostable ligase (preferably from strain AK16D), RNaseH2, buffer supplement to optimized ligation conditions, and suitable upstream and downstream LDR probes (10 nM to 20 nM each, downstream probes may be synthesized with 5' phosphate, or kinase in bulk prior to reactions; upstream probes comprise an RNA base after the desired 3' end, 4 additional bases, and a blocking group to prevent target-independent ligation.) In this example, upstream probes comprise of a 5' Drag-tag, followed by target-specific sequence with a C:A or G:T mismatch at the $3^{rd}$ or penultimate base, the mutation base at the 3' end, followed by an RNA base and 4 more DNA bases that matches the target, and a commercially available C3 spacer to block ligation. The downstream probes comprise a 5' phosphorylated end, followed by target-specific sequence, and a 3' tail. Perform 1 cycle of LDR at 60° C. for 4 minutes. This will allow for ligation events to occur on the replicated products if mutant DNA is present. Wash away unligated primer or misligated, target-independent products. Then elute products (e.g. by heat), detect and quantify either through FRET detection, nano-flight tube detection, nanopore detection, or other reporter systems.

Alternative terminal transferase reactions: The major concern with tailing target nucleic acid would be under-polymerization such that some targets have insufficient tails, and/or are not captured in the hybridization step. This initial concern may be a problem if fragments of RNA or DNA accumulate or are not removed during purification or enzymatic steps. This event may be addressed by optimizing primer concentrations, and by using larger capture arrays if needed. A related concern would be over-tailing, such that the products are thousands of bases and may not extend efficiently. This second concern may be solved by using a mixture of ddTTP to TTP at a ratio of 1:150. If the two nucleotides incorporate at the same rate, then the average tail would be ~100 bases long. An alternative approach is to include 2 "dummy" oligonucleotides, at a standard amount to control the ratio of free ends/TTP. Thus, when processing DNA from CTCs, which may range from a few cells to a hundred cells, the total number of ends increases by at most 25%, which would decrease tail length by only 20%. One of the two dummy oligonucleotides would be present at very low levels, and serve as a control for LDR reactions to verify digital counting of original input DNA. As an example, DNA isolated from 10 to 100 CTCs purified from 1 mL of blood, sheared into fragments ~2 kbp, would yield $1.6 \times 10^8$-$1.6 \times 10^9$ fragments. Combined with $1.6 \times 10^{10}$ fragments of linearized plasmid "dummy" DNA, would allow for 10-fold replication and scoring of copy number variations in these CTCs using the aforementioned biomolecular processor array.

Bst Polymerase (large fragment) is used for replication since it has strand-displacement activity and lacks both 3' and 5' exonuclease activity. Other polymerase enzymes include but are not limited to the thermophilic PyroPhage 3173 DNA Polymerase, Exo Minus, which has both strand-displacement and reverse-transcription activity, or Phi-29 DNA polymerase (not thermophilic).

The downstream LDR probes may also be phosphorylated during the ligation reaction using thermophilic phage kinase (derived from bacteriophage RM378 that infects *Rhodothermus marinus*). Under these conditions the denaturation step in the LDR should be as short as possible (i.e. 94° C. or even lower for 1 second), as the thermophilic kinase is not fully thermostable—or just preincubate at 65° C. for 15 minute to achieve full primer phosphorylation. Alternatively, the 5' side of the downstream LDR primer contains a base the same as the 3' discriminating base on the upstream primer, said base removed by the 5' to 3' nuclease activity of Fen nuclease or Taq polymerase to liberate a 5' phosphate suitable for a subsequent ligation.

Example 9—Prophetic Example: High Sensitivity Methylation Marker for Low Abundance Promoter Hypermethylation in Total Plasma DNA Overview of approach: Isolated genomic DNA, or methyl enriched DNA is incubated with terminal transferase to generate $T_{100}$ tails, and then treated with a methyl sensitive enzyme whose recognition elements comprise only C and G bases (i.e. Bsh1236I=CG^CG). Target DNA containing adjacent Bsh1236I sites are distributed onto the solid support such that the $T_{100}$ tail hybridizes to dA30 primers immobilized to pillars. Since the original genomic strand is handed-off from one primer to the next, we can take advantage of a unique property of BstU1 restriction endonuclease. This enzyme, will not nick hybrid unmethylated/methylated DNA, nor cleave unmethylated ssDNA (Zierhut et al., "Break dosage, cell cycle stage and DNA replication influence DNA double strand break response," *EMBO J*, 27, 1875-1885 (2008), which is hereby incorporated by reference in its entirety). Thus, a pretreatment with isoschizomer Bsh1236I, followed by concurrent incubation with BstU1 and Bst polymerase provides a continuous selection for replication of DNA if and only if it was originally methylated at the genomic level. No other amplification system retains this feature. The desired target fragments are detected using ligation primers that cover one or more methylated restriction sites, and thus will only ligate onto those immobilized target sequences that remain intact due to methylation of the original target DNA.

The above restriction site (CG^CG) was also chosen such that carryover prevention may work at two levels: (i) the sites are still cleavable in DNA containing incorporated dUTP, allowing for use of UNG for carryover prevention and (ii) after amplification, the sites are unmethylated, such that products would readily be re-cleaved should they carryover to another reaction. Subsequent to the initial replication, LDR reactions with carryover protection are performed as described above.

Detailed protocol for highly sensitive detection of promoter methylation: Append $T_{(100-150)}$ tails to ends of input cfDNA, using conditions that achieve relatively uniform addition of about 100-150 T bases to the 3' ends of each DNA molecule in the sample. Treat DNA with methyl-sensitive restriction endonuclease Bsh1236I (CG^CG), to cleave unmethylated sites. In this example, T tails should be of sufficient length, such that one or more $dA_{30}$ primers will capture all fragments in the subsequent solid-phase step.

Capture of tailed targets on the solid support. Distribution of tailed single-stranded DNA among pillars within a given bioreactor is a function of the target's diffusion constant, the spacing of the pillars and the fluid velocity. Conditions are varied to capture >80% of input targets, where one or more $dA_{30}$ primers should hybridize to the $T_{100-150}$ tail. Extend hybridized primer with Bst polymerase (large fragment), which lacks both 3' and 5' exonuclease activity, in the presence of BstUI (CG^CG), to make full-length copies of each captured template, if it was methylated. When raising the temperature to 55-60° C., the dA portion partially denatures, allowing for an adjacent primer to hybridize and polymerase displaces the first primer strand. By this repetitive process, the original strand is "handed-off" to the next primer to achieve a linear amplification of the original DNA. BstU1 will cleave dsDNA if unmethylated, but not hybrid methyl/unmethyl DNA, nor unmethylated ssDNA. This linear replication process faithfully copies the original methylated template strand, until unhindered primers are exhausted.

Add thermostable ligase (preferably from strain AK16D), and suitable upstream and downstream LDR probes (10 nM to 20 nM each, downstream probes may be synthesized with 5' phosphate, or kinased in bulk prior to reactions; upstream probes comprise a 5' drag-tag portion followed by a target-specific sequence. The downstream probes comprise a 5' phosphorylated end, followed by target-specific sequence, preferably overlapping at least one BstUI recognition sequence, and a 3' tail. Perform 1 cycle of LDR at 60° C. for 4 minutes. This will allow for ligation events to occur on the replicated products if the target (originally methylated) DNA is present. Wash away unligated primer or misligated, target-independent products. Then elute products (e.g. by heat), detect and quantify either through FRET detection, nano-flight tube detection, nanopore detection, or other reporter systems.

Example 10—Prophetic Example: High Sensitivity Detection of mRNA, lncRNA, Gene Translocation or Splice-Site Variation in mRNA Isolated from Total Plasma mRNA, Exosomes, Circulating Tumor Cells (CTC's) or Total Blood Cells Containing CTC's Overview of approach: Detection of mRNA requires conversion into cDNA, since neither Bst polymerase, nor thermostable ligase has activity on RNA templates. This approach depends on the fidelity of four enzymes: (i) Reverse Transcriptase to faithfully copy low-level copies of mRNA, lncRNA, or aberrant RNA transcripts in the initial sample, (ii) Terminal transferase to generate T tails on all or selected cDNA fragments (iii) Bst polymerase to replicate the tailed cDNA, and (iv) thermostable ligase in discriminating primers hybridized adjacent to each other. Once a ligation event has taken place, those products will be uniquely identified and distinguished using a nanopore and/or nanotube time-of-flight detector.

One advantage of using LDR is that it can discriminate a translocation event independent of the precise breakpoints. Further, when a translocation or alternative splicing creates new exon-exon junctions, LDR is ideally suited to precisely distinguish these junctions, down to the exact bases at the junctions.

There are at least two sources of aberrantly spliced transcripts in tumors. Tumors may undergo global deregulation of gene expression through overall hypo-methylation. One consequence of hypo-methylation is the degradation of control of transcription start sites in promoter regions, allowing for alternative sequences in the 5' end of transcripts. Such alternatively spliced leader sequences may then be accurately identified and quantified using LDR-based assays. A second source of aberrantly spliced transcripts arises from deregulation of the splicing machinery. Some such transcripts are translated into proteins that facilitate or even drive tumor growth. Again, these alternatively spliced transcripts may then be accurately identified and quantified using LDR-based assays, including providing relative levels of both the aberrant and wild-type transcript in the same LDR reaction.

Detailed protocol for highly sensitive detection of mRNA, lncRNA, gene translocation, or splice-site variation in mRNA: Incubate isolated mRNA or lncRNA with MMLV reverse transcriptase, using a $dU_{30}V$ primer that will hybridize to the poly-A tail, to generate cDNA of the 3' regions of poly-adenylated mRNA targets. Since terminal transferase can extend the free 3' end of RNA, as well as templates as small as DNA trimers, it is imperative that RNA and primers are fully removed prior to the tailing step. Cleave unused primer with UDG & EndoVIII, to generate products with 3' phosphate, which are not substrates for terminal transferase: Degrade RNA with RNaseI & RNaseH, and remove dNTPs and 1-3 base digestion products. Thus, only the cDNA extension products remain with free 3' OH.

Append $T_{(100-150)}$ tails to ends cDNA. A range of incubation conditions and TTP concentrations are tested to determine conditions to achieve relatively uniform addition of about 100-150 T bases to the 3' ends of each DNA molecule in the sample. In this example, T tails should be of sufficient length, such that one or more $dA_{30}$ primers will capture all fragments in the subsequent solid-phase step.

Capture of tailed targets on the solid support. Distribution of tailed single-stranded DNA among pillars within a given biomolecular processor is a function of the target's diffusion constant, the spacing of the pillars and the fluid velocity. These are adjusted to capture >80% of input targets, where one or more primers should hybridize to the $T_{100-150}$ tail. Bst polymerase (large fragment), which lacks both 3' and 5' exonuclease activity, but has strand displacement activity, will make full-length copies of each captured template. By raising the temperature to 55-60° C., the poly dA-T portions will partially denature, allowing for new primers to bind and be extended. This linear replication process faithfully copies the original template strand as it is "handed-off" to the next primer, until unhindered primers are exhausted Add thermostable ligase (preferably from strain AK16D), and suitable upstream and downstream LDR probes (10 nM to 20 nM each, downstream probes may be synthesized with 5' phosphate, or treated with kinase in bulk prior to reactions; upstream probes comprise a 5' drag-tag portion followed by a target-specific sequence. The downstream probes comprise a 5' phosphorylated end, followed by target-specific sequence, and a 3' tail. Perform 1 cycle of LDR at 60° C. for 4 minutes. This will allow for ligation events to occur on the replicated products if the target cDNA is present. Wash away unligated probe or misligated, target-independent products. Then elute products (e.g. by heat), detect and quantify either through FRET detection, nano-flight tube detection, nanopore detection, or other reporter systems.

Alternative approaches: Recently, an approach for appending primer sequences based on strand-switching of reverse transcriptase has been developed (Picelli et al., "Full-length RNA-seq from single cells using Smart-seq2," Nat Protoc. 9(1):171-81) (2014), which is hereby incorporated by reference in its entirety). This may be modified for use with the uMPS, and depends on the fidelity of three enzymes: (i) Reverse Transcriptase to faithfully copy low-level copies of mRNA, lncRNA, or aberrant RNA transcripts in the initial sample, as well as to append T tails onto the cDNA (ii) Bst polymerase to replicate the tailed cDNA, and (iii) thermostable ligase in discriminating primers hybridized adjacent to each other. Once a ligation event has taken place, those products will be uniquely identified and distinguished using a nano-flight tube detector.

Yet another alternative approach is dependent on directly capturing the 3' polyA tail of mRNA and lncRNA. In this embodiment, instead of using a $dA_{30}$ primer, the solid support contains a $T_{60}$ primer. A T60 DNA-RNA hybrid has sufficient binding affinity to work for this protocol, however the preferred temperature for replication will be in the range of 45-55° C. Strand displacing M-MuLV reverse transcriptase or Pyrophage 3173 DNA polymerase, (which has reverse-transcriptase activity) is used instead of Bst polymerase.

Detailed protocol for highly sensitive detection of mRNA, lncRNA, gene translocation, or splice-site variation in mRNA: Incubate isolated mRNA or lncRNA with reverse transcriptase, using a $(dU,T)_{30}VN$ primer that will hybridize to the poly-A tail, to generate cDNA of the 3' regions of poly-adenylated mRNA targets. A reverse transcriptase such as Moloney Murine Leukemia Virus Reverse Transcriptase (M-MLV RT, New England Biolabs), or Superscript II or III Reverse Transcriptase (Life Technologies) appends three C bases to the 3' end of each cDNA extension product. A second primer with (optional 5' phosphate), 5' $dA_{30}$ and three ribose G bases on the 3' end is hybridized to the $C_3$ overhang. Preferably, the 3' end G is an LNA base. The reverse transcriptase undergoes strand switching and copies the dA30 tail to generate a T30 tail on the 3' end. Degrade the original $(dU,T)_{30}VN$ primer with UDG. Optionally, the second primer with 5' $dA_{30}$ portion is degraded with a 5' nuclease (such as lambda exonuclease).

Capture of tailed targets on the solid support. Distribution of tailed single-stranded DNA among pillars within a given biomolecular processor is a function of the target's diffusion constant, the spacing of the pillars and the fluid velocity. These are adjusted to capture >80% of input targets, where primers should hybridize to the $T_{30}$ tail. Bst polymerase (large fragment), which lacks both 3' and 5' exonuclease activity, but has strand displacement activity, will make full-length copies of each captured template. By raising the temperature to 55-60° C., the poly dA-T portions will partially denature, allowing for new primers to bind and be extended. This linear replication process faithfully copies the original template strand as it is "handed-off" to the next primer, until unhindered primers are exhausted.

Add thermostable ligase (preferably from strain AK16D), and suitable upstream and downstream LDR probes (10 nM to 20 nM each, downstream probes may be synthesized with 5' phosphate, or treated with kinase in bulk prior to reactions; upstream probes comprise a 5' drag-tag portion followed by a target-specific sequence. The downstream probes comprise a 5' phosphorylated end, followed by target-specific sequence, and a 3' tail. Perform 1 cycle of LDR at 60° C. for 4 minutes. This will allow for ligation events to occur on the replicated products if the target cDNA is present. Wash away unligated probe or misligated, target-independent products. Then elute products (e.g. by heat), detect and quantify either through FRET detection, nano-flight tube detection, nanopore detection, or other reporter systems.

Example 11—Prophetic Example: Accurate Quantification of miRNA Changes from Isolated Exosomes, or from Circulating Tumor Cells Overview of approach: Detection of miRNA requires conversion into cDNA, and depends on the fidelity of five enzymes: (i) T4 ligase to append a loop primer to mRNA (ii) Reverse Transcriptase to faithfully copy low-level copies of miRNA transcripts in the initial sample, (iii) Terminal transferase to generate T tails on all or selected cDNA fragments (iv) Bst polymerase to replicate the tailed cDNA, and (v) thermostable ligase in discriminating primers hybridized adjacent to each other. Once a ligation event has taken place, those products will be uniquely identified and distinguished using a nano-flight tube or nanopore detector Detection of miRNA presents a unique challenge because such fragments are too small (19-25 bases) for traditional reverse-transcript priming, and are smaller than the footprint required for spLDR (about 50-60 bases). A 3'-blocked loop primer is appended to the miRNA, whose 3' terminal 6 random bases are complementary, such that the phosphorylated 5' end of the primer ligates to the 3' end of the miRNA. The product now has 5' RNA sequence, but the original loop primer has a 5' phosphorylated DNA end, and is now a substrate for degradation using lambda exonuclease. The DNA-RNA chimeric product is copied using a 5'-blocked dU-rich primer, complementary to the A-rich region of the loop primer. The stem region is double-stranded during the ligation step (using T4 ligase) at 16° C., but opens during the subsequent reverse transcription step to allow for a full copy of the loop sequence as well as the miRNA. miRNA and other sample RNA is destroyed with RNaseI and RNaseH, unused primer with UDG, and surviving cDNA purified using a ratchet array or electrophoresis. Enzymes are inactivated by heat denaturation.

MicroRNA (miRNA) have been identified as potential tissue-specific markers of the presence of tumors, their classification and prognostication. miRNA exist in serum and plasma either as complexes with Ago2 proteins or by encapsulation as exosomes.

Detailed protocol for highly sensitive detection of miRNA: Ligate loop primer with random hexamer sequence, complementary to 3' end of target miRNA, containing a stem-loop, a rich primer sequence, and a 3'blocking group. This step is accomplished using T4 RNA ligase, and optionally, T4 kinase to append a phosphate on the loop primer if needed. The unused loop primer is degraded with lambda exonuclease. Incubate ligated miRNA with MMLV reverse transcriptase, using a 5' blocked primer with a dU in the $2^{nd}$ or $3^{rd}$ position from the 3' end that will hybridize to the loop region, to generate cDNA of the full-length miRNA targets. Since terminal transferase can extend the free 3' end of RNA, as well as templates as small as DNA trimers, it is imperative that RNA and primers are fully removed prior to the tailing step. Cleave unused primer with UDG & EndoVIII, to generate products with 3' phosphate, which are not substrates for terminal transferase. Degrade RNA with RNaseI & RNaseH, and remove dNTPs and 1-3 base digestion products. Thus, only the cDNA extension products remain with free 3'OH.

Append $T_{(100-150)}$ tails to ends cDNA. A range of incubation conditions and TTP concentrations are tested to determine conditions to achieve relatively uniform addition of about 100-150 T bases to the 3' ends of each DNA molecule in the sample. In this example, T tails should be of sufficient length, such that one or more $dA_{30}$ primers will capture all fragments in the subsequent solid-phase step.

Capture of tailed targets on the solid support. Distribution of tailed single-stranded DNA among pillars within a given biomolecular processor is a function of the target's diffusion constant, the spacing of the pillars and the fluid velocity. These are adjusted to capture >80% of input targets, where one or more primers should hybridize to the $T_{100-150}$ tail. Bst polymerase (large fragment), which lacks both 3' and 5' exonuclease activity, but has strand displacement activity, will make full-length copies of each captured template. By raising the temperature to 55-60° C., the poly dA-T portions will partially denature, allowing for new primers to bind and be extended. This linear replication process faithfully copies the original template strand as it is "handed-off" to the next primer, until unhindered primers are exhausted.

Add thermostable ligase (preferably from strain AK16D), and suitable upstream and downstream LDR probes (10 nM to 20 nM each, downstream probes may be synthesized with 5' phosphate, or treated with kinase in bulk prior to reactions; upstream primers comprise a 5' drag-tag portion followed by a target-specific sequence. Since the miRNA is only on average 23 bases, the upstream LDR probe will contain some loop sequence, while the downstream probe will contain some oligo T sequence as well. The downstream primers comprise a 5' phosphorylated end, followed by target-specific sequence, and a 3' tail. Perform 1 cycle of LDR at 60° C. for 4 minutes. This will allow for ligation events to occur on the replicated products if the target miRNA was present in the original sample. Wash away unligated probe or misligated, target-independent products. Then elute products (e.g. by heat), detect and quantify either through FRET detection, nano-flight tube detection, nanopore detection, or other reporter systems.

Alternative approaches: An approach for appending primer sequences based on strand-switching of reverse transcriptase may be modified for use with the uMPS, and depends on the fidelity of three enzymes: (i) T4 ligase to append a loop primer to mRNA (ii) Reverse Transcriptase to faithfully copy low-level copies of miRNA transcripts in the initial sample, (ii) Reverse Transcriptase to faithfully copy low-level copies of mRNA, lncRNA, or aberrant RNA transcripts in the initial sample, as well as to append T tails onto the cDNA (iii) Bst polymerase to replicate the tailed cDNA, and (iv) thermostable ligase in discriminating primers hybridized adjacent to each other. Once a ligation event has taken place, those products will be uniquely identified and distinguished using a nano-flight tube detection, nanopore detection, or other reporter systems.

Detailed protocol for highly sensitive detection of miRNA: Ligate loop primer with random hexamer sequence, complementary to 3' end of target miRNA, containing a stem-loop, a rich primer sequence, and a 3'blocking group. This step is accomplished using T4 RNA ligase, and optionally, T4 kinase to append a phosphate on the loop primer if needed. The unused loop primer is degraded with lambda exonuclease. Incubate ligated miRNA with a 5' blocked primer and MMLV reverse transcriptase, which appends three C bases to the 3' end of each miRNA extension product. A second primer with (optional 5' phosphate), 5' $dA_{30}$ and three ribose G bases on the 3' end is hybridized to the $C_3$ overhang. Preferably, the 3' end G is an LNA base. The reverse transcriptase undergoes strand switching and copies the dA30 tail to generate a T30 tail on the 3' end. Optionally, the second primer with 5' $dA_{30}$ portion is degraded with a 5' nuclease (such as lambda exonuclease).

Capture of tailed targets on the solid support. Distribution of tailed single-stranded DNA among pillars within a given bioreactor is a function of the target's diffusion constant, the spacing of the pillars and the fluid velocity. These are adjusted to capture >80% of input targets, where primers should hybridize to the $T_{30}$ tail. Bst polymerase (large fragment), which lacks both 3' and 5' exonuclease activity, but has strand displacement activity, will make full-length copies of each captured template. By raising the temperature to 55-60° C., the poly dA-T portions will partially denature, allowing for new primers to bind and be extended. This linear replication process faithfully copies the original template strand as it is "handed-off" to the next primer, until unhindered primers are exhausted.

Add thermostable ligase (preferably from strain AK16D), and suitable upstream and downstream LDR probes (10 nM to 20 nM each, downstream probes may be synthesized with 5' phosphate, or treated with kinase in bulk prior to reactions; upstream probes comprise a 5' drag-tag portion followed by a target-specific sequence. Since the miRNA is only on average 23 bases, the upstream LDR probe will contain some loop sequence, while the downstream probe will contain some oligo T sequence as well. The downstream probes comprise a 5' phosphorylated end, followed by target-specific sequence, and a 3' tail. Perform 1 cycle of LDR at 60° C. for 4 minutes. This will allow for ligation events to occur on the replicated products if the target miRNA was present in the original sample. Wash away unligated probe or misligated, target-independent products. Then elute products (e.g. by heat), detect and quantify either through FRET detection, nano-flight tube detection, nanopore detection, or other reporter systems.

Example 12—Prophetic Example: Two-Sided Target Replication, Targeted Cell-Free DNA Replication, for Detection of Mutations Via LDR or Sequencing Reactions Detailed protocol for two sided-amplification of genomic DNA or cfDNA. Starting with cfDNA (or for example genomic DNA isolated from CTC, sheared to about 150 bp), repair ends with T4 polymerase and T4 Kinase, and subsequently a single base 3' A overhang is added with Klenow (exo-) and dATP. A:T rich linkers have a single base 3' T overhang, such that ligation using T4 ligase appends linkers on both ends of the fragment. Linkers also contain single-stranded 5' universal primer sequence(s) and 3' $T_{30}$ tails. Optionally, purify target DNA from unligated linker.

Capture of $T_{30}$ tailed targets on the $dA_{30}$ primers on the solid support. Distribution of tailed single-stranded DNA among pillars within a given bioreactor is a function of the target's diffusion constant, the spacing of the pillars and the fluid velocity. These are adjusted to capture >80% of input targets. Bst polymerase (large fragment), which lacks both 3' and 5' exonuclease activity, but has strand displacement activity, will make full-length copies of each captured template. By raising the temperature to 55-60° C., the poly dA-T portions will partially denature, allowing for new primers to bind and be extended. This linear replication process faithfully copies the original template strand as it is "handed-off" to the next primer. Meanwhile, universal primer(s) in solution hybridizes to single-stranded extension product, and is extended by polymerase. The process of handoff replication continues until unhindered primers are exhausted. Untethered extension products are melted off the solid support, which now has dozens to hundreds of single strands with identical sequence within a given biomolecular processor, suitable for sequencing-by-synthesis.

Detailed protocol for two-sided amplification of genomic DNA or cfDNA with one-directional target-specific primers used to achieve selection of the desired targets. Starting with cfDNA (or for example genomic DNA isolated from CTC, sheared to about 150 bp), append $T_{(100-150)}$ tails to ends. A range of incubation conditions and TTP concentrations are tested to determine conditions to achieve relatively uniform addition of about 100-150 T bases to the 3' ends of each DNA molecule in the sample. In this example, T tails should be of sufficient length, such that one or more $dA_{30}$ primers will capture all fragments in the subsequent solid-phase step.

The DNA is denatured, and target-specific primers with blocked 3' ends hybridize to their complementary sequences.

Primers are unblocked with RNaseH2 only when bound to target. The liberated 3' ends are extended with polymerase (for example Taq polymerase or Klenow (exo-)) until they reach the end of the fragment, and then append an additional A base. Linkers have a single base 3' T overhang, such that ligation using T4 ligase appends linkers onto fragments that were extended to have the single A base overhang. The linkers contain 5' blocked single-stranded universal primer sequence(s). Optionally, non-target genomic DNA is digested with 5'→3' exonuclease (i.e. lambda exonuclease).

Capture of tailed targets on the solid support. Distribution of tailed single-stranded DNA among pillars within a given biomolecular processor is a function of the target's diffusion constant, the spacing of the pillars and the fluid velocity. These are adjusted to capture >80% of input targets, where one or more primers should hybridize to the $T_{100-150}$ tail. Bst polymerase (large fragment), which lacks both 3' and 5' exonuclease activity, but has strand displacement activity, will make full-length copies of each captured template. By raising the temperature to 55-60° C., the poly dA-T portions will partially denature, allowing for new primers to bind and be extended. This linear replication process faithfully copies the original template strand as it is "handed-off" to the next primer. Meanwhile, universal primer(s) in solution hybridizes to single-stranded extension product, and is extended by polymerase. The process of handoff replication continues until unhindered primers are exhausted. Untethered extension products are melted off the solid support, which now has dozens to hundreds of single strands with identical sequence within a given biomolecular processor, suitable for sequencing-by-synthesis.

Detailed protocol for two-sided amplification of genomic DNA or cfDNA with two-directional target-specific primers to achieve selection of desired targets. Starting with cfDNA (or for example genomic DNA isolated from CTC, sheared to about 150 bp), DNA is denatured, and target-specific primers with blocked 3' ends hybridize to their complementary sequences. Primers are unblocked with RNaseH2 only when bound to target. The liberated 3' ends are extended with thermostable polymerase. One set of primers contain 5'$dA_{30}$ tails, while the other set contain 5' blocked single-stranded universal primer sequence(s). After a second round of denaturation/extension, products are formed with a 5' blocked universal primer followed by target sequence, and a 3' $T_{30}$ tail. Optionally, non-target genomic DNA is digested with 5'→3' exonuclease (i.e. lambda exonuclease).

Capture of $T_{30}$ tailed targets on the $dA_{30}$ primers on the solid support. Distribution of tailed single-stranded DNA among pillars within a given biomolecular processor is a function of the target's diffusion constant, the spacing of the pillars and the fluid velocity. These are adjusted to capture >80% of input targets. Bst polymerase (large fragment), which lacks both 3' and 5' exonuclease activity, but has strand displacement activity, will make full-length copies of each captured template. By raising the temperature to 55-60° C., the poly dA-T portions will partially denature, allowing for new primers to bind and be extended. This linear replication process faithfully copies the original template strand as it is "handed-off" to the next primer. Meanwhile, universal primer(s) in solution hybridizes to single-stranded extension product, and is extended by polymerase. The process of handoff replication continues until unhindered primers are exhausted. Untethered extension products are melted off the solid support, which now has dozens to hundreds of single strands with identical sequence within a given biomolecular processor, suitable for sequencing-by-synthesis.

Starting with cfDNA (or for example genomic DNA isolated from CTC, sheared to about 150 bp), append $T_{(100-150)}$ tails to ends using terminal transferase. A range of incubation conditions and TTP concentrations are tested to determine conditions to achieve relatively uniform addition of about 100-150 T bases to the 3' ends of each DNA molecule in the sample. In this example, T tails should be of sufficient length, such that one or more $dA_{30}$ primers will capture all fragments in the subsequent solid-phase step.

Capture of tailed targets on the solid support. Distribution of tailed single-stranded DNA among pillars within a given biomolecular processor is a function of the target's diffusion constant, the spacing of the pillars and the fluid velocity. These are adjusted to capture >80% of input targets, where one or more primers should hybridize to the $T_{100-150}$ tail. Bst polymerase (large fragment), which lacks both 3' and 5' exonuclease activity, but has strand displacement activity, will make full-length copies of each captured template. By raising the temperature to 55-60° C., the poly dA-T portions will partially denature, allowing for new primers to bind and be extended. This linear replication process faithfully copies the original template strand as it is "handed-off" to the next primer. Meanwhile, target-specific primers with blocked 3' ends hybridize to their complementary sequences on the single-stranded extension product. Primers are unblocked with RNaseH2 only when bound to target. The liberated 3' ends are extended with Bst polymerase. Target-specific primers also contain universal primer sequences on their 5' ends. Universal primer(s) in solution hybridize to second round single-stranded extension products, and are extended by polymerase. The process of handoff replication continues until unhindered primers are exhausted. Untethered extension products are melted off the solid support, which now has dozens to hundreds of single strands with identical sequence within a given biomolecular processor, suitable for sequencing-by-synthesis. By using the universal primers for subsequent sequencing reactions, those linear amplifications that did not contain a target-specific extension product will not be sequenced. Amplification of such unwanted regions may also be eliminated by denaturing away the original target strand after one or more initial replications.

Example 13—Prophetic Example: Generation of Circularized Target Nucleic Acid Constructs Detailed protocol for generating circular templates of generic DNA isolated from circulating tumor cells or cfDNA (see e.g., FIG. 164). Starting with cfDNA or genomic DNA isolated from CTC, (sheared to about 150 bp), repair ends with T4 polymerase and T4 Kinase, and subsequently a single base 3' A overhang is added with Klenow (exo-) and dATP. Linkers have a single base 3' T overhang, such that ligation using T4 ligase at 4° C. appends linkers on both ends of the fragment. Linkers may be synthesized with 5' phosphate, or the phosphate may be appended using T4 kinase. Preferably, the two linker strands have a bubble region and/or additional mismatches, and a longer strand ligated to the 5' end of the target. Optionally, purify target DNA from unligated linker.

Denature target DNA containing linkers on both ends (94° C. 1 minute) in the presence of oligonucleotide probes (thin black, and double line) containing nucleotide sequences complementary to the 5' and 3' single-stranded portions of the linkers of the target DNA segments are hybridized to their respective target DNA segments. Oligonucleotide contains a primer-binding sequence, a dA30 sequence, an optional phosphate on 5' end, and a mismatched or blocked 3' end. Polymerase extends the 3' linker end of the hybridized target DNA segment to form a ligation junction with the 5' linker end of the target DNA segment. In the case where the linker sequence has a 5' phosphate, KlenTaq extends the 3' end until it is directly adjacent to the ligation-competent 5' end. In the case where the linker sequence has a 5' OH, the 5'→3' nuclease activity of polymerase cleaves the matching 5'-overlapping base to create a ligation competent 5' phosphate. Allow for extension and ligation at the hybridization temperature, and optionally raise the temperature (e.g. 60° C.) to assure completion of extension and ligation, to generate circular products.

Add Exonuclease I (digests single-stranded DNA in the 3'→5' direction), and Exonuclease III (digests double-stranded DNA in the 3'→5' direction), to digest all unligated or nicked products, leaving only the desired single-stranded circular DNA comprising of the original target DNA, the linker sequence, the $T_{30}$ sequence, the primer binding sequence, a second copy of the linker sequence. This product is suitable for capture on the solid support and replicative rolling circle amplification.

Detailed protocol for generating circular templates for accurate quantification of tumor-specific copy changes or detection of mutations in known genes (e.g. Braf, K-ras, p53) in DNA isolated from circulating tumor cells or cfDNA (see e.g., FIG. 165).

Starting with cfDNA or genomic DNA isolated from CTC, (sheared to about 150 bp), repair ends with T4 polymerase and T4 Kinase, and subsequently a single base 3' A overhang is added with Klenow (exo-) and dATP. Linkers have a single base 3' T overhang, such that ligation using T4 ligase at 4° C. appends linkers on both ends of the fragment. Linkers may be synthesized with 5' phosphate, or the phosphate may be appended using T4 kinase. Preferably, the two linker strands have a bubble region and/or additional mismatches, and a longer strand ligated to the 5' end of the target. Optionally, purify target DNA from unligated linker.

Denature target DNA containing linkers on both ends (94° C. 1 minute) in the presence of oligonucleotides (comprising a 5' sequence complementary to a unique portion of the target, an optional spacer region, a sequence complementary to the 5' end of the linker, a connecting sequence comprising (i) a $dA_{30}$ sequence, and (ii) a primer-binding sequence, an optional spacer region, a sequence complementary to the 3' end of the linker, and a blocked 3' sequence complementary to a unique portion of the target, and adjacent to the 5' sequence complementary to the target). Allow the oligonucleotides to hybridize to their complementary regions on the desired fragments by cooling to a desired temperature (e.g. 50° C. for 2 hours). Oligonucleotide may contain an optional blocking group on the 5' side. Primers are unblocked with RNaseH2 only when bound to target. The liberated 3' ends are extended with Taq polymerase and/or KlenTaq (Taq polymerase lacking nuclease activity), and nicks sealed with thermostable ligase (preferably from strain AK16D). Enzymes, dNTPs, and NAD are either added subsequent to the annealing step, or at the start of the procedure. In the case where the linker sequence has a 5' phosphate, KlenTaq extends the 3' end until it is directly adjacent to the ligation-competent 5' end. In the case where the linker sequence has a 5' OH, the 5'→3' nuclease activity of polymerase cleaves the matching 5'-overlapping base to create a ligation competent 5' phosphate. Allow for extension and ligation at the hybridization temperature, and optionally raise the temperature (e.g. 60° C.) to assure completion of extension and ligation, to generate circular products.

Optionally, cleave the oligonucleotide strand at a cleavable link (e.g. U cleaved using UDG and AP endonuclease). Add Exonuclease I (digests single-stranded DNA in the 3'→5' direction), and Exonuclease III (digests double-stranded DNA in the 3'→5' direction), to digest all unligated or nicked products, leaving only the desired single-stranded circular DNA comprising of the original target DNA, the linker sequence, the $T_{30}$ sequence, the primer binding sequence, a second copy of the linker sequence. This product is suitable for capture on the solid support and replicative rolling circle amplification.

Oligonucleotide may contain an optional blocking group on the 5' side to interfere with subsequent 5'-3' nuclease activity of polymerase, such that the oligonucleotide strand does not circularize. Alternatively, a cleavable link may be included in the original oligonucleotide.

Fen nuclease may be used instead of polymerase with 5'-3' nuclease activity to generate the ligation-competent 5' phosphate on the 5' side of the target.

The 5' end linker may be synthesized to contain thiophosphate linkages in the $2^{nd}$ and $3^{rd}$ position from the 5' phosphate end, (which will be liberated by the 5'→3' nuclease activity of the polymerase). To minimize polymerase displacement of those bases as it extends one base too many (which would make it impossible to ligate to the downstream primer), the target bases at the ligation junction would preferentially be AT rich on the 3' side, and GC rich on the 5' side.

When using KlenTaq polymerase (Taq polymerase without 5'→3' nuclease cleavage activity), the 5' end linker may be synthesized to contain an apurinic (AP) site at the position adjacent to the desired 5' phosphate. This 5' phosphate is liberated using a thermostable EndoIII (such as Tma EndoIII). This enzyme cleaves AP sites leaving a 5' phosphate when the primer is bound to the target. The endonuclease also cleaves single-stranded primer, but with lower efficiency, and thus primer hybridized to template would be the preferred substrate.

When using KlenTaq polymerase (Taq polymerase without 5'→3' nuclease cleavage activity), the 5' end linker may be synthesized to contain a 5' phosphate. Alternatively, the 5' phosphate may be added using T4 kinase either prior to ligating to the target DNA, or after that ligation step.

A 1:20 mixture of Taq polymerase (with 5'→3' nuclease activity) and KlenTaq (Taq polymerase without 5'→3' nuclease cleavage activity) may be used under conditions of distributive extension (i.e. higher salt concentration) to minimize degradation of target DNA by nick translation.

Detailed protocol terminal transferase to append tails to the 3' ends of target for generation of circularized target nucleic acid molecules (see e.g., FIG. 169).

Starting with cfDNA (or for example genomic DNA isolated from CTC, sheared to about 150 bp), append $T_{(30-50)}$ tails to ends using terminal transferase. A range of incubation conditions and TTP concentrations are tested to determine conditions to achieve relatively uniform addition of about 100-150 T bases to the 3' ends of each DNA molecule in the sample.

Denature target DNA containing $T_{(30-50)}$ tails on both ends (94° C. 1 minute) in the presence of oligonucleotides (comprising a 5' probe region complementary to the sequences to the 5' side of the targets, a connecting sequence comprising (i) a primer-binding sequence and (ii) a $dA_{50}$ sequence, and a 3' probe region complementary to the sequences to the 3' side of the targets). Allow the oligonucleotides to hybridize to their complementary regions on the desired fragments by cooling to a desired temperature (e.g. 50° C. for 2 hours). Oligonucleotide may contain an optional blocking group on the 5' side. Taq polymerase and/or KlenTaq (Taq polymerase lacking nuclease activity), and thermostable ligase (preferably from strain AK16D), dNTPs, and NAD are either added subsequent to the annealing step, or at the start of the procedure. Allow for extension and ligation at the hybridization temperature, and optionally raise the temperature (e.g. 60° C.) to assure completion of extension and ligation, to generate circular products.

Optionally, cleave the oligonucleotide strand at a cleavable link (e.g. U cleaved using UDG and AP endonuclease). Add Exonuclease I (digests single-stranded DNA in the 3'→5' direction), and Exonuclease III (digests double-stranded DNA in the 3'→5' direction), to digest all unligated or nicked products, leaving only the desired single-stranded circular DNA comprising of the original target DNA, the linker sequence, the $T_{30}$ sequence, the primer binding sequence, a second copy of the linker sequence. This product is suitable for capture on the solid support and replicative rolling circle amplification.

Detailed protocol for using T4 ligase to append linkers to the target nucleic acid molecule for circularization (see e.g., FIG. 170). Starting with cfDNA or genomic DNA isolated from CTC, (sheared to about 150 bp), repair ends with T4 polymerase and T4 Kinase, and subsequently a single base 3' A overhang is added with Klenow (exo-) and dATP. Linkers have a single base 3' T overhang, such that ligation using T4 ligase at 4° C. appends linkers on both ends of the fragment. Linkers may be synthesized with 5' phosphate, or the phosphate may be appended using T4 kinase. Optionally, purify target DNA from unligated linker.

Denature target DNA containing linkers on both ends (94° C. 1 minute) in the presence of oligonucleotides (comprising a 5' probe region complementary to the sequences to the 5' side of the targets, a sequence complementary to the 5' end of the linker, a connecting sequence comprising (i) a primer-binding sequence and (ii) a $dA_{30}$ sequence, a sequence complementary to the 3' end of the linker, and a 3' probe region complementary to the sequences to the 3' side of the targets). Allow the oligonucleotides to hybridize to their complementary regions on the desired fragments by cooling to a desired temperature (e.g. 50° C. for 2 hours). Oligonucleotide may contain an optional blocking group on the 5' side. Taq polymerase and/or KlenTaq (Taq polymerase lacking nuclease activity), and thermostable ligase (preferably from strain AK16D), dNTPs, and NAD are either added subsequent to the annealing step, or at the start of the procedure. In the case where the linker sequence has a 5' phosphate, KlenTaq extends the 3' end until it is directly adjacent to the ligation-competent 5' end. In the case where the linker sequence has a 5' OH, the 5'→3' nuclease activity of polymerase cleaves the matching 5'-overlapping base to create a ligation competent 5' phosphate. Allow for extension and ligation at the hybridization temperature, and optionally raise the temperature (e.g. 60° C.) to assure completion of extension and ligation, to generate circular products.

Optionally, cleave the oligonucleotide strand at a cleavable link (e.g. U cleaved using UDG and AP endonuclease). Add Exonuclease I (digests single-stranded DNA in the 3'→5' direction), and Exonuclease III (digests double-stranded DNA in the 3'→5' direction), to digest all unligated or nicked products, leaving only the desired single-stranded circular DNA comprising of the original target DNA, the linker sequence, the $T_{30}$ sequence, the primer binding sequence, a second copy of the linker sequence. This product is suitable for capture on the solid support and replicative rolling circle amplification.

Detailed protocol for circularizing target nucleic acid molecules without adapter portions (see e.g., FIG. 171). Denature target DNA (94° C. 1 minute) in the presence of oligonucleotides (comprising a 5' probe region complementary to the sequences to the 5' side of the targets, a connecting sequence comprising (i) a primer-binding sequence and (ii) a $dA_{50}$ sequence, and a 3' probe region complementary to the sequences to the 3' side of the targets). The 5' and 3' probe regions contain optional mismatches at regular intervals (e.g., 10, 12, or 15 bases). Allow the oligonucleotides to hybridize to their complementary regions on the desired fragments by cooling to a desired temperature (e.g. 45° C.-50° C. for 2 hours). Oligonucleotide may contain an optional blocking group on the 5' side. Taq polymerase and/or KlenTaq (Taq polymerase lacking nuclease activity), and thermostable ligase (preferably from strain AK16D), dNTPs, and NAD are either added subsequent to the annealing step, or at the start of the procedure. Allow for extension and ligation at the hybridization temperature, and optionally raise the temperature (e.g. 60° C.) to assure completion of extension and ligation, to generate circular products.

Optionally, cleave the oligonucleotide strand at a cleavable link (e.g. U cleaved using UDG and AP endonuclease). Add Exonuclease I (digests single-stranded DNA in the 3'→5' direction), and Exonuclease III (digests double-stranded DNA in the 3'→5' direction), to digest all unligated or nicked products, leaving only the desired single-stranded circular DNA comprising of the original target DNA, the linker sequence, the $T_{30}$ sequence, the primer-binding sequence, a second copy of the linker sequence. This product is suitable for capture on the solid support and replicative rolling circle amplification.

Detailed protocol for circularizing methylated target nucleic acid molecule without adapter portions. Treat potentially methylated cfDNA, optionally with methyl sensitive restriction endonuclease(s), and then with bisulfite, which converts unmethylated dC to dU, and renders the strands non-complementary.

Add bisulfite treated target DNA to oligonucleotides (comprising a 5' probe region complementary to the sequences to the 5' side of the targets, a connecting sequence comprising (i) a primer-binding sequence and (ii) a $dA_{50}$ sequence, and a 3' probe region complementary to the sequences to the 3' side of the targets). The 5' and 3' probe regions contain optional mismatches at regular intervals (i.e. 10, 12, or 15 bases). Allow the oligonucleotides to hybridize to their complementary regions on the desired fragments by cooling to a desired temperature (e.g. 45° C.-50° C. for 2 hours). Oligonucleotide may contain an optional blocking group on the 5' side. Taq polymerase and/or KlenTaq (Taq polymerase lacking nuclease activity), and thermostable ligase (preferably from strain AK16D), dNTPs, and NAD are either added subsequent to the annealing step, or at the start of the procedure. Allow for extension and ligation at the hybridization temperature, and optionally raise the temperature (e.g. 55° C.) to assure completion of extension and ligation, to generate circular products.

Optionally, cleave unmethylated strands with methyl-sensitive restriction endonuclease(s), and cleave the oligonucleotide strand at a cleavable link (e.g. abasic site cleaved using AP endonuclease). Add Exonuclease I (digests single-stranded DNA in the 3'→5' direction), and Exonuclease III (digests double-stranded DNA in the 3'→5' direction), to digest all unligated or nicked products, leaving only the desired single-stranded circular DNA comprising of the original target DNA, the linker sequence, the $dA_{30}$ sequence, the primer binding sequence, a second copy of the linker sequence. This product is suitable for capture on the solid support and replicative rolling circle amplification.

Example 14—Prophetic Example: Rolling Circle Amplification

Capture of $T_{30}$ single-stranded circular targets on the $dA_{30}$ primers on the solid support. Distribution of single-stranded circular DNA among pillars within a given biomolecular processor is a function of the target's diffusion constant, the spacing of the pillars and the fluid velocity. These are adjusted to capture >80% of input targets. Bst polymerase (large fragment), which lacks both 3' and 5' exonuclease activity, but has strand displacement activity, will make rolling circle copies of each captured template. Meanwhile, universal primer(s) in solution hybridizes to single-stranded rolling circle extension product, and are extended by polymerase (see e.g., FIGS. 173 and 176). These extend back toward the solid surface, until they copy the original immobilized $dA_{30}$ primer. Alternatively, target-specific primers may be used to selectively amplify desired rolling circle products (see e.g., FIG. 174). By first generating rolling circle products, denaturing and removing circles, and then subsequently adding the target-specific primers, the process may be optimized to limit amplification of undesired products (see e.g., FIG. 175). By raising the temperature to 55-60° C., the poly dA-T portions will partially denature, allowing for new primers to bind and be extended. This linear replication process faithfully copies the original template strand as it is "handed-off" to the next primer. Further, longer universal primer extension products on the original rolling circle extension displace shorter extension products that are downstream. These displaced, untethered extension products can hybridize to fresh $dA_{30}$ primers on the solid support, and the process of extension and handoff replication can start at the new site. Displacement of untethered strands by growing extension products allows new universal primer(s) in solution to hybridize to single-stranded extension product, and these in turn are extended by polymerase. The process of handoff replication continues until unhindered primers are exhausted. Untethered extension products are melted off the solid support, which now has hundreds to thousands of single strands with identical sequence within a given biomolecular processor, suitable for sequencing-by-synthesis.

To illustrate how rapid the numbers increase, consider tethered strands (underlined) and free strands (plain) after 5 cycles of isothermal rolling circle extension with universal primer strand-displacement amplification. The numbers below were calculated based on the assumption that isothermal extension proceeds at an even rate, and that displaced untethered strands are rapidly captured on fresh $dA_{30}$ primers on the solid support. The initial rolling circle increases by one unit in each "cycle", thus, it "grows" from 1 to 2 to 3 to 4 to 5 (etc.) tandem copies in length. As it increases, fresh universal primers can bind and displace the previous universal primer, generating untethered fragments, of lengths 1, 2, 3, and 4 respectively. These in turn bind to fresh $dA_{30}$ primers on the solid support, allowing extension of tethered strands of equal length. The process is repeated, yielding the numbers below.

Cycle 1. 1:1
Cycle 2. 2:2+1:1
Cycle 3. 3:3+2:2+1:1+1:1
Cycle 4. 4:4+3:3+2:2+2:2+1:1+1:1+1:1+1:1
Cycle 5. 5:5+4:4+3:3+3:3+2:2+2:2+2:2+2:2+1:1+1:1+1:1+1:1+1:1+1:1+1:1+1:1

After melting off untethered sequences, a total of 5+4+3+3+2+2+2+2+1+1+1+1+1+1+1+1=31 copies of the original tethered sequence.

The theoretical totals after each extension cycle are 1, 3, 7, 15, 31, respectively and follow the formula of $2^n-1$, where n=extension cycles. This is assuming that new products are unhindered in hybridizing to fresh $dA_{30}$ primers on the solid surface to generate additional extension products. The rapid replication of extension products will be slowed as unhindered primers become limiting, which depends on the total targets being amplified on the 288 pillars within a biomolecular processor.

Example 15—Prophetic Example: Use of Replicated Templates for Sequencing-by-Synthesis Reactions and Detection on the uMPS Earlier calculations for the number of nano chambers and biomolecular processors were based on each nano chamber exhibiting dimensions of 200×410 μm, contains 8 biomolecular processors, each in a 20 μm×20 μm footprint. Each biomolecular processor contains 288 pillars, which are 1 μm in diameter, 5 um high, and spaced in a hexagonal packing with 0.25 μm spacing (center to center of 1.25 μm).

For obtaining the greatest value from uMPS sequencing, it is important to maximize the number of biomolecular processors per microfabricated device. Thus, new calculations are provided below for a streamlined nanosensor chamber exhibiting dimensions of 175×175 contains 8 biomolecular processors, each in a 25×16 μm footprint (each biomolecular processor with 288 pillars) as described supra.

A 4×4 inch wafer=101.6 mm×101.6 mm. That means 580×580=336,400 chambers×8 biomolecular processors=2,691,200 biomolecular processors. A 4×4 inch wafer contains about 336,000 chambers and 2,600,000 biomolecular processors.

A 6×6 inch wafer=152.4 mm×152.4 mm, but using only 135 mm (5.3 inches) per side=135 mm×135 mm. That means 771×771=594,441 chambers×8 biomolecular processors=4,755,528 biomolecular processors. A 6×6 inch wafer contains about 600,000 chambers and 4,700,000 biomolecular processors.

Based on literature reports of ~5,000 molecules per 1 μm2, it is estimated that a given pillar can accommodate ~78,500 molecules. In either of the above configurations, total packing=288 pillars per biomolecular processor.

Total pillars=288×4,755,528=1,369,592,064=1.37 billion pillars. Load pillars with 400 billion fragments, that is equal to 292 molecules per pillar, or essentially the ability to make 78,500/292=about 268 replicates per input molecule.

Now that total number of pillars has been determined, the average number of molecules per pillar, and the number of replicates per input molecules, it is important to determine the number of single reads, i.e. the sequencing data is interpretable provided no more than one fragment per biomolecular processor is being sequenced at one time.

For 4.75 M biomolecular processors, if 15% seq. reads, =712,500 total primer extensions then 13% single reads, 1% double reads=87% single=619,875 single reads For 4.75 M biomolecular processors, if 20% seq. reads, =950,000 total primer extensions then 16.4% single reads, 1.6% double reads=82% single=779,000 single reads For 4.75 M biomolecular processors, if 25% seq. reads=1, 187,500 total primer extensions then 19.5% single reads, 2.4% double reads=78% single=926,250 single reads For 4.75 M biomolecular processors, if 30% seq. reads=1, 425,000 total primer extensions then 22.2% single reads, 3.3% double reads=74% single=1,054,500 single reads The calculations below are based on 30% of the biomolecular processors generating sequence reads, i.e. 1,425,000 total primer extensions, will give single reads on 74% of extensions, i.e. sampling an average of 7,400 of the 10,000 genome equivalents. For example, during a given run analyzing cfDNA from 1 ml of plasma, a total of 142 primers are sequencing 10,000 genome equivalents.

The calculations below are based on the entire process per base takes 1 second, as each biomolecular processors is individually addressed. Thus, for 100 base reads=100 seconds=1.66 minutes.

The calculations below are based on 100 different primer additions=100×142=14,200. Each primer gives 100 bases of readable sequence, so coverage=1,420,000=1.42 MB worth of unique sequence information=about 710 genes of—but for an average of 7,400 of the 10,000 genomes that were captured.

This is calculated to generate 1,054,500 single reads×100 different primer additions=105 million reads×100 bases=10.5 Billion bases. Based on these calculations, the entire biomolecular processor sequencing process would be estimated to take 2.8 hours.

Example 16—Prophetic Example:
Sequencing-by-Synthesis and Detection on the uMPS Allows for Unprecedented Accuracy Based on the above calculations, an average of 268 molecules will be replicated per bioreactor chamber. Since primer should bind to each molecule, all 268 molecules are being sequenced at the single molecule level, each generating a product that may be detected with the Nano-scale flight tube. The information from all these products from a target region containing a potential mutation is being summed to determine if the sequence deviates from the summation of all these products for wild-type sequence, in essence, significantly enhancing base calling.

Thus, each of the over single million reads are actually the summation of 268 single-molecule reads.

1,054,500 single reads×100 different primer additions=105 million reads×100 bases=10.5 Billion bases×268 single-molecule reads=2.81 terabases of information in 2.8 hours How is all of this sequencing information useful? The key issue in early detection of cancer from the plasma is to accurately call low-abundance mutations. In general, there are three sources of error in a sequencing by synthesis run: (i) Mis-incorporation error, ones that are more likely to occur when the template has a damaged base or abasic site, or alternatively if polymerase has difficulty incorporating the labeled nucleotide analogue, (ii) "Minus" phase shift errors, where a sequencing strand with a free 3' end did not have a terminated base addition, and (iii) "Plus" phase shift errors, where a sequencing strand had 2 bases incorporated instead of one, for example due to low-level cleavage of reversible terminator or inhibitor group from a minority of the incorporated labeled nucleotide analogue. Phase shift and mis-incorporation errors may also occur at certain sequences, for example mononucleotide and di-nucleotide repeats may causes sequence-dependent errors.

FIG. 197 provides a summary of the simulated effect of phase shift errors on the ability to interpret a sequencing run. In the simulation, 200 strands were randomly shifted at the rate of one phase shift per base sequenced (cycle). For the "Minus" section (top of figure) this amounts to an 0.5% error rate, about average for current sequencing by synthesis instruments. Since the phase shift is random, some strands accumulate errors at 1 base out of phase, less at 2 bases out of phase, etc. After 100 cycles of sequencing by synthesis, 100 errors accumulate, but the majority of the strands (126) still have no frame shift, less than half of that (53) have one base shift, and about 10% of the strands have 2 or more bases shifted. The sequenced base leaves a "trail" of incorrect calls, which appear in the next few bases of the read (i.e. N at +1, +2, etc.) With fluorescent sequencing, or ion-based sequencing, each read is based on the accumulated signal, and for certain sequences, the phasing problem causes mis-interpretation of the actual sequence. From 120 to 200 cycles, the mis-calls continue to spread, such that by 200 cycles, the signal generated from the correct position is indistinguishable from that generated at the +1 position of the read. This would cause significant mis-reading of the sequence.

For the "Plus-Minus" calculations, the error rate per cycle was simulated at 0.5% for the minus shift, and 0.5% for the plus shift. Actual conditions may vary such that the minus shift is more frequent than the plus shift, or vice-versa. Total error per base is now at 1%, above average for current sequencing by synthesis instruments. After 100 cycles of sequencing, 200 errors accumulate, such that less than half of the strands (i.e. 90) exhibit no frame shift, while an almost equal number (39+47=86) have one base shift. The net effect is a broadening of the sequencing signal across several bases. From 120 to 200 cycles, the mis-calls continue to spread, such that by 200 cycles, the signal generated from the correct position is indistinguishable from that generated at the +1 position of the read. This would cause significant mis-reading of the sequence. Different simulations will give different levels of variation in the plus and minus direction, but an overall increase in mis-calls will occur in any case.

In contrast to the standard fluorescent and ion-based methods of sequencing-by-synthesis, the sequencing on the uMPS generates digital information. In other words, each base will generate a quantitative count of mobility labels, and instead of providing an average signal, the Nano-scale flight tube will provide a flight time for each single molecule label detected from all the strands for that bioreactor chamber. Further, since the sequencing information is provided at every position, the rates of phasing error can be determined in real time during the sequencing run, and thus the anticipated call for the next base can be accurately determined.

FIGS. 198-200 illustrate the simulated raw data from biomolecular processor sequencing to distinguish K-ras mutations with phase errors at 0.5% loss per cycle, and also as 0.5% loss and 0.5% gain per cycle after 100 cycles of simulated sequencing. FIGS. 198 and 200 (0.5% loss per cycle) provide the output for wild-type sequence TGGAGCTGGTGGCGTAG (SEQ ID NO: 3), while FIGS. 199 and 201 (0.5% loss and 0.5% gain per cycle) provide the output for the G12D mutation (G transition to A at the second position of codon 12; TGGAGCTGATGGCGTAG (SEQ ID NO: 4). The figures show bases on each side of the base that are mutated, i.e. CTGGTGG (nucleotides 6-12 of SEQ ID NO: 3) to CTGATGG (nucleotides 6-12 of SEQ ID NO: 4). The top row of the figure indicates the seven base string being considered. The second row of the figure shows the base position relative to the central site of mutation in the string. The third row of the figure shows the "correct" (compliment) base called at each position by a sequencing by synthesis process. The next four rows show the count of each base called correctly (pink) or incorrectly (yellow) for 200 simulated strands. These figures illustrate two very important features of biomolecular processor-sequencing: (i) The bases that remain unchanged in the sequence provide the same total number of calls independent of the calls for the bases that change; and (ii) The bases that do change are readily distinguishable, not only at the actual mutation position, but also for the neighboring bases.

These figures illustrate the rich information content generated by digitally counting the signal generated at each base interrogation instead of simply measuring an average signal response. Meaningful information about each is base is even imbedded in the incorrect calls which will be useful for not only dephasing error correction but will also provide a quality metric for each base position called.

To see this visually, compare as below for the calls (correct or incorrect) for various bases of the central 5 bases in the 16 base sequence shown in each of the FIGS. 198-201.

|  | T | G | G/A | T | G |
|---|---|---|---|---|---|
| (T Base calls) |  |  |  |  |  |
| FIG. 198 | 126 | 53 | 16 | 130 | 54 |
| FIG. 199 | 126 | 53 | 16 | 130 | 54 |
| FIG. 200 | 92 | 59 | 47 | 92 | 47 |
| FIG. 201 | 92 | 59 | 47 | 92 | 47 |
| (A Base calls) |  |  |  |  |  |
| FIG. 198 | 4 | 1 | 0 | 0 | 0 |
| FIG. 199 | 4 | 1 | 126 | 53 | 15 |
| FIG. 200 | 2 | 0 | 0 | 0 | 0 |
| FIG. 201 | 14 | 39 | 90 | 47 | 8 |
| (G Base calls) |  |  |  |  |  |
| FIG. 198 | 17 | 130 | 180 | 69 | 146 |
| FIG. 199 | 17 | 130 | 54 | 16 | 130 |
| FIG. 200 | 59 | 133 | 151 | 106 | 141 |
| FIG. 201 | 47 | 94 | 61 | 59 | 133 |

FIGS. 202-207 provide summaries of the calculations for base calls surrounding the wild-type/mutant base for a K-ras codon 12 mutation (FIGS. 202-203), APC gene codon 1307 single-base deletion (FIGS. 204-205), and a TP53 gene codon 248 mutation (FIGS. 206-207). The top row of each figure shows the 17 base sequence string surrounding the central mutation. The second row shows the base offsets relative to the central mutation. The third & fourth rows show the central 7 bases and base offsets for the mutation (left column) and the wild-type (right column). For each figure, the simulation results are provided assuming a steady rate of phase shift during 100 to 200 cycles of sequencing by synthesis. The correct base call is shaded in pink, and numbers above a threshold of 20 (i.e. 10% of the 200 strands) are shaded in yellow. In each case, compare the pattern on the left (mutant) with the pattern on the right (wild-type). Even when there is more signal for an incorrect base than the correct base for that position (e.g. FIG. 203, K-ras, T (offset=1) sandwiched between G bases (offset=0 & offset=2) gives substantially less signal than G at 160 cycles, 180 cycles, and 200 cycles), a direct comparison between wild-type and mutant patterns and digital signal gives no question that they are very different from each other, and readily distinguished. Even when there is a base deletion in a mononucleotide track APC 1307 delT mutation, the sequence pattern immediately distinguishes the two sequences (i.e., AGCAGAAA[T/del]AAAAGAAA (SEQ ID NO: 5)) (see FIGS. 204 and 205). With the p53 gene sequence, after 200 cycles with the 0.5% loss per cycle, the critical base (offset=0) would potentially be mis-called as a "C" for both wild-type and mutant sequences (i.e., CAT-GAACC[G/A]GAGGCCCA (SEQ ID NO: 6)) and using the "analog" signal from fluorescent or ion sequencing (FIG. 206, bottom, compare C calls (incorrect) 113>76; and 113>84). However, sequencing with the uMPS provides digital information, and the G and A bases are easily distinguished even though they are not the majority signal.

FIGS. 208-210 provide examples of the simulated signal for any pattern of A and G sequence, highlighting the power of signal molecule digital detection. Homopolymer tracts are particularly difficult for most NGS technologies and the figures demonstrate the detection of a single mutation even in the presence of flanking homopolymer tracts of differing lengths. This is illustrated with the example of 180 sequencing cycles, as required by the length of a typical cfDNA fragment. The top half provides the results with an error rate of minus 0.5% bases per cycle, while the bottom half shows the results for minus 0.5% bases per cycle and plus 0.5% bases per cycle, for a total of 1% error per cycle. To assure the ability to distinguish the "worst case" the calculations started with the sequences NNNANNN (SEQ ID NO: 7) and NNNGNNN (SEQ ID NO: 8) (FIG. 208), and then systematically adds A and G bases. As each base is added to the sequence, the program calculates the total signal for that base for all the positions.

FIGS. 211-213 summarize the results from these simulations. FIG. 211 provides results on patterns of the form A3NNAAGNNG3 (SEQ ID NO: 12) and A3NNAGGNNG3 (SEQ ID NO: 13). FIG. 212 provides results on patterns of the form A3NNGAANNG3 (SEQ ID NO: 14) and A3NNGGANNG3 (SEQ ID NO: 15), while FIG. 213 explores the impact of adding more "A" bases to the sequence. What is truly remarkable is that no matter what the pattern, in all cases a side-by-side comparison between the "G" mutation containing sequence and the "A" wild-type containing sequence shows very distinct patterns of distribution of digital signal for the simulated base calls, not only at the position of mutation, but at the surrounding bases as well. Thus, even in the absence of a "correct" dominant base call at a mutated position imbedded in a homopolymer tract the single molecule counting provides a digital signature that can be used to potentially correct the mis-call or at a minimum, provide a quality score that indicates that a mis-call is likely to have occurred.

Example 17—Prophetic Example: Sanger-Like Sequencing with Terminators and Detection on the uMPS Allows for Rapid and Highly Accurate Mutation Detection The sequencing-by-synthesis approach embodied in the previous section will provide unprecedented accuracy in mutation detection. By using a slightly different strategy based on the Sanger terminator approach, it may be possible to achieve very rapid, yet highly accurate sequencing results, by accurately measuring mobility of tens-to-hundreds of fragment mobilities in a nano-scale flight tube. In one embodiment, illustrated in FIGS. 179-182, primers are extended and then base-specific extension products are generated using a terminator with a capture moiety (such as biotin) to capture a 3' identifying signature modifier (such as thermostable streptavidin). In another embodiment, illustrated in FIGS. 183-185, primers comprising an optional 5' identifying signature modifier are extended and then base-specific extension products are generated using a terminator with a 3' encoded identifying signature modifier. In both embodiments, the extension reactions are repeated to provide different signatures, where the distribution of products from each run, in combination, provides the sequence information for the target.

When using terminators, only a fraction of the extension strands are terminated at each position of the given base. As extension continues, there will be less strands left after each round of termination. Thus, in order to get sufficient signal at a given base, and get sufficiently long sequence information, it is important to start with a sufficient number of molecules of a given target, and to balance the percent terminator incorporated at each position containing that base. On average, a given base will comprise 25% of the sequence, thus conditions sufficient for reading for example 30 different length extension products for a given base, should provide sequence information of about 120 bases for all four bases.

As an example, for achieving read lengths above 100 bases, consider targets that have been replicated to generate at least 1,000 molecules on the solid support. Assume an average distribution of base sequence and using the example of a dA terminator, the following metrics are observed:

| Base Number | Initial Strands | Percent terminator | Signal Molecules |
|---|---|---|---|
| 1 | 1000 | 5% | 50 |
| 5 | 815 | 5% | 41 |
| 10 | 630 | 5% | 32 |
| 15 | 488 | 5% | 24 |
| 20 | 377 | 5% | 19 |
| 25 | 292 | 5% | 15 |
| 30 | 226 | 5% | 11 |
| 35 | 175 | 5% | 9 |
| 40 | 135 | 5% | 7 |
| 45 | 105 | 5% | 5 |
| 50 | 81 | 5% | 4 |
| 1 | 1000 | 4.5% | 45 |
| 5 | 832 | 4.5% | 37 |
| 10 | 661 | 4.5% | 30 |
| 15 | 525 | 4.5% | 24 |
| 20 | 417 | 4.5% | 19 |
| 25 | 331 | 4.5% | 15 |
| 30 | 263 | 4.5% | 12 |
| 35 | 209 | 4.5% | 9 |
| 40 | 166 | 4.5% | 7 |
| 45 | 132 | 4.5% | 6 |
| 50 | 105 | 4.5% | 5 |
| 1 | 1000 | 4% | 40 |
| 5 | 849 | 4% | 34 |
| 10 | 693 | 4% | 28 |
| 15 | 565 | 4% | 23 |
| 20 | 460 | 4% | 18 |
| 25 | 375 | 4% | 15 |
| 30 | 306 | 4% | 12 |
| 35 | 250 | 4% | 10 |
| 40 | 204 | 4% | 8 |
| 45 | 166 | 4% | 7 |
| 50 | 135 | 4% | 5 |
| 1 | 1000 | 3.5% | 35 |
| 5 | 867 | 3.5% | 30 |
| 10 | 726 | 3.5% | 25 |
| 15 | 607 | 3.5% | 21 |
| 20 | 508 | 3.5% | 18 |
| 25 | 425 | 3.5% | 15 |
| 30 | 356 | 3.5% | 12 |
| 35 | 298 | 3.5% | 10 |
| 40 | 249 | 3.5% | 9 |
| 45 | 209 | 3.5% | 7 |
| 50 | 175 | 3.5% | 6 |
| 1 | 1000 | 3% | 30 |
| 5 | 885 | 3% | 27 |
| 10 | 760 | 3% | 23 |
| 15 | 653 | 3% | 20 |
| 20 | 561 | 3% | 17 |
| 25 | 481 | 3% | 14 |
| 30 | 413 | 3% | 12 |
| 35 | 355 | 3% | 11 |
| 40 | 305 | 3% | 9 |
| 45 | 262 | 3% | 8 |
| 50 | 225 | 3% | 7 |
| 1 | 1000 | 2.5% | 25 |
| 5 | 904 | 2.5% | 23 |
| 10 | 796 | 2.5% | 20 |
| 15 | 702 | 2.5% | 18 |
| 20 | 618 | 2.5% | 15 |
| 25 | 545 | 2.5% | 14 |
| 30 | 480 | 2.5% | 12 |
| 35 | 423 | 2.5% | 11 |
| 40 | 373 | 2.5% | 9 |
| 45 | 328 | 2.5% | 8 |
| 50 | 289 | 2.5% | 7 |
| 1 | 1000 | 2% | 20 |
| 5 | 922 | 2% | 18 |
| 10 | 834 | 2% | 17 |
| 15 | 754 | 2% | 15 |
| 20 | 681 | 2% | 14 |
| 25 | 616 | 2% | 12 |
| 30 | 557 | 2% | 11 |
| 35 | 503 | 2% | 10 |
| 40 | 455 | 2% | 9 |
| 45 | 411 | 2% | 8 |
| 50 | 372 | 2% | 7 |

From the above calculations there is an optimal percent terminator to be used for a given preferred read length. For an average read length of about 60 bases, this would result in about 60/4 or about 15 "dA" bases in that sequence. The calculations above reveal that for either 4.5% or 5% terminator, an average of 24 molecules would be terminated at about the 60 base read position. The ideal % terminator for a given length read and the maximum molecules read at that position are: 4.5%-5% terminator; 60 bases read length; 24 molecules/4.5%-5% terminators; 80 bases read length; 19 molecules/3.5%-4% terminator; 100 bases read length; 15 molecules/3%-4% terminator; 120 bases read length; 12 molecules/2.5%-3% terminator; 140 bases read length; 11 molecules/2%-3% terminator; 160 bases read length; 9 molecules. The accuracy of the read is also dependent on the resolution of a given length product in a nano-scale flight tube. A simplified distribution is shown in FIG. 214, assuming "bins" for the average time-of-flight. For example, at 60 bases, the distribution is 12 molecules in the expected bin, and 6 molecules each in the "−1" and "+1" bin. This simulates a Gaussian distribution of flight times for the same length molecules. The figure illustrates the widening of the distribution as the read length increases, and for the purposes of this illustration, a minimum of 3 molecules per bin are calculated to score a bin positive. Thus, at 160 base read length, the signal of 9 molecules is distributed across 5 bins.

FIGS. 215-217 provide summaries of the calculations for base calls surrounding the wild-type/mutant base for a K-ras codon 12 mutation (i.e., TGGAGCTGGTGGCGTAG (SEQ ID NO: 3) and TGGAGCTGATGGCGTAG (SEQ ID NO: 4)) (FIG. 215), APC gene codon 1307 single-base deletion (i.e., AGCAGAAA[T/del]AAAAGAAA (SEQ ID NO: 5)) (FIG. 216), and a p53 gene codon 248 mutation (i.e., CATGAACC[G/A]GAGGCCCA (SEQ ID NO: 6)) (FIG. 217). The top row of each figure shows the 17 base sequence string surrounding the central mutation. The second row shows the base offsets relative to the central mutation. The third & fourth rows show the central 7 bases and base offsets for the mutation (left column) and the wild-type (right column). For each figure, the simulation results are provided assuming the Gaussian distribution of flight times as illustrated in FIG. 214. The correct base call is shaded in pink, and numbers above a threshold of 3 are shaded in yellow. In each case, compare the pattern on the left (mutant) with the pattern on the right (wild-type). Even when there is more signal for an incorrect base than the correct base for that position (e.g. FIG. 215, K-ras, T (offset=1) sandwiched between G bases (offset=0 & offset=2) gives less signal than G at 80 bases, 100 bases, 120 bases, 140 bases, or 160 bases), a direct comparison between wild-type and mutant patterns and digital signal gives no question that they are very different from each other, and readily distinguished. Even when there is a base deletion in a mononucleotide track APC 1307 delT mutation, the sequence pattern immediately distinguishes the two sequences (see FIG. 216). Likewise, with the p53 gene sequence, the pattern for the mutant sequence is readily distinguished from wild-type sequence, even at 160 base read length (see FIG. 217).

For some applications, especially when using a universal primer to distinguish different transcripts or enumerate target copy number, it is not necessary to sequence the target in its entirety, but only to obtain sufficient sequence information to identify the presence of that target or transcript, or about 20 to 30 bases of sequence information. Under these conditions, the short target sequence may be identified from far less target (about 200 target molecules on the solid support) and by using higher amounts of terminator. Assume an average distribution of base sequence and using the example of a dA terminator, the following metrics are observed:

| Base Number | Initial Strands | Percent terminator | Signal Molecules |
|---|---|---|---|
| 1 | 200 | 14% | 28 |
| 2 | 172 | 14% | 24 |
| 4 | 127 | 14% | 18 |
| 6 | 94 | 14% | 13 |
| 8 | 70 | 14% | 10 |
| 10 | 51 | 14% | 7 |
| 1 | 200 | 12% | 24 |
| 2 | 176 | 12% | 21 |
| 4 | 136 | 12% | 16 |
| 6 | 106 | 12% | 13 |
| 8 | 82 | 12% | 10 |
| 10 | 63 | 12% | 8 |
| 1 | 200 | 10% | 20 |
| 2 | 180 | 10% | 18 |
| 4 | 146 | 10% | 15 |
| 6 | 118 | 10% | 12 |
| 8 | 96 | 10% | 10 |
| 10 | 77 | 10% | 8 |

From the above calculations there is an optimal percent terminator to be used for a shorter read length (i.e. 20-40 bases) when just trying to identify each target. For an average read length of about 24 bases, this would result in about 24/4 or about 6 "dA" bases in that sequence. The calculations above reveal that for either 12% or 14% terminator, an average of 13 molecules would be terminated at about the 24 base read position. The ideal % terminator for a given length read and the maximum molecules read at that position are: 12%-14% terminator; 24 bases read length; 13 molecules/10%-14% terminators; 32 bases read length; 10 molecules/10%-12% terminator; 40 bases read length; 8 molecules.

In the second embodiment, illustrated in FIGS. 183-185, primers comprising an optional 5' identifying signature modifier are extended and then base-specific extension products are generated using a terminator with a 3' encoded identifying signature modifier as illustrated in FIGS. 218-220. FIGS. 221 through 225 illustrate the potential pattern of time-of-flight distribution for various combinations of 3' encoded identifying signature modifiers, using the TP53 wildtype sequence (SEQ ID NO 16) and common variants as examples (i.e., SEQ ID NOs: 17-21). In FIG. 221, four separate extension runs are performed using sequential reactions containing only a single terminator base, in each case carrying the same 3' encoded identifying signature modifier. For illustrative purposes, the 3' encoded identifying signature modifier is deemed to alter the time-of-flight by the same amount as an additional base (i.e. +1). The pattern of time-of-flights is illustrated in FIG. 221, with specific mutations altering the pattern at a single position between mutant and wild-type.

FIG. 222 shows an example using two 3' encoded identifying signature modifiers, which alter the mobility by +1 and +2 bases respectively. In this example, the first run uses 3' encoded identifying signature modifier +2 on dA, and 3' encoded identifying signature modifier +1 on dC. The second run reverses the 3' encoded identifying signature modifiers by using modifier +1 on dA, and 3' encoded identifying signature modifier +2 on dC, The third run uses 3' encoded identifying signature modifier +1 on dG, and 3' encoded identifying signature modifier +2 on T, while the fourth run uses 3' encoded identifying signature modifier +2 on dG, and 3' encoded identifying signature modifier +1 on T. The ensuing pattern is more complex, and when two signals would bin to the same mobility, this is indicated by a higher number (i.e. 2). In this figure, presence of the mutation changes the pattern in two positions among the 4 runs, and increases confidence in the identification of a true mutation.

FIG. 223 shows an example using two 3' encoded identifying signature modifiers, which alter the mobility by +1 and +3 bases respectively. In this example, the first run uses 3' encoded identifying signature modifier +3 on dA, and 3' encoded identifying signature modifier +1 on dC. The second run reverses the 3' encoded identifying signature modifiers by using modifier +1 on dA, and 3' encoded identifying signature modifier +3 on dC, The third run uses 3' encoded identifying signature modifier +1 on dG, and 3' encoded identifying signature modifier +3 on T, while the fourth run uses 3' encoded identifying signature modifier +3 on dG, and 3' encoded identifying signature modifier +1 on T. The ensuing pattern is more complex, and when two signals would bin to the same mobility, this is indicated by a higher number (i.e. 2). In this figure, presence of the mutation changes the pattern in two positions among the 4 runs, and increases confidence in the identification of a true mutation.

FIG. 224 shows an example using two 3' encoded identifying signature modifiers, which alter the mobility by +2 and +4 bases respectively. In this example, the first run uses 3' encoded identifying signature modifier +4 on dA, and 3' encoded identifying signature modifier +2 on dC. The second run reverses the 3' encoded identifying signature modifiers by using modifier +2 on dA, and 3' encoded identifying signature modifier +4 on dC, The third run uses 3' encoded identifying signature modifier +2 on dG, and 3' encoded identifying signature modifier +4 on T, while the fourth run uses 3' encoded identifying signature modifier +4 on dG, and 3' encoded identifying signature modifier +2 on T. The ensuing pattern is more complex, and when two signals would bin to the same mobility, this is indicated by a higher number (i.e. 2). In this figure, presence of the mutation changes the pattern in two positions among the 4 runs, and increases confidence in the identification of a true mutation.

FIG. 225 shows an example using four 3' encoded identifying signature modifiers, which alter the mobility by +1 through +4 bases respectively. In this example, the first run uses 3' encoded identifying signature modifier +2 on dA, 3' encoded identifying signature modifier +1 on dC, 3' encoded identifying signature modifier +4 on dG, and 3' encoded identifying signature modifier +3 on T. The second run uses 3' encoded identifying signature modifier +1 on dA, 3' encoded identifying signature modifier +2 on dC, 3' encoded identifying signature modifier +3 on dG, and 3' encoded identifying signature modifier +4 on T. The third run uses 3' encoded identifying signature modifier +3 on dA, 3' encoded identifying signature modifier +4 on dC, 3' encoded identifying signature modifier +1 on dG, and 3' encoded identifying signature modifier +2 on T. The fourth run uses 3' encoded identifying signature modifier=4 on dA, 3' encoded identifying signature modifier +3 on dC, 3' encoded identifying signature modifier +2 on dG, and 3' encoded identifying signature modifier +1 on T. In this figure, presence of the mutation changes the pattern in four positions among the 4 runs, and increases confidence in the identification of a true mutation.

Although the invention has been described in detail for the purpose of illustration, it is understood that such details are solely for that purpose and variations can be made therein by those skilled in the art without departing from the spirit and scope of the invention which is defined by the following claims.

What is claimed:

1. A method for identifying, in a sample, one or more target nucleotide sequences differing from other nucleotide sequences in the sample by one or more nucleotides, one or more copy numbers, one or more transcript sequences, and/or one or more methylated residues, said method comprising:

providing a sample containing one or more target nucleic acid molecules containing the target nucleotide sequence or complements thereof;

providing a solid support comprising one or more immobilized capture molecules, said capture molecules suitable to bind to a portion of the one or more target nucleic acid molecules;

binding the one or more target nucleic acid molecules to the one or more immobilized capture molecules on the solid support thereby immobilizing the one or more target nucleic acid molecules on said solid support;

subjecting the immobilized target nucleic acid molecules or immobilized complementary target nucleic acid molecules thereof to a ligase detection reaction to produce ligation products hybridized to said immobilized target nucleic acid molecules or immobilized complements thereof;

denaturing the ligation products from the immobilized target nucleic acid molecules or immobilized complementary target nucleic acid molecules thereof to release the ligation products from the solid support;

feeding the denatured ligation products through one or more nanopores capable of detecting said ligation products;

detecting, as a result of said feeding, an identifying signature of each ligation product that is generated when each product passes through the one or more nanopores; and identifying, based on said detecting, the presence of one or more target nucleotide sequences differing from other nucleotide sequences in the sample by one or more nucleotides, one or more copy numbers, one or more transcript sequences, and/or one or more methylated residues.

2. The method of claim 1 further comprising:

appending one or more adapter portions to the one or more target nucleic acid molecules to form adapter appended target nucleic acid molecules, wherein said adapter appended target nucleic acid molecules are suitable for said binding to the one or more immobilized capture molecules on the solid support.

3. The method of claim 2, wherein said appending comprises:
  providing one or more oligonucleotide primer sets, each primer set comprising (a) a first oligonucleotide primer comprising one of the one or more adapter portions at its 5' end and a 3' nucleotide sequence that is complementary to a portion of the target nucleic acid molecule, and (b) a second oligonucleotide primer comprising an optional 5' primer-specific portion and a 3' nucleotide sequence that is complementary to a portion of an extension product formed from the first oligonucleotide primer;
  blending the sample, the one or more oligonucleotide primer sets, and a polymerase to form a polymerase extension reaction mixture;
  subjecting the polymerase extension reaction mixture to two or more polymerase extension reaction cycles thereby forming the adapter appended target nucleic acid molecules.

4. The method of claim 2, wherein said appending comprises:
  subjecting the sample to a terminal deoxynucleotidyl transferase reaction in the presence of mononucleotide triphosphate to append an adapter portion comprising a homopolymer sequence of that mononucleotide to the one or more target nucleic acid molecules.

5. The method of claim 1, wherein said one or more immobilized capture molecules comprise capture oligonucleotides, said method further comprising:
  contacting the solid support containing the immobilized target nucleic acid molecules with a polymerase and dNTPs to forma polymerase replication reaction mixture prior to said subjecting, and
  extending the capture oligonucleotides bound to the target nucleic acid molecules in the polymerase replication reaction mixture to form the immobilized complementary target nucleic acid molecules thereof that are suitable for said subjecting.

6. The method of claim 1, wherein said subjecting comprises:
  contacting the immobilized target nucleic acid molecules or immobilized complementary target nucleic acid molecules thereof with a ligase and one or more oligonucleotide probe sets to form a ligation reaction mixture, wherein each oligonucleotide probe set comprises (a) a first oligonucleotide probe having a target nucleotide sequence-specific portion, and (b) a second oligonucleotide probe having a target nucleotide sequence-specific portion, wherein the first and second oligonucleotide probes of a probe set are configured to hybridize, in a base specific manner, on a complementary region of the immobilized target nucleic acid molecules or immobilized complementary target nucleic acid molecules thereof;
  ligating together first and second oligonucleotide probes of the one or more oligonucleotide probe sets that have hybridized to complementary regions of the immobilized target nucleic acid molecules or immobilized complementary target nucleic acid molecules thereof thereby producing the ligation products hybridized to the target nucleic acid molecules.

7. The method of claim 6 further comprising:
  extending the 3' end of the first oligonucleotide probe to form a junction with the 5' end of the second oligonucleotide probe prior to said ligating.

8. The method of claim 6, wherein the first oligonucleotide probe of the probe set comprises a 5' further portion and the second oligonucleotide probe in a probe set comprises a 3' further portion, wherein the 5' further portion of the first oligonucleotide probe of the probe set is complementary to a portion of the 3' further portion of the second oligonucleotide probe.

9. The method of claim 1, wherein the one or more oligonucleotide probe sets further comprise a third oligonucleotide probe having a target nucleotide sequence-specific portion, wherein the second and third oligonucleotide probes of a probe set are configured to hybridize adjacent to one another on a target nucleic acid molecule with a junction between them to allow ligation between the second and third oligonucleotide probes to form a ligated product sequence comprising the first, second, and third oligonucleotide probes of a probe set.

10. The method of claim 1, wherein said detecting the identifying signature of the ligation product comprises:
  measuring a change in current through at least one of the one or more nanopores that is generated from the passing of the ligation product through said at least one nanopore, wherein said identifying is based on said measuring.

11. The method of claim 1, wherein said detecting the identifying signature of the ligation product comprises:
  detecting a change in current through two or more nanopores, where each of the two or more nanopores have different dimensions, wherein the detected change in current through a first nanopore that is generated from the passing of the ligation product through said first nanopore having a first dimension is different from the detected change in current through a second nanopore that is generated from the passing of the same ligation product through said second nanopore having a second dimension, wherein said identifying is based on said detected changes in current at both the first and second nanopores.

12. The method of claim 1, wherein said detecting the identifying signature of the ligation product comprises:
  detecting, based on said feeding, the ligation product as it passes through at least a first and a second nanopore, wherein said first and second nanopores are positioned on opposing ends of a nano-scale time-of flight channel; and
  measuring, based on said detecting, how long it takes for the ligation product to pass the first and second nanopores in the nano-scale time-of-flight channel, wherein said identifying is based on said measuring.

13. The method of claim 1, wherein the ligation products comprise an identifying signature modifier, wherein one ligation product and its identifying signature modifier generate an identifying signature that is distinguishable from the identifying signature produced by a different ligation product and its identifying signature modifier.

14. The method of claim 1, wherein the provided sample contains a plurality of target nucleic acid molecules and said subjecting produces a plurality of different ligation products corresponding to the plurality of target nucleic acid molecules, said method further comprising:
  distinguishing the plurality of different ligation products based on detecting different identifying signatures produced by the plurality of different ligation products, whereby said identifying involves identifying a plurality of target nucleotide sequences differing from other nucleotide sequences in the sample by one or more nucleotides, one or more copy numbers, one or more transcript sequences, and/or one or more methylated residues.

15. The method of claim 1 further comprising:
contacting the sample with at least a first methylation sensitive enzyme to form a restriction enzyme reaction mixture prior to said binding, wherein said first methylation sensitive enzyme cleaves nucleic acid molecules in the sample that contain one or more unmethylated residues within at least one methylation sensitive enzyme recognition sequence, whereby said identifying involves identifying the presence of one or more target nucleotide sequences originally containing one or more methylated residues.

16. The method of claim 1, wherein the one or more nucleic acid molecules containing the target nucleotide sequence is a ribonucleic acid molecule, said method further comprising:
generating complementary deoxyribonucleic acid (cDNA) molecules from the ribonucleic acid molecule containing the target nucleotide sequence prior to said binding, wherein said cDNA molecules contain the target nucleotide sequence or a complement thereof and are suitable for said binding to the one or more immobilized capture molecules on the solid support, and wherein said identifying identifies the presence of one or more target ribonucleotide sequences differing from other ribonucleotide sequences in the sample due to alternative transcript, alternative start site, alternative coding sequence, alternative non-coding sequence, alternative splicing, exon insertion, exon deletion, intron insertion, translocation, mutation, or other rearrangement at the genome level.

17. The method of claim 1, wherein the one or more nucleic acid molecules containing the target nucleotide sequence in the sample is a micro-ribonucleic acid (miRNA) molecule, said method further comprising:
contacting the sample containing the target miRNA molecule with a ligase and a first oligonucleotide probe comprising a 5' phosphate, a 5' stem-loop portion containing an internal primer-specific portion, a blocking group, and a 3' nucleotide sequence that is complementary to a 3' portion of the target miRNA molecule prior to said binding;
ligating the target miRNA molecule at its 3' end to the 5' phosphate of the first oligonucleotide probe to generate a chimeric nucleic acid molecule comprising the target miRNA molecule and the first oligonucleotide probe;
blending the chimeric nucleic acid molecule, with one or more second oligonucleotide primers comprising a nucleotide sequence that is complementary to the internal primer-specific portion of the first oligonucleotide probe, dNTPs, and a reverse transcriptase to form a reverse transcription reaction mixture, wherein the one or more second oligonucleotide primers of a primer set hybridizes to the internal primer specific portion of the chimeric nucleic acid molecule and is extended at its 3' end to generate a complement of the chimeric nucleic acid molecule that is suitable for said binding, and wherein said identifying identifies the presence of one or more target micro-ribonucleotide sequences differing from other micro-ribonucleotide sequences in the sample by one or more bases.

18. The method of claim 1 further comprising:
contacting the sample with one or more enzymes capable of digesting deoxyuracil (dUTP) containing nucleic acid molecules present in the sample prior to said binding.

* * * * *

UNITED STATES PATENT AND TRADEMARK OFFICE
CERTIFICATE OF CORRECTION

PATENT NO. : 10,829,804 B2
APPLICATION NO. : 15/560805
DATED : November 10, 2020
INVENTOR(S) : Barany et al.

It is certified that error appears in the above-identified patent and that said Letters Patent is hereby corrected as shown below:

In the Specification

Column 19, Lines 63-64:
Please correct "TGGAGCTGGTGGCGTAG" to read -- TGGAGCTG<u>G</u>TGGCGTAG --

Column 20, Lines 3-4:
Please correct "TGGAGCTGATGGCGTAG" to read -- TGGAGCTG<u>A</u>TGGCGTAG --

Column 20, Lines 10-11:
Please correct "TGGAGCTGGTGGCGTAG" to read -- TGGAGCTG<u>G</u>TGGCGTAG --

Column 20, Lines 17-18:
Please correct "TGGAGCTGATGGCGTAG" to read -- TGGAGCTG<u>A</u>TGGCGTAG --

Column 21, Lines 22-23:
Please correct "TGGAGCTGGTGGCGTAG" to read -- TGGAGCTG<u>G</u>TGGCGTAG --

Column 21, Line 23:
Please correct "TGGAGCTGATGGCGTAG" to read -- TGGAGCTG<u>A</u>TGGCGTAG --

Column 24, Line 46:
Please correct "78,500" to read -- ~78,500 --

Column 39, Line 54:
Please correct "RAPS" to read -- RAP5 --

Column 47, Line 53:
Please correct "60-100" to read -- 60-100 μm --

Signed and Sealed this
Thirtieth Day of March, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 10,829,804 B2

Column 83, Lines 24-25:
Please correct "5' -AATTTTTTATTATTCAAC-x-TAAAAAATAATAATAAAAAAAAAAAAAAAAAAAAAAAAAAAAAA -3'" to read
-- A-C_ -5'
A ATTTTTTATTATTA
C–x-TAAAAAATAATAATAAAAAAAAAAAAAAAAAAAAAAAAAAAAAA -3' --

Column 104, Line 13:
Please correct "A-DNA" to read -- λ-DNA --

Column 104, Line 66:
Please correct "100 nm ( ▨ )" to read -- 100 nm ( ▨ ) --

Column 105, Line 37:
Please correct "$N_e$" to read -- $N_c$ --

Column 127, Line 65-Column 128, Line 5:
Please correct
"Cycle 1. 1:1
Cycle 2. 2:2 + 1:1
Cycle 3. 3:3 + 2:2 + 1:1 + 1:1
Cycle 4. 4:4 + 3:3 + 2:2 + 2:2 + 1:1 + 1:1 + 1:1 + 1:1
Cycle 5. 5:5 + 4:4 + 3:3 + 3:3 + 2:2 + 2:2 + 2:2 + 2:2 + 1:1 + 1:1 + 1:1 + 1:1 + 1:1 + 1:1 + 1:1 + 1:1
After melting off untethered sequences, a total of 5 + 4 + 3 + 3 + 2 + 2 + 2 + 2 + 1 + 1 + 1
+ 1 + 1 + 1 + 1 + 1 = 31" to read
-- Cycle 1. 1:1
Cycle 2. 2:2 + 1:1
Cycle 3. 3:3 + 2:2 + 1:1 + 1:1
Cycle 4. 4:4 + 3:3 + 2:2 + 2:2 + 1:1 + 1:1 + 1:1 + 1:1
Cycle 5. 5:5 + 4:4 + 3:3 + 3:3 + 2:2 + 2:2 + 2:2 + 2:2 + 1:1 + 1:1 + 1:1 + 1:1 + 1:1 + 1:1 + 1:1 + 1:1
After melting off untethered sequences, a total of 5 + 4 + 3 + 3 + 2 + 2 + 2 + 2 + 1 +1 + 1 + 1 + 1 + 1
+ 1 + 1 = 31 --

Column 128, Line 33:
Please correct "175x175" to read -- 175x175 μm --

In the Claims

Column 147, Line 32, Claim 5:
Please correct "forma" to read -- form a --